US009834819B2

(12) United States Patent
Margulies et al.

(10) Patent No.: US 9,834,819 B2
(45) Date of Patent: Dec. 5, 2017

(54) METHODS FOR DIAGNOSING AUTISM SPECTRUM DISORDERS

(71) Applicant: Laboratory Corporation of America Holdings, Burlington, NC (US)

(72) Inventors: David Michael Margulies, Newton, MA (US); Mark Firman Bear, Boston, MA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 29 days.

(21) Appl. No.: 14/215,875

(22) Filed: Mar. 17, 2014

(65) Prior Publication Data

US 2014/0186839 A1 Jul. 3, 2014

Related U.S. Application Data

(62) Division of application No. 12/877,655, filed on Sep. 8, 2010, now abandoned.

(60) Provisional application No. 61/240,469, filed on Sep. 8, 2009.

(51) Int. Cl.
*C12Q 1/68* (2006.01)

(52) U.S. Cl.
CPC ..... *C12Q 1/6883* (2013.01); *C12Q 2600/156* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 6,326,483 | B1 | 12/2001 | Kwiatkowski |
| 6,818,395 | B1 | 11/2004 | Quake et al. |
| 7,169,560 | B2 | 1/2007 | Lapidus et al. |
| 7,282,337 | B1 | 10/2007 | Harris |
| 2003/0170807 | A1 | 9/2003 | Worley et al. |
| 2007/0141577 | A1 | 6/2007 | Moore |
| 2009/0156412 | A1 | 6/2009 | Boyce, Jr. et al. |
| 2011/0166029 | A1 | 7/2011 | Margulies et al. |
| 2011/0294693 | A1* | 12/2011 | Hu .................................... 506/9 |

FOREIGN PATENT DOCUMENTS

| | | |
|---|---|---|
| EP | 3135772 | 3/2017 |
| WO | WO 2008/124187 | 10/2008 |
| WO | WO 2009/043178 | 4/2009 |
| WO | WO 2009/144480 | 12/2009 |
| WO | 2011/031786 | 3/2011 |

OTHER PUBLICATIONS

State Intellectual Property Office of the People's Republic of China, Office Action, Application No. 20108004644, dated Aug. 6, 2014, 10 pages.

Akanksha, M. et al., Autism Spectrum Disorders (ASD), International Journal of Research in Ayurveda & Pharmacy, 2(5):1541-1546, 2011.

Caglayan, A., Genetic Causes of Syndromic and Non-Syndromic Autism, Developmental Medicine & Child Neurology, 52:130-138, 2010.

Rogers, S. et al., The Behavioral Phenotype in Fragile X: Symptoms of Autism in Very Young Children with Fragile X Syndrome, Idiopathic Autism, and Other Developmental Disorders, Journal of Developmental & Behavioral Pediatrics, 22(6):409-417, 2001.

Abrahams, B. and Geschwind, D., "Advances in Autism Genetics: On the Threshold of a New Neurobiology," 2008, Nature Reviews Genetics, 9:341-355.

Ausubel, F.M. et al,, Short Protocols in Molecular Biology, 41h Edition, Chapter 2, John Wiley and Sons, N.Y., 1999.

Bowers, J. et al., "Virtual Terminator Nucleotides for Next-Generation DNA Sequencing," 2009, Nature Methods, 6:593-595.

Braslavsky et al., "Sequence Information Can Be Obtained from Single DNA Molecules," 2003, Proc. Natl. Acad. Sci. USA, 100:3960-3964.

Maxam, A. et al., "A New Method for Sequencing DNA," 1977, Proc. Natl. Acad. Sci. USA, 74:560-564.

Needleman, S. and Wunsch, C,, "A General Method Applicable to the Search for Similarities in the Amino Acid Sequence of Two Proteins," 1970, J. Mol. Biol., 48:443-453.

Ozsolak, F. etal., "Direct RNA Sequencing," 2009, Nature, 461:814-818.

Pearson, W. and Lipman, D., "Improved tools for biological sequence comparison," 1988, Proc, Natl. Acad. Sci. USA, 85:2444-2448.

Sanger, F. et al., "DNA sequencing with chain-terminating inhibitors," 1977, Proc. Natl. Acad Sci USA, 74:54635467.

Smith, T. and Waterman, M., "Comparison of Biosequences," 1981, Advances in Applied Mathematics, 2:482489.

Wilbur, W. and Lipman, D,, "Rapid Similarity Searches of Nucleic Acid and Protein Data Banks," 1983, Proc. Natl. Acad. Sci USA, 80:726-730.

GenBank Accession No. NC_000008, *Homo sapiens* chromosome 8, GRCh37.p2 primary reference assembly Oct. 29, 2010, 2 pages.

GenBank Accession No. NC_000004, *Homo sapiens* chromosome 4, GRCh37.p2 primary reference assembly Oct. 29, 2010. 2 pages.

GenBank Accession No. NC 000023, *Homo sapiens* chromosome X, GRCh37.p2 primary reference assembly Oct. 29, 2010. 3 pages.

GenBank Accession No. NC_000006, *Homo sapiens* chromosome 6, GRCh37.p2 primary reference assembly Oct. 29, 2010. 2 pages.

GenBank Accession No. NC 000005, *Homo sapiens* chromosome 5, GRCh37.p2 primary reference assembly Oct. 29, 2010. 2 pages.

GenBank Accession No. NC 000011, *Homo sapiens* chromosome 11, GRCh37.p2 primary reference assembly Oct. 29, 2010. 2 pages.

(Continued)

*Primary Examiner* — Channing S Mahatan

(74) *Attorney, Agent, or Firm* — Kilpatrick Townsend & Stockton LLP

(57) ABSTRACT

The invention generally relates to methods for diagnosing autism spectrum disorders. In certain embodiments, the invention provides a method for diagnosing presence or increased risk of developing an autism spectrum disorder in a subject.

14 Claims, 93 Drawing Sheets

(56) References Cited

OTHER PUBLICATIONS

GenBank Accession No. NC_000015, *Homo sapiens* chromosome 15, GRCh37.p2 primary reference assembly Nov. 1, 2010. 2 pages.
GenBank Accession No. NC_000019, *Homo sapiens* chromosome 19, GRCh37.p2 primary reference assembly Oct. 29, 2010. 2 pages.
GenBank Accession No. NC_000003, *Homo sapiens* chromosome 3, GRCh37.p2 primary reference assembly Oct. 29, 2010. 2 pages.
GenBank Accession No. NC_007466, Human rotavirus G3 segment 7, complete sequence Oct. 29, 2010. 2 pages.
GenBank Accession No. NC_000007, *Homo sapiens* chromosome 7, GRCh37.p2 primary reference assembly Oct. 29, 2010. 2 pages.
GenBank Accession No. NC_000022, *Homo sapiens* chromosome 22, GRCh37.p2 primary reference assembly Oct. 29, 2010. 2 pages.
GenBank Accession No. NC 000009, *Homo sapiens* chromosome 9, GRCh37.p2 primary reference assembly Oct. 29, 2010. 2 pages.
GenBank Accession No. NC_000016, *Homo sapiens* chromosome 16, GRCh37.p2 primary reference assembly Oct. 29, 2010. 2 pages.
GenBank Accession No. NM 015193, *Homo sapiens* activity-regulated cytoskeleton-associated protein (ARC), mRNA Oct. 29, 2010. 3 pages.
GenBank Accession No. NM_001968, *Homo sapiens* eukaryotic translation initiation factor 4E (EIF4E), transcript variant 1, mRNA Nov. 1, 2010. 6 pages.
GenBank Accession No. NM_002024, *Homo sapiens* fragile X mental retardation 1 (FMR1), transcript variant ISO1, mRNA Nov. 1, 2010. 5 pages.
GenBank Accession No. NM_000838, *Homo sapiens* glutamate receptor, metabotropic 1 (GRM1), transcript variant 1, mRNA Nov. 1, 2010. 5 pages.
GenBank Accession No. NM_000842, *Homo sapiens* glutamate receptor, metabotropic 5 (GRM5), transcript variant b, mRNA Nov. 1, 2010. 6 pages.
GenBank Accession No. NM 004272, *Homo sapiens* homer homolog 1 (*Drosophila*) (HOMER1), mRNA Oct. 24, 2011. 6 pages.
GenBank Accession No. NM_176795, *Homo sapiens* v-Ha-ras Harvey rat sarcoma viral oncogene homolog (HRAS), transcript variant 2, mRNA Nov. 1, 2010. 4 pages.
GenBank Accession No. NM 002755, *Homo sapiens* mitogen-activated protein kinase kinase 1 (MAP2K1), mRNA 11/01/20107 4 pages.
GenBank Accession No. NM 030662, *Homo sapiens* mitogen-activated protein kinase kinase 2 (MAP2K2), mRNA Nov. 1, 2010. 4 pages.
GenBank Accession No. NM_004992, *Homo sapiens* methyl CpG binding protein 2 (Rett syndrome) (MECP2), transcript variant 1, mRNA, Nov. 1, 2010. 11 pages.
GenBank Accession No. NM 006218, *Homo sapiens* phosphoinositide-3-klnase, catalytic, alpha polypeptide (PIK3CA), mRNA Nov. 1, 2010. 5 pages.
GenBank Accession No. NM_181523, *Homo sapiens* phosphoinositide-3-kinase, regulatory subunit 1 (alpha) (PIK3R1), transcript variant 1, mRNA3, Nov. 1, 2010. 6 pages.
GenBank Accession No. NM_000314, *Homo sapiens* phosphatase and tensin homolog (PTEN), mRNA Nov. 1, 2010. 5 pages.
GenBank Accession No. NM_002880, *Homo sapiens* v-raf-1 murine leukemia viral oncogene homolog 1 (RAF1), mRNA Nov. 1, 2010. 5 pages.
GenBank Accession No. NMJJ05614, *Homo sapiens* Ras homolog enriched in brain (RHEB), mRNA Nov. 1, 2010. 4 pages.
GenBank Accession No. NM 001080420, *Homo sapiens* SH3 and multiple ankyrin repeat domains 3 (SHANK3), mRNA Nov. 1, 2010. 7 pages.
GenBank Accession No. NM 000368, *Homo sapiens* tuberous sclerosis 1 (TSC1), transcript variant 1, mRNA 1.Jan. 1, 2010. 7 pages.
GenBank Accession No. NM_000548, *Homo sapiens* tuberous sclerosis 2 (TSC2), transcript variant 1, mRNA Nov. 1, 2010. 7 pages.
GenBank Accession No. NM_130839, *Homo sapiens* ubiquitin protein ligase E3A (UBE3A), transcript variant 3, mRNA Nov. 1, 2010. 6 pages.
Lewis, J. et al., "Genotype and Psychological Phenotype in Tuberous Sclerosis," J. Med. Genet., 2004, vol. 41, No. 3, pp. 203-207, XP002633212.
Michaelis, R. et al., "Tuberous Sclerosis 2 (TSC2) Gene Variants in patients with Autism and Seizures," Am. J. Human Genet., 2003, vol. 73, No. 5, p. 538.
Neves-Pereira, M. et al., "Deregulation of EIF4E: A Novel Mechanism for Autism," J. Med. Genet., 2009, vol. 46, No. 11, pp. 759-765, XP008132468.
Norton, N. et al., "Mutation Screening of the Homer Gene family and Association Analysis in Schizophrenia," Am. J. Med. Genet. Part B (Neuropsychiatric Genetics)., 2003, vol. 120B, No. 1, pp. 18-21, XP002633211.
Rendtorff, N. et al., "Analysis of 65 Tuberous Sclerosis Complex (TSC) Patients by TSC2 DGGE, TSC1/TSC2 MLPA, and TSC1 Long-range PCR Sequencing, and Report of 28 Novel Mutations," Human Mutation, 2005, vol. 26, No. 4, pp. 374-383, XP002633213.
Serajee, F. et al., "Association of INPP1, PIK3CG, and TSC2 Gene Variants with Autistic Disorder: implications for Phosphatidylinositol Signalling in Autism," J. Med. Genet., 2003, vol. 40, No. 11, pp. 1-5, XP008135539.
Patent Cooperation Treaty, International Search Report and Written Opinion, Application No. PCT/US2010/048164, dated Apr. 29, 2011. 2 7 pages.
Matlashewski et al. Isolation and characterization of a human p53 cDNA clone: expression of the human p53 gene. 1984. The EMBO Journal. vol. 3, No. 13, pp. 3257-3262.
State Intellectual Property Office of the Peoples Republic of China, Notification of First Office Action, Application No. 201080046441.5, dated Sep. 26, 2013. 16 pages.
Patent Cooperation Treaty, International Preliminary Report on Patentability, International Application No. PCT/US2010/048164, dated Mar. 22, 2012. 18 pages.
Szuml1nski, K. et al., Homer proteins: implication for neuropsychiatric disorders, Neurobiology, 16:251-257, 2006.
European Patent Office, Communication Pursuant to Article 94(3) EPC, Application No. 10777130, dated Jul. 29, 2013. 6 pages.
Geschwind, D. et al., "The Autism Genetic Resource Exchange: A Resource for the Study of Autism and Related Neuropsychiatric Conditions," Am. J. Hum. Gent., 69:463-466, 2001.
European Patent Office, Communication pursuant to Article 94(3) EPC, Application No. 10 777 130.5, dated Apr. 30, 2014, 7 pages.
Danish Patent and Trademark Office, Singapore Search Report, Application No. 201201617-6, dated Jun. 14, 2013, 8 pages.
Danish Patent and Trademark Office, Singapore Search Report, Application No. 201201617-6, dated Jun. 17, 2013, 11 pages.
Danish Patent and Trademark Office, Singapore Search Report, Application No. 201201617-6, dated Nov. 4, 2014, 11 pages.
State Intellectual Property Office of the People's Republic of China, Notification of the Third Office Action, Application No. 201080046441, dated Feb. 28, 2015.
Canadian Patent Office, Office Action, Application No. CA 2,773,049, dated Feb. 2, 2016, 4 pages.
State Intellectual Property Office of the Peoples Republic of China, Office Action, Application No. CN 201080046441, dated Nov. 5, 2015, 9 pages.
Canadian Patent Application No. 2,773,049, Office Action dated Feb. 21, 2017, 6 pages.
Durand et al., "Mutations in the gene encoding the synaptic scaffolding protein SHANKS are associated with autism spectrum disorders", Nature Genetics, Nature Publishing Group, New York, US, vol. 39, No. 1, Jan. 2007, pp. 25-27.
European Patent Application No. 16162579.3, Extended European Search Report dated Dec. 12, 2016, 14 pages.
Gauthier et al., "Novel de novo SHANK3 mutation in autistic patients", American Journal of Medical Genetics Part B: Neuropsychiatric Genetics, vol. 150B, No. 3, Apr. 5, 2009, pp. 421-424.

(56) References Cited

OTHER PUBLICATIONS

Moessner et al., "Contribution of SHANK3 Mutations to Autism Spectrum Disorder", American Journal of Human Genetics, American Society of Human Genetics, Chicago, IL, US, vol. 81, No. 6, Dec. 1, 2007, pp. 1289-1297.
Qin et al., "Association study of SHANK3 gene polymorphisms with autism in Chinese Han population", BMC Medical Genetics, Biomed Central, London, GB, vol. 10, No. 1, Jun. 30, 2009, pp. 1-6.

* cited by examiner

FIG. 3A

ARC DNA (NM_015193) SEQ ID NO: 1

```
   1 tcgggcacgg cgtcctccct ccgcagcagc cgagccggac ctgcctcccc gggcgtgctc
  61 cgccggcccc gccgccggcc cgcagcgaca gacaggcgct ccccgcagct ccgcacggga
 121 cccaggccgc cggaccccag cgccggacca ccctctgtcc gccccgagga gtttgccgcc
 181 tgccggagca cctgcgcaca gatggagctg gaccaccgga ccagcggcgg gctccacgcc
 241 taccccgggc cgcggggcgg gcaggtggcc aagcccaacg tgatcctgca gatcgggaag
 301 tgccgggccg agatgctgga gcacgtgcgg cggacgcacc ggcacctgct ggccgaggtg
 361 tccaagcagg tggagcgcga gctgaagggg ctgcaccggt cggtcgggaa gctggagagc
 421 aacctggacg gctacgtgcc cacgagcgac tcgcagcgct ggaagaagtc catcaaggcc
 481 tgcctgtgcc gctgccagga gaccatcgcc aacctggagc gctgggtcaa gcgcgagatg
 541 cacgtgtggc gcgaggtgtt ctaccgcctg gagcgctggg ccgaccgcct ggagtccacg
 601 ggcggcaagt acccggtggg cagcgagtca gcccgccaca ccgtttccgt gggcgtgggg
 661 ggtcccgaga gctactgcca cgaggcagac ggctacgact acaccgtcag cccctacgcc
 721 atcaccccgc ccccagccgc tggcgagctg cccgggcagg agcccgccga ggcccagcag
 781 taccagccgt gggtccccgg cgaggacggg cagcccagcc ccggcgtgga cacgcagatc
 841 ttcgaggacc ctcgagagtt cctgagccac ctagaggagt acttgcggca ggtgggcggc
 901 tctgaggagt actggctgtc ccagatccag aatcacatga acgggccggc caagaagtgg
 961 tgggagttca agcagggctc cgtgaagaac tgggtggagt tcaagaagga gttcctgcag
1021 tacagcgagg gcacgctgtc ccgagaggcc atccagcgcg agctggacct gccgcagaag
1081 cagggcgagc cgctggacca gttcctgtgg cgcaagcggg acctgtacca gacgctctac
1141 gtggacgcgg acgaggagga gatcatccag tacgtggtgg gcaccctgca gcccaagctc
1201 aagcgtttcc tgcgccaccc cctgcccaag accctggagc agctcatcca gagggggcatg
1261 gaggtgcagg atgacctgga gcaggcggcc gagccggccg gcccccacct cccggtggag
1321 gatgaggcgg agaccctcac gcccgccccc aacagcgagt ccgtggccag tgaccggacc
1381 cagcccgagt agagggcatc ccggagcccc cagcctgccc actacatcca gcctgtggct
1441 ttgcccacca ggacttttga gctggggctg actcctgcag ggaagccct ggtccagctg
1501 ggtgccccct cgagctccgg gcggactcgc acacactcgt gtcatccaga tgtgagcacc
1561 gcacccagcg gcaaagagcc ctcccccctg cagggctcca cccatcaccc tccctccgtc
1621 tgtctttccg gcctggaccc caccctccac actctcaggc catcacagaa caccccagct
1681 tcctcattct gctacaacac ccaggccctc tggacatcca gaaaaccaag tgtccggatg
1741 gcaggggcca gcggccacca agctcatggg acacccagag cagaagctag ggcagagcca
1801 atgctgaggg agcctcgact tccggcgccg ccgccctctc ccggcatccg cagagccagc
1861 tgacgccctc cctgcctccc agggcagctg gccagcctcg ggcagcgcgg ccccctcctc
1921 ccagggggaga gtagaagtcg cacacgcagc agagcagacc tgatgtcccg gtgcttcctg
1981 gcccctcagc tccagtgatt cacgcccgcc tggagaagaa tcagagctca gctcatgact
2041 cacccatggc aggcggaggg tcccagaggg gctgagtcct caaatccggc tgaggcagca
2101 gctggcacca tcagagccag gagagtgaca acaggtctca aggttcccac aaagtctttg
2161 ctgctgtgct gggcaccacc caccctcac cttgcaggct gcctgcgtgg gaggcgaagt
2221 cccaggacag cccagagggg ggctacagag aggagtcggc tgcagcagag ggcaggagcc
2281 ccagcttagc cctgagcgcc agcgcgagga ccagggcctg ccactaagcc cgccccgctg
2341 gccgccagct gcccgtcccc agagccactg cagcaggagt cgggccctgc ctccctccca
2401 gcagggaaac cccgcccgct gccaggccat cctctctgcc agaggctttc atgagcccca
2461 aggctggggc cacagctcct acccctgccc agcagccctg agctcagctg caggaaggac
2521 atcccagaag ccatggctcc tggggcgctt ccaggcattc tgccctgccc cgacaccaga
2581 accctggtgc tggtgggcca ctagcgtctg cagcctaagc aggtgctggc tcagggttca
2641 tcgttctgcc ttgtccactg gggaccagc cctgcagacc actctgacaa gtcttcagcc
2701 cacaccctgc cagccccaca gattttattt ttgcacataa gccataacca atcctcaagg
2761 ctggcacagg ctttggggaa gccctggagc ctgtgaagac cctggaaacc tcatgaggct
2821 gtggccaacc cctgcccctt gccccacaca gaccaggcct taaatgtcgg tccaggccct
2881 gtgcacctta ccccagagac agactctttt tgtaagattt tgttaataaa acactgaaac
2941 ttcaaaaaaa aaaaaaaaaa aaaaaaaaaa aaaaaaaaaa aaaaa
```

FIG. 3B

ARC Protein SEQ ID NO: 2

MELDHRTSGGLHAYPGPRGGQVAKPNVILQIGKCRAEMLEHVRR

THRHLLAEVSKQVERELKGLHRSVGKLESNLDGYVPTSDSQRWKKSIKACLCRCQETI

ANLERWVKREMHVWREVFYRLERWADRLESTGGKYPVGSESARHTVSVGVGGPESYCH

EADGYDYTVSPYAITPPPAAGELPGQEPAEAQQYQPWVPGEDGQPSPGVDTQIFEDPR

EFLSHLEEYLRQVGGSEEYWLSQIQNHMNGPAKKWWEFKQGSVKNWVEFKKEFLQYSE

GTLSREAIQRELDLPQKQGEPLDQFLWRKRDLYQTLYVDADEEEIIQYVVGTLQPKLK

RFLRHPLPKTLEQLIQRGMEVQDDLEQAAEPAGPHLPVEDEAETLTPAPNSESVASDR

TQPE

FIG. 3C

EIF4E DNA (NM_001968) SEQ ID NO: 3

```
   1 gcacaggcag cctgcataca ctccttttcc tggtgtcaac attatttaaa agcatgggaa
  61 atagtaatga gacagtgtct tcttcattag aaccttagga gtctactaga tttcttcatc
 121 tctatttgtt gttattagta gccaaactgt gcaaaaaaca cggtcttgag aaatgacagc
 181 acagtatctt agagggaaag gaaatgtagg atgccagtgt ggggacaaat ttctgattgc
 241 cagtgattgt tgtgagcata acaataattt catgaacatt aaagcctcta ttgagggcag
 301 ctgcagttgt aaaggaaaaa aaatggtcct gaacatttaa aactacactg gtgtacatca
 361 taatcaaaca aagtaaacag aaaaaaattt aaactttgct aaaaaaaaaa agcagaagca
 421 cttgatcttt aggaaggcac gcagttgctt attatgaatc atttctagag tccgatgcat
 481 tttcaaagcc ggttacagtc attacgaagc acacccttgt gaggtaagtg tatcatcacc
 541 tttggttcat aaataaaaaa gctgagacgc cgagcgatta agtcactcgc ctaaggagaa
 601 tgagtcaacg tcaagagtca tagttgaccc ggcctaaaga ctccagacca tcagtccagg
 661 gcttagtcag cggggcccgg agtggcttcc ctggctggca tctggactta ggctatttcc
 721 gtgcacgtaa aagcggaata ttggaacggt tgcacagaac ttccaaataa tttttaccgc
 781 cacgcaagat ttagccctga ggtcttaatc tcaggatttg ggacagtaaa agctgtcgtc
 841 cctcccctc gtccagccgg tggcaagcgg gtactgcggg cggttccgtc cgtcccttt
 901 cgcagaaatg gcaacgaatg accaccagca ttagctgagc caggggacgt gggagggttg
 961 attgcctaaa cgactctgca tcgccgcctc tttttgaaac taagagaaaa tggtgggaga
1021 tcaaaagaaa actaaataaa cacacaggca acttgtcctg ggacctcaac taagcaaatg
1081 aagccttatt gtgtgtgctg agcctgcagt tcccaacctt ccggggaaga tgggaggaca
1141 gggcgacaaa gggcacagta ggcttgcctg gcagtaagtg tgaccgcagc tatccaggcg
1201 gaagagcaga ggactgaaac caccctccag caagcgagtg tccgccgcgt tgagaaccgc
1261 gcaccctacc catcggccac gtgaccagtc ctttttaaaa aaaatttctt taccttaaaa
1321 aaaaaaaaaa aaaaaaggtg ggggagagac tccacttccc agaagcctct cgttactcac
1381 gcagccgcag tcttgcgcag gtgccgccag ggccaaacgg acatatccgt cacgtggcca
1441 gaagctggcc aatccggttt gaatctcatt tttttcctct tacccccct tctggagcgg
1501 ttgtgcgatc agatcgatct aagatggcga ctgtcgaacc ggaaaccacc cctactccta
1561 atccccgac tacagaagag gagaaaacgg aatctaatca ggaggttgct aacccagaac
1621 actatattaa acatccccta cagaacagat gggcactctg gtttttaaa aatgataaaa
1681 gcaaaacttg gcaagcaaac ctgcggctga tctccaagtt tgatactgtt gaagactttt
1741 gggctctgta caaccatatc cagttgtcta gtaatttaat gcctggctgt gactactcac
1801 tttttaagga tggtattgag cctatgtggg aagatgagaa aaacaaacgg ggaggacgat
1861 ggctaattac attgaacaaa cagcagagac gaagtgacct cgatcgcttt tggctagaga
1921 cacttctgtg ccttattgga gaatcttttg atgactacag tgatgatgta tgtggcgctg
1981 ttgttaatgt tagagctaaa ggtgataaga tagcaatatg gactactgaa tgtgaaaaca
2041 gagaagctgt tacacatata gggagggtat acaaggaaag gttaggactt cctccaaaga
2101 tagtgattgg ttatcagtcc cacgcagaca cagctactaa gagcggctcc accactaaaa
2161 ataggtttgt tgtttaagaa gacaccttct gagtattctc ataggagact gcgtcaagca
2221 atcgagattt gggagctgaa ccaaagcctc ttcaaaaagc agagtggact gcatttaaat
2281 ttgatttcca tcttaatgtt actcagatat aagagaagtc tcattcgcct ttgtcttgta
2341 cttctgtgtt catttttttt tttttttttg gctagagttt ccactatccc aatcaaagaa
2401 ttacagtaca catccccaga atccataaat gtgttcctgg cccactctgt aatagttcag
2461 tagaattacc attaattaca tacagatttt acctatccac aatagtcaga aaacaacttg
2521 gcatttctat actttacagg aaaaaaaatt ctgttgttcc attttatgca gaagcatatt
2581 ttgctggttt gaaagattat gatgcataca gttttctagc aattttcttt gtttcttttt
2641 acagcattgt ctttgctgta ctcttgctga tggctgctag attttaattt atttgtttcc
2701 ctacttgata atattagtga ttctgatttc agtttttcat ttgttttgct tttgtttttt
2761 tcctcatgta acattggtga aggatccagg aatatgacac aaaggtggaa taaacattaa
2821 ttttgtgcat tctttggtaa ttttttttgt tttttgtaac tacaaagctt tgctacaaat
2881 ttatgcattt cattcaaatc agtgatctat gtttgtgtga tttcctaaac ataattgtgg
2941 attataaaaa atgtaacatc ataattacat tcctaactag aattagtatg tctgtttttg
3001 tatctttatg ctgtatttta acactttgta ttacttaggt tattttgctt tggttaaaaa
3061 tggctcaagt agaaaagcag tcccattcat attaagacag tgtacaaaac tgtaaataaa
```

FIG. 3C (cont.)

```
3121 atgtgtacag tgaattgtct tttagacaac tagatttgtc cttttatttc tccatcttta
3181 tagaaggaat ttgtacttct tattgcaagg cagtctctat attatgtctt cttttgtggt
3241 gtcttccatg tgaacagcat aagtttggag cactagtttg attattatgt ttattacaat
3301 ttttaataaa ttgaataggt agtatcatat atatggaatt aaattgatgt ggctatcttt
3361 gtttttttat aaagtaaggc acagtcattc agtcttaggt aaataatgta ctctcttaat
3421 atgttaatac tcatgagaat tgggatctga tgcatcacca tttgattggt agcaacagtg
3481 gttgtaaaac ttggttgctg aattgagttg tttctatgtt aagtgtcaaa atgatagtgt
3541 agggaaagta caggtggtgg ggacatatgc attaagaatc ttgttagtgt tgcaatctaa
3601 atagaatgga ataaacaggt gttaagacat atttatagtg gtaaattgtt gtagtatggt
3661 attctgtaaa cttgaaaact tgatctactc tttgtaggta tcatttgaaa gcaaacttga
3721 aaatgttttg tacatagtac atacttgtat agtcctgtga gatgaagtat ggctatcaga
3781 ccaaaggata agccaaactg taggtagcag aatggaaatt attattttga gaggaaaatt
3841 tgtctttgaa tggtgattat gacttaatca ttttaaaact gataaacttg acaaaaaccc
3901 tgtatgaaat aaacatgaaa ttaatagcac tgatttcatt gtaaaatttt aaagcagttt
3961 aaagggtacc acaggttatc acagtactct caatgccaca aacacctctt gttcagtatt
4021 ctagaaatac tgaatcagaa ttctgtgttt attataatct cagcatactg tacataatat
4081 ctgctagtta aacttgggta attggttaag gtgacttact gtctatgtca atatgtatag
4141 ttttgagtac ttcaagagtt tacttaaaag tgatgatgtt actggtatgt tggcagtggg
4201 tgggactgaa gtagtgtatc tattataaat tgatctattt tcttaattct aagatgaagt
4261 ccaattttaa gcatcagctt ttaggtgcaa aggaggaatt aacacattaa atgtatacag
4321 ttctaaattt ttgaaataac tgatgtgtag catttgatta ttggtattac cattttagaa
4381 tcatgatgtt attttaaacc tttttcctgg ggacaagaaa ggataataaa ttacgctgaa
4441 tcacttttgg cagttgccac ttaaatagta cagtgacttg caacttttat aactttatca
4501 gcatcttctc taaatacaaa attaggctat atgttatttt ccaacttact gttttctctc
4561 tgtttagcag gatattataa atagattaaa tagatatatt ttcttttttt tttttttttt
4621 ttgagacgga gtctcgcttt gtctcccagg ctggagtgca gtggcgtgat ctcccagtag
4681 ctgggactac aagcacctgc caccatgccc ggctaatttt ttttgtattt ttagtagaga
4741 cggggtttc
```

FIG. 3D

EIF4E Protein SEQ ID NO: 4

MATVEPETTPTPNPPTTEEEKTESNQEVANPEHYIKHPLQNRWA

LWFFKNDKSKTWQANLRLISKFDTVEDFWALYNHIQLSSNLMPGCDYSLFKDGIEPMW

EDEKNKRGGRWLITLNKQQRRSDLDRFWLETLLCLIGESFDDYSDDVCGAVVNVRAKG

DKIAIWTTECENREAVTHIGRVYKERLGLPPKIVIGYQSHADTATKSGSTTKNRFVV

FIG. 3E

FMR1 DNA (NM _002024) SEQ ID NO: 5

```
   1 acttccggtg gagggccgcc tctgagcggg cggcgggccg acggcgagcg cgggcggcgg
  61 cggtgacgga ggcgccgctg ccaggggggcg tgcggcagcg cggcggcggc ggcggcggcg
 121 gcggcggcgg aggcggcggc ggcggcggcg gcggcggcgg ctgggcctcg agcgcccgca
 181 gcccacctct cgggggcggg ctcccggcgc tagcagggct gaagagaaga tggaggagct
 241 ggtggtggaa gtgcggggct ccaatggcgc tttctacaag gcatttgtaa aggatgttca
 301 tgaagattca ataacagttg catttgaaaa caactggcag cctgataggc agattccatt
 361 tcatgatgtc agattcccac ctcctgtagg ttataataaa gatataaatg aaagtgatga
 421 agttgaggtg tattccagag caaatgaaaa agagccttgc tgttggtggt tagctaaagt
 481 gaggatgata aagggtgagt tttatgtgat agaatatgca gcatgtgatg caacttacaa
 541 tgaaattgtc acaattgaac gtctaagatc tgttaatccc aacaaacctg ccacaaaaga
 601 tactttccat aagatcaagc tggatgtgcc agaagactta cggcaaatgt gtgccaaaga
 661 ggcggcacat aaggatttta aaaaggcagt tggtgccttt tctgtaactt atgatccaga
 721 aaattatcag cttgtcattt tgtccatcaa tgaagtcacc tcaaagcgag cacatatgct
 781 gattgacatg cactttcgga gtctgcgcac taagttgtct ctgataatga gaaatgaaga
 841 agctagtaag cagctggaga gttcaaggca gcttgcctcg agatttcatg aacagtttat
 901 cgtaagagaa gatctgatgg gtctagctat tggtactcat ggtgctaata ttcagcaagc
 961 tagaaaagta cctggggtca ctgctattga tctagatgaa gatacctgca catttcatat
1021 ttatggagag gatcaggatg cagtgaaaaa agctagaagc tttctcgaat ttgctgaaga
1081 tgtaatacaa gttccaagga acttagtagg caaagtaata ggaaaaaatg gaaagctgat
1141 tcaggagatt gtggacaagt caggagttgt gagggtgagg attgaggctg aaaatgagaa
1201 aaatgttcca caagaagagg aaattatgcc accaaattcc cttccttcca ataattcaag
1261 ggttggacct aatgccccag aagaaaaaaa acatttagat ataaaggaaa acagcaccca
1321 tttttctcaa cctaacagta caaaagtcca gagggtgtta gtggcttcat cagttgtagc
1381 aggggaatcc cagaaacctg aactcaaggc ttggcagggt atggtaccat ttgtttttgt
1441 gggaacaaag gacagcatcg ctaatgccac tgttcttttg gattatcacc tgaactattt
1501 aaaggaagta gaccagttgc gtttggagag attacaaatt gatgagcagt tgcgacagat
1561 tggagctagt tctagaccac caccaaatcg tacagataag gaaaaaagct atgtgactga
1621 tgatggtcaa ggaatgggtc gaggtagtag acettacaga aatagggggc acggcagacg
1681 cggtcctgga tatacttcag gaactaattc tgaagcatca aatgcttctg aaacagaatc
1741 tgaccacaga gacgaactca gtgattggtc attagctcca acagaggaag agagggagag
1801 cttcctgcgc agaggagacg gacggcggcg tggaggggga ggaagaggac aaggaggaag
1861 aggacgtgga ggaggcttca aaggaaacga cgatcactcc cgaacagata atcgtccacg
1921 taatccaaga gaggctaaag gaagaacaac agatggatcc cttcagatca gagttgactg
1981 caataatgaa aggagtgtcc acactaaaac attacagaat acctccagtg aaggtagtcg
2041 gctgcgcacg ggtaaagatc gtaaccagaa gaaagagaag ccagacagcg tggatggtca
2101 gcaaccactc gtgaatggag taccctaaac tgcataattc tgaagttata tttcctatac
2161 catttccgta attcttattc catattagaa aactttgtta ggccaaagac aaatagtagg
2221 caagatggca cagggcatga aatgaacaca aattatgcta agaatttttt atttttttggt
2281 attggccata agcaacaatt ttcagatttg cacaaaaaga taccttaaaa tttgaaacat
2341 tgcttttaaa actacttagc acttcagggc agattttagt tttattttct aaagtactga
2401 gcagtgatat tctttgttaa tttggaccat tttcctgcat tgggtgatca ttcaccagta
2461 cattctcagt ttttcttaat atatagcatt tatggtaatc atattagact tctgttttca
2521 atctcgtata gaagtcttca tgaaatgcta tgtcatttca tgtcctgtgt cagtttatgt
2581 tttggtccac ttttccagta ttttagtgga ccctgaaatg tgtgtgatgt gacatttgtc
2641 attttcatta gcaaaaaaag ttgtatgatc tgtgcctttt ttatatcttg gcaggtagga
2701 atattatatt tggatgcaga gttcagggaa gataagttgg aaacactaaa tgttaaagat
2761 gtagcaaacc ctgtcaaaca ttagtacttt atagaagaat gcatgctttc catatttttt
2821 tccttacata aacatcaggt taggcagtat aaagaatagg acttgttttt gtttttgttt
2881 tgttgcactg aagtttgata aatagtgtta ttgagagaga tgtgtaattt ttctgtatag
2941 acaggagaag aaagaactat cttcatctga gagaggctaa aatgttttca gctaggaaca
3001 aatcttcctg gtcgaaagtt agtaggatat gcctgctctt tggcctgatg accaatttta
```

FIG. 3E (cont.)

```
3061 acttagagct tttttttttt aattttgtct gccccaagtt ttgtgaaatt tttcatattt
3121 taatttcaag cttattttgg agagatagga aggtcatttc catgtatgca taataatcct
3181 gcaaagtaca ggtactttgt ctaagaaaca ttggaagcag gttaaatgtt ttgtaaactt
3241 tgaaatatat ggtctaatgt ttaagcagaa ttggaaaaga ctaagatcgg ttaacaaata
3301 acaacttttt tttctttttt tcttttgttt tttgaagtgt tggggtttgg ttttgttttt
3361 tgagtctttt tttttaagt gaaatttatt gaggaaaaat atgtgaagga ccttcactct
3421 aagatgttat atttttctta aaaagtaact cctagtaggg gtaccactga atctgtacag
3481 agccgtaaaa actgaagttc tgcctctgat gtattttgtg agtttgtttc tttgaatttt
3541 cattttacag ttacttttcc ttgcatacaa acaagcatat aaaatggcaa caaactgcac
3601 atgatttcac aaatattaaa aagtctttta aaaagtattg ccaaacatta atgttgattt
3661 ctagttattt attctgggaa tgtatagtat ttgaaaacag aaattggtac cttgcacaca
3721 tcatctgtaa gctgtttggt tttaaaatac tgtagataat taaccaaggt agaatgacct
3781 tgtaatgtaa ctgctcttgg gcaatattct ctgtacatat tagcgacaac agattggatt
3841 ttatgttgac atttgtttgg ttatagtgca atatattttg tatgcaagca gtttcaataa
3901 agtttgatct tcctctgcta aattgatgtt gatgcaatcc ttacaaatga ttgcttttaa
3961 aattttaagc taggaaaaga aatctataga aagtgttctg ttacaaaatg taactgttac
4021 cattggaaat ttcacgtcat aggaagttag cctttatcta ccaactttca agaacttgtt
4081 taataaagcg aaaaactcaa ccaaatggta caaaaccaca gtgtaccatt aaaatatgca
4141 ctaagtctct tttttacaaa ggctgtattc agcaaggcgc taacttgctt aaatgtgaat
4201 tactaacttc taaaactgta ctttgattca catgttttca aatggagttg gagttcattc
4261 atattacaat atttgtgtgc taaacgtgta tgtttttcag ttcaaagtca tgatgttttt
4321 aaaatcttat taaagtttca aaaatctgaa gattgtttat ctagatgtaa atttttatta
4381 aaaagttgca cttatgaaaa agcaaaaaat t
```

FIG. 3F

FMR1 Protein SEQ ID NO: 6

MEELVVEVRGSNGAFYKAFVKDVHEDSITVAFENNWQPDRQIPF

HDVRFPPPVGYNKDINESDEVEVYSRANEKEPCCWWLAKVRMIKGEFYVIEYAACDAT

YNEIVTIERLRSVNPNKPATKDTFHKIKLDVPEDLRQMCAKEAAHKDFKKAVGAFSVT

YDPENYQLVILSINEVTSKRAHMLIDMHFRSLRTKLSLIMRNEEASKQLESSRQLASR

FHEQFIVREDLMGLAIGTHGANIQQARKVPGVTAIDLDEDTCTFHIYGEDQDAVKKAR

SFLEFAEDVIQVPRNLVGKVIGKNGKLIQEIVDKSGVVRVRIEAENEKNVPQEEEIMP

PNSLPSNNSRVGPNAPEEKKHLDIKENSTHFSQPNSTKVQRVLVASSVVAGESQKPEL

KAWQGMVPFVFVGTKDSIANATVLLDYHLNYLKEVDQLRLERLQIDEQLRQIGASSRP

PPNRTDKEKSYVTDDGQGMGRGSRPYRNRGHGRRGPGYTSGTNSEASNASETESDHRD

ELSDWSLAPTEEERESFLRRGDGRRRGGGGRGQGGRGRGGGFKGNDDHSRTDNRPRNP

REAKGRTTDGSLQIRVDCNNERSVHTKTLQNTSSEGSRLRTGKDRNQKKEKPDSVDGQ

QPLVNGVP

FIG. 3G

GMR1 DNA (NM_000838) SEQ ID NO: 7

```
   1 agtgctgaag aaagagggca ctagtgtaca gcccagatcg catccttgca ccgtctggat
  61 tagagctgag gcgtctgcaa gccgagcgtg gccacggtcc tctggccccg ggaccatagc
 121 gctgtctacc ccgactcagg tactcagcag catctagctc accgctgcca acacgacttc
 181 cactgtactc ttgatcaatt taccttgatg cactaccggt gaagaacggg gactcgaatt
 241 cccttacaaa cgcctccagc ttgtagaggc ggtcgtggag gacccagagg aggagacgaa
 301 ggggaaggag gcggtggtgg aggaggcaaa ggccttggac gaccattgtt ggcgaggggc
 361 accactccgg gagaggcggc gctgggcgtc ttgggggtgc gcgccgggag cctgcagcgg
 421 gaccagcgtg ggaacgcggc tggcaggctg tggacctcgt cctcaccacc atggtcgggc
 481 tcctttttgt ttttttccca gcgatctttt tggaggtgtc ccttctcccc agaagccccg
 541 gcaggaaagt gttgctggca ggagcgtcgt ctcagcgctc ggtggccaga atggacggag
 601 atgtcatcat tggagccctc ttctcagtcc atcaccagcc tccggccgag aaagtgcccg
 661 agaggaagtg tggggagatc agggagcagt atggcatcca gagggtggag gccatgttcc
 721 acacgttgga taagatcaac gcggacccgg tcctcctgcc caacatcacc ctgggcagtg
 781 agatccggga ctcctgctgg cactcttccg tggctctgga acagagcatt gagttcatta
 841 gggactctct gatttccatt cgagatgaga aggatgggat caaccggtgt ctgcctgacg
 901 gccagtccct ccccccaggc aggactaaga agcccattgc gggagtgatc ggtcccggct
 961 ccagctctgt agccattcaa gtgcagaacc tgctccagct cttcgacatc ccccagatcg
1021 cttattcagc cacaagcatc gacctgagtg acaaaacttt gtacaaatac ttcctgaggg
1081 ttgtcccttc tgacactttg caggcaaggg ccatgcttga catagtcaaa cgttacaatt
1141 ggacctatgt ctctgcagtc cacacggaag ggaattatgg ggagagcgga atggacgctt
1201 tcaaagagct ggctgcccag gaaggcctct gtatcgccca ttctgacaaa atctacagca
1261 acgctgggga gaagagcttt gaccgactct tgcgcaaact ccgagagagg cttcccaagg
1321 ctagagtggt ggtctgcttc tgtgaaggca tgacagtgcg aggactcctg agcgccatgc
1381 ggcgccttgg cgtcgtgggc gagttctcac tcattggaag tgatggatgg gcagacagag
1441 atgaagtcat tgaaggttat gaggtggaag ccaacggggg aatcacgata aagctgcagt
1501 ctccagaggt caggtcattt gatgattatt tcctgaaact gaggctggac actaacacga
1561 ggaatccctg gttccctgag ttctggcaac atcggttcca gtgccgcctt ccaggacacc
1621 ttctggaaaa tcccaacttt aaacgaatct gcacaggcaa tgaaagctta gaagaaaact
1681 atgtccagga cagtaagatg gggtttgtca tcaatgccat ctatgccatg gcacatgggc
1741 tgcagaacat gcaccatgcc ctctgccctg gccacgtggg cctctgcgat gccatgaagc
1801 ccatcgacgg cagcaagctg ctggacttcc tcatcaagtc ctcattcatt ggagtatctg
1861 gagaggaggt gtggtttgat gagaaaggag acgctcctgg aaggtatgat atcatgaatc
1921 tgcagtacac tgaagctaat cgctatgact atgtgcacgt tggaacctgg catgaaggag
1981 tgctgaacat tgatgattac aaaatccaga tgaacaagag tggagtggtg cggtctgtgt
2041 gcagtgagcc ttgcttaaag ggccagatta aggttatacg gaaaggagaa gtgagctgct
2101 gctggatttg cacggcctgc aaagagaatg aatatgtgca agatgagttc acctgcaaag
2161 cttgtgactt gggatggtgg cccaatgcag atctaacagg ctgtgagccc attcctgtgc
2221 gctatcttga gtggagcaac atcgaatcca ttatagccat cgccttttca tgcctgggaa
2281 tccttgttac cttgtttgtc accctaatct ttgtactgta ccgggacaca ccagtggtca
2341 aatcctccag tcgggagctc tgctacatca tcctagctgg catcttcctt ggttatgtgt
2401 gcccattcac tctcattgcc aaacctacta ccacctcctg ctacctccag cgcctcttgg
2461 ttggcctctc ctctgcgatg tgctactctg ctttagtgac taaaaccaat cgtattgcac
2521 gcatcctggc tggcagcaag aagaagatct gcacccggaa gcccaggttc atgagtgcct
2581 gggctcaggt gatcattgcc tcaattctga ttagtgtgca actaaccctg gtggtaaccc
2641 tgatcatcat ggaacccccct atgcccattc tgtcctaccc aagtatcaag gaagtctacc
2701 ttatctgcaa taccagcaac ctgggtgtgg tggccccttt gggctacaat ggactcctca
2761 tcatgagctg tacctactat gccttcaaga cccgcaacgt gcccgccaac ttcaacgagg
2821 ccaaatatat cgcgttcacc atgtacacca cctgtatcat ctggctagct tttgtgccca
2881 tttactttgg gagcaactac aagatcatca caacttgctt tgcagtgagt ctcagtgtaa
2941 cagtggctct ggggtgcatg ttcactccca agatgtacat cattattgcc aagcctgaga
3001 ggaatgtccg cagtgccttc accacctctg atgttgtccg catgcatgtt ggcgatggca
```

FIG. 3G (cont.)

```
3061 agctgccctg ccgctccaac actttcctca acatcttccg aagaaagaag gcaggggcag
3121 ggaatgccaa ttctaatggc aagtctgtgt catggtctga accaggtgga ggacaggtgc
3181 ccaagggaca gcatatgtgg caccgcctct ctgtgcacgt gaagaccaat gagacggcct
3241 gcaaccaaac agccgtcatc aagcccctca ctaaaagtta ccaaggctct ggcaagagcc
3301 tgaccttttc agataccagc accaagaccc tttacaacgt agaggaggag gaggatgccc
3361 agccgattcg ctttagcccg cctggtagcc cttccatggt ggtgcacagg cgcgtgccaa
3421 gcgcggcgac cactccgcct ctgccgtccc acctgaccgc agaggagacc cccctcttcc
3481 tggccgaacc agccctcccc aagggcttgc cccctcctct ccagcagcag cagcaacccc
3541 ctccacagca gaaatcgctg atggaccagc tccagggagt ggtcagcaac ttcagtaccg
3601 cgatcccgga ttttcacgcg gtgctggcag gccccggtgg tcccgggaac gggctgcggt
3661 ccctgtaccc gcccccgcca cctccgcagc acctgcagat gctgccgctg cagctgagca
3721 cctttgggga ggagctggtc tccccgcccg cggacgacga cgacgacagc gagaggttta
3781 agctcctcca ggagtacgtg tatgagcacg agcgggaagg gaacacggaa gaagacgaac
3841 tggaagagga ggaggaggac ctgcaggcgg ccagcaaact gaccccggat gattcgcctg
3901 cgctgacgcc tccgtcgcct ttccgcgact cggtggcctc gggcagctcg gtgcccagct
3961 cccccgtgtc cgagtcggtg ctctgcaccc ctcccaacgt atcctacgcc tctgtcattc
4021 tgcgggacta caagcaaagc tcttccaccc tgtaaggggg aagggtccac atagaaaagc
4081 aagacaagcc agagatctcc cacacctcca gagatgtgca aacagctggg aggaaaagcc
4141 tgggagtggg gggcctcgtc gggaggacag gagaccgctg ctgctgctgc cgctactgct
4201 gctgctgcct taagtaggaa gagagggaag gacaccaagc aaaaaatgtt ccaggccagg
4261 attcggattc ttgaattact cgaagccttc tctgggaaga aagggaattc tgacaaagca
4321 caattccata tggtatgtaa cttttatcac aaatcaaata gtgacatcac aaacataatg
4381 tcctcttttg cacaattgtg catagatata tatatgccca cacacactgg gccatgcttg
4441 ccaaggaaca gcccacgtgg acatgccagt cggatcatga gttcacctga tggcattcgg
4501 agtgagctgg tggagccaga cagagcaggt gcggggaagg gaagggccca ggccagaccc
4561 atcccaaacg gatgatggga tgatggaca gcagctcctt gctcagaagc ccttctcccc
4621 gctgggctga cagactcctc atcttcagga gactcaggaa tggagcggca caggggtctc
4681 tcttcatcca ctgcaaccca tccagtgcca gctttgagat tgcacttgaa gaaaggtgca
4741 tggacccccct gctgctctgc agattccctt tatttaggaa aacaggaata agagcaaaat
4801 tatcaccaaa aagtgcttca tcaggcgtgc tacaggagga aggagctaga aatagaacaa
4861 tccatcagca tgagactttg aaaaaaaaac acatgatcag cttctcatgt tccatattca
4921 cttattggcg atttggggaa aaggccggaa caagagattg ttacgagagt ggcagaaacc
4981 cttttgtaga ttgacttgtg tttgtgccaa gcgggctttc cattgacctt cagttaaaga
5041 acaaaccatg tgacaaaatt gttaccttcc acttactgta gcaaataata cctacaagtt
5101 gaacttctaa gatgcgtata tgtacaattt ggtgccatta tttctcctac gtattagaga
5161 aacaaatcca tctttgaatc taatggtgta ctcatagcaa ctattactgg tttaaatgac
5221 aaataattct atcctattgt cactgaagtc cttgtaacta gcgagtgaat gtgttcctgt
5281 gtccttgtat atgtgcgatc gtaaaatttg tgcaatgtaa tgtcaaattg actggtcaat
5341 gtcaacctag tagtcaatct aactgcaatt agaaattgtc ttttgaatat actatatata
5401 tttttatgt tccaataatg ttttgtacat cattgtcatc aatatctaca gaagctcttt
5461 gacggtttga atactatggc tcaaggtttt catatgcagc tcggatggac atttttcttc
5521 taagatggaa cttatttttc agatattttc tgatgtggag atatgttatt aatgaagtgg
5581 tttgaaaatt tgttatatta aaagtgcaca aaaactgaga gtgaaaataa aaggtacatt
5641 ttataagctt gcacacatta ttaacacata agattgaaca aagcatttag attattccag
5701 gttatatcat ttttttaaag attttccaca gctacttgag tgtctaacat acagtaacat
5761 ctaactcagc taataatttg taaaatcttt atcaatcaca ttttgccttc ttttaatttt
5821 tatgttcatg gacttttatt cctgtgtctt ggctgtcata actttttatt tctgctattt
5881 gctgttgtgt aatatccatg gacatgtaat ccacttactc catctttaca atcccttttt
5941 accaccaata aaaggatttt tcttgctgtt ttgatttctt ctattatttg tggaatgaat
6001 tatacccccc ttaaatatct ttgtttatgc cttatgttca gtcatatttt aatatgcttc
6061 cttcatattg aagctgctga tttctcagcc aaaaatcatc ttagaatctt taaatatcca
6121 ttgcatcatt tgttcagaat ttaacatcca ttccaatgtt ggaggcttgt attacttata
6181 tttcatcata ttctattgcc aagtttagtc agttccacac caagaatgaa ctgcatttcc
```

FIG. 3G (cont.)

```
6241 tttaaaaatt attttaaaac acctttattg aaaagatctc atgactgaga tgtggacttt
6301 ggttccatgt tttcattgta agaaagcaga gagcggaaaa tcaatggctc cagtgattaa
6361 tagatgggtt tttagtaatt gacaaattca tgagggaaag catatgatct ctttattagt
6421 gaatcatgct tattttttac tcttaatgcc actaatatac atccctaata tcacagggct
6481 tgtgcattca gatttttaaa aaattaggat agataaggaa acaacttata ttcaagtgta
6541 agatgatatc aggttggtct aagacttttg gtgaacacgt tcattcaact gtgatcactt
6601 tattactctg aatgcctact attatcctga ttatggggtc tcctgaataa atagagtatt
6661 agtccttatg tcatcattgt tcaaaattgg agatgtacac atacataccc tataccaaga
6721 gggccgaaac tcttcacctt gatgtatgtt ctgatacaag ttgttcagct tcttgtaaat
6781 gtgttttcct tcggcttgtt actgcctttt gtcaaataat cttgacaatg ctgtataata
6841 aatattttct attt
```

FIG. 3H

GMR1 Protein SEQ ID NO: 8

MVGLLLFFFPAIFLEVSLLPRSPGRKVLLAGASSQRSVARMDGD

VIIGALFSVHHQPPAEKVPERKCGEIREQYGIQRVEAMFHTLDKINADPVLLPNITLG

SEIRDSCWHSSVALEQSIEFIRDSLISIRDEKDGINRCLPDGQSLPPGRTKKPIAGVI

GPGSSSVAIQVQNLLQLFDIPQIAYSATSIDLSDKTLYKYFLRVVPSDTLQARAMLDI

VKRYNWTYVSAVHTEGNYGESGMDAFKELAAQEGLCIAHSDKIYSNAGEKSFDRLLRK

LRERLPKARVVVCFCEGMTVRGLLSAMRRLGVVGEFSLIGSDGWADRDEVIEGYEVEA

NGGITIKLQSPEVRSFDDYFLKLRLDTNTRNPWFPEFWQHRFQCRLPGHLLENPNFKR

ICTGNESLEENYVQDSKMGFVINAIYAMAHGLQNMHHALCPGHVGLCDAMKPIDGSKL

LDFLIKSSFIGVSGEEVWFDEKGDAPGRYDIMNLQYTEANRYDYVHVGTWHEGVLNID

DYKIQMNKSGVVRSVCSEPCLKGQIKVIRKGEVSCCWICTACKENEYVQDEFTCKACD

LGWWPNADLTGCEPIPVRYLEWSNIESIIAIAFSCLGILVTLFVTLIFVLYRDTPVVK

SSSRELCYIILAGIFLGYVCPFTLIAKPTTTSCYLQRLLVGLSSAMCYSALVTKTNRI

ARILAGSKKKICTRKPRFMSAWAQVIIASILISVQLTLVVTLIIMEPPMPILSYPSIK

EVYLICNTSNLGVVAPLGYNGLLIMSCTYYAFKTRNVPANFNEAKYIAFTMYTTCIIW

LAFVPIYFGSNYKIITTCFAVSLSVTVALGCMFTPKMYIIIAKPERNVRSAFTTSDVV

RMHVGDGKLPCRSNTFLNIFRRKKAGAGNANSNGKSVSWSEPGGGQVPKGQHMWHRLS

VHVKTNETACNQTAVIKPLTKSYQGSGKSLTFSDTSTKTLYNVEEEEDAQPIRFSPPG

SPSMVVHRRVPSAATTPPLPSHLTAEETPLFLAEPALPKGLPPPLQQQQPPPQQKSL

MDQLQGVVSNFSTAIPDFHAVLAGPGGPGNGLRSLYPPPPPPQHLQMLPLQLSTFGEE

LVSPPADDDDDSERFKLLQEYVYEHEREGNTEEDELEEEEEDLQAASKLTPDDSPALT

PPSPFRDSVASGSSVPSSPVSESVLCTPPNVSYASVILRDYKQSSSTL

FIG. 3I

GRM5 DNA (NM_000842) SEQ ID NO: 9

```
   1 agctcggctg ttctgcgcac gctgagcgga gggaatgagc ttgagatcat cttggggggg
  61 aagccgggga ctggagaggc cggctctgcc ctgctgatcc ccgtggccca acttttcggg
 121 gggctagcta gaccgagtct cactgctcgc agcgcagcca acaggggggt ttagaagatc
 181 atgaccacat ggatcatcta actaaatggt acatggggac aaaatggtcc tttagaaaat
 241 acatctgaat tgctggctaa tttcttgatt tgcgactcaa cgtaggacat cgcttgttcg
 301 tagctatcag aaccctcctg aattttcccc accatgctat ctttattggc ttgaactcct
 361 ttcctaaaat ggtccttctg ttgatcctgt cagtcttact tttgaaagaa gatgtccgtg
 421 ggagtgcaca gtccagtgag aggagggtgg tggctcacat gccgggtgac atcattattg
 481 gagctctctt ttctgttcat caccagccta ctgtggacaa agttcatgag aggaagtgtg
 541 gggcggtccg tgaacagtat ggcattcaga gagtggaggc catgctgcat accctggaaa
 601 ggatcaattc agaccccaca ctcttgccca acatcacact gggctgtgag ataaggcact
 661 cctgctggca ttcggctgtg gccctagagc agagcattga gttcataaga gattccctca
 721 tttcttcaga agaggaagaa ggcttggtac gctgtgtgga tggctcctcc tcttccttcc
 781 gctccaagaa gcccatagta ggggtcattg ggcctggctc cagttctgta gccattcagg
 841 tccagaattt gctccagctt ttcaacatac ctcagattgc ttactcagca accagcatgg
 901 atctgagtga caagactctg ttcaaatatt tcatgagggt tgtgccttca gatgctcagc
 961 aggcaagggc catggtggac atagtgaaga ggtacaactg gacctatgta tcagccgtgc
1021 acacagaagg caactatgga gaaagtggga tggaagcctt caaagatatg tcagcgaagg
1081 aagggatttg catcgcccac tcttacaaaa tctacagtaa tgcaggggag cagagctttg
1141 ataagctgct gaagaagctc acaagtcact tgcccaaggc ccgggtggtg gcctgcttct
1201 gtgagggcat gacggtgaga ggtctgctga tggccatgag gcgcctgggt ctagcgggag
1261 aatttctgct tctgggcagt gatggctggg ctgacaggta tgatgtgaca gatggatatc
1321 agcgagaagc tgttggtggc atcacaatca agctccaatc tcccgatgtc aagtggtttg
1381 atgattatta tctgaagctc cggccagaaa caaaccaccg aaacccttgg tttcaagaat
1441 tttggcagca tcgttttcag tgccgactgg aagggtttcc acaggagaac agcaaataca
1501 acaagacttg caatagttct ctgactctga aaacacatca tgttcaggat tccaaaatgg
1561 gatttgtgat caacgccatc tattcgatgg cctatgggct ccacaacatg cagatgtccc
1621 tctgcccagg ctatgcagga ctctgtgatg ccatgaagcc aattgatgga cggaaacttt
1681 tggagtccct gatgaaaacc aattttactg gggtttctgg agatacgatc ctattcgatg
1741 agaatggaga ctctccagga aggtatgaaa taatgaattt caaggaaatg ggaaaagatt
1801 actttgatta tatcaacgtt ggaagttggg acaatggaga attaaaaatg gatgatgatg
1861 aagtatggtc caagaaaagc aacatcatca gatctgtgtg cagtgaacca tgtgagaaag
1921 gccagatcaa ggtgatccga aagggagaag tcagctgttg ttggacctgt acaccttgta
1981 aggagaatga gtatgtcttt gatgagtaca catgcaaggc atgccaactg gggtcttggc
2041 ccactgatga tctcacaggt tgtgacttga tcccagtaca gtatcttcga tggggtgacc
2101 ctgaacccat tgcagctgtg gtgtttgcct gccttggcct cctggccacc ctgtttgtta
2161 ctgtagtctt catcatttac cgtgatacac cagtagtcaa gtcctcaagc agggaactct
2221 gctacattat ccttgctggc atctgcctgg gctacttatg taccttctgc ctcattgcga
2281 agcccaaaca gatttactgc taccttcaga gaattggcat tggtctctcc ccagccatga
2341 gctactcagc ccttgtaaca aagaccaacc gtattgcaag gatcctggct ggcagcaaga
2401 agaagatctg taccaaaaag cccagattca tgagtgcctg tgcccagcta gtgattgctt
2461 tcattctcat atgcatccag ttgggcatca tcgttgccct ctttataatg gagcctcctg
2521 acataatgca tgactaccca agcattcgag aagtctacct gatctgtaac accaccaacc
2581 taggagttgt cactccactt ggatacaatg gattgttgat tttgagctgc accttctatg
2641 cgttcaagac cagaaatgtt ccagctaact tcaacgaggc caagtatatc gccttcacaa
2701 tgtacacgac ctgcattata tggctagctt ttgtgccaat ctactttggc agcaactaca
2761 aaatcatcac catgtgtttc tcggtcagcc tcagtgccac agtggcccta ggctgcatgt
2821 ttgtgccgaa ggtgtacatc atcctggcca aaccagagag aaacgtgcgc agcgccttca
2881 ccacatctac cgtggtgcgc atgcatgtag gggatggcaa gtcatcctcc gcagccagca
2941 gatccagcag cctagtcaac ctgtggaaga gaaggggctc ctctggggaa accttaagtt
3001 ccaatggaaa atccgtcacg tgggcccaga atgagaagag cagccggggg cagcacctgt
```

FIG. 3I (cont.)

```
3061 ggcagcgcct gtccatccac atcaacaaga aagaaaaccc caaccaaacg gccgtcatca
3121 agcccttccc caagagcacg gagagccgtg gcctgggcgc tggcgctggc gcaggcggga
3181 gcgctggggg cgtgggggcc acgggcggtg cgggctgcgc aggcgccggc ccaggcgggc
3241 ccgagtcccc agacgccggc cccaaggcgc tgtatgatgt ggccgaggct gaggagcact
3301 tcccggcgcc cgcgcggccg cgctcaccgt cgcccatcag cacgctgagc caccgcgcgg
3361 gctcggccag ccgcacggac gacgatgtgc cgtcgctgca ctcggagcct gtggcgcgca
3421 gcagctcctc gcagggctcc ctcatggagc agatcagcag tgtggtcacc cgcttcacgg
3481 ccaacatcag cgagctcaac tccatgatgc tgtccaccgc ggcccccagc cccggcgtcg
3541 gcgccccgct ctgctcgtcc tacctgatcc ccaaagagat ccagttgccc acgaccatga
3601 cgacctttgc cgaaatccag cctctgccgg ccatcgaagt cacgggaggc gcgcagcccg
3661 cggcaggggc gcaggcggct ggggacgcgg cccgggagag ccccgcggcc ggtcccgagg
3721 ctgcggccgc caagccagac ctggaggagc tggtggctct caccccgccg tcccccttca
3781 gagactcggt ggactcgggg agcacaaccc ccaactcgcc agtgtccgag tcggccctct
3841 gtatcccgtc gtctcccaaa tatgacactc ttatcataag agattacact cagagctcct
3901 cgtcgttgtg aatgtccctg gaaagcacgc cggcctgcgc gtgcggagcg gagccccccg
3961 tgttcacaca cacacaatgg caagcatagt cgcctggtta cggcccaggg ggaagatgcc
4021 aagggcaccc cttaatggaa acacgagatc agtagtgcta tctcatgaca accgacgaag
4081 aaaccgacga caaatctttt ggcagatttt cttctagtgg ccttagaaaa catgggcttt
4141 taagaaacac ggctgatatc tttgagggct gacaaggcgt ctcttcaaac agttccatac
4201 caagtgcttt gctctaggga agcagtgcgt gtgaaacagc gtaacggagg gtgaagagca
4261 tagttaataa gcaactgtaa aaagttttat ttgtttactt taattctttt cccagaagag
4321 tctttgattc accaaacatg aatgtacatt ttctaacaaa ctcaaaatct gggaccaaaa
4381 catcaacttt tttctttctt ttttctttct ttttgttttt tctttcctgt aaagaccttg
4441 aaaagcagta acttgggtcc agtatttacg gaggcgttgt gaatgtgtcc catgcataac
4501 acactactgg atagtgagtg ctgcgctaat gtactacgta gggcttctac cagagatttt
4561 cctctccaat tgggttgtga aatactcttc caaaagcctg catcggggat tccacctact
4621 tatttcagat tcacctccat taaccaagaa aaccagtgga agatttcttg actatttcac
4681 catgttgcca atcaatactg gagtagcaaa aaaaatattt tctggaatac tgttttgtaa
4741 ttccctcact ggggtgcatt gtagctggaa attctcttta taaaaatcat tcttgagctc
4801 cagcctggct atctctttca agaaacatgg ccactcttta ggaatgctgt tgcgtttgca
4861 ttgccaacta aaatattaaa atatgcattg ggcttcttc attcctttat tttgagaacc
4921 tgatgcacaa agagctcctt tgttcttttc gagtcccacc actggaagag tggtccatag
4981 accccatgaa gacattgtca tgatttgaga gactgttgtt gaaaggatta acacaatctt
5041 aatacactga aaattttaac tgtgtcaagt cagcttagtg gagatttagc tatgccagtg
5101 agcagtgatt ttaactattc ttggctgctt aaacagggca gctatgaact atgacaaatg
5161 tagatttttc aaagcaatac aaaatactaa aaaagaggaa ccttaatgaa tattaaccac
5221 acagtctttc ttagccattc caaaaagagg caaagcaatt cttattttct tttttaaaat
5281 aatgattaat atgattttgt gcacttcata ctgtcacttt ttaaaactac agaaaagaga
5341 tttagagtat aacagaaaca agtgtgcttt gatagtctca aataggtaga attcatagtt
5401 caagacctga atccactgtc atctctttct tcctcccatt gcagctatcc tcaggtacca
5461 aatgttttga tttttaaata aggatagtaa taaatggagg aggtgtccta taaatttaaa
5521 gttcagttga cccagcctta tacttaagat agccttatga aaaatatgtg ctgtgaggca
5581 gaagtatatt ttggcagaga gaataataaa taaaactttt tcttttagct caatatcctt
5641 actttggtaa gtattttttt ttatttcaca tctacttaac agaaaataaa ctgagaaata
5701 gaagtcagtc cattggcata atttatcatt cttcacttta aaaaattcta ataaatattc
5761 tgcttgagtt ttcttttctg ctatttgttc ttacttgcaa ctttaagtca aacctcccaa
5821 tacaaaacat taaaagctaa cattaatgta ctaaagtatt aatttaaaag aaatcgaacc
5881 tcccatgcta gatttgaaaa taacatcatc acagcaccct gatcccaaat attacaccga
5941 ggcttttaaa atgtaagtga aatctagcta agtttcatgg tttcattaaa agcaaatgtc
6001 tgcctctatc tgaaaaacaa atggaaatct tttgaggtgt taataccctt tggatcctca
6061 tcaaaaggat ggcattcacc tgaggattcc tatcttgact tcttaggtat taaaaacctt
6121 tcttgatatg ctctacattt taaaatttgt tttataaaat ccttatgttg attttcattt
6181 tattctcaag tacaatacgt ttcactctag accagttgaa gaacatgttt aaactttgtt
```

FIG. 3I (cont.)

```
6241 catggtcaaa ttcattttct attttttag taacatatct cttaaaaagc acactacctt
6301 ataaaaaact tcatcagaaa ttaaatttaa tgcaagtaaa ttgccatctg atacttccac
6361 atgctatcat aatcaactgt aataataaaa atgatttatc caattagaaa aggacaagat
6421 atatttttct ctgtatttct ataacttttg ccactccatt gaatacattg tatgttggac
6481 ataagattat tagtaatgca ttcttgagat cttttatttt ggaatgatgc taactctgtc
6541 tctttgccaa ttctaatacc aggttccaag taataactct acagtacaaa gagaactgaa
6601 tattcattct agggctatag gatatgaact tcacaattca tttgggtaca ttctcattga
6661 atttccttca aaacaatctg ttcctggtgc ccagtgataa ttcagtcggg accagcatga
6721 ctaaaaggaa ggggatatgc taaggctcag caaagtgacc ctaaatgaga gatatgtccc
6781 aggatggaaa gaagaagacg tggtttaacc aagttatact gactaatcta agcagtccac
6841 tcatccttcc attttgggaa aggagtgggg gcagcctaag aagaacatat ctggattggg
6901 aagaaccgtc tttctgggct agggatgggg aacagaaagg gagtatggaa agaaaaatta
6961 taagagattt gactgaagca aggaaaaaaa gcaaatcccc aaacgtgcta atccttgaaa
7021 gtaactatct ttcccaaact actgctgtta ccagcaagtg atcaggaaga ctaggagcta
7081 tttctgactg taaatgaatt gtataatagc tctgctgcag ttctgtgact tccaagccag
7141 gaattaaatg ctctttttaa gaataacaaa aaacaaaagc atttcctatg ctagtctccc
7201 agtaaaatgt acatgttttg gagacttcaa aggtattatg tgagttcaca tttagcaaca
7261 gcttattaat aaccctcaag ctgtcagaat ctctatagtt accatttaca attttatact
7321 gtgaaaaaat acagatcagt gaaagcataa agacaagtca gaattcactt tgaagagggt
7381 ctgaggcctg ggagagtctc tactgtctat tgaagaatga ggcatgtata aaatagttgg
7441 ttgaatttca ctgatcttcc caatgtgaac aaatatacta tgtatattgt gtgtatttct
7501 agaaatcaat ggcagctgct gatggtgttg taattagaaa tctatataga ttatagatgt
7561 tttagaaaga tggtgccaat cctaaaagat ttgtgtgggc taaaagtgct tgtacttact
7621 tttttctgca cttataactg atttggtttt aaaattgtgt gcgtgtatct gttctttctc
7681 tgttgtggca gcttgtacta ttaaaataat agagaatgtt aaattatttt gatgtgaact
7741 gcaaatgatt ttttttcata aagtttaaca tttttatcag cattgttttg ctttgtactt
7801 gtataaatat gttttatttt agcacttcaa aatatacttg cctgtttctc agttgtctaa
7861 atcatgttgt acttggtgtt tgtgaagcca gttacttttc aaaaaaatta aaaaacctat
7921 aatatga
```

FIG. 3J

GMR5 Protein SEQ ID NO: 10

MVLLLILSVLLLKEDVRGSAQSSERRVVAHMPGDIIIGALFSVH

HQPTVDKVHERKCGAVREQYGIQRVEAMLHTLERINSDPTLLPNITLGCEIRDSCWHS

AVALEQSIEFIRDSLISSEEEEGLVRCVDGSSSSFRSKKPIVGVIGPGSSSVAIQVQN

LLQLFNIPQIAYSATSMDLSDKTLFKYFMRVVPSDAQQARAMVDIVKRYNWTYVSAVH

TEGNYGESGMEAFKDMSAKEGICIAHSYKIYSNAGEQSFDKLLKKLTSHLPKARVVAC

FCEGMTVRGLLMAMRRLGLAGEFLLLGSDGWADRYDVTDGYQREAVGGITIKLQSPDV

KWFDDYYLKLRPETNHRNPWFQEFWQHRFQCRLEGFPQENSKYNKTCNSSLTLKTHHV

QDSKMGFVINAIYSMAYGLHNMQMSLCPGYAGLCDAMKPIDGRKLLESLMKTNFTGVS

GDTILFDENGDSPGRYEIMNFKEMGKDYFDYINVGSWDNGELKMDDDEVWSKKSNIIR

SVCSEPCEKGQIKVIRKGEVSCCWTCTPCKENEYVFDEYTCKACQLGSWPTDDLTGCD

LIPVQYLRWGDPEPIAAVVFACLGLLATLFVTVVFIIYRDTPVVKSSSRELCYIILAG

ICLGYLCTFCLIAKPKQIYCYLQRIGIGLSPAMSYSALVTKTNRIARILAGSKKKICT

KKPRFMSACAQLVIAFILICIQLGIIVALFIMEPPDIMHDYPSIREVYLICNTTNLGV

VTPLGYNGLLILSCTFYAFKTRNVPANFNEAKYIAFTMYTTCIIWLAFVPIYFGSNYK

IITMCFSVSLSATVALGCMFVPKVYIILAKPERNVRSAFTTSTVVRMHVGDGKSSSAA

SRSSSLVNLWKRRGSSGETLSSNGKSVTWAQNEKSSRGQHLWQRLSIHINKKENPNQT

AVIKPFPKSTESRGLGAGAGAGGSAGGVGATGGAGCAGAGPGGPESPDAGPKALYDVA

EAEEHFPAPARPRSPSPISTLSHRAGSASRTDDDVPSLHSEPVARSSSSQGSLMEQIS

SVVTRFTANISELNSMMLSTAAPSPGVGAPLCSSYLIPKEIQLPTTMTTFAEIQPLPA

IEVTGGAQPAAGAQAAGDAARESPAAGPEAAAAKPDLEELVALTPPSPFRDSVDSGST

TPNSPVSESALCIPSSPKYDTLIIRDYTQSSSSL

FIG. 3K

HOMER 1 DNA (NM_004272) SEQ ID NO: 11

```
   1 tggagcggcg gctgcgcttc ggcttcgagc ccagctctcc tggccccaac gcgggcttag
  61 cctcccgcct tggctcgggc aggcgcccgt cgacccttcg gccccttcg cccgccctgg
 121 agctgggggc agggtgccag tggaagcgtg gggcttggct ctgtgattca ttcattctcc
 181 gccgacggga gcctcagacc cgctgtgctc tgaagagagg agggaagagg gggcagccgc
 241 gaatgaaggg ccgggcacca gccgggctcc attgtgctcg gcggcggggg gcgggaaggg
 301 gctgagggag gtgggatcgg gtcccctcct ccagctctcc ggcgtgcgct gcgcccccag
 361 cctgctgcca gcctggaaat ggctccgttt attctcttcg ggagaatgaa tcgatcctgc
 421 ctagccttct cttcgtcctc cccacctctt ctctgctccg agtcttagga ggagaaacat
 481 ttaaaaagac agattccaat gtggagtgcc gtgcaggttg cgagctgccg ggtttgcact
 541 tcgaggagat tttcctgtgt agtttttttc ctaatgtgag cgcagggaag ccgtggcatt
 601 actgcttttg ggatttttat tcacgtgcac gtcgcgtttg gttgctcgct ccacccccgg
 661 agacctggtg tggtggagaa atttgaaccc gcagccttag ctccgaaaag gccgagttac
 721 ctggctctcc ctgagtgtcg aggaggacat gagtgaaatg accagcgaac tcatttttta
 781 taggactcgg tgaagccgga ttctgcattt ccctacttgt agactcattt tgtggaatag
 841 agttgatcgc tgtctcctcc gcaaagcatt ttaactcgaa taagcaaatg ccgcctctgt
 901 ttgaacgttt tggtatttac aagagagaaa tcattttacc taagagaact aattgaattg
 961 gcagcatcct tgaaatacct ccggacaagg atctgggggt gggggtggaa aagcaactgc
1021 gaaatagcag acggagaaat tcctttggaa gttattccgt agcataagag ctgaaacttc
1081 agagcaagtt ttcattgggc aaaatggggg aacaacctat cttcagcact cgagctcatg
1141 tcttccaaat tgacccaaac acaaagaaga actgggtacc caccagcaag catgcagtta
1201 ctgtgtctta tttctatgac agcacaagaa atgtgtatag gataatcagt ttagatggct
1261 caaaggcaat aataaatagt accatcaccc caaacatgac atttactaaa acatctcaga
1321 agtttggcca gtgggctgat agccgggcaa acaccgttta tggattggga ttctcctctg
1381 agcatcatct ttcgaaattt gcagaaaagt ttcaggaatt taaagaagct gctcgactag
1441 caaaggaaaa atcacaagag aagatggaac ttaccagtac accttcacag gaatccgcag
1501 gcggggatct tcagtctcct ttaacaccgg aaagtatcaa cgggacagat gatgaaagaa
1561 cacctgatgt gacacagaac tcagagccaa gggctgaacc aactcagaat gcattgccat
1621 tttcacatag ttcagcaatc agcaaacatt gggaggctga actggctacc ctcaaaggaa
1681 ataatgccaa actcactgca gccctgctgg agtccactgc caatgtgaaa caatggaaac
1741 agcaacttgc tgcctatcaa gaggaagcag aacgtctgca caagcgggtg actgaacttg
1801 aatgtgttag tagccaagca aatgcagtac atactcataa gacagaatta aatcagacaa
1861 tacaagaact ggaagagaca ctgaaactga aggaagagga aatagaaagg ttaaaacaag
1921 aaattgataa tgccagagaa ctacaagaac agagggattc tttgactcag aaactacagg
1981 aagtagaaat tcggaacaaa gacctggagg gacaactgtc tgacttagag caacgtctgg
2041 agaaaagtca gaatgaacaa gaagcttttc gcaataacct gaagacactc ttagaaattc
2101 tggatggaaa gatatttgaa ctaacagaat tacgagataa cttggccaag ctactagaat
2161 gcagctaagg aaagtgaaat ttcagtgcca attaattaaa agatacactg tctctcttca
2221 taggactgtt taggctctgc atcaagattg cacaaaaaaa aaaaaaaaaa aattgaatat
2281 cactcctcca ggaggaggat cttttgaaat tggaattgta tatttcactg taaattttag
2341 aatccagctt gtagctagtt ggggaaaaaa gatgaaaaac ttgaactaca aattacctcc
2401 atgtatatta ttggccatag ttaactagaa agttataaat agacacttaa tgcaatcttt
2461 tttcctgata ttagccaatg ggagaattaa caatgtctag gtcacatccc ctttttgtgt
2521 tcaacacagt gaagattatc tgctttttaa attaatttat ttacgatatc tagagctgtg
2581 ttttgtgcaa aaacttagtg atgaaagcct gtcttttgtt gtaatctgaa taatttctca
2641 ggatattttt gcactgctga gaagcagtgc cattaccaat taattcttgc caggagtgag
2701 agagagctgt atctttaatt gaaatatact ataactgggt gtatagagtt cttccctttt
2761 ttgtgctgga agatatttca ctctggtgac tactctggta cactctggtg ttctctaatc
2821 ttgtctgttg tatagtttac ttttccatat tgattccatg tatttatgag aagatattgt
2881 ctcccatttt attacacatt ttaaagccaa ctaacgaagg cagctgagtc cctcagaaat
2941 ttttcttttt aagtttctaa taaatttgac acacagtact gaaatacagc agcccgtcat
3001 tgacaggctg gtctagcaat gttaagtata tttacagaat atgcagttac atttatttat
```

FIG. 3K (cont.)

```
3061 atattttgca agaaatcttt tctgaatgat caatgcattt caatttacga ataataatgg
3121 ttattgggga actgtttatt atagataatt ttaaggtgta tagctatttt aaaggggggtc
3181 catttacatc aaacagctga tcagaggact ctatctaaat tgtgatcgtg gcagatagag
3241 atggagtcat gtactctatc tggctctaca catcaatcac atcttgattc aaacctcaca
3301 aggcaatatt ctgaattgtt aactaggtat ttcaaaacag gaattaaatt caataggctc
3361 ttctcagtga acaggtttta atgttgtttt gatgtaattt taaaagactt ttagcaaaca
3421 tgcatttctt tatatgatat atttctttta cgaagctatt ttaaaagtaa gccaagtgct
3481 gtctagtctg cttataaagt aggaattgca tcagagtaca tatattcttg ctgtacaatg
3541 cctgtgatgt tgaggagggt tcttttttaa agtgtatgct tgagtaactg actctatgga
3601 gtctataaat gcactgactt cttgtttgta ccccaaaatg atcgaattgt taagtacaaa
3661 attaagctaa ttaaccaatt tgtaaccatt ttttcactca taaacagcta ctcaatacta
3721 gacaattttg tttttatgt atgtgtatgt acgtaaatac atacatatta atttacatta
3781 gagtgaaaaa taaatggttt gtttctgaag ttagtttctt aagtgagttt tcaggtgtct
3841 ctgaaaaatt tataacaatc atgtattata tgtgctgtaa catcatgtac gttacctcca
3901 tctattttag gatattttcc tcacctatat attataggga gaataattta gatacacatg
3961 ctcagagctg agatatttct ctgataaatc aggtaacaaa atgtatttga ttgatggaat
4021 tttgaagtaa atgtgttttt atccatcagt ttctgagtaa caaagagcac caagttttaa
4081 tttaaatagg agatttaaca ctagggatca gggagtttag tatgaagagt taaaaaaatt
4141 taaaaaacag tgtaagctgt tgaaatggca agtgaattat tttaatgatg taataaaata
4201 tttttaaatt ttgaaaaaaa aaaaaaaa
```

FIG. 3L

HOMER 1 Protein SEQ ID NO: 12

MGEQPIFSTRAHVFQIDPNTKKNWVPTSKHAVTVSYFYDSTRNV

YRIISLDGSKAIINSTITPNMTFTKTSQKFGQWADSRANTVYGLGFSSEHHLSKFAEK

FQEFKEAARLAKEKSQEKMELTSTPSQESAGGDLQSPLTPESINGTDDERTPDVTQNS

EPRAEPTQNALPFSHSSAISKHWEAELATLKGNNAKLTAALLESTANVKQWKQQLAAY

QEEAERLHKRVTELECVSSQANAVHTHKTELNQTIQELEETLKLKEEEIERLKQEIDN

ARELQEQRDSLTQKLQEVEIRNKDLEGQLSDLEQRLEKSQNEQEAFRNNLKTLLEILD

GKIFELTELRDNLAKLLECS

FIG. 3M

HRAS DNA (NM_176795) SEQ ID NO: 13

```
   1 tgccctgcgc ccgcaacccg agccgcaccc gccgcggacg gagcccatgc gcggggcgaa
  61 ccgcgcgccc ccgcccccgc cccgccccgg cctcggcccc ggccctggcc ccgggggcag
 121 tcgcgcctgt gaacggtggg gcaggagacc ctgtaggagg accccgggcc gcaggcccct
 181 gaggagcgat gacggaatat aagctggtgg tggtgggcgc cggcggtgtg ggcaagagtg
 241 cgctgaccat ccagctgatc cagaaccatt ttgtggacga atacgacccc actatagagg
 301 attcctaccg gaagcaggtg gtcattgatg gggagacgtg cctgttggac atcctggata
 361 ccgccggcca ggaggagtac agcgccatgc gggaccagta catgcgcacc ggggagggct
 421 tcctgtgtgt gtttgccatc aacaacacca agtcttttga ggacatccac cagtacaggg
 481 agcagatcaa acgggtgaag gactcggatg acgtgcccat ggtgctggtg gggaacaagt
 541 gtgacctggc tgcacgcact gtggaatctc ggcaggctca ggacctcgcc cgaagctacg
 601 gcatccccta catcgagacc tcggccaaga cccggcaggg cagccgctct ggctctagct
 661 ccagctccgg gaccctctgg gaccccccgg gacccatgtg acccagcggc ccctcgcgct
 721 ggagtggagg atgccttcta cacgttggtg cgtgagatcc ggcagcacaa gctgcggaag
 781 ctgaaccctc ctgatgagag tggccccggc tgcatgagct gcaagtgtgt gctctcctga
 841 cgcaggtgag ggggactccc agggcggccg ccacgcccac cggatgaccc cggctccccg
 901 cccctgccgg tctcctggcc tgcggtcagc agcctccctt gtgccccgcc cagcacaagc
 961 tcaggacatg gaggtgccgg atgcaggaag gaggtgcaga cggaaggagg aggaaggaag
1021 gacggaagca aggaaggaag gaagggctgc tggagcccag tcaccccggg accgtgggcc
1081 gaggtgactg cagaccctcc cagggaggct gtgcacagac tgtcttgaac atcccaaatg
1141 ccaccggaac cccagccctt agctcccctc ccaggcctct gtgggccctt gtcgggcaca
1201 gatgggatca cagtaaatta ttggatggtc ttgaaaaaaa aaaaaaaaaa a
```

FIG. 3N

HRAS Protein SEQ ID NO: 14

MTEYKLVVVGAGGVGKSALTIQLIQNHFVDEYDPTIEDSYRKQV

VIDGETCLLDILDTAGQEEYSAMRDQYMRTGEGFLCVFAINNTKSFEDIHQYREQIKR

VKDSDDVPMVLVGNKCDLAARTVESRQAQDLARSYGIPYIETSAKTRQGSRSGSSSSS

GTLWDPPGPM

FIG. 30

MAP2K1 DNA (NM_02755) SEQ ID NO: 15

```
   1 aggcgaggct tccccttccc cgcccctccc ccggcctcca gtccctccca gggccgcttc
  61 gcagagcggc taggagcacg gcggcggcgg cactttcccc ggcaggagct ggagctgggc
 121 tctggtgcgc gcgcggctgt gccgcccgag ccggagggac tggttggttg agagagagag
 181 aggaagggaa tcccgggctg ccgaaccgca cgttcagccc gctccgctcc tgcagggcag
 241 cctttcggct ctctgcgcgc gaagccgagt cccgggcggg tggggcgggg gtccactgag
 301 accgctaccg gcccctcggc gctgacggga ccgcgcgggg cgcacccgct gaaggcagcc
 361 ccggggcccg cggcccggac ttggtcctgc gcagcgggcg cggggcagcg cagcgggagg
 421 aagcgagagg tgctgccctc cccccggagt tggaagcgcg ttacccgggt ccaaaatgcc
 481 caagaagaag ccgacgccca tccagctgaa cccggccccc gacggctctg cagttaacgg
 541 gaccagctct gcggagacca acttggaggc cttgcagaag aagctggagg agctagagct
 601 tgatgagcag cagcgaaagc gccttgaggc ctttcttacc cagaagcaga aggtgggaga
 661 actgaaggat gacgactttg agaagatcag tgagctgggg gctggcaatg gcggtgtggt
 721 gttcaaggtc tcccacaagc cttctggcct ggtcatggcc agaaagctaa ttcatctgga
 781 gatcaaaccc gcaatccgga accagatcat aagggagctg caggttctgc atgagtgcaa
 841 ctctccgtac atcgtgggct tctatggtgc gttctacagc gatggcgaga tcagtatctg
 901 catggagcac atggatggag gttctctgga tcaagtcctg aagaaagctg gaagaattcc
 961 tgaacaaatt ttaggaaaag ttagcattgc tgtaataaaa ggcctgacat atctgaggga
1021 gaagcacaag atcatgcaca gagatgtcaa gccctccaac atcctagtca actcccgtgg
1081 ggagatcaag ctctgtgact ttggggtcag cgggcagctc atcgactcca tggccaactc
1141 cttcgtgggc acaaggtcct acatgtcgcc agaaagactc caggggactc attactctgt
1201 gcagtcagac atctggagca tgggactgtc tctggtagag atggcggttg ggaggtatcc
1261 catccctcct ccagatgcca aggagctgga gctgatgttt gggtgccagg tggaaggaga
1321 tgcggctgag accccaccca ggccaaggac ccccgggagg ccccttagct catacggaat
1381 ggacagccga cctcccatgg caatttttga gttgttggat tacatagtca acgagcctcc
1441 tccaaaactg cccagtggag tgttcagtct ggaatttcaa gattttgtga ataaatgctt
1501 aataaaaaac cccgcagaga gagcagattt gaagcaactc atggttcatg cttttatcaa
1561 gagatctgat gctgaggaag tggattttgc aggttggctc tgctccacca tcggccttaa
1621 ccagcccagc acaccaaccc atgctgctgg cgtctaagtg tttgggaagc aacaaagagc
1681 gagtcccctg cccggtggtt tgccatgtcg cttttgggcc tccttcccat gcctgtctct
1741 gttcagatgt gcatttcacc tgtgacaaag gatgaagaac acagcatgtg ccaagattct
1801 actcttgtca tttttaatat tactgtcttt attcttatta ctattattgt tcccctaagt
1861 ggattggctt tgtgcttggg gctatttgtg tgtatgctga tgatcaaaac ctgtgccagg
1921 ctgaattaca gtgaaatttt ggtgaatgtg ggtagtcatt cttacaattg cactgctgtt
1981 cctgctccat gactggctgt ctgcctgtat tttcgggatt ctttgacatt tggtggtact
2041 ttattcttgc tgggcatact ttctctctag gagggagcct tgtgagatcc ttcacaggca
2101 gtgcatgtga agcatgcttt gctgctatga aaatgagcat cagagagtgt acatcatgtt
2161 attttattat tattatttgc ttttcatgta gaactcagca gttgacatcc aaatctagcc
2221 agagcccttc actgccatga tagctggggc ttcaccagtc tgtctactgt ggtgatctgt
2281 agacttctgg ttgtatttct atatttattt tcagtatact gtgtgggata cttagtggta
2341 tgtctcttta agttttgatt aatgtttctt aaatggaatt attttgaatg tcacaaattg
2401 atcaagatat taaaatgtcg gatttatctt tccccatatc caagtaccaa tgctgttgta
2461 aacaacgtgt atagtgccta aaattgtatg aaaatccttt taaccatttt aacctagatg
2521 tttaacaaat ctaatctctt attctaataa atatactatg aaataaaaaa aaaaggatga
2581 aagctaaaaa aaaaaaaaaa aaa
```

FIG. 3P

MAP2K1 Protein SEQ ID NO: 16

MPKKKPTPIQLNPAPDGSAVNGTSSAETNLEALQKKLEELELDE

QQRKRLEAFLTQKQKVGELKDDDFEKISELGAGNGGVVFKVSHKPSGLVMARKLIHLE

IKPAIRNQIIRELQVLHECNSPYIVGFYGAFYSDGEISICMEHMDGGSLDQVLKKAGR

IPEQILGKVSIAVIKGLTYLREKHKIMHRDVKPSNILVNSRGEIKLCDFGVSGQLIDS

MANSFVGTRSYMSPERLQGTHYSVQSDIWSMGLSLVEMAVGRYPIPPPDAKELELMFG

CQVEGDAAETPPRPRTPGRPLSSYGMDSRPPMAIFELLDYIVNEPPPKLPSGVFSLEF

QDFVNKCLIKNPAERADLKQLMVHAFIKRSDAEEVDFAGWLCSTIGLNQPSTPTHAAG

MAP2K2 DNA (NM_030662) SEQ ID NO: 17

```
   1 cccctgcctc tcggactcgg gctgcggcgt cagccttctt cgggcctcgg cagcggtagc
  61 ggctcgctcg cctcagcccc agcgcccctc ggctaccctc ggcccaggcc cgcagcgccg
 121 cccgccctcg gccgccccga cgccggcctg ggccgcggcc gcagccccgg gctcgcgtag
 181 gcgccgaccg ctcccggccc gccccctatg ggccccggct agaggcgccg ccgccgccgg
 241 cccgcggagc cccgatgctg gcccggagga agccggtgct gccggcgctc accatcaacc
 301 ctaccatcgc cgagggccca tcccctacca gcgagggcgc ctccgaggca aacctggtgg
 361 acctgcagaa gaagctggag gagctggaac ttgacgagca gcagaagaag cggctggaag
 421 cctttctcac ccagaaagcc aaggtcggcg aactcaaaga cgatgacttc gaaaggatct
 481 cagagctggg cgcgggcaac ggcgggtgg tcaccaaagt ccagcacaga ccctcgggcc
 541 tcatcatggc caggaagctg atccaccttg agatcaagcc ggccatccgg aaccagatca
 601 tccgcgagct gcaggtcctg cacgaatgca actcgccgta catcgtgggc ttctacgggg
 661 ccttctacag tgacggggag atcagcattt gcatggaaca catggacggc ggctccctgg
 721 accaggtgct gaaagaggcc aagaggattc ccgaggagat cctggggaaa gtcagcatcg
 781 cggttctccg gggcttggcg tacctccgag agaagcacca gatcatgcac cgagatgtga
 841 agccctccaa catcctcgtg aactctagag gggagatcaa gctgtgtgac ttcggggtga
 901 gcggccagct catcgactcc atggccaact ccttcgtggg cacgcgctcc tacatggctc
 961 cggagcggtt gcagggcaca cattactcgg tgcagtcgga catctggagc atgggcctgt
1021 ccctggtgga gctggccgtc ggaaggtacc ccatcccccc gcccgacgcc aaagagctgg
1081 aggccatctt tggccggccc gtggtcgacg gggaagaagg agagcctcac agcatctcgc
1141 ctcggccgag gcccccgggg cgccccgtca gcggtcacgg gatggatagc cggcctgcca
1201 tggccatctt tgaactcctg gactatattg tgaacgagcc acctcctaag ctgcccaacg
1261 gtgtgttcac ccccgacttc caggagtttg tcaataaatg cctcatcaag aacccagcgg
1321 agcgggcgga cctgaagatg ctcacaaacc acaccttcat caagcggtcc gaggtggaag
1381 aagtggattt tgccggctgg ttgtgtaaaa ccctgcggct gaaccagccc ggcacaccca
1441 cgcgcaccgc cgtgtgacag tggccgggct ccctgcgtcc cgctggtgac ctgcccaccg
1501 tccctgtcca tgccccgccc ttccagctga ggacaggctg gcgcctccac ccaccctcct
1561 gcctcacccc tgcggagagc accgtggcgg ggcgacagcg catgcaggaa cgggggtctc
1621 ctctcctgcc cgtcctggcc ggggtgcctc tggggacggg cgacgctgct gtgtgtggtc
1681 tcagaggctc tgcttcctta ggttacaaaa caaaacaggg agagaaaaag caaaaaaaaa
1741 aaaaaaaaaa aaaaaaaaa
```

FIG. 3R

MAP2K2 (NM_030662) Protein SEQ ID NO: 18

MLARRKPVLPALTINPTIAEGPSPTSEGASEANLVDLQKKLEEL

ELDEQQKKRLEAFLTQKAKVGELKDDDFERISELGAGNGGVVTKVQHRPSGLIMARKL

IHLEIKPAIRNQIIRELQVLHECNSPYIVGFYGAFYSDGEISICMEHMDGGSLDQVLK

EAKRIPEEILGKVSIAVLRGLAYLREKHQIMHRDVKPSNILVNSRGEIKLCDFGVSGQ

LIDSMANSFVGTRSYMAPERLQGTHYSVQSDIWSMGLSLVELAVGRYPIPPPDAKELE

AIFGRPVVDGEEGEPHSISPRPRPPGRPVSGHGMDSRPAMAIFELLDYIVNEPPPKLP

NGVFTPDFQEFVNKCLIKNPAERADLKMLTNHTFIKRSEVEEVDFAGWLCKTLRLNQP

GTPTRTAV

FIG. 3S

MECP2 DNA (NM_004992) SEQ ID NO: 19

```
   1 ccggcgtcgg cggcgcgcgc gctccctcct ctcggagaga gggctgtggt aaaagccgtc
  61 cggaaaatgg ccgccgccgc cgccgccgcg ccgagcggag gaggaggagg aggcgaggag
 121 gagagactgc tccataaaaa tacagactca ccagttcctg ctttgatgtg acatgtgact
 181 ccccagaata caccttgctt ctgtagacca gctccaacag gattccatgg tagctgggat
 241 gttagggctc agggaagaaa agtcagaaga ccaggacctc cagggcctca aggacaaacc
 301 cctcaagttt aaaaaggtga agaaagataa gaaagaagag aaagagggca agcatgagcc
 361 cgtgcagcca tcagcccacc actctgctga gcccgcagag gcaggcaaag cagagacatc
 421 agaagggtca ggctccgccc cggctgtgcc ggaagcttct gcctccccca aacagcggcg
 481 ctccatcatc cgtgaccggg gacccatgta tgatgacccc accctgcctg aaggctggac
 541 acggaagctt aagcaaagga aatctggccg ctctgctggg aagtatgatg tgtatttgat
 601 caatccccag ggaaaagcct ttcgctctaa agtggagttg attgcgtact tcgaaaaggt
 661 aggcgacaca tccctggacc ctaatgattt tgacttcacg gtaactggga gagggagccc
 721 ctcccggcga gagcagaaac cacctaagaa gcccaaatct cccaaagctc caggaactgg
 781 cagaggccgg ggacgcccca aagggagcgg caccacgaga cccaaggcgg ccacgtcaga
 841 gggtgtgcag gtgaaaaggg tcctggagaa aagtcctggg aagctccttg tcaagatgcc
 901 ttttcaaact tcgccagggg gcaaggctga ggggggtggg gccaccacat ccacccaggt
 961 catggtgatc aaacgccccg gcaggaagcg aaaagctgag gccgaccctc aggccattcc
1021 caagaaacgg ggccgaaagc cggggagtgt ggtggcagcc gctgccgccg aggccaaaaa
1081 gaaagccgtg aaggagtctt ctatccgatc tgtgcaggag accgtactcc ccatcaagaa
1141 gcgcaagacc cgggagacgg tcagcatcga ggtcaaggaa gtggtgaagc ccctgctggt
1201 gtccaccctc ggtgagaaga gcgggaaagg actgaagacc tgtaagagcc ctgggcggaa
1261 aagcaaggag agcagcccca aggggcgcag cagcagcgcc tcctcacccc ccaagaagga
1321 gcaccaccac catcaccacc actcagagtc cccaaaggcc cccgtgccac tgctcccacc
1381 cctgccccca cctccacctg agcccgagag ctccgaggac cccaccagcc cccctgagcc
1441 ccaggacttg agcagcagcg tctgcaaaga ggagaagatg cccagaggag gctcactgga
1501 gagcgacggc tgccccaagg agccagctaa gactcagccc gcggttgcca ccgccgccac
1561 ggccgcagaa aagtacaaac accgagggga gggagagcgc aaagacattg tttcatcctc
1621 catgccaagg ccaaacagag aggagcctgt ggacagccgg acgcccgtga ccgagagagt
1681 tagctgactt tacacggagc ggattgcaaa gcaaaccaac aagaataaag gcagctgttg
1741 tctcttctcc ttatgggtag ggctctgaca aagcttcccg attaactgaa ataaaaaata
1801 tttttttttc tttcagtaaa cttagagttt cgtggcttca gggtgggagt agttggagca
1861 ttggggatgt ttttcttacc gacaagcaca gtcaggttga agacctaacc agggccagaa
1921 gtagctttgc acttttctaa actaggctcc ttcaacaagg cttgctgcag atactactga
1981 ccagacaagc tgttgaccag gcacctcccc tcccgcccaa acctttcccc catgtggtcg
2041 ttagagacag agcgacagag cagttgagag gacactcccg ttttcggtgc catcagtgcc
2101 ccgtctacag ctcccccagc tccccccacc tcccccactc ccaaccacgt tgggacaggg
2161 aggtgtgagg caggagagac agttggattc tttagagaag atggatatga ccagtggcta
2221 tggcctgtgc gatcccaccc gtggtggctc aagtctggcc ccacaccagc cccaatccaa
2281 aactggcaag gacgcttcac aggacaggaa agtggcacct gtctgctcca gctctggcat
2341 ggctaggagg ggggagtccc ttgaactact gggtgtagac tggcctgaac cacaggagag
2401 gatggcccag ggtgaggtgg catggtccat tctcaaggga cgtcctccaa cgggtggcgc
2461 tagaggccat ggaggcagta ggacaaggtg caggcaggct ggcctggggt caggccgggc
2521 agagcacagc ggggtgagag ggattcctaa tcactcagag cagtctgtga cttagtggac
2581 aggggagggg gcaaaggggg aggagaagaa aatgttcttc cagttacttt ccaattctcc
2641 tttagggaca gcttagaatt atttgcacta ttgagtcttc atgttcccac ttcaaaacaa
2701 acagatgctc tgagagcaaa ctggcttgaa ttggtgacat ttagtccctc aagccaccag
2761 atgtgacagt gttgagaact acctggattt gtatatatac ctgcgcttgt tttaaagtgg
2821 gctcagcaca tagggttccc acgaagctcc gaaactctaa gtgtttgctg caattttata
2881 aggacttcct gattggtttc tcttctcccc ttccatttct gccttttgtt catttcatcc
2941 tttcacttct ttcccttcct ccgtcctcct ccttcctagt tcatcccttc tcttccaggc
3001 agccgcggtg cccaaccaca cttgtcggct ccagtcccca gaactctgcc tgccctttgt
```

FIG. 3S (cont.)

```
3061 cctcctgctg ccagtaccag ccccaccctg ttttgagccc tgaggaggcc ttgggctctg
3121 ctgagtccga cctggcctgt ctgtgaagag caagagagca gcaaggtctt gctctcctag
3181 gtagccccct cttccctggt aagaaaaagc aaaaggcatt tcccaccctg aacaacgagc
3241 cttttcaccc ttctactcta gagaagtgga ctggaggagc tgggcccgat ttggtagttg
3301 aggaaagcac agaggcctcc tgtggcctgc cagtcatcga gtggcccaac aggggctcca
3361 tgccagccga ccttgacctc actcagaagt ccagagtcta gcgtagtgca gcagggcagt
3421 agcggtacca atgcagaact cccaagaccc gagctgggac cagtacctgg gtccccagcc
3481 cttcctctgc tccccctttt ccctcggagt tcttcttgaa tggcaatgtt ttgcttttgc
3541 tcgatgcaga caggggccca gaacaccaca catttcactg tctgtctggt ccatagctgt
3601 ggtgtagggg cttagaggca tgggcttgct gtgggttttt aattgatcag ttttcatgtg
3661 ggatcccatc tttttaacct ctgttcagga agtccttatc tagctgcata tcttcatcat
3721 attggtatat ccttttctgt gtttacagag atgtctctta tatctaaatc tgtccaactg
3781 agaagtacct tatcaaagta gcaaatgaga cagcagtctt atgcttccag aaacacccac
3841 aggcatgtcc catgtgagct gctgccatga actgtcaagt gtgtgttgtc ttgtgtattt
3901 cagttattgt ccctggcttc cttactatgg tgtaatcatg aaggagtgaa acatcataga
3961 aactgtctag cacttccttg ccagtcttta gtgatcagga accatagttg acagttccaa
4021 tcagtagctt aagaaaaaac cgtgtttgtc tcttctggaa tggttagaag tgagggagtt
4081 tgccccgttc tgtttgtaga gtctcatagt tggactttct agcatatatg tgtccatttc
4141 cttatgctgt aaaagcaagt cctgcaacca aactcccatc agcccaatcc ctgatccctg
4201 atcccttcca cctgctctgc tgatgacccc cccagcttca cttctgactc ttccccagga
4261 agggaagggg ggtcagaaga gagggtgagt cctccagaac tcttcctcca aggacagaag
4321 gctcctgccc ccatagtggc ctcgaactcc tggcactacc aaaggacact tatccacgag
4381 agcgcagcat ccgaccaggt tgtcactgag aagatgttta ttttggtcag ttgggttttt
4441 atgtattata cttagtcaaa tgtaatgtgg cttctggaat cattgtccag agctgcttcc
4501 ccgtcacctg ggcgtcatct ggtcctggta agaggagtgc gtggcccacc aggccccccct
4561 gtcacccatg acagttcatt cagggccgat ggggcagtcg tggttgggaa cacagcattt
4621 caagcgtcac tttatttcat tcggccccca cctgcagctc cctcaaagag gcagttgccc
4681 agcctctttc ccttccagtt tattccagag ctgccagtgg ggcctgaggc tccttagggt
4741 tttctctcta tttccccctt tcttcctcat tccctcgtct ttcccaaagg catcacgagt
4801 cagtcgcctt tcagcaggca gccttggcgg tttatcgccc tggcaggcag gggccctgca
4861 gctctcatgc tgcccctgcc ttggggtcag gttgacagga ggttggaggg aaagccttaa
4921 gctgcaggat tctcaccagc tgtgtccggc ccagttttgg ggtgtgacct caatttcaat
4981 tttgtctgta cttgaacatt atgaagatgg gggcctcttt cagtgaattt gtgaacagca
5041 gaattgaccg acagctttcc agtacccatg gggctaggtc attaaggcca catccacagt
5101 ctcccccacc cttgttccag ttgttagtta ctacctcctc tcctgacaat actgtatgtc
5161 gtcgagctcc ccccaggtct acccctcccg gccctgcctg ctggtgggct tgtcatagcc
5221 agtgggattg ccggtcttga cagctcagtg agctggagat acttggtcac agccaggcgc
5281 tagcacagct cccttctgtt gatgctgtat tcccatatca aaagacacag ggacacccca
5341 gaaacgccac atcccccaat ccatcagtgc caaactagcc aacggcccca gcttctcagc
5401 tcgctggatg gcggaagctg ctactcgtga gcgccagtgc gggtgcagac aatcttctgt
5461 tgggtggcat cattccaggc ccgaagcatg aacagtgcac ctgggacagg gagcagcccc
5521 aaattgtcac ctgcttctct gcccagcttt tcattgctgt gacagtgatg gcgaaagagg
5581 gtaataacca gacacaaact gccaagttgg gtggagaaag gagtttcttt agctgacaga
5641 atctctgaat tttaaatcac ttagtaagcg gctcaagccc aggagggagc agaggatac
5701 gagcggagtc ccctgcgcgg gaccatctgg aattggttta gcccaagtgg agcctgacag
5761 ccagaactct gtgtcccccg tctaaccaca gctccttttc cagagcattc cagtcaggct
5821 ctctgggctg actgggccag gggaggttac aggtaccagt tctttaagaa gatctttggg
5881 catatacatt tttagcctgt gtcattgccc caaatggatt cctgtttcaa gttcacacct
5941 gcagattcta ggacctgtgt cctagacttc agggagtcag ctgtttctag agttcctacc
6001 atggagtggg tctggaggac ctgcccggtg gggggcaga gccctgctcc ctccgggtct
6061 tcctactctt ctctctgctc tgacgggatt tgttgattct ctccattttg gtgtctttct
6121 cttttagata ttgtatcaat ctttagaaaa ggcatagtct acttgttata aatcgttagg
6181 atactgcctc ccccagggtc taaaattaca tattagaggg gaaaagctga acactgaagt
```

FIG. 3S (cont.)

```
6241 cagttctcaa caatttagaa ggaaaaccta gaaaacattt ggcagaaaat tacatttcga
6301 tgtttttgaa tgaatacgag caagctttta caacagtgct gatctaaaaa tacttagcac
6361 ttggcctgag atgcctggtg agcattacag gcaaggggaa tctggaggta gccgacctga
6421 ggacatggct tctgaacctg tcttttggga gtggtatgga aggtggagcg ttcaccagtg
6481 acctggaagg cccagcacca ccctccttcc cactcttctc atcttgacag agcctgcccc
6541 agcgctgacg tgtcaggaaa acacccaggg aactaggaag gcacttctgc ctgaggggca
6601 gcctgccttg cccactcctg ctctgctcgc ctcggatcag ctgagccttc tgagctggcc
6661 tctcactgcc tccccaaggc cccctgcctg ccctgtcagg aggcagaagg aagcaggtgt
6721 gagggcagtg caaggaggga gcacaacccc cagctcccgc tccgggctcc gacttgtgca
6781 caggcagagc ccagaccctg gaggaaatcc tacctttgaa ttcaagaaca tttggggaat
6841 ttggaaatct ctttgccccc aaacccccat tctgtcctac ctttaatcag gtcctgctca
6901 gcagtgagag cagatgaggt gaaaaggcca agaggtttgg ctcctgccca ctgatagccc
6961 ctctccccgc agtgtttgtg tgtcaagtgg caaagctgtt cttcctggtg accctgatta
7021 tatccagtaa cacatagact gtgcgcatag gcctgctttg tctcctctat cctgggcttt
7081 tgttttgctt tttagttttg cttttagttt ttctgtccct tttatttaac gcaccgacta
7141 gacacacaaa gcagttgaat ttttatatat atatctgtat attgcacaat tataaactca
7201 ttttgcttgt ggctccacac acacaaaaaa agacctgtta aaattatacc tgttgcttaa
7261 ttacaatatt tctgataacc atagcatagg acaaggaaaa ataaaaaaag aaaaaaaaga
7321 aaaaaaaacg acaaatctgt ctgctggtca cttcttctgt ccaagcagat tcgtggtctt
7381 ttcctcgctt ctttcaaggg ctttcctgtg ccaggtgaag gaggctccag gcagcaccca
7441 ggttttgcac tcttgtttct cccgtgcttg tgaaagaggt cccaaggttc tgggtgcagg
7501 agcgctccct tgacctgctg aagtccggaa cgtagtcggc acagcctggt cgccttccac
7561 ctctgggagc tggagtccac tggggtggcc tgactccccc agtccccttc ccgtgacctg
7621 gtcagggtga gcccatgtgg agtcagcctc gcaggcctcc ctgccagtag ggtccgagtg
7681 tgtttcatcc ttcccactct gtcgagcctg gggctggag cggagacggg aggcctggcc
7741 tgtctcggaa cctgtgagct gcaccaggta gaacgccagg gaccccagaa tcatgtgcgt
7801 cagtccaagg ggtcccctcc aggagtagtg aagactccag aaatgtccct ttcttctccc
7861 ccatcctacg agtaattgca tttgcttttg taattcttaa tgagcaatat ctgctagaga
7921 gtttagctgt aacagttctt tttgatcatc ttttttaat aattagaaac accaaaaaaa
7981 tccagaaact tgttcttcca aagcagagag cattataatc accagggcca aaagcttccc
8041 tccctgctgt cattgcttct tctgaggcct gaatccaaaa gaaaaacagc catagggcct
8101 ttcagtggcc gggctacccg tgagcccttc ggaggaccag ggctggggca gcctctgggc
8161 ccacatccgg ggccagctcc ggcgtgtgtt cagtgttagc agtgggtcat gatgctcttt
8221 cccacccagc ctgggatagg ggcagaggag gcgaggaggc cgttgccgct gatgtttggc
8281 cgtgaacagg tgggtgtctg cgtgcgtcca cgtgcgtgtt ttctgactga catgaaatcg
8341 acgcccgagt tagcctcacc cggtgacctc tagccctgcc cggatggagc ggggcccacc
8401 cggttcagtg tttctgggga gctggacagt ggagtgcaaa aggcttgcag aacttgaagc
8461 ctgctccttc ccttgctacc acggcctcct ttccgtttga tttgtcactg cttcaatcaa
8521 taacagccgc tccagagtca gtagtcaatg aatatatgac caaatatcac caggactgtt
8581 actcaatgtg tgccgagccc ttgcccatgc tgggctcccg tgtatctgga cactgtaacg
8641 tgtgctgtgt ttgctcccct tccccttcct tctttgccct ttacttgtct ttctggggtt
8701 tttctgtttg ggtttggttt ggtttttatt tctccttttg tgttccaaac atgaggttct
8761 ctctactggt cctcttaact gtggtgttga ggcttatatt tgtgtaattt ttggtgggtg
8821 aaaggaattt tgctaagtaa atctcttctg tgtttgaact gaagtctgta ttgtaactat
8881 gtttaaagta attgttccag agacaaatat ttctagacac tttttcttta caaacaaaag
8941 cattcggagg gaggggatg gtgactgaga tgagagggga gagctgaaca gatgacccct
9001 gcccagatca gccagaagcc acccaaagca gtggagccca ggagtcccac tccaagccag
9061 caagccgaat agctgatgtg ttgccacttt ccaagtcact gcaaaaccag gttttgttcc
9121 gcccagtgga ttcttgtttt gcttcccctc cccccgagat tattaccacc atcccgtgct
9181 tttaaggaaa ggcaagattg atgtttcctt gaggggagcc aggaggggat gtgtgtgtgc
9241 agagctgaag agctggggag aatggggctg ggcccaccca agcaggaggc tgggacgctc
9301 tgctgtgggc acaggtcagg ctaatgttgg cagatgcagc tcttcctgga caggccaggt
9361 ggtgggcatt ctctctccaa ggtgtgcccc gtgggcatta ctgtttaaga cacttccgtc
```

FIG. 3S (cont.)

```
 9421 acatcccacc ccatcctcca gggctcaaca ctgtgacatc tctattcccc accctcccct
 9481 tcccagggca ataaaatgac catggagggg gcttgcactc tcttggctgt cacccgatcg
 9541 ccagcaaaac ttagatgtga gaaaacccct tcccattcca tggcgaaaac atctccttag
 9601 aaaagccatt accctcatta ggcatggttt tgggctccca aaacacctga cagcccctcc
 9661 ctcctctgag aggcggagag tgctgactgt agtgaccatt gcatgccggg tgcagcatct
 9721 ggaagagcta ggcagggtgt ctgcccccctc ctgagttgaa gtcatgctcc cctgtgccag
 9781 cccagaggcc gagagctatg gacagcattg ccagtaacac aggccaccct gtgcagaagg
 9841 gagctggctc cagcctggaa acctgtctga ggttgggaga ggtgcacttg gggcacaggg
 9901 agaggccggg acacacttag ctggagatgt ctctaaaagc cctgtatcgt attcaccttc
 9961 agtttttgtg ttttgggaca attactttag aaaataagta ggtcgtttta aaaacaaaaa
10021 ttattgattg ctttttttgta gtgttcagaa aaaaggttct ttgtgtatag ccaaatgact
10081 gaaagcactg atatatttaa aaacaaaagg caatttatta aggaaatttg taccatttca
10141 gtaaacctgt ctgaatgtac ctgtatacgt ttcaaaaaca cccccccccc actgaatccc
10201 tgtaacctat ttattatata aagagtttgc cttataaatt t
```

FIG. 3T

MECP2 Protein SEQ ID NO: 20

MVAGMLGLREEKSEDQDLQGLKDKPLKFKKVKKDKKEEKEGKHE

PVQPSAHHSAEPAEAGKAETSEGSGSAPAVPEASASPKQRRSIIRDRGPMYDDPTLPE

GWTRKLKQRKSGRSAGKYDVYLINPQGKAFRSKVELIAYFEKVGDTSLDPNDFDFTVT

GRGSPSRREQKPPKKPKSPKAPGTGRGRGRPKGSGTTRPKAATSEGVQVKRVLEKSPG

KLLVKMPFQTSPGGKAEGGGATTSTQVMVIKRPGRKRKAEADPQAIPKKRGRKPGSVV

AAAAAEAKKKAVKESSIRSVQETVLPIKKRKTRETVSIEVKEVVKPLLVSTLGEKSGK

GLKTCKSPGRKSKESSPKGRSSSASSPPKKEHHHHHHHSESPKAPVPLLPPLPPPPPE

PESSEDPTSPPEPQDLSSSVCKEEKMPRGGSLESDGCPKEPAKTQPAVATAATAAEKY

KHRGEGERKDIVSSSMPRPNREEPVDSRTPVTERVS

FIG. 3U

PIKCA DNA Sequence (NM_006218) SEQ ID NO: 21

```
   1 tctccctcgg cgccgccgcc gccgcccgcg gggctgggac ccgatgcggt tagagccgcg
  61 gagcctggaa gagccccgag cgtttctgct ttgggacaac catacatcta attccttaaa
 121 gtagttttat atgtaaaact tgcaaagaat cagaacaatg cctccacgac catcatcagg
 181 tgaactgtgg ggcatccact tgatgccccc aagaatccta gtagaatgtt tactaccaaa
 241 tggaatgata gtgactttag aatgcctccg tgaggctaca ttaataacca taaagcatga
 301 actatttaaa gaagcaagaa aataccccct ccatcaactt cttcaagatg aatcttctta
 361 cattttcgta agtgttactc aagaagcaga aagggaagaa tttttgatg aaacaagacg
 421 actttgtgac cttcggcttt ttcaaccctt tttaaaagta attgaaccag taggcaaccg
 481 tgaagaaaag atcctcaatc gagaaattgg ttttgctatc ggcatgccag tgtgtgaatt
 541 tgatatggtt aaagatccag aagtacagga cttccgaaga aatattctga acgtttgtaa
 601 agaagctgtg gatcttaggg acctcaattc acctcatagt agagcaatgt atgtctatcc
 661 tccaaatgta gaatcttcac cagaattgcc aaagcacata tataataaat tagataaagg
 721 gcaaataata gtggtgatct gggtaatagt ttctccaaat aatgacaagc agaagtatac
 781 tctgaaaatc aaccatgact gtgtaccaga acaagtaatt gctgaagcaa tcaggaaaaa
 841 aactcgaagt atgttgctat cctctgaaca actaaaactc tgtgttttag aatatcaggg
 901 caagtatatt ttaaaagtgt gtggatgtga tgaatacttc ctagaaaaat atcctctgag
 961 tcagtataag tatataagaa gctgtataat gcttgggagg atgcccaatt tgatgttgat
1021 ggctaaagaa agcctttatt ctcaactgcc aatggactgt tttacaatgc catcttattc
1081 cagacgcatt tccacagcta caccatatat gaatggagaa acatctacaa aatccctttg
1141 ggttataaat agtgcactca gaataaaaat tctttgtgca acctacgtga atgtaaatat
1201 tcgagacatt gataagatct atgttcgaac aggtatctac catggaggag aacccttatg
1261 tgacaatgtg aacactcaaa gagtaccttg ttccaatccc aggtggaatg aatggctgaa
1321 ttatgatata tacattcctg atcttcctcg tgctgctcga ctttgccttt ccatttgctc
1381 tgttaaaggc cgaaagggtg ctaaagagga acactgtcca ttggcatggg gaaatataaa
1441 cttgtttgat tacacagaca ctctagtatc tggaaaaatg gctttgaatc tttggccagt
1501 acctcatgga ttagaagatt tgctgaaccc tattggtgtt actggatcaa atccaaataa
1561 agaaactcca tgcttagagt tggagtttga ctggttcagc agtgtggtaa agttcccaga
1621 tatgtcagtg attgaagagc atgccaattg gtctgtatcc cgagaagcag gatttagcta
1681 ttcccacgca ggactgagta acagactagc tagagacaat gaattaaggg aaaatgacaa
1741 agaacagctc aaagcaattt ctacacgaga tcctctctct gaaatcactg agcaggagaa
1801 agattttcta tggagtcaca gacactattg tgtaactatc cccgaaattc tacccaaatt
1861 gcttctgtct gttaaatgga attctagaga tgaagtagcc cagatgtatt gcttggtaaa
1921 agattggcct ccaatcaaac ctgaacaggc tatggaactt ctggactgta attacccaga
1981 tcctatggtt cgaggttttg ctgttcggtg cttggaaaaa tatttaacag atgacaaact
2041 ttctcagtat ttaattcagc tagtacaggt cctaaaatat gaacaatatt tggataactt
2101 gcttgtgaga tttttactga agaaagcatt gactaatcaa aggattgggc actttttctt
2161 ttggcattta aaatctgaga tgcacaataa aacagttagc cagaggtttg gcctgctttt
2221 ggagtcctat tgtcgtgcat gtgggatgta tttgaagcac ctgaataggc aagtcgaggc
2281 aatggaaaag ctcattaact taactgacat tctcaaacag gagaagaagg atgaaacaca
2341 aaaggtacag atgaagtttt tagttgagca aatgaggcga ccagatttca tggatgctct
2401 acagggcttt ctgtctcctc taaaccctgc tcatcaacta ggaaacctca ggcttgaaga
2461 gtgtcgaatt atgtcctctg caaaaaggcc actgtggttg aattgggaga acccagacat
2521 catgtcagag ttactgtttc agaacaatga gatcatcttt aaaaatgggg atgatttacg
2581 gcaagatatg ctaacacttc aaattattcg tattatggaa aatatctggc aaaatcaagg
2641 tcttgatctt cgaatgttac cttatggttg tctgtcaatc ggtgactgtg tgggacttat
2701 tgaggtggtg cgaaattctc acactattat gcaaattcag tgcaaaggcg gcttgaaagg
2761 tgcactgcag ttcaacagcc acacactaca tcagtggctc aaagacaaga acaaaggaga
2821 aatatatgat gcagccattg acctgtttac acgttcatgt gctggatact gtgtagctac
2881 cttcattttg ggaattggag atcgtcacaa tagtaacatc atggtgaaag acgatggaca
2941 actgtttcat atagattttg gacacttttt ggatcacaag aagaaaaaat ttggttataa
3001 acgagaacgt gtgccatttg ttttgacaca ggatttctta atagtgatta gtaaaggagc
```

FIG. 3U (cont.)

```
3061 ccaagaatgc acaaagacaa gagaatttga gaggtttcag gagatgtgtt acaaggctta
3121 tctagctatt cgacagcatg ccaatctctt cataaatctt ttctcaatga tgcttggctc
3181 tggaatgcca gaactacaat cttttgatga cattgcatac attcgaaaga ccctagcctt
3241 agataaaact gagcaagagg ctttggagta tttcatgaaa caaatgaatg atgcacatca
3301 tggtggctgg acaacaaaaa tggattggat cttccacaca attaaacagc atgcattgaa
3361 ctgaaaagat aactgagaaa atgaaagctc actctggatt ccacactgca ctgttaataa
3421 ctctcagcag gcaaagaccg attgcatagg aattgcacaa tccatgaaca gcattagaat
3481 ttacagcaag aacagaaata aaatactata taatttaaat aatgtaaacg caaacagggt
3541 ttgatagcac ttaaactagt tcatttcaaa attaagcttt agaataatgc gcaatttcat
3601 gttatgcctt aagtccaaaa aggtaaactt tgaagattgt ttgtatcttt ttttaaaaaa
3661 caaaacaaaa caaaaatccc caaaatatat agaaatgatg gagaaggaaa aaaaaaaaaa
3721 aaaa
```

FIG. 3V

PIKCA Protein SEQ ID NO: 22

MPPRPSSGELWGIHLMPPRILVECLLPNGMIVTLECLREATLIT

IKHELFKEARKYPLHQLLQDESSYIFVSVTQEAEREEFFDETRRLCDLRLFQPFLKVI

EPVGNREEKILNREIGFAIGMPVCEFDMVKDPEVQDFRRNILNVCKEAVDLRDLNSPH

SRAMYVYPPNVESSPELPKHIYNKLDKGQIIVVIWVIVSPNNDKQKYTLKINHDCVPE

QVIAEAIRKKTRSMLLSSEQLKLCVLEYQGKYILKVCGCDEYFLEKYPLSQYKYIRSC

IMLGRMPNLMLMAKESLYSQLPMDCFTMPSYSRRISTATPYMNGETSTKSLWVINSAL

RIKILCATYVNVNIRDIDKIYVRTGIYHGGEPLCDNVNTQRVPCSNPRWNEWLNYDIY

IPDLPRAARLCLSICSVKGRKGAKEEHCPLAWGNINLFDYTDTLVSGKMALNLWPVPH

GLEDLLNPIGVTGSNPNKETPCLELEFDWFSSVVKFPDMSVIEEHANWSVSREAGFSY

SHAGLSNRLARDNELRENDKEQLKAISTRDPLSEITEQEKDFLWSHRHYCVTIPEILP

KLLLSVKWNSRDEVAQMYCLVKDWPPIKPEQAMELLDCNYPDPMVRGFAVRCLEKYLT

DDKLSQYLIQLVQVLKYEQYLDNLLVRFLLKKALTNQRIGHFFFWHLKSEMHNKTVSQ

RFGLLLESYCRACGMYLKHLNRQVEAMEKLINLTDILKQEKKDETQKVQMKFLVEQMR

RPDFMDALQGFLSPLNPAHQLGNLRLEECRIMSSAKRPLWLNWENPDIMSELLFQNNE

IIFKNGDDLRQDMLTLQIIRIMENIWQNQGLDLRMLPYGCLSIGDCVGLIEVVRNSHT

IMQIQCKGGLKGALQFNSHTLHQWLKDKNKGEIYDAAIDLFTRSCAGYCVATFILGIG

DRHNSNIMVKDDGQLFHIDFGHFLDHKKKKFGYKRERVPFVLTQDFLIVISKGAQECT

KTREFERFQEMCYKAYLAIRQHANLFINLFSMMLGSGMPELQSFDDIAYIRKTLALDK

TEQEALEYFMKQMNDAHHGGWTTKMDWIFHTIKQHALN

FIG. 3W

PIK3R1 DNA (NM_181523) SEQ ID NO: 23

```
   1 tacaaccagg ctcaactgtt gcatggtagc agatttgcaa acatgagtgc tgaggggtac
  61 cagtacagag cgctgtatga ttataaaaag gaaagagaag aagatattga cttgcacttg
 121 ggtgacatat tgactgtgaa taaagggtcc ttagtagctc ttggattcag tgatggacag
 181 gaagccaggc ctgaagaaat tggctggtta aatggctata atgaaaccac aggggaaagg
 241 ggggactttc cgggaactta cgtagaatat attggaagga aaaaaatctc gcctcccaca
 301 ccaaagcccc ggccacctcg gcctcttcct gttgcaccag gttcttcgaa aactgaagca
 361 gatgttgaac aacaagcttt gactctcccg gatcttgcag agcagtttgc ccctcctgac
 421 attgccccgc ctcttcttat caagctcgtg gaagccattg aaaagaaagg tctggaatgt
 481 tcaactctat acagaacaca gagctccagc aacctggcag aattacgaca gcttcttgat
 541 tgtgatacac cctccgtgga cttggaaatg atcgatgtgc acgttttggc tgacgctttc
 601 aaacgctatc tcctggactt accaaatcct gtcattccag cagccgttta cagtgaaatg
 661 atttctttag ctccagaagt acaaagctcc gaagaatata ttcagctatt gaagaagctt
 721 attaggtcgc ctagcatacc tcatcagtat tggcttacgc ttcagtattt gttaaaacat
 781 ttcttcaagc tctctcaaac ctccagcaaa aatctgttga atgcaagagt actctctgaa
 841 attttcagcc ctatgctttt cagattctca gcagccagct ctgataatac tgaaaacctc
 901 ataaaagtta tagaaatttt aatctcaact gaatggaatg aacgacagcc tgcaccagca
 961 ctgcctccta aaccaccaaa acctactact gtagccaaca acggtatgaa taacaatatg
1021 tccttacaag atgctgaatg gtactgggga gatatctcga gggaagaagt gaatgaaaaa
1081 cttcgagata cagcagacgg gacctttttg gtacgagatg cgtctactaa aatgcatggt
1141 gattatactc ttacactaag gaaaggggga aataacaaat taatcaaaat atttcatcga
1201 gatgggaaat atggcttctc tgacccatta accttcagtt ctgtggttga attaataaac
1261 cactaccgga atgaatctct agctcagtat aatcccaaat tggatgtgaa attactttat
1321 ccagtatcca aataccaaca ggatcaagtt gtcaaagaag ataatattga agctgtaggg
1381 aaaaaattac atgaatataa cactcagttt caagaaaaaa gtcgagaata tgatagatta
1441 tatgaagaat atacccgcac atcccaggaa atccaaatga aaaggacagc tattgaagca
1501 tttaatgaaa ccataaaaat atttgaagaa cagtgccaga cccaagagcg gtacagcaaa
1561 gaatacatag aaaagtttaa acgtgaaggc aatgagaaag aaatacaaag gattatgcat
1621 aattatgata agttgaagtc tcgaatcagt gaaattattg acagtagaag aagattggaa
1681 gaagacttga agaagcaggc agctgagtat cgagaaattg acaaacgtat gaacagcatt
1741 aaaccagacc ttatccagct gagaaagacg agagaccaat acttgatgtg gttgactcaa
1801 aaaggtgttc ggcaaaagaa gttgaacgag tggttgggca atgaaaacac tgaagaccaa
1861 tattcactgg tggaagatga tgaagatttg ccccatcatg atgagaagac atggaatgtt
1921 ggaagcagca accgaaacaa agctgaaaac ctgttgcgag ggaagcgaga tggcactttt
1981 cttgtccggg agagcagtaa acagggctgc tatgcctgct ctgtagtggt ggacggcgaa
2041 gtaaagcatt gtgtcataaa caaaacagca actggctatg gctttgccga gccctataac
2101 ttgtacagct ctctgaaaga actggtgcta cattaccaac acacctccct tgtgcagcac
2161 aacgactccc tcaatgtcac actagcctac ccagtatatg cacagcagag gcgatgaagc
2221 gcttactctt tgatccttct cctgaagttc agccaccctg aggcctctgg aaagcaaagg
2281 gctcctctcc agtctgatct gtgaattgag ctgcagaaac gaagccatct ttctttggat
2341 gggactagag ctttctttca caaaaaagaa gtaggggaag acatgcagcc taaggctgta
2401 tgatgaccac acgttcctaa gctggagtgc ttatcccttc tttttctttt tttctttggt
2461 ttaatttaaa gccacaacca catacaacac aaagagaaaa agaaatgcaa aaatctctgc
2521 gtgcagggac aaagaggcct ttaaccatgg tgcttgttaa tgctttctga agctttacca
2581 gctgaaagtt gggactctgg agagcggagg agagagaggc agaagaaccc tggcctgaga
2641 aggtttggtc cagcctggtt tagcctggat gttgctgtgc acggtggacc cagacacatc
2701 gcactgtgga ttatttcatt ttgtaacaaa tgaacgatat gtagcagaaa ggcacgtcca
2761 ctcacaaggg acgctttggg agaatgtcag ttcatgtatg ttcagaagaa attctgtcat
2821 agaaagtgcc agaaagtgtt taacttgtca aaaaacaaaa acccagcaac agaaaaatgg
2881 agtttggaaa acaggactta aaatgacatt cagtatataa aatatgtaca taatattgga
2941 tgactaacta tcaaatagat ggatttgtat caataccaaa tagcttctgt tttgttttgc
3001 tgaaggctaa attcacagcg ctatgcaatt cttaattttc attaagttgt tatttcagtt
```

FIG. 3W (cont.)

```
3061 ttaaatgtac cttcagaata agcttcccca ccccagtttt tgttgcttga aaatattgtt
3121 gtcccggatt tttgttaata ttcatttttg ttatcctttt ttaaaagtaa atgtacagga
3181 tgccagtaaa aaaaaaaaat ggcttcagaa ttaaaactat gaaatatttt acagtttttc
3241 ttgtacagag tacttggctg ttagcccaag gttaaaaagt tcataacaga tttttttttgg
3301 actgttttgt tgggcagtgc ctgataagct tcaaagctgc tttattcaat aaaaaaaaga
3361 aatgaaaaag atatatgaat atgacaaagt attgctgagt ccaacaatgt tgttttaaga
3421 ctcttaaaat acggtacctg gcaatgttta tttcataaag aattgtgaac ttcttgaatc
3481 tagggagggg gaatgtagtg aagggatgta tcaagtgggg tggtgggagg gggaggcaag
3541 gttatatgca ctttctcatg atttacagag aagtgaataa ctgcaaagtg aagttgcttc
3601 ttctacttca gtcttctctc actttgattt gctagttgtt atcaattaat gacaattaca
3661 aacctactgt atctctaata cagtgtgact ggtcaggtat ttcagttctt aggaaggaag
3721 tgccaagttt gtttttgggt tcctggaaca gcgctcacct ttgtttagaa cactggttta
3781 aagggataat catctctgtc acattagact atccatcatg accagcaaat actcatttta
3841 ggaaaaaaaa aagcatgatc tgaaaaatac ttttggtggt atgttggtta ccctcctagc
3901 tttccatttg gtttagaaca taaagcaaat agacacagtc atactgtcac tgctctggac
3961 tgtgtggagc tcgctaaagt catggtcatt gcaggaatcc aagtggcagt ccttctcatt
4021 cattctaatc attgtatgtg cttcactacg ggggggagaa ggaaacgtta gcatcatgtt
4081 tcccatttag ggcaggagtg agaggtctct cttcctgatt tagatatgca aaagctggta
4141 tgttcagtag gaactgtaca tgtgttggga ggcataaaga ctaattagca accataatat
4201 ggtcactacc ctaatagact aaatgaaatc ttgcaatttc aaattactct ttctccatat
4261 tagatttacc cacagctata tttctgttta agtactaggg tgagggtttt ctgttacttt
4321 gtttttttaat gttgttcctt ttgaaagaat cagtcttgca gctgagtgaa aaatctgtgg
4381 aatgtattat ttgtcctctt tacatgaaac tactcatact taagcaaaag tcagtcttat
4441 agcaagactg ttagccctca aacttgactc tactgatctg accatttccc tctcatcgcc
4501 agacaactga cgatttccct ggttttagtc tgcgtctctg ctttaaagtt attgtgatat
4561 ccttctagat catacacaag tctaacagtt aattagttaa cagtttttaa actaggtttg
4621 tgggtatttt tttggtagca catgtatgct attacataca aatttttatt tctaaaatat
4681 aagatctgag attgaatatt ttcattaaaa gctacagttt tgtgaatctt tgtgcttcaa
4741 cattctttgc aagatgatac ggtatttagg catttgcctt atttttgcat ctcacaaaca
4801 taagtgcaat agatcttttc attgaacagc aaagtaggat tcatcattcc atatgacttg
4861 agttacacca gacctgttct gcccaatgcc tttttgatta cagtgtagct tgcccaccgc
4921 atttgtcgtt ttagatactt tgctagccgg ccactttgga tttcatcaga cagtcctaac
4981 aatattgtct gaacggctga atatgaatag atacagcaga ggcactcctg atatatgatt
5041 tttatccatg cgtcagtttt tcccacccag tgtagcatcc taaagataaa gccagaagct
5101 aagctgcagt gaggctgtga ttgggcgtag aagtgggagc attgggacct cacattacac
5161 acacgagaga tcataaccat gtgaaaaggc aaaaagcatg tgtttgcaac atctgataac
5221 ttcatggcct ttgataaatg tatatatgta tatgtgcatg gactgtgttt ccagtacacc
5281 tttcagccaa aacagatcca cagtagttgt tgagttcaag tacataaagt acataacaag
5341 cgaacgtcta gtacaattct tacttatgtg tatgggattt ttccctttga ggttgctttg
5401 ttttgtctta caaaggtgaa aattgtttgt aagtgaagtg agaagttcat atttctttgg
5461 ctttttttgtg tttttaaaag ttactccttt tagggagctg gtctgatgac ttgcttagct
5521 tggaaatcct tgttttcagt gtgtcgagtc aaaatgtgtt tatgtgagct gtcactgtgg
5581 ggaaccaatt gctttgtcat atagctggtt atgaactagt aacatgtttg ggaagtccta
5641 ctgatgttcc tttggaagaa aaaatctgct ggttttaaca actgtgcttt tgctatgtat
5701 ggtatccaag ttagttgaaa cgcagacact gagatctgtt tgagtttagg gtcattttta
5761 gaaaggggca gtttaaagca caatgtctca catgggacaa agttccaaaa tgccaaattc
5821 ttatttttta aaaagctagt tctataaaat actggtatta tgggtgggga ggaaatagaa
5881 ttgagtcaat tggaaagact atccaactta acatgaaact tgtcaccatg agatagcatt
5941 agctgcccag gatgctgcta tatatatata tatatatata tatgtgtgtg tgtgtgtgtg
6001 tgtgtgtgta tatatatata tatatatata tatatatata tatatatatg tgtgtgtata
6061 tatatatata tgtgtatata tatatgtata tacatatatg tatatatatg cacatatata
6121 tatgtattta aaaaaatcaa aacaaaaaaa aactcattta tacctgtgta tttttttaaag
6181 ctacaatctg ttcaatgttt ttaaaaatct gtttatatga cattgttaaa ataaagttgg
```

FIG. 3W (cont.)

6241 tcttttgacg agagggagga tgtcacggtc agttgtaact ttgccttcac aaggcaactg
6301 gggtgggggg tgggggtagt gtgcctcctt gacatttcgt tcaagttata gattcaatgg
6361 agctatgtct tgttttaagt tgctttaatg cattgtatta gatcttcaaa cagaataaag
6421 gttgttttga aactgaaaaa aaaaaaaaaa aaa

FIG. 3X

PIK3R1 Protein SEQ ID NO: 24

MSAEGYQYRALYDYKKEREEDIDLHLGDILTVNKGSLVALGFSD

GQEARPEEIGWLNGYNETTGERGDFPGTYVEYIGRKKISPPTPKPRPPRPLPVAPGSS

KTEADVEQQALTLPDLAEQFAPPDIAPPLLIKLVEAIEKKGLECSTLYRTQSSSNLAE

LRQLLDCDTPSVDLEMIDVHVLADAFKRYLLDLPNPVIPAAVYSEMISLAPEVQSSEE

YIQLLKKLIRSPSIPHQYWLTLQYLLKHFFKLSQTSSKNLLNARVLSEIFSPMLFRFS

AASSDNTENLIKVIEILISTEWNERQPAPALPPKPPKPTTVANNGMNNNMSLQDAEWY

WGDISREEVNEKLRDTADGTFLVRDASTKMHGDYTLTLRKGGNNKLIKIFHRDGKYGF

SDPLTFSSVVELINHYRNESLAQYNPKLDVKLLYPVSKYQQDQVVKEDNIEAVGKKLH

EYNTQFQEKSREYDRLYEEYTRTSQEIQMKRTAIEAFNETIKIFEEQCQTQERYSKEY

IEKFKREGNEKEIQRIMHNYDKLKSRISEIIDSRRRLEEDLKKQAAEYREIDKRMNSI

KPDLIQLRKTRDQYLMWLTQKGVRQKKLNEWLGNENTEDQYSLVEDDEDLPHHDEKTW

NVGSSNRNKAENLLRGKRDGTFLVRESSKQGCYACSVVVDGEVKHCVINKTATGYGFA

EPYNLYSSLKELVLHYQHTSLVQHNDSLNVTLAYPVYAQQRR

FIG. 3Y

PTEN DNA (NM_000314) SEQ ID NO: 25

```
   1 cctcccctcg cccggcgcgg tcccgtccgc ctctcgctcg cctcccgcct cccctcggtc
  61 ttccgaggcg cccgggctcc cggcgcggcg gcggaggggg cgggcaggcc ggcgggcggt
 121 gatgtggcgg gactctttat gcgctgcggc aggatacgcg ctcggcgctg ggacgcgact
 181 gcgctcagtt ctctcctctc ggaagctgca gccatgatgg aagtttgaga gttgagccgc
 241 tgtgaggcga ggccgggctc aggcgaggga gatgagagac ggcggcggcc gcggcccgga
 301 gcccctctca gcgcctgtga gcagccgcgg gggcagcgcc ctcggggagc cggccggcct
 361 gcggcggcgg cagcggcggc gtttctcgcc tcctcttcgt cttttctaac cgtgcagcct
 421 cttcctcggc ttctcctgaa agggaaggtg gaagccgtgg gctcgggcgg gagccggctg
 481 aggcgcggcg gcggcggcgg cacctcccgc tcctggagcg gggggagaa gcggcggcgg
 541 cggcggccgc ggcggctgca gctccaggga gggggtctga gtcgcctgtc accatttcca
 601 gggctgggaa cgccggagag ttggtctctc cccttctact gcctccaaca cggcggcggc
 661 ggcggcggca catccaggga cccgggccgg ttttaaacct cccgtccgcc gccgccgcac
 721 cccccgtggc ccgggctccg gaggccgccg gcggaggcag ccgttcggag gattattcgt
 781 cttctcccca ttccgctgcc gccgctgcca ggcctctggc tgctgaggag aagcaggccc
 841 agtcgctgca accatccagc agccgccgca gcagccatta cccggctgcg gtccagagcc
 901 aagcggcggc agagcgaggg gcatcagcta ccgccaagtc cagagccatt tccatcctgc
 961 agaagaagcc ccgccaccag cagcttctgc catctctctc ctcctttttc ttcagccaca
1021 ggctcccaga catgacagcc atcatcaaag agatcgttag cagaaacaaa aggagatatc
1081 aagaggatgg attcgactta gacttgacct atatttatcc aaacattatt gctatgggat
1141 ttcctgcaga aagacttgaa ggcgtataca ggaacaatat tgatgatgta gtaaggtttt
1201 tggattcaaa gcataaaaac cattacaaga tatacaatct ttgtgctgaa agacattatg
1261 acaccgccaa atttaattgc agagttgcac aatatccttt tgaagaccat aacccaccac
1321 agctagaact tatcaaaccc ttttgtgaag atcttgacca atggctaagt gaagatgaca
1381 atcatgttgc agcaattcac tgtaaagctg gaaagggacg aactggtgta atgatatgtg
1441 catatttatt acatcggggc aaatttttaa aggcacaaga ggccctagat ttctatgggg
1501 aagtaaggac cagagacaaa aagggagtaa ctattcccag tcagaggcgc tatgtgtatt
1561 attatagcta cctgttaaag aatcatctgg attatagacc agtggcactg ttgtttcaca
1621 agatgatgtt tgaaactatt ccaatgttca gtggcggaac ttgcaatcct cagtttgtgg
1681 tctgccagct aaaggtgaag atatattcct ccaattcagg acccacacga cgggaagaca
1741 agttcatgta ctttgagttc cctcagccgt tacctgtgtg tggtgatatc aaagtagagt
1801 tcttccacaa acagaacaag atgctaaaaa aggacaaaat gtttcacttt tgggtaaata
1861 cattcttcat accaggacca gaggaaacct cagaaaaagt agaaaatgga agtctatgtg
1921 atcaagaaat cgatagcatt tgcagtatag agcgtgcaga taatgacaag gaatatctag
1981 tacttacttt aacaaaaaat gatcttgaca aagcaaataa agacaaagcc aaccgatact
2041 tttctccaaa ttttaaggtg aagctgtact tcacaaaaac agtagaggag ccgtcaaatc
2101 cagaggctag cagttcaact tctgtaacac cagatgttag tgacaatgaa cctgatcatt
2161 atagatattc tgacaccact gactctgatc cagagaatga acctttgat gaagatcagc
2221 atacacaaat tacaaaagtc tgaatttttt tttatcaaga gggataaaac accatgaaaa
2281 taaacttgaa taaactgaaa atggaccttt tttttttaa tggcaatagg acattgtgtc
2341 agattaccag ttataggaac aattctcttt tcctgaccaa tcttgtttta ccctatacat
2401 ccacagggtt ttgacacttg ttgtccagtt gaaaaaggt tgtgtagctg tgtcatgtat
2461 ataccttttt gtgtcaaaag gacatttaaa attcaattag gattaataaa gatggcactt
2521 tcccgtttta ttccagtttt ataaaaagtg gagacagact gatgtgtata cgtaggaatt
2581 ttttcctttt gtgttctgtc accaactgaa gtggctaaag agctttgtga tatactggtt
2641 cacatcctac ccctttgcac ttgtggcaac agataagttt gcagttggct aagagaggtt
2701 tccgaagggt tttgctacat tctaatgcat gtattcgggt taggggaatg gagggaatgc
2761 tcagaaagga aataatttta tgctggactc tggaccatat accatctcca gctatttaca
2821 cacacctttc tttagcatgc tacagttatt aatctggaca ttcgaggaat tggccgctgt
2881 cactgcttgt tgtttgcgca ttttttttta aagcatattg gtgctagaaa aggcagctaa
2941 aggaagtgaa tctgtattgg ggtacaggaa tgaaccttct gcaacatctt aagatccaca
3001 aatgaaggga tataaaaata atgtcatagg taagaaacac agcaacaatg acttaaccat
```

FIG. 3Y (cont.)

```
3061 ataaatgtgg aggctatcaa caaagaatgg gcttgaaaca ttataaaaat tgacaatgat
3121 ttattaaata tgttttctca attgtaacga cttctccatc tcctgtgtaa tcaaggccag
3181 tgctaaaatt cagatgctgt tagtacctac atcagtcaac aacttacact tattttacta
3241 gttttcaatc ataatacctg ctgtggatgc ttcatgtgct gcctgcaagc ttcttttttc
3301 tcattaaata taaaatattt tgtaatgctg cacagaaatt ttcaatttga gattctacag
3361 taagcgtttt ttttctttga agatttatga tgcacttatt caatagctgt cagccgttcc
3421 acccttttga ccttacacat tctattacaa tgaattttgc agttttgcac atttttttaaa
3481 tgtcattaac tgttagggaa ttttacttga atactgaata catataatgt ttatattaaa
3541 aaggacattt gtgttaaaaa ggaaattaga gttgcagtaa actttcaatg ctgcacacaa
3601 aaaaaagaca tttgattttt cagtagaaat tgtcctacat gtgctttatt gatttgctat
3661 tgaaagaata gggttttttt tttttttttt tttttttttt ttaaatgtgc agtgttgaat
3721 catttcttca tagtgctccc ccgagttggg actagggctt caatttcact tcttaaaaaa
3781 aatcatcata tatttgatat gcccagactg catacgattt taagcggagt acaactacta
3841 ttgtaaagct aatgtgaaga tattattaaa aaggtttttt tttccagaaa tttggtgtct
3901 tcaaattata ccttcacctt gacatttgaa tatccagcca ttttgtttct taatggtata
3961 aaattccatt ttcaataact tattggtgct gaaattgttc actagctgtg gtctgaccta
4021 gttaatttac aaatacagat tgaataggac ctactagagc agcatttata gagtttgatg
4081 gcaaatagat taggcagaac ttcatctaaa atattcttag taaataatgt tgacacgttt
4141 tccatacctt gtcagtttca ttcaacaatt tttaaatttt taacaaagct cttaggattt
4201 acacatttat atttaaacat tgatatatag agtattgatt gattgctcat aagttaaatt
4261 ggtaaagtta gagacaacta ttctaacacc tcaccattga aatttatatg ccaccttgtc
4321 tttcataaaa gctgaaaatt gttacctaaa atgaaaatca acttcatgtt ttgaagatag
4381 ttataaatat tgttctttgt tacaatttcg ggcaccgcat attaaaacgt aactttattg
4441 ttccaatatg taacatggag ggccaggtca taaataatga cattataatg ggcttttgca
4501 ctgttattat ttttcctttg gaatgtgaag gtctgaatga gggttttgat tttgaatgtt
4561 tcaatgtttt tgagaagcct tgcttacatt ttatggtgta gtcattggaa atggaaaaat
4621 ggcattatat atattatata tataaatata tattatacat actctcctta ctttatttca
4681 gttaccatcc ccatagaatt tgacaagaat tgctatgact gaaaggtttt cgagtcctaa
4741 ttaaaacttt atttatggca gtattcataa ttagcctgaa atgcattctg taggtaatct
4801 ctgagtttct ggaatatttt cttagacttt ttggatgtgc agcagcttac atgtctgaag
4861 ttacttgaag gcatcacttt taagaaagct tacagttggg ccctgtacca tcccaagtcc
4921 tttgtagctc ctcttgaaca tgtttgccat acttttaaaa gggtagttga ataaatagca
4981 tcaccattct ttgctgtggc acaggttata aacttaagtg gagtttaccg gcagcatcaa
5041 atgtttcagc tttaaaaaat aaaagtaggg tacaagttta atgtttagtt ctagaaattt
5101 tgtgcaatat gttcataacg atggctgtgg ttgccacaaa gtgcctcgtt tacctttaaa
5161 tactgttaat gtgtcatgca tgcagatgga aggggtggaa ctgtgcacta aagtggggc
5221 tttaactgta gtatttggca gagttgcctt ctacctgcca gttcaaaagt tcaacctgtt
5281 ttcatataga atatatatac taaaaaattt cagtctgtta aacagcctta ctctgattca
5341 gcctcttcag atactcttgt gctgtgcagc agtggctctg tgtgtaaatg ctatgcactg
5401 aggatacaca aaaataccaa tatgatgtgt acaggataat gcctcatccc aatcagatgt
5461 ccatttgtta ttgtgtttgt taacaaccct ttatctctta gtgttataaa ctccacttaa
5521 aactgattaa agtctcattc ttgtcaaaaa aaaaaaaaaa aaaaaaaaaa aa
```

FIG. 3Z

PTEN Protein SEQ ID NO: 26

MTAIIKEIVSRNKRRYQEDGFDLDLTYIYPNIIAMGFPAERLEG

VYRNNIDDVVRFLDSKHKNHYKIYNLCAERHYDTAKFNCRVAQYPFEDHNPPQLELIK

PFCEDLDQWLSEDDNHVAAIHCKAGKGRTGVMICAYLLHRGKFLKAQEALDFYGEVRT

RDKKGVTIPSQRRYVYYYSYLLKNHLDYRPVALLFHKMMFETIPMFSGGTCNPQFVVC

QLKVKIYSSNSGPTRREDKFMYFEFPQPLPVCGDIKVEFFHKQNKMLKKDKMFHFWVN

TFFIPGPEETSEKVENGSLCDQEIDSICSIERADNDKEYLVLTLTKNDLDKANKDKAN

RYFSPNFKVKLYFTKTVEEPSNPEASSSTSVTPDVSDNEPDHYRYSDTTDSDPENEPF

DEDQHTQITKV

FIG. 3AA

RAF 1 NM_002880 SEQ ID NO: 27

```
   1 agaatcggag agccggtggc gtcgcaggtc gggaggacga gcaccgagtc gagggctcgc
  61 tcgtctgggc cgcccgagag tcttaatcgc gggcgcttgg gccgccatct tagatggcgg
 121 gagtaagagg aaaacgattg tgaggcggga acggctttct gctgcctttt ttgggccccg
 181 aaaagggtca gctggccggg ctttggggcg cgtgccctga ggcgcggagc gcgtttgcta
 241 cgatgcgggg gctgctcggg gctccgtccc ctgggctggg gacgcgccga atgtgaccgc
 301 ctcccgctcc ctcacccgcc gcggggagga ggagcgggcg agaagctgcc gccgaacgac
 361 aggacgttgg ggcggcctgg ctccctcagg tttaagaatt gtttaagctg catcaatgga
 421 gcacatacag ggagcttgga agacgatcag caatggtttt ggattcaaag atgccgtgtt
 481 tgatggctcc agctgcatct ctcctacaat agttcagcag tttggctatc agcgccgggc
 541 atcagatgat ggcaaactca cagatccttc taagacaagc aacactatcc gtgtttttct
 601 gccgaacaag caaagaacag tggtcaatgt gcgaaatgga atgagcttgc atgactgcct
 661 tatgaaagca ctcaaggtga ggggcctgca accagagtgc tgtgcagtgt tcagacttct
 721 ccacgaacac aaaggtaaaa aagcacgctt agattggaat actgatgctg cgtctttgat
 781 tggagaagaa cttcaagtag atttcctgga tcatgttccc ctcacaacac acaactttgc
 841 tcggaagacg ttcctgaagc ttgccttctg tgacatctgt cagaaattcc tgctcaatgg
 901 atttcgatgt cagacttgtg gctacaaatt tcatgagcac tgtagcacca aagtacctac
 961 tatgtgtgtg gactggagta acatcagaca actcttattg tttccaaatt ccactattgg
1021 tgatagtgga gtcccagcac taccttcttt gactatgcgt cgtatgcgag agtctgtttc
1081 caggatgcct gttagttctc agcacagata ttctacacct cacgccttca cctttaacac
1141 ctccagtccc tcatctgaag gttccctctc ccagaggcag aggtcgacat ccacacctaa
1201 tgtccacatg gtcagcacca ccctgcctgt ggacagcagg atgattgagg atgcaattcg
1261 aagtcacagc gaatcagcct caccttcagc cctgtccagt agccccaaca atctgagccc
1321 aacaggctgg tcacagccga aaacccccgt gccagcacaa agagagcggg caccagtatc
1381 tgggacccag gagaaaaaca aaattaggcc tcgtggacag agagattcaa gctattattg
1441 ggaaatagaa gccagtgaag tgatgctgtc cactcggatt gggtcaggct cttttggaac
1501 tgtttataag ggtaaatggc acggagatgt tgcagtaaag atcctaaagg ttgtcgaccc
1561 aaccccagag caattccagg ccttcaggaa tgaggtggct gttctgcgca aaacacggca
1621 tgtgaacatt ctgcttttca tggggtacat gacaaaggac aacctggcaa ttgtgaccca
1681 gtggtgcgag ggcagcagcc tctacaaaca cctgcatgtc caggagacca agtttcagat
1741 gttccagcta attgacattg cccggcagac ggctcaggga atggactatt tgcatgcaaa
1801 gaacatcatc catagagaca tgaaatccaa caatatattt ctccatgaag gcttaacagt
1861 gaaaattgga gattttggtt tggcaacagt aaagtcacgc tggagtggtt ctcagcaggt
1921 tgaacaacct actggctctg tcctctggat ggccccagag gtgatccgaa tgcaggataa
1981 caacccattc agtttccagt cggatgtcta ctcctatggc atcgtattgt atgaactgat
2041 gacgggggag cttccttatt ctcacatcaa caaccgagat cagatcatct tcatggtggg
2101 ccgaggatat gcctccccag atcttagtaa gctatataag aactgcccca aagcaatgaa
2161 gaggctggta gctgactgtg tgaagaaagt aaaggaagag aggcctcttt ttccccagat
2221 cctgtcttcc attgagctgc tccaacactc tctaccgaag atcaaccgga gcgcttccga
2281 gccatccttg catcgggcag cccacactga ggatatcaat gcttgcacgc tgaccacgtc
2341 cccgaggctg cctgtcttct agttgacttt gcacctgtct tcaggctgcc aggggaggag
2401 gagaagccag caggcaccac ttttctgctc cctttctcca gaggcagaac acatgttttc
2461 agagaagctg ctgctaagga ccttctagac tgctcacagg gccttaactt catgttgcct
2521 tcttttctat ccctttgggc cctgggagaa ggaagccatt tgcagtgctg gtgtgtcctg
2581 ctccctcccc acattcccca tgctcaaggc ccagccttct gtagatgcgc aagtggatgt
2641 tgatggtagt acaaaaagca ggggcccagc cccagctgtt ggctacatga gtatttagag
2701 gaagtaaggt agcaggcagt ccagccctga tgtggagaca catgggattt tggaaatcag
2761 cttctggagg aatgcatgtc acaggcggga ctttcttcag agagtggtgc agcgccagac
2821 attttgcaca taaggcacca aacagcccag gactgccgag actctggccg cccgaaggag
2881 cctgctttgg tactatggaa cttttcttag ggacacgtcc tcctttcac agcttctaag
2941 gtgtccagtg cattgggatg gttttccagg caaggcactc ggccaatccg catctcagcc
3001 ctctcaggga gcagtcttcc atcatgctga attttgtctt ccaggagctg cccctatggg
```

FIG. 3AA (cont.)

```
3061 gcggggccgc agggccagcc ttgtttctct aacaaacaaa caaacaaaca gccttgtttc
3121 tctagtcaca tcatgtgtat acaaggaagc caggaataca ggttttcttg atgatttggg
3181 ttttaatttt gtttttattg cacctgacaa aatacagtta tctgatggtc cctcaattat
3241 gttattttaa taaaataaat taaatttagg tgtaaaaaaa aaaaaaaaaa a
```

FIG. 3BB

RAF protein SEQ ID NO: 28

MEHIQGAWKTISNGFGFKDAVFDGSSCISPTIVQQFGYQRRASD

DGKLTDPSKTSNTIRVFLPNKQRTVVNVRNGMSLHDCLMKALKVRGLQPECCAVFRLL

HEHKGKKARLDWNTDAASLIGEELQVDFLDHVPLTTHNFARKTFLKLAFCDICQKFLL

NGFRCQTCGYKFHEHCSTKVPTMCVDWSNIRQLLLFPNSTIGDSGVPALPSLTMRRMR

ESVSRMPVSSQHRYSTPHAFTFNTSSPSSEGSLSQRQRSTSTPNVHMVSTTLPVDSRM

IEDAIRSHSESASPSALSSSPNNLSPTGWSQPKTPVPAQRERAPVSGTQEKNKIRPRG

QRDSSYYWEIEASEVMLSTRIGSGSFGTVYKGKWHGDVAVKILKVVDPTPEQFQAFRN

EVAVLRKTRHVNILLFMGYMTKDNLAIVTQWCEGSSLYKHLHVQETKFQMFQLIDIAR

QTAQGMDYLHAKNIIHRDMKSNNIFLHEGLTVKIGDFGLATVKSRWSGSQQVEQPTGS

VLWMAPEVIRMQDNNPFSFQSDVYSYGIVLYELMTGELPYSHINNRDQIIFMVGRGYA

SPDLSKLYKNCPKAMKRLVADCVKKVKEERPLFPQILSSIELLQHSLPKINRSASEPS

LHRAAHTEDINACTLTTSPRLPVF

FIG. 3CC

RHEB DNA NM_005614 SEQ ID NO: 29

```
   1 ggcgtaatta aaaagcggcg gaagaaggtg ggagggtcat gacgcagcga gtttcagtcg
  61 tgacttttct gggggcatcg cggcgtcccc tttttttgcc tttaaagtaa aacgtcgccc
 121 cgacgcaccc cccgcgtatt tcgggggcg gaggcggcgg gccacggcgc gaagaggggc
 181 ggtgctgacg ccggccggtc acgtgggcgt gttgtggggg ggaggggcgc cgccgcgcgg
 241 tcggttccgg gcggttggga gcgcgcgagc tagcgagcga gaggcagccg cgcccgccgc
 301 cgcccctgct ctgtatgccg ctctctcccg gcgcggccgc cgccgatcac agcagcagga
 361 gccaccgccg ccgcggttga tgtggttggg ccggggctga ggaggccgcc aagatgccgc
 421 agtccaagtc ccggaagatc gcgatcctgg gctaccggtc tgtggggaaa tcctcattga
 481 cgattcaatt tgttgaaggc caatttgtgg actcctacga tccaaccata gaaaacactt
 541 ttacaaagtt gatcacagta aatggacaag aatatcatct tcaacttgta gacacagccg
 601 ggcaagatga atattctatc tttcctcaga catactccat agatattaat ggctatattc
 661 ttgtgtattc tgttacatca atcaaaagtt ttgaagtgat taaagttatc catggcaaat
 721 tgttggatat ggtggggaaa gtacaaatac ctattatgtt ggttgggaat aagaaagacc
 781 tgcatatgga aagggtgatc agttatgaag aagggaaagc tttggcagaa tcttggaatg
 841 cagctttttt ggaatcttct gctaaagaaa atcagactgc tgtggatgtt tttcgaagga
 901 taattttgga ggcagaaaaa atggacgggg cagcttcaca aggcaagtct tcatgctcgg
 961 tgatgtgatt ctgctgcaaa gcctgaggac actgggaata tattctacct gaagaagcaa
1021 actgcccgtt ctccttgaag ataaactatg cttctttttt cttctgttaa cctgaaagat
1081 atcatttggg tcagagctcc cctcccttca gattatgtta actctgagtc tgtccaaatg
1141 agttcacttc cattttcaaa ttttaagcaa tcatattttc aatttatata ttgtatttct
1201 taatattatg accaagaatt ttatcggcat taatttttca gtgtagtttg ttgtttaaaa
1261 taatgtaatc atcaaaatga tgcatattgt tacactacta ttaactaggc ttcagtatat
1321 cagtgtttat ttcattgtgt taaatgtata cttgtaaata aaatagctgc aaacctcagt
1381 cctttgtgct acttgatgtg gctttcaaag aagagaagcc ttgtcctgag tttctcactt
1441 ggcttcagga aggccccagg ttggattcca gaaaccagtg aagatgtggc cacaggagga
1501 ggtgtgctga ggtggctgct gaccgtggac tccctgcgca gtggcctgca gatgttgggg
1561 ctgggttaca gctgattgaa gctgagtggc cctggggggt ctgtgagggg agttcctccc
1621 cagtgatgaa attctctcct tccaccctca aatccctaga ccttgactga aatgctccgt
1681 ggtcgggagc ctggtcaagg aggaggagct gctgagaggc attgttcgcc cttgctcata
1741 gcttagctcg atgtccgtgt cagacaggag atgattgaga acagccttgc ctgtcactgt
1801 cctagaacac cctggagttt agtgttctgt gtcagagtct tgggagcctc cttcagaccc
1861 agatgacggg cctccctctg tccaaggagc agctgtaaag gagaagaggg atttcatttg
1921 tttggtggct gttaccttgt ctgtaagtca aacttggagt tgagcagtgc tttttaaacg
1981 attccctttt gcagctaaaa tttcacaggg ctatttctaa tacgtaagca aatgttacca
2041 ttgactttat taataaaata tagttttgct ttgcaaaaaa aaaaaaaaaa aa
```

FIG. 3DD

RHEB Protein SEQ ID NO: 30

MPQSKSRKIAILGYRSVGKSSLTIQFVEGQFVDSYDPTIENTFT

KLITVNGQEYHLQLVDTAGQDEYSIFPQTYSIDINGYILVYSVTSIKSFEVIKVIHGK

LLDMVGKVQIPIMLVGNKKDLHMERVISYEEGKALAESWNAAFLESSAKENQTAVDVF

RRIILEAEKMDGAASQGKSSCSVM

FIG. 3EE

Shank DNA (NM_001080420) SEQ ID NO: 31

```
   1 atggacggcc ccggggccag cgccgtggtc gtgcgcgtcg gcatcccgga cctgcagcag
  61 acgaagtgcc tgcgcctgga cccggccgcg cccgtgtggg ccgccaagca gcgcgtgctc
 121 tgcgccctca accacagcct ccaggacgcg ctcaactatg ggcttttcca gccgccctcc
 181 cggggccgcg ccggcaagtt cctggatgag gagcggctcc tgcaggagta cccgcccaac
 241 ctggacacgc ccctgcccta cctggagttt cgatacaagc ggcgagttta tgcccagaac
 301 ctcatcgatg ataagcagtt tgcaaagctt cacacaaagg cgaacctgaa gaagttcatg
 361 gactacgtcc agctgcatag cacggacaag gtggcacgcc tgttggacaa ggggctggac
 421 cccaacttcc atgaccctga ctcaggagag tgccccctga gcctcgcagc ccagctggac
 481 aacgccacgg acctgctaaa ggtgctgaag aatggtggtg cccacctgga cttccgcact
 541 cgcgatgggc tcactgccgt gcactgtgcc acacgccagc ggaatgcggc agcactgacg
 601 accctgctgg acctgggggc ttcacctgac tacaaggaca gccgcggctt gacacccctc
 661 taccacagcg ccctgggggg tggggatgcc ctctgctgtg agctgcttct ccacgaccac
 721 gctcagctgg ggatcaccga cgagaatggc tggcaggaga tccaccaggc ctgccgcttt
 781 gggcacgtgc agcatctgga gcacctgctg ttctatgggg cagacatggg ggcccagaac
 841 gcctcgggga acacagccct gcacatctgt gccctctaca accaggagag ctgtgctcgt
 901 gtcctgctct tccgtggagc taacagggat gtccgcaact acaacagcca gacagccttc
 961 caggtggcca tcatcgcagg gaactttgag cttgcagagg ttatcaagac ccacaaagac
1021 tcggatgttg taccattcag ggaaaccccc agctatgcga agcggcggcg actggctggc
1081 cccagtggct tggcatcccc tcggcctctg cagcgctcag ccagcgatat caacctgaag
1141 ggggaggcac agccagcagc ttctcctgga ccctcgctga gaagcctccc ccaccagctg
1201 ctgctccagc ggctgcaaga ggagaaagat cgtgaccggg atgccgacca ggagagcaac
1261 atcagtggcc ctttagcagg cagggccggc caaagcaaga tcagcgatcc gggccctgga
1321 cctggagggg tggggggggc gcccctccct cccccctggcg cgcccaggag ctgtattcga
1381 attcgagctc ggttccccgc gcccctgcg ccccccgcac cgccgccccg gggcccgaag
1441 cggaaacttt acagcgccgt ccccggccgc aagttcatcg ccgtgaaggc gcacagcccg
1501 cagggtgaag gcgagatccc gctgcaccgc ggcgaggccg tgaaggtgct cagcattggg
1561 gagggcggtt tctgggaggg aaccgtgaaa ggccgcacgg gctggttccc ggccgactgc
1621 gtggaggaag tgcagatgag gcagcatgac acacggcctg aaacgcggga ggaccggacg
1681 aagcggctct ttcggcacta cacagtgggc tcctacgaca gcctcacctc acacagcgat
1741 tatgtcattg atgacaaagt ggctgtcctg cagaaacggg accacgaggg ctttggtttt
1801 gtgctccggg gagccaaagc agagaccccc atcgaggagt tcacgcccac gccagccttc
1861 ccggcgctgc agtatctcga gtcggtggac gtggagggtg tggcctggag ggccgggctg
1921 cgcacgggag acttcctcat cgaggtgaac ggggtgaacg tggtgaaggt cggacacaag
1981 caggtggtgg ctctgattcg ccagggtggc aaccgcctcg tcatgaaggt tgtgtctgtg
2041 acaaggaagc cagaagagga cggggctcgg cgcagagccc caccgccccc caagagggcc
2101 cccagcacca cactgaccct gcgctccaag tccatgacag ctgagctcga ggaacttgcc
2161 tccattcgga gaagaaaagg ggagaagctg gacgagatgc tggcagccgc cgcagagcca
2221 acgctgcggc cagacatcgc agacgcagac tccagagccg ccaccgtcaa acagaggccc
2281 accagtcgga ggatcacacc cgccgagatt agctcattgt ttgaacgcca gggcctccca
2341 ggcccagaga agctgccggg ctccttgcgg aaggggattc cacggaccaa gtctgtaggg
2401 gaggacgaga agctggcgtc cctgctggaa gggcgcttcc cgcggagcac ctcgatgcaa
2461 gacccggtgc gcgagggtcg cggcatcccg cccccgccgc agaccgcgcc gcctcccccg
2521 cccgcgccct actacttcga ctcggggccg cccccggcct tctcgccgcc gcccccgccg
2581 ggccgcgcct acgacacggt gcgctccagc ttcaagcccg gcctggaggc gcgcctgggc
2641 gcgggcgctg ccggcctgta cgagccgggc gcggccctcg gcccgctgcc gtatcccgag
2701 cggcagaagc gcgcgcgctc catgatcatc ctgcaggact cggcgcccga gtcgggcgac
2761 gcccctcgac ccccgcccgc ggccaccccg cccgagcgac ccaagcgccg gccgcggccg
2821 cccggccccg acagccccta cgccaacctg ggcgccttca gcgccagcct cttcgctccg
2881 tccaagccgc agcgccgcaa gagcccccctg gtgaagcagc tgcaggtgga ggacgcgcag
2941 gagcgcgcgg ccctggccgt gggcagcccc ggtcccggcg gcggcagctt cgcccgcgag
3001 ccctccccga cccaccgcgg tccgcgcccg ggtggcctcg actacggcgc gggcgatggc
```

FIG. 3EE (cont.)

```
3061 ccggggctcg cgttcggcgg cccgggcccg gccaaggacc ggcggctgga ggagcggcgc
3121 cgctccactg tgttcctgtc cgtgggggcc atcgagggca gcgccccccgg cgcggatctg
3181 ccatccctac agccctcccg ctccatcgac gagcgcctcc tggggaccgg ccccaccgcc
3241 ggccgcgacc tgctgctgcc ctccccggtg tctgccctga agccgttggt cagcggcccg
3301 agcctggggc cctcgggttc caccttcatc cacccactca ccggcaaacc cctggacccc
3361 agctcacccc tggcccttgc cctggctgcc cgagagcgag ctctggcctc ccaggcgccc
3421 tcccggtccc ccacacccgt gcacagtccc gacgccgacc gccccggacc cctgtttgtg
3481 gatgtacagg cccgggaccc agagcgaggg tccctggctt ccccggcttt ctccccacgg
3541 agcccagcct ggattcctgt gcctgctcgc agggaggcag agaaggtccc ccgggaggag
3601 cggaagtcac ccgaggacaa gaagtccatg atcctcagcg tcctggacac atccctgcag
3661 cggccagctg gcctcatcgt tgtgcacgcc accagcaacg ggcaggagcc cagcaggctg
3721 gggggggccg aagaggagcg cccgggcacc ccggagttgg ccccggcccc catgcagtca
3781 gcggctgtgg cagagcccct gcccagcccc cgggcccagc cccctggtgg caccccggca
3841 gacgccgggc caggccaggg cagctcagag gaagagccag agctggtgtt tgctgtgaac
3901 ctgccacctg cccagctgtc gtccagcgat gaggagacca gggaggagct ggcccgaatt
3961 gggttggtgc cacccccctga agagtttgcc aacggggtcc tgctggccac cccactcgct
4021 ggcccgggcc cctcgcccac cacggtgccc agcccggcct cagggaagcc cagcagtgag
4081 ccacccccctg cccctgagtc tgcagccgac tctgggtgg aggaggctga cacacgcagc
4141 tccagcgacc cccacctgga gaccacaagc accatctcca cggtgtccag catgtccacc
4201 ttgagctcgg agagcgggga actcactgac acccacacct ccttcgctga cggacacact
4261 tttctactcg agaagccacc agtgcctccc aagcccaagc tcaagtcccc gctggggaag
4321 gggccggtga ccttcaggga cccgctgctg aagcagtcct cggacagcga gctcatggcc
4381 cagcagcacc acgccgcctc tgccgggctg gcctctgccg ccgggcctgc ccgccctcgc
4441 tacctcttcc agagaaggtc caagctatgg ggggaccccg tggagagccg gggggctccct
4501 gggcctgaag acgacaaacc aactgtgatc agtgagctca gctcccgcct gcagcagctg
4561 aacaaggaca cgcgttccct gggggaggaa ccagttggtg gcctgggcag cctgctggac
4621 cctgccaaga agtcgcccat cgcagcagct cggctcttca gcagcctcgg tgagctgagc
4681 tccatttcag cgcagcgcag ccccgggggc ccgggcggcg ggcctcgta ctcggtgagg
4741 cccagtggcc gctaccccgt ggcgagacgc gccccgagcc cggtgaagcc cgcgtcgctg
4801 gagcgggtgg aggggctggg ggcgggcgcg gggggcgcag ggcggccctt cggcctcacg
4861 ccccccacca tcctcaagtc gtccagcctc tccatcccgc acgagcccaa ggaggtgcgc
4921 ttcgtggtgc gcagcgtgag cgcgcgcagt cgctccccct cgccgtcgcc gctgccctcg
4981 cccgcgtccg gccccggccc cggcgccccc ggcccacgcc gacccttcca gcagaagccg
5041 ctgcagctct ggagcaagtt cgacgtgggc gactggctgg agagcatcca cctaggcgag
5101 caccgcgacc gcttcgagga ccatgagata gaaggcgcgc acctacccgc gcttaccaag
5161 gacgacttcg tggagctggg cgtcacgcgc gtgggccacc gcatgaacat cgagcgcgcg
5221 ctcaggcagc tggacggcag ctgacgcccc acccccactc ccgccccggc cgtgccctgc
5281 cggcagggcc ccccaccccc accccgggcc gcgggctcgg cctgcccctt acgacggcgc
5341 ccgggccagg aatgttgcat gaatcgtcct gtttgctgtt gctcggagac tcgccctgta
5401 cattgcttag tgccctcacc ggccgcccag cccacccagc gcacagtcag gaagggcgtg
5461 gaccagggag gctggggcgg gaggtgccgg gggtggggtg ccctagcgtg accacctcct
5521 tcgcagctcc tggtggccat tctcccagag gggaacccta gtccagcatg cgaggtcagg
5581 acccgccttg gtgactcggg gggagggggg agacattggg attctcgatg ggggccaagg
5641 agcccccctg ttttgcatat tttaatccac tctatatttg gaacgagaaa aggaacaaat
5701 atctctgtcc gtaatagttt cctctcccct cccttctact tccactggtc ccactgcagc
5761 tgcccagtct tccatctccg gcccctcact gccactgcca ccccacaacg gggcagggga
5821 cgctccagct ggtctggggt tggccagggc cctagtggcc cgccctgggg ccccagctcg
5881 gcccctcgcc tcgctgagct ctagtgtgcc ccaccgaccc ttcaggtgct gctcgtggtg
5941 ggaggggcgg caggccgcgg gtcctgctgt gcacccgcgg gaccagccgg cctgggagac
6001 catcggccgg gggggatgag ggcagggccc tgccgctcca ccgcagccat cttcctcaca
6061 gggtctctcc ccaaggaggg ggctagcttg gtccccatgc tcttgggcaa ctacagcaga
6121 gaagcctccc tgccttggac cccaaagtct cctgtcctgc cctttatgtg tgtgggtgaa
6181 actgggtgcg tctgagcacg tgggagccgt gtgtgtgcct gattactgag tggccaccag
```

FIG. 3EE (cont.)

```
6241 gggccgctct ggactagcgc ggggccgtgg aggcgtgcac cgtgtgcatg cgtggggtgt
6301 acctgtgaga gcaccctgtc tcctcttcca aagaaagtca gaggccatcc tgcaccctgg
6361 gtccagctgt ttgcccagcc tgtccttcca gagcctcacc cagcctgagc ggggttccct
6421 ggtgaatccc tgctgcttgg ggaggcccca agggcccctt ggaggcagcg cccccacctt
6481 gggcttctga gggcatcata gggggacccc tagagtcagt tcaccacagg ccctggggag
6541 agtcaaagac ccccgagggt gcccagcccc ccacactgtg actcctcaca ctcagcgatg
6601 acctgtgggg tgggggggccc tgggacgttt ttaaacctag ggtttggagt ctggactaag
6661 ctccatccac gtcactcaca agtttctgtt tatatttcta gcttttttta ataaaataaa
6721 aaaaaaaaga aaacagaagt tttcacaacc caggggcctg gcacgccggt ctgtgcctgc
6781 ccgccccgcc ctggcccacc ggccccactc cctgggcaca gagtcacacc cactcatcct
6841 tccgccaaca gtccaggtca cacagcagca gtcactgtaa cagactgcca catacacact
6901 cggtctcaca ctcacctgtg ggttttggtt ccgttcaatt tgggttttta actttacagg
6961 gtcagttccg cttcacctcc ttttgtatgg agttccatcc gggggggtttc accccctgct
7021 ccagtcctga ggcctcctga ccctgacgtt gtgatacgcc ccacagagat ctatgtttct
7081 tatattatta ttattgataa taattattat aatattatta tgtaataaat ttataagaaa
7141 tgaag
```

FIG. 3FF

SHANK 3 Protein SEQ ID NO:32

MDGPGASAVVVRVGIPDLQQTKCLRLDPAAPVWAAKQRVLCALN

HSLQDALNYGLFQPPSRGRAGKFLDEERLLQEYPPNLDTPLPYLEFRYKRRVYAQNLI

DDKQFAKLHTKANLKKFMDYVQLHSTDKVARLLDKGLDPNFHDPDSGECPLSLAAQLD

NATDLLKVLKNGGAHLDFRTRDGLTAVHCATRQRNAAALTTLLDLGASPDYKDSRGLT

PLYHSALGGGDALCCELLLHDHAQLGITDENGWQEIHQACRFGHVQHLEHLLFYGADM

GAQNASGNTALHICALYNQESCARVLLFRGANRDVRNYNSQTAFQVAIIAGNFELAEV

IKTHKDSDVVPFRETPSYAKRRRLAGPSGLASPRPLQRSASDINLKGEAQPAASPGPS

LRSLPHQLLLQRLQEEKDRDRDADQESNISGPLAGRAGQSKISDPGPGPGGVGGAPLP

PPGAPRSCIRIRARFPAPPAPPAPPPRGPKRKLYSAVPGRKFIAVKAHSPQGEGEIPL

HRGEAVKVLSIGEGGFWEGTVKGRTGWFPADCVEEVQMRQHDTRPETREDRTKRLFRH

YTVGSYDSLTSHSDYVIDDKVAVLQKRDHEGFGFVLRGAKAETPIEEFTPTPAFPALQ

YLESVDVEGVAWRAGLRTGDFLIEVNGVNVVKVGHKQVVALIRQGGNRLVMKVVSVTR

KPEEDGARRRAPPPPKRAPSTTLTLRSKSMTAELEELASIRRRKGEKLDEMLAAAAEP

TLRPDIADADSRAATVKQRPTSRRITPAEISSLFERQGLPGPEKLPGSLRKGIPRTKS

VGEDEKLASLLEGRFPRSTSMQDPVREGRGIPPPPQTAPPPPPAPYYFDSGPPPAFSP

PPPPGRAYDTVRSSFKPGLEARLGAGAAGLYEPGAALGPLPYPERQKRARSMIILQDS

APESGDAPRPPPAATPPERPKRRPRPPGPDSPYANLGAFSASLFAPSKPQRRKSPLVK

QLQVEDAQERAALAVGSPGPGGGSFAREPSPTHRGPRPGGLDYGAGDGPGLAFGGPGP

AKDRRLEERRRSTVFLSVGAIEGSAPGADLPSLQPSRSIDERLLGTGPTAGRDLLLPS

PVSALKPLVSGPSLGPSGSTFIHPLTGKPLDPSSPLALALAARERALASQAPSRSPTP

VHSPDADRPGPLFVDVQARDPERGSLASPAFSPRSPAWIPVPARREAEKVPREERKSP

EDKKSMILSVLDTSLQRPAGLIVVHATSNGQEPSRLGGAEEERPGTPELAPAPMQSAA

VAEPLPSPRAQPPGGTPADAGPGQGSSEEEPELVFAVNLPPAQLSSSDEETREELARI

GLVPPPEEFANGVLLATPLAGPGPSPTTVPSPASGKPSSEPPPAPESAADSGVEEADT

RSSSDPHLETTSTISTVSSMSTLSSESGELTDTHTSFADGHTFLLEKPPVPPKPKLKS

PLGKGPVTFRDPLLKQSSDSELMAQQHHAASAGLASAAGPARPRYLFQRRSKLWGDPV

FIG. 3FF (cont.)

ESRGLPGPEDDKPTVISELSSRLQQLNKDTRSLGEEPVGGLGSLLDPAKKSPIAAARL

FSSLGELSSISAQRSPGGPGGGASYSVRPSGRYPVARRAPSPVKPASLERVEGLGAGA

GGAGRPFGLTPPTILKSSSLSIPHEPKEVRFVVRSVSARSRSPSPSPLPSPASGPGPG

APGPRRPFQQKPLQLWSKFDVGDWLESIHLGEHRDRFEDHEIEGAHLPALTKDDFVEL

GVTRVGHRMNIERALRQLDGS

FIG. 3GG

TSC1 DNA (NM_000368) SEQ ID NO: 33

```
   1 acgacggggg aggtgctgta cgtccaagat ggcggcgccc tgtaggctgg agggactgtg
  61 aggtaaacag ctgaggggga ggagacggtg gtgaccatga aagacaccag gttgacagca
 121 ctggaaactg aagtaccagt tgtcgctaga acagtttggt agtggcccca atgaagaacc
 181 ttcagaacct gtagcacacg tcctggagcc agcacagcgc cttcgagcga gagaatggcc
 241 caacaagcaa atgtcgggga gcttcttgcc atgctggact cccccatgct gggtgtgcgg
 301 gacgacgtga cagctgtctt taaagagaac ctcaattctg accgtggccc tatgcttgta
 361 aacaccttgg tggattatta cctggaaacc agctctcagc cggcattgca catcctgacc
 421 accttgcaag agccacatga caagcacctc ttggacagga ttaacgaata tgtgggcaaa
 481 gccgccactc gtttatccat cctctcgtta ctgggtcatg tcataagact gcagccatct
 541 tggaagcata agctctctca agcacctctt ttgccttctt tactaaaatg tctcaagatg
 601 gacactgacg tcgttgtcct cacaacaggc gtcttggtgt tgataaccat gctaccaatg
 661 attccacagt ctgggaaaca gcatcttctt gatttctttg acatttttgg ccgtctgtca
 721 tcatggtgcc tgaagaaacc aggccacgtg gcggaagtct atctcgtcca tctccatgcc
 781 agtgtgtacg cactctttca tcgcctttat ggaatgtacc cttgcaactt cgtctccttt
 841 ttgcgttctc attacagtat gaaagaaaac ctggagactt ttgaagaagt ggtcaagcca
 901 atgatggagc atgtgcgaat tcatccggaa ttagtgactg gatccaagga ccatgaactg
 961 gaccctcgaa ggtggaagag attagaaact catgatgttg tgatcgagtg tgccaaaatc
1021 tctctggatc ccacagaagc ctcatatgaa gatggctatt ctgtgtctca ccaaatctca
1081 gcccgctttc ctcatcgttc agccgatgtc accaccagcc cttatgctga cacacagaat
1141 agctatgggt gtgctacttc taccccttac tccacgtctc ggctgatgtt gttaaatatg
1201 ccagggcagc tacctcagac tctgagttcc ccatcgacac ggctgataac tgaaccacca
1261 caagctactc tttggagccc atctatggtt tgtggtatga ccactcctcc aacttctcct
1321 ggaaatgtcc cacctgatct gtcacaccct tacagtaaag tctttggtac aactgcaggt
1381 ggaaaaggaa ctcctctggg aaccccagca acctctcctc ctccagcccc actctgtcat
1441 tcggatgact acgtgcacat ttcactcccc caggccacag tcacaccccc caggaaggaa
1501 gagagaatgg attctgcaag accatgtcta cacagacaac accatcttct gaatgacaga
1561 ggatcagaag agccacctgg cagcaaaggt tctgtcactc taagtgatct tccagggttt
1621 ttaggtgatc tggcctctga agaagatagt attgaaaaag ataaagaaga agctgcaata
1681 tctagagaac tttctgagat caccacagca gaggcagagc ctgtggttcc tcgaggaggc
1741 tttgactctc cctttaccg agacagtctc ccaggttctc agcggaagac ccactcggca
1801 gcctccagtt ctcagggcgc cagcgtgaac cctgagcctt tacactcctc cctggacaag
1861 cttgggcctg acacaccaaa gcaagccttt actcccatag acctgccctg cggcagtgct
1921 gatgaaagcc ctgcgggaga cagggaatgc cagacttctt tggagaccag tatcttcact
1981 cccagtcctt gtaaaattcc acctccgacg agagtgggct ttggaagcgg gcagcctccc
2041 ccgtatgatc atctttttga ggtggcattg ccaaagacag cccatcattt tgtcatcagg
2101 aagactgagg agctgttaaa gaaagcaaaa ggaaacacag aggaagatgg tgtgccctct
2161 acctccccaa tggaagtgct ggacagactg atacagcagg gagcagacgc gcacagcaag
2221 gagctgaaca agttgccttt acccagcaag tctgtcgact ggacccactt tggaggctct
2281 cctccttcag atgagatccg caccctccga gaccagttgc ttttactgca caaccagtta
2341 ctctatgagc gttttaagag gcagcagcat gccctccgga acaggcggct cctccgcaag
2401 gtgatcaaag cagcagctct ggaggaacat aatgctgcca tgaaagatca gttgaagtta
2461 caagagaagg acatccagat gtggaaggtt agtctgcaga aagaacaagc tagatacaat
2521 cagctccagg agcagcgtga cactatggta accaagctcc acagccagat cagacagctg
2581 cagcatgacc gagaggaatt ctacaaccag agccaggaat tacagacgaa gctggaggac
2641 tgcaggaaca tgattgcgga gctgcggata gaactgaaga aggccaacaa caaggtgtgt
2701 cacactgagc tgctgctcag tcaggtttcc caaaagctct caaacagtga gtcggtccag
2761 cagcagatgg agttcttgaa caggcagctg ttggttcttg gggaggtcaa cgagctctat
2821 ttggaacaac tgcagaacaa gcactcagat accacaaagg aagtagaaat gatgaaagcc
2881 gcctatcgga aagagctaga aaaaaacaga agccatgttc tccagcagac tcagaggctt
2941 gatacctccc aaaaacggat tttggaactg gaatctcacc tggccaagaa agaccacctt
3001 cttttggaac agaagaaata tctagaggat gtcaaactcc aggcaagagg acagctgcag
```

FIG. 3GG (cont.)

3061 gccgcagaga gcaggtatga ggctcagaaa aggataaccc aggtgtttga attggagatc
3121 ttagatttat atggcaggtt ggagaaagat ggcctcctga aaaaacttga agaagaaaaa
3181 gcagaagcag ctgaagcagc agaagaaagg cttgactgtt gtaatgacgg gtgctcagat
3241 tccatggtag ggcacaatga agaggcatct ggccacaacg gtgagaccaa gacccccagg
3301 cccagcagcg cccggggcag tagtggaagc agaggtggtg gaggcagcag cagcagcagc
3361 agcgagcttt ctaccccaga gaaacccca caccagaggg caggcccatt cagcagtcgg
3421 tgggagacga ctatgggaga agcgtctgcc agcatcccca ccactgtggg ctcacttccc
3481 agttcaaaaa gcttcctggg tatgaaggct cgagagttat ttcgtaataa gagcgagagc
3541 cagtgtgatg aggacggcat gaccagtagc ctttctgaga gcctaaagac agaactgggc
3601 aaagacttgg gtgtggaagc caagattccc ctgaacctag atggccctca cccgtctccc
3661 ccgaccccgg acagtgttgg acagctacat atcatggact acaatgagac tcatcatgaa
3721 cacagctaag gaatgatggt caatcagtgt taacttgcat attgttggca cagaacagga
3781 ggtgtgaatg cacgtttcaa agctttcctg tttccagggt ctgagtgcaa gttcatgtgt
3841 ggaaatggga cggaggtcct ttggacagct gactgaatgc agaacggttt ttggatctgg
3901 cattgaaatg cctcttgacc ttcccctcca cccgccctaa cccccctca tttacctcgc
3961 agtgtgttct aatccaaggg ccagttggtg ttcctcagta gctttacttt cttcctttcc
4021 cccccaaatg gttgcgtcct ttgaacctgt gcaatatgag gccaaattta atctttgagt
4081 ctaacacacc actttctgct ttcccgaagt tcagataact gggttggctc tcaattagac
4141 caggtagttt gttgcattgc aggtaagtct ggttttgtcc cttccaggag gacatagcct
4201 gcaaagctgg ttgtctttac atgaaagcgt ttacatgaga ctttccgact gctttttga
4261 ttctgaagtt cagcatctaa agcagcaggt ctagaagaac aacggtttat tcatacttgc
4321 attcttttgg cagttctgat aagcttccta gaaagttctg tgtaaacaga agcctgtttc
4381 agaaatctgg agctggcact gtggagacca cacacccttt gggaaagctc ttgtctcttc
4441 ttccccccact acctcttatt tatttggtgt ttgcttgaat gctggtacta ttgtgaccac
4501 aggctggtgt gtaggtggta aaacctgttc tccataggag ggaaggagca gtcactggga
4561 gaggttaccc gagaagcact tgagcatgag gaactgcacc tttaggccat ctcagcttgc
4621 tgggcctttt gttaaaccct tctgtctact ggcctccctt tgtgtgcata cgcctcttgt
4681 tcatgtcagc ttatatgtga cactgcagca gaaaggctct gaaggtccaa agagtttctg
4741 caaagtgtat gtgaccatca tttcccaggc cattagggtt gcctcactgt agcaggttct
4801 aggctaccag aagaggggca gctttttcat accaattcca actttcaggg gctgactctc
4861 cagggagctg atgtcatcac actctccatg ttagtaatgg cagagcagtc taaacagagt
4921 ccgggagaat gctggcaaag gctggctgtg tatacccact aggctgcccc acgtgctccc
4981 gagagatgac actagtcaga aaattggcag tggcagagaa tccaaactca acaagtgctc
5041 ctgaaagaaa cgctagaagc ctaagaactg tggtctggtg ttccagctga ggcaggggga
5101 tttggtagga aggagccagt gaacttggct ttcctgtttc tatctttcat taaaaagaat
5161 agaaggattc agtcataaag aggtaaaaaa ctgtcacggt acgaaatctt agtgcccacg
5221 gaggcctcga gcagagagaa tgaaagtctt tttttttttt tttttttttt agcatggcaa
5281 taaatattct agcatcccta actaaagggg actagacagt tagagactct gtcaccctag
5341 ctataccagc agaaaacctg ttcaggcagg ctttctgggt gtgactgatt cccagcctgt
5401 ggcagggcgt ggtcccaact actcagccta gcacaggctg gcagttggta ctgaattgtc
5461 agatgtggag tattagtgac accacacatt taattcagct ttgtccaaag gaaagcttaa
5521 aacccaatac agtctagttt cctggttccg ttttagaaaa ggaaaacgtg aacaaactta
5581 gaaagggaag gaaatcccat cagtgaatcc tgaaactggt tttaagtgct ttccttctcc
5641 tcatgcccaa gagatctgtg ccatagaaca agataccagg cacttaaagc cttttcctga
5701 attggaaagg aaaagaggcc caagtgcaaa agaaaaaaca ttttagaaac ggacagctta
5761 taaaaataaa gggaagaaag gaggcagcat ggagagaggc ctgtgctaga agctccatgg
5821 acgtgtctgc acaggtcct cagctcatcc atgcggcctg ggtgtccttt tactcagctt
5881 tataacaaat gtggctccaa gctcaggtgc ctttgagttc taggaggctg tgggttttat
5941 tcaactacgg ttgggagaat gagacctgga gtcatgttga aggtgcccaa cctaaaaatg
6001 taggctttca tgttgcaaag aactccagag tcagtagtta ggtttggttt ggttttggac
6061 atgataaacc tgccaagagt caacaggtca cttgatcatg ctgcagtggg tagttctaag
6121 gatggaaagg tgacagtatt actctcgaga ggcaattcag tcctgggcaa aggtattagt
6181 acaataagcg ttaagggcag agtctacctt gaaaccaatt aagcagcttg gtattcataa

FIG. 3GG (cont.)

```
6241 atattgggat tggatggcct ccatccagaa atcactatgg gtgagcatac ctgtctcagc
6301 tgtttggcca atgtgcataa cctactcgga tccccacctg acactaacca gagtcagcac
6361 aggccccgag gagcccgaag tctgctgctg tgcagcatgg aattccttta aaaaggtgca
6421 ctacagtttt agcggggagg gggataggaa gacgcagagc aaatgagctc cggagtccct
6481 gcaggtgaat aaacacacag atctgcatct gatagaactt tgatggattt tcaaaaagcc
6541 gttgacaagg ctctgctata cagtctataa aaattgttat tatgggattg gaagaaacac
6601 gtggtcatga atagaaaaaa aacaaaccca aaggtaggaa ggtcaaggtc atttcttaga
6661 tggagaagtt gtgaaagatg tccttggaga tgagttttag gaccagcatt actaaggcag
6721 gtgggcagac agtgacctct ctaggtgtgt ccacagagtt tttcaggaga gaaaactgcc
6781 tgacctttgg gactaagctg cggaatcttc ttactaagct tgaagagtgg agaggcgaga
6841 ggtgagctac tttgtgagcc aaagcttatg tgacatggtt ggggaaacag tccaaactgt
6901 tctgagaagg tgaactgtta cgacccagga caattagaaa aattcaccca ccatgccgca
6961 cattactggg taaaagcagg gcagcaggga acaaaactcc agactcttgg gccgtcccca
7021 tttgcaacag cacacatagt ttctggtata tttgttggga aagataaaac tctagcagtt
7081 gttgagggga ggatgtataa aatggtcatg gggatgaaag gatctctgag accacagagg
7141 ctcagactca ctgttaagaa tagaaaactg ggtatgcgtt tcatgtagcc agcagaactg
7201 aagtgtgctg tgacaagcca atgtgaattt ctaccaaata gtagagcata ccacttgaag
7261 aaggaaagaa ccgaagagca aacaaaagtt ctgcgtaatg agactcacct tttctcgctg
7321 aaagcactaa gaggtgggag gaggcctgca caggctggag gagggtttgg gcagagcgaa
7381 gacccggcca ggaccttggt gagatggggt gccgcccacc tcctgcggat actcttggag
7441 agttgttccc ccaggggget ctgccccacc tggagaagga agctgcctgg tgtggagtga
7501 ctcaaatcag tatacctatc tgctgcacct tcactctcca gggtacatgc tttaaaaccg
7561 acccgcaaca agtattggaa aaatgtatcc agtctgaaga tgtttgtgta tctgtttaca
7621 tccagagttc tgtgacacat gcccccccaga ttgctgcaaa gatcccaagg cattgattgc
7681 acttgattaa gcttttgtct gtaggtgaaa gaacaagttt aggtcgagga ctggccccta
7741 ggctgctgct gtgacccttg tcccatgtgg cttgtttgcc tgtccgggac tcttcgatgt
7801 gcccagggga gcgtgttcct gtctcttcca tgccgtcctg cagtccttat ctgctcgcct
7861 gagggaagag tagctgtagc tacaagggaa gcctgcctgg aagagccgag cacctgtgcc
7921 catggcttct ggtcatgaaa cgagttaatg atggcagagg agcttcctcc ccacttcgca
7981 gcgccacatt atccatcctc tgagataagt aggctggttt aaccattgga atggaccttt
8041 cagtggaaac cctgagagtc tgagaacccc cagaccaacc cttccctccc tttccccacc
8101 tcttacagtg tttggacagg agggtatggt gctgctctgt gtagcaagta ctttggctta
8161 tgaaagaggc agccacgcat tttgcactag gaagaatcag taatcacttt tcagaagact
8221 tctatggacc acaaatatat tacggaggaa cagattttgc taagacataa tctagtttta
8281 taactcaatc atgaatgaac catgtgtggc aaacttgcag tttaaagggg tcccatcagt
8341 gaaagaaact gatttttttt aacggactgc ttttagttaa attgaagaaa gtcagctctt
8401 gtcaaaaggt ctaaactttc ccgcctcaat cctaaaagca tgtcaacaat ccacatcaga
8461 tgccataaat atgaactgca ggataaaatg gtacaatctt agtgaatggg aattggaatc
8521 aaaagagttt gctgtccttc ttagaatgtt ctaaaatgtc aaggcagttg cttgtgttta
8581 actgtgaaca aataaaaatt tattgttttg cactacaaaa aaaaaa
```

FIG. 3HH

TSC1 Protein SEQ ID NO: 34

MAQQANVGELLAMLDSPMLGVRDDVTAVFKENLNSDRGPMLVNT

LVDYYLETSSQPALHILTTLQEPHDKHLLDRINEYVGKAATRLSILSLLGHVIRLQPS

WKHKLSQAPLLPSLLKCLKMDTDVVVLTTGVLVLITMLPMIPQSGKQHLLDFFDIFGR

LSSWCLKKPGHVAEVYLVHLHASVYALFHRLYGMYPCNFVSFLRSHYSMKENLETFEE

VVKPMMEHVRIHPELVTGSKDHELDPRRWKRLETHDVVIECAKISLDPTEASYEDGYS

VSHQISARFPHRSADVTTSPYADTQNSYGCATSTPYSTSRLMLLNMPGQLPQTLSSPS

TRLITEPPQATLWSPSMVCGMTTPPTSPGNVPPDLSHPYSKVFGTTAGGKGTPLGTPA

TSPPPAPLCHSDDYVHISLPQATVTPPRKEERMDSARPCLHRQHHLLNDRGSEEPPGS

KGSVTLSDLPGFLGDLASEEDSIEKDKEEAAISRELSEITTAEAEPVVPRGGFDSPFY

RDSLPGSQRKTHSAASSSQGASVNPEPLHSSLDKLGPDTPKQAFTPIDLPCGSADESP

AGDRECQTSLETSIFTPSPCKIPPPTRVGFGSGQPPPYDHLFEVALPKTAHHFVIRKT

EELLKKAKGNTEEDGVPSTSPMEVLDRLIQQGADAHSKELNKLPLPSKSVDWTHFGGS

PPSDEIRTLRDQLLLLHNQLLYERFKRQQHALRNRRLLRKVIKAAALEEHNAAMKDQL

KLQEKDIQMWKVSLQKEQARYNQLQEQRDTMVTKLHSQIRQLQHDREEFYNQSQELQT

KLEDCRNMIAELRIELKKANNKVCHTELLLSQVSQKLSNSESVQQQMEFLNRQLLVLG

EVNELYLEQLQNKHSDTTKEVEMMKAAYRKELEKNRSHVLQQTQRLDTSQKRILELES

HLAKKDHLLLEQKKYLEDVKLQARGQLQAAESRYEAQKRITQVFELEILDLYGRLEKD

GLLKKLEEEKAEAAEAAEERLDCCNDGCSDSMVGHNEEASGHNGETKTPRPSSARGSS

GSRGGGGSSSSSSELSTPEKPPHQRAGPFSSRWETTMGEASASIPTTVGSLPSSKSFL

GMKARELFRNKSESQCDEDGMTSSLSESLKTELGKDLGVEAKIPLNLDGPHPSPPTPD

SVGQLHIMDYNETHHEHS

FIG. 3II

TSC2 DNA (NM_000548) SEQ ID NO: 35

```
   1 ccggcggcgt cccggggcca gggggtgcg cctttctccg cgtcggggcg gccccggagcg
  61 cggtggcgcg gcgcgggagg ggttttctgg tgcgtcctgg tccaccatgg ccaaaccaac
 121 aagcaaagat tcaggcttga aggagaagtt taagattctg ttgggactgg gaacaccgag
 181 gccaaatccc aggtctgcag agggtaaaca gacggagttt atcatcaccg cggaaatact
 241 gagagaactg agcatggaat gtggcctcaa caatcgcatc cggatgatag ggcagatttg
 301 tgaagtcgca aaaaccaaga aatttgaaga gcacgcagtg gaagcactct ggaaggcggt
 361 cgcggatctg ttgcagccgg agcggccgct ggaggcccgg cacgcggtgc tggctctgct
 421 gaaggccatc gtgcaggggc agggcgagcg tttgggggtc ctcagagccc tcttctttaa
 481 ggtcatcaag gattaccctt ccaacgaaga ccttcacgaa aggctggagg ttttcaaggc
 541 cctcacagac aatgggagac acatcaccta cttggaggaa gagctggctg actttgtcct
 601 gcagtggatg gatgttggct tgtcctcgga attccttctg gtgctggtga acttggtcaa
 661 attcaatagc tgttacctcg acgagtacat cgcaaggatg gttcagatga tctgtctgct
 721 gtgcgtccgg accgcgtcct ctgtggacat agaggtctcc ctgcaggtgc tggacgccgt
 781 ggtctgctac aactgcctgc cggctgagag cctcccgctg ttcatcgtta ccctctgtcg
 841 caccatcaac gtcaaggagc tctgcgagcc ttgctggaag ctgatgcgga acctccttgg
 901 cacccacctg ggccacagcg ccatctacaa catgtgccac ctcatggagg acagagccta
 961 catggaggac gcgcccctgc tgagaggagc cgtgtttttt gtgggcatgg ctctctgggg
1021 agcccaccgg ctctattctc tcaggaactc gccgacatct gtgttgccat cattttacca
1081 ggccatggca tgtccgaacg aggtggtgtc ctatgagatc gtcctgtcca tcaccaggct
1141 catcaagaag tataggaagg agctccaggt ggtggcgtgg gacattctgc tgaacatcat
1201 cgaacggctc cttcagcagc tccagacctt ggacagcccg gagctcagga ccatcgtcca
1261 tgacctgttg accacggtgg aggagctgtg tgaccagaac gagttccacg ggtctcagga
1321 gagatacttt gaactggtgg agagatgtgc ggaccagagg cctgagtcct ccctcctgaa
1381 cctgatctcc tatagagcgc agtccatcca cccggccaag gacggctgga ttcagaacct
1441 gcaggcgctg atggagagat tcttcaggag cgagtcccga ggcgccgtgc gcatcaaggt
1501 gctggacgtg ctgtcctttg tgctgctcat caacaggcag ttctatgagg aggagctgat
1561 taactcagtg gtcatctcgc agctctccca catccccgag gataaagacc accaggtccg
1621 aaagctggcc acccagttgc tggtggacct ggcagagggc tgccacacac accacttcaa
1681 cagcctgctg gacatcatcg agaaggtgat ggcccgctcc ctctccccac ccccggagct
1741 ggaagaaagg gatgtggccg catactcggc ctccttggag gatgtgaaga cagccgtcct
1801 ggggcttctg gtcatccttc agaccaagct gtacaccctg cctgcaagcc acgccacgcg
1861 tgtgtatgag atgctggtca gccacattca gctccactac aagcacagct acaccctgcc
1921 aatcgcgagc agcatccggc tgcaggcctt tgacttcctg ttgctgctgc gggccgactc
1981 actgcaccgc ctgggcctgc ccaacaagga tggagtcgtg cggttcagcc cctactgcgt
2041 ctgcgactac atggagccag agagaggctc tgagaagaag accagcggcc ccctttctcc
2101 tcccacaggg cctcctggcc cggcgcctgc aggccccgcc gtgcggctgg ggtccgtgcc
2161 ctactccctg ctcttccgcg tcctgctgca gtgcttgaag caggagtctg actggaaggt
2221 gctgaagctg gttctgggca ggctgcctga gtccctgcgc tataaagtgc tcatctttac
2281 ttccccttgc agtgtggacc agctgtgctc tgctctctgc tccatgcttt caggcccaaa
2341 gacactggag cggctccgag gcgccccaga aggcttctcc agaactgact tgcacctggc
2401 cgtggttcca gtgctgacag cattaatctc ttaccataac tacctggaca aaaccaaaca
2461 gcgcgagatg gtctactgcc tggagcaggg cctcatccac cgctgtgcca gccagtgcgt
2521 cgtggccttg tccatctgca gcgtggagat gcctgacatc atcatcaagg cgctgcctgt
2581 tctggtggtg aagctcacgc acatctcagc cacagccagc atggccgtcc cactgctgga
2641 gttcctgtcc actctggcca ggctgccgca cctctacagg aactttgccg cggagcagta
2701 tgccagtgtg ttcgccatct ccctgccgta caccaacccc tccaagttta atcagtacat
2761 cgtgtgtctg gcccatcacg tcatagccat gtggttcatc aggtgccgcc tgcccttccg
2821 gaaggatttt gtcccttca tcactaaggg cctgcggtcc aatgtcctct tgtcttttga
2881 tgacaccccc gagaaggaca gcttcagggc ccggagtact agtctcaacg agagacccaa
2941 gagtctgagg atagccagac cccccaaaca aggcttgaat aactctccac ccgtgaaaga
3001 attcaaggag agctctgcag ccgaggcctt ccggtgccgc agcatcagtg tgtctgaaca
```

FIG. 3II (cont.)

```
3061 tgtggtccgc agcaggatac agacgtccct caccagtgcc agcttggggt ctgcagatga
3121 gaactccgtg gcccaggctg acgatagcct gaaaaacctc cacctggagc tcacggaaac
3181 ctgtctggac atgatggctc gatacgtctt ctccaacttc acggctgtcc cgaagaggtc
3241 tcctgtgggc gagttcctcc tagcgggtgg caggaccaaa acctggctgg ttgggaacaa
3301 gcttgtcact gtgacgacaa gcgtgggaac cgggacccgg tcgttactag gcctggactc
3361 gggggagctg cagtccggcc cggagtcgag ctccagcccc ggggtgcatg tgagacagac
3421 caaggaggcg ccggccaagc tggagtccca ggctgggcag caggtgtccc gtggggcccg
3481 ggatcgggtc cgttccatgt cggggggcca tggtcttcga gttggcgccc tggacgtgcc
3541 ggcctcccag ttcctgggca gtgccacttc tccaggacca cggactgcac cagccgcgaa
3601 acctgagaag gcctcagctg gcacccgggt tcctgtgcag gagaagacga acctggcggc
3661 ctatgtgccc ctgctgaccc agggctgggc ggagatcctg gtccggaggc ccacagggaa
3721 caccagctgg ctgatgagcc tggagaaccc gctcagccct ttctcctcgg acatcaacaa
3781 catgcccctg caggagctgt ctaacgccct catggcggct gagcgcttca aggagcaccg
3841 ggacacagcc ctgtacaagt cactgtcggt gccggcagcc agcacggcca aacccccctcc
3901 tctgcctcgc tccaacacag tggcctcttt ctcctccctg taccagtcca gctgccaagg
3961 acagctgcac aggagcgttt cctgggcaga ctccgccgtg gtcatggagg agggaagtcc
4021 gggcgaggtt cctgtgctgg tggagccccc agggttggag gacgttgagg cagcgctagg
4081 catggacagg cgcacggatg cctacagcag gtcgtcctca gtctccagcc aggaggagaa
4141 gtcgctccac gcggaggagc tggttggcag gggcatcccc atcgagcgag tcgtctcctc
4201 ggagggtggc cggccctctg tggacctctc cttccagccc tcgcagcccc tgagcaagtc
4261 cagctcctct cccgagctgc agactctgca ggacatcctc ggggaccctg gggacaaggc
4321 cgacgtgggc cggctgagcc ctgaggttaa ggcccggtca cagtcaggga ccctggacgg
4381 ggaaagtgct gcctggtcgg cctcgggcga agacagtcgg ggccagcccg agggtccctt
4441 gccttccagc tccccccgct cgcccagtgg cctccggccc cgaggttaca ccatctccga
4501 ctcggcccca tcacgcaggg gcaagagagt agagagggac gccttaaaga gcagagccac
4561 agcctccaat gcagagaaag tgccaggcat caaccccagt ttcgtgttcc tgcagctcta
4621 ccattccccc ttctttggcg acgagtcaaa caagccaatc ctgctgccca atgagtcaca
4681 gtcctttgag cggtcggtgc agctcctcga ccagatccca tcatacgaca cccacaagat
4741 cgccgtcctg tatgttggag aaggccagag caacagcgag ctcgccatcc tgtccaatga
4801 gcatggctcc tacaggtaca cggagttcct gacgggcctg ggccggctca tcgagctgaa
4861 ggactgccag ccggacaagg tgtacctggg aggcctggac gtgtgtggtg aggacggcca
4921 gttcacctac tgctggcacg atgacatcat gcaagccgtc ttccacatcg ccaccctgat
4981 gcccaccaag gacgtggaca agcaccgctg cgacaagaag cgccacctgg gcaacgactt
5041 tgtgtccatt gtctacaatg actccggtga ggacttcaag cttggcacca tcaagggcca
5101 gttcaacttt gtccacgtga tcgtcacccc gctggactac gagtgcaacc tggtgtccct
5161 gcagtgcagg aaagacatgg agggccttgt ggacaccagc gtggccaaga tcgtgtctga
5221 ccgcaacctg cccttcgtgg cccgccagat ggccctgcac gcaaatatgg cctcacaggt
5281 gcatcatagc cgctccaacc ccaccgatat ctacccctcc aagtggattg cccggctccg
5341 ccacatcaag cggctccgcc agcggatctg cgaggaagcc gcctactcca accccagcct
5401 acctctggtg caccctccgt cccatagcaa agcccctgca cagactccag ccgagcccac
5461 acctggctat gaggtgggcc agcggaagcg cctcatctcc tcggtggagg acttcaccga
5521 gtttgtgtga ggccggggcc ctccctcctg cactggcctt ggacggtatt gcctgtcagt
5581 gaaataaata aagtcctgac cccagtgcac agacatagag gcacagattg caaaaaaaaa
5641 aaaaaaaaaa aaaaaaaaaa aaaaaaaaaa aaaaa
```

FIG. 3JJ

TSC2 Protein SEQ ID NO: 36

MAKPTSKDSGLKEKFKILLGLGTPRPNPRSAEGKQTEFIITAEI

LRELSMECGLNNRIRMIGQICEVAKTKKFEEHAVEALWKAVADLLQPERPLEARHAVL

ALLKAIVQGQGERLGVLRALFFKVIKDYPSNEDLHERLEVFKALTDNGRHITYLEEEL

ADFVLQWMDVGLSSEFLLVLVNLVKFNSCYLDEYIARMVQMICLLCVRTASSVDIEVS

LQVLDAVVCYNCLPAESLPLFIVTLCRTINVKELCEPCWKLMRNLLGTHLGHSAIYNM

CHLMEDRAYMEDAPLLRGAVFFVGMALWGAHRLYSLRNSPTSVLPSFYQAMACPNEVV

SYEIVLSITRLIKKYRKELQVVAWDILLNIIERLLQQLQTLDSPELRTIVHDLLTTVE

ELCDQNEFHGSQERYFELVERCADQRPESSLLNLISYRAQSIHPAKDGWIQNLQALME

RFFRSESRGAVRIKVLDVLSFVLLINRQFYEEELINSVVISQLSHIPEDKDHQVRKLA

TQLLVDLAEGCHTHHFNSLLDIIEKVMARSLSPPPELEERDVAAYSASLEDVKTAVLG

LLVILQTKLYTLPASHATRVYEMLVSHIQLHYKHSYTLPIASSIRLQAFDFLLLLRAD

SLHRLGLPNKDGVVRFSPYCVCDYMEPERGSEKKTSGPLSPPTGPPGPAPAGPAVRLG

SVPYSLLFRVLLQCLKQESDWKVLKLVLGRLPESLRYKVLIFTSPCSVDQLCSALCSM

LSGPKTLERLRGAPEGFSRTDLHLAVVPVLTALISYHNYLDKTKQREMVYCLEQGLIH

RCASQCVVALSICSVEMPDIIIKALPVLVVKLTHISATASMAVPLLEFLSTLARLPHL

YRNFAAEQYASVFAISLPYTNPSKFNQYIVCLAHHVIAMWFIRCRLPFRKDFVPFITK

GLRSNVLLSFDDTPEKDSFRARSTSLNERPKSLRIARPPKQGLNNSPPVKEFKESSAA

EAFRCRSISVSEHVVRSRIQTSLTSASLGSADENSVAQADDSLKNLHLELTETCLDMM

ARYVFSNFTAVPKRSPVGEFLLAGGRTKTWLVGNKLVTVTTSVGTGTRSLLGLDSGEL

QSGPESSSSPGVHVRQTKEAPAKLESQAGQQVSRGARDRVRSMSGGHGLRVGALDVPA

SQFLGSATSPGPRTAPAAKPEKASAGTRVPVQEKTNLAAYVPLLTQGWAEILVRRPTG

NTSWLMSLENPLSPFSSDINNMPLQELSNALMAAERFKEHRDTALYKSLSVPAASTAK

PPPLPRSNTVASFSSLYQSSCQGQLHRSVSWADSAVVMEEGSPGEVPVLVEPPGLEDV

EAALGMDRRTDAYSRSSSVSSQEEKSLHAEELVGRGIPIERVVSSEGGRPSVDLSFQP

SQPLSKSSSSPELQTLQDILGDPGDKADVGRLSPEVKARSQSGTLDGESAAWSASGED

SRGQPEGPLPSSSPRSPSGLRPRGYTISDSAPSRRGKRVERDALKSRATASNAEKVPG

FIG. 3JJ (cont.)

INPSFVFLQLYHSPFFGDESNKPILLPNESQSFERSVQLLDQIPSYDTHKIAVLYVGE

GQSNSELAILSNEHGSYRYTEFLTGLGRLIELKDCQPDKVYLGGLDVCGEDGQFTYCW

HDDIMQAVFHIATLMPTKDVDKHRCDKKRHLGNDFVSIVYNDSGEDFKLGTIKGQFNF

VHVIVTPLDYECNLVSLQCRKDMEGLVDTSVAKIVSDRNLPFVARQMALHANMASQVH

HSRSNPTDIYPSKWIARLRHIKRLRQRICEEAAYSNPSLPLVHPPSHSKAPAQTPAEP

TPGYEVGQRKRLISSVEDFTEFV

FIG. 3KK

UBE3A DNA (NM_130839) SEQ ID NO: 37

```
   1 ccaagatggt ggcgctgggc tcggggtgac tacaggagac gacggggcct tttcccttcg
  61 ccaggacccg acacaccagg cttcgctcgc tcgcgcaccc ctccgccgcg tagccatccg
 121 ccagcgcggg cgcccgccat ccgccgccta cttacgcttc acctctgccg acccggcgcg
 181 ctcggctgcg ggcggcggcg cctccttcgg ctcctcctcg gaatagctcg cggcctgtag
 241 cccctggcag gagggcccct cagccccccg gtgtggacag gcagcggcgg ctggcgacga
 301 acgccgggat ttcggcggcc ccggcgctcc ctttcccggc ctcgttttcc ggataaggaa
 361 gcgcgggtcc cgcatgagcc ccggcggtgg cggcagcgaa agagaacgag gcggtggcgg
 421 gcggaggcgg cgggcgaggg cgactacgac cagtgaggcg gccgccgcag cccaggcgcg
 481 ggggcgacga caggttaaaa atctgtaaga gcctgatttt agaattcacc agctcctcag
 541 aagtttggcg aaatatgagt tattaagcct acgctcagat caaggtagca gctagactgg
 601 tgtgacaacc tgtttttaat cagtgactca aagctgtgat caccctgatg tcaccgaatg
 661 gccacagctt gtaaaagatc aggagaacct cagtctgacg acattgaagc tagccgaatg
 721 aagcgagcag ctgcaaagca tctaatagaa cgctactacc accagttaac tgagggctgt
 781 ggaaatgaag cctgcacgaa tgagttttgt gcttcctgtc caacttttct tcgtatggat
 841 aataatgcag cagctattaa agccctcgag ctttataaga ttaatgcaaa actctgtgat
 901 cctcatccct ccaagaaagg agcaagctca gcttaccttg agaactcgaa aggtgccccc
 961 aacaactcct gctctgagat aaaaatgaac aagaaaggcg ctagaattga ttttaaagat
1021 gtgacttact taacagaaga gaaggtatat gaaattcttg aattatgtag agaaagagag
1081 gattattccc ctttaatccg tgttattgga agagtttttt ctagtgctga ggcattggta
1141 cagagcttcc ggaaagttaa acaacacacc aaggaagaac tgaaatctct tcaagcaaaa
1201 gatgaagaca aagatgaaga tgaaaaggaa aaagctgcat gttctgctgc tgctatggaa
1261 gaagactcag aagcatcttc ctcaaggata ggtgatagct cacagggaga caacaatttg
1321 caaaaattag gccctgatga tgtgtctgtg gatattgatg ccattagaag ggtctacacc
1381 agattgctct ctaatgaaaa aattgaaact gcctttctca atgcacttgt atatttgtca
1441 cctaacgtgg aatgtgactt gacgtatcac aatgtatact ctcgagatcc taattatctg
1501 aatttgttca ttatcgtaat ggagaataga aatctccaca gtcctgaata tctggaaatg
1561 gctttgccat tattttgcaa agcgatgagc aagctacccc ttgcagccca aggaaaactg
1621 atcagactgt ggtctaaata caatgcagac cagattcgga gaatgatgga gacatttcag
1681 caacttatta cttataaagt cataagcaat gaatttaaca gtcgaaatct agtgaatgat
1741 gatgatgcca ttgttgctgc ttcgaagtgc ttgaaaatgg tttactatgc aaatgtagtg
1801 ggaggggaag tggacacaaa tcacaatgaa gaagatgatg aagagcccat ccctgagtcc
1861 agcgagctga cacttcagga acttttggga gaagaaagaa gaaacaagaa aggtcctcga
1921 gtggaccccc tggaaactga acttggtgtt aaaaccctgg attgtcgaaa accacttatc
1981 ccttttgaag agtttattaa tgaaccactg aatgaggttc tagaaatgga taaagattat
2041 actttttca aagtagaaac agagaacaaa ttctctttta tgacatgtcc ctttatattg
2101 aatgctgtca caaagaattt gggattatat tatgacaata gaattcgcat gtacagtgaa
2161 cgaagaatca ctgttctcta cagcttagtt caaggacagc agttgaatcc atatttgaga
2221 ctcaaagtta gacgtgacca tatcatagat gatgcacttg tccggctaga gatgatcgct
2281 atggaaaatc ctgcagactt gaagaagcag ttgtatgtgg aatttgaagg agaacaagga
2341 gttgatgagg gaggtgtttc caaagaattt tttcagctgg ttgtggagga aatcttcaat
2401 ccagatattg gtatgttcac atacgatgaa tctacaaaat tgttttggtt taatccatct
2461 tcttttgaaa ctgagggtca gtttactctg attggcatag tactgggtct ggctatttac
2521 aataactgta tactggatgt acattttccc atggttgtct acaggaagct aatggggaaa
2581 aaaggaactt ttcgtgactt gggagactct cacccagttc tatatcagag tttaaaagat
2641 ttattggagt atgaagggaa tgtggaagat gacatgatga tcactttcca gatatcacag
2701 acagatcttt ttggtaaccc aatgatgtat gatctaaagg aaaatggtga taaaattcca
2761 attacaaatg aaaacaggaa ggaatttgtc aatctttatt ctgactacat tctcaataaa
2821 tcagtagaaa aacagttcaa ggcttttcgg agaggttttc atatggtgac caatgaatct
2881 cccttaaagt acttattcag accagaagaa attgaattgc ttatatgtgg aagccggaat
2941 ctagatttcc aagcactaga agaaactaca gaatatgacg gtggctatac cagggactct
3001 gttctgatta gggagttctg ggaaatcgtt cattcattta cagatgaaca gaaaagactc
```

FIG. 3KK (cont.)

```
3061 ttcttgcagt ttacaacggg cacagacaga gcacctgtgg gaggactagg aaaattaaag
3121 atgattatag ccaaaaatgg cccagacaca gaaaggttac ctacatctca tacttgcttt
3181 aatgtgcttt tacttccgga atactcaagc aaagaaaaac ttaaagagag attgttgaag
3241 gccatcacgt atgccaaagg atttggcatg ctgtaaaaca aaacaaaaca aaataaaaca
3301 aaaaaaagga aggaaaaaaa aagaaaaaat ttaaaaaatt ttaaaaatat aacgagggat
3361 aaatttttgg tggtgatagt gtcccagtac aaaaaggctg taagatagtc aaccacagta
3421 gtcacctatg tctgtgcctc ccttctttat tggggacatg tgggctggaa cagcagattt
3481 cagctacata tatgaacaaa tcctttatta ttattataat tatttttttg cgtgaaagtg
3541 ttacatattc tttcacttgt atgtacagag aggtttttct gaatatttat tttaagggtt
3601 aaatcacttt tgcttgtgtt tattactgct tgaggttgag ccttttgagt atttaaaaaa
3661 tatataccaa cagaactact ctcccaagga aaatattgcc accatttgta gaccacgtaa
3721 ccttcaagta tgtgctactt ttttgtccct gtatctaact caaatcagga actgtatttt
3781 ttttaatgat ttgcttttga aacttgaagt cttgaaaaca gtgtgatgca attactgctg
3841 ttctagcccc caaagagttt tctgtgcaaa atcttgagaa tcaatcaata aagaaagatg
3901 gaaggaaggg agaaattgga atgttttaac tgcagccctc agaactttag taacagcaca
3961 acaaattaaa aacaaaaaca actcatgcca cagtatgtcg tcttcatgtg tcttgcaatg
4021 aactgtttca gtagccaatc ctctttctta gtatatgaaa ggacagggat ttttgttctt
4081 gttgttctcg ttgttgtttt aagtttactg gggaaagtgc atttggccaa atgaaatggt
4141 agtcaagcct attgcaacaa agttaggaag tttgttgttt gtttattata aacaaaaagc
4201 atgtgaaagt gcacttaaga tagagttttt attaattact tacttattac ctagatttta
4261 aatagacaat ccaaagtctc cccttcgtgt tgccatcatc ttgttgaatc agccatttta
4321 tcgaggcacg tgatcagtgt tgcaacataa tgaaaaagat ggctactgtg ccttgtgtta
4381 cttaatcata cagtaagctg acctggaaat gaatgaaact attactccta agaattacat
4441 tgtatagccc cacagattaa atttaattaa ttaattcaaa acatgttaaa cgttactttc
4501 atgtactatg gaaaagtaca agtaggttta cattactgat ttccagaagt aagtagtttc
4561 ccctttccta gtcttctgtg tatgtgatgt tgttaatttc ttttattgca ttataaaata
4621 aaaggattat gtatttttaa ctaaggtgag acattgatat atccttttgc tacaagctat
4681 agctaatgtg ctgagcttgt gccttggtga ttgattgatt gattgactga ttgttttaac
4741 tgattactgt agatcaacct gatgatttgt ttgtttgaaa ttggcaggaa aaatgcagct
4801 ttcaaatcat tgggggggaga aaaaggatgt ctttcaggat tattttaatt aatttttttc
4861 ataattgaga cagaactgtt tgttatgtac cataatgcta aataaaactg tggcactttt
4921 caccataatt taatttagtg gaaaaagaag acaatgcttt ccatattgtg ataaggtaac
4981 atggggtttt tctgggccag cctttagaac actgttaggg tacatacgct accttgatga
5041 aagggacctt cgtgcaactg tagtcatctt aaaggcttct catccactgt gcttcttaat
5101 gtgtaattaa agtgaggaga aattaaatac tctgagggcg ttttatataa taaattcgtg
5161 aaga
```

FIG. 3LL

UBE3A Protein SEQ ID NO: 38

MATACKRSGEPQSDDIEASRMKRAAAKHLIERYYHQLTEGCGNE

ACTNEFCASCPTFLRMDNNAAAIKALELYKINAKLCDPHPSKKGASSAYLENSKGAPN

NSCSEIKMNKKGARIDFKDVTYLTEEKVYEILELCREREDYSPLIRVIGRVFSSAEAL

VQSFRKVKQHTKEELKSLQAKDEDKDEDEKEKAACSAAAMEEDSEASSSRIGDSSQGD

NNLQKLGPDDVSVDIDAIRRVYTRLLSNEKIETAFLNALVYLSPNVECDLTYHNVYSR

DPNYLNLFIIVMENRNLHSPEYLEMALPLFCKAMSKLPLAAQGKLIRLWSKYNADQIR

RMMETFQQLITYKVISNEFNSRNLVNDDDAIVAASKCLKMVYYANVVGGEVDTNHNEE

DDEEPIPESSELTLQELLGEERRNKKGPRVDPLETELGVKTLDCRKPLIPFEEFINEP

LNEVLEMDKDYTFFKVETENKFSFMTCPFILNAVTKNLGLYYDNRIRMYSERRITVLY

SLVQGQQLNPYLRLKVRRDHIIDDALVRLEMIAMENPADLKKQLYVEFEGEQGVDEGG

VSKEFFQLVVEEIFNPDIGMFTYDESTKLFWFNPSSFETEGQFTLIGIVLGLAIYNNC

ILDVHFPMVVYRKLMGKKGTFRDLGDSHPVLYQSLKDLLEYEGNVEDDMMITFQISQT

DLFGNPMMYDLKENGDKIPITNENRKEFVNLYSDYILNKSVEKQFKAFRRGFHMVTNE

SPLKYLFRPEEIELLICGSRNLDFQALEETTEYDGGYTRDSVLIREFWEIVHSFTDEQ

KRLFLQFTTGTDRAPVGGLGKLKMIIAKNGPDTERLPTSHTCFNVLLLPEYSSKEKLK

ERLLKAITYAKGFGML

| Gene | SEQ ID NO: | Exon | Chromosomal coordinates (hg18) | Exonic sequences plus 30 bases of "padding" (intronic or UTR) on either side |
|---|---|---|---|---|
| RAF1 | 39 | 2 | chr3:12634984-12635250 | CCAGGTTTAAGAATTGTTTAAGCTGCATCAATGGAGCACATACAGGGAGCTTGGAAGACGATCAGCAATGGTTTTGGATTCAAAGATGCCGTGTTTGATGGCTCCAGCTGCATCTCTCCTACAATAGTTCAGCAGTTTGGCTATCAGCGCCGGGCATCAGATGATGGCAAACTCACAGATCCTTCTAAGACAAGCAACACTATCCGTGTTTTCTTGCCGAACAAGCAAAGAACAGTGGTATGTGAACATTCTACTTAGGAAATTTAG |
| RAF1 | 40 | 3 | chr3:12628419-12628591 | TTGGTCCTAAAGGTGGTCCTTTGTTTGTAGGTCAATGTGCGAAATGGAATGAGCTTGCATGACTGCCTTATGAAAGCACTCAAGGTGAGGGGCCTGCAACCAGAGTGCTGTGCAGTGTTCAGACTTCTCCACGAACACAAAGGGTAAGAGCTCAAAAGTCAATTGACTTCTTC |
| RAF1 | 41 | 4 | chr3:12625702-12625864 | CATTTCATGTTTTTTTTAAATCCTTTCTAGTAAAAAAGCACGCTTAGATTGGAATACTGATGCTGCGTCTTTGATTGGAGAAGAACTTCAAGTAGATTTCCTGGATCATGTTCCCCTCACAACACACAACTTTGTAAGTTGCAGATCTCTTCTCTTTCTGGCA |
| RAF1 | 42 | 5 | chr3:12625235-12625452 | GCATAATTTACACCTGTGTTCTTGTTGTAGGCTCGGAAGACGTTCCTGAAGCTTGCCTTCTGTGACATCTGTCAGAAATTCCTGCTCAATGGATTTCGATGTCAGACTTGTGGCTACAAATTTCATGAGCACTGTAGCACCAAAGTACCTACTATGTGTGTGGACTGGAGTAACATCAGACAACTCTTGTAAGGCATTGTTCTTTTATCCAAGGAAGA |
| RAF1 | 43 | 6 | chr3:12622670-12622828 | AAAAACCAGTCTTTCCCTGCTTTTGTTTAGATTGTTTCCAAATTCCACTATTGGTGATAGTGGAGTCCCAGCACTACCTTCTTTGACTATGCGTCGTATGCGAGAGTCTGTTTCCAGGATGCCTGTTAGGTAATTTTTTACCTATAGCTTTTCTTTTAG |
| RAF1 | 44 | 7 | chr3:12620605-12620818 | CCAATCATGGAATTTTCTTTCTCCTCCTAGTTCTCAGCACAGATATTCTACACCTCACGCCTTCACCTTTAACACCTCCAGTCCCTCATCTGAAGGTTCCCTCTCCCAGAGGCAGAGGTCGACATCCACACCTAATGTCCACATGGTCAGCACCACCCTGCCTGTGGACAGCAGGATGATTGAGGTAATAGGGCACCTTGGGGGTGGTAATGTC |
| RAF1 | 45 | 8 | chr3:12616857-12616944 | GAGTTGACCAGCTTTCCTTTTCTGTTTCAGGATGCAATTCGAAGTCACAGCGAATCAGGTACTTTTCCATAGTCATTTAGCCAACAAT |
| RAF1 | 46 | 9 | chr3:12616621-12616808 | GTGTGGCTTCTGTTTGTCTTGTCTATTAAGCCTCACCTTCAGCCCTGTCCAGTAGCCCCAACAATCTGAGCCCAACAGGCTGGTCACAGCCGAAAACCCCCGTGCCAGCACAAAGAGAGCGGGCACCAGTATCTGGGACCCAGGAGAAAAACAAAATTGTGAGTATAGACAACAGTACCTCCTGCCAA |
| RAF1 | 47 | 10 | chr3:12616160-12616337 | GAGTATAATAATGATCTCTACTTGTTTCAGAGGCCTCGTGGACAGAGAGATTCAAGCTATTATTGGGAAATAGAAGCCAGTGAAGTGATGCTGTCCACTCGGATTGGGTCAGGCTCTTTTGGAACTGTTTATAAGGGTAAATGGCACGGTAAGCTTGGGGCCCTCCCTTTACTAACTG |
| RAF1 | 48 | 11 | chr3:12608177-12608321 | GATTGCACTGACTGCCAACTAATTTTGCAGGAGATGTTGCAGTAAAGATCCTAAAGGTTGTCGACCCAACCCCAGAGCAATTCCAGGCCTTCAGGAATGAGGTGGCTGTTCTGCGGTGAGTAGAAAGCTGGCGGTCCAGTCCCTC |

FIG. 4

| | | | | |
|---|---|---|---|---|
| RAF1 | 49 | 12 | chr3:12607267-12607503 | CCCTCTCCTCTCTTCCCCTCCCCTCCCCAGCAAAACACGGCATGTGAACATTCTGCTTTTCATGGGGTACAT GACAAAGGACAACCTGGCAATTGTGACCCAGTGGTGCGAGGGCAGCAGCCTCTACAAACACCTGCATGT CCAGGAGACCAAGTTTCAGATGTTCCAGCTAATTGACATTGCCCGGCAGACGGCTCAGGGAATGGAGTG AGTAGATGGTCTGATGCCTCTCTGGGA |
| RAF1 | 50 | 13 | chr3:12604060-12604166 | TATTTTTAATAATTTCTTTTCCCTTCACAGCTATTTGCATGCAAAGAACATCATCCATAGAGACATGAAATC CAACAGTATCCTTTGGTTGTTGAGTTCATTTGACT |
| RAF1 | 51 | 14 | chr3:12602150-12602328 | TTGAAACCAGAGTCCTTAACAAGCATTGAGATATATTTCTCCATGAAGGCTTAACAGTGAAAATTGGAGA TTTTGGTTTGGCAACAGTAAAGTCACGCTGGAGTGGTTCTCAGCAGGTTGAACAACCTACTGGCTCTGTC CTCTGGATGGTGAGAATCTGGGCTCCCACCAGCAGTCTC |
| RAF1 | 52 | 15 | chr3:12601591-12601782 | TGCACTTTTGTCATATGGTGATACATGTAGGCCCCAGAGGTGATCCGAATGCAGGATAACAACCCATTCA GTTTCCAGTCGGATGTCTACTCCTATGGCATCGTATTGTATGAACTGATGACGGGGGAGCTTCCTTATTCT CACATCAACAACCGAGATCAGGTAAGTCTGTGCTGGTGCGAAAGGACCCAA |
| RAF1 | 53 | 16 | chr3:12601316-12601510 | CCATTAGCTCAGCTGTTTTCTTTCCCTTAGATCATCTTCATGGTGGGCCGAGGATATGCCTCCCCAGATCTT AGTAAGCTATATAAGAACTGCCCCAAAGCAATGAAGAGGCTGGTAGCTGACTGTGTGAAGAAAGTAAA GGAAGAGAGGCCTCTTTTTCCCCAGGTAAGGCTCAGGGCTGCTAGAATGTGATTA |
| RAF1 | 54 | 17 | chr3:12600983-12601186 | TAATGAGAGCATTCTTGGGCTTTGTTTCAGATCCTGTCTTCCATTGAGCTGCTCCAACACTCTCTACCGAA GATCAACCGGAGCGCTTCCGAGCCATCCTTGCATCGGGCAGCCCACACTGAGGATATCAATGCTTGCACG CTGACCACGTCCCCGAGGCTGCCTGTCTTCTAGTTGACTTTGCACCTGTCTTCAGGCTGCCAG |
| PIK3CA | 55 | 2 | chr3:180399278-180399689 | TATATGTAAAACTTGCAAAGAATCAGAACAATGCCTCCACGACCATCATCAGGTGAACTGTGGGGCATCC ACTTGATGCCCCCAAGAATCCTAGTAGAATGTTTACTACCAAATGGAATGATAGTGACTTTAGAATGCCT CCGTGAGGCTACATTAATAACCATAAAGCATGAACTATTTAAAGAAGCAAGAAAATACCCCCTCCATCAA CTTCTTCAAGATGAATCTTCTTACATTTTCGTAAGTGTTACTCAAGAAGCAGAAAGGGAAGAATTTTTTGA TGAAACAAGACGACTTTGTGACCTTCGGCTTTTTCAACCCTTTTTAAAAGTAATTGAACCAGTAGGCAACC GTGAAGAAAAGATCCTCAATCGAGAAATTGGTATGATACAATATCCTATTCTAAAATGCA |
| PIK3CA | 56 | 3 | chr3:180400142-180400411 | TGTTATATTCTTTATGTAATTTTATTAAAGGTTTTGCTATCGGCATGCCAGTGTGTGAATTTGATATGGTTA AAGATCCAGAAGTACAGGACTTCCGAAGAAATATTCTGAACGTTTGTAAAGAAGCTGTGGATCTTAGGG ACCTCAATTCACCTCATAGTAGAGCAATGTATGTCTATCCTCCAAATGTAGAATCTTCACCAGAATTGCCA AAGCACATATATAATAAATTAGATAAAGGTAAGAAAATGACTAATCTACTCTAATCAT |
| PIK3CA | 57 | 4 | chr3:180401742-180402052 | GTGATTGCATCTAATGTTTTCCTGTTATAGGGCAAATAATAGTGGTGATCTGGGTAATAGTTTCTCCAAAT AATGACAAGCAGAAGTATACTCTGAAAATCAACCATGACTGTGTACCAGAACAAGTAATTGCTGAAGCA ATCAGGAAAAAAACTCGAAGTATGTTGCTATCCTCTGAACAACTAAAACTCTGTGTTTTAGAATATCAGG GCAAGTATATTTTAAAAGTGTGTGGATGTGATGAATACTTCCTAGAAAAATATCCTCTGAGTCAGTATAA GGTGAGTAACAAGTTTCAAAATATTAATTTT |

FIG. 4 cont.

| | | | | |
|---|---|---|---|---|
| PIK3CA | 58 | 5 | chr3:180403996-180404301 | GAAATGGCTCGCCCCCTTAATCTCTTACAGTATATAAGAAGCTGTATAATGCTTGGGAGGATGCCCAATT<br>TGATGTTGATGGCTAAAGAAAGCCTTTATTCTCAACTGCCAATGGACTGTTTTACAATGCCATCTTATTCC<br>AGACGCATTTCCACAGCTACACCATATATGAATGGAGAAACATCTACAAAATCCCTTTGGGTTATAAATA<br>GTGCACTCAGAATAAAAATTCTTTGTGCAACCTACGTGAATGTAAATATTCGAGACATTGATAAGGTAAA<br>GTCAAATGCTGATGCTTATTATTTT |
| PIK3CA | 59 | 6 | chr3:180404955-180405100 | CATTAGTATATACCTACTTTTTTCTTTTAGATCTATGTTCGAACAGGTATCTACCATGGAGGAGAACCCTTA<br>TGTGACAATGTGAACACTCAAAGAGTACCTTGTTCCAATCCCAGGTAAGGAAGTATATAGATTTATATTTC<br>CAA |
| PIK3CA | 60 | 7 | chr3:180410047-180410212 | GTATTATTTTTGCTTTAAAATTTTACATAGGTGGAATGAATGGCTGAATTATGATATATACATTCCTGATCT<br>TCCTCGTGCTGCTCGACTTTGCCTTTCCATTTGCTCTGTTAAAGGCCGAAAGGGTGCTAAAGAGGTAAAG<br>TATTTCAGAAGGAACAATTATGTT |
| PIK3CA | 61 | 8 | chr3:180410638-180410850 | ACTAGTGAATATTTTTCTTTGTTTTTTAAGGAACACTGTCCATTGGCATGGGGAAATATAAACTTGTTTGA<br>TTACACAGACACTCTAGTATCTGGAAAAATGGCTTTGAATCTTTGGCCAGTACCTCATGGATTAGAAGATT<br>TGCTGAACCCTATTGGTGTTACTGGATCAAATCCAAATAAAGTAAGGTTTTTATTGTCATAAATTAGATAT |
| PIK3CA | 62 | 9 | chr3:180410883-180411077 | ATATATAATAGCTTTTCTTCCATCTCTTAGGAAACTCCATGCTTAGAGTTGGAGTTTGACTGGTTCAGCAG<br>TGTGGTAAAGTTCCCAGATATGTCAGTGATTGAAGAGCATGCCAATTGGTCTGTATCCCGAGAAGCAGG<br>ATTTAGCTATTCCCACGCAGGACTGGTAAGGCAAATCACTGAGTTTATTAAGTAT |
| PIK3CA | 63 | 10 | chr3:180418662-180418846 | AGCTATATAAGATATTATTTTATTTTACAGAGTAACAGACTAGCTAGAGACAATGAATTAAGGGAAAATG<br>ACAAAGAACAGCTCAAAGCAATTTCTACACGAGATCCTCTCTCTGAAATCACTGAGCAGGAGAAAGATTT<br>TCTATGGAGTCACAGGTAAGTGCTAAAATGGAGATTCTCTGTTTC |
| PIK3CA | 64 | 11 | chr3:180419648-180419789 | GTTTATGTTTATTTTGTTTCTCCCACACAGACACTATTGTGTAACTATCCCCGAAATTCTACCCAAATTGCTT<br>CTGTCTGTTAAATGGAATTCTAGAGATGAAGTAGCCCAGGTAAATGTATGTTTGAGATTACTAGATAAC |
| PIK3CA | 65 | 12 | chr3:180420023-180420247 | AATATGATTTATTGTCTTTCTCATACACAGATGTATTGCTTGGTAAAAGATTGGCCTCCAATCAAACCTGA<br>ACAGGCTATGGAACTTCTGGACTGTAATTACCCAGATCCTATGGTTCGAGGTTTTGCTGTTCGGTGCTTG<br>GAAAAATATTTAACAGATGACAAACTTTCTCAGTATTTAATTCAGCTAGTACAGGTAAAATAATGTAAAAT<br>AGTAAATAATGTT |
| PIK3CA | 66 | 13 | chr3:180420401-180420564 | ACCCTGATTTGTTTTTTTGGAATCACCTAGGTCCTAAAATATGAACAATATTTGGATAACTTGCTTGTGAG<br>ATTTTTACTGAAGAAAGCATTGACTAATCAAAGGATTGGGCACTTTTTCTTTTGGCATTTAAAGTAAGTCT<br>AATTATTTTCCCATTAAATTCT |

FIG. 4 cont.

| | | | | |
|---|---|---|---|---|
| PIK3CA | 67 | 14 | chr3:180421438-180421669 | TATATTTTTAATTTTGCACGATTCTTTTAGATCTGAGATGCACAATAAAACAGTTAGCCAGAGGTTTGGCC<br>TGCTTTTGGAGTCCTATTGTCGTGCATGTGGGATGTATTTGAAGCACCTGAATAGGCAAGTCGAGGCAAT<br>GGAAAAGCTCATTAACTTAACTGACATTCTCAAACAGGAGAAGAAGGATGAAACACAAAAGGTGTGTGA<br>CTCTAGTTTGTGTTTGAGACTC |
| PIK3CA | 68 | 15 | chr3:180424533-180424699 | TTACTGTGACTATCCTTTTTTTTTAATCAGGTACAGATGAAGTTTTTAGTTGAGCAAATGAGGCGACCAGA<br>TTTCATGGATGCTCTACAGGGCTTTCTGTCTCCTCTAAACCCTGCTCATCAACTAGGAAACCTCAGGTACTT<br>TCTTGGGGGTTTCATTGATATATT |
| PIK3CA | 69 | 16 | chr3:180425152-180425333 | TACCTAGTAAAGTTTTTAACTATTTTAAAGGCTTGAAGAGTGTCGAATTATGTCCTCTGCAAAAAGGCCAC<br>TGTGGTTGAATTGGGAGAACCCAGACATCATGTCAGAGTTACTGTTTCAGAACAATGAGATCATCTTTAA<br>AAATGGGGATGGTAAGGAAGAGTATTAATGAGCTTATGATG |
| PIK3CA | 70 | 17 | chr3:180426414-180426552 | AAATGGTGATACATATTATTTGAATTTCAGATTTACGGCAAGATATGCTAACACTTCAAATTATTCGTATT<br>ATGGAAAATATCTGGCAAAATCAAGGTCTTGATCTTCGGTAGGTAACCAGTAAGGCAACCTGTATGTT |
| PIK3CA | 71 | 18 | chr3:180429724-180429954 | TTAATTGTAAACGTGTTACTCCTCTTTCAGAATGTTACCTTATGGTTGTCTGTCAATCGGTGACTGTGTGG<br>GACTTATTGAGGTGGTGCGAAATTCTCACACTATTATGCAAATTCAGTGCAAAGGCGGCTTGAAAGGTGC<br>ACTGCAGTTCAACAGCCACACACTACATCAGTGGCTCAAAGACAAGAACAAAGGAGAAATGTGAGTTGT<br>ATTATTCTTTCTTCCTATGTT |
| PIK3CA | 72 | 19 | chr3:180430456-180430633 | TACTACTCATGAGGTGTTTATTCTTTGTAGATATGATGCAGCCATTGACCTGTTTACACGTTCATGTGCTG<br>GATACTGTGTAGCTACCTTCATTTTGGGAATTGGAGATCGTCACAATAGTAACATCATGGTGAAAGACGA<br>TGGACAAGTAATGGTTTTCTCTGTTTAAAATGTTTTG |
| PIK3CA | 73 | 20 | chr3:180430677-180430888 | AACTATAACATAATTTCTTATTTTTGAAAGCTGTTTCATATAGATTTTGGACACTTTTTGGATCACAAGAAG<br>AAAAAATTTGGTTATAAACGAGAACGTGTGCCATTTGTTTTGACACAGGATTTCTTAATAGTGATTAGTAA<br>AGGAGCCCAAGAATGCACAAAGACAAGAGAATTTGAGAGGTGAGCTCGAGCAATTAAAAACACAAAAT<br>A |
| PIK3CA | 74 | 21 | chr3:180434546-180434876 | AACTGACCAAACTGTTCTTATTACTTATAGGTTTCAGGAGATGTGTTACAAGGCTTATCTAGCTATTCGAC<br>AGCATGCCAATCTCTTCATAAATCTTTTCTCAATGATGCTTGGCTCTGGAATGCCAGAACTACAATCTTTTG<br>ATGACATTGCATACATTCGAAAGACCCTAGCCTTAGATAAAACTGAGCAAGAGGCTTTGGAGTATTTCAT<br>GAAACAAATGAATGATGCACATCATGGTGGCTGGACAACAAAAATGGATTGGATCTTCCACACAATTAA<br>ACAGCATGCATTGAACTGAAAAGATAACTGAGAAAATGAAAGCTCACTC |
| EIF4E | 75 | 1 | chr4:100069239-100069316 | GGAGCGGTTGTGCGATCAGATCGATCTAAGATGGCGACTGTCGAACCGGTGAGTATTGCCTTTGGCCCC<br>CACCCCCAC |
| EIF4E | 76 | 2 | chr4:100042020-100042186 | AAAATAATGTTTTATATTATTTTCCACTAGGAAACCACCCCTACTCCTAATCCCCCGACTACAGAAGAGGA<br>GAAAACGGAATCTAATCAGGAGGTTGCTAACCCAGAACACTATATTAAACATCCCCTACAGAACAGGTA<br>AGCTTTCTAACACCTAGGTTTTCTGAG |

FIG. 4 cont.

| | | | | |
|---|---|---|---|---|
| EIF4E | 77 | 3 | chr4:100031381-100031536 | CATTTTTTGACACTGATTTTTTATTTTTAGATGGGCACTCTGGTTTTTTAAAAATGATAAAAGCAAAACTTGGCAAGCAAACCTGCGGCTGATCTCCAAGTTTGATACTGTTGAAGACTTTTGGGCGTAAGTAACCATTTGTTTTAGTATGTTTGT |
| EIF4E | 78 | 4 | chr4:100028033-100028156 | TGTTTTTAATTGTTATTTTCTTTTACCTAGTCTGTACAACCATATCCAGTTGTCTAGTAATTTAATGCCTGGCTGTGACTACTCACTTTTTAAGGTATGCTTAATTGGTGATTTTATATATTTA |
| EIF4E | 79 | 5 | chr4:100027223-100027396 | GTGTAATACTGTTGTCTTCTAACCCTGTAGGATGGTATTGAGCCTATGTGGGAAGATGAGAAAAACAAACGGGGAGGACGATGGCTAATTACATTGAACAAACAGCAGAGACGAAGTGACCTCGATCGCTTTTGGCTAGAGACAGTAAGGTTTTAAAAGTATAAAGCAGTTTTA |
| EIF4E | 80 | 6 | chr4:100025066-100025265 | ATTAAATGTAATTTGGGATTTTTTTTTAAGCTTCTGTGCCTTATTGGAGAATCTTTTGATGACTACAGTGATGATGTATGTGGCGCTGTTGTTAATGTTAGAGCTAAAGGTGATAAGATAGCAATATGGACTACTGAATGTGAAAACAGAGAAGCTGTTACACATATAGGGTAAGTTTTGCTCTTTGCCTACTTATTTTA |
| EIF4E | 81 | 7 | chr4:100021172-100021346 | TTTTTCTTCTTCTTTTTTTTTTTCTTCTAGGAGGGTATACAAGGAAAGGTTAGGACTTCCTCCAAAGATAGTGATTGGTTATCAGTCCCACGCAGACACAGCTACTAAGAGCGGCTCCACCACTAAAAATAGGTTTGTTGTTTAAGAAGACACCTTCTGAGTATTCTCATAGGAG |
| HOMER 1 | 82 | 1 | chr5:78844319-78844383 | AAACTTCAGAGCAAGTTTTCATTGGGCAAAATGGGGTAAGGATTTTTGTGCTTAACACAGCTTCG |
| HOMER 1 | 83 | 2 | chr5:78788411-78788627 | CAGTCCATCATTTTCTTTTCTGCCCTGCAGGGAACAACCTATCTTCAGCACTCGAGCTCATGTCTTCCAAATTGACCCAAACACAAAGAAGAACTGGGTACCCACCAGCAAGCATGCAGTTACTGTGTCTTATTTCTATGACAGCACAAGAAATGTGTATAGGATAATCAGTTTAGATGGCTCAAAGGTAAGCTACGTTTACTTTGAATGATTTGGC |
| HOMER 1 | 84 | 3 | chr5:78782539-78782730 | CTGGTTGCTCATACTTGCTTTATTTTTTAGGCAATAATAAATAGTACCATCACCCCAAACATGACATTTACTAAAACATCTCAGAAGTTTGGCCAGTGGGCTGATAGCCGGGCAAACACCGTTTATGGATTGGGATTCTCCTCTGAGCATCATCTTTCGAAAGTGAGTTAAATCATAAAATTTGAATGAAAA |
| HOMER 1 | 85 | 4 | chr5:78778602-78778754 | GGTTAATGTATGTAGTCTCTATACATTCAGTTTGCAGAAAAGTTTCAGGAATTTAAAGAAGCTGCTCGACTAGCAAAGGAAAAATCACAAGAGAAGATGGAACTTACCAGTACACCTTCACAGGTGGGTATATCATTTCTATTCTTAATTATG |
| HOMER 1 | 86 | 5 | chr5:78770559-78770758 | ATTTTTTATCCCCCACCCCTTTTTTTAAAGGAATCCGCAGGCGGGGATCTTCAGTCTCCTTTAACACCGGAAAGTATCAACGGGACAGATGATGAAAGAACACCTGATGTGACACAGAACTCAGAGCCAAGGGCTGAACCAACTCAGAATGCATTGCCATTTTCACATAGGTACAGATTCAATTCAGCAATTATGATTAA |
| HOMER 1 | 87 | 6 | chr5:78733448-78733664 | GGATAGAATTTTCTTTTTGTTTTATTTTAGTTCAGCAATCAGCAAACATTGGGAGGCTGAACTGGCTACCCTCAAAGGAAATAATGCCAAACTCACTGCAGCCCTGCTGGAGTCCACTGCCAATGTGAAACAATGGAAACAGCAACTTGCTGCCTATCAAGAGGAAGCAGAACGTCTGCACAAGCGGGTAATTTCAGGGCTGATGTCTATAGGGATT |

FIG. 4 cont.

| | | | | |
|---|---|---|---|---|
| HOMER 1 | 88 | 7 | chr5:78729076-78729246 | AAGTTAATCTGTGTTCTCATTTAATTTTAGGTGACTGAACTTGAATGTGTTAGTAGCCAAGCAAATGCAGT<br>ACATACTCATAAGACAGAATTAAATCAGACAATACAAGAACTGGAAGAGACACTGAAACTGAAGGAAG<br>AGGTATTTGCTGCTTTTTACTCATCTGTAATC |
| HOMER 1 | 89 | 8 | chr5:78728372-78728512 | AATGTTAAGACATTGCTCTGTCTTTTCTAGGAAATAGAAAGGTTAAAACAAGAAATTGATAATGCCAGAG<br>AACTACAAGAACAGAGGGATTCTTTGACTCAGAAACTACAGGTGAGCTGTAGTAAAAATTGTTATTCACT<br>T |
| HOMER 1 | 90 | 9 | chr5:78707558-78707806 | TATATACATGTTACACTTTTGTTTCTGAAGGAAGTAGAAATTCGGAACAAAGACCTGGAGGGACAACTGT<br>CTGACTTAGAGCAACGTCTGGAGAAAAGTCAGAATGAACAAGAAGCTTTTCGCAATAACCTGAAGACAC<br>TCTTAGAAATTCTGGATGGAAAGATATTTGAACTAACAGAATTACGAGATAACTTGGCCAAGCTACTAGA<br>ATGCAGCTAAGGAAAGTGAAATTTCAGTGCCAATTAATTA |
| PIK3R1 | 91 | 1 | chr5:67558230-67558623 | CAACTGTTGCATGGTAGCAGATTTGCAAACATGAGTGCTGAGGGGTACCAGTACAGAGCGCTGTATGAT<br>TATAAAAAGGAAAGAGAAGAAGATATTGACTTGCACTTGGGTGACATATTGACTGTGAATAAAGGGTCC<br>TTAGTAGCTCTTGGATTCAGTGATGGACAGGAAGCCAGGCCTGAAGAAATTGGCTGGTTAAATGGCTAT<br>AATGAAACCACAGGGGAAAGGGGGGACTTTCCGGGAACTTACGTAGAATATATTGGAAGGAAAAAAAT<br>CTCGCCTCCCACACCAAAGCCCCGGCCACCTCGGCCTCTTCCTGTTGCACCAGGTTCTTCGAAAACTGAAG<br>CAGATGTTGAACAACAAGGTCAGTATTGATAAGTGGTTGCTTAATGAC |
| PIK3R1 | 92 | 2 | chr5:67604944-67605096 | AATACAATGGTGGGATTTTGTTGTTTGCAGCTTTGACTCTCCCGGATCTTGCAGAGCAGTTTGCCCCTCCT<br>GACATTGCCCCGCCTCTTCTTATCAAGCTCGTGGAAGCCATTGAAAAGAAAGGTAACCAGACTGCTAGAG<br>GGCATCAGTTCC |
| PIK3R1 | 93 | 3 | chr5:67605493-67605627 | ACATGGTCTGTGGTCTGTTTTGTGTCCTAGGTCTGGAATGTTCAACTCTATACAGAACACAGAGCTCCAGC<br>AACCTGGCAGAATTACGACAGCTTCTTGATTGTGGTGAGTGTCACAGAGCTAGAAATGCAAATG |
| PIK3R1 | 94 | 4 | chr5:67611156-67611347 | GTCTGAAATATTTCTTAAATTGTTTCCTAGATACACCCTCCGTGGACTTGGAAATGATCGATGTGCACGTT<br>TTGGCTGACGCTTTCAAACGCTATCTCCTGGACTTACCAAATCCTGTCATTCCAGCAGCCGTTTACAGTGA<br>AATGATTTCTTTAGCTCCAGGTTTGTTTTTTCTCTTCTGGGAACCTCATT |
| PIK3R1 | 95 | 5 | chr5:67612082-67612343 | TTCTCTTTTTTTTTTTTTTTTAAACTTGTAGAAGTACAAAGCTCCGAAGAATATATTCAGCTATTGAAGAAGC<br>TTATTAGGTCGCCTAGCATACCTCATCAGTATTGGCTTACGCTTCAGTATTTGTTAAAACATTTCTTCAAGC<br>TCTCTCAAACCTCCAGCAAAAATCTGTTGAATGCAAGAGTACTCTCTGAAATTTTCAGCCCTATGCTTTTCA<br>GATTCTCAGCAGCCAGGTAAGTGAAAGGAGACAAACATGTATTTTG |
| PIK3R1 | 96 | 6 | chr5:67612481-67612620 | AAGGTTTCTAATAAACTCTCTTTCTTACAGCTCTGATAATACTGAAAACCTCATAAAAGTTATAGAAATTTT<br>AATCTCAACTGAATGGAATGAACGACAGCCTGCACCAGGTAATGCTTTTTGAGCATTTAACATTCTCT |
| PIK3R1 | 97 | 7 | chr5:67623813-67623975 | TGCGAACAACTTTTTCTTTTTCATCTGCAGCACTGCCTCCTAAACCACCAAAACCTACTACTGTAGCCAACA<br>ACGGTATGAATAACAATATGTCCTTACAAGATGCTGAATGGTACTGGGGAGATATCTCGAGGTAAGGCT<br>ACAGAAACTTCATTTTCAGAGA |

FIG. 4 cont.

| | | | | |
|---|---|---|---|---|
| PIK3R1 | 98 | 8 | chr5:67624655-67624813 | GATGAGCATTGTTTTGTGTTTTCATTTCAGGGAAGAAGTGAATGAAAAACTTCGAGATACAGCAGACGG<br>GACCTTTTTGGTACGAGATGCGTCTACTAAAATGCATGGTGATTATACTCTTACACTAAGGTAAGCCAGG<br>GAATATAGCTGAAATTAGGG |
| PIK3R1 | 99 | 9 | chr5:67624857-67625097 | AATACCTTTATTTTTATATTGTTTTTACAGGAAAGGGGGAAATAACAAATTAATCAAAATATTTCATCGAG<br>ATGGGAAATATGGCTTCTCTGACCCATTAACCTTCAGTTCTGTGGTTGAATTAATAAACCACTACCGGAAT<br>GAATCTCTAGCTCAGTATAATCCCAAATTGGATGTGAAATTACTTTATCCAGTATCCAAATACCAACAGGT<br>AATAAAAACTGAATGAATTATCCAGTTA |
| PIK3R1 | 100 | 10 | chr5:67625263-67625448 | TATCCATTGAATTTATTTTAATCTTTCTAGGATCAAGTTGTCAAAGAAGATAATATTGAAGCTGTAGGGAA<br>AAAATTACATGAATATAACACTCAGTTTCAAGAAAAAAGTCGAGAATATGATAGATTATATGAAGAATAT<br>ACCCGCACATCCCAGGTGAGTTTTCTATGAAAATCAGATTAAAAA |
| PIK3R1 | 101 | 11 | chr5:67626090-67626292 | TGACATTATCTTTTTAAAATTATGTTGCAGGAAATCCAAATGAAAAGGACAGCTATTGAAGCATTTAATG<br>AAACCATAAAAATATTTGAAGAACAGTGCCAGACCCAAGAGCGGTACAGCAAAGAATACATAGAAAAGT<br>TTAAACGTGAAGGCAATGAGAAAGAAATACAAAGGTTGGTGTTTCCCTTGTTCTTGTGCTAGAG |
| PIK3R1 | 102 | 12 | chr5:67626702-67626938 | TAATAACAAATACGTTTCTTTTGCCTGCAGGATTATGCATAATTATGATAAGTTGAAGTCTCGAATCAGTG<br>AAATTATTGACAGTAGAAGAAGATTGGAAGAAGACTTGAAGAAGCAGGCAGCTGAGTATCGAGAAATT<br>GACAAACGTATGAACAGCATTAAACCAGACCTTATCCAGCTGAGAAAGACGAGAGACCAATACTTGATG<br>TAAGTATTTGAAATGGAATCCTATACATG |
| PIK3R1 | 103 | 13 | chr5:67626974-67627102 | ATGCGTTCTCTTTTCAAAACTGTTTTTCAGGTGGTTGACTCAAAAAGGTGTTCGGCAAAAGAAGTTGAAC<br>GAGTGGTTGGGCAATGAAAACACTGAAGAGTAAGTAGTTACTAAAGATGGTGATAGCAG |
| PIK3R1 | 104 | 14 | chr5:67627725-67627955 | ATTTAGAAACTTTCTGTCCTGCCTGCCTAGCCAATATTCACTGGTGGAAGATGATGAAGATTTGCCCCATC<br>ATGATGAGAAGACATGGAATGTTGGAAGCAGCAACCGAAACAAAGCTGAAAACCTGTTGCGAGGGAAG<br>CGAGATGGCACTTTTCTTGTCCGGGAGAGCAGTAAACAGGGCTGCTATGCCTGCTCTGTAGTGTATGTAT<br>CTCCAGCAAACTTTTCTTTACA |
| PIK3R1 | 105 | 15 | chr5:67628966-67629215 | AAAAGACAGTTTTTCTTCTCTCCTCTCTAGGGTGGACGGCGAAGTAAAGCATTGTGTCATAAACAAAACA<br>GCAACTGGCTATGGCTTTGCCGAGCCCTATAACTTGTACAGCTCTCTGAAAGAACTGGTGCTACATTACC<br>AACACACCTCCCTTGTGCAGCACAACGACTCCCTCAATGTCACACTAGCCTACCCAGTATATGCACAGCAG<br>AGGCGATGAAGCGCTTACTCTTTGATCCTTCTCCTGAAG |

FIG. 4 cont.

| | | | | |
|---|---|---|---|---|
| GRM1 | 106 | 1 | chr6:146392317-146393076 | TGGCAGGCTGTGGACCTCGTCCTCACCACCATGGTCGGGCTCCTTTTGTTTTTTTTCCCAGCGATCTTTTTG<br>GAGGTGTCCCTTCTCCCCAGAAGCCCCGGCAGGAAAGTGTTGCTGGCAGGAGCGTCGTCTCAGCGCTCG<br>GTGGCCAGAATGGACGGAGATGTCATCATTGGAGCCCTCTTCTCAGTCCATCACCAGCCTCCGGCCGAGA<br>AAGTGCCCGAGAGGAAGTGTGGGGAGATCAGGGAGCAGTATGGCATCCAGAGGGTGGAGGCCATGTT<br>CCACACGTTGGATAAGATCAACGCGGACCCGGTCCTCCTGCCCAACATCACCCTGGGCAGTGAGATCCG<br>GGACTCCTGCTGGCACTCTTCCGTGGCTCTGGAACAGAGCATTGAGTTCATTAGGGACTCTCTGATTTCCA<br>TTCGAGATGAGAAGGATGGGATCAACCGGTGTCTGCCTGACGGCCAGTCCCTCCCCCCAGGCAGGACTA<br>AGAAGCCCATTGCGGGAGTGATCGGTCCCGGCTCCAGCTCTGTAGCCATTCAAGTGCAGAACCTGCTCCA<br>GCTCTTCGACATCCCCCAGATCGCTTATTCAGCCACAAGCATCGACCTGAGTGACAAAACTTTGTACAAAT<br>ACTTCCTGAGGGTTGTCCCTTCTGACACTTTGCAGGCAAGGGCCATGCTTGACATAGTCAAACGTTACAA<br>TTGGACCTATGTCTCTGCAGTCCACACGGAAGGTAGGCATTATATTTGGGAAAGAAGGGTAC |
| GRM1 | 107 | 2 | chr6:146522147-146522456 | CTTGAACATCTGCTGATTGTTTCTGGACAGGGAATTATGGGGAGAGCGGAATGGACGCTTTCAAAGAGC<br>TGGCTGCCCAGGAAGGCCTCTGTATCGCCCATTCTGACAAAATCTACAGCAACGCTGGGGAGAAGAGCT<br>TTGACCGACTCTTGCGCAAACTCCGAGAGAGGCTTCCCAAGGCTAGAGTGGTGGTCTGCTTCTGTGAAG<br>GCATGACAGTGCGAGGACTCCTGAGCGCCATGCGGCGCCTTGGCGTCGTGGGCGAGTTCTCACTCATTG<br>GAAGGTAAGTTTCTCTCTCTCTCTCTCTCTCTCT |
| GRM1 | 108 | 3 | chr6:146667410-146667705 | TCTCCCTACCCCAATCCCTGCATTTTTTAGTGATGGATGGGCAGACAGAGATGAAGTCATTGAAGGTTAT<br>GAGGTGGAAGCCAACGGGGGAATCACGATAAAGCTGCAGTCTCCAGAGGTCAGGTCATTTGATGATTAT<br>TTCCTGAAACTGAGGCTGGACACTAACACGAGGAATCCCTGGTTCCCTGAGTTCTGGCAACATCGGTTCC<br>AGTGCCGCCTTCCAGGACACCTTCTGGAAAATCCCAACTTTAAACGAATCTGCACAGGTAACTCATGTTCA<br>CAAAATAACAACTCAG |
| GRM1 | 109 | 4 | chr6:146715049-146715355 | CTTGGTAGTGATCTATTTTTATTGTTACAGGCAATGAAAGCTTAGAAGAAAACTATGTCCAGGACAGTAA<br>GATGGGGTTTGTCATCAATGCCATCTATGCCATGGCACATGGGCTGCAGAACATGCACCATGCCCTCTGC<br>CCTGGCCACGTGGGCCTCTGCGATGCCATGAAGCCCATCGACGGCAGCAAGCTGCTGGACTTCCTCATCA<br>AGTCCTCATTCATTGGAGTATCTGGAGAGGAGGTGTGGTTTGATGAGAAAGGAGACGCTCCTGGAAGGT<br>AATCTTTTCAGTAATCAATCTAAGTAAC |
| GRM1 | 110 | 5 | chr6:146720325-146720553 | TATAAGACATGCACATTGTGCTCTTTGTAGGTATGATATCATGAATCTGCAGTACACTGAAGCTAATCGCT<br>ATGACTATGTGCACGTTGGAACCTGGCATGAAGGAGTGCTGAACATTGATGATTACAAAATCCAGATGA<br>ACAAGAGTGGAGTGGTGCGGTCTGTGTGCAGTGAGCCTTGCTTAAAGGGCCAGATTAAGGTAAGCCAC<br>AAATGCATTCTTGCATGGTAT |
| GRM1 | 111 | 6 | chr6:146749689-146749875 | TTTAAAATTCATGAAATATCTATGTTATAGGTTATACGGAAAGGAGAAGTGAGCTGCTGCTGGATTTGCA<br>CGGCCTGCAAAGAGAATGAATATGTGCAAGATGAGTTCACCTGCAAAGCTTGTGACTTGGGATGGTGGC<br>CCAATGCAGATCTAACAGGTAGGAACTGCCTCACTTGGAAACCTTGTG |

FIG. 4 cont.

| | | | | |
|---|---|---|---|---|
| GRM1 | 112 | 7 | chr6:146761568-146762558 | TTCATGCTCAAATGATTTTTCTCATCACAGGCTGTGAGCCCATTCCTGTGCGCTATCTTGAGTGGAGCAAC<br>ATCGAATCCATTATAGCCATCGCCTTTTCATGCCTGGGAATCCTTGTTACCTTGTTTGTCACCCTAATCTTT<br>GTACTGTACCGGGACACACCAGTGGTCAAATCCTCCAGTCGGGAGCTCTGCTACATCATCCTAGCTGGCA<br>TCTTCCTTGGTTATGTGTGCCCATTCACTCTCATTGCCAAACCTACTACCACCTCCTGCTACCTCCAGCGCC<br>TCTTGGTTGGCCTCTCCTCTGCGATGTGCTACTCTGCTTTAGTGACTAAAACCAATCGTATTGCACGCATCC<br>TGGCTGGCAGCAAGAAGAAGATCTGCACCCGGAAGCCCAGGTTCATGAGTGCCTGGGCTCAGGTGATC<br>ATTGCCTCAATTCTGATTAGTGTGCAACTAACCCTGGTGGTAACCCTGATCATCATGGAACCCCCTATGCC<br>CATTCTGTCCTACCCAAGTATCAAGGAAGTCTACCTTATCTGCAATACCAGCAACCTGGGTGTGGTGGCC<br>CCTTTGGGCTACAATGGACTCCTCATCATGAGCTGTACCTACTATGCCTTCAAGACCCGCAACGTGCCCGC<br>CAACTTCAACGAGGCCAAATATATCGCGTTCACCATGTACACCACCTGTATCATCTGGCTAGCTTTTGTGC<br>CCATTTACTTTGGGAGCAACTACAAGATCATCACAACTTGCTTTGCAGTGAGTCTCAGTGTAACAGTGGCT<br>CTGGGGTGCATGTTCACTCCCAAGATGTACATCATTATTGCCAAGCCTGAGAGGAATGTCCGCAGTGCCT<br>TCACCACCTCTGATGTTGTCCGCATGCATGTTGGCGATGGCAAGCTGCCCTGCCGCTCCAACACTTTCCTC<br>AACATCTTCCGAAGAAAGAAGGCAGGGGCAGGGAATGCCAAGTGAGTTATCTGACCTGTTTGTCTCTCTT<br>T |
| GRM1 | 113 | 8 | chr6:146796671-146797655 | CAAATAAATCCATCTCTATTTTATTCATAGTTCTAATGGCAAGTCTGTGTCATGGTCTGAACCAGGTGGAG<br>GACAGGTGCCCAAGGGACAGCATATGTGGCACCGCCTCTCTGTGCACGTGAAGACCAATGAGACGGCCT<br>GCAACCAAACAGCCGTCATCAAGCCCCTCACTAAAAGTTACCAAGGCTCTGGCAAGAGCCTGACCTTTTC<br>AGATACCAGCACCAAGACCCTTTACAACGTAGAGGAGGAGGAGGATGCCCAGCCGATTCGCTTTAGCCC<br>GCCTGGTAGCCCTTCCATGGTGGTGCACAGGCGCGTGCCAAGCGCGGCGACCACTCCGCCTCTGCCGTC<br>CCACCTGACCGCAGAGGAGACCCCCCTCTTCCTGGCCGAACCAGCCCTCCCCAAGGGCTTGCCCCCTCCT<br>CTCCAGCAGCAGCAGCAACCCCCTCCACAGCAGAAATCGCTGATGGACCAGCTCCAGGGAGTGGTCAGC<br>AACTTCAGTACCGCGATCCCGGATTTTCACGCGGTGCTGGCAGGCCCCGGTGGTCCCGGGAACGGGCTG<br>CGGTCCCTGTACCCGCCCCCGCCACCTCCGCAGCACCTGCAGATGCTGCCGCTGCAGCTGAGCACCTTTG<br>GGGAGGAGCTGGTCTCCCCGCCCGCGGACGACGACGACGACAGCGAGAGGTTTAAGCTCCTCCAGGAG<br>TACGTGTATGAGCACGAGCGGGAAGGGAACACGGAAGAAGACGAACTGGAAGAGGAGGAGGAGGAC<br>CTGCAGGCGGCCAGCAAACTGACCCCGGATGATTCGCCTGCGCTGACGCCTCCGTCGCCTTTCCGCGACT<br>CGGTGGCCTCGGGCAGCTCGGTGCCCAGCTCCCCCGTGTCCGAGTCGGTGCTCTGCACCCCTCCCAACGT<br>ATCCTACGCCTCTGTCATTCTGCGGGACTACAAGCAAAGCTCTTCCACCCTGTAAGGGGGAAGGGTCCAC<br>ATAGAAAAGCAAGAC |
| RHEB | 114 | 1 | chr7:150847449-150847560 | GGTTGGGCCGGGGCTGAGGAGGCCGCCAAGATGCCGCAGTCCAAGTCCCGGAAGATCGCGATCCTGGG<br>CTACCGGTCTGTGGGTGAGTGGCCGGTGGCCGCGCGGCCTCCTC |
| RHEB | 115 | 2 | chr7:150818932-150819063 | CACACACTAAGCTCTTGTTCTCTTTTATAGGGAAATCCTCATTGACGATTCAATTTGTTGAAGGCCAATTTG<br>TGGACTCCTACGATCCAACCATAGAAAACAGTAAGTATTGTTTTCAAGTACTTAAAAACT |
| RHEB | 116 | 3 | chr7:150812726-150812853 | ACTAATGTTTAATTTCCTTTTTCCCTGTAGCTTTTACAAAGTTGATCACAGTAAATGGACAAGAATATCATC<br>TTCAACTTGTAGACACAGCCGGGCAAGTAAGTGACCTCTGGTATCTCAGAATCTTA |

FIG. 4 cont.

| | | | | |
|---|---|---|---|---|
| RHEB | 117 | 4 | chr7:150805322-150805464 | CTACTCAAAGATAATTTTTTTTCCCCACAGGATGAATATTCTATCTTTCCTCAGACATACTCCATAGATATT AATGGCTATATTCTTGTGTATTCTGTTACATCAATCAAAAGGTAAGACTCCTGCTGCCTGCTTGAGTTGAT |
| RHEB | 118 | 5 | chr7:150799538-150799654 | GATGTCTAATTTATACTTTTTGTTTTATAGTTTTGAAGTGATTAAAGTTATCCATGGCAAATTGTTGGATAT GGTGGGGAAAGTACAGTAAGTAGTACCATTTTATCTGCTTGTTAG |
| RHEB | 119 | 6 | chr7:150799383-150799490 | ACTGGTTTGTCTTTTTTTTCTTACAAATAGAATACCTATTATGTTGGTTGGGAATAAGAAAGACCTGCATA TGGAAAGGTATGTAGCTTTTATAAAGTCAAATCTAAG |
| RHEB | 120 | 7 | chr7:150798560-150798701 | ACTTTAACTAGAATTTTATTTTTTCTTTAGGGTGATCAGTTATGAAGAAGGGAAAGCTTTGGCAGAATCTT GGAATGCAGCTTTTTTGGAATCTTCTGCTAAAGAAAATCAGGTAACAGATTCTATAAACCTCATTTTGCAT |
| RHEB | 121 | 8 | chr7:150795108-150795260 | CACTGTGATTGGGTTTCTTTCTCTTTTCAGACTGCTGTGGATGTTTTTCGAAGGATAATTTTGGAGGCAGA AAAAATGGACGGGGCAGCTTCACAAGGCAAGTCTTCATGCTCGGTGATGTGATTCTGCTGCAAAGCCTG AGGACACTGGGAA |
| ARC | 122 | 1 | chr8:143691414-143692664 | TTTGCCGCCTGCCGGAGCACCTGCGCACAGATGGAGCTGGACCACCGGACCAGCGGCGGGCTCCACGCC TACCCCGGGCCGCGGGGCGGGCAGGTGGCCAAGCCCAACGTGATCCTGCAGATCGGGAAGTGCCGGGC CGAGATGCTGGAGCACGTGCGGCGGACGCACCGGCACCTGCTGGCCGAGGTGTCCAAGCAGGTGGAGC GCGAGCTGAAGGGGCTGCACCGGTCGGTCGGGAAGCTGGAGAGCAACCTGGACGGCTACGTGCCCACG AGCGACTCGCAGCGCTGGAAGAAGTCCATCAAGGCCTGCCTGTGCCGCTGCCAGGAGACCATCGCCAAC CTGGAGCGCTGGGTCAAGCGCGAGATGCACGTGTGGCGCGAGGTGTTCTACCGCCTGGAGCGCTGGGC CGACCGCCTGGAGTCCACGGGCGGCAAGTACCCGGTGGGCAGCGAGTCAGCCCGCCACACCGTTTCCGT GGGCGTGGGGGGTCCCGAGAGCTACTGCCACGAGGCAGACGGCTACGACTACACCGTCAGCCCCTACG CCATCACCCCGCCCCCAGCCGCTGGCGAGCTGCCCGGGCAGGAGCCCGCCGAGGCCCAGCAGTACCAGC CGTGGGTCCCCGGCGAGGACGGGCAGCCCAGCCCCGGCGTGGACACGCAGATCTTCGAGGACCCTCGA GAGTTCCTGAGCCACCTAGAGGAGTACTTGCGGCAGGTGGGCGGCTCTGAGGAGTACTGGCTGTCCCAG ATCCAGAATCACATGAACGGGCCGGCCAAGAAGTGGTGGGAGTTCAAGCAGGGCTCCGTGAAGAACTG GGTGGAGTTCAAGAAGGAGTTCCTGCAGTACAGCGAGGGCACGCTGTCCCGAGAGGCCATCCAGCGCG AGCTGGACCTGCCGCAGAAGCAGGGCGAGCCGCTGGACCAGTTCCTGTGGCGCAAGCGGGACCTGTAC CAGACGCTCTACGTGGACGCGGACGAGGAGGAGATCATCCAGTACGTGGTGGGCACCCTGCAGCCCAA GCTCAAGCGTTTCCTGCGCCACCCCCTGCCCAAGACCCTGGAGCAGCTCATCCAGAGGGGCATGGAGGTG |
| TSC1 | 123 | 3 | chr9:134793945-134794110 | GGAGCCAGCACAGCGCCTTCGAGCGAGAGAATGGCCCAACAAGCAAATGTCGGGGAGCTTCTTGCCAT GCTGGACTCCCCCATGCTGGGTGTGCGGGACGACGTGACAGCTGTCTTTAAAGAGAACCTCAATTCTGGT TAGCAAAATAATATCCTTTTTAGCTTAT |

FIG. 4 cont.

| | | | | |
|---|---|---|---|---|
| TSC1 | 124 | 4 | chr9:134792379-134792542 | GTATCATCCATTGCCCTTTTCTTGATTTAGACCGTGGCCCTATGCTTGTAAACACCTTGGTGGATTATTACC<br>TGGAAACCAGCTCTCAGCCGGCATTGCACATCCTGACCACCTTGCAAGAGCCACATGACAAGGTAATGG<br>CTGAAATATCATAGGCATTTCAT |
| TSC1 | 125 | 5 | chr9:134790765-134790977 | AGGACTGCCCTTGTTCTTTTACATTTTCAGCACCTCTTGGACAGGATTAACGAATATGTGGGCAAAGCCGC<br>CACTCGTTTATCCATCCTCTCGTTACTGGGTCATGTCATAAGACTGCAGCCATCTTGGAAGCATAAGCTCT<br>CTCAAGCACCTCTTTTGCCTTCTTTACTAAAATGTCTCAAGGTAGGATGTTTGTAAGGATTTGAATGAAAT |
| TSC1 | 126 | 6 | chr9:134788526-134788730 | ACGTTTCCTGTTTGACCTTTTCTCCTGCAGATGGACACTGACGTCGTTGTCCTCACAACAGGCGTCTTGGT<br>GTTGATAACCATGCTACCAATGATTCCACAGTCTGGGAAACAGCATCTTCTTGATTTCTTTGACATTTTTG<br>GCCGTCTGTCATCATGGTGCCTGAAGAAACCAGGTACAGATCTCCTCATATACCTGTTGGGCC |
| TSC1 | 127 | 7 | chr9:134786997-134787211 | GAGGCTCTTCTCAACGGGTTCCTTTTCTAGGCCACGTGGCGGAAGTCTATCTCGTCCATCTCCATGCCAGT<br>GTGTACGCACTCTTTCATCGCCTTTATGGAATGTACCCTTGCAACTTCGTCTCCTTTTTGCGTTCTCATTACA<br>GTATGAAAGAAAACCTGGAGACTTTTGAAGAAGTGGTCAAGGTAAATTGAAACTGCTTGTTTGTTTGCTA<br>C |
| TSC1 | 128 | 8 | chr9:134786541-134786674 | CTTTATAATTTGTCAACCCAACTCTTCTAGCCAATGATGGAGCATGTGCGAATTCATCCGGAATTAGTGAC<br>TGGATCCAAGGACCATGAACTGGACCCTCGAAGGTATAGAAACTAGTGTCAAAATTTTAAAGA |
| TSC1 | 129 | 9 | chr9:134777460-134777695 | GCATTTCTTGACTTTCATTGCATTTTACAGGTGGAAGAGATTAGAAACTCATGATGTTGTGATCGAGTGTG<br>CCAAAATCTCTCTGGATCCCACAGAAGCCTCATATGAAGATGGCTATTCTGTGTCTCACCAAATCTCAGCC<br>CGCTTTCCTCATCGTTCAGCCGATGTCACCACCAGCCCTTATGCTGACACACAGAATAGCTATGGTAAAAA<br>GTGTCTTTGGTACTTATCTGTTT |
| TSC1 | 130 | 10 | chr9:134776631-134776806 | AACCCCCTGTGTTCTTCTCTTCCATTTTAGGGTGTGCTACTTCTACCCCTTACTCCACGTCTCGGCTGATGTT<br>GTTAAATATGCCAGGGCAGCTACCTCAGACTCTGAGTTCCCCATCGACACGGCTGATAACTGAACCACCA<br>CAAGTATGGTGTCAACTAGTGTGCCTGCTCTCT |
| TSC1 | 131 | 11 | chr9:134776180-134776351 | CACTGCTGATGTACTTTATTAACTTCCCAGGCTACTCTTTGGAGCCCATCTATGGTTTGTGGTATGACCACT<br>CCTCCAACTTCTCCTGGAAATGTCCCACCTGATCTGTCACACCCTTACAGTAAAGTCTTTGGTACAACTGG<br>TATGTATGTCTTAGGTTGGATTTGATTAG |
| TSC1 | 132 | 12 | chr9:134775749-134775930 | GTTCATATATGTTCTGCCCTTGTCTCTAAGCAGGTGGAAAAGGAACTCCTCTGGGAACCCCAGCAACCTCT<br>CCTCCTCCAGCCCCACTCTGTCATTCGGATGACTACGTGCACATTTCACTCCCCCAGGCCACAGTCACACC<br>CCCCAGGAAGGTGCGATCCAGCTCGTCTGCTATCCCTCTG |
| TSC1 | 133 | 13 | chr9:134772479-134772608 | TTGTGATATAAATGATACTTATCTTTTCAGGAAGAGAGAATGGATTCTGCAAGACCATGTCTACACAGAC<br>AACACCATCTTCTGAATGACAGAGGATCAGGTAAAATTTCTGCGTTACTACAGGCCTTGC |

FIG. 4 cont.

| | | | | |
|---|---|---|---|---|
| TSC1 | 134 | 14 | chr9:134771909-134772073 | TTGACTTCAGTTGTCTTTGTTTCTCTTCAGAAGAGCCACCTGGCAGCAAAGGTTCTGTCACTCTAAGTGAT<br>CTTCCAGGGTTTTTAGGTGATCTGGCCTCTGAAGAAGATAGTATTGAAAAAGATAAAGAAGAAGGTAAT<br>GTATGTGGGATTGCTATGAGTTGAT |
| TSC1 | 135 | 15 | chr9:134770759-134771377 | CATTTCTTTTGTTTCCTCTCTTCCTCTCAGCTGCAATATCTAGAGAACTTTCTGAGATCACCACAGCAGAGG<br>CAGAGCCTGTGGTTCCTCGAGGAGGCTTTGACTCTCCCTTTTACCGAGACAGTCTCCCAGGTTCTCAGCG<br>GAAGACCCACTCGGCAGCCTCCAGTTCTCAGGGCGCCAGCGTGAACCCTGAGCCTTTACACTCCTCCCTG<br>GACAAGCTTGGGCCTGACACACCAAAGCAAGCCTTTACTCCCATAGACCTGCCCTGCGGCAGTGCTGATG<br>AAAGCCCTGCGGGAGACAGGGAATGCCAGACTTCTTTGGAGACCAGTATCTTCACTCCCAGTCCTTGTAA<br>AATTCCACCTCCGACGAGAGTGGGCTTTGGAAGCGGGCAGCCTCCCCCGTATGATCATCTTTTTGAGGTG<br>GCATTGCCAAAGACAGCCCATCATTTTGTCATCAGGAAGACTGAGGAGCTGTTAAAGAAAGCAAAAGGA<br>AACACAGAGGAAGATGGTGTGCCCTCTACCTCCCCAATGGAAGTGCTGGACAGACTGATACAGCAGGGA<br>GCAGACGCGCACAGCAAGGAGCTGAACAAGTAAGGGACTGGGGCACTCTCTTCTGTGTT |
| TSC1 | 136 | 16 | chr9:134769589-134769692 | AACTTTGTTACTCAAAAACTTTCTTCCTAGGTTGCCTTTACCCAGCAAGTCTGTCGACTGGACCCACTTTGG<br>AGGTAAAGTTGTTACTTTAGCTCCAAATCCAG |
| TSC1 | 137 | 17 | chr9:134768829-134769055 | TCTGCCACCCTCCCTCTGCTTTACAATCAGGCTCTCCTCCTTCAGATGAGATCCGCACCCTCCGAGACCAGT<br>TGCTTTTACTGCACAACCAGTTACTCTATGAGCGTTTTAAGAGGCAGCAGCATGCCCTCCGGAACAGGCG<br>GCTCCTCCGCAAGGTGATCAAAGCAGCAGCTCTGGAGGAACATAATGCTGCCATGGTGAGGACTGGGG<br>AGGGGACAGGTGGAGCT |
| TSC1 | 138 | 18 | chr9:134767783-134768025 | TAAAATGATGACATTTCTGGTCTCTGCTAGAAAGATCAGTTGAAGTTACAAGAGAAGGACATCCAGATGT<br>GGAAGGTTAGTCTGCAGAAAGAACAAGCTAGATACAATCAGCTCCAGGAGCAGCGTGACACTATGGTA<br>ACCAAGCTCCACAGCCAGATCAGACAGCTGCAGCATGACCGAGAGGAATTCTACAACCAGAGCCAGGAA<br>TTACAGGTATAAACTGCAGCACCAGGCAAAGCCAAC |
| TSC1 | 139 | 19 | chr9:134766767-134766937 | CAAACTTCATGTCCACGTCTCTTTGGGCAGACGAAGCTGGAGGACTGCAGGAACATGATTGCGGAGCTG<br>CGGATAGAACTGAAGAAGGCCAACAACAAGGTGTGTCACACTGAGCTGCTGCTCAGTCAGGTTTCCCAA<br>AAGGTAAGAAGAAATGAGGCAGACCTGAATCTG |
| TSC1 | 140 | 20 | chr9:134765893-134766075 | TTTTTCACTTTGCTCATGTTTTTTGGTTAGCTCTCAAACAGTGAGTCGGTCCAGCAGCAGATGGAGTTCTT<br>GAACAGGCAGCTGTTGGTTCTTGGGGAGGTCAACGAGCTCTATTTGGAACAACTGCAGAACAAGCACTC<br>AGATACCACAAAGGTATGCCAGGGCTCGGGAGCCAGACCTTAG |
| TSC1 | 141 | 21 | chr9:134762601-134762848 | ATTCCAGTCTTTTTTTTTTTTTTTTTTCAGGAAGTAGAAATGATGAAAGCCGCCTATCGGAAAGAGCTAGA<br>AAAAAACAGAAGCCATGTTCTCCAGCAGACTCAGAGGCTTGATACCTCCCAAAAACGGATTTTGGAACTG<br>GAATCTCACCTGGCCAAGAAAGACCACCTTCTTTTGGAACAGAAGAAATATCTAGAGGATGTCAAACTCC<br>AGGCAAGGTAACTTTCATCAGGAAAGGCTTTTGTGTT |

FIG. 4 cont.

| | | | | |
|---|---|---|---|---|
| TSC1 | 142 | 22 | chr9:134762362-134762583 | CCTATATTCTGGCTGGTCTGTATCTTTCAGAGGACAGCTGCAGGCCGCAGAGAGCAGGTATGAGGCTCA<br>GAAAAGGATAACCCAGGTGTTTGAATTGGAGATCTTAGATTTATATGGCAGGTTGGAGAAAGATGGCCT<br>CCTGAAAAAACTTGAAGAAGAAAAAGCAGAAGCAGCTGAAGCAGCAGAAGAAAGGTAGGAACAAAGA<br>ACTGATTCATGACCTTG |
| TSC1 | 143 | 23 | chr9:134761413-134761992 | CTCCTTTTTTCCTCCCCGGCTTTCTTACAGGCTTGACTGTTGTAATGACGGGTGCTCAGATTCCATGGTAG<br>GGCACAATGAAGAGGCATCTGGCCACAACGGTGAGACCAAGACCCCCAGGCCCAGCAGCGCCCGGGGC<br>AGTAGTGGAAGCAGAGGTGGTGGAGGCAGCAGCAGCAGCAGCAGCGAGCTTTCTACCCCAGAGAAACC<br>CCCACACCAGAGGGCAGGCCCATTCAGCAGTCGGTGGGAGACGACTATGGGAGAAGCGTCTGCCAGCA<br>TCCCCACCACTGTGGGCTCACTTCCCAGTTCAAAAAGCTTCCTGGGTATGAAGGCTCGAGAGTTATTTCGT<br>AATAAGAGCGAGAGCCAGTGTGATGAGGACGGCATGACCAGTAGCCTTTCTGAGAGCCTAAAGACAGA<br>ACTGGGCAAAGACTTGGGTGTGGAAGCCAAGATTCCCCTGAACCTAGATGGCCCTCACCCGTCTCCCCCG<br>ACCCCGGACAGTGTTGGACAGCTACATATCATGGACTACAATGAGACTCATCATGAACACAGCTAAGGA<br>ATGATGGTCAATCAGTGTTAACTTGCA |
| FMR1 | 144 | 1 | chrX:146801360-146801470 | GCTCCCGGCGCTAGCAGGGCTGAAGAGAAGATGGAGGAGCTGGTGGTGGAAGTGCGGGGCTCCAATG<br>GCGCTTTCTACAAGGTACTTGGCTCTAGGGCAGGCCCCATCTTC |
| FMR1 | 145 | 2 | chrX:146811113-146811225 | CAAGTTAATTTAACGTTTTTTCTTACACAGGCATTTGTAAAGGATGTTCATGAAGATTCAATAACAGTTGC<br>ATTTGAAAACAAGTAAGTGTCTCGTTATATAATTTTAATGAT |
| FMR1 | 146 | 3 | chrX:146814720-146814873 | TTAAATAATTGTATGTTTGCTTATTTACAGCTGGCAGCCTGATAGGCAGATTCCATTTCATGATGTCAGAT<br>TCCCACCTCCTGTAGGTTATAATAAAGATATAAATGAAAGTGATGAAGTTGAGGTGAGTTTTCCCTGCCA<br>TAAAGTCATTTAG |
| FMR1 | 147 | 4 | chrX:146817502-146817633 | GAAATATTCTGTGTTGTAATTTTTGTGTAGGTGTATTCCAGAGCAAATGAAAAAGAGCCTTGCTGTTGGT<br>GGTTAGCTAAAGTGAGGATGATAAAGGGTGAGGTAGGAAAATGCCTATTTAAATTTTTTTCT |
| FMR1 | 148 | 5 | chrX:146817839-146818047 | GATTAGAAGTGACTTTTATTTATTTCTCAGTTTTATGTGATAGAATATGCAGCATGTGATGCAACTTACAA<br>TGAAATTGTCACAATTGAACGTCTAAGATCTGTTAATCCCAACAAACCTGCCACAAAAGATACTTTCCATA<br>AGATCAAGCTGGATGTGCCAGAAGACTTACGGCAAATGTAAGTTGATACACAAGAAATGCTGAGAAC |
| FMR1 | 149 | 6 | chrX:146819129-146819282 | TCATCTTAATTTTTTTTTTTAAATTTCTAGGTGTGCCAAAGAGGCGGCACATAAGGATTTTAAAAAGGCAG<br>TTGGTGCCTTTTCTGTAACTTATGATCCAGAAAATTATCAGCTTGTCATTTTGGTGAGCATTTTTGAGTTGT<br>TTATTTTTAGT |
| FMR1 | 150 | 7 | chrX:146819309-146819485 | ATAATAATGTTGTTAATTTAAATCATTTAGTCCATCAATGAAGTCACCTCAAAGCGAGCACATATGCTGAT<br>TGACATGCACTTTCGGAGTCTGCGCACTAAGTTGTCTCTGATAATGAGAAATGAAGAAGCTAGTAAGCA<br>GCTGGAGGTATGTCACTTTCCCTAGCACTGCTTGTAA |

FIG. 4 cont.

| | | | | |
|---|---|---|---|---|
| FMR1 | 151 | 8 | chrX:146821606-146821836 | TGTATTCATCAGACGTCCATTTCTCTTCAGAGTTCAAGGCAGCTTGCCTCGAGATTTCATGAACAGTTTAT<br>CGTAAGAGAAGATCTGATGGGTCTAGCTATTGGTACTCATGGTGCTAATATTCAGCAAGCTAGAAAAGT<br>ACCTGGGGTCACTGCTATTGATCTAGATGAAGATACCTGCACATTTCATATTTATGGAGAGGTAAATATTT<br>TACTGCATAGTTTTTTTTTC |
| FMR1 | 152 | 9 | chrX:146821866-146822004 | TTTGTCTTAAAATGTTTCCCCTTTTATTAGGATCAGGATGCAGTGAAAAAAGCTAGAAGCTTTCTCGAATT<br>TGCTGAAGATGTAATACAAGTTCCAAGGAACTTAGTAGGTAAGTCAGAAGTATCTGTTGACATATAGT |
| FMR1 | 153 | 10 | chrX:146825685-146825854 | AAAACCAAACTTGATTTATTTATTTCTTAGGCAAAGTAATAGGAAAAAATGGAAAGCTGATTCAGGAGAT<br>TGTGGACAAGTCAGGAGTTGTGAGGGTGAGGATTGAGGCTGAAAATGAGAAAAATGTTCCACAAGAAG<br>AGGTATGTTACAGTGCGAATATTTTGTGGCAC |
| FMR1 | 154 | 11 | chrX:146826647-146826841 | TCTCTTTTGTGTTTTCTGTTTTTTACCAAGGAAATTATGCCACCAAATTCCCTTCCTTCCAATAATTCAAGGG<br>TTGGACCTAATGCCCCAGAAGAAAAAAAACATTTAGATATAAAGGAAAACAGCACCCATTTTTCTCAACC<br>TAACAGTACAAAAGTCCAGAGGGTAAGAATTACTTGTCACTTTGAATTACAA |
| FMR1 | 155 | 12 | chrX:146827280-146827402 | ACATCCCTTGCATTCCTTATACTGCTTTAGGTGTTAGTGGCTTCATCAGTTGTAGCAGGGGAATCCCAGAA<br>ACCTGAACTCAAGGCTTGGCAGGTAGGAAAACATTCCTTGAGAAATACACTT |
| FMR1 | 156 | 13 | chrX:146829757-146829903 | ATAGGATCATTGTTGCAATTTCTTTTTCAGGGTATGGTACCATTTGTTTTTGTGGGAACAAAGGACAGCAT<br>CGCTAATGCCACTGTTCTTTTGGATTATCACCTGAACTATTTAAAGGTGAGAACAGAAAGAACTTTAACTT<br>CTAAT |
| FMR1 | 157 | 14 | chrX:146832313-146832568 | TTTTACTGTTATCTTGTATATTTTAAATAGGAAGTAGACCAGTTGCGTTTGGAGAGATTACAAATTGATGA<br>GCAGTTGCGACAGATTGGAGCTAGTTCTAGACCACCACCAAATCGTACAGATAAGGAAAAAAGCTATGT<br>GACTGATGATGGTCAAGGAATGGGTCGAGGTAGTAGACCTTACAGAAATAGGGGGCACGGCAGACGCG<br>GTCCTGGATATACTTCAGGTACAAACTAAGCATTTTACTCAGTAACTT |
| FMR1 | 158 | 15 | chrX:146834051-146834293 | CAATGGTATATAACTTTTAACTCTCGATAGGAACTAATTCTGAAGCATCAAATGCTTCTGAAACAGAATCT<br>GACCACAGAGACGAACTCAGTGATTGGTCATTAGCTCCAACAGAGGAAGAGAGGGAGAGCTTCCTGCG<br>CAGAGGAGACGGACGGCGGCGTGGAGGGGGAGGAAGAGGACAAGGAGGAAGAGGACGTGGAGGAG<br>GCTTCAAAGGTATGGAGATCTTCATTAAGAAATCAAAGT |
| FMR1 | 159 | 16 | chrX:146834716-146834858 | CTGTTGAACCTTTTGAAAATATTCTCATAGGAAACGACGATCACTCCCGAACAGATAATCGTCCACGTAAT<br>CCAAGAGAGGCTAAAGGAAGAACAACAGATGGATCCCTTCAGGTAAAACCTGTCTGCCTCTTTTCATCTT<br>AA |
| FMR1 | 160 | 17 | chrX:146837865-146838086 | TGTGTATATAACAACTATAACTTGTTTTAGATCAGAGTTGACTGCAATAATGAAAGGAGTGTCCACACTA<br>AAACATTACAGAATACCTCCAGTGAAGGTAGTCGGCTGCGCACGGGTAAAGATCGTAACCAGAAGAAA<br>GAGAAGCCAGACAGCGTGGATGGTCAGCAACCACTCGTGAATGGAGTACCCTAAACTGCATAATTCTGA<br>AGTTATATTTCCTAT |

FIG. 4 cont.

| | | | | |
|---|---|---|---|---|
| MECP2 | 161 | 2 | chrX:153010806-153010891 | GCTTCTGTAGACCAGCTCCAACAGGATTCCATGGTAGCTGGGATGTTAGGGCTCAGGTAAGTAACCTTCC<br>TTTTTTTTTTTTTAGT |
| MECP2 | 162 | 3 | chrX:152950822-152951232 | TGATACTTACATACTTGTTTAACACTTCAGGGAAGAAAAGTCAGAAGACCAGGACCTCCAGGGCCTCAAG<br>GACAAACCCCTCAAGTTTAAAAAGGTGAAGAAAGATAAGAAAGAAGAGAAAGAGGGCAAGCATGAGC<br>CCGTGCAGCCATCAGCCCACCACTCTGCTGAGCCCGCAGAGGCAGGCAAAGCAGAGACATCAGAAGGG<br>TCAGGCTCCGCCCCGGCTGTGCCGGAAGCTTCTGCCTCCCCCAAACAGCGGCGCTCCATCATCCGTGACC<br>GGGGACCCATGTATGATGACCCCACCCTGCCTGAAGGCTGGACACGGAAGCTTAAGCAAAGGAAATCTG<br>GCCGCTCTGCTGGGAAGTATGATGTGTATTTGATCAAGTAAGTAAGAGCAACTCCTATCTCTACAGG |
| MECP2 | 163 | 4 | chrX:152948982-152950125 | TTCCTTGTGTCTTTCTGTTTGTCCCCACAGTCCCCAGGGAAAAGCCTTTCGCTCTAAAGTGGAGTTGATTG<br>CGTACTTCGAAAAGGTAGGCGACACATCCCTGGACCCTAATGATTTTGACTTCACGGTAACTGGGAGAG<br>GGAGCCCCTCCCGGCGAGAGCAGAAACCACCTAAGAAGCCCAAATCTCCCAAAGCTCCAGGAACTGGCA<br>GAGGCCGGGGACGCCCCAAAGGGAGCGGCACCACGAGACCCAAGGCGGCCACGTCAGAGGGTGTGCA<br>GGTGAAAAGGGTCCTGGAGAAAAGTCCTGGGAAGCTCCTTGTCAAGATGCCTTTTCAAACTTCGCCAGG<br>GGGCAAGGCTGAGGGGGGTGGGGCCACCACATCCACCCAGGTCATGGTGATCAAACGCCCCGGCAGGA<br>AGCGAAAAGCTGAGGCCGACCCTCAGGCCATTCCCAAGAAACGGGGCCGAAAGCCGGGGAGTGTGGTG<br>GCAGCCGCTGCCGCCGAGGCCAAAAAGAAAGCCGTGAAGGAGTCTTCTATCCGATCTGTGCAGGAGACC<br>GTACTCCCCATCAAGAAGCGCAAGACCCGGGAGACGGTCAGCATCGAGGTCAAGGAAGTGGTGAAGCC<br>CCTGCTGGTGTCCACCCTCGGTGAGAAGAGCGGGAAAGGACTGAAGACCTGTAAGAGCCCTGGGCGGA<br>AAAGCAAGGAGAGCAGCCCCAAGGGGCGCAGCAGCAGCGCCTCCTCACCCCCCAAGAAGGAGCACCAC<br>CACCATCACCACCACTCAGAGTCCCCAAAGGCCCCCGTGCCACTGCTCCCACCCCTGCCCCCACCTCCACC<br>TGAGCCCGAGAGCTCCGAGGACCCCACCAGCCCCCCTGAGCCCCAGGACTTGAGCAGCAGCGTCTGCAA<br>AGAGGAGAAGATGCCCAGAGGAGGCTCACTGGAGAGCGACGGCTGCCCCAAGGAGCCAGCTAAGACT<br>CAGCCCGCGGTTGCCACCGCCGCCACGGCCGCAGAAAAGTACAAACACCGAGGGGAGGGAGAGCGCA<br>AAGACATTGTTTCATCCTCCATGCCAAGGCCAAACAGAGAGGAGCCTGTGGACAGCCGGACGCCCGTGA( |
| PTEN | 164 | 1 | chr10:89614177-89614315 | TCCTTTTTCTTCAGCCACAGGCTCCCAGACATGACAGCCATCATCAAAGAGATCGTTAGCAGAAACAAAA<br>GGAGATATCAAGAGGATGGATTCGACTTAGACTTGACCTGTATCCATTTCTGCGGCTGCTCCTCTTTAC |
| PTEN | 165 | 2 | chr10:89643732-89643876 | GATATTTCTTTCCTTAACTAAAGTACTCAGATATTTATCCAAACATTATTGCTATGGGATTTCCTGCAGAAA<br>GACTTGAAGGCGTATACAGGAACAATATTGATGATGTAGTAAGGTAAGAATGCTTTGATTTTCTATTTCA<br>AAT |
| PTEN | 166 | 3 | chr10:89675220-89675324 | TGGCTTTTTGTTTGTTTGTTTTGTTTTAAGGTTTTTGGATTCAAAGCATAAAAACCATTACAAGATATACAA<br>TCTGTAAGTATGTTTTCTTATTTGTATGCTTGC |
| PTEN | 167 | 4 | chr10:89680753-89680856 | CTTTATATCACTTTTAAACTTTTCTTTTAGTTGTGCTGAAAGACATTATGACACCGCCAAATTTAATTGCAG<br>AGGTAGGTATGAATGTACTGTACTATGTTGTA |

FIG. 4 cont.

| | | | | |
|---|---|---|---|---|
| PTEN | 168 | 5 | chr10:89682720-89683018 | TCTTATTCTGAGGTTATCTTTTTACCACAGTTGCACAATATCCTTTTGAAGACCATAACCCACCACAGCTAG<br>AACTTATCAAACCCTTTTGTGAAGATCTTGACCAATGGCTAAGTGAAGATGACAATCATGTTGCAGCAAT<br>TCACTGTAAAGCTGGAAAGGGACGAACTGGTGTAATGATATGTGCATATTTATTACATCGGGGCAAATTT<br>TTAAAGGCACAAGAGGCCCTAGATTTCTATGGGGAAGTAAGGACCAGAGACAAAAAGGTAAGTTATTTT<br>TTGATGTTTTTCCTTTCC |
| PTEN | 169 | 6 | chr10:89701825-89702026 | TTTGGCTTCTCTTTTTTTTCTGTCCACCAGGGAGTAACTATTCCCAGTCAGAGGCGCTATGTGTATTATTAT<br>AGCTACCTGTTAAAGAATCATCTGGATTATAGACCAGTGGCACTGTTGTTTCACAAGATGATGTTTGAAA<br>CTATTCCAATGTTCAGTGGCGGAACTTGCAGTAAGTGCTTGAAATTCTCATCCTTCCATG |
| PTEN | 170 | 7 | chr10:89707560-89707786 | AATAATACTGGTATGTATTTAACCATGCAGATCCTCAGTTTGTGGTCTGCCAGCTAAAGGTGAAGATATA<br>TTCCTCCAATTCAGGACCCACACGACGGGAAGACAAGTTCATGTACTTTGAGTTCCCTCAGCCGTTACCTG<br>TGTGTGGTGATATCAAAGTAGAGTTCTTCCACAAACAGAACAAGATGCTAAAAAAGGTTTGTACTTTACT<br>TTCATTGGGAGAAATA |
| PTEN | 171 | 8 | chr10:89710601-89710885 | TCTTTTTCTTTTCTTTTTTTTTTTTTTTTAGGACAAAATGTTTCACTTTTGGGTAAATACATTCTTCATACCAGG<br>ACCAGAGGAAACCTCAGAAAAAGTAGAAAATGGAAGTCTATGTGATCAAGAAATCGATAGCATTTGCAG<br>TATAGAGCGTGCAGATAATGACAAGGAATATCTAGTACTTACTTTAACAAAAAATGATCTTGACAAAGCA<br>AATAAAGACAAAGCCAACCGATACTTTTCTCCAAATTTTAAGGTCAGTTAAATTAAACATTTTGTGGGGGT<br>T |
| PTEN | 172 | 9 | chr10:89714994-89715239 | GGGTTTTCATTTTAAATTTTCTTTCTCTAGGTGAAGCTGTACTTCACAAAAACAGTAGAGGAGCCGTCAAA<br>TCCAGAGGCTAGCAGTTCAACTTCTGTAACACCAGATGTTAGTGACAATGAACCTGATCATTATAGATATT<br>CTGACACCACTGACTCTGATCCAGAGAATGAACCTTTTGATGAAGATCAGCATACACAAATTACAAAAGT<br>CTGAATTTTTTTTTATCAAGAGGGATAAAACACC |
| GRM5 | 173 | 1 | chr11:88419998-88420718 | ATCTTTATTGGCTTGAACTCCTTTCCTAAAATGGTCCTTCTGTTGATCCTGTCAGTCTTACTTTTGAAAGAA<br>GATGTCCGTGGGAGTGCACAGTCCAGTGAGAGGAGGGTGGTGGCTCACATGCCGGGTGACATCATTATT<br>GGAGCTCTCTTTTCTGTTCATCACCAGCCTACTGTGGACAAAGTTCATGAGAGGAAGTGTGGGGCGGTCC<br>GTGAACAGTATGGCATTCAGAGAGTGGAGGCCATGCTGCATACCCTGGAAAGGATCAATTCAGACCCCA<br>CACTCTTGCCCAACATCACACTGGGCTGTGAGATAAGGGACTCCTGCTGGCATTCGGCTGTGGCCCTAGA<br>GCAGAGCATTGAGTTCATAAGAGATTCCCTCATTTCTTCAGAAGAGGAAGAAGGCTTGGTACGCTGTGT<br>GGATGGCTCCTCCTCTTCCTTCCGCTCCAAGAAGCCCATAGTAGGGGTCATTGGGCCTGGCTCCAGTTCT<br>GTAGCCATTCAGGTCCAGAATTTGCTCCAGCTTTTCAACATACCTCAGATTGCTTACTCAGCAACCAGCAT<br>GGATCTGAGTGACAAGACTCTGTTCAAATATTTCATGAGGGTTGTGCCTTCAGATGCTCAGCAGGCAAGG<br>GCCATGGTGGACATAGTGAAGAGGTACAACTGGACCTATGTATCAGCCGTGCACACAGAAGGTAAGTTT<br>CCTTTGCATACATCGAGTATAT |

FIG. 4 cont.

| | | | | |
|---|---|---|---|---|
| GRM5 | 174 | 2 | chr11:88222692-88223001 | ATCCCTCTGCTTATCTATGTTTTCACACAGGCAACTATGGAGAAAGTGGGATGGAAGCCTTCAAAGATAT<br>GTCAGCGAAGGAAGGGATTTGCATCGCCCACTCTTACAAAATCTACAGTAATGCAGGGGAGCAGAGCTT<br>TGATAAGCTGCTGAAGAAGCTCACAAGTCACTTGCCCAAGGCCCGGGTGGTGGCCTGCTTCTGTGAGGG<br>CATGACGGTGAGAGGTCTGCTGATGGCCATGAGGCGCCTGGGTCTAGCGGGAGAATTTCTGCTTCTGGG<br>CAGGTGAGTGATAATAAGAAAATTTACATGGAG |
| GRM5 | 175 | 3 | chr11:88025954-88026249 | TAAGCTGAGGGTTTTTTTATTTCCCCACAGTGATGGCTGGGCTGACAGGTATGATGTGACAGATGGATAT<br>CAGCGAGAAGCTGTTGGTGGCATCACAATCAAGCTCCAATCTCCCGATGTCAAGTGGTTTGATGATTATT<br>ATCTGAAGCTCCGGCCAGAAACAAACCACCGAAACCCTTGGTTTCAAGAATTTTGGCAGCATCGTTTTCA<br>GTGCCGACTGGAAGGGTTTCCACAGGAGAACAGCAAATACAACAAGACTTGCAATAGTAAGCAGATTTA<br>TTATTTCATTTAAAATG |
| GRM5 | 176 | 4 | chr11:87977504-87977810 | CAAAGCTATGCTTAATTTGTTTCCCAACAGGTTCTCTGACTCTGAAAACACATCATGTTCAGGATTCCAAA<br>ATGGGATTTGTGATCAACGCCATCTATTCGATGGCCTATGGGCTCCACAACATGCAGATGTCCCTCTGCCC<br>AGGCTATGCAGGACTCTGTGATGCCATGAAGCCAATTGATGGACGGAAACTTTTGGAGTCCCTGATGAA<br>AACCAATTTTACTGGGGTTTCTGGAGATACGATCCTATTCGATGAGAATGGAGACTCTCCAGGAAGGTAT<br>TGTGTTACAATTCTCCTCTGCAGAGT |
| GRM5 | 177 | 5 | chr11:87969970-87970198 | CTGCATAATTATCATATTCTTATTCCTAAGGTATGAAATAATGAATTTCAAGGAAATGGGAAAAGATTACT<br>TTGATTATATCAACGTTGGAAGTTGGGACAATGGAGAATTAAAAATGGATGATGATGAAGTATGGTCCA<br>AGAAAAGCAACATCATCAGATCTGTGTGCAGTGAACCATGTGAGAAAGGCCAGATCAAGGTAAAATGG<br>AATCTATGTTTCTTTCATTTT |
| GRM5 | 178 | 6 | chr11:87963387-87963573 | AAAAATCTAAATTTCAAATATTTGCCTTAGGTGATCCGAAAGGGAGAAGTCAGCTGTTGTTGGACCTGTA<br>CACCTTGTAAGGAGAATGAGTATGTCTTTGATGAGTACACATGCAAGGCATGCCAACTGGGGTCTTGGC<br>CCACTGATGATCTCACAGGTAATCTATCACAATCTCACCACATATAAA |

FIG. 4 cont.

| | | | | |
|---|---|---|---|---|
| GRM5 | 179 | 7 | chr11:87939839-87940838 | CCTTTACAATATGTGTTTGTGTCTCTGCAGGTTGTGACTTGATCCCAGTACAGTATCTTCGATGGGGTGAC<br>CCTGAACCCATTGCAGCTGTGGTGTTTGCCTGCCTTGGCCTCCTGGCCACCCTGTTTGTTACTGTAGTCTTC<br>ATCATTTACCGTGATACACCAGTAGTCAAGTCCTCAAGCAGGGAACTCTGCTACATTATCCTTGCTGGCAT<br>CTGCCTGGGCTACTTATGTACCTTCTGCCTCATTGCGAAGCCCAAACAGATTTACTGCTACCTTCAGAGAA<br>TTGGCATTGGTCTCTCCCCAGCCATGAGCTACTCAGCCCTTGTAACAAAGACCAACCGTATTGCAAGGAT<br>CCTGGCTGGCAGCAAGAAGAAGATCTGTACCAAAAAGCCCAGATTCATGAGTGCCTGTGCCCAGCTAGT<br>GATTGCTTTCATTCTCATATGCATCCAGTTGGGCATCATCGTTGCCCTCTTTATAATGGAGCCTCCTGACAT<br>AATGCATGACTACCCAAGCATTCGAGAAGTCTACCTGATCTGTAACACCACCAACCTAGGAGTTGTCACT<br>CCACTTGGATACAATGGATTGTTGATTTTGAGCTGCACCTTCTATGCGTTCAAGACCAGAAATGTTCCAGC<br>TAACTTCAACGAGGCCAAGTATATCGCCTTCACAATGTACACGACCTGCATTATATGGCTAGCTTTTGTGC<br>CAATCTACTTTGGCAGCAACTACAAAATCATCACCATGTGTTTCTCGGTCAGCCTCAGTGCCACAGTGGCC<br>CTAGGCTGCATGTTTGTGCCGAAGGTGTACATCATCCTGGCCAAACCAGAGAGAAACGTGCGCAGCGCC<br>TTCACCACATCTACCGTGGTGCGCATGCATGTAGGGGATGGCAAGTCATCCTCCGCAGCCAGCAGATCCA<br>GCAGCCTAGTCAACCTGTGGAAGAGAAGGGGCTCCTCTGGGGAAACCTTAAGGTAAAAGTTGTGGGGG<br>CTTACAGGGATGCT |
| GRM5 | 180 | 8 | chr11:87881378-87882350 | AGTCACCTTTCCTCTCCCTTCTCTCCTCAGTTCCAATGGAAAATCCGTCACGTGGGCCCAGAATGAGAAGA<br>GCAGCCGGGGGCAGCACCTGTGGCAGCGCCTGTCCATCCACATCAACAAGAAAGAAAACCCCAACCAAA<br>CGGCCGTCATCAAGCCCTTCCCCAAGAGCACGGAGAGCCGTGGCCTGGGCGCTGGCGCTGGCGCAGGC<br>GGGAGCGCTGGGGGCGTGGGGGCCACGGGCGGTGCGGGCTGCGCAGGCGCCGGCCCAGGCGGGCCC<br>GAGTCCCCAGACGCCGGCCCCAAGGCGCTGTATGATGTGGCCGAGGCTGAGGAGCACTTCCCGGCGCCC<br>GCGCGGCCGCGCTCACCGTCGCCCATCAGCACGCTGAGCCACCGCGCGGGCTCGGCCAGCCGCACGGAC<br>GACGATGTGCCGTCGCTGCACTCGGAGCCTGTGGCGCGCAGCAGCTCCTCGCAGGGCTCCCTCATGGAG<br>CAGATCAGCAGTGTGGTCACCCGCTTCACGGCCAACATCAGCGAGCTCAACTCCATGATGCTGTCCACCG<br>CGGCCCCCAGCCCCGGCGTCGGCGCCCCGCTCTGCTCGTCCTACCTGATCCCCAAAGAGATCCAGTTGCC<br>CACGACCATGACGACCTTTGCCGAAATCCAGCCTCTGCCGGCCATCGAAGTCACGGGAGGCGCGCAGCC<br>CGCGGCAGGGGCGCAGGCGGCTGGGGACGCGGCCCGGGAGAGCCCCGCGGCCGGTCCCGAGGCTGCG<br>GCCGCCAAGCCAGACCTGGAGGAGCTGGTGGCTCTCACCCCGCCGTCCCCCTTCAGAGACTCGGTGGAC<br>TCGGGGAGCACAACCCCCAACTCGCCAGTGTCCGAGTCGGCCCTCTGTATCCCGTCGTCTCCCAAATATG<br>ACACTCTTATCATAAGAGATTACACTCAGAGCTCCTCGTCGTTGTGAATGTCCCTGGAAAGCACGCCGGC<br>CTGCGCG |
| HRAS | 181 | 2 | chr11:524182-524352 | GGACCCCGGGCCGCAGGCCCCTGAGGAGCGATGACGGAATATAAGCTGGTGGTGGTGGGCGCCGGCG<br>GTGTGGGCAAGAGTGCGCTGACCATCCAGCTGATCCAGAACCATTTTGTGGACGAATACGACCCCACTAT<br>AGAGGTGAGCCTGGCGCCGCCGTCCAGGTGCCAG |

FIG. 4 cont.

| | | | | |
|---|---|---|---|---|
| HRAS | 182 | 3 | chr11:523736-523974 | AGGGGGTCCCTGAGCCCTGTCCTCCTGCAGGATTCCTACCGGAAGCAGGTGGTCATTGATGGGGAGACG<br>TGCCTGTTGGACATCCTGGATACCGCCGGCCAGGAGGAGTACAGCGCCATGCGGGACCAGTACATGCGC<br>ACCGGGGAGGGCTTCCTGTGTGTGTTTGCCATCAACAACACCAAGTCTTTTGAGGACATCCACCAGTACA<br>GGTGAACCCCGTGAGGCTGGCCCGGGAGCCC |
| HRAS | 183 | 4 | chr11:523423-523642 | CGTAGCCAGCTCTCGCTTTCCACCTCTCAGGGAGCAGATCAAACGGGTGAAGGACTCGGATGACGTGCC<br>CATGGTGCTGGTGGGGAACAAGTGTGACCTGGCTGCACGCACTGTGGAATCTCGGCAGGCTCAGGACCT<br>CGCCCGAAGCTACGGCATCCCCTACATCGAGACCTCGGCCAAGACCCGGCAGGTGAGGCAGCTCTCCAC<br>CCCACAGCTAGCC |
| HRAS | 184 | 5 | chr11:523266-523388 | AGCACTCACTGACCCTCTCCCTTGACACAGGGCAGCCGCTCTGGCTCTAGCTCCAGCTCCGGGACCCTCT<br>GGGACCCCCCGGGACCCATGTGACCCAGCGGCCCCTCGCGCTGTAAGTCTCCC |
| MAP2K1 | 185 | 1 | chr15:64466710-64466849 | GGAGTTGGAAGCGCGTTACCCGGGTCCAAAATGCCCAAGAAGAAGCCGACGCCCATCCAGCTGAACCC<br>GGCCCCCGACGGCTCTGCAGTTAACGGGACCAGCTCTGCGGAGTAAGTATGGGGCGGGCGGTGAACCT<br>CGGG |
| MAP2K1 | 186 | 2 | chr15:64514389-64514659 | TATTGACTTGTGCTCCCCACTTTGGAACAGGACCAACTTGGAGGCCTTGCAGAAGAAGCTGGAGGAGCT<br>AGAGCTTGATGAGCAGCAGCGAAAGCGCCTTGAGGCCTTTCTTACCCAGAAGCAGAAGGTGGGAGAAC<br>TGAAGGATGACGACTTTGAGAAGATCAGTGAGCTGGGGGCTGGCAATGGCGGTGTGGTGTTCAAGGTC<br>TCCCACAAGCCTTCTGGCCTGGTCATGGCCAGAAAGGTGAGTTTGCCTTGATTAACAGGTAATTGG |
| MAP2K1 | 187 | 3 | chr15:64516108-64516314 | AAAACCTCTCTTTCTTCCACCTTTCTCCAGCTAATTCATCTGGAGATCAAACCCGCAATCCGGAACCAGATC<br>ATAAGGGAGCTGCAGGTTCTGCATGAGTGCAACTCTCCGTACATCGTGGGCTTCTATGGTGCGTTCTACA<br>GCGATGGCGAGATCAGTATCTGCATGGAGCACATGGTATGTGACACCCTCTCAGCCTCTGGAGCA |
| MAP2K1 | 188 | 4 | chr15:64522642-64522779 | CACTAACTGGTCTGGTATTCTCGATCTTAGGATGGAGGTTCTCTGGATCAAGTCCTGAAGAAAGCTGGAA<br>GAATTCCTGAACAAATTTTAGGAAAAGTTAGCATTGCTGTGAGTATGTTATGAAGTTTTTCTTCTAAG |
| MAP2K1 | 189 | 5 | chr15:64524018-64524129 | TTCTTTTCTTTTACATTCCCTTTCCTCTAGGTAATAAAAGGCCTGACATATCTGAGGGAGAAGCACAAGAT<br>CATGCACAGAGGTAAGAAGTTATTTGCTAGTTATTTTGCTT |
| MAP2K1 | 190 | 6 | chr15:64561117-64561301 | CCCTCCTTTTCTATTTTCTCTTCCCTGCAGATGTCAAGCCCTCCAACATCCTAGTCAACTCCCGTGGGGAGA<br>TCAAGCTCTGTGACTTTGGGGTCAGCGGGCAGCTCATCGACTCCATGGCCAACTCCTTCGTGGGCACAAG<br>GTCCTACATGTCGGTATGAACAGAAGTTTCCATTGCTTGAGCT |

FIG. 4 cont.

| | | | | |
|---|---|---|---|---|
| MAP2K1 | 191 | 7 | chr15:64564352-64564613 | GGTGATTATCACTGTCTGTCTCTCCTGCAGCCAGAAAGACTCCAGGGGACTCATTACTCTGTGCAGTCAG<br>ACATCTGGAGCATGGGACTGTCTCTGGTAGAGATGGCGGTTGGGAGGTATCCCATCCCTCCTCCAGATG<br>CCAAGGAGCTGGAGCTGATGTTTGGGTGCCAGGTGGAAGGAGATGCGGCTGAGACCCCACCCAGGCCA<br>AGGACCCCCGGGAGGCCCCTTAGCTGTGAGTAGCCTGGTGTGTCCCCATCTTGGA |
| MAP2K1 | 192 | 8 | chr15:64566590-64566714 | AAGTATTTTTTCTTTTTATAAAATTTGTAGCATACGGAATGGACAGCCGACCTCCCATGGCAATTTTTGAG<br>TTGTTGGATTACATAGTCAACGAGGTAAGTACTGCCTGGTTTCCTTCACCTTGG |
| MAP2K1 | 193 | 9 | chr15:64568577-64568698 | CATTTTTCTTATCTCAACATGTGTTTGCAGCCTCCTCCAAAACTGCCCAGTGGAGTGTTCAGTCTGGAATTT<br>CAAGATTTTGTGAATAAATGGTAAGTTGGCTCCTTGTTCTCTGGAAGCGT |
| MAP2K1 | 194 | 10 | chr15:64569080-64569185 | CAGCTCTTACCTTGTCTTTCTTCCTTTAAGCTTAATAAAAAACCCCGCAGAGAGAGCAGATTTGAAGCAAC<br>TCATGGTGAGTCTATTTATTCCGGATTCTTACAGT |
| MAP2K1 | 195 | 11 | chr15:64569864-64570037 | CACCACGTCCTCTCGTTTCCTTACATGCAGGTTCATGCTTTTATCAAGAGATCTGATGCTGAGGAAGTGGA<br>TTTTGCAGGTTGGCTCTGCTCCACCATCGGCCTTAACCAGCCCAGCACACCAACCCATGCTGCTGGCGTCT<br>AAGTGTTTGGGAAGCAACAAAGAGCGAGTCCC |
| UBE3A | 196 | 3 | chr15:23205298-23205377 | TCAAAGCTGTGATCACCCTGATGTCACCGAATGGCCACAGCTTGTAAAAGGTAATTTTGAATTATTTTACA<br>GCCTTTAAA |
| UBE3A | 197 | 4 | chr15:23201671-23201772 | TGCTAACTGTTTCTCAATTGCATTTTACAGATCAGGAGAACCTCAGTCTGACGACATTGAAGCTAGCCGA<br>ATGTAAGTGTAACTTGGTTGAGACTGTGGTTC |
| UBE3A | 198 | 5 | chr15:23171675-23172033 | CTGTGCTTATTGTTTGAATGTTTGGTACAGGAAGCGAGCAGCTGCAAAGCATCTAATAGAACGCTACTAC<br>CACCAGTTAACTGAGGGCTGTGGAAATGAAGCCTGCACGAATGAGTTTTGTGCTTCCTGTCCAACTTTTCT<br>TCGTATGGATAATAATGCAGCAGCTATTAAAGCCCTCGAGCTTTATAAGATTAATGCAAAACTCTGTGAT<br>CCTCATCCCTCCAAGAAAGGAGCAAGCTCAGCTTACCTTGAGAACTCGAAAGGTGCCCCCAACAACTCCT<br>GCTCTGAGATAAAAATGAACAAGAAAGGCGCTAGAATTGATTTTAAAGGTAAGATGTTTTATTTTCAATT<br>GAGAATTG |

FIG. 4 cont.

| | | | | |
|---|---|---|---|---|
| UBE3A | 199 | 6 | chr15:23166776-23168082 | AATGTTCTCTTTTTTCCTCTGATTTTCTAGATGTGACTTACTTAACAGAAGAGAAGGTATATGAAATTCTTG<br>AATTATGTAGAGAAAGAGAGGATTATTCCCCTTTAATCCGTGTTATTGGAAGAGTTTTTTCTAGTGCTGAG<br>GCATTGGTACAGAGCTTCCGGAAAGTTAAACAACACACCAAGGAAGAACTGAAATCTCTTCAAGCAAAA<br>GATGAAGACAAAGATGAAGATGAAAAGGAAAAAGCTGCATGTTCTGCTGCTGCTATGGAAGAAGACTC<br>AGAAGCATCTTCCTCAAGGATAGGTGATAGCTCACAGGGAGACAACAATTTGCAAAAATTAGGCCCTGA<br>TGATGTGTCTGTGGATATTGATGCCATTAGAAGGGTCTACACCAGATTGCTCTCTAATGAAAAAATTGAA<br>ACTGCCTTTCTCAATGCACTTGTATATTTGTCACCTAACGTGGAATGTGACTTGACGTATCACAATGTATA<br>CTCTCGAGATCCTAATTATCTGAATTTGTTCATTATCGTAATGGAGAATAGAAATCTCCACAGTCCTGAAT<br>ATCTGGAAATGGCTTTGCCATTATTTTGCAAAGCGATGAGCAAGCTACCCCTTGCAGCCCAAGGAAAACT<br>GATCAGACTGTGGTCTAAATACAATGCAGACCAGATTCGGAGAATGATGGAGACATTTCAGCAACTTATT<br>ACTTATAAAGTCATAAGCAATGAATTTAACAGTCGAAATCTAGTGAATGATGATGATGCCATTGTTGCTG<br>CTTCGAAGTGCTTGAAAATGGTTTACTATGCAAATGTAGTGGGAGGGGAAGTGGACACAAATCACAATG<br>AAGAAGATGATGAAGAGCCCATCCCTGAGTCCAGCGAGCTGACACTTCAGGAACTTTTGGGAGAAGAAA<br>GAAGAAACAAGAAAGGTCCTCGAGTGGACCCCCTGGAAACTGAACTTGGTGTTAAAACCCTGGATTGTC<br>GAAAACCACTTATCCCTTTTGAAGAGTTTATTAATGAACCACTGAATGAGGTTCTAGAAATGGATAAAGA<br>TTATACTTTTTTCAAAGTAGAAACAGAGAACAAATTCTCTTTTATGACATGTCCCTTTATATTGAATGCTGT( |
| UBE3A | 200 | 7 | chr15:23156593-23156797 | TCTTTTCATGTTTATCTTTTCAATCACTAGCTAGAGATGATCGCTATGGAAAATCCTGCAGACTTGAAGAA<br>GCAGTTGTATGTGGAATTTGAAGGAGAACAAGGAGTTGATGAGGGAGGTGTTTCCAAAGAATTTTTTCA<br>GCTGGTTGTGGAGGAAATCTTCAATCCAGATATTGGTAAATACATTAGTAATGTGATTATGGTGT |
| UBE3A | 201 | 8 | chr15:23152901-23153166 | TAATGTATTTTTAAAAATCATTTCTTATAGGTATGTTCACATACGATGAATCTACAAAATTGTTTTGGTTTA<br>ATCCATCTTCTTTTGAAACTGAGGGTCAGTTTACTCTGATTGGCATAGTACTGGGTCTGGCTATTTACAAT<br>AACTGTATACTGGATGTACATTTTCCCATGGTTGTCTACAGGAAGCTAATGGGGAAAAAAGGAACTTTTC<br>GTGACTTGGGAGACTCTCACCCAGTAAGTTCTTTGTCATTTTTTTAATTCAGT |
| UBE3A | 202 | 9 | chr15:23152102-23152326 | TGGCCTCAATTTACCATTTCTGGTTGCTAGGTTCTATATCAGAGTTTAAAAGATTTATTGGAGTATGAAGG<br>GAATGTGGAAGATGACATGATGATCACTTTCCAGATATCACAGACAGATCTTTTTGGTAACCCAATGATG<br>TATGATCTAAAGGAAAATGGTGATAAAATTCCAATTACAAATGAAAACAGGAAGGTAATAAATGTTTTTA<br>TGTCACATTTTGTC |
| UBE3A | 203 | 10 | chr15:23150738-23150953 | AGAAGTTCTTGTGATTAATGTTTTCTACAGGAATTTGTCAATCTTTATTCTGACTACATTCTCAATAAATCA<br>GTAGAAAAACAGTTCAAGGCTTTTCGGAGAGGTTTTCATATGGTGACCAATGAATCTCCCTTAAAGTACT<br>TATTCAGACCAGAAGAAATTGAATTGCTTATATGTGGAAGCCGGGTAAGAAAGCAGGTGTCTGCAAAAA<br>GTCAT |
| UBE3A | 204 | 11 | chr15:23150563-23150696 | TAACTAAGACATATTTTCTTGAATTTGCAGAATCTAGATTTCCAAGCACTAGAAGAAACTACAGAATATGA<br>CGGTGGCTATACCAGGGACTCTGTTCTGATTAGGTGAGGTACTTAGTTCTTCAGAGGAAGATT |

FIG. 4 cont.

| | | | | |
|---|---|---|---|---|
| UBE3A | 205 | 12 | chr15:23136295-23136498 | TGAAACCAGTATTGTATTTTTTCTCATTAGGGAGTTCTGGGAAATCGTTCATTCATTTACAGATGAACAGA AAAGACTCTTCTTGCAGTTTACAACGGGCACAGACAGAGCACCTGTGGGAGGACTAGGAAAATTAAAGA TGATTATAGCCAAAAATGGCCCAGACACAGAAAGGTAGGTAATTATTAACTTGTGACTGTATAC |
| UBE3A | 206 | 13 | chr15:23135347-23135527 | TCCTGTTTTTTTCCCCTTTTCTCTATTTAGGTTACCTACATCTCATACTTGCTTTAATGTGCTTTTACTTCCGG AATACTCAAGCAAAGAAAAACTTAAAGAGAGATTGTTGAAGGCCATCACGTATGCCAAAGGATTTGGCA TGCTGTAAAACAAAACAAAACAAAATAAAACAAAAAAA |
| TSC2 | 207 | 2 | chr16:2038588-2038785 | GAGGGGTTTTCTGGTGCGTCCTGGTCCACCATGGCCAAACCAACAAGCAAAGATTCAGGCTTGAAGGAG AAGTTTAAGATTCTGTTGGGACTGGGAACACCGAGGCCAAATCCCAGGTCTGCAGAGGGTAAACAGACG GAGTTTATCATCACCGCGGAAATACTGAGAGTGAGTGAGCTACCTGTGTCTTTGCTAGGC |
| TSC2 | 208 | 3 | chr16:2040372-2040518 | GCCCCTTTTTCTTCTTTCATCTCTCTCCAGGAACTGAGCATGGAATGTGGCCTCAACAATCGCATCCGGAT GATAGGGCAGATTTGTGAAGTCGCAAAAACCAAGAAATTTGAAGAGGTAGGTTTATCCAGTTGAGCTAC TAGAGAG |
| TSC2 | 209 | 4 | chr16:2043314-2043484 | CCTCACCGCTGTCCCCTCTGCTGGTGACAGCACGCAGTGGAAGCACTCTGGAAGGCGGTCGCGGATCTG TTGCAGCCGGAGCGGCCGCTGGAGGCCCGGCACGCGGTGCTGGCTCTGCTGAAGGCCATCGTGCAGGG GCAGGTAAGGCCCAGGGCGACGCTGGGATGGGTG |
| TSC2 | 210 | 5 | chr16:2044268-2044472 | CTCTGCTGATCCTGTGGCTTTTGTCTTTAGGGCGAGCGTTTGGGGGTCCTCAGAGCCCTCTTCTTTAAGGT CATCAAGGATTACCCTTCCAACGAAGACCTTCACGAAAGGCTGGAGGTTTTCAAGGCCCTCACAGACAAT GGGAGACACATCACCTACTTGGAGGAAGAGCTGGGTGGGTGCCACCTTGGGTTGGAGGTTTCTC |
| TSC2 | 211 | 6 | chr16:2045374-2045551 | CCTCGCAAACTGCCGCCGCTTCTCCCCCAGCTGACTTTGTCCTGCAGTGGATGGATGTTGGCTTGTCCTCG GAATTCCTTCTGGTGCTGGTGAACTTGGTCAAATTCAATAGCTGTTACCTCGACGAGTACATCGCAAGGA TGGTTCAGTAAGAAAAGAATTGAGATCCTGTTCTGAT |
| TSC2 | 212 | 7 | chr16:2046168-2046276 | TGCCGGGACTGAGCTCGGTGCTCCCTGCAGGATGATCTGTCTGCTGTGCGTCCGGACCGCGTCCTCTGTG GACATAGAGGTCAGTGCCTCCCCTCCCCAGGGCCGGCCC |
| TSC2 | 213 | 8 | chr16:2046616-2046801 | ACGGGCGTGAGCCGTCTCCCTCTCCACCAGGTCTCCCTGCAGGTGCTGGACGCCGTGGTCTGCTACAACT GCCTGCCGGCTGAGAGCCTCCCGCTGTTCATCGTTACCCTCTGTCGCACCATCAACGTCAAGGAGCTCTG CGAGCCTTGCTGGAAGGTGGGGTTTCTGAAACTGCTCTGGAAGGTT |
| TSC2 | 214 | 9 | chr16:2047077-2047210 | CCAGCCCCTGACACGCATTGTGTCTCGCAGCTGATGCGGAACCTCCTTGGCACCCACCTGGGCCACAGCG CCATCTACAACATGTGCCACCTCATGGAGGACAGGTGAGTGTGGTGGGTGGGGCGCAGGGCAGT |

FIG. 4 cont.

| | | | | |
|---|---|---|---|---|
| TSC2 | 215 | 10 | chr16:2048719-2048905 | ACATTCCGTCTCTCTGGGGAACACTTTTAGAGCCTACATGGAGGACGCGCCCCTGCTGAGAGGAGCCGTGTTTTTTGTGGGCATGGCTCTCTGGGGAGCCCACCGGCTCTATTCTCTCAGGAACTCGCCGACATCTGTGTTGCCATCATTTTACCAGGTAAGGCGGTTTCTGTGTGCAGTGAGCTGG |
| TSC2 | 216 | 11 | chr16:2050642-2050845 | CCCTGTGTGCTGGCCGGGCTCGTGTTCCAGGCCATGGCATGTCCGAACGAGGTGGTGTCCTATGAGATCGTCCTGTCCATCACCAGGCTCATCAAGAAGTATAGGAAGGAGCTCCAGGTGGTGGCGTGGGACATTCTGCTGAACATCATCGAACGGCTCCTTCAGCAGCTCCAGGTGGGGTGGGGGCAGGAGCTCCGGGGAGCA |
| TSC2 | 217 | 12 | chr16:2051843-2052040 | CAGCCTGTGTCATCGTGCCTGGTACTGCAGACCTTGGACAGCCCGGAGCTCAGGACCATCGTCCATGACCTGTTGACCACGGTGGAGGAGCTGTGTGACCAGAACGAGTTCCACGGGTCTCAGGAGAGATACTTTGAACTGGTGGAGAGATGTGCGGACCAGAGGCCTGTGAGACCCCCTCCTGGGTGGGGCCTTTGG |
| TSC2 | 218 | 13 | chr16:2052469-2052632 | GAGGGGCAACACCGGCTCTTCTTTTGACAGGAGTCCTCCCTCCTGAACCTGATCTCCTATAGAGCGCAGTCCATCCACCCGGCCAAGGACGGCTGGATTCAGAACCTGCAGGCGCTGATGGAGAGATTCTTCAGGTAGGGGGTCCTCTGTAGCCTTGCCTGGCA |
| TSC2 | 219 | 14 | chr16:2052944-2053085 | CACCCGCCCCAGCAGGCTGCCGTCCCGCAGGAGCGAGTCCCGAGGCGCCGTGCGCATCAAGGTGCTGGACGTGCTGTCCTTTGTGCTGCTCATCAACAGGCAGTTCTATGAGGTGCGTGTCCAGGCGGCCGCAGCTGGGGGC |
| TSC2 | 220 | 15 | chr16:2054244-2054459 | CGCTCATTGGCCTCCCTTGTGCCTGTGCAGGAGGAGCTGATTAACTCAGTGGTCATCTCGCAGCTCTCCCACATCCCCGAGGATAAAGACCACCAGGTCCGAAAGCTGGCCACCCAGTTGCTGGTGGACCTGGCAGAGGGCTGCCACACACACCACTTCAACAGCCTGCTGGACATCATCGAGAAGGTGAGAGCCGTTGTACCCGGGGCCGGGTGC |
| TSC2 | 221 | 16 | chr16:2055491-2055667 | TGTGTGTAAGTCCTGGCCTTCTCTTCAAAGGTGATGGCCCGCTCCCTCTCCCCACCCCCGGAGCTGGAAGAAAGGGATGTGGCCGCATACTCGGCCTCCTTGGAGGATGTGAAGACAGCCGTCCTGGGGCTTCTGGTCATCCTTCAGGTGGGTGTTCTGCACGAGGCCTCTGCTCCC |
| TSC2 | 222 | 17 | chr16:2060428-2060610 | GCCGTGGTGAGCTGCGTCCTCTCTCTGCAGACCAAGCTGTACACCCTGCCTGCAAGCCACGCCACGCGTGTGTATGAGATGCTGGTCAGCCACATTCAGCTCCACTACAAGCACAGCTACACCCTGCCAATCGCGAGCAGCATCCGGCTGCAGGTATGGTGGCTGGGGTTGCGCAGCCAGTTC |
| TSC2 | 223 | 18 | chr16:2061482-2061648 | CTCTGGCTTTCACCATCCTCTTCCTGACAGGCCTTTGACTTCCTGTTGCTGCTGCGGGCCGACTCACTGCACCGCCTGGGCCTGCCCAACAAGGATGGAGTCGTGCGGTTCAGCCCCTACTGCGTCTGCGACTACATGTACGCGGGACCTCGCCCACGGCCCATGAG |
| TSC2 | 224 | 19 | chr16:2061756-2061966 | TGGCCTCAGCTGCTTCTCTTGCTTCTGCAGGGAGCCAGAGAGAGGCTCTGAGAAGAAGACCAGCGGCCCCCTTTCTCCTCCCACAGGGCCTCCTGGCCCGGCGCCTGCAGGCCCCGCCGTGCGGCTGGGGTCCGTGCCCTACTCCCTGCTCTTCCGCGTCCTGCTGCAGTGCTTGAAGCAGGTGAGTGGGGCCGGGCAGGGACCATCCGTC |

FIG. 4 cont.

| | | | | |
|---|---|---|---|---|
| TSC2 | 225 | 20 | chr16:2062213-2062395 | GCCCTGTCCTGACGCCTCCTCTCCTCGCAGGAGTCTGACTGGAAGGTGCTGAAGCTGGTTCTGGGCAGGC<br>TGCCTGAGTCCCTGCGCTATAAAGTGCTCATCTTTACTTCCCCTTGCAGTGTGGACCAGCTGTGCTCTGCT<br>CTCTGCTCCATGGTACCATGGCCGGCCTGGGGTTGGGGTGGG |
| TSC2 | 226 | 21 | chr16:2062821-2063015 | AGAGGTTTCATGCCTGGATTTGGTCATCAGCTTTCAGGCCCAAAGACACTGGAGCGGCTCCGAGGCGCC<br>CCAGAAGGCTTCTCCAGAACTGACTTGCACCTGGCCGTGGTTCCAGTGCTGACAGCATTAATCTCTTACCA<br>TAACTACCTGGACAAAACCAAACAGGTAGGAGGTCAGAGCAGGACAGGCGAGCTT |
| TSC2 | 227 | 22 | chr16:2064172-2064421 | GTGGGGCCTGAGGTGTCCTGTCTCCTGCAGCGCGAGATGGTCTACTGCCTGGAGCAGGGCCTCATCCAC<br>CGCTGTGCCAGCCAGTGCGTCGTGGCCTTGTCCATCTGCAGCGTGGAGATGCCTGACATCATCATCAAGG<br>CGCTGCCTGTTCTGGTGGTGAAGCTCACGCACATCTCAGCCACAGCCAGCATGGCCGTCCCACTGCTGGA<br>GTTCCTGTCCAGTGAGTCCCCGCCCTGCCTGCGCATGCACC |
| TSC2 | 228 | 23 | chr16:2065771-2065924 | CTCCCCTGACCACCCTCTCCATTACCGCAGCTCTGGCCAGGCTGCCGCACCTCTACAGGAACTTTGCCGCG<br>GAGCAGTATGCCAGTGTGTTCGCCATCTCCCTGCCGTACACCAACCCCTCCAAGTGAGTGGTCGCCCCAG<br>GCCCTGTGCCTCC |
| TSC2 | 229 | 24 | chr16:2066040-2066202 | GATGGAGTGCCAGCCCCCTTCTCATCTCAGGTTTAATCAGTACATCGTGTGTCTGGCCCATCACGTCATAG<br>CCATGTGGTTCATCAGGTGCCGCCTGCCCTTCCGGAAGGATTTTGTCCCTTTCATCACTAAGGTGGGCTCA<br>GGGCCGGTGAAGGCTGTGTCT |
| TSC2 | 230 | 25 | chr16:2066463-2066617 | CTCACTGTCTGGGTGTGCTCACTCTGCCAGGGCCTGCGGTCCAATGTCCTCTTGTCTTTTGATGACACCCC<br>CGAGAAGGACAGCTTCAGGGCCCGGAGTACTAGTCTCAACGAGAGACCCAAGAGGTACGGCCTGCGGG<br>GGTGTGCCTGGAGTCG |
| TSC2 | 231 | 26 | chr16:2067570-2067758 | GGGCGTTGGGGCTCCTTCCTCACCCGATAGTCTGAGGATAGCCAGACCCCCCAAACAAGGCTTGAATAA<br>CTCTCCACCCGTGAAAGAATTCAAGGAGAGCTCTGCAGCCGAGGCCTTCCGGTGCCGCAGCATCAGTGT<br>GTCTGAACATGTGGTCCGCAGGTAGCGGGACTGTCGGGTGGGGGGCACGGA |
| TSC2 | 232 | 27 | chr16:2069004-2069228 | CCTGACCCTGGTCACGGCCTCTCCCTCCAGCAGGATACAGACGTCCCTCACCAGTGCCAGCTTGGGGTCT<br>GCAGATGAGAACTCCGTGGCCCAGGCTGACGATAGCCTGAAAAACCTCCACCTGGAGCTCACGGAAACC<br>TGTCTGGACATGATGGCTCGATACGTCTTCTCCAACTTCACGGCTGTCCCGAAGAGGTCCAGGCGGCACT<br>ACAGGGCTGGGCGGGC |
| TSC2 | 233 | 28 | chr16:2069248-2069460 | AAGCTGGGTTTCACGCTCCCTGTCTTCTAGGTCTCCTGTGGGCGAGTTCCTCCTAGCGGGTGGCAGGACC<br>AAAACCTGGCTGGTTGGGAACAAGCTTGTCACTGTGACGACAAGCGTGGGAACCGGGACCCGGTCGTTA<br>CTAGGCCTGGACTCGGGGGAGCTGCAGTCCGGCCCGGAGTCGAGGTGACTGCACCTTCCTTTCCTCCGC<br>GCCTG |
| TSC2 | 2334 | 29 | chr16:2069529-2069701 | TCCACCCTGTGCGTGGGATTCTCTTCTCAGCTCCAGCCCCGGGGTGCATGTGAGACAGACCAAGGAGGC<br>GCCGGCCAAGCTGGAGTCCCAGGCTGGGCAGCAGGTGTCCCGTGGGGCCCGGGATCGGGTCCGTTCCA<br>TGTCGGGTGAGCCTTGGCCCCAGCCACCTCCACACA |

FIG. 4 cont.

| | | | | |
|---|---|---|---|---|
| TSC2 | 235 | 30 | chr16:2070137-2070409 | TGGTCACCAGTCCTCTGCCCTCTTCTTCAGGGGGCCATGGTCTTCGAGTTGGCGCCCTGGACGTGCCGGC<br>CTCCCAGTTCCTGGGCAGTGCCACTTCTCCAGGACCACGGACTGCACCAGCCGCGAAACCTGAGAAGGC<br>CTCAGCTGGCACCCGGGTTCCTGTGCAGGAGAAGACGAACCTGGCGGCCTATGTGCCCCTGCTGACCCA<br>GGGCTGGGCGGAGATCCTGGTCCGGAGGCCCACAGGTACTGGGCGGGGCTGGCCTGAGCGCCATC |
| TSC2 | 236 | 31 | chr16:2071567-2071830 | CTCAGGCCAAAGGTGCTGCCGCCTCCGCAGGGAACACCAGCTGGCTGATGAGCCTGGAGAACCCGCTCA<br>GCCCTTTCTCCTCGGACATCAACAACATGCCCCTGCAGGAGCTGTCTAACGCCCTCATGGCGGCTGAGCG<br>CTTCAAGGAGCACCGGGACACAGCCCTGTACAAGTCACTGTCGGTGCCGGCAGCCAGCACGGCCAAACC<br>CCCTCCTCTGCCTCGCTCCAACACAGGTGAGTGGCATGGCGGGCCTTGGCACGGGC |
| TSC2 | 237 | 32 | chr16:2072408-2072536 | GACGTGGCCGCACACGGCCTTCCCTTGCAGTGGCCTCTTTCTCCTCCCTGTACCAGTCCAGCTGCCAAGGA<br>CAGCTGCACAGGAGCGTTTCCTGGGCAGGTATCGCCTCTCAGAGGGAAGCGGTTGGCT |
| TSC2 | 238 | 33 | chr16:2073667-2073848 | CATCCAGCAGCCCCGTCTGTGTCCTCCCAGACTCCGCCGTGGTCATGGAGGAGGGAAGTCCGGGCGAGG<br>TTCCTGTGCTGGTGGAGCCCCCAGGGTTGGAGGACGTTGAGGCAGCGCTAGGCATGGACAGGCGCACG<br>GATGCCTACAGCAGGGTGAGTGTGGCTCAGAGCCTGGACCCTGCT |
| TSC2 | 239 | 34 | chr16:2074200-2074747 | AGGGGTTCTCTTTGGGATGGTCCTTTCTAGTCGTCCTCAGTCTCCAGCCAGGAGGAGAAGTCGCTCCACG<br>CGGAGGAGCTGGTTGGCAGGGGCATCCCCATCGAGCGAGTCGTCTCCTCGGAGGGTGGCCGGCCCTCT<br>GTGGACCTCTCCTTCCAGCCCTCGCAGCCCCTGAGCAAGTCCAGCTCCTCTCCCGAGCTGCAGACTCTGCA<br>GGACATCCTCGGGGACCCTGGGGACAAGGCCGACGTGGGCCGGCTGAGCCCTGAGGTTAAGGCCCGGT<br>CACAGTCAGGGACCCTGGACGGGGAAAGTGCTGCCTGGTCGGCCTCGGGCGAAGACAGTCGGGGCCAG<br>CCCGAGGGTCCCTTGCCTTCCAGCTCCCCCCGCTCGCCCAGTGGCCTCCGGCCCCGAGGTTACACCATCTC<br>CGACTCGGCCCCATCACGCAGGGGCAAGAGAGTAGAGAGGGACGCCTTAAAGAGCAGAGCCACAGCCT<br>CCAATGCAGAGAAAGTGCCAGGCATCAACCCCAGGTGGGCCTCTTGCTTCCGGGCGGGGCTCCT |
| TSC2 | 240 | 35 | chr16:2074923-2075058 | CTGGGTGCCCACCATCCCCTCCCTGTGCAGTTTCGTGTTCCTGCAGCTCTACCATTCCCCCTTCTTTGGCGA<br>CGAGTCAAACAAGCCAATCCTGCTGCCCAATGAGGTAGGCGTGGCCTCCCTCTCCTGCATCCGC |
| TSC2 | 241 | 36 | chr16:2075202-2075354 | GGGGCTCAGGCAGGGCTCTGTGTGCCACAGTCACAGTCCTTTGAGCGGTCGGTGCAGCTCCTCGACCAG<br>ATCCCATCATACGACACCCACAAGATCGCCGTCCTGTATGTTGGAGAAGGCCAGGTGAGGCTGCGGGGC<br>CGGCCTAGGTGCCTG |
| TSC2 | 242 | 37 | chr16:2076165-2076411 | TGCCACCCTGCCTCTCCCCTCTCCCCACAGAGCAACAGCGAGCTCGCCATCCTGTCCAATGAGCATGGCTC<br>CTACAGGTACACGGAGTTCCTGACGGGCCTGGGCCGGCTCATCGAGCTGAAGGACTGCCAGCCGGACA<br>AGGTGTACCTGGGAGGCCTGGACGTGTGTGGTGAGGACGGCCAGTTCACCTACTGCTGGCACGATGAC<br>ATCATGCAAGGTACGGCCTGGCGCCTACCCGCTCCTGCTG |

FIG. 4 cont.

| | | | | |
|---|---|---|---|---|
| TSC2 | 243 | 38 | chr16:2076704-2076903 | ACAAACCCATCCGGCCCTGCTCACCCTCAGCCGTCTTCCACATCGCCACCCTGATGCCCACCAAGGACGTG<br>GACAAGCACCGCTGCGACAAGAAGCGCCACCTGGGCAACGACTTTGTGTCCATTGTCTACAATGACTCCG<br>GTGAGGACTTCAAGCTTGGCACCATCAAGGTGAGTGAGGGGCCGTCAGTGAGGCTGGGC |
| TSC2 | 244 | 39 | chr16:2077835-2077973 | CGGGGATGACCCTTTCTCTTGTCCGGGCAGGGCCAGTTCAACTTTGTCCACGTGATCGTCACCCCGCTGG<br>ACTACGAGTGCAACCTGGTGTCCCTGCAGTGCAGGAAAGGTAGGGCCGGGTGGGGCCCTGCAGTGCAG<br>G |
| TSC2 | 245 | 40 | chr16:2078020-2078171 | GGGCCTGGCGTGACCACCAAGTCTCCCCAGACATGGAGGGCCTTGTGGACACCAGCGTGGCCAAGATCG<br>TGTCTGACCGCAACCTGCCCTTCGTGGCCCGCCAGATGGCCCTGCACGCAAATGTGAGTGGGGGTGGGT<br>CCAGGCGTGAGCTG |
| TSC2 | 246 | 41 | chr16:2078199-2078357 | AGTGAGCTCACCCCCTGCCTACGTCCCCAGATGGCCTCACAGGTGCATCATAGCCGCTCCAACCCCACCG<br>ATATCTACCCCTCCAAGTGGATTGCCCGGCTCCGCCACATCAAGCGGCTCCGCCAGCGGGTAGGGAATAT<br>GGGGCTCCCTCAGCGGGGT |
| TSC2 | 247 | 42 | chr16:2078418-2078642 | ACTTACTGCCCAAGCCGCCTCTGCCTTCAGATCTGCGAGGAAGCCGCCTACTCCAACCCCAGCCTACCTCT<br>GGTGCACCCTCCGTCCCATAGCAAAGCCCCTGCACAGACTCCAGCCGAGCCCACACCTGGCTATGAGGTG<br>GGCCAGCGGAAGCGCCTCATCTCCTCGGTGGAGGACTTCACCGAGTTTGTGTGAGGCCGGGGCCCTCCC<br>TCCTGCACTGGCCTT |
| MAP2K2 | 248 | 1 | chr19:4074751-4074902 | GCGCCGCCGCCGCCGGCCCGCGGAGCCCCGATGCTGGCCCGGAGGAAGCCGGTGCTGCCGGCGCTCAC<br>CATCAACCCTACCATCGCCGAGGGCCCATCCCCTACCAGCGAGGGCGCCTCCGAGTGAGTGGGCAGGGG<br>TCAGCCGGAGGCTTG |
| MAP2K2 | 249 | 2 | chr19:4068387-4068657 | GCTAACCCCTACCCTGGGGGGTCTCTGCAGGGCAAACCTGGTGGACCTGCAGAAGAAGCTGGAGGAGC<br>TGGAACTTGACGAGCAGCAGAAGAAGCGGCTGGAAGCCTTTCTCACCCAGAAAGCCAAGGTCGGCGAA<br>CTCAAAGACGATGACTTCGAAAGGATCTCAGAGCTGGGCGCGGGCAACGGCGGGGTGGTCACCAAAGT<br>CCAGCACAGACCCTCGGGCCTCATCATGGCCAGGAAGGTGAGCACTGCGGGGTCGGGGAGGTCGGGG |
| MAP2K2 | 250 | 3 | chr19:4061477-4061683 | CAAGCCAGTCTCGCCCCTCTCCCCTTGCAGCTGATCCACCTTGAGATCAAGCCGGCCATCCGGAACCAGA<br>TCATCCGCGAGCTGCAGGTCCTGCACGAATGCAACTCGCCGTACATCGTGGGCTTCTACGGGGCCTTCTA<br>CAGTGACGGGGAGATCAGCATTTGCATGGAACACATGGTGAGTGCGTCCGGGGCAGGGGCAGGGGCA |
| MAP2K2 | 251 | 4 | chr19:4053344-4053481 | GCCTGCACTCACTCCTTGTGTGCCCTCTAGGACGGCGGCTCCCTGGACCAGGTGCTGAAAGAGGCCAAG<br>AGGATTCCCGAGGAGATCCTGGGGAAAGTCAGCATCGCGGTGAGTCCACCGCAGACCCACATCGCGCCC |
| MAP2K2 | 252 | 5 | chr19:4052197-4052308 | TCCCGTGACTCCCTCCGCGCTCCCCTGCAGGTTCTCCGGGGCTTGGCGTACCTCCGAGAGAAGCACCAGA<br>TCATGCACCGAGGTAAGGCCCAGCCCGCCCTCCCCAGAGCCC |

FIG. 4 cont.

| | | | |
|---|---|---|---|
| MAP2K2 253 | 6 | chr19:4051987-4052171 | CGCCCCTCACCCGCAGCCTGCCGCCTCCAGATGTGAAGCCCTCCAACATCCTCGTGAACTCTAGAGGGGA<br>GATCAAGCTGTGTGACTTCGGGGTGAGCGGCCAGCTCATCGACTCCATGGCCAACTCCTTCGTGGGCAC<br>GCGCTCCTACATGGCTGTGAGTCCCCGCTGGCTCTCCCCTCCAGCT |
| MAP2K2 254 | 7 | chr19:4050169-4050442 | TGGGCTCTTTCCTCCCTGGCTCTGCTGCAGCCGGAGCGGTTGCAGGGCACACATTACTCGGTGCAGTCGG<br>ACATCTGGAGCATGGGCCTGTCCCTGGTGGAGCTGGCCGTCGGAAGGTACCCCATCCCCCCGCCCGACG<br>CCAAAGAGCTGGAGGCCATCTTTGGCCGGCCCGTGGTCGACGGGGAAGAAGGAGAGCCTCACAGCATC<br>TCGCCTCGGCCGAGGCCCCCCGGGCGCCCCGTCAGCGGTACGGCCTGAATCTGCAACTTCCGGTCTG |
| MAP2K2 255 | 8 | chr19:4048247-4048371 | CATCTCACCTCCATCTCTCTCCCTGTGCAGGTCACGGGATGGATAGCCGGCCTGCCATGGCCATCTTTGAA<br>CTCCTGGACTATATTGTGAACGAGGTTTGTGCTTGATGCCTTTTGGCTTTTCTT |
| MAP2K2 256 | 9 | chr19:4046356-4046477 | GCTGACCCCACCCTCTGTTCTCCTCCACAGCCACCTCCTAAGCTGCCCAACGGTGTGTTCACCCCCGACTTC<br>CAGGAGTTTGTCAATAAATGGTAGGTGGAGCCGGGCTGCCCACACCCCTG |
| MAP2K2 257 | 10 | chr19:4045421-4045526 | CCTCCCGGTCCTGCCTCTTGGAACCCCCAGCCTCATCAAGAACCCAGCGGAGCGGGCGGACCTGAAGAT<br>GCTCACAGTGAGTGATGCCAGCGGGTTCTGGGACCGG |
| MAP2K2 258 | 11 | chr19:4041566-4041736 | CGGGTGCTCACGGCTCCCCTTTCCTTGCAGAACCACACCTTCATCAAGCGGTCCGAGGTGGAAGAAGTG<br>GATTTTGCCGGCTGGTTGTGTAAAACCCTGCGGCTGAACCAGCCCGGCACACCCACGCGCACCGCCGTGT<br>GACAGTGGCCGGGCTCCCTGCGTCCCGCTGGT |
| SHANK3 259 | 1 | chr22:49459906-49460028 | AGCGGCCCCGGCCCGGGCCCCGGCGCGGGGATGGACGGCCCCGGGGCCAGCGCCGTGGTCGTGCGCG<br>TCGGCATCCCGGACCTGCAGCAGACGGTGAGCCCCGCCGCCCTGGGCCCGGCCGTG |
| SHANK3 250 | 2 | chr22:49460312-49460575 | ACCTGAGCTCACGAGCCCGCTCCGCTGCAGAAGTGCCTGCGCCTGGACCCGGCCGCGCCCGTGTGGGCC<br>GCCAAGCAGCGCGTGCTCTGCGCCCTCAACCACAGCCTCCAGGACGCGCTCAACTATGGGCTTTTCCAGC<br>CGCCCTCCCGGGGCCGCGCCGGCAAGTTCCTGGATGAGGAGCGGCTCCTGCAGGAGTACCCGCCCAACC<br>TGGACACGCCCCTGCCCTACCTGGAGGTAAGTGGCCGGCGCGGGGGTGAGCTGAGG |
| SHANK3 251 | 3 | chr22:49461886-49462017 | ATTTTCTCTACCTTTTCTTTATCTGAGCAGTTTCGATACAAGCGGCGAGTTTATGCCCAGAACCTCATCGAT<br>GATAAGCAGTTTGCAAAGCTTCACACAAAGGTAAAGGATCACGGGGAGGGGGCTCCTGAG |
| SHANK3 252 | 4 | chr22:49463849-49464017 | TGCCAGGCTGACTGACGGCCGGTGTTCCAGGCGAACCTGAAGAAGTTCATGGACTACGTCCAGCTGCAT<br>AGCACGGACAAGGTGGCACGCCTGTTGGACAAGGGGCTGGACCCCAACTTCCATGACCCTGACTCAGGA<br>GGTGAGGAGTGGAGTCGGGGAGGGGCATGGC |
| SHANK3 253 | 5 | chr22:49464033-49464244 | AGCCTGACCCTTATCTGTCTGTGAACCCAGAGTGCCCCCTGAGCCTCGCAGCCCAGCTGGACAACGCCAC<br>GGACCTGCTAAAGGTGCTGAAGAATGGTGGTGCCCACCTGGACTTCCGCACTCGCGATGGGCTCACTGC<br>CGTGCACTGTGCCACACGCCAGCGGAATGCGGCAGCACTGACGGTCAGTGAGGGCGGGGCCTGGCCTG<br>GAGGG |

FIG. 4 cont.

| | | | | |
|---|---|---|---|---|
| SHANK3 | 254 | 6 | chr22:49464283-49464510 | GGTGTGGATACTGAGGCTGCTCACCCTCAGACCCTGCTGGACCTGGGGGCTTCACCTGACTACAAGGAC<br>AGCCGCGGCTTGACACCCCTCTACCACAGCGCCCTGGGGGGTGGGGATGCCCTCTGCTGTGAGCTGCTT<br>CTCCACGACCACGCTCAGCTGGGGATCACCGACGAGAATGGCTGGCAGGAGATCCACCAGGTGTGCAG<br>GGAGCCGAGGTGGGGTCCCGGC |
| SHANK3 | 255 | 7 | chr22:49464576-49464752 | GGACCCTACAGCACCTTGCTCTTCCCCCAGGCCTGCCGCTTTGGGCACGTGCAGCATCTGGAGCACCTGC<br>TGTTCTATGGGGCAGACATGGGGGCCCAGAACGCCTCGGGGAACACAGCCCTGCACATCTGTGCCCTCT<br>ACAACCAGGTGCGACTGTGTGTCCTGCACATGCCTGCA |
| SHANK3 | 256 | 8 | chr22:49468604-49468741 | CCAGCTGTGATTCCCTCTTCCCCGCAACAGGAGAGCTGTGCTCGTGTCCTGCTCTTCCGTGGAGCTAACA<br>GGGATGTCCGCAACTACAACAGCCAGACAGCCTTCCAGGTACACCGGTGGTTTACAGGAGCTCAAGGC |
| SHANK3 | 257 | 9 | chr22:49469849-49469975 | CTCAAGGCCTTGACCTCCCCTTTCCCTCAGGTGGCCATCATCGCAGGGAACTTTGAGCTTGCAGAGGTTAT<br>CAAGACCCACAAAGACTCGGATGTTGGTGAGTTCTGCCCACCTGGGCGACCCTGCT |
| SHANK3 | 258 | 10 | chr22:49480039-49480372 | CAGAGTCTTACCTATGCCCCCTTACCCCAGTACCATTCAGGGAAACCCCCAGCTATGCGAAGCGGCGGCG<br>ACTGGCTGGCCCCAGTGGCTTGGCATCCCCTCGGCCTCTGCAGCGCTCAGCCAGCGATATCAACCTGAAG<br>GGGGAGGCACAGCCAGCAGCTTCTCCTGGACCCTCGCTGAGAAGCCTCCCCCACCAGCTGCTGCTCCAG<br>CGGCTGCAAGAGGAGAAAGATCGTGACCGGGATGCCGACCAGGAGAGCAACATCAGTGGCCCTTTAGC<br>AGGCAGGGCCGGCCAAAGCAAGATCAGGTAGGAGGGGGCTGGCAGGCCCTGGAGGGG |
| SHANK3 | 259 | 11 | chr22:49482507-49482615 | CCCAGGCCTAGAGGGGGACTGGGCACCCAGCGATCCGGGCCCTGGACCTGGAGGGGTGGGGGGGCG<br>CCCCTCCCTCCCGTTCACCGGCTCCAGGCGGCTTTGCTGGTG |
| SHANK3 | 260 | 12 | chr22:49482787-49483039 | GGGCGCGGGGCGGCCGCGGCATGGAGCGAGCCTGGCGCGCCCAGGAGCTGTATTCGAATTCGAGCTCG<br>GTTCCCCGCGCCCCCTGCGCCCCCCGCACCGCCGCCCCGGGGCCCGAAGCGGAAACTTTACAGCGCCGTC<br>CCCGGCCGCAAGTTCATCGCCGTGAAGGCGCACAGCCCGCAGGGTGAAGGCGAGATCCCGCTGCACCG<br>CGGCGAGGCCGTGAAGGGTGAGGGGCGCGGGGGGGCGCGGGGGGGCG |
| SHANK3 | 261 | 13 | chr22:49483954-49484127 | ACTGACGGCCTGTCTGGCTTCTTCCTCCAGTGCTCAGCATTGGGGAGGGCGGTTTCTGGGAGGGAACCG<br>TGAAAGGCCGCACGGGCTGGTTCCCGGCCGACTGCGTGGAGGAAGTGCAGATGAGGCAGCATGACACA<br>CGGCCTGGTGAGTGACCCCACGGCTCCCCGGGCAGCT |
| SHANK3 | 262 | 14 | chr22:49489124-49489259 | CTGTCCATCAGCTCCCGATACTCCCTTCAGAAACGCGGGAGGACCGGACGAAGCGGCTCTTTCGGCACTA<br>CACAGTGGGCTCCTACGACAGCCTCACCTCACACAGGTACGTGCAGGGACCCTGGCTGGCGGGAGC |
| SHANK3 | 263 | 15 | chr22:49489430-49489572 | ACCTCACTCCTCCCTGCTTTCCTTCATCAGCGATTATGTCATTGATGACAAAGTGGCTGTCCTGCAGAAAC<br>GGGACCACGAGGGCTTTGGTTTTGTGCTCCGGGGAGCCAAAGGTAATGGGGAGTGGGTGCCCGGGGGT<br>CAGG |

FIG. 4 cont.

| | | | | |
|---|---|---|---|---|
| SHANK3 | 264 | 16 | chr22:49490002-49490186 | GTGAAGCGCCTTCCTAATTGCCCCCCGCAGCAGAGACCCCCATCGAGGAGTTCACGCCCACGCCAGCCTT<br>CCCGGCGCTGCAGTATCTCGAGTCGGTGGACGTGGAGGGTGTGGCCTGGAGGGCCGGGCTGCGCACGG<br>GAGACTTCCTCATCGAGGTGAGGTCGTTCTGGCCGGTGCTGCCCAGT |
| SHANK3 | 265 | 17 | chr22:49490228-49490420 | CGTCCCCACCCAGCTGCCTGTCTATCCCAGGTGAACGGGGTGAACGTGGTGAAGGTCGGACACAAGCAG<br>GTGGTGGCTCTGATTCGCCAGGGTGGCAACCGCCTCGTCATGAAGGTTGTGTCTGTGACAAGGAAGCCA<br>GAAGAGGACGGGGCTCGGCGCAGAGGTGAGGGGTCACGCTTCAGGCCTCTGTGCC |
| SHANK3 | 266 | 18 | chr22:49491336-49491476 | GGAGGTCCAAGGCCTCCCTCTTCTTTGCAGCCCCACCGCCCCCCAAGAGGGCCCCCAGCACCACACTGAC<br>CCTGCGCTCCAAGTCCATGACAGCTGAGCTCGAGGAACTTGGTGAGTGGCGGGGGTGGCGGTGGAGGT<br>GGA |
| SHANK3 | 267 | 19 | chr22:49496879-49496962 | ACTCCCTTTACTCTGTTTCTTGATTCCAAGCCTCCATTCGGAGAAGAAAAGGGGGTGAGTCATCTGCCTGT<br>GTCCCCAGGGCCT |
| SHANK3 | 268 | 20 | chr22:49500181-49500371 | CAGCTGAGATGGAGCCTCCTTGCTGTGCAGAGAAGCTGGACGAGATGCTGGCAGCCGCCGCAGAGCCA<br>ACGCTGCGGCCAGACATCGCAGACGCAGACTCCAGAGCCGCCACCGTCAAACAGAGGCCCACCAGTCG<br>GAGGATCACACCCGCCGAGATTAGCGTAAGGGCCACGGGCGGCTGGGAGCGCTGG |
| SHANK3 | 269 | 21 | chr22:49500933-49501077 | CCTCCATATTCCCCTCCCTGACCCCCACAGTCATTGTTTGAACGCCAGGGCCTCCCAGGCCCAGAGAAGCT<br>GCCGGGCTCCTTGCGGAAGGGGATTCCACGGACCAAGTCTGTAGGTATGGCTGCGCTGTGGGGCTGCAT<br>GGGGT |
| SHANK3 | 270 | 22 | chr22:49505448-49507761 | GGCTGGTCTCACCGGCCCTTCCGTCCGCAGGGGAGGACGAGAAGCTGGCGTCCCTGCTGGAAGGGCGC<br>TTCCCGCGGAGCACCTCGATGCAAGACCCGGTGCGCGAGGGTCGCGGCATCCCGCCCCCGCCGCAGACC<br>GCGCCGCCTCCCCCGCCCGCGCCCTACTACTTCGACTCGGGGCCGCCCCCGGCCTTCTCGCCGCCGCCCCC<br>GCCGGGCCGCGCCTACGACACGGTGCGCTCCAGCTTCAAGCCCGGCCTGGAGGCGCGCCTGGGCGCGG<br>GCGCTGCCGGCCTGTACGAGCCGGGCGCGGCCCTCGGCCCGCTGCCGTATCCCGAGCGGCAGAAGCGC<br>GCGCGCTCCATGATCATCCTGCAGGACTCGGCGCCCGAGTCGGGCGACGCCCCTCGACCCCCGCCCGCG<br>GCCACCCCGCCCGAGCGACCCAAGCGCCGGCCGCGGCCGCCCGGCCCCGACAGCCCCTACGCCAACCTG<br>GGCGCCTTCAGCGCCAGCCTCTTCGCTCCGTCCAAGCCGCAGCGCCGCAAGAGCCCCCTGGTGAAGCAG<br>CTGCAGGTGGAGGACGCGCAGGAGCGCGCGGCCCTGGCCGTGGGCAGCCCCGGTCCCGGCGGCGGCA<br>GCTTCGCCCGCGAGCCCTCCCCGACCCACCGCGGTCCGCGCCCGGGTGGCCTCGACTACGGCGCGGGCG<br>ATGGCCCGGGGCTCGCGTTCGGCGGCCCGGGCCCGGCCAAGGACCGGCGGCTGGAGGAGCGGCGCCG<br>CTCCACTGTGTTCCTGTCCGTGGGGGCCATCGAGGGCAGCGCCCCCGGCGCGGATCTGCCATCCCTACAG<br>CCCTCCCGCTCCATCGACGAGCGCCTCCTGGGGACCGGCCCCACCGCCGGCCGCGACCTGCTGCTGCCCT<br>CCCCGGTGTCTGCCCTGAAGCCGTTGGTCAGCGGCCCGAGCCTGGGGCCCTCGGGTTCCACCTTCATCCA<br>CCCACTCACCGGCAAACCCCTGGACCCCAGCTCACCCCTGGCCCTTGCCCTGGCTGCCCGAGAGCGAGCT<br>CTGGCCTCCCAGGCGCCCTCCCGGTCCCCCACACCCGTGCACAGTCCCGACGCCGACCGCCCCGGACCCCT |

FIG. 4 cont.

| | | | | |
|---|---|---|---|---|
| | | | | CACCTGGCGCTGACCCCTCTCCCTCCGCAGGCTCTTCAGCAGCCTCGGTGAGCTGAGCTCCATTTCAGCGC<br>AGCGCAGCCCCGGGGGCCCGGGCGGCGGGGCCTCGTACTCGGTGAGGCCCAGTGGCCGCTACCCCGTG<br>GCGAGACGCGCCCCGAGCCCGGTGAAGCCCGCGTCGCTGGAGCGGGTGGAGGGGCTGGGGGCGGGCG<br>CGGGGGGCGCAGGGCGGCCCTTCGGCCTCACGCCCCCCACCATCCTCAAGTCGTCCAGCCTCTCCATCCC<br>GCACGAGCCCAAGGAGGTGCGCTTCGTGGTGCGCAGCGTGAGCGCGCGCAGTCGCTCCCCCTCGCCGTC<br>GCCGCTGCCCTCGCCCGCGTCCGGCCCCGGCCCCGGCGCCCCCGGCCCACGCCGACCCTTCCAGCAGAA<br>GCCGCTGCAGCTCTGGAGCAAGTTCGACGTGGGCGACTGGCTGGAGAGCATCCACCTAGGCGAGCACC<br>GCGACCGCTTCGAGGACCATGAGATAGAAGGCGCGCACCTACCCGCGCTTACCAAGGACGACTTCGTGG<br>AGCTGGGCGTCACGCGCGTGGGCCACCGCATGAACATCGAGCGCGCGCTCAGGCAGCTGGACGGCAGC |
| SHANK3 | 271 | 23 | chr22:49515985-49516636 | TGACGCCCCACCCCCACTCCCGCCCCGGCCGTG |

FIG. 4 cont.

SEQUENCE LISTING

<160> NUMBER OF SEQ ID NOS: 281

<210> SEQ ID NO 1
<211> LENGTH: 2985
<212> TYPE: DNA
<213> ORGANISM: Homo sapiens

<400> SEQUENCE: 1
tcgggcacgg cgtcctccct ccgcagcagc cgagccggac ctgcctcccc gggcgtgctc 60
cgccggcccc gccgccggcc cgcagcgaca gacaggcgct ccccgcagct ccgcacggga 120
cccaggccgc cggaccccag cgccggacca ccctctgtcc gccccgagga gtttgccgcc 180
tgccggagca cctgcgcaca gatggagctg gaccaccgga ccagcggcgg gctccacgcc 240
taccccgggc cgcggggcgg gcaggtggcc aagcccaacg tgatcctgca gatcgggaag 300
tgccgggccg agatgctgga gcacgtgcgg cggacgcacc ggcacctgct ggccgaggtg 360
tccaagcagg tggagcgcga gctgaagggg ctgcaccggt cggtcgggaa gctggagagc 420
aacctggacg gctacgtgcc cacgagcgac tcgcagcgct ggaagaagtc catcaaggcc 480
tgcctgtgcc gctgccagga gaccatcgcc aacctggagc gctgggtcaa gcgcgagatg 540
cacgtgtggc gcgaggtgtt ctaccgcctg gagcgctggg ccgaccgcct ggagtccacg 600
ggcggcaagt acccggtggg cagcgagtca gcccgccaca ccgtttccgt gggcgtgggg 660
ggtcccgaga gctactgcca cgaggcagac ggctacgact acaccgtcag cccctacgcc 720
atcaccccgc ccccagccgc tggcgagctg cccgggcagg agcccgccga ggcccagcag 780
taccagccgt gggtccccgg cgaggacggg cagcccagcc ccggcgtgga cacgcagatc 840
ttcgaggacc ctcgagagtt cctgagccac ctagaggagt acttgcggca ggtgggcggc 900
tctgaggagt actggctgtc ccagatccag aatcacatga acgggccggc caagaagtgg 960
tgggagttca agcagggctc cgtgaagaac tgggtggagt tcaagaagga gttcctgcag 1020
tacagcgagg gcacgctgtc ccgagaggcc atccagcgcg agctggacct gccgcagaag 1080
cagggcgagc cgctggacca gttcctgtgg cgcaagcggg acctgtacca gacgctctac 1140
gtggacgcgg acgaggagga gatcatccag tacgtggtgg gcaccctgca gcccaagctc 1200
aagcgtttcc tgcgccaccc cctgcccaag accctggagc agctcatcca gaggggcatg 1260
gaggtgcagg atgacctgga gcaggcggcc gagccggccg gcccccacct cccggtggag 1320
gatgaggcgg agaccctcac gcccgccccc aacagcgagt ccgtggccag tgaccggacc 1380
cagcccgagt agagggcatc ccggagcccc cagcctgccc actacatcca gcctgtggct 1440
ttgcccacca ggacttttga gctggggctg actcctgcag ggaagccct ggtccagctg 1500 ggtgcccccct cgagctccgg gcggactcgc acacactcgt gtcatccaga tgtgagcacc 1560
gcacccagcg gcaaagagcc ctcccccctg cagggctcca cccatcaccc tccctccgtc 1620
tgtctttccg gcctggaccc caccctccac actctcaggc catcacagaa caccccagct 1680
tcctcattct gctacaacac ccaggccctc tggacatcca gaaaaccaag tgtccggatg 1740
gcaggggcca gcggccacca agctcatggg acacccagag cagaagctag ggcagagcca 1800
atgctgaggg agcctcgact tccggcgccg ccgccctctc ccggcatccg cagagccagc 1860
tgacgccctc cctgcctccc agggcagctg gccagcctcg ggcagcgcgg ccccctcctc 1920
ccaggggaga gtagaagtcg cacacgcagc agagcagacc tgatgtcccg gtgcttcctg 1980
gcccctcagc tccagtgatt cacgcccgcc tggagaagaa tcagagctca gctcatgact 2040
cacccatggc aggcggaggg tcccagaggg gctgagtcct caaatccggc tgaggcagca 2100

```
gctggcacca tcagagccag gagagtgaca acaggtctca aggttcccac aaagtctttg   2160

ctgctgtgct gggcaccacc caccccctcac cttgcaggct gcctgcgtgg gaggcgaagt   2220

cccaggacag cccagagggg ggctacagag aggagtcggc tgcagcagag ggcaggagcc   2280

ccagcttagc cctgagcgcc agcgcgagga ccagggcctg ccactaagcc cgccccgctg   2340

gccgccagct gcccgtcccc agagccactg cagcaggagt cgggccctgc ctccctccca   2400

gcagggaaac cccgcccgct gccaggccat cctctctgcc agaggctttc atgagcccca   2460

aggctggggc cacagctcct acccctgccc agcagccctg agctcagctg caggaaggac   2520

atcccagaag ccatggctcc tggggcgctt ccaggcattc tgccctgccc cgacaccaga   2580

accctggtgc tggtgggcca ctagcgtctg cagcctaagc aggtgctggc tcagggttca   2640

tcgttctgcc ttgtccactg gggaccagc cctgcagacc actctgacaa gtcttcagcc   2700

cacaccctgc cagccccaca gattttattt ttgcacataa gccataacca atcctcaagg   2760

ctggcacagg ctttggggaa gccctggagc ctgtgaagac cctggaaacc tcatgaggct   2820

gtggccaacc cctgcccctt gccccacaca gaccaggcct taaatgtcgg tccaggccct   2880

gtgcacctta ccccagagac agactctttt tgtaagattt tgttaataaa acactgaaac   2940

ttcaaaaaaa aaaaaaaaaa aaaaaaaaaa aaaaaaaaaa aaaaa                   2985
```

<210> SEQ ID NO 2
<211> LENGTH: 396
<212> TYPE: PRT
<213> ORGANISM: Homo sapiens

<400> SEQUENCE: 2

```
Met Glu Leu Asp His Arg Thr Ser Gly Gly Leu His Ala Tyr Pro Gly
1               5                   10                  15

Pro Arg Gly Gly Gln Val Ala Lys Pro Asn Val Ile Leu Gln Ile Gly
            20                  25                  30

Lys Cys Arg Ala Glu Met Leu Glu His Val Arg Arg Thr His Arg His
        35                  40                  45

Leu Leu Ala Glu Val Ser Lys Gln Val Glu Arg Glu Leu Lys Gly Leu
    50                  55                  60

His Arg Ser Val Gly Lys Leu Glu Ser Asn Leu Asp Gly Tyr Val Pro
65                  70                  75                  80

Thr Ser Asp Ser Gln Arg Trp Lys Lys Ser Ile Lys Ala Cys Leu Cys
                85                  90                  95

Arg Cys Gln Glu Thr Ile Ala Asn Leu Glu Arg Trp Val Lys Arg Glu
            100                 105                 110

Met His Val Trp Arg Glu Val Phe Tyr Arg Leu Glu Arg Trp Ala Asp
        115                 120                 125

Arg Leu Glu Ser Thr Gly Gly Lys Tyr Pro Val Gly Ser Glu Ser Ala
    130                 135                 140

Arg His Thr Val Ser Val Gly Val Gly Gly Pro Glu Ser Tyr Cys His
145                 150                 155                 160

Glu Ala Asp Gly Tyr Asp Tyr Thr Val Ser Pro Tyr Ala Ile Thr Pro
                165                 170                 175

Pro Pro Ala Ala Gly Glu Leu Pro Gly Gln Glu Pro Ala Glu Ala Gln
            180                 185                 190

Gln Tyr Gln Pro Trp Val Pro Gly Glu Asp Gly Gln Pro Ser Pro Gly
        195                 200                 205

Val Asp Thr Gln Ile Phe Glu Asp Pro Arg Glu Phe Leu Ser His Leu
```

-continued

```
    210                 215                 220

Glu Glu Tyr Leu Arg Gln Val Gly Gly Ser Glu Glu Tyr Trp Leu Ser
225                 230                 235                 240

Gln Ile Gln Asn His Met Asn Gly Pro Ala Lys Lys Trp Trp Glu Phe
                245                 250                 255

Lys Gln Gly Ser Val Lys Asn Trp Val Glu Phe Lys Lys Glu Phe Leu
            260                 265                 270

Gln Tyr Ser Glu Gly Thr Leu Ser Arg Glu Ala Ile Gln Arg Glu Leu
        275                 280                 285

Asp Leu Pro Gln Lys Gln Gly Glu Pro Leu Asp Gln Phe Leu Trp Arg
    290                 295                 300

Lys Arg Asp Leu Tyr Gln Thr Leu Tyr Val Asp Ala Asp Glu Glu Glu
305                 310                 315                 320

Ile Ile Gln Tyr Val Val Gly Thr Leu Gln Pro Lys Leu Lys Arg Phe
                325                 330                 335

Leu Arg His Pro Leu Pro Lys Thr Leu Glu Gln Leu Ile Gln Arg Gly
            340                 345                 350

Met Glu Val Gln Asp Asp Leu Glu Gln Ala Ala Glu Pro Ala Gly Pro
        355                 360                 365

His Leu Pro Val Glu Asp Glu Ala Glu Thr Leu Thr Pro Ala Pro Asn
    370                 375                 380

Ser Glu Ser Val Ala Ser Asp Arg Thr Gln Pro Glu
385                 390                 395
```

<210> SEQ ID NO 3
<211> LENGTH: 4749
<212> TYPE: DNA
<213> ORGANISM: Homo sapiens

<400> SEQUENCE: 3

```
gcacaggcag cctgcataca ctccttttcc tggtgtcaac attatttaaa agcatgggaa      60
atagtaatga gacagtgtct tcttcattag aaccttagga gtctactaga tttcttcatc     120
tctatttgtt gttattagta gccaaactgt gcaaaaaaca cggtcttgag aaatgacagc     180
acagtatctt agagggaaag gaaatgtagg atgccagtgt ggggacaaat ttctgattgc     240
cagtgattgt tgtgagcata acaataattt catgaacatt aaagcctcta ttgagggcag     300
ctgcagttgt aaaggaaaaa aaatggtcct gaacatttaa aactacactg gtgtacatca     360
taatcaaaca aagtaaacag aaaaaaattt aaactttgct aaaaaaaaaa agcagaagca     420
cttgatcttt aggaaggcac gcagttgctt attatgaatc atttctagag tccgatgcat     480
tttcaaagcc ggttacagtc attacgaagc acacccttgt gaggtaagtg tatcatcacc     540
tttggttcat aaataaaaaa gctgagacgc cgagcgatta agtcactcgc ctaaggagaa     600
tgagtcaacg tcaagagtca tagttgaccc ggcctaaaga ctccagacca tcagtccagg     660
gcttagtcag cggggcccgg agtggcttcc ctggctggca tctggactta ggctatttcc     720
gtgcacgtaa aagcggaata ttggaacggt tgcacagaac ttccaaataa tttttaccgc     780
cacgcaagat ttagccctga ggtcttaatc tcaggatttg ggacagtaaa agctgtcgtc     840
cctccccctc gtccagccgg tggcaagcgg gtactgcggg cggttccgtc cgtccccttt     900
cgcagaaatg gcaacgaatg accaccagca ttagctgagc caggggacgt gggagggttg     960
attgcctaaa cgactctgca tcgccgcctc tttttgaaac taagagaaaa tggtgggaga    1020
tcaaaagaaa actaaataaa cacacaggca acttgtcctg ggacctcaac taagcaaatg    1080
```

-continued

```
aagccttatt gtgtgtgctg agcctgcagt tcccaacctt ccggggaaga tgggaggaca   1140
gggcgacaaa gggcacagta ggcttgcctg gcagtaagtg tgaccgcagc tatccaggcg   1200
gaagagcaga ggactgaaac caccctccag caagcgagtg tccgccgcgt tgagaaccgc   1260
gcaccctacc catcggccac gtgaccagtc ctttttaaaa aaaatttctt taccttaaaa   1320
aaaaaaaaaa aaaaaaggtg gggagagagac tccacttccc agaagcctct cgttactcac   1380
gcagccgcag tcttgcgcag gtgccgccag ggccaaacgg acatatccgt cacgtggcca   1440
gaagctggcc aatccggttt gaatctcatt tttttcctct taccccccct tctggagcgg   1500
ttgtgcgatc agatcgatct aagatggcga ctgtcgaacc ggaaaccacc cctactccta   1560
atcccccgac tacagaagag gagaaaacgg aatctaatca ggaggttgct aacccagaac   1620
actatattaa acatccccta cagaacagat gggcactctg gtttttttaaa aatgataaaa   1680
gcaaaacttg gcaagcaaac ctgcggctga tctccaagtt tgatactgtt gaagactttt   1740
gggctctgta caaccatatc cagttgtcta gtaatttaat gcctggctgt gactactcac   1800
tttttaagga tggtattgag cctatgtggg aagatgagaa aaacaaacgg ggaggacgat   1860
ggctaattac attgaacaaa cagcagagac gaagtgacct cgatcgcttt tggctagaga   1920
cacttctgtg ccttattgga gaatcttttg atgactacag tgatgatgta tgtggcgctg   1980
ttgttaatgt tagagctaaa ggtgataaga tagcaatatg gactactgaa tgtgaaaaca   2040
gagaagctgt tacacatata gggagggtat acaaggaaag gttaggactt cctccaaaga   2100
tagtgattgg ttatcagtcc cacgcagaca cagctactaa gagcggctcc accactaaaa   2160
ataggtttgt tgtttaagaa gacaccttct gagtattctc ataggagact gcgtcaagca   2220
atcgagattt gggagctgaa ccaaagcctc ttcaaaaagc agagtggact gcatttaaat   2280
ttgatttcca tcttaatgtt actcagatat aagagaagtc tcattcgcct ttgtcttgta   2340
cttctgtgtt catttttttt ttttttttg gctagagttt ccactatccc aatcaaagaa   2400
ttacagtaca catccccaga atccataaat gtgttcctgg cccactctgt aatagttcag   2460
tagaattacc attaattaca tacagatttt acctatccac aatagtcaga aaacaacttg   2520
gcatttctat actttacagg aaaaaaaatt ctgttgttcc attttatgca gaagcatatt   2580
ttgctggttt gaaagattat gatgcataca gttttctagc aattttcttt gtttcttttt   2640
acagcattgt ctttgctgta ctcttgctga tggctgctag attttaattt atttgtttcc   2700
ctacttgata atattagtga ttctgatttc agtttttcat ttgttttgct tttgtttttt   2760
tcctcatgta acattggtga aggatccagg aatatgacac aaaggtggaa taaacattaa   2820
ttttgtgcat tctttggtaa ttttttttgt tttttgtaac tacaaagctt tgctacaaat   2880
ttatgcattt cattcaaatc agtgatctat gtttgtgtga tttcctaaac ataattgtgg   2940
attataaaaa atgtaacatc ataattacat tcctaactag aattagtatg tctgtttttg   3000
tatctttatg ctgtatttta acactttgta ttacttaggt tattttgctt tggttaaaaa   3060
tggctcaagt agaaaagcag tcccattcat attaagacag tgtacaaaac tgtaaataaa   3120
atgtgtacag tgaattgtct tttagacaac tagatttgtc cttttatttc tccatcttta   3180
tagaaggaat ttgtacttct tattgcaagg cagtctctat attatgtctt cttttgtggt   3240
gtcttccatg tgaacagcat aagtttggag cactagtttg attattatgt ttattacaat   3300
ttttaataaa ttgaataggt agtatcatat atatggaatt aaattgatgt ggctatcttt   3360
gttttttttat aaagtaaggc acagtcattc agtcttaggt aaataatgta ctctcttaat   3420
atgttaatac tcatgagaat tgggatctga tgcatcacca tttgattggt agcaacagtg   3480
```

```
gttgtaaaac ttggttgctg aattgagttg tttctatgtt aagtgtcaaa atgatagtgt   3540

agggaaagta caggtggtgg ggacatatgc attaagaatc ttgttagtgt tgcaatctaa   3600

atagaatgga ataaacaggt gttaagacat atttatagtg gtaaattgtt gtagtatggt   3660

attctgtaaa cttgaaaact tgatctactc tttgtaggta tcatttgaaa gcaaacttga   3720

aaatgttttg tacatagtac atacttgtat agtcctgtga gatgaagtat ggctatcaga   3780

ccaaaggata agccaaactg taggtagcag aatggaaatt attattttga gaggaaaatt   3840

tgtctttgaa tggtgattat gacttaatca ttttaaaact gataaacttg acaaaaaccc   3900

tgtatgaaat aaacatgaaa ttaatagcac tgatttcatt gtaaaatttt aaagcagttt   3960

aaagggtacc acaggttatc acagtactct caatgccaca aacacctctt gttcagtatt   4020

ctagaaatac tgaatcagaa ttctgtgttt attataaatct cagcatactg tacataaatat   4080

ctgctagtta aacttgggta attggttaag gtgacttact gtctatgtca atatgtatag   4140

ttttgagtac ttcaagagtt tacttaaaag tgatgatgtt actggtatgt tggcagtggg   4200

tgggactgaa gtagtgtatc tattataaat tgatctattt tcttaattct aagatgaagt   4260

ccaattttaa gcatcagctt ttaggtgcaa aggaggaatt aacacattaa atgtatacag   4320

ttctaaattt ttgaaataac tgatgtgtag catttgatta ttggtattac catttttagaa   4380

tcatgatgtt attttaaacc tttttcctgg ggacaagaaa ggataataaa ttacgctgaa   4440

tcacttttgg cagttgccac ttaaatagta cagtgacttg caacttttat aactttatca   4500

gcatcttctc taaatacaaa attaggctat atgttatttt ccaacttact gttttctctc   4560

tgtttagcag gatattataa atagattaaa tagatatatt ttcttttttt ttttttttt   4620

ttgagacgga gtctcgcttt gtctcccagg ctggagtgca gtggcgtgat ctcccagtag   4680

ctgggactac aagcacctgc caccatgccc ggctaatttt ttttgtattt ttagtagaga   4740

cggggtttc                                                           4749
```

<210> SEQ ID NO 4
<211> LENGTH: 217
<212> TYPE: PRT
<213> ORGANISM: Homo sapiens

<400> SEQUENCE: 4

```
Met Ala Thr Val Glu Pro Glu Thr Thr Pro Thr Pro Asn Pro Pro Thr
1               5                   10                  15

Thr Glu Glu Glu Lys Thr Glu Ser Asn Gln Glu Val Ala Asn Pro Glu
            20                  25                  30

His Tyr Ile Lys His Pro Leu Gln Asn Arg Trp Ala Leu Trp Phe Phe
        35                  40                  45

Lys Asn Asp Lys Ser Lys Thr Trp Gln Ala Asn Leu Arg Leu Ile Ser
    50                  55                  60

Lys Phe Asp Thr Val Glu Asp Phe Trp Ala Leu Tyr Asn His Ile Gln
65                  70                  75                  80

Leu Ser Ser Asn Leu Met Pro Gly Cys Asp Tyr Ser Leu Phe Lys Asp
                85                  90                  95

Gly Ile Glu Pro Met Trp Glu Asp Glu Lys Asn Lys Arg Gly Gly Arg
            100                 105                 110

Trp Leu Ile Thr Leu Asn Lys Gln Gln Arg Arg Ser Asp Leu Asp Arg
        115                 120                 125

Phe Trp Leu Glu Thr Leu Leu Cys Leu Ile Gly Glu Ser Phe Asp Asp
    130                 135                 140
```

```
Tyr Ser Asp Asp Val Cys Gly Ala Val Val Asn Val Arg Ala Lys Gly
145                 150                 155                 160

Asp Lys Ile Ala Ile Trp Thr Thr Glu Cys Glu Asn Arg Glu Ala Val
                165                 170                 175

Thr His Ile Gly Arg Val Tyr Lys Glu Arg Leu Gly Leu Pro Pro Lys
            180                 185                 190

Ile Val Ile Gly Tyr Gln Ser His Ala Asp Thr Ala Thr Lys Ser Gly
        195                 200                 205

Ser Thr Thr Lys Asn Arg Phe Val Val
    210                 215


<210> SEQ ID NO 5
<211> LENGTH: 4411
<212> TYPE: DNA
<213> ORGANISM: Homo sapiens

<400> SEQUENCE: 5

acttccggtg gagggccgcc tctgagcggg cggcgggccg acggcgagcg cgggcggcgg     60

cggtgacgga ggcgccgctg ccaggggggcg tgcggcagcg cggcggcggc ggcggcggcg    120

gcggcggcgg aggcggcggc ggcggcggcg gcggcggcgg ctgggcctcg agcgcccgca    180

gcccacctct cgggggcggg ctcccggcgc tagcagggct gaagagaaga tggaggagct    240

ggtggtggaa gtgcggggct ccaatggcgc tttctacaag gcatttgtaa aggatgttca    300

tgaagattca ataacagttg catttgaaaa caactggcag cctgataggc agattccatt    360

tcatgatgtc agattcccac ctcctgtagg ttataataaa gatataaatg aaagtgatga    420

agttgaggtg tattccagag caaatgaaaa agagccttgc tgttggtggt tagctaaagt    480

gaggatgata aagggtgagt tttatgtgat agaatatgca gcatgtgatg caacttacaa    540

tgaaattgtc acaattgaac gtctaagatc tgttaatccc aacaaacctg ccacaaaaga    600

tactttccat aagatcaagc tggatgtgcc agaagactta cggcaaatgt gtgccaaaga    660

ggcggcacat aaggatttta aaaaggcagt tggtgccttt tctgtaactt atgatccaga    720

aaattatcag cttgtcattt tgtccatcaa tgaagtcacc tcaaagcgag cacatatgct    780

gattgacatg cactttcgga gtctgcgcac taagttgtct ctgataatga gaaatgaaga    840

agctagtaag cagctggaga gttcaaggca gcttgcctcg agatttcatg aacagtttat    900

cgtaagagaa gatctgatgg gtctagctat tggtactcat ggtgctaata ttcagcaagc    960

tagaaaagta cctggggtca ctgctattga tctagatgaa gatacctgca catttcatat   1020

ttatggagag gatcaggatg cagtgaaaaa agctagaagc tttctcgaat ttgctgaaga   1080

tgtaatacaa gttccaagga acttagtagg caaagtaata ggaaaaaatg gaaagctgat   1140

tcaggagatt gtggacaagt caggagttgt gagggtgagg attgaggctg aaaatgagaa   1200

aaatgttcca caagaagagg aaattatgcc accaaattcc cttccttcca ataattcaag   1260

ggttggacct aatgccccag aagaaaaaaa acatttagat ataaaggaaa acagcaccca   1320

tttttctcaa cctaacagta caaaagtcca gagggtgtta gtggcttcat cagttgtagc   1380

aggggaatcc cagaaacctg aactcaaggc ttggcagggt atggtaccat ttgtttttgt   1440

gggaacaaag gacagcatcg ctaatgccac tgttcttttg gattatcacc tgaactattt   1500

aaaggaagta gaccagttgc gtttggagag attacaaatt gatgagcagt tgcgacagat   1560

tggagctagt tctagaccac caccaaatcg tacagataag gaaaaaagct atgtgactga   1620

tgatggtcaa ggaatgggtc gaggtagtag accttacaga aatagggggc acggcagacg   1680
```

```
cggtcctgga tatacttcag gaactaattc tgaagcatca aatgcttctg aaacagaatc   1740
tgaccacaga gacgaactca gtgattggtc attagctcca acagaggaag agagggagag   1800
cttcctgcgc agaggagacg gacggcggcg tggaggggga ggaagaggac aaggaggaag   1860
aggacgtgga ggaggcttca aaggaaacga cgatcactcc cgaacagata atcgtccacg   1920
taatccaaga gaggctaaag gaagaacaac agatggatcc cttcagatca gagttgactg   1980
caataatgaa aggagtgtcc acactaaaac attacagaat acctccagtg aaggtagtcg   2040
gctgcgcacg ggtaaagatc gtaaccagaa gaaagagaag ccagacagcg tggatggtca   2100
gcaaccactc gtgaatggag taccctaaac tgcataattc tgaagttata tttcctatac   2160
catttccgta attcttattc catattagaa aactttgtta ggccaaagac aaatagtagg   2220
caagatggca cagggcatga aatgaacaca aattatgcta agaatttttt attttttggt   2280
attggccata agcaacaatt ttcagatttg cacaaaaaga taccttaaaa tttgaaacat   2340
tgcttttaaa actacttagc acttcagggc agattttagt tttattttct aaagtactga   2400
gcagtgatat tctttgttaa tttggaccat tttcctgcat tgggtgatca ttcaccagta   2460
cattctcagt ttttcttaat atatagcatt tatggtaatc atattagact tctgttttca   2520
atctcgtata gaagtcttca tgaaatgcta tgtcatttca tgtcctgtgt cagtttatgt   2580
tttggtccac ttttccagta ttttagtgga ccctgaaatg tgtgtgatgt gacatttgtc   2640
attttcatta gcaaaaaaag ttgtatgatc tgtgcctttt ttatatcttg gcaggtagga   2700
atattatatt tggatgcaga gttcagggaa gataagttgg aaacactaaa tgttaaagat   2760
gtagcaaacc ctgtcaaaca ttagtacttt atagaagaat gcatgctttc catatttttt   2820
tccttacata aacatcaggt taggcagtat aaagaatagg acttgttttt gtttttgttt   2880
tgttgcactg aagtttgata aatagtgtta ttgagagaga tgtgtaattt ttctgtatag   2940
acaggagaag aaagaactat cttcatctga gagaggctaa aatgttttca gctaggaaca   3000
aatcttcctg gtcgaaagtt agtaggatat gcctgctctt tggcctgatg accaatttta   3060
acttagagct tttttttttt aattttgtct gccccaagtt ttgtgaaatt tttcatattt   3120
taatttcaag cttattttgg agagatagga aggtcatttc catgtatgca taataatcct   3180
gcaaagtaca ggtactttgt ctaagaaaca ttggaagcag gttaaatgtt ttgtaaactt   3240
tgaaatatat ggtctaatgt ttaagcagaa ttggaaaaga ctaagatcgg ttaacaaata   3300
acaacttttt tttctttttt tcttttgttt tttgaagtgt tggggtttgg ttttgttttt   3360
tgagtctttt ttttttaagt gaaatttatt gaggaaaaat atgtgaagga ccttcactct   3420
aagatgttat atttttctta aaaagtaact cctagtaggg gtaccactga atctgtacag   3480
agccgtaaaa actgaagttc tgcctctgat gtattttgtg agtttgtttc tttgaatttt   3540
cattttacag ttacttttcc ttgcatacaa acaagcatat aaaatggcaa caaactgcac   3600
atgatttcac aaatattaaa aagtctttta aaaagtattg ccaaacatta atgttgattt   3660
ctagttattt attctgggaa tgtatagtat ttgaaaacag aaattggtac cttgcacaca   3720
tcatctgtaa gctgtttggt tttaaaatac tgtagataat taaccaaggt agaatgacct   3780
tgtaatgtaa ctgctcttgg gcaatattct ctgtacatat tagcgacaac agattggatt   3840
ttatgttgac atttgtttgg ttatagtgca atatattttg tatgcaagca gtttcaataa   3900
agtttgatct tcctctgcta aattgatgtt gatgcaatcc ttacaaatga ttgcttttaa   3960
aattttaagc taggaaaaga aatctataga aagtgttctg ttacaaaatg taactgttac   4020
```

cattggaaat ttcacgtcat aggaagttag cctttatcta ccaactttca agaacttgtt 4080
taataaagcg aaaaactcaa ccaaatggta caaaaccaca gtgtaccatt aaaatatgca 4140
ctaagtctct tttttacaaa ggctgtattc agcaaggcgc taacttgctt aaatgtgaat 4200
tactaacttc taaaactgta ctttgattca catgttttca aatggagttg gagttcattc 4260
atattacaat atttgtgtgc taaacgtgta tgtttttcag ttcaaagtca tgatgttttt 4320
aaaatcttat taaagtttca aaaatctgaa gattgtttat ctagatgtaa atttttatta 4380
aaaagttgca cttatgaaaa agcaaaaaat t 4411

<210> SEQ ID NO 6
<211> LENGTH: 632
<212> TYPE: PRT
<213> ORGANISM: Homo sapiens

<400> SEQUENCE: 6

Met Glu Glu Leu Val Val Glu Val Arg Gly Ser Asn Gly Ala Phe Tyr
1 5 10 15

Lys Ala Phe Val Lys Asp Val His Glu Asp Ser Ile Thr Val Ala Phe
20 25 30

Glu Asn Asn Trp Gln Pro Asp Arg Gln Ile Pro Phe His Asp Val Arg
35 40 45

Phe Pro Pro Pro Val Gly Tyr Asn Lys Asp Ile Asn Glu Ser Asp Glu
50 55 60

Val Glu Val Tyr Ser Arg Ala Asn Glu Lys Glu Pro Cys Cys Trp Trp
65 70 75 80

Leu Ala Lys Val Arg Met Ile Lys Gly Glu Phe Tyr Val Ile Glu Tyr
85 90 95

Ala Ala Cys Asp Ala Thr Tyr Asn Glu Ile Val Thr Ile Glu Arg Leu
100 105 110

Arg Ser Val Asn Pro Asn Lys Pro Ala Thr Lys Asp Thr Phe His Lys
115 120 125

Ile Lys Leu Asp Val Pro Glu Asp Leu Arg Gln Met Cys Ala Lys Glu
130 135 140

Ala Ala His Lys Asp Phe Lys Lys Ala Val Gly Ala Phe Ser Val Thr
145 150 155 160

Tyr Asp Pro Glu Asn Tyr Gln Leu Val Ile Leu Ser Ile Asn Glu Val
165 170 175

Thr Ser Lys Arg Ala His Met Leu Ile Asp Met His Phe Arg Ser Leu
180 185 190

Arg Thr Lys Leu Ser Leu Ile Met Arg Asn Glu Glu Ala Ser Lys Gln
195 200 205

Leu Glu Ser Ser Arg Gln Leu Ala Ser Arg Phe His Glu Gln Phe Ile
210 215 220

Val Arg Glu Asp Leu Met Gly Leu Ala Ile Gly Thr His Gly Ala Asn
225 230 235 240

Ile Gln Gln Ala Arg Lys Val Pro Gly Val Thr Ala Ile Asp Leu Asp
245 250 255

Glu Asp Thr Cys Thr Phe His Ile Tyr Gly Glu Asp Gln Asp Ala Val
260 265 270

Lys Lys Ala Arg Ser Phe Leu Glu Phe Ala Glu Asp Val Ile Gln Val
275 280 285

Pro Arg Asn Leu Val Gly Lys Val Ile Gly Lys Asn Gly Lys Leu Ile
290 295 300

-continued

```
Gln Glu Ile Val Asp Lys Ser Gly Val Val Arg Val Arg Ile Glu Ala
305                 310                 315                 320

Glu Asn Glu Lys Asn Val Pro Gln Glu Glu Glu Ile Met Pro Pro Asn
                325                 330                 335

Ser Leu Pro Ser Asn Asn Ser Arg Val Gly Pro Asn Ala Pro Glu Glu
            340                 345                 350

Lys Lys His Leu Asp Ile Lys Glu Asn Ser Thr His Phe Ser Gln Pro
        355                 360                 365

Asn Ser Thr Lys Val Gln Arg Val Leu Val Ala Ser Ser Val Val Ala
    370                 375                 380

Gly Glu Ser Gln Lys Pro Glu Leu Lys Ala Trp Gln Gly Met Val Pro
385                 390                 395                 400

Phe Val Phe Val Gly Thr Lys Asp Ser Ile Ala Asn Ala Thr Val Leu
                405                 410                 415

Leu Asp Tyr His Leu Asn Tyr Leu Lys Glu Val Asp Gln Leu Arg Leu
            420                 425                 430

Glu Arg Leu Gln Ile Asp Glu Gln Leu Arg Gln Ile Gly Ala Ser Ser
        435                 440                 445

Arg Pro Pro Pro Asn Arg Thr Asp Lys Glu Lys Ser Tyr Val Thr Asp
    450                 455                 460

Asp Gly Gln Gly Met Gly Arg Gly Ser Arg Pro Tyr Arg Asn Arg Gly
465                 470                 475                 480

His Gly Arg Arg Gly Pro Gly Tyr Thr Ser Gly Thr Asn Ser Glu Ala
                485                 490                 495

Ser Asn Ala Ser Glu Thr Glu Ser Asp His Arg Asp Glu Leu Ser Asp
            500                 505                 510

Trp Ser Leu Ala Pro Thr Glu Glu Glu Arg Glu Ser Phe Leu Arg Arg
        515                 520                 525

Gly Asp Gly Arg Arg Arg Gly Gly Gly Gly Arg Gly Gln Gly Gly Arg
    530                 535                 540

Gly Arg Gly Gly Gly Phe Lys Gly Asn Asp Asp His Ser Arg Thr Asp
545                 550                 555                 560

Asn Arg Pro Arg Asn Pro Arg Glu Ala Lys Gly Arg Thr Thr Asp Gly
                565                 570                 575

Ser Leu Gln Ile Arg Val Asp Cys Asn Asn Glu Arg Ser Val His Thr
            580                 585                 590

Lys Thr Leu Gln Asn Thr Ser Ser Glu Gly Ser Arg Leu Arg Thr Gly
        595                 600                 605

Lys Asp Arg Asn Gln Lys Lys Glu Lys Pro Asp Ser Val Asp Gly Gln
    610                 615                 620

Gln Pro Leu Val Asn Gly Val Pro
625                 630
```

<210> SEQ ID NO 7
<211> LENGTH: 6854
<212> TYPE: DNA
<213> ORGANISM: Homo sapiens

<400> SEQUENCE: 7

```
agtgctgaag aaagagggca ctagtgtaca gcccagatcg catccttgca ccgtctggat      60

tagagctgag gcgtctgcaa gccgagcgtg gccacggtcc tctggccccg ggaccatagc     120

gctgtctacc ccgactcagg tactcagcag catctagctc accgctgcca acacgacttc     180

cactgtactc ttgatcaatt taccttgatg cactaccggt gaagaacggg gactcgaatt     240
```

```
cccttacaaa cgcctccagc ttgtagaggc ggtcgtggag gacccagagg aggagacgaa    300
ggggaaggag gcggtggtgg aggaggcaaa ggccttggac gaccattgtt ggcgaggggc    360
accactccgg gagaggcggc gctgggcgtc ttgggggtgc gcgccgggag cctgcagcgg    420
gaccagcgtg ggaacgcggc tggcaggctg tggacctcgt cctcaccacc atggtcgggc    480
tcctttgtt tttttccca gcgatctttt tggaggtgtc ccttctcccc agaagccccg    540
gcaggaaagt gttgctggca ggagcgtcgt ctcagcgctc ggtggccaga atggacggag    600
atgtcatcat tggagccctc ttctcagtcc atcaccagcc tccggccgag aaagtgcccg    660
agaggaagtg tggggagatc agggagcagt atggcatcca gagggtggag gccatgttcc    720
acacgttgga taagatcaac gcggacccgg tcctcctgcc caacatcacc ctgggcagtg    780
agatccggga ctcctgctgg cactcttccg tggctctgga acagagcatt gagttcatta    840
gggactctct gatttccatt cgagatgaga aggatgggat caaccggtgt ctgcctgacg    900
gccagtccct ccccccaggc aggactaaga agcccattgc gggagtgatc ggtcccggct    960
ccagctctgt agccattcaa gtgcagaacc tgctccagct cttcgacatc ccccagatcg   1020
cttattcagc cacaagcatc gacctgagtg acaaaacttt gtacaaatac ttcctgaggg   1080
ttgtcccttc tgacactttg caggcaaggg ccatgcttga catagtcaaa cgttacaatt   1140
ggacctatgt ctctgcagtc cacacggaag ggaattatgg ggagagcgga atggacgctt   1200
tcaaagagct ggctgcccag gaaggcctct gtatcgccca ttctgacaaa atctacagca   1260
acgctgggga gaagagcttt gaccgactct tgcgcaaact ccgagagagg cttcccaagg   1320
ctagagtggt ggtctgcttc tgtgaaggca tgacagtgcg aggactcctg agcgccatgc   1380
ggcgccttgg cgtcgtgggc gagttctcac tcattggaag tgatggatgg gcagacagag   1440
atgaagtcat tgaaggttat gaggtggaag ccaacggggg aatcacgata aagctgcagt   1500
ctccagaggt caggtcattt gatgattatt tcctgaaact gaggctggac actaacacga   1560
ggaatccctg gttccctgag ttctggcaac atcggttcca gtgccgcctt ccaggacacc   1620
ttctggaaaa tcccaacttt aaacgaatct gcacaggcaa tgaaagctta gaagaaaact   1680
atgtccagga cagtaagatg ggtttgtca tcaatgccat ctatgccatg gcacatgggc   1740
tgcagaacat gcaccatgcc ctctgccctg gccacgtggg cctctgcgat gccatgaagc   1800
ccatcgacgg cagcaagctg ctggacttcc tcatcaagtc ctcattcatt ggagtatctg   1860
gagaggaggt gtggtttgat gagaaaggag acgctcctgg aaggtatgat atcatgaatc   1920
tgcagtacac tgaagctaat cgctatgact atgtgcacgt tggaacctgg catgaaggag   1980
tgctgaacat tgatgattac aaaatccaga tgaacaagag tggagtggtg cggtctgtgt   2040
gcagtgagcc ttgcttaaag ggccagatta aggttatacg gaaaggagaa gtgagctgct   2100
gctggatttg cacggcctgc aaagagaatg aatatgtgca agatgagttc acctgcaaag   2160
cttgtgactt gggatggtgg cccaatgcag atctaacagg ctgtgagccc attcctgtgc   2220
gctatcttga gtggagcaac atcgaatcca ttatagccat cgccttttca tgcctgggaa   2280
tccttgttac cttgtttgtc accctaatct ttgtactgta ccgggacaca ccagtggtca   2340
aatcctccag tcgggagctc tgctacatca tcctagctgg catcttcctt ggttatgtgt   2400
gcccattcac tctcattgcc aaacctacta ccacctcctg ctacctccag cgcctcttgg   2460
ttggcctctc ctctgcgatg tgctactctg ctttagtgac taaaaccaat cgtattgcac   2520
gcatcctggc tggcagcaag aagaagatct gcacccggaa gcccaggttc atgagtgcct   2580
gggctcaggt gatcattgcc tcaattctga ttagtgtgca actaaccctg gtggtaaccc   2640
```

-continued

```
tgatcatcat ggaacccccct atgcccattc tgtcctaccc aagtatcaag gaagtctacc   2700
ttatctgcaa taccagcaac ctgggtgtgg tggccccttt gggctacaat ggactcctca   2760
tcatgagctg tacctactat gccttcaaga cccgcaacgt gcccgccaac ttcaacgagg   2820
ccaaatatat cgcgttcacc atgtacacca cctgtatcat ctggctagct tttgtgccca   2880
tttactttgg gagcaactac aagatcatca caacttgctt tgcagtgagt ctcagtgtaa   2940
cagtggctct ggggtgcatg ttcactccca agatgtacat cattattgcc aagcctgaga   3000
ggaatgtccg cagtgccttc accacctctg atgttgtccg catgcatgtt ggcgatggca   3060
agctgccctg ccgctccaac actttcctca acatcttccg aagaaagaag gcaggggcag   3120
ggaatgccaa ttctaatggc aagtctgtgt catggtctga accaggtgga ggacaggtgc   3180
ccaagggaca gcatatgtgg caccgcctct ctgtgcacgt gaagaccaat gagacggcct   3240
gcaaccaaac agccgtcatc aagcccctca ctaaaagtta ccaaggctct ggcaagagcc   3300
tgaccttttc agataccagc accaagaccc tttacaacgt agaggaggag gaggatgccc   3360
agccgattcg ctttagcccg cctggtagcc cttccatggt ggtgcacagg cgcgtgccaa   3420
gcgcggcgac cactccgcct ctgccgtccc acctgaccgc agaggagacc cccctcttcc   3480
tggccgaacc agccctcccc aagggcttgc cccctcctct ccagcagcag cagcaacccc   3540
ctccacagca gaaatcgctg atggaccagc tccagggagt ggtcagcaac ttcagtaccg   3600
cgatcccgga ttttcacgcg gtgctggcag gccccggtgg tcccgggaac gggctgcggt   3660
ccctgtaccc gcccccgcca cctccgcagc acctgcagat gctgccgctg cagctgagca   3720
cctttgggga ggagctggtc tccccgcccg cggacgacga cgacgacagc gagaggttta   3780
agctcctcca ggagtacgtg tatgagcacg agcgggaagg gaacacggaa gaagacgaac   3840
tggaagagga ggaggaggac ctgcaggcgg ccagcaaact gaccccggat gattcgcctg   3900
cgctgacgcc tccgtcgcct ttccgcgact cggtggcctc gggcagctcg gtgcccagct   3960
cccccgtgtc cgagtcggtg ctctgcaccc ctcccaacgt atcctacgcc tctgtcattc   4020
tgcgggacta caagcaaagc tcttccaccc tgtaaggggg aagggtccac atagaaaagc   4080
aagacaagcc agagatctcc cacacctcca gagatgtgca aacagctggg aggaaaagcc   4140
tgggagtggg gggcctcgtc gggaggacag gagaccgctg ctgctgctgc cgctactgct   4200
gctgctgcct taagtaggaa gagagggaag gacaccaagc aaaaaatgtt ccaggccagg   4260
attcggattc ttgaattact cgaagccttc tctgggaaga aagggaattc tgacaaagca   4320
caattccata tggtatgtaa cttttatcac aaatcaaata gtgacatcac aaacataatg   4380
tcctcttttg cacaattgtg catagatata tatatgccca cacacactgg gccatgcttg   4440
ccaaggaaca gcccacgtgg acatgccagt cggatcatga gttcacctga tggcattcgg   4500
agtgagctgg tggagccaga cagagcaggt gcggggaagg gaagggccca ggccagaccc   4560
atcccaaacg gatgatggga tgatgggaca gcagctcctt gctcagaagc ccttctcccc   4620
gctgggctga cagactcctc atcttcagga gactcaggaa tggagcggca caggggtctc   4680
tcttcatcca ctgcaaccca tccagtgcca gctttgagat tgcacttgaa gaaaggtgca   4740
tggacccccct gctgctctgc agattccctt tatttaggaa aacaggaata agagcaaaat   4800
tatcaccaaa aagtgcttca tcaggcgtgc tacaggagga aggagctaga aatagaacaa   4860
tccatcagca tgagactttg aaaaaaaaac acatgatcag cttctcatgt tccatattca   4920
cttattggcg atttggggaa aaggccggaa caagagattg ttacgagagt ggcagaaacc   4980
```

```
cttttgtaga ttgacttgtg tttgtgccaa gcgggctttc cattgacctt cagttaaaga   5040

acaaaccatg tgacaaaatt gttaccttcc acttactgta gcaaataata cctacaagtt   5100

gaacttctaa gatgcgtata tgtacaattt ggtgccatta tttctcctac gtattagaga   5160

aacaaatcca tctttgaatc taatggtgta ctcatagcaa ctattactgg tttaaatgac   5220

aaataattct atcctattgt cactgaagtc cttgtaacta gcgagtgaat gtgttcctgt   5280

gtccttgtat atgtgcgatc gtaaaatttg tgcaatgtaa tgtcaaattg actggtcaat   5340

gtcaacctag tagtcaatct aactgcaatt agaaattgtc ttttgaatat actatatata   5400

tttttatgt tccaataatg ttttgtacat cattgtcatc aatatctaca gaagctcttt   5460

gacggtttga atactatggc tcaaggtttt catatgcagc tcggatggac atttttcttc   5520

taagatggaa cttatttttc agatattttc tgatgtggag atatgttatt aatgaagtgg   5580

tttgaaaatt tgttatatta aaagtgcaca aaaactgaga gtgaaaataa aaggtacatt   5640

ttataagctt gcacacatta ttaacacata agattgaaca aagcatttag attattccag   5700

gttatatcat ttttttaaag attttccaca gctacttgag tgtctaacat acagtaacat   5760

ctaactcagc taataatttg taaaatcttt atcaatcaca ttttgccttc ttttaatttt   5820

tatgttcatg gacttttatt cctgtgtctt ggctgtcata acttttttatt tctgctattt   5880

gctgttgtgt aatatccatg gacatgtaat ccacttactc catctttaca atcccttttt   5940

accaccaata aaaggatttt tcttgctgtt ttgatttctt ctattatttg tggaatgaat   6000

tataccccccc ttaaatatct ttgtttatgc cttatgttca gtcatatttt aatatgcttc   6060

cttcatattg aagctgctga tttctcagcc aaaaatcatc ttagaatctt taaatatcca   6120

ttgcatcatt tgttcagaat ttaacatcca ttccaatgtt ggaggcttgt attacttata   6180

tttcatcata ttctattgcc aagtttagtc agttccacac caagaatgaa ctgcatttcc   6240

tttaaaaatt attttaaaac acctttattg aaaagatctc atgactgaga tgtggacttt   6300

ggttccatgt tttcattgta agaaagcaga gagcggaaaa tcaatggctc cagtgattaa   6360

tagatgggtt tttagtaatt gacaaattca tgagggaaag catatgatct ctttattagt   6420

gaatcatgct tattttttac tcttaatgcc actaatatac atccctaata tcacagggct   6480

tgtgcattca gatttttaaa aaattaggat agataaggaa acaacttata ttcaagtgta   6540

agatgatatc aggttggtct aagacttttg gtgaacacgt tcattcaact gtgatcactt   6600

tattactctg aatgcctact attatcctga ttatggggtc tcctgaataa atagagtatt   6660

agtccttatg tcatcattgt tcaaaattgg agatgtacac atacataccc tataccaaga   6720

gggccgaaac tcttcacctt gatgtatgtt ctgatacaag ttgttcagct tcttgtaaat   6780

gtgtttttcct tcggcttgtt actgcctttt gtcaaataat cttgacaatg ctgtataata   6840

aatattttct attt                                                     6854
```

<210> SEQ ID NO 8
<211> LENGTH: 1194
<212> TYPE: PRT
<213> ORGANISM: Homo sapiens

<400> SEQUENCE: 8

```
Met Val Gly Leu Leu Leu Phe Phe Phe Pro Ala Ile Phe Leu Glu Val
1               5                   10                  15

Ser Leu Leu Pro Arg Ser Pro Gly Arg Lys Val Leu Leu Ala Gly Ala
            20                  25                  30

Ser Ser Gln Arg Ser Val Ala Arg Met Asp Gly Asp Val Ile Ile Gly
```

```
        35                  40                  45

Ala Leu Phe Ser Val His His Gln Pro Pro Ala Glu Lys Val Pro Glu
    50                  55                  60

Arg Lys Cys Gly Glu Ile Arg Glu Gln Tyr Gly Ile Gln Arg Val Glu
65                  70                  75                  80

Ala Met Phe His Thr Leu Asp Lys Ile Asn Ala Asp Pro Val Leu Leu
                85                  90                  95

Pro Asn Ile Thr Leu Gly Ser Glu Ile Arg Asp Ser Cys Trp His Ser
            100                 105                 110

Ser Val Ala Leu Glu Gln Ser Ile Glu Phe Ile Arg Asp Ser Leu Ile
        115                 120                 125

Ser Ile Arg Asp Glu Lys Asp Gly Ile Asn Arg Cys Leu Pro Asp Gly
    130                 135                 140

Gln Ser Leu Pro Pro Gly Arg Thr Lys Lys Pro Ile Ala Gly Val Ile
145                 150                 155                 160

Gly Pro Gly Ser Ser Ser Val Ala Ile Gln Val Gln Asn Leu Leu Gln
                165                 170                 175

Leu Phe Asp Ile Pro Gln Ile Ala Tyr Ser Ala Thr Ser Ile Asp Leu
            180                 185                 190

Ser Asp Lys Thr Leu Tyr Lys Tyr Phe Leu Arg Val Val Pro Ser Asp
        195                 200                 205

Thr Leu Gln Ala Arg Ala Met Leu Asp Ile Val Lys Arg Tyr Asn Trp
    210                 215                 220

Thr Tyr Val Ser Ala Val His Thr Glu Gly Asn Tyr Gly Glu Ser Gly
225                 230                 235                 240

Met Asp Ala Phe Lys Glu Leu Ala Ala Gln Glu Gly Leu Cys Ile Ala
                245                 250                 255

His Ser Asp Lys Ile Tyr Ser Asn Ala Gly Glu Lys Ser Phe Asp Arg
            260                 265                 270

Leu Leu Arg Lys Leu Arg Glu Arg Leu Pro Lys Ala Arg Val Val Val
        275                 280                 285

Cys Phe Cys Glu Gly Met Thr Val Arg Gly Leu Leu Ser Ala Met Arg
    290                 295                 300

Arg Leu Gly Val Val Gly Glu Phe Ser Leu Ile Gly Ser Asp Gly Trp
305                 310                 315                 320

Ala Asp Arg Asp Glu Val Ile Glu Gly Tyr Glu Val Glu Ala Asn Gly
                325                 330                 335

Gly Ile Thr Ile Lys Leu Gln Ser Pro Glu Val Arg Ser Phe Asp Asp
            340                 345                 350

Tyr Phe Leu Lys Leu Arg Leu Asp Thr Asn Thr Arg Asn Pro Trp Phe
        355                 360                 365

Pro Glu Phe Trp Gln His Arg Phe Gln Cys Arg Leu Pro Gly His Leu
    370                 375                 380

Leu Glu Asn Pro Asn Phe Lys Arg Ile Cys Thr Gly Asn Glu Ser Leu
385                 390                 395                 400

Glu Glu Asn Tyr Val Gln Asp Ser Lys Met Gly Phe Val Ile Asn Ala
                405                 410                 415

Ile Tyr Ala Met Ala His Gly Leu Gln Asn Met His His Ala Leu Cys
            420                 425                 430

Pro Gly His Val Gly Leu Cys Asp Ala Met Lys Pro Ile Asp Gly Ser
        435                 440                 445

Lys Leu Leu Asp Phe Leu Ile Lys Ser Ser Phe Ile Gly Val Ser Gly
    450                 455                 460
```

-continued

```
Glu Glu Val Trp Phe Asp Glu Lys Gly Asp Ala Pro Gly Arg Tyr Asp
465                 470                 475                 480

Ile Met Asn Leu Gln Tyr Thr Glu Ala Asn Arg Tyr Asp Tyr Val His
                485                 490                 495

Val Gly Thr Trp His Glu Gly Val Leu Asn Ile Asp Asp Tyr Lys Ile
            500                 505                 510

Gln Met Asn Lys Ser Gly Val Val Arg Ser Val Cys Ser Glu Pro Cys
        515                 520                 525

Leu Lys Gly Gln Ile Lys Val Ile Arg Lys Gly Glu Val Ser Cys Cys
    530                 535                 540

Trp Ile Cys Thr Ala Cys Lys Glu Asn Glu Tyr Val Gln Asp Glu Phe
545                 550                 555                 560

Thr Cys Lys Ala Cys Asp Leu Gly Trp Trp Pro Asn Ala Asp Leu Thr
                565                 570                 575

Gly Cys Glu Pro Ile Pro Val Arg Tyr Leu Glu Trp Ser Asn Ile Glu
            580                 585                 590

Ser Ile Ile Ala Ile Ala Phe Ser Cys Leu Gly Ile Leu Val Thr Leu
        595                 600                 605

Phe Val Thr Leu Ile Phe Val Leu Tyr Arg Asp Thr Pro Val Val Lys
    610                 615                 620

Ser Ser Ser Arg Glu Leu Cys Tyr Ile Ile Leu Ala Gly Ile Phe Leu
625                 630                 635                 640

Gly Tyr Val Cys Pro Phe Thr Leu Ile Ala Lys Pro Thr Thr Thr Ser
                645                 650                 655

Cys Tyr Leu Gln Arg Leu Leu Val Gly Leu Ser Ser Ala Met Cys Tyr
            660                 665                 670

Ser Ala Leu Val Thr Lys Thr Asn Arg Ile Ala Arg Ile Leu Ala Gly
        675                 680                 685

Ser Lys Lys Lys Ile Cys Thr Arg Lys Pro Arg Phe Met Ser Ala Trp
    690                 695                 700

Ala Gln Val Ile Ile Ala Ser Ile Leu Ile Ser Val Gln Leu Thr Leu
705                 710                 715                 720

Val Val Thr Leu Ile Ile Met Glu Pro Pro Met Pro Ile Leu Ser Tyr
                725                 730                 735

Pro Ser Ile Lys Glu Val Tyr Leu Ile Cys Asn Thr Ser Asn Leu Gly
            740                 745                 750

Val Val Ala Pro Leu Gly Tyr Asn Gly Leu Leu Ile Met Ser Cys Thr
        755                 760                 765

Tyr Tyr Ala Phe Lys Thr Arg Asn Val Pro Ala Asn Phe Asn Glu Ala
    770                 775                 780

Lys Tyr Ile Ala Phe Thr Met Tyr Thr Thr Cys Ile Ile Trp Leu Ala
785                 790                 795                 800

Phe Val Pro Ile Tyr Phe Gly Ser Asn Tyr Lys Ile Ile Thr Thr Cys
                805                 810                 815

Phe Ala Val Ser Leu Ser Val Thr Val Ala Leu Gly Cys Met Phe Thr
            820                 825                 830

Pro Lys Met Tyr Ile Ile Ile Ala Lys Pro Glu Arg Asn Val Arg Ser
        835                 840                 845

Ala Phe Thr Thr Ser Asp Val Val Arg Met His Val Gly Asp Gly Lys
    850                 855                 860

Leu Pro Cys Arg Ser Asn Thr Phe Leu Asn Ile Phe Arg Arg Lys Lys
865                 870                 875                 880
```

-continued

```
Ala Gly Ala Gly Asn Ala Asn Ser Asn Gly Lys Ser Val Ser Trp Ser
                885                 890                 895

Glu Pro Gly Gly Gly Gln Val Pro Lys Gly Gln His Met Trp His Arg
            900                 905                 910

Leu Ser Val His Val Lys Thr Asn Glu Thr Ala Cys Asn Gln Thr Ala
        915                 920                 925

Val Ile Lys Pro Leu Thr Lys Ser Tyr Gln Gly Ser Gly Lys Ser Leu
    930                 935                 940

Thr Phe Ser Asp Thr Ser Thr Lys Thr Leu Tyr Asn Val Glu Glu Glu
945                 950                 955                 960

Glu Asp Ala Gln Pro Ile Arg Phe Ser Pro Pro Gly Ser Pro Ser Met
                965                 970                 975

Val Val His Arg Arg Val Pro Ser Ala Ala Thr Thr Pro Pro Leu Pro
            980                 985                 990

Ser His Leu Thr Ala Glu Glu Thr  Pro Leu Phe Leu Ala  Glu Pro Ala
        995                 1000                1005

Leu Pro  Lys Gly Leu Pro Pro  Pro Leu Gln Gln Gln  Gln Gln Pro
    1010                 1015                 1020

Pro Pro  Gln Gln Lys Ser Leu  Met Asp Gln Leu Gln  Gly Val Val
    1025                 1030                 1035

Ser Asn  Phe Ser Thr Ala Ile  Pro Asp Phe His Ala  Val Leu Ala
    1040                 1045                 1050

Gly Pro  Gly Gly Pro Gly Asn  Gly Leu Arg Ser Leu  Tyr Pro Pro
    1055                 1060                 1065

Pro Pro  Pro Pro Gln His Leu  Gln Met Leu Pro Leu  Gln Leu Ser
    1070                 1075                 1080

Thr Phe  Gly Glu Glu Leu Val  Ser Pro Pro Ala Asp  Asp Asp Asp
    1085                 1090                 1095

Asp Ser  Glu Arg Phe Lys Leu  Leu Gln Glu Tyr Val  Tyr Glu His
    1100                 1105                 1110

Glu Arg  Glu Gly Asn Thr Glu  Glu Asp Glu Leu Glu  Glu Glu Glu
    1115                 1120                 1125

Glu Asp  Leu Gln Ala Ala Ser  Lys Leu Thr Pro Asp  Asp Ser Pro
    1130                 1135                 1140

Ala Leu  Thr Pro Pro Ser Pro  Phe Arg Asp Ser Val  Ala Ser Gly
    1145                 1150                 1155

Ser Ser  Val Pro Ser Ser Pro  Val Ser Glu Ser Val  Leu Cys Thr
    1160                 1165                 1170

Pro Pro  Asn Val Ser Tyr Ala  Ser Val Ile Leu Arg  Asp Tyr Lys
    1175                 1180                 1185

Gln Ser  Ser Ser Thr Leu
    1190
```

<210> SEQ ID NO 9
<211> LENGTH: 7927
<212> TYPE: DNA
<213> ORGANISM: Homo sapiens

<400> SEQUENCE: 9

```
agctcggctg ttctgcgcac gctgagcgga gggaatgagc ttgagatcat cttgggggg      60

aagccgggga ctggagaggc cggctctgcc ctgctgatcc ccgtggccca acttttcggg    120

gggctagcta gaccgagtct cactgctcgc agcgcagcca acagggggt ttagaagatc    180

atgaccacat ggatcatcta actaaatggt acatggggac aaaatggtcc tttagaaaat    240
```

-continued

```
acatctgaat tgctggctaa tttcttgatt tgcgactcaa cgtaggacat cgcttgttcg    300
tagctatcag aaccctcctg aattttcccc accatgctat ctttattggc ttgaactcct    360
ttcctaaaat ggtccttctg ttgatcctgt cagtcttact tttgaaagaa gatgtccgtg    420
ggagtgcaca gtccagtgag aggagggtgg tggctcacat gccgggtgac atcattattg    480
gagctctctt ttctgttcat caccagccta ctgtggacaa agttcatgag aggaagtgtg    540
gggcggtccg tgaacagtat ggcattcaga gagtggaggc catgctgcat accctggaaa    600
ggatcaattc agaccccaca ctcttgccca acatcacact gggctgtgag ataagggact    660
cctgctggca ttcggctgtg gccctagagc agagcattga gttcataaga gattccctca    720
tttcttcaga agaggaagaa ggcttggtac gctgtgtgga tggctcctcc tcttccttcc    780
gctccaagaa gcccatagta ggggtcattg ggcctggctc cagttctgta gccattcagg    840
tccagaattt gctccagctt ttcaacatac ctcagattgc ttactcagca accagcatgg    900
atctgagtga caagactctg ttcaaatatt tcatgagggt tgtgccttca gatgctcagc    960
aggcaagggc catggtggac atagtgaaga ggtacaactg gacctatgta tcagccgtgc   1020
acacagaagg caactatgga gaaagtggga tggaagcctt caaagatatg tcagcgaagg   1080
aagggatttg catcgcccac tcttacaaaa tctacagtaa tgcaggggag cagagctttg   1140
ataagctgct gaagaagctc acaagtcact tgcccaaggc ccgggtggtg gcctgcttct   1200
gtgagggcat gacggtgaga ggtctgctga tggccatgag gcgcctgggt ctagcgggag   1260
aatttctgct tctgggcagt gatggctggg ctgacaggta tgatgtgaca gatggatatc   1320
agcgagaagc tgttggtggc atcacaatca agctccaatc tcccgatgtc aagtggtttg   1380
atgattatta tctgaagctc cggccagaaa caaaccaccg aaacccttgg tttcaagaat   1440
tttggcagca tcgttttcag tgccgactgg aagggtttcc acaggagaac agcaaataca   1500
acaagacttg caatagttct ctgactctga aaacacatca tgttcaggat tccaaaatgg   1560
gatttgtgat caacgccatc tattcgatgg cctatgggct ccacaacatg cagatgtccc   1620
tctgcccagg ctatgcagga ctctgtgatg ccatgaagcc aattgatgga cggaaacttt   1680
tggagtccct gatgaaaacc aattttactg ggtttctgg agatacgatc ctattcgatg   1740
agaatggaga ctctccagga aggtatgaaa taatgaattt caaggaaatg ggaaaagatt   1800
actttgatta tatcaacgtt ggaagttggg acaatggaga attaaaaatg gatgatgatg   1860
aagtatggtc caagaaaagc aacatcatca gatctgtgtg cagtgaacca tgtgagaaag   1920
gccagatcaa ggtgatccga aagggagaag tcagctgttg ttggacctgt acaccttgta   1980
aggagaatga gtatgtcttt gatgagtaca catgcaaggc atgccaactg ggtcttggc   2040
ccactgatga tctcacaggt tgtgacttga tcccagtaca gtatcttcga tggggtgacc   2100
ctgaacccat tgcagctgtg gtgtttgcct gccttggcct cctggccacc ctgtttgtta   2160
ctgtagtctt catcatttac cgtgatacac cagtagtcaa gtcctcaagc agggaactct   2220
gctacattat ccttgctggc atctgcctgg gctacttatg taccttctgc ctcattgcga   2280
agcccaaaca gatttactgc taccttcaga gaattggcat tggtctctcc ccagccatga   2340
gctactcagc ccttgtaaca aagaccaacc gtattgcaag gatcctggct ggcagcaaga   2400
agaagatctg taccaaaaag cccagattca tgagtgcctg tgcccagcta gtgattgctt   2460
tcattctcat atgcatccag ttgggcatca tcgttgccct ctttataatg gagcctcctg   2520
acataatgca tgactaccca agcattcgag aagtctacct gatctgtaac accaccaacc   2580
taggagttgt cactccactt ggatacaatg gattgttgat tttgagctgc accttctatg   2640
```

-continued cgttcaagac cagaaatgtt ccagctaact tcaacgaggc caagtatatc gccttcacaa 2700
tgtacacgac ctgcattata tggctagctt ttgtgccaat ctactttggc agcaactaca 2760
aaatcatcac catgtgtttc tcggtcagcc tcagtgccac agtggcccta ggctgcatgt 2820
ttgtgccgaa ggtgtacatc atcctggcca aaccagagag aaacgtgcgc agcgccttca 2880
ccacatctac cgtggtgcgc atgcatgtag ggatggcaa gtcatcctcc gcagccagca 2940
gatccagcag cctagtcaac ctgtggaaga gaaggggctc ctctggggaa accttaagtt 3000
ccaatggaaa atccgtcacg tgggcccaga atgagaagag cagccggggg cagcacctgt 3060
ggcagcgcct gtccatccac atcaacaaga aagaaaaccc caaccaaacg gccgtcatca 3120
agcccttccc caagagcacg gagagccgtg gcctgggcgc tggcgctggc gcaggcggga 3180
gcgctggggg cgtgggggcc acgggcggtg cgggctgcgc aggcgccggc ccaggcgggc 3240
ccgagtcccc agacgccggc cccaaggcgc tgtatgatgt ggccgaggct gaggagcact 3300
tcccggcgcc cgcgcggccg cgctcaccgt cgcccatcag cacgctgagc caccgcgcgg 3360
gctcggccag ccgcacggac gacgatgtgc cgtcgctgca ctcggagcct gtggcgcgca 3420
gcagctcctc gcagggctcc ctcatggagc agatcagcag tgtggtcacc cgcttcacgg 3480
ccaacatcag cgagctcaac tccatgatgc tgtccaccgc ggcccccagc cccggcgtcg 3540
gcgccccgct ctgctcgtcc tacctgatcc ccaaagagat ccagttgccc acgaccatga 3600
cgacctttgc cgaaatccag cctctgccgg ccatcgaagt cacgggaggc gcgcagcccg 3660
cggcaggggc gcaggcggct ggggacgcgg cccgggagag ccccgcggcc ggtcccgagg 3720
ctgcggccgc caagccagac ctggaggagc tggtggctct caccccgccg tccccccttca 3780 gagactcggt ggactcgggg agcacaaccc ccaactcgcc agtgtccgag tcggccctct 3840
gtatcccgtc gtctcccaaa tatgacactc ttatcataag agattacact cagagctcct 3900
cgtcgttgtg aatgtccctg gaaagcacgc cggcctgcgc gtgcggagcg gagcccccccg 3960 tgttcacaca cacacaatgg caagcatagt cgcctggtta cggcccaggg ggaagatgcc 4020
aagggcaccc cttaatggaa acacgagatc agtagtgcta tctcatgaca accgacgaag 4080
aaaccgacga caaatctttt ggcagatttt cttctagtgg ccttagaaaa catgggcttt 4140
taagaaacac ggctgatatc tttgagggct gacaaggcgt ctcttcaaac agttccatac 4200
caagtgcttt gctctaggga agcagtgcgt gtgaaacagc gtaacggagg gtgaagagca 4260
tagttaataa gcaactgtaa aaagttttat ttgtttactt taattctttt cccagaagag 4320
tctttgattc accaaacatg aatgtacatt ttctaacaaa ctcaaaatct gggaccaaaa 4380
catcaacttt tttctttctt ttttctttct ttttgttttt tctttcctgt aaagaccttg 4440
aaaagcagta acttgggtcc agtatttacg gaggcgttgt gaatgtgtcc catgcataac 4500
acactactgg atagtgagtg ctgcgctaat gtactacgta gggcttctac cagagatttt 4560
cctctccaat tgggttgtga aatactcttc caaaagcctg catcggggat tccacctact 4620
tatttcagat tcacctccat taaccaagaa aaccagtgga agatttcttg actatttcac 4680
catgttgcca atcaatactg gagtagcaaa aaaaatattt tctggaatac tgttttgtaa 4740
ttccctcact ggggtgcatt gtagctggaa attctcttta taaaaatcat tcttgagctc 4800
cagcctggct atctctttca agaaacatgg ccactcttta ggaatgctgt tgcgtttgca 4860
ttgccaacta aaatattaaa atatgcattg ggcttcttc attcctttat tttgagaacc 4920
tgatgcacaa agagctcctt tgttcttttc gagtcccacc actggaagag tggtccatag 4980

```
accccatgaa gacattgtca tgatttgaga gactgttgtt gaaaggatta acacaatctt   5040
aatacactga aaattttaac tgtgtcaagt cagcttagtg gagatttagc tatgccagtg   5100
agcagtgatt ttaactattc ttggctgctt aaacagggca gctatgaact atgacaaatg   5160
tagatttttc aaagcaatac aaaatactaa aaaagaggaa ccttaatgaa tattaaccac   5220
acagtctttc ttagccattc caaaaagagg caaagcaatt cttattttct tttttaaaat   5280
aatgattaat atgattttgt gcacttcata ctgtcacttt ttaaaactac agaaaagaga   5340
tttagagtat aacagaaaca agtgtgcttt gatagtctca aataggtaga attcatagtt   5400
caagacctga atccactgtc atctctttct tcctcccatt gcagctatcc tcaggtacca   5460
aatgttttga tttttaaata aggatagtaa taaatggagg aggtgtccta taaatttaaa   5520
gttcagttga cccagcctta tacttaagat agccttatga aaaatatgtg ctgtgaggca   5580
gaagtatatt ttggcagaga gaataataaa taaaactttt tcttttagct caatatcctt   5640
actttggtaa gtattttttt ttatttcaca tctacttaac agaaaataaa ctgagaaata   5700
gaagtcagtc cattggcata atttatcatt cttcacttta aaaaattcta ataaatattc   5760
tgcttgagtt ttcttttctg ctatttgttc ttacttgcaa ctttaagtca aacctcccaa   5820
tacaaaacat taaaagctaa cattaatgta ctaaagtatt aatttaaaag aaatcgaacc   5880
tcccatgcta gatttgaaaa taacatcatc acagcaccct gatcccaaat attacaccga   5940
ggcttttaaa atgtaagtga aatctagcta agtttcatgg tttcattaaa agcaaatgtc   6000
tgcctctatc tgaaaaacaa atggaaatct tttgaggtgt taataccctt tggatcctca   6060
tcaaaaggat ggcattcacc tgaggattcc tatcttgact tcttaggtat taaaaacctt   6120
tcttgatatg ctctacattt taaaatttgt tttataaaat ccttatgttg attttcattt   6180
tattctcaag tacaatacgt ttcactctag accagttgaa gaacatgttt aaactttgtt   6240
catggtcaaa ttcattttct attttttag taacatatct cttaaaaagc acactacctt   6300
ataaaaaact tcatcagaaa ttaaatttaa tgcaagtaaa ttgccatctg atacttccac   6360
atgctatcat aatcaactgt aataataaaa atgatttatc caattagaaa aggacaagat   6420
atatttttct ctgtatttct ataacttttg ccactccatt gaatacattg tatgttggac   6480
ataagattat tagtaatgca ttcttgagat cttttatttt ggaatgatgc taactctgtc   6540
tctttgccaa ttctaatacc aggttccaag taataactct acagtacaaa gagaactgaa   6600
tattcattct agggctatag gatatgaact tcacaattca tttgggtaca ttctcattga   6660
atttccttca aaacaatctg ttcctggtgc ccagtgataa ttcagtcggg accagcatga   6720
ctaaaaggaa ggggatatgc taaggctcag caaagtgacc ctaaatgaga gatatgtccc   6780
aggatggaaa gaagaagacg tggtttaacc aagttatact gactaatcta agcagtccac   6840
tcatccttcc attttgggaa aggagtgggg gcagcctaag aagaacatat ctggattggg   6900
aagaaccgtc tttctgggct agggatgggg aacagaaagg gagtatggaa agaaaaatta   6960
taagagattt gactgaagca aggaaaaaaa gcaaatcccc aaacgtgcta atccttgaaa   7020
gtaactatct ttcccaaact actgctgtta ccagcaagtg atcaggaaga ctaggagcta   7080
tttctgactg taaatgaatt gtataatagc tctgctgcag ttctgtgact tccaagccag   7140
gaattaaatg ctctttttaa gaataacaaa aaacaaaagc atttcctatg ctagtctccc   7200
agtaaaatgt acatgttttg gagacttcaa aggtattatg tgagttcaca tttagcaaca   7260
gcttattaat aaccctcaag ctgtcagaat ctctatagtt accatttaca attttatact   7320
gtgaaaaaat acagatcagt gaaagcataa agacaagtca gaattcactt tgaagagggt   7380
```

```
ctgaggcctg ggagagtctc tactgtctat tgaagaatga ggcatgtata aaatagttgg   7440

ttgaatttca ctgatcttcc caatgtgaac aaatatacta tgtatattgt gtgtatttct   7500

agaaatcaat ggcagctgct gatggtgttg taattagaaa tctatataga ttatagatgt   7560

tttagaaaga tggtgccaat cctaaaagat ttgtgtgggc taaaagtgct tgtacttact   7620

tttttctgca cttataactg atttggtttt aaaattgtgt gcgtgtatct gttctttctc   7680

tgttgtggca gcttgtacta ttaaaataat agagaatgtt aaattatttt gatgtgaact   7740

gcaaatgatt ttttttcata aagtttaaca tttttatcag cattgttttg ctttgtactt   7800

gtataaatat gttttatttt agcacttcaa aatatacttg cctgtttctc agttgtctaa   7860

atcatgttgt acttggtgtt tgtgaagcca gttacttttc aaaaaaatta aaaaacctat   7920

aatatga                                                             7927


<210> SEQ ID NO 10
<211> LENGTH: 1180
<212> TYPE: PRT
<213> ORGANISM: Homo sapiens

<400> SEQUENCE: 10

Met Val Leu Leu Leu Ile Leu Ser Val Leu Leu Leu Lys Glu Asp Val
1               5                   10                  15

Arg Gly Ser Ala Gln Ser Ser Glu Arg Arg Val Val Ala His Met Pro
            20                  25                  30

Gly Asp Ile Ile Ile Gly Ala Leu Phe Ser Val His His Gln Pro Thr
        35                  40                  45

Val Asp Lys Val His Glu Arg Lys Cys Gly Ala Val Arg Glu Gln Tyr
    50                  55                  60

Gly Ile Gln Arg Val Glu Ala Met Leu His Thr Leu Glu Arg Ile Asn
65                  70                  75                  80

Ser Asp Pro Thr Leu Leu Pro Asn Ile Thr Leu Gly Cys Glu Ile Arg
                85                  90                  95

Asp Ser Cys Trp His Ser Ala Val Ala Leu Glu Gln Ser Ile Glu Phe
            100                 105                 110

Ile Arg Asp Ser Leu Ile Ser Ser Glu Glu Glu Glu Gly Leu Val Arg
        115                 120                 125

Cys Val Asp Gly Ser Ser Ser Ser Phe Arg Ser Lys Lys Pro Ile Val
    130                 135                 140

Gly Val Ile Gly Pro Gly Ser Ser Ser Val Ala Ile Gln Val Gln Asn
145                 150                 155                 160

Leu Leu Gln Leu Phe Asn Ile Pro Gln Ile Ala Tyr Ser Ala Thr Ser
                165                 170                 175

Met Asp Leu Ser Asp Lys Thr Leu Phe Lys Tyr Phe Met Arg Val Val
            180                 185                 190

Pro Ser Asp Ala Gln Gln Ala Arg Ala Met Val Asp Ile Val Lys Arg
        195                 200                 205

Tyr Asn Trp Thr Tyr Val Ser Ala Val His Thr Glu Gly Asn Tyr Gly
    210                 215                 220

Glu Ser Gly Met Glu Ala Phe Lys Asp Met Ser Ala Lys Glu Gly Ile
225                 230                 235                 240

Cys Ile Ala His Ser Tyr Lys Ile Tyr Ser Asn Ala Gly Glu Gln Ser
                245                 250                 255

Phe Asp Lys Leu Leu Lys Lys Leu Thr Ser His Leu Pro Lys Ala Arg
            260                 265                 270
```

-continued

```
Val Val Ala Cys Phe Cys Glu Gly Met Thr Val Arg Gly Leu Leu Met
        275                 280                 285

Ala Met Arg Arg Leu Gly Leu Ala Gly Glu Phe Leu Leu Leu Gly Ser
    290                 295                 300

Asp Gly Trp Ala Asp Arg Tyr Asp Val Thr Asp Gly Tyr Gln Arg Glu
305                 310                 315                 320

Ala Val Gly Gly Ile Thr Ile Lys Leu Gln Ser Pro Asp Val Lys Trp
                325                 330                 335

Phe Asp Asp Tyr Tyr Leu Lys Leu Arg Pro Glu Thr Asn His Arg Asn
            340                 345                 350

Pro Trp Phe Gln Glu Phe Trp Gln His Arg Phe Gln Cys Arg Leu Glu
        355                 360                 365

Gly Phe Pro Gln Glu Asn Ser Lys Tyr Asn Lys Thr Cys Asn Ser Ser
    370                 375                 380

Leu Thr Leu Lys Thr His His Val Gln Asp Ser Lys Met Gly Phe Val
385                 390                 395                 400

Ile Asn Ala Ile Tyr Ser Met Ala Tyr Gly Leu His Asn Met Gln Met
                405                 410                 415

Ser Leu Cys Pro Gly Tyr Ala Gly Leu Cys Asp Ala Met Lys Pro Ile
            420                 425                 430

Asp Gly Arg Lys Leu Leu Glu Ser Leu Met Lys Thr Asn Phe Thr Gly
        435                 440                 445

Val Ser Gly Asp Thr Ile Leu Phe Asp Glu Asn Gly Asp Ser Pro Gly
    450                 455                 460

Arg Tyr Glu Ile Met Asn Phe Lys Glu Met Gly Lys Asp Tyr Phe Asp
465                 470                 475                 480

Tyr Ile Asn Val Gly Ser Trp Asp Asn Gly Glu Leu Lys Met Asp Asp
                485                 490                 495

Asp Glu Val Trp Ser Lys Lys Ser Asn Ile Ile Arg Ser Val Cys Ser
            500                 505                 510

Glu Pro Cys Glu Lys Gly Gln Ile Lys Val Ile Arg Lys Gly Glu Val
        515                 520                 525

Ser Cys Cys Trp Thr Cys Thr Pro Cys Lys Glu Asn Glu Tyr Val Phe
    530                 535                 540

Asp Glu Tyr Thr Cys Lys Ala Cys Gln Leu Gly Ser Trp Pro Thr Asp
545                 550                 555                 560

Asp Leu Thr Gly Cys Asp Leu Ile Pro Val Gln Tyr Leu Arg Trp Gly
                565                 570                 575

Asp Pro Glu Pro Ile Ala Ala Val Val Phe Ala Cys Leu Gly Leu Leu
            580                 585                 590

Ala Thr Leu Phe Val Thr Val Val Phe Ile Ile Tyr Arg Asp Thr Pro
        595                 600                 605

Val Val Lys Ser Ser Ser Arg Glu Leu Cys Tyr Ile Ile Leu Ala Gly
    610                 615                 620

Ile Cys Leu Gly Tyr Leu Cys Thr Phe Cys Leu Ile Ala Lys Pro Lys
625                 630                 635                 640

Gln Ile Tyr Cys Tyr Leu Gln Arg Ile Gly Ile Gly Leu Ser Pro Ala
                645                 650                 655

Met Ser Tyr Ser Ala Leu Val Thr Lys Thr Asn Arg Ile Ala Arg Ile
            660                 665                 670

Leu Ala Gly Ser Lys Lys Lys Ile Cys Thr Lys Lys Pro Arg Phe Met
        675                 680                 685
```

-continued

```
Ser Ala Cys Ala Gln Leu Val Ile Ala Phe Ile Leu Ile Cys Ile Gln
    690                 695                 700

Leu Gly Ile Ile Val Ala Leu Phe Ile Met Glu Pro Pro Asp Ile Met
705                 710                 715                 720

His Asp Tyr Pro Ser Ile Arg Glu Val Tyr Leu Ile Cys Asn Thr Thr
                725                 730                 735

Asn Leu Gly Val Val Thr Pro Leu Gly Tyr Asn Gly Leu Leu Ile Leu
            740                 745                 750

Ser Cys Thr Phe Tyr Ala Phe Lys Thr Arg Asn Val Pro Ala Asn Phe
        755                 760                 765

Asn Glu Ala Lys Tyr Ile Ala Phe Thr Met Tyr Thr Thr Cys Ile Ile
    770                 775                 780

Trp Leu Ala Phe Val Pro Ile Tyr Phe Gly Ser Asn Tyr Lys Ile Ile
785                 790                 795                 800

Thr Met Cys Phe Ser Val Ser Leu Ser Ala Thr Val Ala Leu Gly Cys
                805                 810                 815

Met Phe Val Pro Lys Val Tyr Ile Ile Leu Ala Lys Pro Glu Arg Asn
            820                 825                 830

Val Arg Ser Ala Phe Thr Thr Ser Thr Val Val Arg Met His Val Gly
        835                 840                 845

Asp Gly Lys Ser Ser Ser Ala Ala Ser Arg Ser Ser Ser Leu Val Asn
    850                 855                 860

Leu Trp Lys Arg Arg Gly Ser Ser Gly Glu Thr Leu Ser Ser Asn Gly
865                 870                 875                 880

Lys Ser Val Thr Trp Ala Gln Asn Glu Lys Ser Ser Arg Gly Gln His
                885                 890                 895

Leu Trp Gln Arg Leu Ser Ile His Ile Asn Lys Lys Glu Asn Pro Asn
            900                 905                 910

Gln Thr Ala Val Ile Lys Pro Phe Pro Lys Ser Thr Glu Ser Arg Gly
        915                 920                 925

Leu Gly Ala Gly Ala Gly Ala Gly Gly Ser Ala Gly Gly Val Gly Ala
    930                 935                 940

Thr Gly Gly Ala Gly Cys Ala Gly Ala Gly Pro Gly Gly Pro Glu Ser
945                 950                 955                 960

Pro Asp Ala Gly Pro Lys Ala Leu Tyr Asp Val Ala Glu Ala Glu Glu
                965                 970                 975

His Phe Pro Ala Pro Ala Arg Pro Arg Ser Pro Ser Pro Ile Ser Thr
            980                 985                 990

Leu Ser His Arg Ala Gly Ser Ala  Ser Arg Thr Asp Asp  Asp Val Pro
        995                 1000                1005

Ser Leu  His Ser Glu Pro Val  Ala Arg Ser Ser Ser  Ser Gln Gly
    1010                 1015                 1020

Ser Leu  Met Glu Gln Ile Ser  Ser Val Val Thr Arg  Phe Thr Ala
    1025                 1030                 1035

Asn Ile  Ser Glu Leu Asn Ser  Met Met Leu Ser Thr  Ala Ala Pro
    1040                 1045                 1050

Ser Pro  Gly Val Gly Ala Pro  Leu Cys Ser Ser Tyr  Leu Ile Pro
    1055                 1060                 1065

Lys Glu  Ile Gln Leu Pro Thr  Thr Met Thr Thr Phe  Ala Glu Ile
    1070                 1075                 1080

Gln Pro  Leu Pro Ala Ile Glu  Val Thr Gly Gly Ala  Gln Pro Ala
    1085                 1090                 1095

Ala Gly  Ala Gln Ala Ala Gly  Asp Ala Ala Arg Glu  Ser Pro Ala
```

```
    1100                1105                1110

Ala Gly  Pro Glu Ala Ala Ala  Ala Lys Pro Asp Leu  Glu Glu Leu
    1115                1120                1125

Val Ala  Leu Thr Pro Pro Ser  Pro Phe Arg Asp Ser  Val Asp Ser
    1130                1135                1140

Gly Ser  Thr Thr Pro Asn Ser  Pro Val Ser Glu Ser  Ala Leu Cys
    1145                1150                1155

Ile Pro  Ser Ser Pro Lys Tyr  Asp Thr Leu Ile Ile  Arg Asp Tyr
    1160                1165                1170

Thr Gln  Ser Ser Ser Ser Leu
    1175                1180


<210> SEQ ID NO 11
<211> LENGTH: 4228
<212> TYPE: DNA
<213> ORGANISM: Homo sapiens

<400> SEQUENCE: 11

tggagcggcg gctgcgcttc ggcttcgagc ccagctctcc tggccccaac gcgggcttag     60

cctcccgcct tggctcgggc aggcgcccgt cgacccttcg gcccctttcg cccgccctgg    120

agctgggggc agggtgccag tggaagcgtg gggcttggct ctgtgattca ttcattctcc    180

gccgacggga gcctcagacc cgctgtgctc tgaagagagg agggaagagg gggcagccgc    240

gaatgaaggg ccgggcacca gccgggctcc attgtgctcg gcggcggggg gcgggaaggg    300

gctgagggag gtgggatcgg gtcccctcct ccagctctcc ggcgtgcgct gcgcccccag    360

cctgctgcca gcctggaaat ggctccgttt attctcttcg ggagaatgaa tcgatcctgc    420

ctagccttct cttcgtcctc cccacctctt ctctgctccg agtcttagga ggagaaacat    480

ttaaaaagac agattccaat gtggagtgcc gtgcaggttg cgagctgccg ggtttgcact    540

tcgaggagat tttcctgtgt agttttttc ctaatgtgag cgcagggaag ccgtggcatt    600

actgcttttg ggatttttat tcacgtgcac gtcgcgtttg gttgctcgct ccaccccccgg    660

agacctggtg tggtggagaa atttgaaccc gcagccttag ctccgaaaag gccgagttac    720

ctggctctcc ctgagtgtcg aggaggacat gagtgaaatg accagcgaac tcattttta    780

taggactcgg tgaagccgga ttctgcattt ccctacttgt agactcattt tgtggaatag    840

agttgatcgc tgtctcctcc gcaaagcatt ttaactcgaa taagcaaatg ccgcctctgt    900

ttgaacgttt tggtatttac aagagagaaa tcattttacc taagagaact aattgaattg    960

gcagcatcct tgaaatacct ccggacaagg atctgggggt gggggtggaa aagcaactgc   1020

gaaatagcag acggagaaat tcctttggaa gttattccgt agcataagag ctgaaacttc   1080

agagcaagtt ttcattgggc aaaatggggg aacaacctat cttcagcact cgagctcatg   1140

tcttccaaat tgacccaaac acaaagaaga actgggtacc caccagcaag catgcagtta   1200

ctgtgtctta tttctatgac agcacaagaa atgtgtatag gataatcagt ttagatggct   1260

caaaggcaat aataaatagt accatcaccc caaacatgac atttactaaa acatctcaga   1320

agtttggcca gtgggctgat agccgggcaa acaccgttta tggattggga ttctcctctg   1380

agcatcatct ttcgaaattt gcagaaaagt ttcaggaatt taaagaagct gctcgactag   1440

caaaggaaaa atcacaagag aagatggaac ttaccagtac accttcacag gaatccgcag   1500

gcggggatct tcagtctcct ttaacaccgg aaagtatcaa cgggacagat gatgaaagaa   1560

cacctgatgt gacacagaac tcagagccaa gggctgaacc aactcagaat gcattgccat   1620
```

```
tttcacatag ttcagcaatc agcaaacatt gggaggctga actggctacc ctcaaaggaa   1680
ataatgccaa actcactgca gccctgctgg agtccactgc caatgtgaaa caatggaaac   1740
agcaacttgc tgcctatcaa gaggaagcag aacgtctgca caagcgggtg actgaacttg   1800
aatgtgttag tagccaagca aatgcagtac atactcataa gacagaatta aatcagacaa   1860
tacaagaact ggaagagaca ctgaaactga aggaagagga aatagaaagg ttaaaacaag   1920
aaattgataa tgccagagaa ctacaagaac agagggattc tttgactcag aaactacagg   1980
aagtagaaat tcggaacaaa gacctggagg gacaactgtc tgacttagag caacgtctgg   2040
agaaaagtca gaatgaacaa gaagcttttc gcaataacct gaagacactc ttagaaattc   2100
tggatggaaa gatatttgaa ctaacagaat tacgagataa cttggccaag ctactagaat   2160
gcagctaagg aaagtgaaat ttcagtgcca attaattaaa agatacactg tctctcttca   2220
taggactgtt taggctctgc atcaagattg cacaaaaaaa aaaaaaaaaa aattgaatat   2280
cactcctcca ggaggaggat cttttgaaat tggaattgta tatttcactg taaattttag   2340
aatccagctt gtagctagtt ggggaaaaaa gatgaaaaac ttgaactaca aattacctcc   2400
atgtatatta ttggccatag ttaactagaa agttataaat agacacttaa tgcaatcttt   2460
tttcctgata ttagccaatg ggagaattaa caatgtctag gtcacatccc ctttttgtgt   2520
tcaacacagt gaagattatc tgctttttaa attaatttat ttacgatatc tagagctgtg   2580
ttttgtgcaa aaacttagtg atgaaagcct gtcttttgtt gtaatctgaa taatttctca   2640
ggatattttt gcactgctga gaagcagtgc cattaccaat taattcttgc caggagtgag   2700
agagagctgt atctttaatt gaaatatact ataactgggt gtatagagtt cttccctttt   2760
ttgtgctgga agatatttca ctctggtgac tactctggta cactctggtg ttctctaatc   2820
ttgtctgttg tatagtttac ttttccatat tgattccatg tatttatgag aagatattgt   2880
ctcccatttt attacacatt ttaaagccaa ctaacgaagg cagctgagtc cctcagaaat   2940
ttttcttttt aagtttctaa taaatttgac acacagtact gaaatacagc agcccgtcat   3000
tgacaggctg gtctagcaat gttaagtata tttacagaat atgcagttac atttatttat   3060
atattttgca agaaatcttt tctgaatgat caatgcattt caatttacga ataataatgg   3120
ttattgggga actgtttatt atagataatt ttaaggtgta tagctatttt aaagggggtc   3180
catttacatc aaacagctga tcagaggact ctatctaaat tgtgatcgtg gcagatagag   3240
atggagtcat gtactctatc tggctctaca catcaatcac atcttgattc aaacctcaca   3300
aggcaatatt ctgaattgtt aactaggtat ttcaaaacag gaattaaatt caataggctc   3360
ttctcagtga acaggtttta atgttgtttt gatgtaattt taaaagactt ttagcaaaca   3420
tgcatttctt tatatgatat atttctttta cgaagctatt ttaaaagtaa gccaagtgct   3480
gtctagtctg cttataaagt aggaattgca tcagagtaca tatattcttg ctgtacaatg   3540
cctgtgatgt tgaggagggt tctttttttaa agtgtatgct tgagtaactg actctatgga   3600
gtctataaat gcactgactt cttgtttgta ccccaaaatg atcgaattgt taagtacaaa   3660
attaagctaa ttaaccaatt tgtaaccatt ttttcactca taaacagcta ctcaatacta   3720
gacaattttg ttttttatgt atgtgtatgt acgtaaatac atacatatta atttacatta   3780
gagtgaaaaa taaatggttt gtttctgaag ttagtttctt aagtgagttt tcaggtgtct   3840
ctgaaaaatt tataacaatc atgtattata tgtgctgtaa catcatgtac gttacctcca   3900
tctattttag gatattttcc tcacctatat attataggga gaataattta gatacacatg   3960
ctcagagctg agatatttct ctgataaatc aggtaacaaa atgtatttga ttgatggaat   4020
```

tttgaagtaa atgtgttttt atccatcagt ttctgagtaa caaagagcac caagttttaa 4080
tttaaatagg agatttaaca ctagggatca gggagtttag tatgaagagt taaaaaaatt 4140
taaaaaacag tgtaagctgt tgaaatggca agtgaattat tttaatgatg taataaaata 4200
tttttaaatt ttgaaaaaaa aaaaaaaa 4228

<210> SEQ ID NO 12
<211> LENGTH: 354
<212> TYPE: PRT
<213> ORGANISM: Homo sapiens

<400> SEQUENCE: 12

```
Met Gly Glu Gln Pro Ile Phe Ser Thr Arg Ala His Val Phe Gln Ile
1               5                   10                  15

Asp Pro Asn Thr Lys Lys Asn Trp Val Pro Thr Ser Lys His Ala Val
            20                  25                  30

Thr Val Ser Tyr Phe Tyr Asp Ser Thr Arg Asn Val Tyr Arg Ile Ile
        35                  40                  45

Ser Leu Asp Gly Ser Lys Ala Ile Ile Asn Ser Thr Ile Thr Pro Asn
    50                  55                  60

Met Thr Phe Thr Lys Thr Ser Gln Lys Phe Gly Gln Trp Ala Asp Ser
65                  70                  75                  80

Arg Ala Asn Thr Val Tyr Gly Leu Gly Phe Ser Ser Glu His His Leu
                85                  90                  95

Ser Lys Phe Ala Glu Lys Phe Gln Glu Phe Lys Glu Ala Ala Arg Leu
            100                 105                 110

Ala Lys Glu Lys Ser Gln Glu Lys Met Glu Leu Thr Ser Thr Pro Ser
        115                 120                 125

Gln Glu Ser Ala Gly Gly Asp Leu Gln Ser Pro Leu Thr Pro Glu Ser
    130                 135                 140

Ile Asn Gly Thr Asp Asp Glu Arg Thr Pro Asp Val Thr Gln Asn Ser
145                 150                 155                 160

Glu Pro Arg Ala Glu Pro Thr Gln Asn Ala Leu Pro Phe Ser His Ser
                165                 170                 175

Ser Ala Ile Ser Lys His Trp Glu Ala Glu Leu Ala Thr Leu Lys Gly
            180                 185                 190

Asn Asn Ala Lys Leu Thr Ala Ala Leu Leu Glu Ser Thr Ala Asn Val
        195                 200                 205

Lys Gln Trp Lys Gln Gln Leu Ala Ala Tyr Gln Glu Glu Ala Glu Arg
    210                 215                 220

Leu His Lys Arg Val Thr Glu Leu Glu Cys Val Ser Ser Gln Ala Asn
225                 230                 235                 240

Ala Val His Thr His Lys Thr Glu Leu Asn Gln Thr Ile Gln Glu Leu
                245                 250                 255

Glu Glu Thr Leu Lys Leu Lys Glu Glu Glu Ile Glu Arg Leu Lys Gln
            260                 265                 270

Glu Ile Asp Asn Ala Arg Glu Leu Gln Glu Gln Arg Asp Ser Leu Thr
        275                 280                 285

Gln Lys Leu Gln Glu Val Glu Ile Arg Asn Lys Asp Leu Glu Gly Gln
    290                 295                 300

Leu Ser Asp Leu Glu Gln Arg Leu Glu Lys Ser Gln Asn Glu Gln Glu
305                 310                 315                 320

Ala Phe Arg Asn Asn Leu Lys Thr Leu Leu Glu Ile Leu Asp Gly Lys
                325                 330                 335
```

```
Ile Phe Glu Leu Thr Glu Leu Arg Asp Asn Leu Ala Lys Leu Leu Glu
            340                 345                 350

Cys Ser


<210> SEQ ID NO 13
<211> LENGTH: 1251
<212> TYPE: DNA
<213> ORGANISM: Homo sapiens

<400> SEQUENCE: 13

tgccctgcgc ccgcaacccg agccgcaccc gccgcggacg gagcccatgc gcggggcgaa      60

ccgcgcgccc ccgccccgc cccgccccgg cctcggcccc ggccctggcc ccgggggcag     120

tcgcgcctgt gaacggtggg gcaggagacc ctgtaggagg accccgggcc gcaggcccct     180

gaggagcgat gacggaatat aagctggtgg tggtgggcgc cggcggtgtg ggcaagagtg     240

cgctgaccat ccagctgatc cagaaccatt ttgtggacga atacgacccc actatagagg     300

attcctaccg gaagcaggtg gtcattgatg gggagacgtg cctgttggac atcctggata     360

ccgccggcca ggaggagtac agcgccatgc gggaccagta catgcgcacc ggggagggct     420

tcctgtgtgt gtttgccatc aacaacacca agtcttttga ggacatccac cagtacaggg     480

agcagatcaa acgggtgaag gactcggatg acgtgcccat ggtgctggtg gggaacaagt     540

gtgacctggc tgcacgcact gtggaatctc ggcaggctca ggacctcgcc cgaagctacg     600

gcatccccta catcgagacc tcggccaaga cccggcaggg cagccgctct ggctctagct     660

ccagctccgg gaccctctgg gaccccccgg gacccatgtg acccagcggc ccctcgcgct     720

ggagtggagg atgccttcta cacgttggtg cgtgagatcc ggcagcacaa gctgcggaag     780

ctgaaccctc ctgatgagag tggccccggc tgcatgagct gcaagtgtgt gctctcctga     840

cgcaggtgag ggggactccc agggcggccg ccacgcccac cggatgaccc cggctccccg     900

cccctgccgg tctcctggcc tgcggtcagc agcctccctt gtgccccgcc cagcacaagc     960

tcaggacatg gaggtgccgg atgcaggaag gaggtgcaga cggaaggagg aggaaggaag    1020

gacggaagca aggaaggaag gaagggctgc tggagcccag tcaccccggg accgtgggcc    1080

gaggtgactg cagaccctcc cagggaggct gtgcacagac tgtcttgaac atcccaaatg    1140

ccaccggaac cccagccctt agctcccctc ccaggcctct gtgggccctt gtcgggcaca    1200

gatgggatca cagtaaatta ttggatggtc ttgaaaaaaa aaaaaaaaaa a             1251


<210> SEQ ID NO 14
<211> LENGTH: 170
<212> TYPE: PRT
<213> ORGANISM: Homo sapiens

<400> SEQUENCE: 14

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80
```

-continued

```
Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Ser Ser Ser Ser
145                 150                 155                 160

Gly Thr Leu Trp Asp Pro Pro Gly Pro Met
                165                 170
```

<210> SEQ ID NO 15
<211> LENGTH: 2603
<212> TYPE: DNA
<213> ORGANISM: Homo sapiens

<400> SEQUENCE: 15

```
aggcgaggct tccccttccc cgcccctccc ccggcctcca gtccctccca gggccgcttc     60

gcagagcggc taggagcacg gcggcggcgg cactttcccc ggcaggagct ggagctgggc    120

tctggtgcgc gcgcggctgt gccgcccgag ccggagggac tggttggttg agagagagag    180

aggaagggaa tcccgggctg ccgaaccgca cgttcagccc gctccgctcc tgcagggcag    240

cctttcggct ctctgcgcgc gaagccgagt cccgggcggg tggggcgggg gtccactgag    300

accgctaccg gcccctcggc gctgacggga ccgcgcgggg cgcacccgct gaaggcagcc    360

ccggggcccg cggcccggac ttggtcctgc gcagcgggcg cggggcagcg cagcgggagg    420

aagcgagagg tgctgccctc cccccggagt tggaagcgcg ttacccgggt ccaaaatgcc    480

caagaagaag ccgacgccca tccagctgaa cccggccccc gacggctctg cagttaacgg    540

gaccagctct gcggagacca acttggaggc cttgcagaag aagctggagg agctagagct    600

tgatgagcag cagcgaaagc gccttgaggc ctttcttacc cagaagcaga aggtgggaga    660

actgaaggat gacgactttg agaagatcag tgagctgggg gctggcaatg gcggtgtggt    720

gttcaaggtc tcccacaagc cttctggcct ggtcatggcc agaaagctaa ttcatctgga    780

gatcaaaccc gcaatccgga accagatcat aagggagctg caggttctgc atgagtgcaa    840

ctctccgtac atcgtgggct tctatggtgc gttctacagc gatggcgaga tcagtatctg    900

catggagcac atggatggag gttctctgga tcaagtcctg aagaaagctg gaagaattcc    960

tgaacaaatt ttaggaaaag ttagcattgc tgtaataaaa ggcctgacat atctgaggga   1020

gaagcacaag atcatgcaca gagatgtcaa gccctccaac atcctagtca actcccgtgg   1080

ggagatcaag ctctgtgact ttggggtcag cgggcagctc atcgactcca tggccaactc   1140

cttcgtgggc acaaggtcct acatgtcgcc agaaagactc caggggactc attactctgt   1200

gcagtcagac atctggagca tgggactgtc tctggtagag atggcggttg ggaggtatcc   1260

catccctcct ccagatgcca aggagctgga gctgatgttt gggtgccagg tggaaggaga   1320

tgcggctgag accccaccca ggccaaggac ccccgggagg ccccttagct catacggaat   1380

ggacagccga cctcccatgg caatttttga gttgttggat tacatagtca acgagcctcc   1440

tccaaaactg cccagtggag tgttcagtct ggaatttcaa gattttgtga ataaatgctt   1500

aataaaaaac cccgcagaga gagcagattt gaagcaactc atggttcatg cttttatcaa   1560

gagatctgat gctgaggaag tggattttgc aggttggctc tgctccacca tcggccttaa   1620
```

```
ccagcccagc acaccaaccc atgctgctgg cgtctaagtg tttgggaagc aacaaagagc   1680

gagtcccctg cccggtggtt tgccatgtcg cttttgggcc tccttcccat gcctgtctct   1740

gttcagatgt gcatttcacc tgtgacaaag gatgaagaac acagcatgtg ccaagattct   1800

actcttgtca tttttaatat tactgtcttt attcttatta ctattattgt tcccctaagt   1860

ggattggctt tgtgcttggg gctatttgtg tgtatgctga tgatcaaaac ctgtgccagg   1920

ctgaattaca gtgaaatttt ggtgaatgtg ggtagtcatt cttacaattg cactgctgtt   1980

cctgctccat gactggctgt ctgcctgtat tttcgggatt ctttgacatt tggtggtact   2040

ttattcttgc tgggcatact ttctctctag gagggagcct tgtgagatcc ttcacaggca   2100

gtgcatgtga agcatgcttt gctgctatga aaatgagcat cagagagtgt acatcatgtt   2160

attttattat tattatttgc ttttcatgta gaactcagca gttgacatcc aaatctagcc   2220

agagcccttc actgccatga tagctggggc ttcaccagtc tgtctactgt ggtgatctgt   2280

agacttctgg ttgtatttct atatttattt tcagtatact gtgtgggata cttagtggta   2340

tgtctcttta agttttgatt aatgtttctt aaatggaatt attttgaatg tcacaaattg   2400

atcaagatat taaaatgtcg gatttatctt tccccatatc caagtaccaa tgctgttgta   2460

aacaacgtgt atagtgccta aaattgtatg aaaatccttt taaccatttt aacctagatg   2520

tttaacaaat ctaatctctt attctaataa atatactatg aaataaaaaa aaaaggatga   2580

aagctaaaaa aaaaaaaaaa aaa                                           2603
```

<210> SEQ ID NO 16
<211> LENGTH: 392
<212> TYPE: PRT
<213> ORGANISM: Homo sapiens

<400> SEQUENCE: 16

```
Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190
```

```
Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Gly
385                 390


<210> SEQ ID NO 17
<211> LENGTH: 1759
<212> TYPE: DNA
<213> ORGANISM: Homo sapiens

<400> SEQUENCE: 17

cccctgcctc tcggactcgg gctgcggcgt cagccttctt cgggcctcgg cagcggtagc      60

ggctcgctcg cctcagcccc agcgcccctc ggctaccctc ggcccaggcc cgcagcgccg     120

cccgccctcg gccgccccga cgccggcctg ggccgcggcc gcagccccgg gctcgcgtag     180

gcgccgaccg ctcccggccc gcccccctatg ggccccggct agaggcgccg ccgccgccgg     240

cccgcggagc cccgatgctg gcccggagga agccggtgct gccggcgctc accatcaacc     300

ctaccatcgc cgagggccca tcccctacca gcgagggcgc ctccgaggca aacctggtgg     360

acctgcagaa gaagctggag gagctggaac ttgacgagca gcagaagaag cggctggaag     420

cctttctcac ccagaaagcc aaggtcggcg aactcaaaga cgatgacttc gaaaggatct     480

cagagctggg cgcgggcaac ggcggggtgg tcaccaaagt ccagcacaga ccctcgggcc     540

tcatcatggc caggaagctg atccaccttg agatcaagcc ggccatccgg aaccagatca     600

tccgcgagct gcaggtcctg cacgaatgca actcgccgta catcgtgggc ttctacgggg     660

ccttctacag tgacggggag atcagcattt gcatggaaca catggacggc ggctccctgg     720

accaggtgct gaaagaggcc aagaggattc ccgaggagat cctggggaaa gtcagcatcg     780

cggttctccg gggcttggcg tacctccgag agaagcacca gatcatgcac cgagatgtga     840

agccctccaa catcctcgtg aactctagag gggagatcaa gctgtgtgac ttcggggtga     900

gcggccagct catcgactcc atggccaact ccttcgtggg cacgcgctcc tacatggctc     960
```

cggagcggtt gcagggcaca cattactcgg tgcagtcgga catctggagc atgggcctgt 1020
ccctggtgga gctggccgtc ggaaggtacc ccatcccccc gcccgacgcc aaagagctgg 1080
aggccatctt tggccggccc gtggtcgacg gggaagaagg agagcctcac agcatctcgc 1140
ctcggccgag gccccccggg cgccccgtca gcggtcacgg gatggatagc cggcctgcca 1200
tggccatctt tgaactcctg gactatattg tgaacgagcc acctcctaag ctgcccaacg 1260
gtgtgttcac ccccgacttc caggagtttg tcaataaatg cctcatcaag aacccagcgg 1320
agcgggcgga cctgaagatg ctcacaaacc acaccttcat caagcggtcc gaggtggaag 1380
aagtggattt tgccggctgg ttgtgtaaaa ccctgcggct gaaccagccc ggcacaccca 1440
cgcgcaccgc cgtgtgacag tggccgggct ccctgcgtcc cgctggtgac ctgcccaccg 1500
tccctgtcca tgccccgccc ttccagctga ggacaggctg gcgcctccac ccaccctcct 1560
gcctcacccc tgcggagagc accgtggcgg ggcgacagcg catgcaggaa cgggggtctc 1620
ctctcctgcc cgtcctggcc ggggtgcctc tggggacggg cgacgctgct gtgtgtggtc 1680
tcagaggctc tgcttcctta ggttacaaaa caaaacaggg agagaaaaag caaaaaaaaa 1740
aaaaaaaaaa aaaaaaaaa 1759

<210> SEQ ID NO 18
<211> LENGTH: 400
<212> TYPE: PRT
<213> ORGANISM: Homo sapiens

<400> SEQUENCE: 18

Met Leu Ala Arg Arg Lys Pro Val Leu Pro Ala Leu Thr Ile Asn Pro
1 5 10 15

Thr Ile Ala Glu Gly Pro Ser Pro Thr Ser Glu Gly Ala Ser Glu Ala
20 25 30

Asn Leu Val Asp Leu Gln Lys Lys Leu Glu Glu Leu Glu Leu Asp Glu
35 40 45

Gln Gln Lys Lys Arg Leu Glu Ala Phe Leu Thr Gln Lys Ala Lys Val
50 55 60

Gly Glu Leu Lys Asp Asp Asp Phe Glu Arg Ile Ser Glu Leu Gly Ala
65 70 75 80

Gly Asn Gly Gly Val Val Thr Lys Val Gln His Arg Pro Ser Gly Leu
85 90 95

Ile Met Ala Arg Lys Leu Ile His Leu Glu Ile Lys Pro Ala Ile Arg
100 105 110

Asn Gln Ile Ile Arg Glu Leu Gln Val Leu His Glu Cys Asn Ser Pro
115 120 125

Tyr Ile Val Gly Phe Tyr Gly Ala Phe Tyr Ser Asp Gly Glu Ile Ser
130 135 140

Ile Cys Met Glu His Met Asp Gly Gly Ser Leu Asp Gln Val Leu Lys
145 150 155 160

Glu Ala Lys Arg Ile Pro Glu Glu Ile Leu Gly Lys Val Ser Ile Ala
165 170 175

Val Leu Arg Gly Leu Ala Tyr Leu Arg Glu Lys His Gln Ile Met His
180 185 190

Arg Asp Val Lys Pro Ser Asn Ile Leu Val Asn Ser Arg Gly Glu Ile
195 200 205

Lys Leu Cys Asp Phe Gly Val Ser Gly Gln Leu Ile Asp Ser Met Ala
210 215 220

Asn Ser Phe Val Gly Thr Arg Ser Tyr Met Ala Pro Glu Arg Leu Gln

-continued

```
225                 230                 235                 240

Gly Thr His Tyr Ser Val Gln Ser Asp Ile Trp Ser Met Gly Leu Ser
                245                 250                 255

Leu Val Glu Leu Ala Val Gly Arg Tyr Pro Ile Pro Pro Pro Asp Ala
            260                 265                 270

Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Pro Gly Arg Pro
    290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Pro Lys Leu Pro Asn Gly
                325                 330                 335

Val Phe Thr Pro Asp Phe Gln Glu Phe Val Asn Lys Cys Leu Ile Lys
            340                 345                 350

Asn Pro Ala Glu Arg Ala Asp Leu Lys Met Leu Thr Asn His Thr Phe
        355                 360                 365

Ile Lys Arg Ser Glu Val Glu Glu Val Asp Phe Ala Gly Trp Leu Cys
    370                 375                 380

Lys Thr Leu Arg Leu Asn Gln Pro Gly Thr Pro Thr Arg Thr Ala Val
385                 390                 395                 400
```

<210> SEQ ID NO 19
<211> LENGTH: 10241
<212> TYPE: DNA
<213> ORGANISM: Homo sapiens

<400> SEQUENCE: 19

```
ccggcgtcgg cggcgcgcgc gctccctcct ctcggagaga gggctgtggt aaaagccgtc      60

cggaaaatgg ccgccgccgc cgccgccgcg ccgagcggag gaggaggagg aggcgaggag     120

gagagactgc tccataaaaa tacagactca ccagttcctg ctttgatgtg acatgtgact     180

ccccagaata caccttgctt ctgtagacca gctccaacag gattccatgg tagctgggat     240

gttagggctc agggaagaaa agtcagaaga ccaggacctc cagggcctca aggacaaacc     300

cctcaagttt aaaaaggtga agaaagataa gaaagaagag aaagagggca agcatgagcc     360

cgtgcagcca tcagcccacc actctgctga gcccgcagag gcaggcaaag cagagacatc     420

agaagggtca ggctccgccc cggctgtgcc ggaagcttct gcctccccca aacagcggcg     480

ctccatcatc cgtgaccggg gacccatgta tgatgacccc accctgcctg aaggctggac     540

acggaagctt aagcaaagga aatctggccg ctctgctggg aagtatgatg tgtatttgat     600

caatccccag ggaaaagcct ttcgctctaa agtggagttg attgcgtact tcgaaaaggt     660

aggcgacaca tccctggacc ctaatgattt tgacttcacg gtaactggga gagggagccc     720

ctcccggcga gagcagaaac cacctaagaa gcccaaatct cccaaagctc caggaactgg     780

cagaggccgg ggacgcccca aagggagcgg caccacgaga cccaaggcgg ccacgtcaga     840

gggtgtgcag gtgaaaaggg tcctggagaa aagtcctggg aagctccttg tcaagatgcc     900

ttttcaaact tcgccagggg gcaaggctga ggggggtggg gccaccacat ccacccaggt     960

catggtgatc aaacgccccg gcaggaagcg aaaagctgag gccgaccctc aggccattcc    1020

caagaaacgg ggccgaaagc cggggagtgt ggtggcagcc gctgccgccg aggccaaaaa    1080

gaaagccgtg aaggagtctt ctatccgatc tgtgcaggag accgtactcc ccatcaagaa    1140

gcgcaagacc cgggagacgg tcagcatcga ggtcaaggaa gtggtgaagc ccctgctggt    1200
```

```
gtccaccctc ggtgagaaga gcgggaaagg actgaagacc tgtaagagcc ctgggcggaa   1260
aagcaaggag agcagcccca aggggcgcag cagcagcgcc tcctcacccc ccaagaagga   1320
gcaccaccac catcaccacc actcagagtc cccaaaggcc cccgtgccac tgctcccacc   1380
cctgccccca cctccacctg agcccgagag ctccgaggac cccaccagcc cccctgagcc   1440
ccaggacttg agcagcagcg tctgcaaaga ggagaagatg cccagaggag gctcactgga   1500
gagcgacggc tgccccaagg agccagctaa gactcagccc gcggttgcca ccgccgccac   1560
ggccgcagaa aagtacaaac accgagggga gggagagcgc aaagacattg tttcatcctc   1620
catgccaagg ccaaacagag aggagcctgt ggacagccgg acgcccgtga ccgagagagt   1680
tagctgactt tacacggagc ggattgcaaa gcaaaccaac aagaataaag gcagctgttg   1740
tctcttctcc ttatgggtag ggctctgaca aagcttcccg attaactgaa ataaaaaata   1800
tttttttttc tttcagtaaa cttagagttt cgtggcttca gggtgggagt agttggagca   1860
ttggggatgt ttttcttacc gacaagcaca gtcaggttga agacctaacc agggccagaa   1920
gtagctttgc acttttctaa actaggctcc ttcaacaagg cttgctgcag atactactga   1980
ccagacaagc tgttgaccag gcacctcccc tcccgcccaa acctttcccc catgtggtcg   2040
ttagagacag agcgacagag cagttgagag gacactcccg ttttcggtgc catcagtgcc   2100
ccgtctacag ctcccccagc tccccccacc tcccccactc ccaaccacgt tgggacaggg   2160
aggtgtgagg caggagagac agttggattc tttagagaag atggatatga ccagtggcta   2220
tggcctgtgc gatcccaccc gtggtggctc aagtctggcc ccacaccagc cccaatccaa   2280
aactggcaag gacgcttcac aggacaggaa agtggcacct gtctgctcca gctctggcat   2340
ggctaggagg ggggagtccc ttgaactact gggtgtagac tggcctgaac cacaggagag   2400
gatggcccag ggtgaggtgg catggtccat tctcaaggga cgtcctccaa cgggtggcgc   2460
tagaggccat ggaggcagta ggacaaggtg caggcaggct ggcctggggt caggccgggc   2520
agagcacagc ggggtgagag ggattcctaa tcactcagag cagtctgtga cttagtggac   2580
aggggagggg gcaaaggggg aggagaagaa aatgttcttc cagttacttt ccaattctcc   2640
tttagggaca gcttagaatt atttgcacta ttgagtcttc atgttcccac ttcaaaacaa   2700
acagatgctc tgagagcaaa ctggcttgaa ttggtgacat ttagtccctc aagccaccag   2760
atgtgacagt gttgagaact acctggattt gtatatatac ctgcgcttgt tttaaagtgg   2820
gctcagcaca tagggttccc acgaagctcc gaaactctaa gtgtttgctg caattttata   2880
aggacttcct gattggtttc tcttctcccc ttccatttct gccttttgtt catttcatcc   2940
tttcacttct ttcccttcct ccgtcctcct ccttcctagt tcatcccttc tcttccaggc   3000
agccgcggtg cccaaccaca cttgtcggct ccagtcccca gaactctgcc tgccctttgt   3060
cctcctgctg ccagtaccag ccccaccctg ttttgagccc tgaggaggcc ttgggctctg   3120
ctgagtccga cctggcctgt ctgtgaagag caagagagca gcaaggtctt gctctcctag   3180
gtagcccccct cttccctggt aagaaaaagc aaaaggcatt tcccaccctg aacaacgagc   3240
cttttcaccc ttctactcta gagaagtgga ctggaggagc tgggcccgat ttggtagttg   3300
aggaaagcac agaggcctcc tgtggcctgc cagtcatcga gtggcccaac aggggctcca   3360
tgccagccga ccttgacctc actcagaagt ccagagtcta gcgtagtgca gcagggcagt   3420
agcggtacca atgcagaact cccaagaccc gagctgggac cagtacctgg gtccccagcc   3480
cttcctctgc tccccctttt ccctcggagt tcttcttgaa tggcaatgtt ttgcttttgc   3540
```

-continued

```
tcgatgcaga cagggggcca gaacaccaca catttcactg tctgtctggt ccatagctgt   3600
ggtgtagggg cttagaggca tgggcttgct gtgggttttt aattgatcag ttttcatgtg   3660
ggatcccatc tttttaacct ctgttcagga agtccttatc tagctgcata tcttcatcat   3720
attggtatat ccttttctgt gtttacagag atgtctctta tatctaaatc tgtccaactg   3780
agaagtacct tatcaaagta gcaaatgaga cagcagtctt atgcttccag aaacacccac   3840
aggcatgtcc catgtgagct gctgccatga actgtcaagt gtgtgttgtc ttgtgtattt   3900
cagttattgt ccctggcttc cttactatgg tgtaatcatg aaggagtgaa acatcataga   3960
aactgtctag cacttccttg ccagtcttta gtgatcagga accatagttg acagttccaa   4020
tcagtagctt aagaaaaaac cgtgtttgtc tcttctggaa tggttagaag tgagggagtt   4080
tgccccgttc tgtttgtaga gtctcatagt tggactttct agcatatatg tgtccatttc   4140
cttatgctgt aaaagcaagt cctgcaacca aactcccatc agcccaatcc ctgatccctg   4200
atcccttcca cctgctctgc tgatgacccc cccagcttca cttctgactc ttccccagga   4260
agggaagggg ggtcagaaga gagggtgagt cctccagaac tcttcctcca aggacagaag   4320
gctcctgccc ccatagtggc ctcgaactcc tggcactacc aaaggacact tatccacgag   4380
agcgcagcat ccgaccaggt tgtcactgag aagatgttta ttttggtcag ttgggttttt   4440
atgtattata cttagtcaaa tgtaatgtgg cttctggaat cattgtccag agctgcttcc   4500
ccgtcacctg ggcgtcatct ggtcctggta agaggagtgc gtggcccacc aggcccccct   4560
gtcacccatg acagttcatt cagggccgat ggggcagtcg tggttgggaa cacagcattt   4620
caagcgtcac tttatttcat tcgggcccca cctgcagctc cctcaaagag gcagttgccc   4680
agcctctttc ccttccagtt tattccagag ctgccagtgg ggcctgaggc tccttagggt   4740
tttctctcta tttccccctt tcttcctcat tccctcgtct ttcccaaagg catcacgagt   4800
cagtcgcctt tcagcaggca gccttggcgg tttatcgccc tggcaggcag gggccctgca   4860
gctctcatgc tgcccctgcc ttggggtcag gttgacagga ggttggaggg aaagccttaa   4920
gctgcaggat tctcaccagc tgtgtccggc ccagttttgg ggtgtgacct caatttcaat   4980
tttgtctgta cttgaacatt atgaagatgg gggcctcttt cagtgaattt gtgaacagca   5040
gaattgaccg acagctttcc agtacccatg gggctaggtc attaaggcca catccacagt   5100
ctcccccacc cttgttccag ttgttagtta ctacctcctc tcctgacaat actgtatgtc   5160
gtcgagctcc ccccaggtct acccctcccg gccctgcctg ctggtgggct tgtcatagcc   5220
agtgggattg ccggtcttga cagctcagtg agctggagat acttggtcac agccaggcgc   5280
tagcacagct cccttctgtt gatgctgtat tcccatatca aaagacacag gggacaccca   5340
gaaacgccac atcccccaat ccatcagtgc caaactagcc aacggcccca gcttctcagc   5400
tcgctggatg gcggaagctg ctactcgtga gcgccagtgc gggtgcagac aatcttctgt   5460
tgggtggcat cattccaggc ccgaagcatg aacagtgcac ctgggacagg gagcagcccc   5520
aaattgtcac ctgcttctct gcccagcttt tcattgctgt gacagtgatg gcgaaagagg   5580
gtaataacca gacacaaact gccaagttgg gtggagaaag gagtttcttt agctgacaga   5640
atctctgaat tttaaatcac ttagtaagcg gctcaagccc aggagggagc agagggatac   5700
gagcggagtc ccctgcgcgg gaccatctgg aattggttta gcccaagtgg agcctgacag   5760
ccagaactct gtgtcccccg tctaaccaca gctccttttc cagagcattc cagtcaggct   5820
ctctgggctg actgggccag gggaggttac aggtaccagt tctttaagaa gatctttggg   5880
catatacatt tttagcctgt gtcattgccc caaatggatt cctgtttcaa gttcacacct   5940
```

```
gcagattcta ggacctgtgt cctagacttc agggagtcag ctgtttctag agttcctacc   6000
atggagtggg tctggaggac ctgcccggtg ggggggcaga gccctgctcc ctccgggtct   6060
tcctactctt ctctctgctc tgacgggatt tgttgattct ctccattttg gtgtctttct   6120
cttttagata ttgtatcaat ctttagaaaa ggcatagtct acttgttata aatcgttagg   6180
atactgcctc ccccagggtc taaaattaca tattagaggg gaaaagctga acactgaagt   6240
cagttctcaa caatttagaa ggaaaaccta gaaaacattt ggcagaaaat tacatttcga   6300
tgtttttgaa tgaatacgag caagctttta caacagtgct gatctaaaaa tacttagcac   6360
ttggcctgag atgcctggtg agcattacag gcaaggggaa tctggaggta gccgacctga   6420
ggacatggct tctgaacctg tcttttggga gtggtatgga aggtggagcg ttcaccagtg   6480
acctggaagg cccagcacca ccctccttcc cactcttctc atcttgacag agcctgcccc   6540
agcgctgacg tgtcaggaaa acacccaggg aactaggaag gcacttctgc ctgaggggca   6600
gcctgccttg cccactcctg ctctgctcgc ctcggatcag ctgagccttc tgagctggcc   6660
tctcactgcc tccccaaggc cccctgcctg ccctgtcagg aggcagaagg aagcaggtgt   6720
gagggcagtg caaggaggga gcacaacccc cagctcccgc tccgggctcc gacttgtgca   6780
caggcagagc ccagaccctg gaggaaatcc tacctttgaa ttcaagaaca tttggggaat   6840
ttggaaatct ctttgccccc aaacccccat tctgtcctac ctttaatcag gtcctgctca   6900
gcagtgagag cagatgaggt gaaaaggcca agaggtttgg ctcctgccca ctgatagccc   6960
ctctccccgc agtgtttgtg tgtcaagtgg caaagctgtt cttcctggtg accctgatta   7020
tatccagtaa cacatagact gtgcgcatag gcctgctttg tctcctctat cctgggcttt   7080
tgttttgctt tttagttttg cttttagttt ttctgtccct tttatttaac gcaccgacta   7140
gacacacaaa gcagttgaat ttttatatat atatctgtat attgcacaat tataaactca   7200
ttttgcttgt ggctccacac acacaaaaaa agacctgtta aaattatacc tgttgcttaa   7260
ttacaatatt tctgataacc atagcatagg acaagggaaa ataaaaaaag aaaaaaaaga   7320
aaaaaaaacg acaaatctgt ctgctggtca cttcttctgt ccaagcagat tcgtggtctt   7380
ttcctcgctt ctttcaaggg ctttcctgtg ccaggtgaag gaggctccag gcagcaccca   7440
ggttttgcac tcttgtttct cccgtgcttg tgaaagaggt cccaaggttc tgggtgcagg   7500
agcgctccct tgacctgctg aagtccggaa cgtagtcggc acagcctggt cgccttccac   7560
ctctgggagc tggagtccac tggggtggcc tgactccccc agtccccttc ccgtgacctg   7620
gtcagggtga gcccatgtgg agtcagcctc gcaggcctcc ctgccagtag ggtccgagtg   7680
tgtttcatcc ttcccactct gtcgagcctg gggctggag cggagacggg aggcctggcc    7740
tgtctcggaa cctgtgagct gcaccaggta gaacgccagg gaccccagaa tcatgtgcgt   7800
cagtccaagg ggtcccctcc aggagtagtg aagactccag aaatgtccct ttcttctccc   7860
ccatcctacg agtaattgca tttgcttttg taattcttaa tgagcaatat ctgctagaga   7920
gtttagctgt aacagttctt tttgatcatc tttttttaat aattagaaac accaaaaaaa   7980
tccagaaact tgttcttcca aagcagagag cattataatc accagggcca aaagcttccc   8040
tccctgctgt cattgcttct tctgaggcct gaatccaaaa gaaaaacagc cataggccct   8100
ttcagtggcc gggctacccg tgagcccttc ggaggaccag ggctggggca gcctctgggc   8160
ccacatccgg ggccagctcc ggcgtgtgtt cagtgttagc agtgggtcat gatgctcttt   8220
cccacccagc ctgggatagg ggcagaggag gcgaggaggc cgttgccgct gatgtttggc   8280
```

-continued cgtgaacagg tgggtgtctg cgtgcgtcca cgtgcgtgtt ttctgactga catgaaatcg 8340
acgcccgagt tagcctcacc cggtgacctc tagccctgcc cggatggagc ggggcccacc 8400
cggttcagtg tttctgggga gctggacagt ggagtgcaaa aggcttgcag aacttgaagc 8460
ctgctccttc ccttgctacc acggcctcct ttccgtttga tttgtcactg cttcaatcaa 8520
taacagccgc tccagagtca gtagtcaatg aatatatgac caaatatcac caggactgtt 8580
actcaatgtg tgccgagccc ttgcccatgc tgggctcccg tgtatctgga cactgtaacg 8640
tgtgctgtgt ttgctcccct tccccttcct tctttgccct ttacttgtct ttctggggtt 8700
tttctgtttg ggtttggttt ggtttttatt tctccttttg tgttccaaac atgaggttct 8760
ctctactggt cctcttaact gtggtgttga ggcttatatt tgtgtaattt ttggtgggtg 8820
aaaggaattt tgctaagtaa atctcttctg tgtttgaact gaagtctgta ttgtaactat 8880
gtttaaagta attgttccag agacaaatat ttctagacac tttttcttta caaacaaaag 8940
cattcggagg gagggggatg gtgactgaga tgagagggga gagctgaaca gatgacccct 9000
gcccagatca gccagaagcc acccaaagca gtggagccca ggagtcccac tccaagccag 9060
caagccgaat agctgatgtg ttgccacttt ccaagtcact gcaaaaccag gttttgttcc 9120
gcccagtgga ttcttgtttt gcttcccctc cccccgagat tattaccacc atcccgtgct 9180
tttaaggaaa ggcaagattg atgtttcctt gaggggagcc aggaggggat gtgtgtgtgc 9240
agagctgaag agctggggag aatggggctg ggcccaccca agcaggaggc tgggacgctc 9300
tgctgtgggc acaggtcagg ctaatgttgg cagatgcagc tcttcctgga caggccaggt 9360
ggtgggcatt ctctctccaa ggtgtgcccc gtgggcatta ctgtttaaga cacttccgtc 9420
acatcccacc ccatcctcca gggctcaaca ctgtgacatc tctattcccc accctcccct 9480
tcccagggca ataaaatgac catggagggg gcttgcactc tcttggctgt cacccgatcg 9540
ccagcaaaac ttagatgtga gaaaacccct tcccattcca tggcgaaaac atctccttag 9600
aaaagccatt accctcatta ggcatggttt tgggctccca aaacacctga cagcccctcc 9660
ctcctctgag aggcggagag tgctgactgt agtgaccatt gcatgccggg tgcagcatct 9720
ggaagagcta ggcagggtgt ctgccccctc ctgagttgaa gtcatgctcc cctgtgccag 9780
cccagaggcc gagagctatg gacagcattg ccagtaacac aggccaccct gtgcagaagg 9840
gagctggctc cagcctggaa acctgtctga ggttgggaga ggtgcacttg ggcacaggg 9900 agaggccggg acacacttag ctggagatgt ctctaaaagc cctgtatcgt attcaccttc 9960
agtttttgtg ttttgggaca attactttag aaaataagta ggtcgtttta aaaacaaaaa 10020
ttattgattg ctttttgta gtgttcagaa aaaaggttct ttgtgtatag ccaaatgact 10080
gaaagcactg atatatttaa aaacaaaagg caatttatta aggaaatttg taccatttca 10140
gtaaacctgt ctgaatgtac ctgtatacgt ttcaaaaaca cccccccccc actgaatccc 10200
tgtaacctat ttattatata aagagtttgc cttataaatt t 10241

<210> SEQ ID NO 20
<211> LENGTH: 486
<212> TYPE: PRT
<213> ORGANISM: Homo sapiens

<400> SEQUENCE: 20

Met Val Ala Gly Met Leu Gly Leu Arg Glu Glu Lys Ser Glu Asp Gln
1 5 10 15

Asp Leu Gln Gly Leu Lys Asp Lys Pro Leu Lys Phe Lys Lys Val Lys
20 25 30

-continued

```
Lys Asp Lys Lys Glu Glu Lys Glu Gly Lys His Glu Pro Val Gln Pro
        35                  40                  45

Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
    210                 215                 220

Pro Phe Gln Thr Ser Pro Gly Gly Lys Ala Glu Gly Gly Gly Ala Thr
225                 230                 235                 240

Thr Ser Thr Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
            260                 265                 270

Gly Ser Val Val Ala Ala Ala Ala Ala Glu Ala Lys Lys Lys Ala Val
        275                 280                 285

Lys Glu Ser Ser Ile Arg Ser Val Gln Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
            340                 345                 350

Gly Arg Ser Ser Ser Ala Ser Ser Pro Pro Lys Lys Glu His His His
        355                 360                 365

His His His His Ser Glu Ser Pro Lys Ala Pro Val Pro Leu Leu Pro
    370                 375                 380

Pro Leu Pro Pro Pro Pro Pro Glu Pro Glu Ser Ser Glu Asp Pro Thr
385                 390                 395                 400

Ser Pro Pro Glu Pro Gln Asp Leu Ser Ser Ser Val Cys Lys Glu Glu
                405                 410                 415

Lys Met Pro Arg Gly Gly Ser Leu Glu Ser Asp Gly Cys Pro Lys Glu
            420                 425                 430

Pro Ala Lys Thr Gln Pro Ala Val Ala Thr Ala Ala Thr Ala Ala Glu
        435                 440                 445
```

-continued

```
Lys Tyr Lys His Arg Gly Glu Gly Glu Arg Lys Asp Ile Val Ser Ser
    450                 455                 460

Ser Met Pro Arg Pro Asn Arg Glu Glu Pro Val Asp Ser Arg Thr Pro
465                 470                 475                 480

Val Thr Glu Arg Val Ser
                485
```

<210> SEQ ID NO 21
<211> LENGTH: 3724
<212> TYPE: DNA
<213> ORGANISM: Homo sapiens

<400> SEQUENCE: 21

```
tctccctcgg cgccgccgcc gccgcccgcg gggctgggac ccgatgcggt tagagccgcg     60

gagcctggaa gagccccgag cgtttctgct ttgggacaac catacatcta attccttaaa    120

gtagttttat atgtaaaact tgcaaagaat cagaacaatg cctccacgac catcatcagg    180

tgaactgtgg ggcatccact tgatgccccc aagaatccta gtagaatgtt tactaccaaa    240

tggaatgata gtgactttag aatgcctccg tgaggctaca ttaataacca taaagcatga    300

actatttaaa gaagcaagaa aataccccct ccatcaactt cttcaagatg aatcttctta    360

cattttcgta agtgttactc aagaagcaga aagggaagaa tttttgatg aaacaagacg    420

actttgtgac cttcggcttt ttcaaccctt tttaaaagta attgaaccag taggcaaccg    480

tgaagaaaag atcctcaatc gagaaattgg ttttgctatc ggcatgccag tgtgtgaatt    540

tgatatggtt aaagatccag aagtacagga cttccgaaga aatattctga acgtttgtaa    600

agaagctgtg gatcttaggg acctcaattc acctcatagt agagcaatgt atgtctatcc    660

tccaaatgta gaatcttcac cagaattgcc aaagcacata tataataaat tagataaagg    720

gcaaataata gtggtgatct gggtaatagt ttctccaaat aatgacaagc agaagtatac    780

tctgaaaatc aaccatgact gtgtaccaga acaagtaatt gctgaagcaa tcaggaaaaa    840

aactcgaagt atgttgctat cctctgaaca actaaaactc tgtgttttag aatatcaggg    900

caagtatatt ttaaaagtgt gtggatgtga tgaatacttc ctagaaaaat atcctctgag    960

tcagtataag tatataagaa gctgtataat gcttgggagg atgcccaatt tgatgttgat   1020

ggctaaagaa agcctttatt ctcaactgcc aatggactgt tttacaatgc catcttattc   1080

cagacgcatt tccacagcta caccatatat gaatggagaa acatctacaa aatccctttg   1140

ggttataaat agtgcactca gaataaaaat tctttgtgca acctacgtga atgtaaatat   1200

tcgagacatt gataagatct atgttcgaac aggtatctac catggaggag aacccttatg   1260

tgacaatgtg aacactcaaa gagtaccttg ttccaatccc aggtggaatg aatggctgaa   1320

ttatgatata tacattcctg atcttcctcg tgctgctcga ctttgccttt ccatttgctc   1380

tgttaaaggc cgaaagggtg ctaaagagga acactgtcca ttggcatggg gaaatataaa   1440

cttgtttgat tacacagaca ctctagtatc tggaaaaatg gctttgaatc tttggccagt   1500

acctcatgga ttagaagatt tgctgaaccc tattggtgtt actggatcaa atccaaataa   1560

agaaactcca tgcttagagt tggagtttga ctggttcagc agtgtggtaa agttcccaga   1620

tatgtcagtg attgaagagc atgccaattg gtctgtatcc cgagaagcag gatttagcta   1680

ttcccacgca ggactgagta acagactagc tagagacaat gaattaaggg aaaatgacaa   1740

agaacagctc aaagcaattt ctacacgaga tcctctctct gaaatcactg agcaggagaa   1800

agattttcta tggagtcaca gacactattg tgtaactatc cccgaaattc tacccaaatt   1860
```

```
gcttctgtct gttaaatgga attctagaga tgaagtagcc cagatgtatt gcttggtaaa   1920
agattggcct ccaatcaaac ctgaacaggc tatggaactt ctggactgta attacccaga   1980
tcctatggtt cgaggttttg ctgttcggtg cttggaaaaa tatttaacag atgacaaact   2040
ttctcagtat ttaattcagc tagtacaggt cctaaaatat gaacaatatt tggataactt   2100
gcttgtgaga tttttactga agaaagcatt gactaatcaa aggattgggc actttttctt   2160
ttggcattta aaatctgaga tgcacaataa aacagttagc cagaggtttg gcctgctttt   2220
ggagtcctat tgtcgtgcat gtgggatgta tttgaagcac ctgaataggc aagtcgaggc   2280
aatggaaaag ctcattaact taactgacat tctcaaacag gagaagaagg atgaaacaca   2340
aaaggtacag atgaagtttt tagttgagca aatgaggcga ccagatttca tggatgctct   2400
acagggcttt ctgtctcctc taaaccctgc tcatcaacta ggaaacctca ggcttgaaga   2460
gtgtcgaatt atgtcctctg caaaaaggcc actgtggttg aattgggaga acccagacat   2520
catgtcagag ttactgtttc agaacaatga gatcatcttt aaaaatgggg atgatttacg   2580
gcaagatatg ctaacacttc aaattattcg tattatggaa aatatctggc aaaatcaagg   2640
tcttgatctt cgaatgttac cttatggttg tctgtcaatc ggtgactgtg tgggacttat   2700
tgaggtggtg cgaaattctc acactattat gcaaattcag tgcaaaggcg gcttgaaagg   2760
tgcactgcag ttcaacagcc acacactaca tcagtggctc aaagacaaga acaaaggaga   2820
aatatatgat gcagccattg acctgtttac acgttcatgt gctggatact gtgtagctac   2880
cttcattttg ggaattggag atcgtcacaa tagtaacatc atggtgaaag acgatggaca   2940
actgtttcat atagattttg gacacttttt ggatcacaag aagaaaaaat ttggttataa   3000
acgagaacgt gtgccatttg ttttgacaca ggatttctta atagtgatta gtaaaggagc   3060
ccaagaatgc acaaagacaa gagaatttga gaggtttcag gagatgtgtt acaaggctta   3120
tctagctatt cgacagcatg ccaatctctt cataaatctt ttctcaatga tgcttggctc   3180
tggaatgcca gaactacaat cttttgatga cattgcatac attcgaaaga ccctagcctt   3240
agataaaact gagcaagagg ctttggagta tttcatgaaa caaatgaatg atgcacatca   3300
tggtggctgg acaacaaaaa tggattggat cttccacaca attaaacagc atgcattgaa   3360
ctgaaaagat aactgagaaa atgaaagctc actctggatt ccacactgca ctgttaataa   3420
ctctcagcag gcaaagaccg attgcatagg aattgcacaa tccatgaaca gcattagaat   3480
ttacagcaag aacagaaata aaatactata taatttaaat aatgtaaacg caaacagggt   3540
ttgatagcac ttaaactagt tcatttcaaa attaagcttt agaataatgc gcaatttcat   3600
gttatgcctt aagtccaaaa aggtaaactt tgaagattgt ttgtatcttt ttttaaaaaa   3660
caaaacaaaa caaaaatccc caaaatatat agaaatgatg gagaaggaaa aaaaaaaaaa   3720
aaaa                                                                3724
```

<210> SEQ ID NO 22
<211> LENGTH: 1068
<212> TYPE: PRT
<213> ORGANISM: Homo sapiens

<400> SEQUENCE: 22

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
```

-continued

```
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460
```

```
Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880
```

-continued

```
Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Met  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065
```

<210> SEQ ID NO 23
<211> LENGTH: 6453
<212> TYPE: DNA
<213> ORGANISM: Homo sapiens

<400> SEQUENCE: 23

```
tacaaccagg ctcaactgtt gcatggtagc agatttgcaa acatgagtgc tgaggggtac     60
cagtacagag cgctgtatga ttataaaaag gaaagagaag aagatattga cttgcacttg    120
ggtgacatat tgactgtgaa taaagggtcc ttagtagctc ttggattcag tgatggacag    180
gaagccaggc ctgaagaaat tggctggtta aatggctata atgaaaccac aggggaaagg    240
ggggactttc cgggaactta cgtagaatat attggaagga aaaaaatctc gcctcccaca    300
ccaaagcccc ggccacctcg gcctcttcct gttgcaccag gttcttcgaa aactgaagca    360
gatgttgaac aacaagcttt gactctcccg gatcttgcag agcagtttgc ccctcctgac    420
attgccccgc ctcttcttat caagctcgtg gaagccattg aaaagaaagg tctggaatgt    480
tcaactctat acagaacaca gagctccagc aacctggcag aattacgaca gcttcttgat    540
tgtgatacac cctccgtgga cttggaaatg atcgatgtgc acgttttggc tgacgctttc    600
aaacgctatc tcctggactt accaaatcct gtcattccag cagccgttta cagtgaaatg    660
atttctttag ctccagaagt acaaagctcc gaagaatata ttcagctatt gaagaagctt    720
attaggtcgc ctagcatacc tcatcagtat tggcttacgc ttcagtattt gttaaaacat    780
ttcttcaagc tctctcaaac ctccagcaaa aatctgttga atgcaagagt actctctgaa    840
attttcagcc ctatgctttt cagattctca gcagccagct ctgataatac tgaaaacctc    900
ataaaagtta tagaaatttt aatctcaact gaatggaatg aacgacagcc tgcaccagca    960
ctgcctccta aaccaccaaa acctactact gtagccaaca acggtatgaa taacaatatg   1020
tccttacaag atgctgaatg gtactgggga gatatctcga gggaagaagt gaatgaaaaa   1080
```

```
cttcgagata cagcagacgg gaccttttg gtacgagatg cgtctactaa aatgcatggt   1140
gattatactc ttacactaag gaaaggggga aataacaaat taatcaaaat atttcatcga   1200
gatgggaaat atggcttctc tgacccatta accttcagtt ctgtggttga attaataaac   1260
cactaccgga atgaatctct agctcagtat aatcccaaat tggatgtgaa attactttat   1320
ccagtatcca aataccaaca ggatcaagtt gtcaaagaag ataatattga agctgtaggg   1380
aaaaaattac atgaatataa cactcagttt caagaaaaaa gtcgagaata tgatagatta   1440
tatgaagaat atacccgcac atcccaggaa atccaaatga aaaggacagc tattgaagca   1500
tttaatgaaa ccataaaaat atttgaagaa cagtgccaga cccaagagcg gtacagcaaa   1560
gaatacatag aaaagtttaa acgtgaaggc aatgagaaag aaatacaaag gattatgcat   1620
aattatgata agttgaagtc tcgaatcagt gaaattattg acagtagaag aagattggaa   1680
gaagacttga agaagcaggc agctgagtat cgagaaattg acaaacgtat gaacagcatt   1740
aaaccagacc ttatccagct gagaaagacg agagaccaat acttgatgtg gttgactcaa   1800
aaaggtgttc ggcaaaagaa gttgaacgag tggttgggca atgaaaacac tgaagaccaa   1860
tattcactgg tggaagatga tgaagatttg ccccatcatg atgagaagac atggaatgtt   1920
ggaagcagca accgaaacaa agctgaaaac ctgttgcgag ggaagcgaga tggcactttt   1980
cttgtccggg agagcagtaa acagggctgc tatgcctgct ctgtagtggt ggacggcgaa   2040
gtaaagcatt gtgtcataaa caaaacagca actggctatg gctttgccga gccctataac   2100
ttgtacagct ctctgaaaga actggtgcta cattaccaac acacctccct tgtgcagcac   2160
aacgactccc tcaatgtcac actagcctac ccagtatatg cacagcagag gcgatgaagc   2220
gcttactctt tgatccttct cctgaagttc agccaccctg aggcctctgg aaagcaaagg   2280
gctcctctcc agtctgatct gtgaattgag ctgcagaaac gaagccatct ttctttggat   2340
gggactagag ctttctttca caaaaaagaa gtaggggaag acatgcagcc taaggctgta   2400
tgatgaccac acgttcctaa gctggagtgc ttatcccttc tttttctttt tttctttggt   2460
ttaatttaaa gccacaacca catacaacac aaagagaaaa agaaatgcaa aaatctctgc   2520
gtgcagggac aaagaggcct ttaaccatgg tgcttgttaa tgctttctga agctttacca   2580
gctgaaagtt gggactctgg agagcggagg agagagaggc agaagaaccc tggcctgaga   2640
aggtttggtc cagcctggtt tagcctggat gttgctgtgc acggtggacc cagacacatc   2700
gcactgtgga ttatttcatt ttgtaacaaa tgaacgatat gtagcagaaa ggcacgtcca   2760
ctcacaaggg acgctttggg agaatgtcag ttcatgtatg ttcagaagaa attctgtcat   2820
agaaagtgcc agaaagtgtt taacttgtca aaaaacaaaa acccagcaac agaaaaatgg   2880
agtttggaaa acaggactta aaatgacatt cagtatataa aatatgtaca taatattgga   2940
tgactaacta tcaaatagat ggatttgtat caataccaaa tagcttctgt tttgttttgc   3000
tgaaggctaa attcacagcg ctatgcaatt cttaatttc attaagttgt tatttcagtt    3060
ttaaatgtac cttcagaata agcttcccca ccccagtttt tgttgcttga aaatattgtt   3120
gtcccggatt tttgttaata ttcatttttg ttatcctttt ttaaaagtaa atgtacagga   3180
tgccagtaaa aaaaaaaaat ggcttcagaa ttaaaactat gaaatatttt acagtttttc   3240
ttgtacagag tacttggctg ttagcccaag gttaaaaagt tcataacaga tttttttgg    3300
actgttttgt tgggcagtgc ctgataagct tcaaagctgc tttattcaat aaaaaaaaga   3360
aatgaaaaag atatatgaat atgacaaagt attgctgagt ccaacaatgt tgttttaaga   3420
```

ctcttaaaat acggtacctg gcaatgttta tttcataaag aattgtgaac ttcttgaatc 3480
tagggagggg gaatgtagtg aagggatgta tcaagtgggg tggtgggagg gggaggcaag 3540
gttatatgca ctttctcatg atttacagag aagtgaataa ctgcaaagtg aagttgcttc 3600
ttctacttca gtcttctctc actttgattt gctagttgtt atcaattaat gacaattaca 3660
aacctactgt atctctaata cagtgtgact ggtcaggtat ttcagttctt aggaaggaag 3720
tgccaagttt gtttttgggt tcctggaaca gcgctcacct ttgtttagaa cactggttta 3780
aagggataat catctctgtc acattagact atccatcatg accagcaaat actcatttta 3840
ggaaaaaaaa aagcatgatc tgaaaaatac ttttggtggt atgttggtta ccctcctagc 3900
tttccatttg gtttagaaca taaagcaaat agacacagtc atactgtcac tgctctggac 3960
tgtgtggagc tcgctaaagt catggtcatt gcaggaatcc aagtggcagt ccttctcatt 4020
cattctaatc attgtatgtg cttcactacg ggggggagaa ggaaacgtta gcatcatgtt 4080
tcccatttag ggcaggagtg agaggtctct cttcctgatt tagatatgca aaagctggta 4140
tgttcagtag gaactgtaca tgtgttggga ggcataaaga ctaattagca accataaatat 4200
ggtcactacc ctaatagact aaatgaaatc ttgcaatttc aaattactct ttctccatat 4260
tagatttacc cacagctata tttctgttta agtactaggg tgagggtttt ctgttacttt 4320
gtttttttaat gttgttcctt ttgaaagaat cagtcttgca gctgagtgaa aaatctgtgg 4380
aatgtattat ttgtcctctt tacatgaaac tactcatact taagcaaaag tcagtcttat 4440
agcaagactg ttagccctca aacttgactc tactgatctg accatttccc tctcatcgcc 4500
agacaactga cgatttccct ggttttagtc tgcgtctctg ctttaaagtt attgtgatat 4560
ccttctagat catacacaag tctaacagtt aattagttaa cagtttttaa actaggtttg 4620
tgggtatttt tttggtagca catgtatgct attacataca aatttttatt tctaaaatat 4680
aagatctgag attgaatatt ttcattaaaa gctacagttt tgtgaatctt tgtgcttcaa 4740
cattctttgc aagatgatac ggtatttagg catttgcctt atttttgcat ctcacaaaca 4800
taagtgcaat agatcttttc attgaacagc aaagtaggat tcatcattcc atatgacttg 4860
agttacacca gacctgttct gcccaatgcc tttttgatta cagtgtagct tgcccaccgc 4920
atttgtcgtt ttagatactt tgctagccgg ccactttgga tttcatcaga cagtcctaac 4980
aatattgtct gaacggctga atatgaatag atacagcaga ggcactcctg atatatgatt 5040
tttatccatg cgtcagtttt tcccacccag tgtagcatcc taaagataaa gccagaagct 5100
aagctgcagt gaggctgtga ttgggcgtag aagtgggagc attgggacct cacattacac 5160
acacgagaga tcataaccat gtgaaaaggc aaaaagcatg tgtttgcaac atctgataac 5220
ttcatggcct ttgataaatg tatatatgta tatgtgcatg gactgtgttt ccagtacacc 5280
tttcagccaa aacagatcca cagtagttgt tgagttcaag tacataaagt acataacaag 5340
cgaacgtcta gtacaattct tacttatgtg tatgggattt ttccctttga ggttgctttg 5400
ttttgtctta caaaggtgaa aattgtttgt aagtgaagtg agaagttcat atttctttgg 5460
ctttttgtg tttttaaaag ttactccttt tagggagctg gtctgatgac ttgcttagct 5520
tggaaatcct tgttttcagt gtgtcgagtc aaaatgtgtt tatgtgagct gtcactgtgg 5580
ggaaccaatt gctttgtcat atagctggtt atgaactagt aacatgtttg ggaagtccta 5640
ctgatgttcc tttggaagaa aaaatctgct ggttttaaca actgtgcttt tgctatgtat 5700
ggtatccaag ttagttgaaa cgcagacact gagatctgtt tgagtttagg gtcattttta 5760
gaaaggggca gtttaaagca caatgtctca catgggacaa agttccaaaa tgccaaattc 5820
ttatttttta aaaagctagt tctataaaat actggtatta tgggtgggga ggaaatagaa 5880
ttgagtcaat tggaaagact atccaactta acatgaaact tgtcaccatg agatagcatt 5940
agctgcccag gatgctgcta tatatatata tatatatata tatgtgtgtg tgtgtgtgtg 6000
tgtgtgtgta tatatatata tatatatata tatatatata tatatatatg tgtgtgtata 6060
tatatatata tgtgtatata tatatgtata tacatatatg tatatatatg cacatatata 6120
tatgtattta aaaaaatcaa aacaaaaaaa aactcattta tacctgtgta ttttttaaag 6180
ctacaatctg ttcaatgttt ttaaaaatct gtttatatga cattgttaaa ataaagttgg 6240
tcttttgacg agagggagga tgtcacggtc agttgtaact ttgccttcac aaggcaactg 6300
gggtgggggg tgggggtagt gtgcctcctt gacatttcgt tcaagttata gattcaatgg 6360
agctatgtct tgttttaagt tgctttaatg cattgtatta gatcttcaaa cagaataaag 6420
gttgttttga aactgaaaaa aaaaaaaaaa aaa 6453

<210> SEQ ID NO 24
<211> LENGTH: 724
<212> TYPE: PRT
<213> ORGANISM: Homo sapiens

<400> SEQUENCE: 24

Met Ser Ala Glu Gly Tyr Gln Tyr Arg Ala Leu Tyr Asp Tyr Lys Lys
1 5 10 15

Glu Arg Glu Glu Asp Ile Asp Leu His Leu Gly Asp Ile Leu Thr Val
20 25 30

Asn Lys Gly Ser Leu Val Ala Leu Gly Phe Ser Asp Gly Gln Glu Ala
35 40 45

Arg Pro Glu Glu Ile Gly Trp Leu Asn Gly Tyr Asn Glu Thr Thr Gly
50 55 60

Glu Arg Gly Asp Phe Pro Gly Thr Tyr Val Glu Tyr Ile Gly Arg Lys
65 70 75 80

Lys Ile Ser Pro Pro Thr Pro Lys Pro Arg Pro Pro Arg Pro Leu Pro
85 90 95

Val Ala Pro Gly Ser Ser Lys Thr Glu Ala Asp Val Glu Gln Gln Ala
100 105 110

Leu Thr Leu Pro Asp Leu Ala Glu Gln Phe Ala Pro Pro Asp Ile Ala
115 120 125

Pro Pro Leu Leu Ile Lys Leu Val Glu Ala Ile Glu Lys Lys Gly Leu
130 135 140

Glu Cys Ser Thr Leu Tyr Arg Thr Gln Ser Ser Ser Asn Leu Ala Glu
145 150 155 160

Leu Arg Gln Leu Leu Asp Cys Asp Thr Pro Ser Val Asp Leu Glu Met
165 170 175

Ile Asp Val His Val Leu Ala Asp Ala Phe Lys Arg Tyr Leu Leu Asp
180 185 190

Leu Pro Asn Pro Val Ile Pro Ala Ala Val Tyr Ser Glu Met Ile Ser
195 200 205

Leu Ala Pro Glu Val Gln Ser Ser Glu Glu Tyr Ile Gln Leu Leu Lys
210 215 220

Lys Leu Ile Arg Ser Pro Ser Ile Pro His Gln Tyr Trp Leu Thr Leu
225 230 235 240

Gln Tyr Leu Leu Lys His Phe Phe Lys Leu Ser Gln Thr Ser Ser Lys
245 250 255

```
Asn Leu Leu Asn Ala Arg Val Leu Ser Glu Ile Phe Ser Pro Met Leu
            260                 265                 270

Phe Arg Phe Ser Ala Ala Ser Ser Asp Asn Thr Glu Asn Leu Ile Lys
        275                 280                 285

Val Ile Glu Ile Leu Ile Ser Thr Glu Trp Asn Glu Arg Gln Pro Ala
    290                 295                 300

Pro Ala Leu Pro Pro Lys Pro Pro Lys Pro Thr Thr Val Ala Asn Asn
305                 310                 315                 320

Gly Met Asn Asn Asn Met Ser Leu Gln Asp Ala Glu Trp Tyr Trp Gly
                325                 330                 335

Asp Ile Ser Arg Glu Glu Val Asn Glu Lys Leu Arg Asp Thr Ala Asp
            340                 345                 350

Gly Thr Phe Leu Val Arg Asp Ala Ser Thr Lys Met His Gly Asp Tyr
        355                 360                 365

Thr Leu Thr Leu Arg Lys Gly Gly Asn Asn Lys Leu Ile Lys Ile Phe
    370                 375                 380

His Arg Asp Gly Lys Tyr Gly Phe Ser Asp Pro Leu Thr Phe Ser Ser
385                 390                 395                 400

Val Val Glu Leu Ile Asn His Tyr Arg Asn Glu Ser Leu Ala Gln Tyr
                405                 410                 415

Asn Pro Lys Leu Asp Val Lys Leu Leu Tyr Pro Val Ser Lys Tyr Gln
            420                 425                 430

Gln Asp Gln Val Val Lys Glu Asp Asn Ile Glu Ala Val Gly Lys Lys
        435                 440                 445

Leu His Glu Tyr Asn Thr Gln Phe Gln Glu Lys Ser Arg Glu Tyr Asp
    450                 455                 460

Arg Leu Tyr Glu Glu Tyr Thr Arg Thr Ser Gln Glu Ile Gln Met Lys
465                 470                 475                 480

Arg Thr Ala Ile Glu Ala Phe Asn Glu Thr Ile Lys Ile Phe Glu Glu
                485                 490                 495

Gln Cys Gln Thr Gln Glu Arg Tyr Ser Lys Glu Tyr Ile Glu Lys Phe
            500                 505                 510

Lys Arg Glu Gly Asn Glu Lys Glu Ile Gln Arg Ile Met His Asn Tyr
        515                 520                 525

Asp Lys Leu Lys Ser Arg Ile Ser Glu Ile Ile Asp Ser Arg Arg Arg
    530                 535                 540

Leu Glu Glu Asp Leu Lys Lys Gln Ala Ala Glu Tyr Arg Glu Ile Asp
545                 550                 555                 560

Lys Arg Met Asn Ser Ile Lys Pro Asp Leu Ile Gln Leu Arg Lys Thr
                565                 570                 575

Arg Asp Gln Tyr Leu Met Trp Leu Thr Gln Lys Gly Val Arg Gln Lys
            580                 585                 590

Lys Leu Asn Glu Trp Leu Gly Asn Glu Asn Thr Glu Asp Gln Tyr Ser
        595                 600                 605

Leu Val Glu Asp Asp Glu Asp Leu Pro His His Asp Glu Lys Thr Trp
    610                 615                 620

Asn Val Gly Ser Ser Asn Arg Asn Lys Ala Glu Asn Leu Leu Arg Gly
625                 630                 635                 640

Lys Arg Asp Gly Thr Phe Leu Val Arg Glu Ser Ser Lys Gln Gly Cys
                645                 650                 655

Tyr Ala Cys Ser Val Val Val Asp Gly Glu Val Lys His Cys Val Ile
            660                 665                 670

Asn Lys Thr Ala Thr Gly Tyr Gly Phe Ala Glu Pro Tyr Asn Leu Tyr
```

675 680 685

Ser Ser Leu Lys Glu Leu Val Leu His Tyr Gln His Thr Ser Leu Val
690 695 700

Gln His Asn Asp Ser Leu Asn Val Thr Leu Ala Tyr Pro Val Tyr Ala
705 710 715 720

Gln Gln Arg Arg

<210> SEQ ID NO 25
<211> LENGTH: 5572
<212> TYPE: DNA
<213> ORGANISM: Homo sapiens

<400> SEQUENCE: 25
cctcccctcg cccggcgcgg tcccgtccgc ctctcgctcg cctcccgcct cccctcggtc 60
ttccgaggcg cccgggctcc cggcgcggcg gcggaggggg cgggcaggcc ggcgggcggt 120
gatgtggcgg gactctttat gcgctgcggc aggatacgcg ctcggcgctg ggacgcgact 180
gcgctcagtt ctctcctctc ggaagctgca gccatgatgg aagtttgaga gttgagccgc 240
tgtgaggcga ggccgggctc aggcgaggga gatgagagac ggcggcggcc gcggcccgga 300
gcccctctca gcgcctgtga gcagccgcgg gggcagcgcc ctcggggagc cggccggcct 360
gcggcggcgg cagcggcggc gtttctcgcc tcctcttcgt cttttctaac cgtgcagcct 420
cttcctcggc ttctcctgaa agggaaggtg gaagccgtgg gctcgggcgg gagccggctg 480
aggcgcggcg gcggcggcgg cacctcccgc tcctggagcg ggggggagaa gcggcggcgg 540
cggcggccgc ggcggctgca gctccaggga gggggtctga gtcgcctgtc accatttcca 600
gggctgggaa cgccggagag ttggtctctc cccttctact gcctccaaca cggcggcggc 660
ggcggcggca catccaggga cccgggccgg ttttaaacct cccgtccgcc gccgccgcac 720
cccccgtggc ccgggctccg gaggccgccg gcggaggcag ccgttcggag gattattcgt 780
cttctcccca ttccgctgcc gccgctgcca ggcctctggc tgctgaggag aagcaggccc 840
agtcgctgca accatccagc agccgccgca gcagccatta cccggctgcg gtccagagcc 900
aagcggcggc agagcgaggg gcatcagcta ccgccaagtc cagagccatt tccatcctgc 960
agaagaagcc ccgccaccag cagcttctgc catctctctc ctcctttttc ttcagccaca 1020
ggctcccaga catgacagcc atcatcaaag agatcgttag cagaaacaaa aggagatatc 1080
aagaggatgg attcgactta gacttgacct atatttatcc aaacattatt gctatgggat 1140
ttcctgcaga aagacttgaa ggcgtataca ggaacaatat tgatgatgta gtaaggtttt 1200
tggattcaaa gcataaaaac cattacaaga tatacaatct ttgtgctgaa agacattatg 1260
acaccgccaa atttaattgc agagttgcac aatatccttt tgaagaccat aacccaccac 1320
agctagaact tatcaaaccc ttttgtgaag atcttgacca atggctaagt gaagatgaca 1380
atcatgttgc agcaattcac tgtaaagctg gaaagggacg aactggtgta atgatatgtg 1440
catatttatt acatcggggc aaatttttaa aggcacaaga ggccctagat ttctatgggg 1500
aagtaaggac cagagacaaa aagggagtaa ctattcccag tcagaggcgc tatgtgtatt 1560
attatagcta cctgttaaag aatcatctgg attatagacc agtggcactg ttgtttcaca 1620
agatgatgtt tgaaactatt ccaatgttca gtggcggaac ttgcaatcct cagtttgtgg 1680
tctgccagct aaaggtgaag atatattcct ccaattcagg acccacacga cgggaagaca 1740
agttcatgta ctttgagttc cctcagccgt tacctgtgtg tggtgatatc aaagtagagt 1800
tcttccacaa acagaacaag atgctaaaaa aggacaaaat gtttcacttt tgggtaaata 1860

```
cattcttcat accaggacca gaggaaacct cagaaaaagt agaaaatgga agtctatgtg   1920
atcaagaaat cgatagcatt tgcagtatag agcgtgcaga taatgacaag gaatatctag   1980
tacttacttt aacaaaaaat gatcttgaca aagcaaataa agacaaagcc aaccgatact   2040
tttctccaaa ttttaaggtg aagctgtact tcacaaaaac agtagaggag ccgtcaaatc   2100
cagaggctag cagttcaact tctgtaacac cagatgttag tgacaatgaa cctgatcatt   2160
atagatattc tgacaccact gactctgatc cagagaatga accttttgat gaagatcagc   2220
atacacaaat tacaaaagtc tgaatttttt tttatcaaga gggataaaac accatgaaaa   2280
taaacttgaa taaactgaaa atggaccttt ttttttttaa tggcaatagg acattgtgtc   2340
agattaccag ttataggaac aattctcttt tcctgaccaa tcttgtttta ccctatacat   2400
ccacagggtt ttgacacttg ttgtccagtt gaaaaaaggt tgtgtagctg tgtcatgtat   2460
ataccttttt gtgtcaaaag gacatttaaa attcaattag gattaataaa gatggcactt   2520
tcccgtttta ttccagtttt ataaaaagtg gagacagact gatgtgtata cgtaggaatt   2580
ttttcctttt gtgttctgtc accaactgaa gtggctaaag agctttgtga tatactggtt   2640
cacatcctac ccctttgcac ttgtggcaac agataagttt gcagttggct aagagaggtt   2700
tccgaagggt tttgctacat tctaatgcat gtattcgggt taggggaatg gagggaatgc   2760
tcagaaagga aataatttta tgctggactc tggaccatat accatctcca gctatttaca   2820
cacacctttc tttagcatgc tacagttatt aatctggaca ttcgaggaat tggccgctgt   2880
cactgcttgt tgtttgcgca ttttttttta aagcatattg gtgctagaaa aggcagctaa   2940
aggaagtgaa tctgtattgg ggtacaggaa tgaaccttct gcaacatctt aagatccaca   3000
aatgaaggga tataaaaata atgtcatagg taagaaacac agcaacaatg acttaaccat   3060
ataaatgtgg aggctatcaa caaagaatgg gcttgaaaca ttataaaaat tgacaatgat   3120
ttattaaata tgttttctca attgtaacga cttctccatc tcctgtgtaa tcaaggccag   3180
tgctaaaatt cagatgctgt tagtacctac atcagtcaac aacttacact tattttacta   3240
gttttcaatc ataatacctg ctgtggatgc ttcatgtgct gcctgcaagc ttcttttttc   3300
tcattaaata taaaatattt tgtaatgctg cacagaaatt ttcaatttga gattctacag   3360
taagcgtttt ttttctttga agatttatga tgcacttatt caatagctgt cagccgttcc   3420
acccttttga ccttacacat tctattacaa tgaattttgc agttttgcac attttttaaa   3480
tgtcattaac tgttagggaa ttttacttga atactgaata catataatgt ttatattaaa   3540
aaggacattt gtgttaaaaa ggaaattaga gttgcagtaa actttcaatg ctgcacacaa   3600
aaaaaagaca tttgattttt cagtagaaat tgtcctacat gtgctttatt gatttgctat   3660
tgaaagaata gggttttttt tttttttttt tttttttttt ttaaatgtgc agtgttgaat   3720
catttcttca tagtgctccc ccgagttggg actagggctt caatttcact tcttaaaaaa   3780
aatcatcata tatttgatat gcccagactg catacgattt taagcggagt acaactacta   3840
ttgtaaagct aatgtgaaga tattattaaa aaggtttttt tttccagaaa tttggtgtct   3900
tcaaattata ccttcacctt gacatttgaa tatccagcca ttttgtttct taatggtata   3960
aaattccatt ttcaataact tattggtgct gaaattgttc actagctgtg gtctgaccta   4020
gttaatttac aaatacagat tgaataggac ctactagagc agcatttata gagtttgatg   4080
gcaaatagat taggcagaac ttcatctaaa atattcttag taaataatgt tgacacgttt   4140
tccatacctt gtcagtttca ttcaacaatt tttaaatttt taacaaagct cttaggattt   4200
```

```
acacatttat atttaaacat tgatatatag agtattgatt gattgctcat aagttaaatt   4260

ggtaaagtta gagacaacta ttctaacacc tcaccattga aatttatatg ccaccttgtc   4320

tttcataaaa gctgaaaatt gttacctaaa atgaaaatca acttcatgtt ttgaagatag   4380

ttataaatat tgttctttgt tacaatttcg ggcaccgcat attaaaacgt aactttattg   4440

ttccaatatg taacatggag ggccaggtca taaataatga cattataatg ggcttttgca   4500

ctgttattat ttttcctttg gaatgtgaag gtctgaatga gggttttgat tttgaatgtt   4560

tcaatgtttt tgagaagcct tgcttacatt ttatggtgta gtcattggaa atggaaaaat   4620

ggcattatat atattatata tataaatata tattatacat actctcctta ctttatttca   4680

gttaccatcc ccatagaatt tgacaagaat tgctatgact gaaaggtttt cgagtcctaa   4740

ttaaaacttt atttatggca gtattcataa ttagcctgaa atgcattctg taggtaatct   4800

ctgagtttct ggaatatttt cttagacttt ttggatgtgc agcagcttac atgtctgaag   4860

ttacttgaag gcatcacttt taagaaagct tacagttggg ccctgtacca tcccaagtcc   4920

tttgtagctc ctcttgaaca tgtttgccat acttttaaaa gggtagttga ataaatagca   4980

tcaccattct ttgctgtggc acaggttata aacttaagtg gagtttaccg gcagcatcaa   5040

atgtttcagc tttaaaaaat aaaagtaggg tacaagttta atgtttagtt ctagaaattt   5100

tgtgcaatat gttcataacg atggctgtgg ttgccacaaa gtgcctcgtt tacctttaaa   5160

tactgttaat gtgtcatgca tgcagatgga aggggtggaa ctgtgcacta aagtgggggc   5220

tttaactgta gtatttggca gagttgcctt ctacctgcca gttcaaaagt tcaacctgtt   5280

ttcatataga atatatatac taaaaaattt cagtctgtta aacagcctta ctctgattca   5340

gcctcttcag atactcttgt gctgtgcagc agtggctctg tgtgtaaatg ctatgcactg   5400

aggatacaca aaaataccaa tatgatgtgt acaggataat gcctcatccc aatcagatgt   5460

ccatttgtta ttgtgtttgt taacaaccct ttatctctta gtgttataaa ctccacttaa   5520

aactgattaa agtctcattc ttgtcaaaaa aaaaaaaaaa aaaaaaaaaa aa           5572
```

```
<210> SEQ ID NO 26
<211> LENGTH: 403
<212> TYPE: PRT
<213> ORGANISM: Homo sapiens

<400> SEQUENCE: 26

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
```

```
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val


<210> SEQ ID NO 27
<211> LENGTH: 3291
<212> TYPE: DNA
<213> ORGANISM: Homo sapiens

<400> SEQUENCE: 27

agaatcggag agccggtggc gtcgcaggtc gggaggacga gcaccgagtc gagggctcgc      60

tcgtctgggc cgcccgagag tcttaatcgc gggcgcttgg gccgccatct tagatggcgg     120

gagtaagagg aaaacgattg tgaggcggga acggctttct gctgcctttt ttgggccccg     180

aaaagggtca gctggccggg ctttggggcg cgtgccctga ggcgcggagc gcgtttgcta     240

cgatgcgggg gctgctcggg gctccgtccc ctgggctggg gacgcgccga atgtgaccgc     300

ctcccgctcc ctcacccgcc gcggggagga ggagcgggcg agaagctgcc gccgaacgac     360

aggacgttgg ggcggcctgg ctccctcagg tttaagaatt gtttaagctg catcaatgga     420

gcacatacag ggagcttgga agacgatcag caatggtttt ggattcaaag atgccgtgtt     480

tgatggctcc agctgcatct ctcctacaat agttcagcag tttggctatc agcgccgggc     540

atcagatgat ggcaaactca cagatccttc taagacaagc aacactatcc gtgttttctt     600
```

-continued

```
gccgaacaag caaagaacag tggtcaatgt gcgaaatgga atgagcttgc atgactgcct    660
tatgaaagca ctcaaggtga ggggcctgca accagagtgc tgtgcagtgt tcagacttct    720
ccacgaacac aaaggtaaaa aagcacgctt agattggaat actgatgctg cgtctttgat    780
tggagaagaa cttcaagtag atttcctgga tcatgttccc ctcacaacac acaactttgc    840
tcggaagacg ttcctgaagc ttgccttctg tgacatctgt cagaaattcc tgctcaatgg    900
atttcgatgt cagacttgtg gctacaaatt tcatgagcac tgtagcacca aagtacctac    960
tatgtgtgtg gactggagta acatcagaca actcttattg tttccaaatt ccactattgg   1020
tgatagtgga gtcccagcac taccttcttt gactatgcgt cgtatgcgag agtctgtttc   1080
caggatgcct gttagttctc agcacagata ttctacacct cacgccttca cctttaacac   1140
ctccagtccc tcatctgaag gttccctctc ccagaggcag aggtcgacat ccacacctaa   1200
tgtccacatg gtcagcacca ccctgcctgt ggacagcagg atgattgagg atgcaattcg   1260
aagtcacagc gaatcagcct caccttcagc cctgtccagt agccccaaca atctgagccc   1320
aacaggctgg tcacagccga aaacccccgt gccagcacaa agagagcggg caccagtatc   1380
tgggacccag gagaaaaaca aaattaggcc tcgtggacag agagattcaa gctattattg   1440
ggaaatagaa gccagtgaag tgatgctgtc cactcggatt gggtcaggct cttttggaac   1500
tgtttataag ggtaaatggc acggagatgt tgcagtaaag atcctaaagg ttgtcgaccc   1560
aaccccagag caattccagg ccttcaggaa tgaggtggct gttctgcgca aaacacggca   1620
tgtgaacatt ctgcttttca tggggtacat gacaaaggac aacctggcaa ttgtgaccca   1680
gtggtgcgag ggcagcagcc tctacaaaca cctgcatgtc caggagacca agtttcagat   1740
gttccagcta attgacattg cccggcagac ggctcaggga atggactatt tgcatgcaaa   1800
gaacatcatc catagagaca tgaaatccaa caatatattt ctccatgaag gcttaacagt   1860
gaaaattgga gattttggtt tggcaacagt aaagtcacgc tggagtggtt ctcagcaggt   1920
tgaacaacct actggctctg tcctctggat ggccccagag gtgatccgaa tgcaggataa   1980
caacccattc agtttccagt cggatgtcta ctcctatggc atcgtattgt atgaactgat   2040
gacgggggag cttccttatt ctcacatcaa caaccgagat cagatcatct tcatggtggg   2100
ccgaggatat gcctccccag atcttagtaa gctatataag aactgcccca aagcaatgaa   2160
gaggctggta gctgactgtg tgaagaaagt aaaggaagag aggcctcttt ttccccagat   2220
cctgtcttcc attgagctgc tccaacactc tctaccgaag atcaaccgga gcgcttccga   2280
gccatccttg catcgggcag cccacactga ggatatcaat gcttgcacgc tgaccacgtc   2340
cccgaggctg cctgtcttct agttgacttt gcacctgtct tcaggctgcc aggggaggag   2400
gagaagccag caggcaccac ttttctgctc cctttctcca gaggcagaac acatgttttc   2460
agagaagctg ctgctaagga ccttctagac tgctcacagg gccttaactt catgttgcct   2520
tcttttctat ccctttgggc cctgggagaa ggaagccatt tgcagtgctg gtgtgtcctg   2580
ctccctcccc acattcccca tgctcaaggc ccagccttct gtagatgcgc aagtggatgt   2640
tgatggtagt acaaaaagca ggggcccagc cccagctgtt ggctacatga gtatttagag   2700
gaagtaaggt agcaggcagt ccagccctga tgtggagaca catgggattt tggaaatcag   2760
cttctggagg aatgcatgtc acaggcggga ctttcttcag agagtggtgc agcgccagac   2820
attttgcaca taaggcacca aacagcccag gactgccgag actctggccg cccgaaggag   2880
cctgctttgg tactatggaa cttttcttag ggacacgtc ctcctttcac agcttctaag   2940
```

```
gtgtccagtg cattgggatg gttttccagg caaggcactc ggccaatccg catctcagcc   3000

ctctcaggga gcagtcttcc atcatgctga attttgtctt ccaggagctg cccctatggg   3060

gcggggccgc agggccagcc ttgtttctct aacaaacaaa caaacaaaca gccttgtttc   3120

tctagtcaca tcatgtgtat acaaggaagc caggaataca ggttttcttg atgatttggg   3180

ttttaatttt gtttttattg cacctgacaa aatacagtta tctgatggtc cctcaattat   3240

gttattttaa taaaataaat taaatttagg tgtaaaaaaa aaaaaaaaaa a            3291
```

<210> SEQ ID NO 28
<211> LENGTH: 648
<212> TYPE: PRT
<213> ORGANISM: Homo sapiens

<400> SEQUENCE: 28

```
Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
            20                  25                  30

Val Gln Gln Phe Gly Tyr Gln Arg Arg Ala Ser Asp Asp Gly Lys Leu
        35                  40                  45

Thr Asp Pro Ser Lys Thr Ser Asn Thr Ile Arg Val Phe Leu Pro Asn
    50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125

Asp Phe Leu Asp His Val Pro Leu Thr Thr His Asn Phe Ala Arg Lys
    130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
    210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
            260                 265                 270

Asp Ser Arg Met Ile Glu Asp Ala Ile Arg Ser His Ser Glu Ser Ala
        275                 280                 285

Ser Pro Ser Ala Leu Ser Ser Ser Pro Asn Asn Leu Ser Pro Thr Gly
    290                 295                 300

Trp Ser Gln Pro Lys Thr Pro Val Pro Ala Gln Arg Glu Arg Ala Pro
305                 310                 315                 320
```

```
Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
            340                 345                 350

Thr Arg Ile Gly Ser Gly Ser Phe Gly Thr Val Tyr Lys Gly Lys Trp
        355                 360                 365

His Gly Asp Val Ala Val Lys Ile Leu Lys Val Val Asp Pro Thr Pro
    370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
            420                 425                 430

Leu His Val Gln Glu Thr Lys Phe Gln Met Phe Gln Leu Ile Asp Ile
        435                 440                 445

Ala Arg Gln Thr Ala Gln Gly Met Asp Tyr Leu His Ala Lys Asn Ile
    450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
            500                 505                 510

Ala Pro Glu Val Ile Arg Met Gln Asp Asn Asn Pro Phe Ser Phe Gln
        515                 520                 525

Ser Asp Val Tyr Ser Tyr Gly Ile Val Leu Tyr Glu Leu Met Thr Gly
    530                 535                 540

Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
                565                 570                 575

Cys Pro Lys Ala Met Lys Arg Leu Val Ala Asp Cys Val Lys Lys Val
            580                 585                 590

Lys Glu Glu Arg Pro Leu Phe Pro Gln Ile Leu Ser Ser Ile Glu Leu
        595                 600                 605

Leu Gln His Ser Leu Pro Lys Ile Asn Arg Ser Ala Ser Glu Pro Ser
    610                 615                 620

Leu His Arg Ala Ala His Thr Glu Asp Ile Asn Ala Cys Thr Leu Thr
625                 630                 635                 640

Thr Ser Pro Arg Leu Pro Val Phe
                645
```

<210> SEQ ID NO 29
<211> LENGTH: 2092
<212> TYPE: DNA
<213> ORGANISM: Homo sapiens

<400> SEQUENCE: 29

```
ggcgtaatta aaaagcggcg gaagaaggtg ggagggtcat gacgcagcga gtttcagtcg      60

tgacttttct gggggcatcg cggcgtcccc tttttttgcc tttaaagtaa aacgtcgccc     120

cgacgcaccc cccgcgtatt tcgggggcg gaggcggcgg gccacggcgc gaagaggggc     180

ggtgctgacg ccggccggtc acgtgggcgt gttgtggggg ggaggggcgc cgccgcgcgg     240
```

-continued

```
tcggttccgg gcggttggga gcgcgcgagc tagcgagcga gaggcagccg cgcccgccgc    300
cgcccctgct ctgtatgccg ctctctcccg gcgcggccgc cgccgatcac agcagcagga    360
gccaccgccg ccgcggttga tgtggttggg ccggggctga ggaggccgcc aagatgccgc    420
agtccaagtc ccggaagatc gcgatcctgg gctaccggtc tgtggggaaa tcctcattga    480
cgattcaatt tgttgaaggc caatttgtgg actcctacga tccaaccata gaaaacactt    540
ttacaaagtt gatcacagta aatggacaag aatatcatct tcaacttgta gacacagccg    600
ggcaagatga atattctatc tttcctcaga catactccat agatattaat ggctatattc    660
ttgtgtattc tgttacatca atcaaaagtt ttgaagtgat taaagttatc catggcaaat    720
tgttggatat ggtggggaaa gtacaaatac ctattatgtt ggttgggaat aagaaagacc    780
tgcatatgga aagggtgatc agttatgaag aagggaaagc tttggcagaa tcttggaatg    840
cagctttttt ggaatcttct gctaaagaaa atcagactgc tgtggatgtt tttcgaagga    900
taattttgga ggcagaaaaa atggacgggg cagcttcaca aggcaagtct tcatgctcgg    960
tgatgtgatt ctgctgcaaa gcctgaggac actgggaata tattctacct gaagaagcaa   1020
actgcccgtt ctccttgaag ataaactatg cttctttttt cttctgttaa cctgaaagat   1080
atcatttggg tcagagctcc cctcccttca gattatgtta actctgagtc tgtccaaatg   1140
agttcacttc cattttcaaa ttttaagcaa tcatattttc aatttatata ttgtatttct   1200
taatattatg accaagaatt ttatcggcat taatttttca gtgtagtttg ttgtttaaaa   1260
taatgtaatc atcaaaatga tgcatattgt tacactacta ttaactaggc ttcagtatat   1320
cagtgtttat ttcattgtgt taaatgtata cttgtaaata aaatagctgc aaacctcagt   1380
cctttgtgct acttgatgtg gctttcaaag aagagaagcc ttgtcctgag tttctcactt   1440
ggcttcagga aggccccagg ttggattcca gaaaccagtg aagatgtggc cacaggagga   1500
ggtgtgctga ggtggctgct gaccgtggac tccctgcgca gtggcctgca gatgttgggg   1560
ctgggttaca gctgattgaa gctgagtggc cctgggggt ctgtgagggg agttcctccc   1620
cagtgatgaa attctctcct tccaccctca aatccctaga ccttgactga aatgctccgt   1680
ggtcgggagc ctggtcaagg aggaggagct gctgagaggc attgttcgcc cttgctcata   1740
gcttagctcg atgtccgtgt cagacaggag atgattgaga acagccttgc ctgtcactgt   1800
cctagaacac cctggagttt agtgttctgt gtcagagtct tgggagcctc cttcagaccc   1860
agatgacggg cctccctctg tccaaggagc agctgtaaag gagaagaggg atttcatttg   1920
tttggtggct gttaccttgt ctgtaagtca aacttggagt tgagcagtgc tttttaaacg   1980
attccctttt gcagctaaaa tttcacaggg ctatttctaa tacgtaagca aatgttacca   2040
ttgactttat taataaaata tagttttgct ttgcaaaaaa aaaaaaaaaa aa           2092

<210> SEQ ID NO 30
<211> LENGTH: 184
<212> TYPE: PRT
<213> ORGANISM: Homo sapiens

<400> SEQUENCE: 30

Met Pro Gln Ser Lys Ser Arg Lys Ile Ala Ile Leu Gly Tyr Arg Ser
1               5                   10                  15

Val Gly Lys Ser Ser Leu Thr Ile Gln Phe Val Glu Gly Gln Phe Val
            20                  25                  30

Asp Ser Tyr Asp Pro Thr Ile Glu Asn Thr Phe Thr Lys Leu Ile Thr
        35                  40                  45
```

```
Val Asn Gly Gln Glu Tyr His Leu Gln Leu Val Asp Thr Ala Gly Gln
    50                  55                  60

Asp Glu Tyr Ser Ile Phe Pro Gln Thr Tyr Ser Ile Asp Ile Asn Gly
65                  70                  75                  80

Tyr Ile Leu Val Tyr Ser Val Thr Ser Ile Lys Ser Phe Glu Val Ile
                85                  90                  95

Lys Val Ile His Gly Lys Leu Leu Asp Met Val Gly Lys Val Gln Ile
            100                 105                 110

Pro Ile Met Leu Val Gly Asn Lys Lys Asp Leu His Met Glu Arg Val
        115                 120                 125

Ile Ser Tyr Glu Glu Gly Lys Ala Leu Ala Glu Ser Trp Asn Ala Ala
    130                 135                 140

Phe Leu Glu Ser Ser Ala Lys Glu Asn Gln Thr Ala Val Asp Val Phe
145                 150                 155                 160

Arg Arg Ile Ile Leu Glu Ala Glu Lys Met Asp Gly Ala Ala Ser Gln
                165                 170                 175

Gly Lys Ser Ser Cys Ser Val Met
            180


<210> SEQ ID NO 31
<211> LENGTH: 7145
<212> TYPE: DNA
<213> ORGANISM: Homo sapiens

<400> SEQUENCE: 31

atggacggcc ccggggccag cgccgtggtc gtgcgcgtcg gcatcccgga cctgcagcag     60

acgaagtgcc tgcgcctgga cccggccgcg cccgtgtggg ccgccaagca gcgcgtgctc    120

tgcgccctca accacagcct ccaggacgcg ctcaactatg ggcttttcca gccgccctcc    180

cggggccgcg ccggcaagtt cctggatgag gagcggctcc tgcaggagta cccgcccaac    240

ctggacacgc ccctgcccta cctggagttt cgatacaagc ggcgagttta tgcccagaac    300

ctcatcgatg ataagcagtt tgcaaagctt cacacaaagg cgaacctgaa gaagttcatg    360

gactacgtcc agctgcatag cacggacaag gtggcacgcc tgttggacaa ggggctggac    420

cccaacttcc atgaccctga ctcaggagag tgccccctga gcctcgcagc ccagctggac    480

aacgccacgg acctgctaaa ggtgctgaag aatggtggtg cccacctgga cttccgcact    540

cgcgatgggc tcactgccgt gcactgtgcc acacgccagc ggaatgcggc agcactgacg    600

accctgctgg acctgggggc ttcacctgac tacaaggaca gccgcggctt gacacccctc    660

taccacagcg ccctgggggg tggggatgcc ctctgctgtg agctgcttct ccacgaccac    720

gctcagctgg ggatcaccga cgagaatggc tggcaggaga tccaccaggc ctgccgcttt    780

gggcacgtgc agcatctgga gcacctgctg ttctatgggg cagacatggg ggcccagaac    840

gcctcgggga acacagccct gcacatctgt gccctctaca accaggagag ctgtgctcgt    900

gtcctgctct tccgtggagc taacagggat gtccgcaact acaacagcca gacagccttc    960

caggtggcca tcatcgcagg gaactttgag cttgcagagg ttatcaagac ccacaaagac   1020

tcggatgttg taccattcag ggaaaccccc agctatgcga agcggcggcg actggctggc   1080

cccagtggct tggcatcccc tcggcctctg cagcgctcag ccagcgatat caacctgaag   1140

ggggaggcac agccagcagc ttctcctgga ccctcgctga gaagcctccc ccaccagctg   1200

ctgctccagc ggctgcaaga ggagaaagat cgtgaccggg atgccgacca ggagagcaac   1260

atcagtggcc ctttagcagg cagggccggc caaagcaaga tcagcgatcc gggccctgga   1320
```

-continued

```
cctggagggg tggggggggc gcccctccct ccccctggcg cgcccaggag ctgtattcga   1380
attcgagctc ggttccccgc gccccctgcg ccccccgcac cgccgccccg gggcccgaag   1440
cggaaacttt acagcgccgt ccccggccgc aagttcatcg ccgtgaaggc gcacagcccg   1500
cagggtgaag gcgagatccc gctgcaccgc ggcgaggccg tgaaggtgct cagcattggg   1560
gagggcggtt tctgggaggg aaccgtgaaa ggccgcacgg gctggttccc ggccgactgc   1620
gtggaggaag tgcagatgag gcagcatgac acacggcctg aaacgcggga ggaccggacg   1680
aagcggctct ttcggcacta cacagtgggc tcctacgaca gcctcacctc acacagcgat   1740
tatgtcattg atgacaaagt ggctgtcctg cagaaacggg accacgaggg ctttggtttt   1800
gtgctccggg gagccaaagc agagaccccc atcgaggagt tcacgcccac gccagccttc   1860
ccggcgctgc agtatctcga gtcggtggac gtggagggtg tggcctggag ggccgggctg   1920
cgcacgggag acttcctcat cgaggtgaac ggggtgaacg tggtgaaggt cggacacaag   1980
caggtggtgg ctctgattcg ccagggtggc aaccgcctcg tcatgaaggt tgtgtctgtg   2040
acaaggaagc cagaagagga cggggctcgg cgcagagccc caccgccccc caagagggcc   2100
cccagcacca cactgaccct gcgctccaag tccatgacag ctgagctcga ggaacttgcc   2160
tccattcgga gaagaaaagg ggagaagctg gacgagatgc tggcagccgc cgcagagcca   2220
acgctgcggc cagacatcgc agacgcagac tccagagccg ccaccgtcaa acagaggccc   2280
accagtcgga ggatcacacc cgccgagatt agctcattgt ttgaacgcca gggcctccca   2340
ggcccagaga agctgccggg ctccttgcgg aaggggattc cacggaccaa gtctgtaggg   2400
gaggacgaga agctggcgtc cctgctggaa gggcgcttcc cgcggagcac ctcgatgcaa   2460
gacccggtgc gcgagggtcg cggcatcccg cccccgccgc agaccgcgcc gcctcccccg   2520
cccgcgccct actacttcga ctcggggccg cccccggcct tctcgccgcc gcccccgccg   2580
ggccgcgcct acgacacggt gcgctccagc ttcaagcccg gcctggaggc gcgcctgggc   2640
gcgggcgctg ccggcctgta cgagccgggc gcggccctcg gcccgctgcc gtatcccgag   2700
cggcagaagc gcgcgcgctc catgatcatc ctgcaggact cggcgcccga gtcgggcgac   2760
gcccctcgac ccccgcccgc ggccaccccg cccgagcgac ccaagcgccg gccgcggccg   2820
cccggccccg acagccccta cgccaacctg ggcgccttca gcgccagcct cttcgctccg   2880
tccaagccgc agcgccgcaa gagcccccctg gtgaagcagc tgcaggtgga ggacgcgcag   2940
gagcgcgcgg ccctggccgt gggcagcccc ggtcccggcg gcggcagctt cgcccgcgag   3000
ccctccccga cccaccgcgg tccgcgcccg ggtggcctcg actacggcgc gggcgatggc   3060
ccggggctcg cgttcggcgg cccgggcccg gccaaggacc ggcggctgga ggagcggcgc   3120
cgctccactg tgttcctgtc cgtgggggcc atcgagggca gcgcccccgg cgcggatctg   3180
ccatccctac agccctcccg ctccatcgac gagcgcctcc tggggaccgg ccccaccgcc   3240
ggccgcgacc tgctgctgcc ctccccggtg tctgccctga agccgttggt cagcggcccg   3300
agcctggggc cctcgggttc caccttcatc cacccactca ccggcaaacc cctggacccc   3360
agctcacccc tggcccttgc cctggctgcc cgagagcgag ctctggcctc ccaggcgccc   3420
tcccggtccc ccacacccgt gcacagtccc gacgccgacc gccccggacc cctgtttgtg   3480
gatgtacagg cccgggaccc agagcgaggg tccctggctt ccccggcttt ctccccacgg   3540
agcccagcct ggattcctgt gcctgctcgc agggaggcag agaaggtccc ccgggaggag   3600
cggaagtcac ccgaggacaa gaagtccatg atcctcagcg tcctggacac atccctgcag   3660
```

```
cggccagctg gcctcatcgt tgtgcacgcc accagcaacg ggcaggagcc cagcaggctg   3720
ggggggggccg aagaggagcg cccgggcacc ccggagttgg ccccggcccc catgcagtca   3780
gcggctgtgg cagagcccct gcccagcccc cgggcccagc cccctggtgg caccccggca   3840
gacgccgggc caggccaggg cagctcagag gaagagccag agctggtgtt tgctgtgaac   3900
ctgccacctg cccagctgtc gtccagcgat gaggagacca gggaggagct ggcccgaatt   3960
gggttggtgc cacccccctga agagtttgcc aacggggtcc tgctggccac cccactcgct   4020
ggcccgggcc cctcgcccac cacggtgccc agcccggcct cagggaagcc cagcagtgag   4080
ccacccccctg cccctgagtc tgcagccgac tctggggtgg aggaggctga cacacgcagc   4140
tccagcgacc cccacctgga gaccacaagc accatctcca cggtgtccag catgtccacc   4200
ttgagctcgg agagcgggga actcactgac acccacacct ccttcgctga cggacacact   4260
tttctactcg agaagccacc agtgcctccc aagcccaagc tcaagtcccc gctggggaag   4320
gggccggtga ccttcaggga cccgctgctg aagcagtcct cggacagcga gctcatggcc   4380
cagcagcacc acgccgcctc tgccgggctg gcctctgccg ccgggcctgc ccgccctcgc   4440
tacctcttcc agagaaggtc caagctatgg ggggaccccg tggagagccg ggggctccct   4500
gggcctgaag acgacaaacc aactgtgatc agtgagctca gctcccgcct gcagcagctg   4560
aacaaggaca cgcgttccct gggggaggaa ccagttggtg gcctgggcag cctgctggac   4620
cctgccaaga agtcgcccat cgcagcagct cggctcttca gcagcctcgg tgagctgagc   4680
tccatttcag cgcagcgcag ccccgggggc ccgggcggcg gggcctcgta ctcggtgagg   4740
cccagtggcc gctaccccgt ggcgagacgc gccccgagcc cggtgaagcc cgcgtcgctg   4800
gagcgggtgg aggggctggg ggcgggcgcg gggggcgcag ggcggccctt cggcctcacg   4860
ccccccacca tcctcaagtc gtccagcctc tccatcccgc acgagcccaa ggaggtgcgc   4920
ttcgtggtgc gcagcgtgag cgcgcgcagt cgctcccccct cgccgtcgcc gctgccctcg   4980
cccgcgtccg gccccggccc cggcgccccc ggcccacgcc gacccttcca gcagaagccg   5040
ctgcagctct ggagcaagtt cgacgtgggc gactggctgg agagcatcca cctaggcgag   5100
caccgcgacc gcttcgagga ccatgagata gaaggcgcgc acctacccgc gcttaccaag   5160
gacgacttcg tggagctggg cgtcacgcgc gtgggccacc gcatgaacat cgagcgcgcg   5220
ctcaggcagc tggacggcag ctgacgcccc acccccactc ccgcccggc cgtgccctgc   5280
cggcagggcc ccccaccccc accccgggcc gcgggctcgg cctgcccctt acgacggcgc   5340
ccgggccagg aatgttgcat gaatcgtcct gtttgctgtt gctcggagac tcgccctgta   5400
cattgcttag tgccctcacc ggccgcccag cccacccagc gcacagtcag gaagggcgtg   5460
gaccagggag gctggggcgg gaggtgccgg gggtggggtg ccctagcgtg accacctcct   5520
tcgcagctcc tggtggccat tctcccagag gggggaaccta gtccagcatg cgaggtcagg   5580
acccgccttg gtgactcggg gggaggggggg agacattggg attctcgatg gggccaagg   5640
agcccccctg ttttgcatat tttaatccac tctatatttg gaacgagaaa aggaacaaat   5700
atctctgtcc gtaatagttt cctctcccct cccttctact tccactggtc ccactgcagc   5760
tgcccagtct tccatctccg gcccctcact gccactgcca ccccacaacg gggcagggga   5820
cgctccagct ggtctggggt tggccagggc cctagtggcc cgccctgggg ccccagctcg   5880
gcccctcgcc tcgctgagct ctagtgtgcc ccaccgaccc ttcaggtgct gctcgtggtg   5940
ggaggggcgg caggccgcgg gtcctgctgt gcacccgcgg gaccagccgg cctgggagac   6000
catcggccgg gggggatgag ggcagggccc tgccgctcca ccgcagccat cttcctcaca   6060
```

```
gggtctctcc ccaaggaggg ggctagcttg gtccccatgc tcttgggcaa ctacagcaga   6120

gaagcctccc tgccttggac cccaaagtct cctgtcctgc cctttatgtg tgtgggtgaa   6180

actgggtgcg tctgagcacg tgggagccgt gtgtgtgcct gattactgag tggccaccag   6240

gggccgctct ggactagcgc ggggccgtgg aggcgtgcac cgtgtgcatg cgtggggtgt   6300

acctgtgaga gcaccctgtc tcctcttcca aagaaagtca gaggccatcc tgcaccctgg   6360

gtccagctgt ttgcccagcc tgtccttcca gagcctcacc cagcctgagc ggggttccct   6420

ggtgaatccc tgctgcttgg ggaggcccca agggcccctt ggaggcagcg cccccacctt   6480

gggcttctga gggcatcata gggggacccc tagagtcagt tcaccacagg ccctggggag   6540

agtcaaagac ccccgagggt gcccagcccc ccacactgtg actcctcaca ctcagcgatg   6600

acctgtgggg tggggggccc tgggacgttt ttaaacctag ggtttggagt ctggactaag   6660

ctccatccac gtcactcaca agtttctgtt tatatttcta gcttttttta ataaaataaa   6720

aaaaaaaaga aaacagaagt tttcacaacc caggggcctg gcacgccggt ctgtgcctgc   6780

ccgccccgcc ctggcccacc ggccccactc cctgggcaca gagtcacacc cactcatcct   6840

tccgccaaca gtccaggtca cacagcagca gtcactgtaa cagactgcca catacacact   6900

cggtctcaca ctcacctgtg ggttttggtt ccgttcaatt tgggttttta actttacagg   6960

gtcagttccg cttcacctcc ttttgtatgg agttccatcc ggggggtttc accccctgct   7020

ccagtcctga ggcctcctga ccctgacgtt gtgatacgcc ccacagagat ctatgtttct   7080

tatattatta ttattgataa taattattat aatattatta tgtaataaat ttataagaaa   7140

tgaag                                                               7145
```

<210> SEQ ID NO 32
<211> LENGTH: 1747
<212> TYPE: PRT
<213> ORGANISM: Homo sapiens

<400> SEQUENCE: 32

```
Met Asp Gly Pro Gly Ala Ser Ala Val Val Val Arg Val Gly Ile Pro
1               5                   10                  15

Asp Leu Gln Gln Thr Lys Cys Leu Arg Leu Asp Pro Ala Ala Pro Val
            20                  25                  30

Trp Ala Ala Lys Gln Arg Val Leu Cys Ala Leu Asn His Ser Leu Gln
        35                  40                  45

Asp Ala Leu Asn Tyr Gly Leu Phe Gln Pro Pro Ser Arg Gly Arg Ala
    50                  55                  60

Gly Lys Phe Leu Asp Glu Glu Arg Leu Leu Gln Glu Tyr Pro Pro Asn
65                  70                  75                  80

Leu Asp Thr Pro Leu Pro Tyr Leu Glu Phe Arg Tyr Lys Arg Arg Val
                85                  90                  95

Tyr Ala Gln Asn Leu Ile Asp Asp Lys Gln Phe Ala Lys Leu His Thr
            100                 105                 110

Lys Ala Asn Leu Lys Lys Phe Met Asp Tyr Val Gln Leu His Ser Thr
        115                 120                 125

Asp Lys Val Ala Arg Leu Leu Asp Lys Gly Leu Asp Pro Asn Phe His
    130                 135                 140

Asp Pro Asp Ser Gly Glu Cys Pro Leu Ser Leu Ala Ala Gln Leu Asp
145                 150                 155                 160

Asn Ala Thr Asp Leu Leu Lys Val Leu Lys Asn Gly Gly Ala His Leu
                165                 170                 175
```

```
Asp Phe Arg Thr Arg Asp Gly Leu Thr Ala Val His Cys Ala Thr Arg
            180                 185                 190

Gln Arg Asn Ala Ala Ala Leu Thr Thr Leu Leu Asp Leu Gly Ala Ser
        195                 200                 205

Pro Asp Tyr Lys Asp Ser Arg Gly Leu Thr Pro Leu Tyr His Ser Ala
    210                 215                 220

Leu Gly Gly Gly Asp Ala Leu Cys Cys Glu Leu Leu Leu His Asp His
225                 230                 235                 240

Ala Gln Leu Gly Ile Thr Asp Glu Asn Gly Trp Gln Glu Ile His Gln
                245                 250                 255

Ala Cys Arg Phe Gly His Val Gln His Leu Glu His Leu Leu Phe Tyr
            260                 265                 270

Gly Ala Asp Met Gly Ala Gln Asn Ala Ser Gly Asn Thr Ala Leu His
        275                 280                 285

Ile Cys Ala Leu Tyr Asn Gln Glu Ser Cys Ala Arg Val Leu Leu Phe
    290                 295                 300

Arg Gly Ala Asn Arg Asp Val Arg Asn Tyr Asn Ser Gln Thr Ala Phe
305                 310                 315                 320

Gln Val Ala Ile Ile Ala Gly Asn Phe Glu Leu Ala Glu Val Ile Lys
                325                 330                 335

Thr His Lys Asp Ser Asp Val Val Pro Phe Arg Glu Thr Pro Ser Tyr
            340                 345                 350

Ala Lys Arg Arg Arg Leu Ala Gly Pro Ser Gly Leu Ala Ser Pro Arg
        355                 360                 365

Pro Leu Gln Arg Ser Ala Ser Asp Ile Asn Leu Lys Gly Glu Ala Gln
    370                 375                 380

Pro Ala Ala Ser Pro Gly Pro Ser Leu Arg Ser Leu Pro His Gln Leu
385                 390                 395                 400

Leu Leu Gln Arg Leu Gln Glu Glu Lys Asp Arg Asp Arg Asp Ala Asp
                405                 410                 415

Gln Glu Ser Asn Ile Ser Gly Pro Leu Ala Gly Arg Ala Gly Gln Ser
            420                 425                 430

Lys Ile Ser Asp Pro Gly Pro Gly Pro Gly Gly Val Gly Gly Ala Pro
        435                 440                 445

Leu Pro Pro Pro Gly Ala Pro Arg Ser Cys Ile Arg Ile Arg Ala Arg
    450                 455                 460

Phe Pro Ala Pro Pro Ala Pro Pro Ala Pro Pro Pro Arg Gly Pro Lys
465                 470                 475                 480

Arg Lys Leu Tyr Ser Ala Val Pro Gly Arg Lys Phe Ile Ala Val Lys
                485                 490                 495

Ala His Ser Pro Gln Gly Glu Gly Glu Ile Pro Leu His Arg Gly Glu
            500                 505                 510

Ala Val Lys Val Leu Ser Ile Gly Glu Gly Gly Phe Trp Glu Gly Thr
        515                 520                 525

Val Lys Gly Arg Thr Gly Trp Phe Pro Ala Asp Cys Val Glu Glu Val
    530                 535                 540

Gln Met Arg Gln His Asp Thr Arg Pro Glu Thr Arg Glu Asp Arg Thr
545                 550                 555                 560

Lys Arg Leu Phe Arg His Tyr Thr Val Gly Ser Tyr Asp Ser Leu Thr
                565                 570                 575

Ser His Ser Asp Tyr Val Ile Asp Asp Lys Val Ala Val Leu Gln Lys
            580                 585                 590
```

-continued

```
Arg Asp His Glu Gly Phe Gly Phe Val Leu Arg Gly Ala Lys Ala Glu
        595                 600                 605

Thr Pro Ile Glu Glu Phe Thr Pro Thr Pro Ala Phe Pro Ala Leu Gln
    610                 615                 620

Tyr Leu Glu Ser Val Asp Val Glu Gly Val Ala Trp Arg Ala Gly Leu
625                 630                 635                 640

Arg Thr Gly Asp Phe Leu Ile Glu Val Asn Gly Val Asn Val Val Lys
                645                 650                 655

Val Gly His Lys Gln Val Val Ala Leu Ile Arg Gln Gly Gly Asn Arg
            660                 665                 670

Leu Val Met Lys Val Val Ser Val Thr Arg Lys Pro Glu Glu Asp Gly
        675                 680                 685

Ala Arg Arg Arg Ala Pro Pro Pro Pro Lys Arg Ala Pro Ser Thr Thr
    690                 695                 700

Leu Thr Leu Arg Ser Lys Ser Met Thr Ala Glu Leu Glu Glu Leu Ala
705                 710                 715                 720

Ser Ile Arg Arg Arg Lys Gly Glu Lys Leu Asp Glu Met Leu Ala Ala
                725                 730                 735

Ala Ala Glu Pro Thr Leu Arg Pro Asp Ile Ala Asp Ala Asp Ser Arg
            740                 745                 750

Ala Ala Thr Val Lys Gln Arg Pro Thr Ser Arg Arg Ile Thr Pro Ala
        755                 760                 765

Glu Ile Ser Ser Leu Phe Glu Arg Gln Gly Leu Pro Gly Pro Glu Lys
    770                 775                 780

Leu Pro Gly Ser Leu Arg Lys Gly Ile Pro Arg Thr Lys Ser Val Gly
785                 790                 795                 800

Glu Asp Glu Lys Leu Ala Ser Leu Leu Glu Gly Arg Phe Pro Arg Ser
                805                 810                 815

Thr Ser Met Gln Asp Pro Val Arg Glu Gly Arg Gly Ile Pro Pro Pro
            820                 825                 830

Pro Gln Thr Ala Pro Pro Pro Pro Pro Ala Pro Tyr Tyr Phe Asp Ser
        835                 840                 845

Gly Pro Pro Pro Ala Phe Ser Pro Pro Pro Pro Pro Gly Arg Ala Tyr
    850                 855                 860

Asp Thr Val Arg Ser Ser Phe Lys Pro Gly Leu Glu Ala Arg Leu Gly
865                 870                 875                 880

Ala Gly Ala Ala Gly Leu Tyr Glu Pro Gly Ala Ala Leu Gly Pro Leu
                885                 890                 895

Pro Tyr Pro Glu Arg Gln Lys Arg Ala Arg Ser Met Ile Ile Leu Gln
            900                 905                 910

Asp Ser Ala Pro Glu Ser Gly Asp Ala Pro Arg Pro Pro Pro Ala Ala
        915                 920                 925

Thr Pro Pro Glu Arg Pro Lys Arg Arg Pro Arg Pro Pro Gly Pro Asp
    930                 935                 940

Ser Pro Tyr Ala Asn Leu Gly Ala Phe Ser Ala Ser Leu Phe Ala Pro
945                 950                 955                 960

Ser Lys Pro Gln Arg Arg Lys Ser Pro Leu Val Lys Gln Leu Gln Val
                965                 970                 975

Glu Asp Ala Gln Glu Arg Ala Ala Leu Ala Val Gly Ser Pro Gly Pro
            980                 985                 990

Gly Gly Gly Ser Phe Ala Arg Glu  Pro Ser Pro Thr His  Arg Gly Pro
        995                 1000                1005

Arg Pro  Gly Gly Leu Asp Tyr  Gly Ala Gly Asp Gly  Pro Gly Leu
```

```
    1010                1015                1020

Ala Phe  Gly Gly Pro Gly Pro  Ala Lys Asp Arg Arg  Leu Glu Glu
    1025                1030                1035

Arg Arg  Arg Ser Thr Val Phe  Leu Ser Val Gly Ala  Ile Glu Gly
    1040                1045                1050

Ser Ala  Pro Gly Ala Asp Leu  Pro Ser Leu Gln Pro  Ser Arg Ser
    1055                1060                1065

Ile Asp  Glu Arg Leu Leu Gly  Thr Gly Pro Thr Ala  Gly Arg Asp
    1070                1075                1080

Leu Leu  Leu Pro Ser Pro Val  Ser Ala Leu Lys Pro  Leu Val Ser
    1085                1090                1095

Gly Pro  Ser Leu Gly Pro Ser  Gly Ser Thr Phe Ile  His Pro Leu
    1100                1105                1110

Thr Gly  Lys Pro Leu Asp Pro  Ser Ser Pro Leu Ala  Leu Ala Leu
    1115                1120                1125

Ala Ala  Arg Glu Arg Ala Leu  Ala Ser Gln Ala Pro  Ser Arg Ser
    1130                1135                1140

Pro Thr  Pro Val His Ser Pro  Asp Ala Asp Arg Pro  Gly Pro Leu
    1145                1150                1155

Phe Val  Asp Val Gln Ala Arg  Asp Pro Glu Arg Gly  Ser Leu Ala
    1160                1165                1170

Ser Pro  Ala Phe Ser Pro Arg  Ser Pro Ala Trp Ile  Pro Val Pro
    1175                1180                1185

Ala Arg  Arg Glu Ala Glu Lys  Val Pro Arg Glu Glu  Arg Lys Ser
    1190                1195                1200

Pro Glu  Asp Lys Lys Ser Met  Ile Leu Ser Val Leu  Asp Thr Ser
    1205                1210                1215

Leu Gln  Arg Pro Ala Gly Leu  Ile Val Val His Ala  Thr Ser Asn
    1220                1225                1230

Gly Gln  Glu Pro Ser Arg Leu  Gly Gly Ala Glu Glu  Glu Arg Pro
    1235                1240                1245

Gly Thr  Pro Glu Leu Ala Pro  Ala Pro Met Gln Ser  Ala Ala Val
    1250                1255                1260

Ala Glu  Pro Leu Pro Ser Pro  Arg Ala Gln Pro Pro  Gly Gly Thr
    1265                1270                1275

Pro Ala  Asp Ala Gly Pro Gly  Gln Gly Ser Ser Glu  Glu Glu Pro
    1280                1285                1290

Glu Leu  Val Phe Ala Val Asn  Leu Pro Pro Ala Gln  Leu Ser Ser
    1295                1300                1305

Ser Asp  Glu Glu Thr Arg Glu  Glu Leu Ala Arg Ile  Gly Leu Val
    1310                1315                1320

Pro Pro  Pro Glu Glu Phe Ala  Asn Gly Val Leu Leu  Ala Thr Pro
    1325                1330                1335

Leu Ala  Gly Pro Gly Pro Ser  Pro Thr Thr Val Pro  Ser Pro Ala
    1340                1345                1350

Ser Gly  Lys Pro Ser Ser Glu  Pro Pro Pro Ala Pro  Glu Ser Ala
    1355                1360                1365

Ala Asp  Ser Gly Val Glu Glu  Ala Asp Thr Arg Ser  Ser Ser Asp
    1370                1375                1380

Pro His  Leu Glu Thr Thr Ser  Thr Ile Ser Thr Val  Ser Ser Met
    1385                1390                1395

Ser Thr  Leu Ser Ser Glu Ser  Gly Glu Leu Thr Asp  Thr His Thr
    1400                1405                1410
```

```
Ser Phe Ala Asp Gly His Thr Phe Leu Leu Glu Lys Pro Pro Val
    1415                1420                1425

Pro Pro Lys Pro Lys Leu Lys Ser Pro Leu Gly Lys Gly Pro Val
    1430                1435                1440

Thr Phe Arg Asp Pro Leu Leu Lys Gln Ser Ser Asp Ser Glu Leu
    1445                1450                1455

Met Ala Gln Gln His His Ala Ala Ser Ala Gly Leu Ala Ser Ala
    1460                1465                1470

Ala Gly Pro Ala Arg Pro Arg Tyr Leu Phe Gln Arg Arg Ser Lys
    1475                1480                1485

Leu Trp Gly Asp Pro Val Glu Ser Arg Gly Leu Pro Gly Pro Glu
    1490                1495                1500

Asp Asp Lys Pro Thr Val Ile Ser Glu Leu Ser Ser Arg Leu Gln
    1505                1510                1515

Gln Leu Asn Lys Asp Thr Arg Ser Leu Gly Glu Glu Pro Val Gly
    1520                1525                1530

Gly Leu Gly Ser Leu Leu Asp Pro Ala Lys Lys Ser Pro Ile Ala
    1535                1540                1545

Ala Ala Arg Leu Phe Ser Ser Leu Gly Glu Leu Ser Ser Ile Ser
    1550                1555                1560

Ala Gln Arg Ser Pro Gly Gly Pro Gly Gly Gly Ala Ser Tyr Ser
    1565                1570                1575

Val Arg Pro Ser Gly Arg Tyr Pro Val Ala Arg Arg Ala Pro Ser
    1580                1585                1590

Pro Val Lys Pro Ala Ser Leu Glu Arg Val Glu Gly Leu Gly Ala
    1595                1600                1605

Gly Ala Gly Gly Ala Gly Arg Pro Phe Gly Leu Thr Pro Pro Thr
    1610                1615                1620

Ile Leu Lys Ser Ser Ser Leu Ser Ile Pro His Glu Pro Lys Glu
    1625                1630                1635

Val Arg Phe Val Val Arg Ser Val Ser Ala Arg Ser Arg Ser Pro
    1640                1645                1650

Ser Pro Ser Pro Leu Pro Ser Pro Ala Ser Gly Pro Gly Pro Gly
    1655                1660                1665

Ala Pro Gly Pro Arg Arg Pro Phe Gln Gln Lys Pro Leu Gln Leu
    1670                1675                1680

Trp Ser Lys Phe Asp Val Gly Asp Trp Leu Glu Ser Ile His Leu
    1685                1690                1695

Gly Glu His Arg Asp Arg Phe Glu Asp His Glu Ile Glu Gly Ala
    1700                1705                1710

His Leu Pro Ala Leu Thr Lys Asp Asp Phe Val Glu Leu Gly Val
    1715                1720                1725

Thr Arg Val Gly His Arg Met Asn Ile Glu Arg Ala Leu Arg Gln
    1730                1735                1740

Leu Asp Gly Ser
    1745
```

<210> SEQ ID NO 33
<211> LENGTH: 8626
<212> TYPE: DNA
<213> ORGANISM: Homo sapiens

<400> SEQUENCE: 33
acgacggggg aggtgctgta cgtccaagat ggcggcgccc tgtaggctgg agggactgtg     60

```
aggtaaacag ctgaggggga ggagacggtg gtgaccatga aagacaccag gttgacagca    120
ctggaaactg aagtaccagt tgtcgctaga acagtttggt agtggcccca atgaagaacc    180
ttcagaacct gtagcacacg tcctggagcc agcacagcgc cttcgagcga gagaatggcc    240
caacaagcaa atgtcgggga gcttcttgcc atgctggact cccccatgct gggtgtgcgg    300
gacgacgtga cagctgtctt taaagagaac ctcaattctg accgtggccc tatgcttgta    360
aacaccttgg tggattatta cctggaaacc agctctcagc cggcattgca catcctgacc    420
accttgcaag agccacatga caagcacctc ttggacagga ttaacgaata tgtgggcaaa    480
gccgccactc gtttatccat cctctcgtta ctgggtcatg tcataagact gcagccatct    540
tggaagcata agctctctca agcacctctt ttgccttctt tactaaaatg tctcaagatg    600
gacactgacg tcgttgtcct cacaacaggc gtcttggtgt tgataaccat gctaccaatg    660
attccacagt ctgggaaaca gcatcttctt gatttctttg acatttttgg ccgtctgtca    720
tcatggtgcc tgaagaaacc aggccacgtg gcggaagtct atctcgtcca tctccatgcc    780
agtgtgtacg cactctttca tcgcctttat ggaatgtacc cttgcaactt cgtctccttt    840
ttgcgttctc attacagtat gaaagaaaac ctggagactt ttgaagaagt ggtcaagcca    900
atgatggagc atgtgcgaat tcatccggaa ttagtgactg gatccaagga ccatgaactg    960
gaccctcgaa ggtggaagag attagaaact catgatgttg tgatcgagtg tgccaaaatc   1020
tctctggatc ccacagaagc ctcatatgaa gatggctatt ctgtgtctca ccaaatctca   1080
gcccgctttc ctcatcgttc agccgatgtc accaccagcc cttatgctga cacacagaat   1140
agctatgggt gtgctacttc taccccttac tccacgtctc ggctgatgtt gttaaatatg   1200
ccagggcagc tacctcagac tctgagttcc ccatcgacac ggctgataac tgaaccacca   1260
caagctactc tttggagccc atctatggtt tgtggtatga ccactcctcc aacttctcct   1320
ggaaatgtcc cacctgatct gtcacaccct tacagtaaag tctttggtac aactgcaggt   1380
ggaaaaggaa ctcctctggg aaccccagca acctctcctc ctccagcccc actctgtcat   1440
tcggatgact acgtgcacat ttcactcccc caggccacag tcacaccccc caggaaggaa   1500
gagagaatgg attctgcaag accatgtcta cacagacaac accatcttct gaatgacaga   1560
ggatcagaag agccacctgg cagcaaaggt tctgtcactc taagtgatct tccagggttt   1620
ttaggtgatc tggcctctga agaagatagt attgaaaaag ataaagaaga agctgcaata   1680
tctagagaac tttctgagat caccacagca gaggcagagc ctgtggttcc tcgaggaggc   1740
tttgactctc ccttttaccg agacagtctc ccaggttctc agcggaagac ccactcggca   1800
gcctccagtt ctcagggcgc cagcgtgaac cctgagcctt tacactcctc cctggacaag   1860
cttgggcctg acacaccaaa gcaagccttt actcccatag acctgccctg cggcagtgct   1920
gatgaaagcc ctgcgggaga cagggaatgc cagacttctt tggagaccag tatcttcact   1980
cccagtcctt gtaaaattcc acctccgacg agagtgggct ttggaagcgg gcagcctccc   2040
ccgtatgatc atctttttga ggtggcattg ccaaagacag cccatcattt tgtcatcagg   2100
aagactgagg agctgttaaa gaaagcaaaa ggaaacacag aggaagatgg tgtgccctct   2160
acctccccaa tggaagtgct ggacagactg atacagcagg gagcagacgc gcacagcaag   2220
gagctgaaca agttgccttt acccagcaag tctgtcgact ggacccactt tggaggctct   2280
cctccttcag atgagatccg caccctccga gaccagttgc ttttactgca caaccagtta   2340
ctctatgagc gttttaagag gcagcagcat gccctccgga acaggcggct cctccgcaag   2400
```

```
gtgatcaaag cagcagctct ggaggaacat aatgctgcca tgaaagatca gttgaagtta   2460
caagagaagg acatccagat gtggaaggtt agtctgcaga aagaacaagc tagatacaat   2520
cagctccagg agcagcgtga cactatggta accaagctcc acagccagat cagacagctg   2580
cagcatgacc gagaggaatt ctacaaccag agccaggaat tacagacgaa gctggaggac   2640
tgcaggaaca tgattgcgga gctgcggata gaactgaaga aggccaacaa caaggtgtgt   2700
cacactgagc tgctgctcag tcaggtttcc caaaagctct caaacagtga gtcggtccag   2760
cagcagatgg agttcttgaa caggcagctg ttggttcttg gggaggtcaa cgagctctat   2820
ttggaacaac tgcagaacaa gcactcagat accacaaagg aagtagaaat gatgaaagcc   2880
gcctatcgga aagagctaga aaaaaacaga agccatgttc tccagcagac tcagaggctt   2940
gatacctccc aaaaacggat tttggaactg gaatctcacc tggccaagaa agaccacctt   3000
cttttggaac agaagaaata tctagaggat gtcaaactcc aggcaagagg acagctgcag   3060
gccgcagaga gcaggtatga ggctcagaaa aggataaccc aggtgtttga attggagatc   3120
ttagatttat atggcaggtt ggagaaagat ggcctcctga aaaaacttga agaagaaaaa   3180
gcagaagcag ctgaagcagc agaagaaagg cttgactgtt gtaatgacgg gtgctcagat   3240
tccatggtag ggcacaatga agaggcatct ggccacaacg gtgagaccaa gacccccagg   3300
cccagcagcg cccggggcag tagtggaagc agaggtggtg gaggcagcag cagcagcagc   3360
agcgagcttt ctaccccaga gaaaccccca caccagaggg caggcccatt cagcagtcgg   3420
tgggagacga ctatgggaga agcgtctgcc agcatcccca ccactgtggg ctcacttccc   3480
agttcaaaaa gcttcctggg tatgaaggct cgagagttat ttcgtaataa gagcgagagc   3540
cagtgtgatg aggacggcat gaccagtagc ctttctgaga gcctaaagac agaactgggc   3600
aaagacttgg gtgtggaagc caagattccc ctgaacctag atggccctca cccgtctccc   3660
ccgaccccgg acagtgttgg acagctacat atcatggact acaatgagac tcatcatgaa   3720
cacagctaag gaatgatggt caatcagtgt taacttgcat attgttggca cagaacagga   3780
ggtgtgaatg cacgtttcaa agctttcctg tttccagggt ctgagtgcaa gttcatgtgt   3840
ggaaatggga cggaggtcct ttggacagct gactgaatgc agaacggttt ttggatctgg   3900
cattgaaatg cctcttgacc ttcccctcca cccgccctaa cccccctctca tttacctcgc   3960
agtgtgttct aatccaaggg ccagttggtg ttcctcagta gctttacttt cttcctttcc   4020
cccccaaatg gttgcgtcct ttgaacctgt gcaatatgag gccaaattta atctttgagt   4080
ctaacacacc actttctgct ttcccgaagt tcagataact gggttggctc tcaattagac   4140
caggtagttt gttgcattgc aggtaagtct ggttttgtcc cttccaggag gacatagcct   4200
gcaaagctgg ttgtctttac atgaaagcgt ttacatgaga ctttccgact gctttttga   4260
ttctgaagtt cagcatctaa agcagcaggt ctagaagaac aacggtttat tcatacttgc   4320
attcttttgg cagttctgat aagcttccta gaaagttctg tgtaaacaga agcctgtttc   4380
agaaatctgg agctggcact gtggagacca cacacccttt gggaaagctc ttgtctcttc   4440
ttcccccact acctcttatt tatttggtgt ttgcttgaat gctggtacta ttgtgaccac   4500
aggctggtgt gtaggtggta aaacctgttc tccataggag ggaaggagca gtcactggga   4560
gaggttaccc gagaagcact tgagcatgag gaactgcacc tttaggccat ctcagcttgc   4620
tgggcctttt gttaaaccct tctgtctact ggcctccctt tgtgtgcata cgcctcttgt   4680
tcatgtcagc ttatatgtga cactgcagca gaaaggctct gaaggtccaa agagtttctg   4740
caaagtgtat gtgaccatca tttcccaggc cattagggtt gcctcactgt agcaggttct   4800
```

```
aggctaccag aagaggggca gctttttcat accaattcca actttcaggg gctgactctc   4860
cagggagctg atgtcatcac actctccatg ttagtaatgg cagagcagtc taaacagagt   4920
ccgggagaat gctggcaaag gctggctgtg tatacccact aggctgcccc acgtgctccc   4980
gagagatgac actagtcaga aaattggcag tggcagagaa tccaaactca acaagtgctc   5040
ctgaaagaaa cgctagaagc ctaagaactg tggtctggtg ttccagctga ggcagggggga   5100
tttggtagga aggagccagt gaacttggct ttcctgtttc tatctttcat taaaaagaat   5160
agaaggattc agtcataaag aggtaaaaaa ctgtcacggt acgaaatctt agtgcccacg   5220
gaggcctcga gcagagagaa tgaaagtctt tttttttttt tttttttttt agcatggcaa   5280
taaatattct agcatcccta actaaagggg actagacagt tagagactct gtcaccctag   5340
ctataccagc agaaaacctg ttcaggcagg ctttctgggt gtgactgatt cccagcctgt   5400
ggcagggcgt ggtcccaact actcagccta gcacaggctg gcagttggta ctgaattgtc   5460
agatgtggag tattagtgac accacacatt taattcagct ttgtccaaag gaaagcttaa   5520
aacccaatac agtctagttt cctggttccg ttttagaaaa ggaaaacgtg aacaaactta   5580
gaaagggaag gaaatcccat cagtgaatcc tgaaactggt tttaagtgct ttccttctcc   5640
tcatgcccaa gagatctgtg ccatagaaca agataccagg cacttaaagc cttttcctga   5700
attggaaagg aaaagaggcc caagtgcaaa agaaaaaaca ttttagaaac ggacagctta   5760
taaaaataaa gggaagaaag gaggcagcat ggagagaggc ctgtgctaga agctccatgg   5820
acgtgtctgc acagggtcct cagctcatcc atgcggcctg ggtgtccttt tactcagctt   5880
tataacaaat gtggctccaa gctcaggtgc ctttgagttc taggaggctg tgggttttat   5940
tcaactacgg ttgggagaat gagacctgga gtcatgttga aggtgcccaa cctaaaaatg   6000
taggctttca tgttgcaaag aactccagag tcagtagtta ggtttggttt ggttttggac   6060
atgataaacc tgccaagagt caacaggtca cttgatcatg ctgcagtggg tagttctaag   6120
gatggaaagg tgacagtatt actctcgaga ggcaattcag tcctgggcaa aggtattagt   6180
acaataagcg ttaagggcag agtctacctt gaaaccaatt aagcagcttg gtattcataa   6240
atattgggat tggatggcct ccatccagaa atcactatgg gtgagcatac ctgtctcagc   6300
tgtttggcca atgtgcataa cctactcgga tccccacctg acactaacca gagtcagcac   6360
aggccccgag gagcccgaag tctgctgctg tgcagcatgg aattccttta aaaaggtgca   6420
ctacagtttt agcggggagg gggataggaa gacgcagagc aaatgagctc cggagtccct   6480
gcaggtgaat aaacacacag atctgcatct gatagaactt tgatggattt tcaaaaagcc   6540
gttgacaagg ctctgctata cagtctataa aaattgttat tatgggattg gaagaaacac   6600
gtggtcatga atagaaaaaa aacaaaccca aaggtaggaa ggtcaaggtc atttcttaga   6660
tggagaagtt gtgaaagatg tccttggaga tgagttttag gaccagcatt actaaggcag   6720
gtgggcagac agtgacctct ctaggtgtgt ccacagagtt tttcaggaga gaaaactgcc   6780
tgacctttgg gactaagctg cggaatcttc ttactaagct tgaagagtgg agaggcgaga   6840
ggtgagctac tttgtgagcc aaagcttatg tgacatggtt ggggaaacag tccaaactgt   6900
tctgagaagg tgaactgtta cgacccagga caattagaaa aattcaccca ccatgccgca   6960
cattactggg taaaagcagg gcagcaggga acaaaactcc agactcttgg gccgtcccca   7020
tttgcaacag cacacatagt ttctggtata tttgttggga aagataaaac tctagcagtt   7080
gttgagggga ggatgtataa aatggtcatg ggatgaaag gatctctgag accacagagg   7140
```

```
ctcagactca ctgttaagaa tagaaaactg ggtatgcgtt tcatgtagcc agcagaactg   7200

aagtgtgctg tgacaagcca atgtgaattt ctaccaaata gtagagcata ccacttgaag   7260

aaggaaagaa ccgaagagca aacaaaagtt ctgcgtaatg agactcacct tttctcgctg   7320

aaagcactaa gaggtgggag gaggcctgca caggctggag gagggtttgg gcagagcgaa   7380

gacccggcca ggaccttggt gagatggggt gccgcccacc tcctgcggat actcttggag   7440

agttgttccc ccagggggct ctgccccacc tggagaagga agctgcctgg tgtggagtga   7500

ctcaaatcag tatacctatc tgctgcacct tcactctcca gggtacatgc tttaaaaccg   7560

acccgcaaca agtattggaa aaatgtatcc agtctgaaga tgtttgtgta tctgtttaca   7620

tccagagttc tgtgacacat gcccccccaga ttgctgcaaa gatcccaagg cattgattgc   7680

acttgattaa gcttttgtct gtaggtgaaa gaacaagttt aggtcgagga ctggccccta   7740

ggctgctgct gtgacccttg tcccatgtgg cttgtttgcc tgtccgggac tcttcgatgt   7800

gcccagggga gcgtgttcct gtctcttcca tgccgtcctg cagtccttat ctgctcgcct   7860

gagggaagag tagctgtagc tacaagggaa gcctgcctgg aagagccgag cacctgtgcc   7920

catggcttct ggtcatgaaa cgagttaatg atggcagagg agcttcctcc ccacttcgca   7980

gcgccacatt atccatcctc tgagataagt aggctggttt aaccattgga atggaccttt   8040

cagtggaaac cctgagagtc tgagaacccc cagaccaacc cttccctccc tttccccacc   8100

tcttacagtg tttggacagg agggtatggt gctgctctgt gtagcaagta ctttggctta   8160

tgaaagaggc agccacgcat tttgcactag gaagaatcag taatcacttt tcagaagact   8220

tctatggacc acaaatatat tacggaggaa cagattttgc taagacataa tctagtttta   8280

taactcaatc atgaatgaac catgtgtggc aaacttgcag tttaaagggg tcccatcagt   8340

gaaagaaact gatttttttt aacggactgc ttttagttaa attgaagaaa gtcagctctt   8400

gtcaaaaggt ctaaactttc ccgcctcaat cctaaaagca tgtcaacaat ccacatcaga   8460

tgccataaat atgaactgca ggataaaatg gtacaatctt agtgaatggg aattggaatc   8520

aaaagagttt gctgtccttc ttagaatgtt ctaaaatgtc aaggcagttg cttgtgttta   8580

actgtgaaca aataaaaatt tattgttttg cactacaaaa aaaaaa                  8626
```

<210> SEQ ID NO 34
<211> LENGTH: 1164
<212> TYPE: PRT
<213> ORGANISM: Homo sapiens

<400> SEQUENCE: 34

```
Met Ala Gln Gln Ala Asn Val Gly Glu Leu Leu Ala Met Leu Asp Ser
1               5                   10                  15

Pro Met Leu Gly Val Arg Asp Asp Val Thr Ala Val Phe Lys Glu Asn
            20                  25                  30

Leu Asn Ser Asp Arg Gly Pro Met Leu Val Asn Thr Leu Val Asp Tyr
        35                  40                  45

Tyr Leu Glu Thr Ser Ser Gln Pro Ala Leu His Ile Leu Thr Thr Leu
    50                  55                  60

Gln Glu Pro His Asp Lys His Leu Leu Asp Arg Ile Asn Glu Tyr Val
65                  70                  75                  80

Gly Lys Ala Ala Thr Arg Leu Ser Ile Leu Ser Leu Leu Gly His Val
                85                  90                  95

Ile Arg Leu Gln Pro Ser Trp Lys His Lys Leu Ser Gln Ala Pro Leu
            100                 105                 110
```

```
Leu Pro Ser Leu Leu Lys Cys Leu Lys Met Asp Thr Asp Val Val Val
        115                 120                 125

Leu Thr Thr Gly Val Leu Val Leu Ile Thr Met Leu Pro Met Ile Pro
    130                 135                 140

Gln Ser Gly Lys Gln His Leu Leu Asp Phe Phe Asp Ile Phe Gly Arg
145                 150                 155                 160

Leu Ser Ser Trp Cys Leu Lys Lys Pro Gly His Val Ala Glu Val Tyr
                165                 170                 175

Leu Val His Leu His Ala Ser Val Tyr Ala Leu Phe His Arg Leu Tyr
            180                 185                 190

Gly Met Tyr Pro Cys Asn Phe Val Ser Phe Leu Arg Ser His Tyr Ser
        195                 200                 205

Met Lys Glu Asn Leu Glu Thr Phe Glu Glu Val Val Lys Pro Met Met
    210                 215                 220

Glu His Val Arg Ile His Pro Glu Leu Val Thr Gly Ser Lys Asp His
225                 230                 235                 240

Glu Leu Asp Pro Arg Arg Trp Lys Arg Leu Glu Thr His Asp Val Val
                245                 250                 255

Ile Glu Cys Ala Lys Ile Ser Leu Asp Pro Thr Glu Ala Ser Tyr Glu
            260                 265                 270

Asp Gly Tyr Ser Val Ser His Gln Ile Ser Ala Arg Phe Pro His Arg
        275                 280                 285

Ser Ala Asp Val Thr Thr Ser Pro Tyr Ala Asp Thr Gln Asn Ser Tyr
    290                 295                 300

Gly Cys Ala Thr Ser Thr Pro Tyr Ser Thr Ser Arg Leu Met Leu Leu
305                 310                 315                 320

Asn Met Pro Gly Gln Leu Pro Gln Thr Leu Ser Ser Pro Ser Thr Arg
                325                 330                 335

Leu Ile Thr Glu Pro Pro Gln Ala Thr Leu Trp Ser Pro Ser Met Val
            340                 345                 350

Cys Gly Met Thr Thr Pro Pro Thr Ser Pro Gly Asn Val Pro Pro Asp
        355                 360                 365

Leu Ser His Pro Tyr Ser Lys Val Phe Gly Thr Thr Ala Gly Gly Lys
    370                 375                 380

Gly Thr Pro Leu Gly Thr Pro Ala Thr Ser Pro Pro Pro Ala Pro Leu
385                 390                 395                 400

Cys His Ser Asp Asp Tyr Val His Ile Ser Leu Pro Gln Ala Thr Val
                405                 410                 415

Thr Pro Pro Arg Lys Glu Glu Arg Met Asp Ser Ala Arg Pro Cys Leu
            420                 425                 430

His Arg Gln His His Leu Leu Asn Asp Arg Gly Ser Glu Glu Pro Pro
        435                 440                 445

Gly Ser Lys Gly Ser Val Thr Leu Ser Asp Leu Pro Gly Phe Leu Gly
    450                 455                 460

Asp Leu Ala Ser Glu Glu Asp Ser Ile Glu Lys Asp Lys Glu Glu Ala
465                 470                 475                 480

Ala Ile Ser Arg Glu Leu Ser Glu Ile Thr Thr Ala Glu Ala Glu Pro
                485                 490                 495

Val Val Pro Arg Gly Gly Phe Asp Ser Pro Phe Tyr Arg Asp Ser Leu
            500                 505                 510

Pro Gly Ser Gln Arg Lys Thr His Ser Ala Ala Ser Ser Ser Gln Gly
        515                 520                 525

Ala Ser Val Asn Pro Glu Pro Leu His Ser Ser Leu Asp Lys Leu Gly
```

```
    530                 535                 540

Pro Asp Thr Pro Lys Gln Ala Phe Thr Pro Ile Asp Leu Pro Cys Gly
545                 550                 555                 560

Ser Ala Asp Glu Ser Pro Ala Gly Asp Arg Glu Cys Gln Thr Ser Leu
                565                 570                 575

Glu Thr Ser Ile Phe Thr Pro Ser Pro Cys Lys Ile Pro Pro Pro Thr
            580                 585                 590

Arg Val Gly Phe Gly Ser Gly Gln Pro Pro Pro Tyr Asp His Leu Phe
        595                 600                 605

Glu Val Ala Leu Pro Lys Thr Ala His His Phe Val Ile Arg Lys Thr
    610                 615                 620

Glu Glu Leu Leu Lys Lys Ala Lys Gly Asn Thr Glu Glu Asp Gly Val
625                 630                 635                 640

Pro Ser Thr Ser Pro Met Glu Val Leu Asp Arg Leu Ile Gln Gln Gly
                645                 650                 655

Ala Asp Ala His Ser Lys Glu Leu Asn Lys Leu Pro Leu Pro Ser Lys
            660                 665                 670

Ser Val Asp Trp Thr His Phe Gly Gly Ser Pro Pro Ser Asp Glu Ile
        675                 680                 685

Arg Thr Leu Arg Asp Gln Leu Leu Leu Leu His Asn Gln Leu Leu Tyr
    690                 695                 700

Glu Arg Phe Lys Arg Gln Gln His Ala Leu Arg Asn Arg Arg Leu Leu
705                 710                 715                 720

Arg Lys Val Ile Lys Ala Ala Ala Leu Glu Glu His Asn Ala Ala Met
                725                 730                 735

Lys Asp Gln Leu Lys Leu Gln Glu Lys Asp Ile Gln Met Trp Lys Val
            740                 745                 750

Ser Leu Gln Lys Glu Gln Ala Arg Tyr Asn Gln Leu Gln Glu Gln Arg
        755                 760                 765

Asp Thr Met Val Thr Lys Leu His Ser Gln Ile Arg Gln Leu Gln His
    770                 775                 780

Asp Arg Glu Glu Phe Tyr Asn Gln Ser Gln Glu Leu Gln Thr Lys Leu
785                 790                 795                 800

Glu Asp Cys Arg Asn Met Ile Ala Glu Leu Arg Ile Glu Leu Lys Lys
                805                 810                 815

Ala Asn Asn Lys Val Cys His Thr Glu Leu Leu Leu Ser Gln Val Ser
            820                 825                 830

Gln Lys Leu Ser Asn Ser Glu Ser Val Gln Gln Gln Met Glu Phe Leu
        835                 840                 845

Asn Arg Gln Leu Leu Val Leu Gly Glu Val Asn Glu Leu Tyr Leu Glu
    850                 855                 860

Gln Leu Gln Asn Lys His Ser Asp Thr Thr Lys Glu Val Glu Met Met
865                 870                 875                 880

Lys Ala Ala Tyr Arg Lys Glu Leu Glu Lys Asn Arg Ser His Val Leu
                885                 890                 895

Gln Gln Thr Gln Arg Leu Asp Thr Ser Gln Lys Arg Ile Leu Glu Leu
            900                 905                 910

Glu Ser His Leu Ala Lys Lys Asp His Leu Leu Leu Glu Gln Lys Lys
        915                 920                 925

Tyr Leu Glu Asp Val Lys Leu Gln Ala Arg Gly Gln Leu Gln Ala Ala
    930                 935                 940

Glu Ser Arg Tyr Glu Ala Gln Lys Arg Ile Thr Gln Val Phe Glu Leu
945                 950                 955                 960
```

```
Glu Ile Leu Asp Leu Tyr Gly Arg Leu Glu Lys Asp Gly Leu Leu Lys
                965                 970                 975

Lys Leu Glu Glu Glu Lys Ala Glu Ala Ala Glu Ala Ala Glu Glu Arg
            980                 985                 990

Leu Asp Cys Cys Asn Asp Gly Cys  Ser Asp Ser Met Val  Gly His Asn
        995                 1000                 1005

Glu Glu  Ala Ser Gly His Asn  Gly Glu Thr Lys Thr  Pro Arg Pro
    1010                 1015                 1020

Ser Ser  Ala Arg Gly Ser Ser  Gly Ser Arg Gly Gly  Gly Gly Ser
    1025                 1030                 1035

Ser Ser  Ser Ser Ser Glu Leu  Ser Thr Pro Glu Lys  Pro Pro His
    1040                 1045                 1050

Gln Arg  Ala Gly Pro Phe Ser  Ser Arg Trp Glu Thr  Thr Met Gly
    1055                 1060                 1065

Glu Ala  Ser Ala Ser Ile Pro  Thr Thr Val Gly Ser  Leu Pro Ser
    1070                 1075                 1080

Ser Lys  Ser Phe Leu Gly Met  Lys Ala Arg Glu Leu  Phe Arg Asn
    1085                 1090                 1095

Lys Ser  Glu Ser Gln Cys Asp  Glu Asp Gly Met Thr  Ser Ser Leu
    1100                 1105                 1110

Ser Glu  Ser Leu Lys Thr Glu  Leu Gly Lys Asp Leu  Gly Val Glu
    1115                 1120                 1125

Ala Lys  Ile Pro Leu Asn Leu  Asp Gly Pro His Pro  Ser Pro Pro
    1130                 1135                 1140

Thr Pro  Asp Ser Val Gly Gln  Leu His Ile Met Asp  Tyr Asn Glu
    1145                 1150                 1155

Thr His  His Glu His Ser
    1160
```

<210> SEQ ID NO 35
<211> LENGTH: 5675
<212> TYPE: DNA
<213> ORGANISM: Homo sapiens

<400> SEQUENCE: 35

```
ccggcggcgt cccggggcca ggggggtgcg cctttctccg cgtcggggcg gcccggagcg      60

cggtggcgcg gcgcgggagg ggttttctgg tgcgtcctgg tccaccatgg ccaaaccaac     120

aagcaaagat tcaggcttga aggagaagtt taagattctg ttgggactgg gaacaccgag     180

gccaaatccc aggtctgcag agggtaaaca gacggagttt atcatcaccg cggaaatact     240

gagagaactg agcatggaat gtggcctcaa caatcgcatc cggatgatag ggcagatttg     300

tgaagtcgca aaaaccaaga aatttgaaga gcacgcagtg gaagcactct ggaaggcggt     360

cgcggatctg ttgcagccgg agcggccgct ggaggcccgg cacgcggtgc tggctctgct     420

gaaggccatc gtgcaggggc agggcgagcg tttgggggtc ctcagagccc tcttctttaa     480

ggtcatcaag gattaccctt ccaacgaaga ccttcacgaa aggctggagg ttttcaaggc     540

cctcacagac aatgggagac acatcaccta cttggaggaa gagctggctg actttgtcct     600

gcagtggatg gatgttggct tgtcctcgga attccttctg gtgctggtga acttggtcaa     660

attcaatagc tgttacctcg acgagtacat cgcaaggatg gttcagatga tctgtctgct     720

gtgcgtccgg accgcgtcct ctgtggacat agaggtctcc ctgcaggtgc tggacgccgt     780

ggtctgctac aactgcctgc cggctgagag cctcccgctg ttcatcgtta ccctctgtcg     840
```

caccatcaac gtcaaggagc tctgcgagcc ttgctggaag ctgatgcgga acctccttgg 900
cacccacctg ggccacagcg ccatctacaa catgtgccac ctcatggagg acagagccta 960
catggaggac gcgcccctgc tgagaggagc cgtgtttttt gtgggcatgg ctctctgggg 1020
agcccaccgg ctctattctc tcaggaactc gccgacatct gtgttgccat cattttacca 1080
ggccatggca tgtccgaacg aggtggtgtc ctatgagatc gtcctgtcca tcaccaggct 1140
catcaagaag tataggaagg agctccaggt ggtggcgtgg gacattctgc tgaacatcat 1200
cgaacggctc cttcagcagc tccagacctt ggacagcccg gagctcagga ccatcgtcca 1260
tgacctgttg accacggtgg aggagctgtg tgaccagaac gagttccacg ggtctcagga 1320
gagatacttt gaactggtgg agagatgtgc ggaccagagg cctgagtcct ccctcctgaa 1380
cctgatctcc tatagagcgc agtccatcca cccggccaag gacggctgga ttcagaacct 1440
gcaggcgctg atggagagat tcttcaggag cgagtcccga ggcgccgtgc gcatcaaggt 1500
gctggacgtg ctgtcctttg tgctgctcat caacaggcag ttctatgagg aggagctgat 1560
taactcagtg gtcatctcgc agctctccca catccccgag gataaagacc accaggtccg 1620
aaagctggcc acccagttgc tggtggacct ggcagagggc tgccacacac accacttcaa 1680
cagcctgctg gacatcatcg agaaggtgat ggcccgctcc ctctccccac ccccggagct 1740
ggaagaaagg gatgtggccg catactcggc ctccttggag gatgtgaaga cagccgtcct 1800
ggggcttctg gtcatccttc agaccaagct gtacaccctg cctgcaagcc acgccacgcg 1860
tgtgtatgag atgctggtca gccacattca gctccactac aagcacagct acaccctgcc 1920
aatcgcgagc agcatccggc tgcaggcctt tgacttcctg ttgctgctgc gggccgactc 1980
actgcaccgc ctgggcctgc ccaacaagga tggagtcgtg cggttcagcc cctactgcgt 2040
ctgcgactac atggagccag agagaggctc tgagaagaag accagcggcc cccttctctcc 2100
tcccacaggg cctcctggcc cggcgcctgc aggcccgcc gtgcggctgg ggtccgtgcc 2160
ctactccctg ctcttccgcg tcctgctgca gtgcttgaag caggagtctg actggaaggt 2220
gctgaagctg gttctgggca ggctgcctga gtccctgcgc tataaagtgc tcatctttac 2280
ttccccttgc agtgtggacc agctgtgctc tgctctctgc tccatgcttt caggcccaaa 2340
gacactggag cggctccgag gcgccccaga aggcttctcc agaactgact tgcacctggc 2400
cgtggttcca gtgctgacag cattaatctc ttaccataac tacctggaca aaaccaaaca 2460
gcgcgagatg gtctactgcc tggagcaggg cctcatccac cgctgtgcca gccagtgcgt 2520
cgtggccttg tccatctgca gcgtggagat gcctgacatc atcatcaagg cgctgcctgt 2580
tctggtggtg aagctcacgc acatctcagc cacagccagc atggccgtcc cactgctgga 2640
gttcctgtcc actctggcca ggctgccgca cctctacagg aactttgccg cggagcagta 2700
tgccagtgtg ttcgccatct ccctgccgta caccaacccc tccaagttta atcagtacat 2760
cgtgtgtctg gcccatcacg tcatagccat gtggttcatc aggtgccgcc tgcccttccg 2820
gaaggatttt gtccctttca tcactaaggg cctgcggtcc aatgtcctct tgtcttttga 2880
tgacaccccc gagaaggaca gcttcagggc ccggagtact agtctcaacg agagacccaa 2940
gagtctgagg atagccagac cccccaaaca aggcttgaat aactctccac ccgtgaaaga 3000
attcaaggag agctctgcag ccgaggcctt ccggtgccgc agcatcagtg tgtctgaaca 3060
tgtggtccgc agcaggatac agacgtccct caccagtgcc agcttggggt ctgcagatga 3120
gaactccgtg gcccaggctg acgatagcct gaaaaacctc cacctggagc tcacggaaac 3180
ctgtctggac atgatggctc gatacgtctt ctccaacttc acggctgtcc cgaagaggtc 3240

```
tcctgtgggc gagttcctcc tagcgggtgg caggaccaaa acctggctgg ttgggaacaa   3300
gcttgtcact gtgacgacaa gcgtgggaac cgggacccgg tcgttactag gcctggactc   3360
gggggagctg cagtccggcc cggagtcgag ctccagcccc ggggtgcatg tgagacagac   3420
caaggaggcg ccggccaagc tggagtccca ggctgggcag caggtgtccc gtggggcccg   3480
ggatcgggtc cgttccatgt cggggggcca tggtcttcga gttggcgccc tggacgtgcc   3540
ggcctcccag ttcctgggca gtgccacttc tccaggacca cggactgcac cagccgcgaa   3600
acctgagaag gcctcagctg gcacccgggt tcctgtgcag gagaagacga acctggcggc   3660
ctatgtgccc ctgctgaccc agggctgggc ggagatcctg gtccggaggc ccacagggaa   3720
caccagctgg ctgatgagcc tggagaaccc gctcagccct ttctcctcgg acatcaacaa   3780
catgcccctg caggagctgt ctaacgccct catggcggct gagcgcttca aggagcaccg   3840
ggacacagcc ctgtacaagt cactgtcggt gccggcagcc agcacggcca aacccccctcc   3900
tctgcctcgc tccaacacag tggcctcttt ctcctccctg taccagtcca gctgccaagg   3960
acagctgcac aggagcgttt cctgggcaga ctccgccgtg gtcatggagg agggaagtcc   4020
gggcgaggtt cctgtgctgg tggagccccc agggttggag gacgttgagg cagcgctagg   4080
catggacagg cgcacggatg cctacagcag gtcgtcctca gtctccagcc aggaggagaa   4140
gtcgctccac gcggaggagc tggttggcag ggcatcccc atcgagcgag tcgtctcctc   4200
ggagggtggc cggccctctg tggacctctc cttccagccc tcgcagcccc tgagcaagtc   4260
cagctcctct cccgagctgc agactctgca ggacatcctc ggggaccctg gggacaaggc   4320
cgacgtgggc cggctgagcc ctgaggttaa ggcccggtca cagtcaggga ccctggacgg   4380
ggaaagtgct gcctggtcgg cctcgggcga agacagtcgg ggccagcccg agggtccctt   4440
gccttccagc tccccccgct cgcccagtgg cctccggccc cgaggttaca ccatctccga   4500
ctcggcccca tcacgcaggg gcaagagagt agagagggac gccttaaaga gcagagccac   4560
agcctccaat gcagagaaag tgccaggcat caaccccagt ttcgtgttcc tgcagctcta   4620
ccattccccc ttctttggcg acgagtcaaa caagccaatc ctgctgccca atgagtcaca   4680
gtcctttgag cggtcggtgc agctcctcga ccagatccca tcatacgaca cccacaagat   4740
cgccgtcctg tatgttggag aaggccagag caacagcgag ctcgccatcc tgtccaatga   4800
gcatggctcc tacaggtaca cggagttcct gacgggcctg ggccggctca tcgagctgaa   4860
ggactgccag ccggacaagg tgtacctggg aggcctggac gtgtgtggtg aggacggcca   4920
gttcacctac tgctggcacg atgacatcat gcaagccgtc ttccacatcg ccaccctgat   4980
gcccaccaag gacgtggaca agcaccgctg cgacaagaag cgccacctgg gcaacgactt   5040
tgtgtccatt gtctacaatg actccggtga ggacttcaag cttggcacca tcaagggcca   5100
gttcaacttt gtccacgtga tcgtcacccc gctggactac gagtgcaacc tggtgtccct   5160
gcagtgcagg aaagacatgg agggccttgt ggacaccagc gtggccaaga tcgtgtctga   5220
ccgcaacctg cccttcgtgg cccgccagat ggccctgcac gcaaatatgg cctcacaggt   5280
gcatcatagc cgctccaacc ccaccgatat ctacccctcc aagtggattg cccggctccg   5340
ccacatcaag cggctccgcc agcggatctg cgaggaagcc gcctactcca accccagcct   5400
acctctggtg caccctccgt cccatagcaa agcccctgca cagactccag ccgagcccac   5460
acctggctat gaggtgggcc agcggaagcg cctcatctcc tcggtggagg acttcaccga   5520
gtttgtgtga ggccggggcc ctccctcctg cactggcctt ggacggtatt gcctgtcagt   5580
```

-continued

```
gaaataaata aagtcctgac cccagtgcac agacatagag gcacagattg caaaaaaaaa   5640

aaaaaaaaaa aaaaaaaaaa aaaaaaaaaa aaaaa                              5675


<210> SEQ ID NO 36
<211> LENGTH: 1807
<212> TYPE: PRT
<213> ORGANISM: Homo sapiens

<400> SEQUENCE: 36

Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
            20                  25                  30

Gly Lys Gln Thr Glu Phe Ile Ile Thr Ala Glu Ile Leu Arg Glu Leu
        35                  40                  45

Ser Met Glu Cys Gly Leu Asn Asn Arg Ile Arg Met Ile Gly Gln Ile
    50                  55                  60

Cys Glu Val Ala Lys Thr Lys Lys Phe Glu Glu His Ala Val Glu Ala
65                  70                  75                  80

Leu Trp Lys Ala Val Ala Asp Leu Leu Gln Pro Glu Arg Pro Leu Glu
                85                  90                  95

Ala Arg His Ala Val Leu Ala Leu Leu Lys Ala Ile Val Gln Gly Gln
            100                 105                 110

Gly Glu Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Arg Met Val Gln Met Ile Cys Leu Leu Cys Val Arg
        195                 200                 205

Thr Ala Ser Ser Val Asp Ile Glu Val Ser Leu Gln Val Leu Asp Ala
    210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys His Leu Met Glu Asp Arg Ala Tyr Met Glu Asp
        275                 280                 285

Ala Pro Leu Leu Arg Gly Ala Val Phe Phe Val Gly Met Ala Leu Trp
    290                 295                 300

Gly Ala His Arg Leu Tyr Ser Leu Arg Asn Ser Pro Thr Ser Val Leu
305                 310                 315                 320

Pro Ser Phe Tyr Gln Ala Met Ala Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Val Val Ala Trp Asp Ile Leu Leu Asn Ile Ile Glu Arg Leu
```

```
        355                 360                 365

Leu Gln Gln Leu Gln Thr Leu Asp Ser Pro Glu Leu Arg Thr Ile Val
    370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
                405                 410                 415

Gln Arg Pro Glu Ser Ser Leu Leu Asn Leu Ile Ser Tyr Arg Ala Gln
            420                 425                 430

Ser Ile His Pro Ala Lys Asp Gly Trp Ile Gln Asn Leu Gln Ala Leu
        435                 440                 445

Met Glu Arg Phe Phe Arg Ser Glu Ser Arg Gly Ala Val Arg Ile Lys
    450                 455                 460

Val Leu Asp Val Leu Ser Phe Val Leu Leu Ile Asn Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
            500                 505                 510

Val Asp Leu Ala Glu Gly Cys His Thr His His Phe Asn Ser Leu Leu
        515                 520                 525

Asp Ile Ile Glu Lys Val Met Ala Arg Ser Leu Ser Pro Pro Pro Glu
    530                 535                 540

Leu Glu Glu Arg Asp Val Ala Ala Tyr Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Met Leu Val Ser
            580                 585                 590

His Ile Gln Leu His Tyr Lys His Ser Tyr Thr Leu Pro Ile Ala Ser
        595                 600                 605

Ser Ile Arg Leu Gln Ala Phe Asp Phe Leu Leu Leu Leu Arg Ala Asp
    610                 615                 620

Ser Leu His Arg Leu Gly Leu Pro Asn Lys Asp Gly Val Val Arg Phe
625                 630                 635                 640

Ser Pro Tyr Cys Val Cys Asp Tyr Met Glu Pro Glu Arg Gly Ser Glu
                645                 650                 655

Lys Lys Thr Ser Gly Pro Leu Ser Pro Pro Thr Gly Pro Pro Gly Pro
            660                 665                 670

Ala Pro Ala Gly Pro Ala Val Arg Leu Gly Ser Val Pro Tyr Ser Leu
        675                 680                 685

Leu Phe Arg Val Leu Leu Gln Cys Leu Lys Gln Glu Ser Asp Trp Lys
    690                 695                 700

Val Leu Lys Leu Val Leu Gly Arg Leu Pro Glu Ser Leu Arg Tyr Lys
705                 710                 715                 720

Val Leu Ile Phe Thr Ser Pro Cys Ser Val Asp Gln Leu Cys Ser Ala
                725                 730                 735

Leu Cys Ser Met Leu Ser Gly Pro Lys Thr Leu Glu Arg Leu Arg Gly
            740                 745                 750

Ala Pro Glu Gly Phe Ser Arg Thr Asp Leu His Leu Ala Val Val Pro
        755                 760                 765

Val Leu Thr Ala Leu Ile Ser Tyr His Asn Tyr Leu Asp Lys Thr Lys
    770                 775                 780
```

```
Gln Arg Glu Met Val Tyr Cys Leu Glu Gln Gly Leu Ile His Arg Cys
785                 790                 795                 800

Ala Ser Gln Cys Val Val Ala Leu Ser Ile Cys Ser Val Glu Met Pro
                805                 810                 815

Asp Ile Ile Ile Lys Ala Leu Pro Val Leu Val Val Lys Leu Thr His
            820                 825                 830

Ile Ser Ala Thr Ala Ser Met Ala Val Pro Leu Leu Glu Phe Leu Ser
        835                 840                 845

Thr Leu Ala Arg Leu Pro His Leu Tyr Arg Asn Phe Ala Ala Glu Gln
    850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Phe Ile
            900                 905                 910

Thr Lys Gly Leu Arg Ser Asn Val Leu Leu Ser Phe Asp Asp Thr Pro
        915                 920                 925

Glu Lys Asp Ser Phe Arg Ala Arg Ser Thr Ser Leu Asn Glu Arg Pro
    930                 935                 940

Lys Ser Leu Arg Ile Ala Arg Pro Pro Lys Gln Gly Leu Asn Asn Ser
945                 950                 955                 960

Pro Pro Val Lys Glu Phe Lys Glu Ser Ser Ala Ala Glu Ala Phe Arg
                965                 970                 975

Cys Arg Ser Ile Ser Val Ser Glu His Val Val Arg Ser Arg Ile Gln
            980                 985                 990

Thr Ser Leu Thr Ser Ala Ser Leu  Gly Ser Ala Asp Glu  Asn Ser Val
        995                 1000                1005

Ala Gln  Ala Asp Asp Ser Leu  Lys Asn Leu His Leu  Glu Leu Thr
    1010                 1015                 1020

Glu Thr  Cys Leu Asp Met Met  Ala Arg Tyr Val Phe  Ser Asn Phe
    1025                 1030                 1035

Thr Ala  Val Pro Lys Arg Ser  Pro Val Gly Glu Phe  Leu Leu Ala
    1040                 1045                 1050

Gly Gly  Arg Thr Lys Thr Trp  Leu Val Gly Asn Lys  Leu Val Thr
    1055                 1060                 1065

Val Thr  Thr Ser Val Gly Thr  Gly Thr Arg Ser Leu  Leu Gly Leu
    1070                 1075                 1080

Asp Ser  Gly Glu Leu Gln Ser  Gly Pro Glu Ser Ser  Ser Ser Pro
    1085                 1090                 1095

Gly Val  His Val Arg Gln Thr  Lys Glu Ala Pro Ala  Lys Leu Glu
    1100                 1105                 1110

Ser Gln  Ala Gly Gln Gln Val  Ser Arg Gly Ala Arg  Asp Arg Val
    1115                 1120                 1125

Arg Ser  Met Ser Gly Gly His  Gly Leu Arg Val Gly  Ala Leu Asp
    1130                 1135                 1140

Val Pro  Ala Ser Gln Phe Leu  Gly Ser Ala Thr Ser  Pro Gly Pro
    1145                 1150                 1155

Arg Thr  Ala Pro Ala Ala Lys  Pro Glu Lys Ala Ser  Ala Gly Thr
    1160                 1165                 1170

Arg Val  Pro Val Gln Glu Lys  Thr Asn Leu Ala Ala  Tyr Val Pro
    1175                 1180                 1185
```

```
Leu Leu  Thr Gln Gly Trp Ala  Glu Ile Leu Val Arg  Arg Pro Thr
    1190                 1195                 1200

Gly Asn  Thr Ser Trp Leu Met  Ser Leu Glu Asn Pro  Leu Ser Pro
    1205                 1210                 1215

Phe Ser  Ser Asp Ile Asn Asn  Met Pro Leu Gln Glu  Leu Ser Asn
    1220                 1225                 1230

Ala Leu  Met Ala Ala Glu Arg  Phe Lys Glu His Arg  Asp Thr Ala
    1235                 1240                 1245

Leu Tyr  Lys Ser Leu Ser Val  Pro Ala Ala Ser Thr  Ala Lys Pro
    1250                 1255                 1260

Pro Pro  Leu Pro Arg Ser Asn  Thr Val Ala Ser Phe  Ser Ser Leu
    1265                 1270                 1275

Tyr Gln  Ser Ser Cys Gln Gly  Gln Leu His Arg Ser  Val Ser Trp
    1280                 1285                 1290

Ala Asp  Ser Ala Val Val Met  Glu Glu Gly Ser Pro  Gly Glu Val
    1295                 1300                 1305

Pro Val  Leu Val Glu Pro Pro  Gly Leu Glu Asp Val  Glu Ala Ala
    1310                 1315                 1320

Leu Gly  Met Asp Arg Arg Thr  Asp Ala Tyr Ser Arg  Ser Ser Ser
    1325                 1330                 1335

Val Ser  Ser Gln Glu Glu Lys  Ser Leu His Ala Glu  Glu Leu Val
    1340                 1345                 1350

Gly Arg  Gly Ile Pro Ile Glu  Arg Val Val Ser Ser  Glu Gly Gly
    1355                 1360                 1365

Arg Pro  Ser Val Asp Leu Ser  Phe Gln Pro Ser Gln  Pro Leu Ser
    1370                 1375                 1380

Lys Ser  Ser Ser Ser Pro Glu  Leu Gln Thr Leu Gln  Asp Ile Leu
    1385                 1390                 1395

Gly Asp  Pro Gly Asp Lys Ala  Asp Val Gly Arg Leu  Ser Pro Glu
    1400                 1405                 1410

Val Lys  Ala Arg Ser Gln Ser  Gly Thr Leu Asp Gly  Glu Ser Ala
    1415                 1420                 1425

Ala Trp  Ser Ala Ser Gly Glu  Asp Ser Arg Gly Gln  Pro Glu Gly
    1430                 1435                 1440

Pro Leu  Pro Ser Ser Ser Pro  Arg Ser Pro Ser Gly  Leu Arg Pro
    1445                 1450                 1455

Arg Gly  Tyr Thr Ile Ser Asp  Ser Ala Pro Ser Arg  Arg Gly Lys
    1460                 1465                 1470

Arg Val  Glu Arg Asp Ala Leu  Lys Ser Arg Ala Thr  Ala Ser Asn
    1475                 1480                 1485

Ala Glu  Lys Val Pro Gly Ile  Asn Pro Ser Phe Val  Phe Leu Gln
    1490                 1495                 1500

Leu Tyr  His Ser Pro Phe Phe  Gly Asp Glu Ser Asn  Lys Pro Ile
    1505                 1510                 1515

Leu Leu  Pro Asn Glu Ser Gln  Ser Phe Glu Arg Ser  Val Gln Leu
    1520                 1525                 1530

Leu Asp  Gln Ile Pro Ser Tyr  Asp Thr His Lys Ile  Ala Val Leu
    1535                 1540                 1545

Tyr Val  Gly Glu Gly Gln Ser  Asn Ser Glu Leu Ala  Ile Leu Ser
    1550                 1555                 1560

Asn Glu  His Gly Ser Tyr Arg  Tyr Thr Glu Phe Leu  Thr Gly Leu
    1565                 1570                 1575

Gly Arg  Leu Ile Glu Leu Lys  Asp Cys Gln Pro Asp  Lys Val Tyr
```

```
    1580                1585                1590

Leu Gly  Gly Leu Asp Val Cys  Gly Glu Asp Gly Gln  Phe Thr Tyr
    1595                1600                1605

Cys Trp  His Asp Asp Ile Met  Gln Ala Val Phe His  Ile Ala Thr
    1610                1615                1620

Leu Met  Pro Thr Lys Asp Val  Asp Lys His Arg Cys  Asp Lys Lys
    1625                1630                1635

Arg His  Leu Gly Asn Asp Phe  Val Ser Ile Val Tyr  Asn Asp Ser
    1640                1645                1650

Gly Glu  Asp Phe Lys Leu Gly  Thr Ile Lys Gly Gln  Phe Asn Phe
    1655                1660                1665

Val His  Val Ile Val Thr Pro  Leu Asp Tyr Glu Cys  Asn Leu Val
    1670                1675                1680

Ser Leu  Gln Cys Arg Lys Asp  Met Glu Gly Leu Val  Asp Thr Ser
    1685                1690                1695

Val Ala  Lys Ile Val Ser Asp  Arg Asn Leu Pro Phe  Val Ala Arg
    1700                1705                1710

Gln Met  Ala Leu His Ala Asn  Met Ala Ser Gln Val  His His Ser
    1715                1720                1725

Arg Ser  Asn Pro Thr Asp Ile  Tyr Pro Ser Lys Trp  Ile Ala Arg
    1730                1735                1740

Leu Arg  His Ile Lys Arg Leu  Arg Gln Arg Ile Cys  Glu Glu Ala
    1745                1750                1755

Ala Tyr  Ser Asn Pro Ser Leu  Pro Leu Val His Pro  Pro Ser His
    1760                1765                1770

Ser Lys  Ala Pro Ala Gln Thr  Pro Ala Glu Pro Thr  Pro Gly Tyr
    1775                1780                1785

Glu Val  Gly Gln Arg Lys Arg  Leu Ile Ser Ser Val  Glu Asp Phe
    1790                1795                1800

Thr Glu  Phe Val
    1805
```

<210> SEQ ID NO 37
<211> LENGTH: 5164
<212> TYPE: DNA
<213> ORGANISM: Homo sapiens

<400> SEQUENCE: 37

```
ccaagatggt ggcgctgggc tcggggtgac tacaggagac gacggggcct tttcccttcg     60

ccaggacccg acacaccagg cttcgctcgc tcgcgcaccc ctccgccgcg tagccatccg    120

ccagcgcggg cgcccgccat ccgccgccta cttacgcttc acctctgccg acccggcgcg    180

ctcggctgcg ggcggcggcg cctccttcgg ctcctcctcg gaatagctcg cggcctgtag    240

cccctggcag gagggcccct cagccccccg gtgtggacag gcagcggcgg ctggcgacga    300

acgccgggat ttcggcggcc ccggcgctcc ctttcccggc ctcgttttcc ggataaggaa    360

gcgcgggtcc cgcatgagcc ccggcggtgg cggcagcgaa agagaacgag gcggtggcgg    420

gcggaggcgg cgggcgaggg cgactacgac cagtgaggcg gccgccgcag cccaggcgcg    480

ggggcgacga caggttaaaa atctgtaaga gcctgatttt agaattcacc agctcctcag    540

aagtttggcg aaatatgagt tattaagcct acgctcagat caaggtagca gctagactgg    600

tgtgacaacc tgtttttaat cagtgactca aagctgtgat caccctgatg tcaccgaatg    660

gccacagctt gtaaaagatc aggagaacct cagtctgacg acattgaagc tagccgaatg    720
```

aagcgagcag ctgcaaagca tctaatagaa cgctactacc accagttaac tgagggctgt 780
ggaaatgaag cctgcacgaa tgagttttgt gcttcctgtc caacttttct tcgtatggat 840
aataatgcag cagctattaa agccctcgag ctttataaga ttaatgcaaa actctgtgat 900
cctcatccct ccaagaaagg agcaagctca gcttaccttg agaactcgaa aggtgccccc 960
aacaactcct gctctgagat aaaaatgaac aagaaaggcg ctagaattga ttttaaagat 1020
gtgacttact taacagaaga gaaggtatat gaaattcttg aattatgtag agaaagagag 1080
gattattccc ctttaatccg tgttattgga agagtttttt ctagtgctga ggcattggta 1140
cagagcttcc ggaaagttaa acaacacacc aaggaagaac tgaaatctct tcaagcaaaa 1200
gatgaagaca aagatgaaga tgaaaaggaa aaagctgcat gttctgctgc tgctatggaa 1260
gaagactcag aagcatcttc ctcaaggata ggtgatagct cacagggaga caacaatttg 1320
caaaaattag gccctgatga tgtgtctgtg gatattgatg ccattagaag ggtctacacc 1380
agattgctct ctaatgaaaa aattgaaact gcctttctca atgcacttgt atatttgtca 1440
cctaacgtgg aatgtgactt gacgtatcac aatgtatact ctcgagatcc taattatctg 1500
aatttgttca ttatcgtaat ggagaataga aatctccaca gtcctgaata tctggaaatg 1560
gctttgccat tattttgcaa agcgatgagc aagctacccc ttgcagccca aggaaaactg 1620
atcagactgt ggtctaaata caatgcagac cagattcgga gaatgatgga gacatttcag 1680
caacttatta cttataaagt cataagcaat gaatttaaca gtcgaaatct agtgaatgat 1740
gatgatgcca ttgttgctgc ttcgaagtgc ttgaaaatgg tttactatgc aaatgtagtg 1800
ggaggggaag tggacacaaa tcacaatgaa gaagatgatg aagagcccat ccctgagtcc 1860
agcgagctga cacttcagga acttttggga gaagaaagaa gaaacaagaa aggtcctcga 1920
gtggaccccc tggaaactga acttggtgtt aaaaccctgg attgtcgaaa accacttatc 1980
ccttttgaag agtttattaa tgaaccactg aatgaggttc tagaaatgga taaagattat 2040 actttttttca aagtagaaac agagaacaaa ttctctttta tgacatgtcc ctttatattg 2100
aatgctgtca caaagaattt gggattatat tatgacaata gaattcgcat gtacagtgaa 2160
cgaagaatca ctgttctcta cagcttagtt caaggacagc agttgaatcc atatttgaga 2220
ctcaaagtta gacgtgacca tatcatagat gatgcacttg tccggctaga gatgatcgct 2280
atggaaaatc ctgcagactt gaagaagcag ttgtatgtgg aatttgaagg agaacaagga 2340
gttgatgagg gaggtgtttc caaagaattt tttcagctgg ttgtggagga aatcttcaat 2400
ccagatattg gtatgttcac atacgatgaa tctacaaaat tgttttggtt taatccatct 2460
tcttttgaaa ctgagggtca gtttactctg attggcatag tactgggtct ggctatttac 2520
aataactgta tactggatgt acattttccc atggttgtct acaggaagct aatggggaaa 2580
aaaggaactt ttcgtgactt gggagactct cacccagttc tatatcagag tttaaaagat 2640
ttattggagt atgaagggaa tgtggaagat gacatgatga tcactttcca gatatcacag 2700
acagatcttt ttggtaaccc aatgatgtat gatctaaagg aaaatggtga taaaattcca 2760
attacaaatg aaaacaggaa ggaatttgtc aatctttatt ctgactacat tctcaataaa 2820
tcagtagaaa aacagttcaa ggcttttcgg agaggttttc atatggtgac caatgaatct 2880
cccttaaagt acttattcag accagaagaa attgaattgc ttatatgtgg aagccggaat 2940
ctagatttcc aagcactaga agaaactaca gaatatgacg gtggctatac cagggactct 3000
gttctgatta gggagttctg ggaaatcgtt cattcattta cagatgaaca gaaaagactc 3060
ttcttgcagt ttacaacggg cacagacaga gcacctgtgg gaggactagg aaaattaaag 3120

-continued

```
atgattatag ccaaaaatgg cccagacaca gaaaggttac ctacatctca tacttgcttt   3180

aatgtgcttt tacttccgga atactcaagc aaagaaaaac ttaaagagag attgttgaag   3240

gccatcacgt atgccaaagg atttggcatg ctgtaaaaca aaacaaaaca aaataaaaca   3300

aaaaaaagga aggaaaaaaa aagaaaaaat ttaaaaaatt ttaaaaatat aacgagggat   3360

aaatttttgg tggtgatagt gtcccagtac aaaaaggctg taagatagtc aaccacagta   3420

gtcacctatg tctgtgcctc ccttctttat tggggacatg tgggctggaa cagcagattt   3480

cagctacata tatgaacaaa tcctttatta ttattataat tattttttg cgtgaaagtg   3540

ttacatattc tttcacttgt atgtacagag aggtttttct gaatatttat tttaagggtt   3600

aaatcacttt tgcttgtgtt tattactgct tgaggttgag ccttttgagt atttaaaaaa   3660

tatataccaa cagaactact ctcccaagga aaatattgcc accatttgta gaccacgtaa   3720

ccttcaagta tgtgctactt ttttgtccct gtatctaact caaatcagga actgtatttt   3780

ttttaatgat ttgcttttga aacttgaagt cttgaaaaca gtgtgatgca attactgctg   3840

ttctagcccc caaagagttt tctgtgcaaa atcttgagaa tcaatcaata aagaaagatg   3900

gaaggaaggg agaaattgga atgttttaac tgcagccctc agaactttag taacagcaca   3960

acaaattaaa aacaaaaaca actcatgcca cagtatgtcg tcttcatgtg tcttgcaatg   4020

aactgtttca gtagccaatc ctctttctta gtatatgaaa ggacagggat ttttgttctt   4080

gttgttctcg ttgttgtttt aagtttactg ggaaagtgc atttggccaa atgaaatggt   4140

agtcaagcct attgcaacaa agttaggaag tttgttgttt gtttattata aacaaaaagc   4200

atgtgaaagt gcacttaaga tagagttttt attaattact tacttattac ctagatttta   4260

aatagacaat ccaaagtctc cccttcgtgt tgccatcatc ttgttgaatc agccatttta   4320

tcgaggcacg tgatcagtgt tgcaacataa tgaaaaagat ggctactgtg ccttgtgtta   4380

cttaatcata cagtaagctg acctggaaat gaatgaaact attactccta agaattacat   4440

tgtatagccc cacagattaa atttaattaa ttaattcaaa acatgttaaa cgttactttc   4500

atgtactatg gaaaagtaca agtaggttta cattactgat ttccagaagt aagtagtttc   4560

ccctttccta gtcttctgtg tatgtgatgt tgttaatttc ttttattgca ttataaaata   4620

aaaggattat gtatttttaa ctaaggtgag acattgatat atccttttgc tacaagctat   4680

agctaatgtg ctgagcttgt gccttggtga ttgattgatt gattgactga ttgttttaac   4740

tgattactgt agatcaacct gatgatttgt ttgtttgaaa ttggcaggaa aaatgcagct   4800

ttcaaatcat tggggggaga aaaaggatgt ctttcaggat tattttaatt aattttttc   4860

ataattgaga cagaactgtt tgttatgtac cataatgcta aataaaactg tggcactttt   4920

caccataatt taatttagtg gaaaaagaag acaatgcttt ccatattgtg ataaggtaac   4980

atggggtttt tctgggccag cctttagaac actgttaggg tacatacgct accttgatga   5040

aagggacctt cgtgcaactg tagtcatctt aaaggcttct catccactgt gcttcttaat   5100

gtgtaattaa agtgaggaga aattaaatac tctgagggcg ttttatataa taaattcgtg   5160

aaga                                                                5164
```

<210> SEQ ID NO 38
<211> LENGTH: 872
<212> TYPE: PRT
<213> ORGANISM: Homo sapiens

<400> SEQUENCE: 38

-continued

```
Met Ala Thr Ala Cys Lys Arg Ser Gly Glu Pro Gln Ser Asp Asp Ile
1               5                   10                  15

Glu Ala Ser Arg Met Lys Arg Ala Ala Ala Lys His Leu Ile Glu Arg
            20                  25                  30

Tyr Tyr His Gln Leu Thr Glu Gly Cys Gly Asn Glu Ala Cys Thr Asn
        35                  40                  45

Glu Phe Cys Ala Ser Cys Pro Thr Phe Leu Arg Met Asp Asn Asn Ala
    50                  55                  60

Ala Ala Ile Lys Ala Leu Glu Leu Tyr Lys Ile Asn Ala Lys Leu Cys
65                  70                  75                  80

Asp Pro His Pro Ser Lys Lys Gly Ala Ser Ser Ala Tyr Leu Glu Asn
                85                  90                  95

Ser Lys Gly Ala Pro Asn Asn Ser Cys Ser Glu Ile Lys Met Asn Lys
            100                 105                 110

Lys Gly Ala Arg Ile Asp Phe Lys Asp Val Thr Tyr Leu Thr Glu Glu
        115                 120                 125

Lys Val Tyr Glu Ile Leu Glu Leu Cys Arg Glu Arg Glu Asp Tyr Ser
    130                 135                 140

Pro Leu Ile Arg Val Ile Gly Arg Val Phe Ser Ser Ala Glu Ala Leu
145                 150                 155                 160

Val Gln Ser Phe Arg Lys Val Lys Gln His Thr Lys Glu Glu Leu Lys
                165                 170                 175

Ser Leu Gln Ala Lys Asp Glu Asp Lys Asp Glu Asp Glu Lys Glu Lys
            180                 185                 190

Ala Ala Cys Ser Ala Ala Ala Met Glu Glu Asp Ser Glu Ala Ser Ser
        195                 200                 205

Ser Arg Ile Gly Asp Ser Ser Gln Gly Asp Asn Asn Leu Gln Lys Leu
    210                 215                 220

Gly Pro Asp Asp Val Ser Val Asp Ile Asp Ala Ile Arg Arg Val Tyr
225                 230                 235                 240

Thr Arg Leu Leu Ser Asn Glu Lys Ile Glu Thr Ala Phe Leu Asn Ala
                245                 250                 255

Leu Val Tyr Leu Ser Pro Asn Val Glu Cys Asp Leu Thr Tyr His Asn
            260                 265                 270

Val Tyr Ser Arg Asp Pro Asn Tyr Leu Asn Leu Phe Ile Ile Val Met
        275                 280                 285

Glu Asn Arg Asn Leu His Ser Pro Glu Tyr Leu Glu Met Ala Leu Pro
    290                 295                 300

Leu Phe Cys Lys Ala Met Ser Lys Leu Pro Leu Ala Ala Gln Gly Lys
305                 310                 315                 320

Leu Ile Arg Leu Trp Ser Lys Tyr Asn Ala Asp Gln Ile Arg Arg Met
                325                 330                 335

Met Glu Thr Phe Gln Gln Leu Ile Thr Tyr Lys Val Ile Ser Asn Glu
            340                 345                 350

Phe Asn Ser Arg Asn Leu Val Asn Asp Asp Asp Ala Ile Val Ala Ala
        355                 360                 365

Ser Lys Cys Leu Lys Met Val Tyr Tyr Ala Asn Val Val Gly Gly Glu
    370                 375                 380

Val Asp Thr Asn His Asn Glu Glu Asp Asp Glu Glu Pro Ile Pro Glu
385                 390                 395                 400

Ser Ser Glu Leu Thr Leu Gln Glu Leu Leu Gly Glu Glu Arg Arg Asn
                405                 410                 415

Lys Lys Gly Pro Arg Val Asp Pro Leu Glu Thr Glu Leu Gly Val Lys
```

```
            420                 425                 430

Thr Leu Asp Cys Arg Lys Pro Leu Ile Pro Phe Glu Glu Phe Ile Asn
        435                 440                 445

Glu Pro Leu Asn Glu Val Leu Glu Met Asp Lys Asp Tyr Thr Phe Phe
    450                 455                 460

Lys Val Glu Thr Glu Asn Lys Phe Ser Phe Met Thr Cys Pro Phe Ile
465                 470                 475                 480

Leu Asn Ala Val Thr Lys Asn Leu Gly Leu Tyr Tyr Asp Asn Arg Ile
                485                 490                 495

Arg Met Tyr Ser Glu Arg Arg Ile Thr Val Leu Tyr Ser Leu Val Gln
            500                 505                 510

Gly Gln Gln Leu Asn Pro Tyr Leu Arg Leu Lys Val Arg Arg Asp His
        515                 520                 525

Ile Ile Asp Asp Ala Leu Val Arg Leu Glu Met Ile Ala Met Glu Asn
    530                 535                 540

Pro Ala Asp Leu Lys Lys Gln Leu Tyr Val Glu Phe Glu Gly Glu Gln
545                 550                 555                 560

Gly Val Asp Glu Gly Gly Val Ser Lys Glu Phe Phe Gln Leu Val Val
                565                 570                 575

Glu Glu Ile Phe Asn Pro Asp Ile Gly Met Phe Thr Tyr Asp Glu Ser
            580                 585                 590

Thr Lys Leu Phe Trp Phe Asn Pro Ser Ser Phe Glu Thr Glu Gly Gln
        595                 600                 605

Phe Thr Leu Ile Gly Ile Val Leu Gly Leu Ala Ile Tyr Asn Asn Cys
    610                 615                 620

Ile Leu Asp Val His Phe Pro Met Val Val Tyr Arg Lys Leu Met Gly
625                 630                 635                 640

Lys Lys Gly Thr Phe Arg Asp Leu Gly Asp Ser His Pro Val Leu Tyr
                645                 650                 655

Gln Ser Leu Lys Asp Leu Leu Glu Tyr Glu Gly Asn Val Glu Asp Asp
            660                 665                 670

Met Met Ile Thr Phe Gln Ile Ser Gln Thr Asp Leu Phe Gly Asn Pro
        675                 680                 685

Met Met Tyr Asp Leu Lys Glu Asn Gly Asp Lys Ile Pro Ile Thr Asn
    690                 695                 700

Glu Asn Arg Lys Glu Phe Val Asn Leu Tyr Ser Asp Tyr Ile Leu Asn
705                 710                 715                 720

Lys Ser Val Glu Lys Gln Phe Lys Ala Phe Arg Arg Gly Phe His Met
                725                 730                 735

Val Thr Asn Glu Ser Pro Leu Lys Tyr Leu Phe Arg Pro Glu Glu Ile
            740                 745                 750

Glu Leu Leu Ile Cys Gly Ser Arg Asn Leu Asp Phe Gln Ala Leu Glu
        755                 760                 765

Glu Thr Thr Glu Tyr Asp Gly Gly Tyr Thr Arg Asp Ser Val Leu Ile
    770                 775                 780

Arg Glu Phe Trp Glu Ile Val His Ser Phe Thr Asp Glu Gln Lys Arg
785                 790                 795                 800

Leu Phe Leu Gln Phe Thr Thr Gly Thr Asp Arg Ala Pro Val Gly Gly
                805                 810                 815

Leu Gly Lys Leu Lys Met Ile Ile Ala Lys Asn Gly Pro Asp Thr Glu
            820                 825                 830

Arg Leu Pro Thr Ser His Thr Cys Phe Asn Val Leu Leu Leu Pro Glu
        835                 840                 845
```

```
Tyr Ser Ser Lys Glu Lys Leu Lys Glu Arg Leu Leu Lys Ala Ile Thr
    850                 855                 860

Tyr Ala Lys Gly Phe Gly Met Leu
865                 870


<210> SEQ ID NO 39
<211> LENGTH: 267
<212> TYPE: DNA
<213> ORGANISM: Homo sapiens

<400> SEQUENCE: 39

ccaggtttaa gaattgttta agctgcatca atggagcaca tacagggagc ttggaagacg      60

atcagcaatg gttttggatt caaagatgcc gtgtttgatg gctccagctg catctctcct     120

acaatagttc agcagtttgg ctatcagcgc cgggcatcag atgatggcaa actcacagat     180

ccttctaaga caagcaacac tatccgtgtt ttcttgccga acaagcaaag aacagtggta     240

tgtgaacatt ctacttagga aatttag                                         267


<210> SEQ ID NO 40
<211> LENGTH: 173
<212> TYPE: DNA
<213> ORGANISM: Homo sapiens

<400> SEQUENCE: 40

ttggtcctaa aggtggtcct ttgtttgtag gtcaatgtgc gaaatggaat gagcttgcat      60

gactgcctta tgaaagcact caaggtgagg ggcctgcaac cagagtgctg tgcagtgttc     120

agacttctcc acgaacacaa agggtaagag ctcaaaagtc aattgacttc ttc            173


<210> SEQ ID NO 41
<211> LENGTH: 163
<212> TYPE: DNA
<213> ORGANISM: Homo sapiens

<400> SEQUENCE: 41

catttcatgt ttttttaaa tcctttctag taaaaaagca cgcttagatt ggaatactga      60

tgctgcgtct ttgattggag aagaacttca agtagatttc ctggatcatg ttcccctcac     120

aacacacaac tttgtaagtt gcagatctct tctctttctg gca                       163


<210> SEQ ID NO 42
<211> LENGTH: 218
<212> TYPE: DNA
<213> ORGANISM: Homo sapiens

<400> SEQUENCE: 42

gcataattta cacctgtgtt cttgttgtag gctcggaaga cgttcctgaa gcttgccttc      60

tgtgacatct gtcagaaatt cctgctcaat ggatttcgat gtcagacttg tggctacaaa     120

tttcatgagc actgtagcac caaagtacct actatgtgtg tggactggag taacatcaga     180

caactcttgt aaggcattgt tcttttatcc aaggaaga                             218


<210> SEQ ID NO 43
<211> LENGTH: 159
<212> TYPE: DNA
<213> ORGANISM: Homo sapiens

<400> SEQUENCE: 43

aaaaaccagt ctttccctgc ttttgtttag attgtttcca aattccacta ttggtgatag      60
```

```
tggagtccca gcactacctt ctttgactat gcgtcgtatg cgagagtctg tttccaggat      120

gcctgttagg taatttttta cctatagctt ttcttttag                            159
```

<210> SEQ ID NO 44
<211> LENGTH: 214
<212> TYPE: DNA
<213> ORGANISM: Homo sapiens

<400> SEQUENCE: 44

```
ccaatcatgg aattttcttt ctcctcctag ttctcagcac agatattcta cacctcacgc      60

cttcaccttt aacacctcca gtccctcatc tgaaggttcc ctctcccaga ggcagaggtc     120

gacatccaca cctaatgtcc acatggtcag caccaccctg cctgtggaca gcaggatgat    180

tgaggtaata gggcaccttg ggggtggtaa tgtc                                  214
```

<210> SEQ ID NO 45
<211> LENGTH: 88
<212> TYPE: DNA
<213> ORGANISM: Homo sapiens

<400> SEQUENCE: 45

```
gagttgacca gctttccttt tctgtttcag gatgcaattc gaagtcacag cgaatcaggt      60

acttttccat agtcatttag ccaacaat                                         88
```

<210> SEQ ID NO 46
<211> LENGTH: 188
<212> TYPE: DNA
<213> ORGANISM: Homo sapiens

<400> SEQUENCE: 46

```
gtgtggcttc tgtttgtctt gtctattaag cctcaccttc agccctgtcc agtagcccca      60

acaatctgag cccaacaggc tggtcacagc cgaaaacccc cgtgccagca caaagagagc     120

gggcaccagt atctgggacc caggagaaaa acaaaattgt gagtatagac aacagtacct    180

cctgccaa                                                              188
```

<210> SEQ ID NO 47
<211> LENGTH: 178
<212> TYPE: DNA
<213> ORGANISM: Homo sapiens

<400> SEQUENCE: 47

```
gagtataata atgatctcta cttgtttcag aggcctcgtg gacagagaga ttcaagctat      60

tattgggaaa tagaagccag tgaagtgatg ctgtccactc ggattgggtc aggctctttt     120

ggaactgttt ataagggtaa atggcacggt aagcttgggg ccctccctttt actaactg     178
```

<210> SEQ ID NO 48
<211> LENGTH: 145
<212> TYPE: DNA
<213> ORGANISM: Homo sapiens

<400> SEQUENCE: 48

```
gattgcactg actgccaact aattttgcag gagatgttgc agtaaagatc ctaaaggttg      60

tcgacccaac cccagagcaa ttccaggcct tcaggaatga ggtggctgtt ctgcggtgag     120

tagaaagctg gcggtccagt ccctc                                           145
```

<210> SEQ ID NO 49
<211> LENGTH: 237

<212> TYPE: DNA
<213> ORGANISM: Homo sapiens

<400> SEQUENCE: 49
ccctctcctc tcttcccctc ccctccccag caaaacacgg catgtgaaca ttctgctttt 60
catggggtac atgacaaagg acaacctggc aattgtgacc cagtggtgcg agggcagcag 120
cctctacaaa cacctgcatg tccaggagac caagtttcag atgttccagc taattgacat 180
tgcccggcag acggctcagg gaatggagtg agtagatggt ctgatgcctc tctggga 237

<210> SEQ ID NO 50
<211> LENGTH: 107
<212> TYPE: DNA
<213> ORGANISM: Homo sapiens

<400> SEQUENCE: 50
tatttttaat aatttctttt cccttcacag ctatttgcat gcaaagaaca tcatccatag 60
agacatgaaa tccaacagta tcctttggtt gttgagttca tttgact 107

<210> SEQ ID NO 51
<211> LENGTH: 179
<212> TYPE: DNA
<213> ORGANISM: Homo sapiens

<400> SEQUENCE: 51
ttgaaaccag agtccttaac aagcattgag atatatttct ccatgaaggc ttaacagtga 60
aaattggaga ttttggtttg gcaacagtaa agtcacgctg gagtggttct cagcaggttg 120
aacaacctac tggctctgtc ctctggatgg tgagaatctg ggctcccacc agcagtctc 179

<210> SEQ ID NO 52
<211> LENGTH: 192
<212> TYPE: DNA
<213> ORGANISM: Homo sapiens

<400> SEQUENCE: 52
tgcacttttg tcatatggtg atacatgtag gccccagagg tgatccgaat gcaggataac 60
aacccattca gtttccagtc ggatgtctac tcctatggca tcgtattgta tgaactgatg 120
acgggggagc ttccttattc tcacatcaac aaccgagatc aggtaagtct gtgctggtgc 180
gaaaggaccc aa 192

<210> SEQ ID NO 53
<211> LENGTH: 195
<212> TYPE: DNA
<213> ORGANISM: Homo sapiens

<400> SEQUENCE: 53
ccattagctc agctgttttc tttcccttag atcatcttca tggtgggccg aggatatgcc 60
tccccagatc ttagtaagct atataagaac tgccccaaag caatgaagag gctggtagct 120
gactgtgtga agaaagtaaa ggaagagagg cctctttttc cccaggtaag gctcagggct 180
gctagaatgt gatta 195

<210> SEQ ID NO 54
<211> LENGTH: 204
<212> TYPE: DNA
<213> ORGANISM: Homo sapiens

<400> SEQUENCE: 54
taatgagagc attcttgggc tttgtttcag atcctgtctt ccattgagct gctccaacac 60
tctctaccga agatcaaccg gagcgcttcc gagccatcct tgcatcgggc agcccacact 120
gaggatatca atgcttgcac gctgaccacg tccccgaggc tgcctgtctt ctagttgact 180
ttgcacctgt cttcaggctg ccag 204

<210> SEQ ID NO 55
<211> LENGTH: 412
<212> TYPE: DNA
<213> ORGANISM: Homo sapiens

<400> SEQUENCE: 55
tatatgtaaa acttgcaaag aatcagaaca atgcctccac gaccatcatc aggtgaactg 60
tggggcatcc acttgatgcc cccaagaatc ctagtagaat gtttactacc aaatggaatg 120
atagtgactt tagaatgcct ccgtgaggct acattaataa ccataaagca tgaactattt 180
aaagaagcaa gaaaataccc cctccatcaa cttcttcaag atgaatcttc ttacattttc 240
gtaagtgtta ctcaagaagc agaaagggaa gaatttttg atgaaacaag acgactttgt 300
gaccttcggc tttttcaacc ctttttaaaa gtaattgaac cagtaggcaa ccgtgaagaa 360
aagatcctca atcgagaaat tggtatgata caatatccta ttctaaaatg ca 412

<210> SEQ ID NO 56
<211> LENGTH: 270
<212> TYPE: DNA
<213> ORGANISM: Homo sapiens

<400> SEQUENCE: 56
tgttatattc tttatgtaat tttattaaag gttttgctat cggcatgcca gtgtgtgaat 60
ttgatatggt taaagatcca gaagtacagg acttccgaag aaatattctg aacgtttgta 120
aagaagctgt ggatcttagg gacctcaatt cacctcatag tagagcaatg tatgtctatc 180
ctccaaatgt agaatcttca ccagaattgc caaagcacat atataataaa ttagataaag 240
gtaagaaaat gactaatcta ctctaatcat 270

<210> SEQ ID NO 57
<211> LENGTH: 311
<212> TYPE: DNA
<213> ORGANISM: Homo sapiens

<400> SEQUENCE: 57
gtgattgcat ctaatgtttt cctgttatag ggcaaataat agtggtgatc tgggtaatag 60
tttctccaaa taatgacaag cagaagtata ctctgaaaat caaccatgac tgtgtaccag 120
aacaagtaat tgctgaagca atcaggaaaa aaactcgaag tatgttgcta tcctctgaac 180
aactaaaact ctgtgtttta gaatatcagg gcaagtatat tttaaaagtg tgtggatgtg 240
atgaatactt cctagaaaaa tatcctctga gtcagtataa ggtgagtaac aagtttcaaa 300
atattaattt t 311

<210> SEQ ID NO 58
<211> LENGTH: 306
<212> TYPE: DNA
<213> ORGANISM: Homo sapiens

<400> SEQUENCE: 58
gaaatggctc gcccccttaa tctcttacag tatataagaa gctgtataat gcttgggagg 60
atgcccaatt tgatgttgat ggctaaagaa agcctttatt ctcaactgcc aatggactgt 120
tttacaatgc catcttattc cagacgcatt tccacagcta caccatatat gaatggagaa 180
acatctacaa aatccctttg ggttataaat agtgcactca gaataaaaat tctttgtgca 240
acctacgtga atgtaaatat tcgagacatt gataaggtaa agtcaaatgc tgatgcttat 300
tatttt 306

<210> SEQ ID NO 59
<211> LENGTH: 146
<212> TYPE: DNA
<213> ORGANISM: Homo sapiens

<400> SEQUENCE: 59
cattagtata tacctacttt tttcttttag atctatgttc gaacaggtat ctaccatgga 60
ggagaaccct tatgtgacaa tgtgaacact caaagagtac cttgttccaa tcccaggtaa 120
ggaagtatat agatttatat ttccaa 146

<210> SEQ ID NO 60
<211> LENGTH: 166
<212> TYPE: DNA
<213> ORGANISM: Homo sapiens

<400> SEQUENCE: 60
gtattatttt tgctttaaaa ttttacatag gtggaatgaa tggctgaatt atgatatata 60
cattcctgat cttcctcgtg ctgctcgact ttgcctttcc atttgctctg ttaaaggccg 120
aaagggtgct aaagaggtaa agtatttcag aaggaacaat tatgtt 166

<210> SEQ ID NO 61
<211> LENGTH: 213
<212> TYPE: DNA
<213> ORGANISM: Homo sapiens

<400> SEQUENCE: 61
actagtgaat atttttcttt gttttttaag gaacactgtc cattggcatg gggaaatata 60
aacttgtttg attacacaga cactctagta tctggaaaaa tggctttgaa tctttggcca 120
gtacctcatg gattagaaga tttgctgaac cctattggtg ttactggatc aaatccaaat 180
aaagtaaggt ttttattgtc ataaattaga tat 213

<210> SEQ ID NO 62
<211> LENGTH: 195
<212> TYPE: DNA
<213> ORGANISM: Homo sapiens

<400> SEQUENCE: 62
atatataata gcttttcttc catctcttag gaaactccat gcttagagtt ggagtttgac 60
tggttcagca gtgtggtaaa gttcccagat atgtcagtga ttgaagagca tgccaattgg 120
tctgtatccc gagaagcagg atttagctat tcccacgcag gactggtaag gcaaatcact 180
gagtttatta agtat 195

<210> SEQ ID NO 63
<211> LENGTH: 185
<212> TYPE: DNA
<213> ORGANISM: Homo sapiens

<400> SEQUENCE: 63
agctatataa gatattattt tattttacag agtaacagac tagctagaga caatgaatta 60
agggaaaatg acaaagaaca gctcaaagca atttctacac gagatcctct ctctgaaatc 120
actgagcagg agaaagattt tctatggagt cacaggtaag tgctaaaatg gagattctct 180
gtttc 185

<210> SEQ ID NO 64
<211> LENGTH: 142
<212> TYPE: DNA
<213> ORGANISM: Homo sapiens

<400> SEQUENCE: 64
gtttatgttt attttgtttc tcccacacag acactattgt gtaactatcc ccgaaattct 60
acccaaattg cttctgtctg ttaaatggaa ttctagagat gaagtagccc aggtaaatgt 120
atgtttgaga ttactagata ac 142

<210> SEQ ID NO 65
<211> LENGTH: 225
<212> TYPE: DNA
<213> ORGANISM: Homo sapiens

<400> SEQUENCE: 65
aatatgattt attgtctttc tcatacacag atgtattgct tggtaaaaga ttggcctcca 60
atcaaacctg aacaggctat ggaacttctg gactgtaatt acccagatcc tatggttcga 120
ggttttgctg ttcggtgctt ggaaaaatat ttaacagatg acaaactttc tcagtattta 180
attcagctag tacaggtaaa ataatgtaaa atagtaaata atgtt 225

<210> SEQ ID NO 66
<211> LENGTH: 164
<212> TYPE: DNA
<213> ORGANISM: Homo sapiens

<400> SEQUENCE: 66
accctgattt gtttttttgg aatcacctag gtcctaaaat atgaacaata tttggataac 60
ttgcttgtga gatttttact gaagaaagca ttgactaatc aaaggattgg gcactttttc 120
ttttggcatt taaagtaagt ctaattattt tcccattaaa ttct 164

<210> SEQ ID NO 67
<211> LENGTH: 232
<212> TYPE: DNA
<213> ORGANISM: Homo sapiens

<400> SEQUENCE: 67
tatattttta attttgcacg attcttttag atctgagatg cacaataaaa cagttagcca 60
gaggtttggc ctgcttttgg agtcctattg tcgtgcatgt gggatgtatt tgaagcacct 120
gaataggcaa gtcgaggcaa tggaaaagct cattaactta actgacattc tcaaacagga 180
gaagaaggat gaaacacaaa aggtgtgtga ctctagtttg tgtttgagac tc 232

<210> SEQ ID NO 68
<211> LENGTH: 167
<212> TYPE: DNA
<213> ORGANISM: Homo sapiens

<400> SEQUENCE: 68
ttactgtgac tatccttttt ttttaatcag gtacagatga agtttttagt tgagcaaatg 60
aggcgaccag atttcatgga tgctctacag ggctttctgt ctcctctaaa ccctgctcat 120
caactaggaa acctcaggta ctttcttggg ggtttcattg atatatt 167

<210> SEQ ID NO 69
<211> LENGTH: 182
<212> TYPE: DNA
<213> ORGANISM: Homo sapiens

<400> SEQUENCE: 69
tacctagtaa agtttttaac tattttaaag gcttgaagag tgtcgaatta tgtcctctgc 60
aaaaaggcca ctgtggttga attgggagaa cccagacatc atgtcagagt tactgtttca 120
gaacaatgag atcatcttta aaaatgggga tggtaaggaa gagtattaat gagcttatga 180
tg 182

<210> SEQ ID NO 70
<211> LENGTH: 139
<212> TYPE: DNA
<213> ORGANISM: Homo sapiens

<400> SEQUENCE: 70
aaatggtgat acatattatt tgaatttcag atttacggca agatatgcta acacttcaaa 60
ttattcgtat tatggaaaat atctggcaaa atcaaggtct tgatcttcgg taggtaacca 120
gtaaggcaac ctgtatgtt 139

<210> SEQ ID NO 71
<211> LENGTH: 231
<212> TYPE: DNA
<213> ORGANISM: Homo sapiens

<400> SEQUENCE: 71
ttaattgtaa acgtgttact cctctttcag aatgttacct tatggttgtc tgtcaatcgg 60
tgactgtgtg ggacttattg aggtggtgcg aaattctcac actattatgc aaattcagtg 120
caaaggcggc ttgaaaggtg cactgcagtt caacagccac acactacatc agtggctcaa 180
agacaagaac aaaggagaaa tgtgagttgt attattcttt cttcctatgt t 231

<210> SEQ ID NO 72
<211> LENGTH: 178
<212> TYPE: DNA
<213> ORGANISM: Homo sapiens

<400> SEQUENCE: 72
tactactcat gaggtgttta ttctttgtag atatgatgca gccattgacc tgtttacacg 60
ttcatgtgct ggatactgtg tagctacctt cattttggga attggagatc gtcacaatag 120
taacatcatg gtgaaagacg atggacaagt aatggttttc tctgtttaaa atgttttg 178

<210> SEQ ID NO 73
<211> LENGTH: 212
<212> TYPE: DNA
<213> ORGANISM: Homo sapiens

<400> SEQUENCE: 73
aactataaca taatttctta tttttgaaag ctgtttcata tagattttgg acactttttg 60
gatcacaaga agaaaaaatt tggttataaa cgagaacgtg tgccatttgt tttgacacag 120
gatttcttaa tagtgattag taaaggagcc caagaatgca caaagacaag agaatttgag 180
aggtgagctc gagcaattaa aaacacaaaa ta 212

<210> SEQ ID NO 74

<211> LENGTH: 331
<212> TYPE: DNA
<213> ORGANISM: Homo sapiens

<400> SEQUENCE: 74
aactgaccaa actgttctta ttacttatag gtttcaggag atgtgttaca aggcttatct 60
agctattcga cagcatgcca atctcttcat aaatcttttc tcaatgatgc ttggctctgg 120
aatgccagaa ctacaatctt ttgatgacat tgcatacatt cgaaagaccc tagccttaga 180
taaaactgag caagaggctt tggagtattt catgaaacaa atgaatgatg cacatcatgg 240
tggctggaca acaaaaatgg attggatctt ccacacaatt aaacagcatg cattgaactg 300
aaaagataac tgagaaaatg aaagctcact c 331

<210> SEQ ID NO 75
<211> LENGTH: 78
<212> TYPE: DNA
<213> ORGANISM: Homo sapiens

<400> SEQUENCE: 75
ggagcggttg tgcgatcaga tcgatctaag atggcgactg tcgaaccggt gagtattgcc 60
tttggccccc acccccac 78

<210> SEQ ID NO 76
<211> LENGTH: 167
<212> TYPE: DNA
<213> ORGANISM: Homo sapiens

<400> SEQUENCE: 76
aaaataatgt tttatattat tttccactag gaaaccaccc ctactcctaa tcccccgact 60
acagaagagg agaaaacgga atctaatcag gaggttgcta acccagaaca ctatattaaa 120
catcccctac agaacaggta agctttctaa cacctaggtt ttctgag 167

<210> SEQ ID NO 77
<211> LENGTH: 156
<212> TYPE: DNA
<213> ORGANISM: Homo sapiens

<400> SEQUENCE: 77 catttttga cactgatttt ttatttttag atgggcactc tggtttttta aaaatgataa 60
aagcaaaact tggcaagcaa acctgcggct gatctccaag tttgatactg ttgaagactt 120
ttgggcgtaa gtaaccattt gttttagtat gtttgt 156

<210> SEQ ID NO 78
<211> LENGTH: 124
<212> TYPE: DNA
<213> ORGANISM: Homo sapiens

<400> SEQUENCE: 78
tgtttttaat tgttattttc ttttacctag tctgtacaac catatccagt tgtctagtaa 60
tttaatgcct ggctgtgact actcactttt taaggtatgc ttaattggtg attttatata 120
ttta 124

<210> SEQ ID NO 79
<211> LENGTH: 174
<212> TYPE: DNA
<213> ORGANISM: Homo sapiens

<400> SEQUENCE: 79
gtgtaatact gttgtcttct aaccctgtag gatggtattg agcctatgtg ggaagatgag 60
aaaaacaaac ggggaggacg atggctaatt acattgaaca aacagcagag acgaagtgac 120
ctcgatcgct tttggctaga gacagtaagg ttttaaaagt ataaagcagt ttta 174

<210> SEQ ID NO 80
<211> LENGTH: 200
<212> TYPE: DNA
<213> ORGANISM: Homo sapiens

<400> SEQUENCE: 80
attaaatgta atttgggatt ttttttaag cttctgtgcc ttattggaga atcttttgat 60
gactacagtg atgatgtatg tggcgctgtt gttaatgtta gagctaaagg tgataagata 120
gcaatatgga ctactgaatg tgaaaacaga gaagctgtta cacatatagg gtaagttttg 180
ctctttgcct acttatttta 200

<210> SEQ ID NO 81
<211> LENGTH: 175
<212> TYPE: DNA
<213> ORGANISM: Homo sapiens

<400> SEQUENCE: 81
tttttcttct tcttttttt tttcttctag gagggtatac aaggaaaggt taggacttcc 60
tccaaagata gtgattggtt atcagtccca cgcagacaca gctactaaga gcggctccac 120
cactaaaaat aggtttgttg tttaagaaga caccttctga gtattctcat aggag 175

<210> SEQ ID NO 82
<211> LENGTH: 65
<212> TYPE: DNA
<213> ORGANISM: Homo sapiens

<400> SEQUENCE: 82
aaacttcaga gcaagttttc attgggcaaa atggggtaag gatttttgtg cttaacacag 60
cttcg 65

<210> SEQ ID NO 83
<211> LENGTH: 217
<212> TYPE: DNA
<213> ORGANISM: Homo sapiens

<400> SEQUENCE: 83
cagtccatca ttttctttc tgccctgcag ggaacaacct atcttcagca ctcgagctca 60
tgtcttccaa attgacccaa acacaaagaa gaactgggta cccaccagca agcatgcagt 120
tactgtgtct tatttctatg acagcacaag aaatgtgtat aggataatca gtttagatgg 180
ctcaaaggta agctacgttt actttgaatg atttggc 217

<210> SEQ ID NO 84
<211> LENGTH: 192
<212> TYPE: DNA
<213> ORGANISM: Homo sapiens

<400> SEQUENCE: 84
ctggttgctc atacttgctt tattttttag gcaataataa atagtaccat caccccaaac 60
atgacattta ctaaaacatc tcagaagttt ggccagtggg ctgatagccg ggcaaacacc 120
gtttatggat tgggattctc ctctgagcat catctttcga aagtgagtta aatcataaaa 180
tttgaatgaa aa 192

<210> SEQ ID NO 85
<211> LENGTH: 153
<212> TYPE: DNA
<213> ORGANISM: Homo sapiens

<400> SEQUENCE: 85
ggttaatgta tgtagtctct atacattcag tttgcagaaa agtttcagga atttaaagaa 60
gctgctcgac tagcaaagga aaaatcacaa gagaagatgg aacttaccag tacaccttca 120
caggtgggta tatcatttct attcttaatt atg 153

<210> SEQ ID NO 86
<211> LENGTH: 200
<212> TYPE: DNA
<213> ORGANISM: Homo sapiens

<400> SEQUENCE: 86 atttttatc ccccacccct ttttttaaag gaatccgcag gcggggatct tcagtctcct 60
ttaacaccgg aaagtatcaa cgggacagat gatgaaagaa cacctgatgt gacacagaac 120
tcagagccaa gggctgaacc aactcagaat gcattgccat tttcacatag gtacagattc 180
aattcagcaa ttatgattaa 200

<210> SEQ ID NO 87
<211> LENGTH: 217
<212> TYPE: DNA
<213> ORGANISM: Homo sapiens

<400> SEQUENCE: 87
ggatagaatt ttctttttgt tttattttag ttcagcaatc agcaaacatt gggaggctga 60
actggctacc ctcaaaggaa ataatgccaa actcactgca gccctgctgg agtccactgc 120
caatgtgaaa caatggaaac agcaacttgc tgcctatcaa gaggaagcag aacgtctgca 180
caagcgggta atttcagggc tgatgtctat agggatt 217

<210> SEQ ID NO 88
<211> LENGTH: 171
<212> TYPE: DNA
<213> ORGANISM: Homo sapiens

<400> SEQUENCE: 88
aagttaatct gtgttctcat ttaattttag gtgactgaac ttgaatgtgt tagtagccaa 60
gcaaatgcag tacatactca taagacagaa ttaaatcaga caatacaaga actggaagag 120
acactgaaac tgaaggaaga ggtatttgct gctttttact catctgtaat c 171

<210> SEQ ID NO 89
<211> LENGTH: 141
<212> TYPE: DNA
<213> ORGANISM: Homo sapiens

<400> SEQUENCE: 89
aatgttaaga cattgctctg tcttttctag gaaatagaaa ggttaaaaca agaaattgat 60
aatgccagag aactacaaga acagagggat tctttgactc agaaactaca ggtgagctgt 120
agtaaaaatt gttattcact t 141

<210> SEQ ID NO 90
<211> LENGTH: 249

<212> TYPE: DNA
<213> ORGANISM: Homo sapiens

<400> SEQUENCE: 90
tatatacatg ttacactttt gtttctgaag gaagtagaaa ttcggaacaa agacctggag 60
ggacaactgt ctgacttaga gcaacgtctg gagaaaagtc agaatgaaca agaagctttt 120
cgcaataacc tgaagacact cttagaaatt ctggatggaa agatatttga actaacagaa 180
ttacgagata acttggccaa gctactagaa tgcagctaag gaaagtgaaa tttcagtgcc 240
aattaatta 249

<210> SEQ ID NO 91
<211> LENGTH: 394
<212> TYPE: DNA
<213> ORGANISM: Homo sapiens

<400> SEQUENCE: 91
caactgttgc atggtagcag atttgcaaac atgagtgctg aggggtacca gtacagagcg 60
ctgtatgatt ataaaaagga aagagaagaa gatattgact tgcacttggg tgacatattg 120
actgtgaata aagggtcctt agtagctctt ggattcagtg atggacagga agccaggcct 180
gaagaaattg gctggttaaa tggctataat gaaaccacag ggaaaggggg ggactttccg 240
ggaacttacg tagaatatat tggaaggaaa aaaatctcgc ctcccacacc aaagccccgg 300
ccacctcggc ctcttcctgt tgcaccaggt tcttcgaaaa ctgaagcaga tgttgaacaa 360
caaggtcagt attgataagt ggttgcttaa tgac 394

<210> SEQ ID NO 92
<211> LENGTH: 153
<212> TYPE: DNA
<213> ORGANISM: Homo sapiens

<400> SEQUENCE: 92
aatacaatgg tgggattttg ttgtttgcag ctttgactct cccggatctt gcagagcagt 60
ttgcccctcc tgacattgcc ccgcctcttc ttatcaagct cgtggaagcc attgaaaaga 120
aaggtaacca gactgctaga gggcatcagt tcc 153

<210> SEQ ID NO 93
<211> LENGTH: 135
<212> TYPE: DNA
<213> ORGANISM: Homo sapiens

<400> SEQUENCE: 93
acatggtctg tggtctgttt tgtgtcctag gtctggaatg ttcaactcta tacagaacac 60
agagctccag caacctggca gaattacgac agcttcttga ttgtggtgag tgtcacagag 120
ctagaaatgc aaatg 135

<210> SEQ ID NO 94
<211> LENGTH: 192
<212> TYPE: DNA
<213> ORGANISM: Homo sapiens

<400> SEQUENCE: 94
gtctgaaata tttcttaaat tgtttcctag atacaccctc cgtggacttg gaaatgatcg 60
atgtgcacgt tttggctgac gctttcaaac gctatctcct ggacttacca aatcctgtca 120
ttccagcagc cgtttacagt gaaatgattt ctttagctcc aggtttgttt tttctcttct 180
gggaacctca tt 192

<210> SEQ ID NO 95
<211> LENGTH: 262
<212> TYPE: DNA
<213> ORGANISM: Homo sapiens

<400> SEQUENCE: 95
ttctcttttt tttttttttt aaacttgtag aagtacaaag ctccgaagaa tatattcagc 60
tattgaagaa gcttattagg tcgcctagca tacctcatca gtattggctt acgcttcagt 120
atttgttaaa acatttcttc aagctctctc aaacctccag caaaaatctg ttgaatgcaa 180
gagtactctc tgaaattttc agccctatgc ttttcagatt ctcagcagcc aggtaagtga 240
aaggagacaa acatgtattt tg 262

<210> SEQ ID NO 96
<211> LENGTH: 140
<212> TYPE: DNA
<213> ORGANISM: Homo sapiens

<400> SEQUENCE: 96
aaggtttcta ataaactctc tttcttacag ctctgataat actgaaaacc tcataaaagt 60
tatagaaatt ttaatctcaa ctgaatggaa tgaacgacag cctgcaccag gtaatgcttt 120
ttgagcattt aacattctct 140

<210> SEQ ID NO 97
<211> LENGTH: 163
<212> TYPE: DNA
<213> ORGANISM: Homo sapiens

<400> SEQUENCE: 97
tgcgaacaac tttttctttt tcatctgcag cactgcctcc taaaccacca aaacctacta 60
ctgtagccaa caacggtatg aataacaata tgtccttaca agatgctgaa tggtactggg 120
gagatatctc gaggtaaggc tacagaaact tcattttcag aga 163

<210> SEQ ID NO 98
<211> LENGTH: 159
<212> TYPE: DNA
<213> ORGANISM: Homo sapiens

<400> SEQUENCE: 98
gatgagcatt gttttgtgtt ttcatttcag ggaagaagtg aatgaaaaac ttcgagatac 60
agcagacggg accttttggg tacgagatgc gtctactaaa atgcatggtg attatactct 120
tacactaagg taagccaggg aatatagctg aaattaggg 159

<210> SEQ ID NO 99
<211> LENGTH: 241
<212> TYPE: DNA
<213> ORGANISM: Homo sapiens

<400> SEQUENCE: 99
aataccttta tttttatatt gtttttacag gaaaggggga aataacaaat taatcaaaat 60
atttcatcga gatgggaaat atggcttctc tgacccatta accttcagtt ctgtggttga 120
attaataaac cactaccgga atgaatctct agctcagtat aatcccaaat tggatgtgaa 180
attactttat ccagtatcca aataccaaca ggtaataaaa actgaatgaa ttatccagtt 240
a 241

<210> SEQ ID NO 100
<211> LENGTH: 186
<212> TYPE: DNA
<213> ORGANISM: Homo sapiens

<400> SEQUENCE: 100
tatccattga atttatttta atctttctag gatcaagttg tcaaagaaga taatattgaa 60
gctgtaggga aaaaattaca tgaatataac actcagtttc aagaaaaaag tcgagaatat 120
gatagattat atgaagaata tacccgcaca tcccaggtga gttttctatg aaaatcagat 180
taaaaa 186

<210> SEQ ID NO 101
<211> LENGTH: 203
<212> TYPE: DNA
<213> ORGANISM: Homo sapiens

<400> SEQUENCE: 101
tgacattatc tttttaaaat tatgttgcag gaaatccaaa tgaaaaggac agctattgaa 60
gcatttaatg aaaccataaa aatatttgaa gaacagtgcc agacccaaga gcggtacagc 120
aaagaataca tagaaaagtt taaacgtgaa ggcaatgaga aagaaataca aaggttggtg 180
tttcccttgt tcttgtgcta gag 203

<210> SEQ ID NO 102
<211> LENGTH: 237
<212> TYPE: DNA
<213> ORGANISM: Homo sapiens

<400> SEQUENCE: 102
taataacaaa tacgtttctt ttgcctgcag gattatgcat aattatgata agttgaagtc 60
tcgaatcagt gaaattattg acagtagaag aagattggaa gaagacttga agaagcaggc 120
agctgagtat cgagaaattg acaaacgtat gaacagcatt aaaccagacc ttatccagct 180
gagaaagacg agagaccaat acttgatgta agtatttgaa atggaatcct atacatg 237

<210> SEQ ID NO 103
<211> LENGTH: 129
<212> TYPE: DNA
<213> ORGANISM: Homo sapiens

<400> SEQUENCE: 103
atgcgttctc ttttcaaaac tgtttttcag gtggttgact caaaaaggtg ttcggcaaaa 60
gaagttgaac gagtggttgg gcaatgaaaa cactgaagag taagtagtta ctaaagatgg 120
tgatagcag 129

<210> SEQ ID NO 104
<211> LENGTH: 231
<212> TYPE: DNA
<213> ORGANISM: Homo sapiens

<400> SEQUENCE: 104
atttagaaac tttctgtcct gcctgcctag ccaatattca ctggtggaag atgatgaaga 60
tttgccccat catgatgaga agacatggaa tgttggaagc agcaaccgaa acaaagctga 120
aaacctgttg cgagggaagc gagatggcac ttttcttgtc cgggagagca gtaaacaggg 180
ctgctatgcc tgctctgtag tgtatgtatc tccagcaaac ttttctttac a 231

<210> SEQ ID NO 105
<211> LENGTH: 250
<212> TYPE: DNA
<213> ORGANISM: Homo sapiens

<400> SEQUENCE: 105
aaaagacagt ttttcttctc tcctctctag ggtggacggc gaagtaaagc attgtgtcat 60
aaacaaaaca gcaactggct atggctttgc cgagccctat aacttgtaca gctctctgaa 120
agaactggtg ctacattacc aacacacctc ccttgtgcag cacaacgact ccctcaatgt 180
cacactagcc tacccagtat atgcacagca gaggcgatga agcgcttact ctttgatcct 240
tctcctgaag 250

<210> SEQ ID NO 106
<211> LENGTH: 760
<212> TYPE: DNA
<213> ORGANISM: Homo sapiens

<400> SEQUENCE: 106
tggcaggctg tggacctcgt cctcaccacc atggtcgggc tccttttgtt ttttttccca 60
gcgatctttt tggaggtgtc ccttctcccc agaagccccg gcaggaaagt gttgctggca 120
ggagcgtcgt ctcagcgctc ggtggccaga atggacggag atgtcatcat tggagccctc 180
ttctcagtcc atcaccagcc tccggccgag aaagtgcccg agaggaagtg tggggagatc 240
agggagcagt atggcatcca gagggtggag gccatgttcc acacgttgga taagatcaac 300
gcggacccgg tcctcctgcc caacatcacc ctgggcagtg agatccggga ctcctgctgg 360
cactcttccg tggctctgga acagagcatt gagttcatta gggactctct gatttccatt 420
cgagatgaga aggatgggat caaccggtgt ctgcctgacg gccagtccct ccccccaggc 480
aggactaaga agcccattgc gggagtgatc ggtcccggct ccagctctgt agccattcaa 540
gtgcagaacc tgctccagct cttcgacatc ccccagatcg cttattcagc cacaagcatc 600
gacctgagtg acaaaacttt gtacaaatac ttcctgaggg ttgtcccttc tgacactttg 660
caggcaaggg ccatgcttga catagtcaaa cgttacaatt ggacctatgt ctctgcagtc 720
cacacggaag gtaggcatta tatttgggaa agaagggtac 760

<210> SEQ ID NO 107
<211> LENGTH: 310
<212> TYPE: DNA
<213> ORGANISM: Homo sapiens

<400> SEQUENCE: 107
cttgaacatc tgctgattgt ttctggacag ggaattatgg ggagagcgga atggacgctt 60
tcaaagagct ggctgcccag gaaggcctct gtatcgccca ttctgacaaa atctacagca 120
acgctgggga gaagagcttt gaccgactct tgcgcaaact ccgagagagg cttcccaagg 180
ctagagtggt ggtctgcttc tgtgaaggca tgacagtgcg aggactcctg agcgccatgc 240
ggcgccttgg cgtcgtgggc gagttctcac tcattggaag gtaagtttct ctctctctct 300
ctctctctct 310

<210> SEQ ID NO 108
<211> LENGTH: 296
<212> TYPE: DNA
<213> ORGANISM: Homo sapiens

<400> SEQUENCE: 108
tctccctacc ccaatccctg catttttag tgatggatgg gcagacagag atgaagtcat 60
tgaaggttat gaggtggaag ccaacggggg aatcacgata aagctgcagt ctccagaggt 120
caggtcattt gatgattatt tcctgaaact gaggctggac actaacacga ggaatccctg 180
gttccctgag ttctggcaac atcggttcca gtgccgcctt ccaggacacc ttctggaaaa 240
tcccaacttt aaacgaatct gcacaggtaa ctcatgttca caaaataaca actcag 296

<210> SEQ ID NO 109
<211> LENGTH: 307
<212> TYPE: DNA
<213> ORGANISM: Homo sapiens

<400> SEQUENCE: 109
cttggtagtg atctattttt attgttacag gcaatgaaag cttagaagaa aactatgtcc 60
aggacagtaa gatggggttt gtcatcaatg ccatctatgc catggcacat gggctgcaga 120
acatgcacca tgccctctgc cctggccacg tgggcctctg cgatgccatg aagcccatcg 180
acggcagcaa gctgctggac ttcctcatca agtcctcatt cattggagta tctggagagg 240
aggtgtggtt tgatgagaaa ggagacgctc ctggaaggta atcttttcag taatcaatct 300
aagtaac 307

<210> SEQ ID NO 110
<211> LENGTH: 229
<212> TYPE: DNA
<213> ORGANISM: Homo sapiens

<400> SEQUENCE: 110
tataagacat gcacattgtg ctctttgtag gtatgatatc atgaatctgc agtacactga 60
agctaatcgc tatgactatg tgcacgttgg aacctggcat gaaggagtgc tgaacattga 120
tgattacaaa atccagatga acaagagtgg agtggtgcgg tctgtgtgca gtgagccttg 180
cttaaagggc cagattaagg taagccacaa atgcattctt gcatggtat 229

<210> SEQ ID NO 111
<211> LENGTH: 187
<212> TYPE: DNA
<213> ORGANISM: Homo sapiens

<400> SEQUENCE: 111
tttaaaattc atgaaatatc tatgttatag gttatacgga aaggagaagt gagctgctgc 60
tggatttgca cggcctgcaa agagaatgaa tatgtgcaag atgagttcac ctgcaaagct 120
tgtgacttgg gatggtggcc caatgcagat ctaacaggta ggaactgcct cacttggaaa 180
ccttgtg 187

<210> SEQ ID NO 112
<211> LENGTH: 991
<212> TYPE: DNA
<213> ORGANISM: Homo sapiens

<400> SEQUENCE: 112
ttcatgctca aatgattttt ctcatcacag gctgtgagcc cattcctgtg cgctatcttg 60
agtggagcaa catcgaatcc attatagcca tcgccttttc atgcctggga atccttgtta 120
ccttgtttgt caccctaatc tttgtactgt accgggacac accagtggtc aaatcctcca 180
gtcgggagct ctgctacatc atcctagctg gcatcttcct tggttatgtg tgcccattca 240

```
ctctcattgc caaacctact accacctcct gctacctcca gcgcctcttg gttggcctct    300
cctctgcgat gtgctactct gctttagtga ctaaaaccaa tcgtattgca cgcatcctgg    360
ctggcagcaa gaagaagatc tgcacccgga agcccaggtt catgagtgcc tgggctcagg    420
tgatcattgc ctcaattctg attagtgtgc aactaaccct ggtggtaacc ctgatcatca    480
tggaaccccc tatgcccatt ctgtcctacc caagtatcaa ggaagtctac cttatctgca    540
ataccagcaa cctgggtgtg gtggcccctt tgggctacaa tggactcctc atcatgagct    600
gtacctacta tgccttcaag acccgcaacg tgcccgccaa cttcaacgag gccaaatata    660
tcgcgttcac catgtacacc acctgtatca tctggctagc ttttgtgccc atttactttg    720
ggagcaacta caagatcatc acaacttgct ttgcagtgag tctcagtgta acagtggctc    780
tggggtgcat gttcactccc aagatgtaca tcattattgc caagcctgag aggaatgtcc    840
gcagtgcctt caccacctct gatgttgtcc gcatgcatgt tggcgatggc aagctgccct    900
gccgctccaa cactttcctc aacatcttcc gaagaaagaa ggcaggggca gggaatgcca    960
agtgagttat ctgacctgtt tgtctctctt t                                   991
```

<210> SEQ ID NO 113
<211> LENGTH: 985
<212> TYPE: DNA
<213> ORGANISM: Homo sapiens

<400> SEQUENCE: 113

```
caaataaatc catctctatt ttattcatag ttctaatggc aagtctgtgt catggtctga     60
accaggtgga ggacaggtgc ccaagggaca gcatatgtgg caccgcctct ctgtgcacgt    120
gaagaccaat gagacggcct gcaaccaaac agccgtcatc aagcccctca ctaaaagtta    180
ccaaggctct ggcaagagcc tgaccttttc agataccagc accaagaccc tttacaacgt    240
agaggaggag gaggatgccc agccgattcg ctttagcccg cctggtagcc cttccatggt    300
ggtgcacagg cgcgtgccaa gcgcggcgac cactccgcct ctgccgtccc acctgaccgc    360
agaggagacc cccctcttcc tggccgaacc agccctcccc aagggcttgc cccctcctct    420
ccagcagcag cagcaacccc ctccacagca gaaatcgctg atggaccagc tccagggagt    480
ggtcagcaac ttcagtaccg cgatcccgga ttttcacgcg gtgctggcag gccccggtgg    540
tcccgggaac gggctgcggt ccctgtaccc gcccccgcca cctccgcagc acctgcagat    600
gctgccgctg cagctgagca cctttgggga ggagctggtc tccccgcccg cggacgacga    660
cgacgacagc gagaggttta agctcctcca ggagtacgtg tatgagcacg agcgggaagg    720
gaacacggaa gaagacgaac tggaagagga ggaggaggac ctgcaggcgg ccagcaaact    780
gaccccggat gattcgcctg cgctgacgcc tccgtcgcct ttccgcgact cggtggcctc    840
gggcagctcg gtgcccagct cccccgtgtc cgagtcggtg ctctgcaccc ctcccaacgt    900
atcctacgcc tctgtcattc tgcgggacta caagcaaagc tcttccaccc tgtaaggggg    960
aagggtccac atagaaaagc aagac                                          985
```

<210> SEQ ID NO 114
<211> LENGTH: 112
<212> TYPE: DNA
<213> ORGANISM: Homo sapiens

<400> SEQUENCE: 114

```
ggttgggccg gggctgagga ggccgccaag atgccgcagt ccaagtcccg gaagatcgcg     60
atcctgggct accggtctgt gggtgagtgg ccggtggccg cgcggcctcc tc            112
```

<210> SEQ ID NO 115
<211> LENGTH: 132
<212> TYPE: DNA
<213> ORGANISM: Homo sapiens

<400> SEQUENCE: 115
cacacactaa gctcttgttc tcttttatag ggaaatcctc attgacgatt caatttgttg 60
aaggccaatt tgtggactcc tacgatccaa ccatagaaaa cagtaagtat tgttttcaag 120
tacttaaaaa ct 132

<210> SEQ ID NO 116
<211> LENGTH: 128
<212> TYPE: DNA
<213> ORGANISM: Homo sapiens

<400> SEQUENCE: 116
actaatgttt aatttccttt ttccctgtag cttttacaaa gttgatcaca gtaaatggac 60
aagaatatca tcttcaactt gtagacacag ccgggcaagt aagtgacctc tggtatctca 120
gaatctta 128

<210> SEQ ID NO 117
<211> LENGTH: 143
<212> TYPE: DNA
<213> ORGANISM: Homo sapiens

<400> SEQUENCE: 117
ctactcaaag ataatttttt ttccccacag gatgaatatt ctatctttcc tcagacatac 60
tccatagata ttaatggcta tattcttgtg tattctgtta catcaatcaa aaggtaagac 120
tcctgctgcc tgcttgagtt gat 143

<210> SEQ ID NO 118
<211> LENGTH: 117
<212> TYPE: DNA
<213> ORGANISM: Homo sapiens

<400> SEQUENCE: 118
gatgtctaat ttatactttt tgttttatag ttttgaagtg attaaagtta tccatggcaa 60
attgttggat atggtgggga aagtacagta agtagtacca ttttatctgc ttgttag 117

<210> SEQ ID NO 119
<211> LENGTH: 108
<212> TYPE: DNA
<213> ORGANISM: Homo sapiens

<400> SEQUENCE: 119
actggtttgt cttttttttc ttacaaatag aatacctatt atgttggttg ggaataagaa 60
agacctgcat atggaaaggt atgtagcttt tataaagtca aatctaag 108

<210> SEQ ID NO 120
<211> LENGTH: 142
<212> TYPE: DNA
<213> ORGANISM: Homo sapiens

<400> SEQUENCE: 120
actttaacta gaattttatt ttttctttag ggtgatcagt tatgaagaag ggaaagcttt 60
ggcagaatct tggaatgcag cttttttgga atcttctgct aaagaaaatc aggtaacaga 120
ttctataaac ctcattttgc at 142

<210> SEQ ID NO 121
<211> LENGTH: 153
<212> TYPE: DNA
<213> ORGANISM: Homo sapiens

<400> SEQUENCE: 121
cactgtgatt gggtttcttt ctcttttcag actgctgtgg atgtttttcg aaggataatt 60
ttggaggcag aaaaaatgga cggggcagct tcacaaggca agtcttcatg ctcggtgatg 120
tgattctgct gcaaagcctg aggacactgg gaa 153

<210> SEQ ID NO 122
<211> LENGTH: 1251
<212> TYPE: DNA
<213> ORGANISM: Homo sapiens

<400> SEQUENCE: 122
tttgccgcct gccggagcac ctgcgcacag atggagctgg accaccggac cagcggcggg 60
ctccacgcct accccgggcc gcggggcggg caggtggcca agcccaacgt gatcctgcag 120
atcgggaagt gccgggccga gatgctggag cacgtgcggc ggacgcaccg gcacctgctg 180
gccgaggtgt ccaagcaggt ggagcgcgag ctgaaggggc tgcaccggtc ggtcgggaag 240
ctggagagca acctggacgg ctacgtgccc acgagcgact cgcagcgctg gaagaagtcc 300
atcaaggcct gcctgtgccg ctgccaggag accatcgcca acctggagcg ctgggtcaag 360
cgcgagatgc acgtgtggcg cgaggtgttc taccgcctgg agcgctgggc cgaccgcctg 420
gagtccacgg gcggcaagta cccggtgggc agcgagtcag cccgccacac cgtttccgtg 480
ggcgtggggg gtcccgagag ctactgccac gaggcagacg gctacgacta caccgtcagc 540
ccctacgcca tcaccccgcc cccagccgct ggcgagctgc ccgggcagga gcccgccgag 600
gcccagcagt accagccgtg ggtccccggc gaggacgggc agcccagccc cggcgtggac 660
acgcagatct tcgaggaccc tcgagagttc ctgagccacc tagaggagta cttgcggcag 720
gtgggcggct ctgaggagta ctggctgtcc cagatccaga atcacatgaa cgggccggcc 780
aagaagtggt gggagttcaa gcagggctcc gtgaagaact gggtggagtt caagaaggag 840
ttcctgcagt acagcgaggg cacgctgtcc cgagaggcca tccagcgcga gctggacctg 900
ccgcagaagc agggcgagcc gctggaccag ttcctgtggc gcaagcggga cctgtaccag 960
acgctctacg tggacgcgga cgaggaggag atcatccagt acgtggtggg caccctgcag 1020
cccaagctca agcgtttcct gcgccacccc ctgcccaaga ccctggagca gctcatccag 1080
aggggcatgg aggtgcagga tgacctggag caggcggccg agccggccgg cccccacctc 1140
ccggtggagg atgaggcgga gaccctcacg cccgccccca acagcgagtc cgtggccagt 1200
gaccggaccc agcccgagta gagggcatcc cggagccccc agcctgccca c 1251

<210> SEQ ID NO 123
<211> LENGTH: 166
<212> TYPE: DNA
<213> ORGANISM: Homo sapiens

<400> SEQUENCE: 123
ggagccagca cagcgccttc gagcgagaga atggcccaac aagcaaatgt cggggagctt 60
cttgccatgc tggactcccc catgctgggt gtgcgggacg acgtgacagc tgtctttaaa 120
gagaacctca attctggtta gcaaaataat atccttttta gcttat 166

<210> SEQ ID NO 124
<211> LENGTH: 164
<212> TYPE: DNA
<213> ORGANISM: Homo sapiens

<400> SEQUENCE: 124
gtatcatcca ttgccctttt cttgatttag accgtggccc tatgcttgta aacaccttgg 60
tggattatta cctggaaacc agctctcagc cggcattgca catcctgacc accttgcaag 120
agccacatga caaggtaatg gctgaaatat cataggcatt tcat 164

<210> SEQ ID NO 125
<211> LENGTH: 213
<212> TYPE: DNA
<213> ORGANISM: Homo sapiens

<400> SEQUENCE: 125
aggactgccc ttgttctttt acattttcag cacctcttgg acaggattaa cgaatatgtg 60
ggcaaagccg ccactcgttt atccatcctc tcgttactgg gtcatgtcat aagactgcag 120
ccatcttgga agcataagct ctctcaagca cctcttttgc cttctttact aaaatgtctc 180
aaggtaggat gtttgtaagg atttgaatga aat 213

<210> SEQ ID NO 126
<211> LENGTH: 205
<212> TYPE: DNA
<213> ORGANISM: Homo sapiens

<400> SEQUENCE: 126
acgtttcctg tttgaccttt tctcctgcag atggacactg acgtcgttgt cctcacaaca 60
ggcgtcttgg tgttgataac catgctacca atgattccac agtctgggaa acagcatctt 120
cttgatttct ttgacatttt tggccgtctg tcatcatggt gcctgaagaa accaggtaca 180
gatctcctca tatacctgtt gggcc 205

<210> SEQ ID NO 127
<211> LENGTH: 215
<212> TYPE: DNA
<213> ORGANISM: Homo sapiens

<400> SEQUENCE: 127
gaggctcttc tcaacgggtt ccttttctag gccacgtggc ggaagtctat ctcgtccatc 60
tccatgccag tgtgtacgca ctctttcatc gcctttatgg aatgtaccct tgcaacttcg 120
tctccttttt gcgttctcat tacagtatga aagaaaacct ggagactttt gaagaagtgg 180
tcaaggtaaa ttgaaactgc ttgtttgttt gctac 215

<210> SEQ ID NO 128
<211> LENGTH: 134
<212> TYPE: DNA
<213> ORGANISM: Homo sapiens

<400> SEQUENCE: 128
ctttataatt tgtcaaccca actcttctag ccaatgatgg agcatgtgcg aattcatccg 60
gaattagtga ctggatccaa ggaccatgaa ctggaccctc gaaggtatag aaactagtgt 120
caaaatttta aaga 134

<210> SEQ ID NO 129

<211> LENGTH: 236
<212> TYPE: DNA
<213> ORGANISM: Homo sapiens

<400> SEQUENCE: 129
gcatttcttg actttcattg cattttacag gtggaagaga ttagaaactc atgatgttgt 60
gatcgagtgt gccaaaatct ctctggatcc cacagaagcc tcatatgaag atggctattc 120
tgtgtctcac caaatctcag cccgctttcc tcatcgttca gccgatgtca ccaccagccc 180
ttatgctgac acacagaata gctatggtaa aaagtgtctt tggtacttat ctgttt 236

<210> SEQ ID NO 130
<211> LENGTH: 176
<212> TYPE: DNA
<213> ORGANISM: Homo sapiens

<400> SEQUENCE: 130
aaccccctgt gttcttctct tccattttag ggtgtgctac ttctacccct tactccacgt 60
ctcggctgat gttgttaaat atgccagggc agctacctca gactctgagt tccccatcga 120
cacggctgat aactgaacca ccacaagtat ggtgtcaact agtgtgcctg ctctct 176

<210> SEQ ID NO 131
<211> LENGTH: 172
<212> TYPE: DNA
<213> ORGANISM: Homo sapiens

<400> SEQUENCE: 131
cactgctgat gtactttatt aacttcccag gctactcttt ggagcccatc tatggtttgt 60
ggtatgacca ctcctccaac ttctcctgga aatgtcccac ctgatctgtc acacccttac 120
agtaaagtct ttggtacaac tggtatgtat gtcttaggtt ggatttgatt ag 172

<210> SEQ ID NO 132
<211> LENGTH: 182
<212> TYPE: DNA
<213> ORGANISM: Homo sapiens

<400> SEQUENCE: 132
gttcatatat gttctgccct tgtctctaag caggtggaaa aggaactcct ctgggaaccc 60
cagcaacctc tcctcctcca gccccactct gtcattcgga tgactacgtg cacatttcac 120
tcccccaggc cacagtcaca ccccccagga aggtgcgatc cagctcgtct gctatccctc 180
tg 182

<210> SEQ ID NO 133
<211> LENGTH: 130
<212> TYPE: DNA
<213> ORGANISM: Homo sapiens

<400> SEQUENCE: 133
ttgtgatata aatgatactt atcttttcag gaagagagaa tggattctgc aagaccatgt 60
ctacacagac aacaccatct tctgaatgac agaggatcag gtaaaatttc tgcgttacta 120
caggccttgc 130

<210> SEQ ID NO 134
<211> LENGTH: 165
<212> TYPE: DNA
<213> ORGANISM: Homo sapiens

<400> SEQUENCE: 134
ttgacttcag ttgtctttgt ttctcttcag aagagccacc tggcagcaaa ggttctgtca 60
ctctaagtga tcttccaggg tttttaggtg atctggcctc tgaagaagat agtattgaaa 120
aagataaaga agaaggtaat gtatgtggga ttgctatgag ttgat 165

<210> SEQ ID NO 135
<211> LENGTH: 619
<212> TYPE: DNA
<213> ORGANISM: Homo sapiens

<400> SEQUENCE: 135
catttctttt gtttcctctc ttcctctcag ctgcaatatc tagagaactt tctgagatca 60
ccacagcaga ggcagagcct gtggttcctc gaggaggctt tgactctccc ttttaccgag 120
acagtctccc aggttctcag cggaagaccc actcggcagc ctccagttct cagggcgcca 180
gcgtgaaccc tgagccttta cactcctccc tggacaagct tgggcctgac acaccaaagc 240
aagcctttac tcccatagac ctgccctgcg gcagtgctga tgaaagccct gcgggagaca 300
gggaatgcca gacttctttg gagaccagta tcttcactcc cagtccttgt aaaattccac 360
ctccgacgag agtgggcttt ggaagcgggc agcctccccc gtatgatcat ctttttgagg 420
tggcattgcc aaagacagcc catcattttg tcatcaggaa gactgaggag ctgttaaaga 480
aagcaaaagg aaacacagag gaagatggtg tgccctctac ctccccaatg gaagtgctgg 540
acagactgat acagcaggga gcagacgcgc acagcaagga gctgaacaag taagggactg 600
gggcactctc ttctgtgtt 619

<210> SEQ ID NO 136
<211> LENGTH: 104
<212> TYPE: DNA
<213> ORGANISM: Homo sapiens

<400> SEQUENCE: 136
aactttgtta ctcaaaaact ttcttcctag gttgccttta cccagcaagt ctgtcgactg 60
gacccacttt ggaggtaaag ttgttacttt agctccaaat ccag 104

<210> SEQ ID NO 137
<211> LENGTH: 227
<212> TYPE: DNA
<213> ORGANISM: Homo sapiens

<400> SEQUENCE: 137
tctgccaccc tccctctgct ttacaatcag gctctcctcc ttcagatgag atccgcaccc 60
tccgagacca gttgctttta ctgcacaacc agttactcta tgagcgtttt aagaggcagc 120
agcatgccct ccggaacagg cggctcctcc gcaaggtgat caaagcagca gctctggagg 180
aacataatgc tgccatggtg aggactgggg aggggacagg tggagct 227

<210> SEQ ID NO 138
<211> LENGTH: 243
<212> TYPE: DNA
<213> ORGANISM: Homo sapiens

<400> SEQUENCE: 138
taaaatgatg acatttctgg tctctgctag aaagatcagt tgaagttaca agagaaggac 60
atccagatgt ggaaggttag tctgcagaaa gaacaagcta gatacaatca gctccaggag 120
cagcgtgaca ctatggtaac caagctccac agccagatca gacagctgca gcatgaccga 180
gaggaattct acaaccagag ccaggaatta caggtataaa ctgcagcacc aggcaaagcc 240
aac 243

<210> SEQ ID NO 139
<211> LENGTH: 171
<212> TYPE: DNA
<213> ORGANISM: Homo sapiens

<400> SEQUENCE: 139
caaacttcat gtccacgtct ctttgggcag acgaagctgg aggactgcag gaacatgatt 60
gcggagctgc ggatagaact gaagaaggcc aacaacaagg tgtgtcacac tgagctgctg 120
ctcagtcagg tttcccaaaa ggtaagaaga aatgaggcag acctgaatct g 171

<210> SEQ ID NO 140
<211> LENGTH: 183
<212> TYPE: DNA
<213> ORGANISM: Homo sapiens

<400> SEQUENCE: 140
tttttcactt tgctcatgtt ttttggttag ctctcaaaca gtgagtcggt ccagcagcag 60
atggagttct tgaacaggca gctgttggtt cttggggagg tcaacgagct ctatttggaa 120
caactgcaga acaagcactc agataccaca aaggtatgcc agggctcggg agccagacct 180
tag 183

<210> SEQ ID NO 141
<211> LENGTH: 248
<212> TYPE: DNA
<213> ORGANISM: Homo sapiens

<400> SEQUENCE: 141
attccagtct tttttttttt tttttttcag gaagtagaaa tgatgaaagc cgcctatcgg 60
aaagagctag aaaaaaacag aagccatgtt ctccagcaga ctcagaggct tgatacctcc 120
caaaaacgga ttttggaact ggaatctcac ctggccaaga aagaccacct tcttttggaa 180
cagaagaaat atctagagga tgtcaaactc caggcaaggt aactttcatc aggaaaggct 240
tttgtgtt 248

<210> SEQ ID NO 142
<211> LENGTH: 222
<212> TYPE: DNA
<213> ORGANISM: Homo sapiens

<400> SEQUENCE: 142
cctatattct ggctggtctg tatctttcag aggacagctg caggccgcag agagcaggta 60
tgaggctcag aaaaggataa cccaggtgtt tgaattggag atcttagatt tatatggcag 120
gttggagaaa gatggcctcc tgaaaaaact tgaagaagaa aaagcagaag cagctgaagc 180
agcagaagaa aggtaggaac aaagaactga ttcatgacct tg 222

<210> SEQ ID NO 143
<211> LENGTH: 580
<212> TYPE: DNA
<213> ORGANISM: Homo sapiens

<400> SEQUENCE: 143
ctcctttttt cctccccggc tttcttacag gcttgactgt tgtaatgacg ggtgctcaga 60
ttccatggta gggcacaatg aagaggcatc tggccacaac ggtgagacca agacccccag 120
gcccagcagc gcccggggca gtagtggaag cagaggtggt ggaggcagca gcagcagcag 180
cagcgagctt tctaccccag agaaaccccc acaccagagg gcaggcccat tcagcagtcg 240
gtgggagacg actatgggag aagcgtctgc cagcatcccc accactgtgg gctcacttcc 300
cagttcaaaa agcttcctgg gtatgaaggc tcgagagtta tttcgtaata agagcgagag 360
ccagtgtgat gaggacggca tgaccagtag cctttctgag agcctaaaga cagaactggg 420
caaagacttg ggtgtggaag ccaagattcc cctgaaccta gatggccctc acccgtctcc 480
cccgaccccg gacagtgttg gacagctaca tatcatggac tacaatgaga ctcatcatga 540
acacagctaa ggaatgatgg tcaatcagtg ttaacttgca 580

<210> SEQ ID NO 144
<211> LENGTH: 111
<212> TYPE: DNA
<213> ORGANISM: Homo sapiens

<400> SEQUENCE: 144
gctcccggcg ctagcagggc tgaagagaag atggaggagc tggtggtgga agtgcggggc 60
tccaatggcg ctttctacaa ggtacttggc tctagggcag gccccatctt c 111

<210> SEQ ID NO 145
<211> LENGTH: 113
<212> TYPE: DNA
<213> ORGANISM: Homo sapiens

<400> SEQUENCE: 145
caagttaatt taacgttttt tcttacacag gcatttgtaa aggatgttca tgaagattca 60
ataacagttg catttgaaaa caagtaagtg tctcgttata taattttaat gat 113

<210> SEQ ID NO 146
<211> LENGTH: 154
<212> TYPE: DNA
<213> ORGANISM: Homo sapiens

<400> SEQUENCE: 146
ttaaataatt gtatgtttgc ttatttacag ctggcagcct gataggcaga ttccatttca 60
tgatgtcaga ttcccacctc ctgtaggtta taataaagat ataaatgaaa gtgatgaagt 120
tgaggtgagt tttccctgcc ataaagtcat ttag 154

<210> SEQ ID NO 147
<211> LENGTH: 132
<212> TYPE: DNA
<213> ORGANISM: Homo sapiens

<400> SEQUENCE: 147
gaaatattct gtgttgtaat ttttgtgtag gtgtattcca gagcaaatga aaaagagcct 60
tgctgttggt ggttagctaa agtgaggatg ataaagggtg aggtaggaaa atgcctattt 120
aaattttttt ct 132

<210> SEQ ID NO 148
<211> LENGTH: 209
<212> TYPE: DNA
<213> ORGANISM: Homo sapiens

<400> SEQUENCE: 148
gattagaagt gacttttatt tatttctcag ttttatgtga tagaatatgc agcatgtgat 60

```
gcaacttaca atgaaattgt cacaattgaa cgtctaagat ctgttaatcc caacaaacct      120

gccacaaaag atactttcca taagatcaag ctggatgtgc cagaagactt acggcaaatg      180

taagttgata cacaagaaat gctgagaac                                        209

<210> SEQ ID NO 149
<211> LENGTH: 154
<212> TYPE: DNA
<213> ORGANISM: Homo sapiens

<400> SEQUENCE: 149

tcatcttaat tttttttttt aaatttctag gtgtgccaaa gaggcggcac ataaggattt       60

taaaaaggca gttggtgcct tttctgtaac ttatgatcca gaaaattatc agcttgtcat      120

tttggtgagc atttttgagt tgtttatttt tagt                                  154

<210> SEQ ID NO 150
<211> LENGTH: 177
<212> TYPE: DNA
<213> ORGANISM: Homo sapiens

<400> SEQUENCE: 150

ataataatgt tgttaattta aatcatttag tccatcaatg aagtcacctc aaagcgagca       60

catatgctga ttgacatgca ctttcggagt ctgcgcacta agttgtctct gataatgaga      120

aatgaagaag ctagtaagca gctggaggta tgtcactttc cctagcactg cttgtaa        177

<210> SEQ ID NO 151
<211> LENGTH: 231
<212> TYPE: DNA
<213> ORGANISM: Homo sapiens

<400> SEQUENCE: 151

tgtattcatc agacgtccat ttctcttcag agttcaaggc agcttgcctc gagatttcat       60

gaacagttta tcgtaagaga agatctgatg ggtctagcta ttggtactca tggtgctaat      120

attcagcaag ctagaaaagt acctggggtc actgctattg atctagatga agatacctgc      180

acatttcata tttatggaga ggtaaatatt ttactgcata gttttttttt c               231

<210> SEQ ID NO 152
<211> LENGTH: 139
<212> TYPE: DNA
<213> ORGANISM: Homo sapiens

<400> SEQUENCE: 152

tttgtcttaa aatgtttccc cttttattag gatcaggatg cagtgaaaaa agctagaagc       60

tttctcgaat ttgctgaaga tgtaatacaa gttccaagga acttagtagg taagtcagaa      120

gtatctgttg acatatagt                                                   139

<210> SEQ ID NO 153
<211> LENGTH: 170
<212> TYPE: DNA
<213> ORGANISM: Homo sapiens

<400> SEQUENCE: 153

aaaaccaaac ttgatttatt tatttcttag gcaaagtaat aggaaaaaat ggaaagctga       60

ttcaggagat tgtggacaag tcaggagttg tgagggtgag gattgaggct gaaaatgaga      120

aaaatgttcc acaagaagag gtatgttaca gtgcgaatat tttgtggcac                170
```

<210> SEQ ID NO 154
<211> LENGTH: 195
<212> TYPE: DNA
<213> ORGANISM: Homo sapiens

<400> SEQUENCE: 154
tctcttttgt gttttctgtt ttttaccaag gaaattatgc caccaaattc ccttccttcc 60
aataattcaa gggttggacc taatgcccca gaagaaaaaa aacatttaga tataaaggaa 120
aacagcaccc atttttctca acctaacagt acaaaagtcc agagggtaag aattacttgt 180
cactttgaat tacaa 195

<210> SEQ ID NO 155
<211> LENGTH: 123
<212> TYPE: DNA
<213> ORGANISM: Homo sapiens

<400> SEQUENCE: 155
acatcccttg cattccttat actgctttag gtgttagtgg cttcatcagt tgtagcaggg 60
gaatcccaga aacctgaact caaggcttgg caggtaggaa aacattcctt gagaaataca 120
ctt 123

<210> SEQ ID NO 156
<211> LENGTH: 147
<212> TYPE: DNA
<213> ORGANISM: Homo sapiens

<400> SEQUENCE: 156
ataggatcat tgttgcaatt tctttttcag ggtatggtac catttgtttt tgtgggaaca 60
aaggacagca tcgctaatgc cactgttctt ttggattatc acctgaacta tttaaaggtg 120
agaacagaaa gaactttaac ttctaat 147

<210> SEQ ID NO 157
<211> LENGTH: 256
<212> TYPE: DNA
<213> ORGANISM: Homo sapiens

<400> SEQUENCE: 157
ttttactgtt atcttgtata ttttaaatag gaagtagacc agttgcgttt ggagagatta 60
caaattgatg agcagttgcg acagattgga gctagttcta gaccaccacc aaatcgtaca 120
gataaggaaa aaagctatgt gactgatgat ggtcaaggaa tgggtcgagg tagtagacct 180
tacagaaata gggggcacgg cagacgcggt cctggatata cttcaggtac aaactaagca 240
ttttactcag taactt 256

<210> SEQ ID NO 158
<211> LENGTH: 243
<212> TYPE: DNA
<213> ORGANISM: Homo sapiens

<400> SEQUENCE: 158
caatggtata taacttttaa ctctcgatag gaactaattc tgaagcatca aatgcttctg 60
aaacagaatc tgaccacaga gacgaactca gtgattggtc attagctcca acagaggaag 120
agagggagag cttcctgcgc agaggagacg gacggcggcg tggaggggga ggaagaggac 180
aaggaggaag aggacgtgga ggaggcttca aaggtatgga gatcttcatt aagaaatcaa 240
agt 243

<210> SEQ ID NO 159
<211> LENGTH: 143
<212> TYPE: DNA
<213> ORGANISM: Homo sapiens

<400> SEQUENCE: 159
ctgttgaacc ttttgaaaat attctcatag gaaacgacga tcactcccga acagataatc 60
gtccacgtaa tccaagagag gctaaaggaa gaacaacaga tggatccctt caggtaaaac 120
ctgtctgcct cttttcatct taa 143

<210> SEQ ID NO 160
<211> LENGTH: 222
<212> TYPE: DNA
<213> ORGANISM: Homo sapiens

<400> SEQUENCE: 160
tgtgtatata acaactataa cttgttttag atcagagttg actgcaataa tgaaaggagt 60
gtccacacta aaacattaca gaatacctcc agtgaaggta gtcggctgcg cacgggtaaa 120
gatcgtaacc agaagaaaga gaagccagac agcgtggatg gtcagcaacc actcgtgaat 180
ggagtaccct aaactgcata attctgaagt tatatttcct at 222

<210> SEQ ID NO 161
<211> LENGTH: 86
<212> TYPE: DNA
<213> ORGANISM: Homo sapiens

<400> SEQUENCE: 161
gcttctgtag accagctcca acaggattcc atggtagctg ggatgttagg gctcaggtaa 60
gtaaccttcc tttttttttt tttagt 86

<210> SEQ ID NO 162
<211> LENGTH: 411
<212> TYPE: DNA
<213> ORGANISM: Homo sapiens

<400> SEQUENCE: 162
tgatacttac atacttgttt aacacttcag ggaagaaaag tcagaagacc aggacctcca 60
gggcctcaag gacaaacccc tcaagtttaa aaaggtgaag aaagataaga aagaagagaa 120
agagggcaag catgagcccg tgcagccatc agcccaccac tctgctgagc ccgcagaggc 180
aggcaaagca gagacatcag aagggtcagg ctccgccccg gctgtgccgg aagcttctgc 240
ctcccccaaa cagcggcgct ccatcatccg tgaccgggga cccatgtatg atgaccccac 300
cctgcctgaa ggctggacac ggaagcttaa gcaaaggaaa tctggccgct ctgctgggaa 360
gtatgatgtg tatttgatca agtaagtaag agcaactcct atctctacag g 411

<210> SEQ ID NO 163
<211> LENGTH: 1144
<212> TYPE: DNA
<213> ORGANISM: Homo sapiens

<400> SEQUENCE: 163
ttccttgtgt ctttctgttt gtccccacag tccccaggga aaagcctttc gctctaaagt 60
ggagttgatt gcgtacttcg aaaaggtagg cgacacatcc ctggacccta atgattttga 120
cttcacggta actgggagag ggagcccctc ccggcgagag cagaaaccac ctaagaagcc 180
caaatctccc aaagctccag gaactggcag aggccgggga cgccccaaag ggagcggcac 240

-continued

```
cacgagaccc aaggcggcca cgtcagaggg tgtgcaggtg aaaagggtcc tggagaaaag    300

tcctgggaag ctccttgtca agatgccttt tcaaacttcg ccaggggggca aggctgaggg    360

gggtggggcc accacatcca cccaggtcat ggtgatcaaa cgccccggca ggaagcgaaa    420

agctgaggcc gaccctcagg ccattcccaa gaaacggggc cgaaagccgg ggagtgtggt    480

ggcagccgct gccgccgagg ccaaaaagaa agccgtgaag gagtcttcta tccgatctgt    540

gcaggagacc gtactcccca tcaagaagcg caagacccgg gagacggtca gcatcgaggt    600

caaggaagtg gtgaagcccc tgctggtgtc caccctcggt gagaagagcg ggaaaggact    660

gaagacctgt aagagccctg ggcggaaaag caaggagagc agccccaagg ggcgcagcag    720

cagcgcctcc tcaccccccca agaaggagca ccaccaccat caccaccact cagagtcccc    780

aaaggccccc gtgccactgc tcccaccccct gcccccacct ccacctgagc ccgagagctc    840

cgaggacccc accagccccc ctgagcccca ggacttgagc agcagcgtct gcaaagagga    900

gaagatgccc agaggaggct cactggagag cgacggctgc cccaaggagc cagctaagac    960

tcagcccgcg gttgccaccg ccgccacggc cgcagaaaag tacaaacacc gaggggaggg   1020

agagcgcaaa gacattgttt catcctccat gccaaggcca aacagagagg agcctgtgga   1080

cagccggacg cccgtgaccg agagagttag ctgactttac acggagcgga ttgcaaagca   1140

aacc                                                                1144
```

<210> SEQ ID NO 164
<211> LENGTH: 139
<212> TYPE: DNA
<213> ORGANISM: Homo sapiens

<400> SEQUENCE: 164

```
tccttttct tcagccacag gctcccagac atgacagcca tcatcaaaga gatcgttagc     60

agaaacaaaa ggagatatca agaggatgga ttcgacttag acttgacctg tatccatttc    120

tgcggctgct cctctttac                                                 139
```

<210> SEQ ID NO 165
<211> LENGTH: 145
<212> TYPE: DNA
<213> ORGANISM: Homo sapiens

<400> SEQUENCE: 165

```
gatatttctt tccttaacta aagtactcag atatttatcc aaacattatt gctatgggat     60

ttcctgcaga aagacttgaa ggcgtataca ggaacaatat tgatgatgta gtaaggtaag    120

aatgctttga ttttctattt caaat                                          145
```

<210> SEQ ID NO 166
<211> LENGTH: 105
<212> TYPE: DNA
<213> ORGANISM: Homo sapiens

<400> SEQUENCE: 166

```
tggcttttg tttgtttgtt ttgttttaag gtttttggat tcaaagcata aaaaccatta     60

caagatatac aatctgtaag tatgttttct tatttgtatg cttgc                    105
```

<210> SEQ ID NO 167
<211> LENGTH: 104
<212> TYPE: DNA
<213> ORGANISM: Homo sapiens

<400> SEQUENCE: 167
ctttatatca cttttaaact tttcttttag ttgtgctgaa agacattatg acaccgccaa 60
atttaattgc agaggtaggt atgaatgtac tgtactatgt tgta 104

<210> SEQ ID NO 168
<211> LENGTH: 299
<212> TYPE: DNA
<213> ORGANISM: Homo sapiens

<400> SEQUENCE: 168
tcttattctg aggttatctt tttaccacag ttgcacaata tcctttttgaa gaccataacc 60 caccacagct agaacttatc aaaccctttt gtgaagatct tgaccaatgg ctaagtgaag 120
atgacaatca tgttgcagca attcactgta aagctggaaa gggacgaact ggtgtaatga 180
tatgtgcata tttattacat cggggcaaat ttttaaaggc acaagaggcc ctagatttct 240
atggggaagt aaggaccaga gacaaaaagg taagttattt tttgatgttt ttcctttcc 299

<210> SEQ ID NO 169
<211> LENGTH: 202
<212> TYPE: DNA
<213> ORGANISM: Homo sapiens

<400> SEQUENCE: 169
tttggcttct cttttttttc tgtccaccag ggagtaacta ttcccagtca gaggcgctat 60
gtgtattatt atagctacct gttaaagaat catctggatt atagaccagt ggcactgttg 120
tttcacaaga tgatgtttga aactattcca atgttcagtg gcggaacttg cagtaagtgc 180
ttgaaattct catccttcca tg 202

<210> SEQ ID NO 170
<211> LENGTH: 227
<212> TYPE: DNA
<213> ORGANISM: Homo sapiens

<400> SEQUENCE: 170
aataatactg gtatgtattt aaccatgcag atcctcagtt tgtggtctgc cagctaaagg 60
tgaagatata ttcctccaat tcaggaccca cacgacggga agacaagttc atgtactttg 120
agttccctca gccgttacct gtgtgtggtg atatcaaagt agagttcttc cacaaacaga 180
acaagatgct aaaaaaggtt tgtactttac tttcattggg agaaata 227

<210> SEQ ID NO 171
<211> LENGTH: 285
<212> TYPE: DNA
<213> ORGANISM: Homo sapiens

<400> SEQUENCE: 171
tctttttctt ttcttttttt tttttttag gacaaaatgt ttcacttttg ggtaaataca 60
ttcttcatac caggaccaga ggaaacctca gaaaaagtag aaaatggaag tctatgtgat 120
caagaaatcg atagcatttg cagtatagag cgtgcagata atgacaagga atatctagta 180
cttactttaa caaaaaatga tcttgacaaa gcaaataaag acaaagccaa ccgatacttt 240
tctccaaatt ttaaggtcag ttaaattaaa cattttgtgg gggtt 285

<210> SEQ ID NO 172
<211> LENGTH: 246
<212> TYPE: DNA
<213> ORGANISM: Homo sapiens

<400> SEQUENCE: 172
gggttttcat tttaaatttt ctttctctag gtgaagctgt acttcacaaa aacagtagag 60
gagccgtcaa atccagaggc tagcagttca acttctgtaa caccagatgt tagtgacaat 120
gaacctgatc attatagata ttctgacacc actgactctg atccagagaa tgaacctttt 180
gatgaagatc agcatacaca aattacaaaa gtctgaattt ttttttatca agagggataa 240
aacacc 246

<210> SEQ ID NO 173
<211> LENGTH: 721
<212> TYPE: DNA
<213> ORGANISM: Homo sapiens

<400> SEQUENCE: 173
atctttattg gcttgaactc ctttcctaaa atggtccttc tgttgatcct gtcagtctta 60
cttttgaaag aagatgtccg tgggagtgca cagtccagtg agaggagggt ggtggctcac 120
atgccgggtg acatcattat tggagctctc ttttctgttc atcaccagcc tactgtggac 180
aaagttcatg agaggaagtg tggggcggtc cgtgaacagt atggcattca gagagtggag 240
gccatgctgc ataccctgga aaggatcaat tcagacccca cactcttgcc caacatcaca 300
ctgggctgtg agataaggga ctcctgctgg cattcggctg tggccctaga gcagagcatt 360
gagttcataa gagattccct catttcttca gaagaggaag aaggcttggt acgctgtgtg 420
gatggctcct cctcttcctt ccgctccaag aagcccatag taggggtcat tgggcctggc 480
tccagttctg tagccattca ggtccagaat ttgctccagc ttttcaacat acctcagatt 540
gcttactcag caaccagcat ggatctgagt gacaagactc tgttcaaata tttcatgagg 600
gttgtgcctt cagatgctca gcaggcaagg gccatggtgg acatagtgaa gaggtacaac 660
tggacctatg tatcagccgt gcacacagaa ggtaagtttc ctttgcatac atcgagtata 720
t 721

<210> SEQ ID NO 174
<211> LENGTH: 310
<212> TYPE: DNA
<213> ORGANISM: Homo sapiens

<400> SEQUENCE: 174
atccctctgc ttatctatgt tttcacacag gcaactatgg agaaagtggg atggaagcct 60
tcaaagatat gtcagcgaag gaagggattt gcatcgccca ctcttacaaa atctacagta 120
atgcagggga gcagagcttt gataagctgc tgaagaagct cacaagtcac ttgcccaagg 180
cccgggtggt ggcctgcttc tgtgagggca tgacggtgag aggtctgctg atggccatga 240
ggcgcctggg tctagcggga gaatttctgc ttctgggcag gtgagtgata ataagaaaat 300
ttacatggag 310

<210> SEQ ID NO 175
<211> LENGTH: 296
<212> TYPE: DNA
<213> ORGANISM: Homo sapiens

<400> SEQUENCE: 175
taagctgagg gttttttat ttccccacag tgatggctgg gctgacaggt atgatgtgac 60
agatggatat cagcgagaag ctgttggtgg catcacaatc aagctccaat ctcccgatgt 120
caagtggttt gatgattatt atctgaagct ccggccagaa acaaaccacc gaaacccttg 180
gtttcaagaa ttttggcagc atcgttttca gtgccgactg gaagggtttc cacaggagaa 240
cagcaaatac aacaagactt gcaatagtaa gcagatttat tatttcattt aaaatg 296

<210> SEQ ID NO 176
<211> LENGTH: 307
<212> TYPE: DNA
<213> ORGANISM: Homo sapiens

<400> SEQUENCE: 176
caaagctatg cttaatttgt ttcccaacag gttctctgac tctgaaaaca catcatgttc 60
aggattccaa aatgggattt gtgatcaacg ccatctattc gatggcctat gggctccaca 120
acatgcagat gtccctctgc ccaggctatg caggactctg tgatgccatg aagccaattg 180
atggacggaa acttttggag tccctgatga aaaccaattt tactggggtt tctggagata 240
cgatcctatt cgatgagaat ggagactctc caggaaggta ttgtgttaca attctcctct 300
gcagagt 307

<210> SEQ ID NO 177
<211> LENGTH: 229
<212> TYPE: DNA
<213> ORGANISM: Homo sapiens

<400> SEQUENCE: 177
ctgcataatt atcatattct tattcctaag gtatgaaata atgaatttca aggaaatggg 60
aaaagattac tttgattata tcaacgttgg aagttgggac aatggagaat taaaaatgga 120
tgatgatgaa gtatggtcca agaaaagcaa catcatcaga tctgtgtgca gtgaaccatg 180
tgagaaaggc cagatcaagg taaaatggaa tctatgtttc tttcatttt 229

<210> SEQ ID NO 178
<211> LENGTH: 187
<212> TYPE: DNA
<213> ORGANISM: Homo sapiens

<400> SEQUENCE: 178
aaaaatctaa atttcaaata tttgccttag gtgatccgaa agggagaagt cagctgttgt 60
tggacctgta caccttgtaa ggagaatgag tatgtctttg atgagtacac atgcaaggca 120
tgccaactgg ggtcttggcc cactgatgat ctcacaggta atctatcaca atctcaccac 180
atataaa 187

<210> SEQ ID NO 179
<211> LENGTH: 1000
<212> TYPE: DNA
<213> ORGANISM: Homo sapiens

<400> SEQUENCE: 179
cctttacaat atgtgtttgt gtctctgcag gttgtgactt gatcccagta cagtatcttc 60
gatggggtga ccctgaaccc attgcagctg tggtgtttgc ctgccttggc ctcctggcca 120
ccctgtttgt tactgtagtc ttcatcattt accgtgatac accagtagtc aagtcctcaa 180
gcagggaact ctgctacatt atccttgctg gcatctgcct gggctactta tgtaccttct 240
gcctcattgc gaagcccaaa cagatttact gctaccttca gagaattggc attggtctct 300
ccccagccat gagctactca gcccttgtaa caaagaccaa ccgtattgca aggatcctgg 360
ctggcagcaa gaagaagatc tgtaccaaaa agcccagatt catgagtgcc tgtgcccagc 420
tagtgattgc tttcattctc atatgcatcc agttgggcat catcgttgcc ctctttataa 480
tggagcctcc tgacataatg catgactacc caagcattcg agaagtctac ctgatctgta 540
acaccaccaa cctaggagtt gtcactccac ttggatacaa tggattgttg attttgagct 600
gcaccttcta tgcgttcaag accagaaatg ttccagctaa cttcaacgag gccaagtata 660
tcgccttcac aatgtacacg acctgcatta tatggctagc ttttgtgcca atctactttg 720
gcagcaacta caaaatcatc accatgtgtt tctcggtcag cctcagtgcc acagtggccc 780
taggctgcat gtttgtgccg aaggtgtaca tcatcctggc caaaccagag agaaacgtgc 840
gcagcgcctt caccacatct accgtggtgc gcatgcatgt aggggatggc aagtcatcct 900
ccgcagccag cagatccagc agcctagtca acctgtggaa gagaaggggc tcctctgggg 960
aaaccttaag gtaaaagttg tgggggctta cagggatgct 1000

<210> SEQ ID NO 180
<211> LENGTH: 973
<212> TYPE: DNA
<213> ORGANISM: Homo sapiens

<400> SEQUENCE: 180
agtcaccttt cctctccctt ctctcctcag ttccaatgga aaatccgtca cgtgggccca 60
gaatgagaag agcagccggg ggcagcacct gtggcagcgc ctgtccatcc acatcaacaa 120
gaaagaaaac cccaaccaaa cggccgtcat caagcccttc cccaagagca cggagagccg 180
tggcctgggc gctggcgctg gcgcaggcgg gagcgctggg ggcgtggggg ccacgggcgg 240
tgcgggctgc gcaggcgccg gcccaggcgg gcccgagtcc ccagacgccg gccccaaggc 300
gctgtatgat gtggccgagg ctgaggagca cttcccggcg cccgcgcggc cgcgctcacc 360
gtcgcccatc agcacgctga gccaccgcgc gggctcggcc agccgcacgg acgacgatgt 420
gccgtcgctg cactcggagc ctgtggcgcg cagcagctcc tcgcagggct ccctcatgga 480
gcagatcagc agtgtggtca cccgcttcac ggccaacatc agcgagctca actccatgat 540
gctgtccacc gcggccccca gccccggcgt cggcgccccg ctctgctcgt cctacctgat 600
ccccaaagag atccagttgc ccacgaccat gacgaccttt gccgaaatcc agcctctgcc 660
ggccatcgaa gtcacgggag gcgcgcagcc cgcggcaggg gcgcaggcgg ctggggacgc 720
ggcccgggag agccccgcgg ccggtcccga ggctgcggcc gccaagccag acctggagga 780
gctggtggct ctcaccccgc cgtcccctt cagagactcg gtggactcgg ggagcacaac 840
ccccaactcg ccagtgtccg agtcggccct ctgtatcccg tcgtctccca aatatgacac 900
tcttatcata agagattaca ctcagagctc ctcgtcgttg tgaatgtccc tggaaagcac 960
gccggcctgc gcg 973

<210> SEQ ID NO 181
<211> LENGTH: 171
<212> TYPE: DNA
<213> ORGANISM: Homo sapiens

<400> SEQUENCE: 181
ggaccccggg ccgcaggccc ctgaggagcg atgacggaat ataagctggt ggtggtgggc 60
gccggcggtg tgggcaagag tgcgctgacc atccagctga tccagaacca ttttgtggac 120
gaatacgacc ccactataga ggtgagcctg gcgccgccgt ccaggtgcca g 171

<210> SEQ ID NO 182

<211> LENGTH: 239
<212> TYPE: DNA
<213> ORGANISM: Homo sapiens

<400> SEQUENCE: 182
agggggtccc tgagccctgt cctcctgcag gattcctacc ggaagcaggt ggtcattgat 60
ggggagacgt gcctgttgga catcctggat accgccggcc aggaggagta cagcgccatg 120
cgggaccagt acatgcgcac cggggagggc ttcctgtgtg tgtttgccat caacaacacc 180
aagtcttttg aggacatcca ccagtacagg tgaaccccgt gaggctggcc cgggagccc 239

<210> SEQ ID NO 183
<211> LENGTH: 220
<212> TYPE: DNA
<213> ORGANISM: Homo sapiens

<400> SEQUENCE: 183
cgtagccagc tctcgctttc cacctctcag ggagcagatc aaacgggtga aggactcgga 60
tgacgtgccc atggtgctgg tggggaacaa gtgtgacctg gctgcacgca ctgtggaatc 120
tcggcaggct caggacctcg cccgaagcta cggcatcccc tacatcgaga cctcggccaa 180
gacccggcag gtgaggcagc tctccacccc acagctagcc 220

<210> SEQ ID NO 184
<211> LENGTH: 123
<212> TYPE: DNA
<213> ORGANISM: Homo sapiens

<400> SEQUENCE: 184
agcactcact gaccctctcc cttgacacag ggcagccgct ctggctctag ctccagctcc 60
gggaccctct gggacccccc gggacccatg tgacccagcg gcccctcgcg ctgtaagtct 120
ccc 123

<210> SEQ ID NO 185
<211> LENGTH: 140
<212> TYPE: DNA
<213> ORGANISM: Homo sapiens

<400> SEQUENCE: 185
ggagttggaa gcgcgttacc cgggtccaaa atgcccaaga agaagccgac gcccatccag 60
ctgaacccgg cccccgacgg ctctgcagtt aacgggacca gctctgcgga gtaagtatgg 120
ggcgggcggt gaacctcggg 140

<210> SEQ ID NO 186
<211> LENGTH: 271
<212> TYPE: DNA
<213> ORGANISM: Homo sapiens

<400> SEQUENCE: 186
tattgacttg tgctccccac tttggaacag gaccaacttg gaggccttgc agaagaagct 60
ggaggagcta gagcttgatg agcagcagcg aaagcgcctt gaggcctttc ttacccagaa 120
gcagaaggtg ggagaactga aggatgacga ctttgagaag atcagtgagc tgggggctgg 180
caatggcggt gtggtgttca aggtctccca caagccttct ggcctggtca tggccagaaa 240
ggtgagtttg ccttgattaa caggtaattg g 271

<210> SEQ ID NO 187
<211> LENGTH: 207

<212> TYPE: DNA
<213> ORGANISM: Homo sapiens

<400> SEQUENCE: 187
aaaacctctc tttcttccac ctttctccag ctaattcatc tggagatcaa acccgcaatc 60
cggaaccaga tcataaggga gctgcaggtt ctgcatgagt gcaactctcc gtacatcgtg 120
ggcttctatg gtgcgttcta cagcgatggc gagatcagta tctgcatgga gcacatggta 180
tgtgacaccc tctcagcctc tggagca 207

<210> SEQ ID NO 188
<211> LENGTH: 138
<212> TYPE: DNA
<213> ORGANISM: Homo sapiens

<400> SEQUENCE: 188
cactaactgg tctggtattc tcgatcttag gatggaggtt ctctggatca agtcctgaag 60
aaagctggaa gaattcctga acaaatttta ggaaaagtta gcattgctgt gagtatgtta 120
tgaagttttt cttctaag 138

<210> SEQ ID NO 189
<211> LENGTH: 112
<212> TYPE: DNA
<213> ORGANISM: Homo sapiens

<400> SEQUENCE: 189
ttcttttctt ttacattccc tttcctctag gtaataaaag gcctgacata tctgagggag 60
aagcacaaga tcatgcacag aggtaagaag ttatttgcta gttattttgc tt 112

<210> SEQ ID NO 190
<211> LENGTH: 185
<212> TYPE: DNA
<213> ORGANISM: Homo sapiens

<400> SEQUENCE: 190
ccctcctttt ctattttctc ttccctgcag atgtcaagcc ctccaacatc ctagtcaact 60
cccgtgggga gatcaagctc tgtgactttg ggtcagcgg gcagctcatc gactccatgg 120
ccaactcctt cgtgggcaca aggtcctaca tgtcggtatg aacagaagtt tccattgctt 180
gagct 185

<210> SEQ ID NO 191
<211> LENGTH: 262
<212> TYPE: DNA
<213> ORGANISM: Homo sapiens

<400> SEQUENCE: 191
ggtgattatc actgtctgtc tctcctgcag ccagaaagac tccaggggac tcattactct 60
gtgcagtcag acatctggag catgggactg tctctggtag agatggcggt tgggaggtat 120
cccatccctc ctccagatgc caaggagctg gagctgatgt ttgggtgcca ggtggaagga 180
gatgcggctg agaccccacc caggccaagg acccccggga ggccccttag ctgtgagtag 240
cctggtgtgt ccccatcttg ga 262

<210> SEQ ID NO 192
<211> LENGTH: 125
<212> TYPE: DNA
<213> ORGANISM: Homo sapiens

<400> SEQUENCE: 192
aagtattttt tctttttata aaatttgtag catacggaat ggacagccga cctcccatgg 60
caatttttga gttgttggat tacatagtca acgaggtaag tactgcctgg tttccttcac 120
cttgg 125

<210> SEQ ID NO 193
<211> LENGTH: 122
<212> TYPE: DNA
<213> ORGANISM: Homo sapiens

<400> SEQUENCE: 193
catttttctt atctcaacat gtgtttgcag cctcctccaa aactgcccag tggagtgttc 60
agtctggaat ttcaagattt tgtgaataaa tggtaagttg gctccttgtt ctctggaagc 120
gt 122

<210> SEQ ID NO 194
<211> LENGTH: 106
<212> TYPE: DNA
<213> ORGANISM: Homo sapiens

<400> SEQUENCE: 194
cagctcttac cttgtctttc ttcctttaag cttaataaaa aaccccgcag agagagcaga 60
tttgaagcaa ctcatggtga gtctatttat tccggattct tacagt 106

<210> SEQ ID NO 195
<211> LENGTH: 174
<212> TYPE: DNA
<213> ORGANISM: Homo sapiens

<400> SEQUENCE: 195
caccacgtcc tctcgtttcc ttacatgcag gttcatgctt ttatcaagag atctgatgct 60
gaggaagtgg attttgcagg ttggctctgc tccaccatcg gccttaacca gcccagcaca 120
ccaacccatg ctgctggcgt ctaagtgttt gggaagcaac aaagagcgag tccc 174

<210> SEQ ID NO 196
<211> LENGTH: 80
<212> TYPE: DNA
<213> ORGANISM: Homo sapiens

<400> SEQUENCE: 196
tcaaagctgt gatcaccctg atgtcaccga atggccacag cttgtaaaag gtaattttga 60
attattttac agcctttaaa 80

<210> SEQ ID NO 197
<211> LENGTH: 102
<212> TYPE: DNA
<213> ORGANISM: Homo sapiens

<400> SEQUENCE: 197
tgctaactgt ttctcaattg cattttacag atcaggagaa cctcagtctg acgacattga 60
agctagccga atgtaagtgt aacttggttg agactgtggt tc 102

<210> SEQ ID NO 198
<211> LENGTH: 359
<212> TYPE: DNA
<213> ORGANISM: Homo sapiens

<400> SEQUENCE: 198

```
ctgtgcttat tgtttgaatg tttggtacag gaagcgagca gctgcaaagc atctaataga     60
acgctactac caccagttaa ctgagggctg tggaaatgaa gcctgcacga atgagttttg    120
tgcttcctgt ccaacttttc ttcgtatgga taataatgca gcagctatta aagccctcga    180
gctttataag attaatgcaa aactctgtga tcctcatccc tccaagaaag gagcaagctc    240
agcttacctt gagaactcga aaggtgcccc caacaactcc tgctctgaga taaaaatgaa    300
caagaaaggc gctagaattg attttaaagg taagatgttt tattttcaat tgagaattg     359
```

```
<210> SEQ ID NO 199
<211> LENGTH: 1307
<212> TYPE: DNA
<213> ORGANISM: Homo sapiens

<400> SEQUENCE: 199

aatgttctct tttttcctct gattttctag atgtgactta cttaacagaa gagaaggtat     60
atgaaattct tgaattatgt agagaaagag aggattattc ccctttaatc cgtgttattg    120
gaagagtttt ttctagtgct gaggcattgg tacagagctt ccggaaagtt aaacaacaca    180
ccaaggaaga actgaaatct cttcaagcaa aagatgaaga caaagatgaa gatgaaaagg    240
aaaaagctgc atgttctgct gctgctatgg aagaagactc agaagcatct tcctcaagga    300
taggtgatag ctcacaggga gacaacaatt tgcaaaaatt aggccctgat gatgtgtctg    360
tggatattga tgccattaga agggtctaca ccagattgct ctctaatgaa aaaattgaaa    420
ctgcctttct caatgcactt gtatatttgt cacctaacgt ggaatgtgac ttgacgtatc    480
acaatgtata ctctcgagat cctaattatc tgaatttgtt cattatcgta atggagaata    540
gaaatctcca cagtcctgaa tatctggaaa tggctttgcc attattttgc aaagcgatga    600
gcaagctacc ccttgcagcc caaggaaaac tgatcagact gtggtctaaa tacaatgcag    660
accagattcg gagaatgatg gagacatttc agcaacttat tacttataaa gtcataagca    720
atgaatttaa cagtcgaaat ctagtgaatg atgatgatgc cattgttgct gcttcgaagt    780
gcttgaaaat ggtttactat gcaaatgtag tgggagggga agtggacaca aatcacaatg    840
aagaagatga tgaagagccc atccctgagt ccagcgagct gacacttcag gaacttttgg    900
gagaagaaag aagaaacaag aaaggtcctc gagtggaccc cctggaaact gaacttggtg    960
ttaaaaccct ggattgtcga aaaccactta tccctttga agagtttatt aatgaaccac   1020
tgaatgaggt tctagaaatg gataaagatt atactttttt caaagtagaa acagagaaca   1080
aattctcttt tatgacatgt ccctttatat tgaatgctgt cacaaagaat ttgggattat   1140
attatgacaa tagaattcgc atgtacagtg aacgaagaat cactgttctc tacagcttag   1200
ttcaaggaca gcagttgaat ccatatttga gactcaaagt tagacgtgac catatcatag   1260
atgatgcact tgtccgggta agttgggctg ctagattaaa aacctaa                 1307
```

```
<210> SEQ ID NO 200
<211> LENGTH: 205
<212> TYPE: DNA
<213> ORGANISM: Homo sapiens

<400> SEQUENCE: 200

tcttttcatg tttatctttt caatcactag ctagagatga tcgctatgga aaatcctgca     60
gacttgaaga agcagttgta tgtggaattt gaaggagaac aaggagttga tgagggaggt    120
gtttccaaag aatttttca gctggttgtg gaggaaatct tcaatccaga tattggtaaa    180
```

tacattagta atgtgattat ggtgt 205

<210> SEQ ID NO 201
<211> LENGTH: 266
<212> TYPE: DNA
<213> ORGANISM: Homo sapiens

<400> SEQUENCE: 201
taatgtattt ttaaaaatca tttcttatag gtatgttcac atacgatgaa tctacaaaat 60
tgttttggtt taatccatct tcttttgaaa ctgagggtca gtttactctg attggcatag 120
tactgggtct ggctatttac aataactgta tactggatgt acattttccc atggttgtct 180
acaggaagct aatggggaaa aaaggaactt ttcgtgactt gggagactct cacccagtaa 240
gttctttgtc attttttaa ttcagt 266

<210> SEQ ID NO 202
<211> LENGTH: 225
<212> TYPE: DNA
<213> ORGANISM: Homo sapiens

<400> SEQUENCE: 202
tggcctcaat ttaccatttc tggttgctag gttctatatc agagtttaaa agatttattg 60
gagtatgaag ggaatgtgga agatgacatg atgatcactt tccagatatc acagacagat 120
ctttttggta acccaatgat gtatgatcta aaggaaaatg gtgataaaat tccaattaca 180
aatgaaaaca ggaaggtaat aaatgttttt atgtcacatt ttgtc 225

<210> SEQ ID NO 203
<211> LENGTH: 216
<212> TYPE: DNA
<213> ORGANISM: Homo sapiens

<400> SEQUENCE: 203
agaagttctt gtgattaatg ttttctacag gaatttgtca atctttattc tgactacatt 60
ctcaataaat cagtagaaaa acagttcaag gcttttcgga gaggttttca tatggtgacc 120
aatgaatctc ccttaaagta cttattcaga ccagaagaaa ttgaattgct tatatgtgga 180
agccgggtaa gaaagcaggt gtctgcaaaa agtcat 216

<210> SEQ ID NO 204
<211> LENGTH: 134
<212> TYPE: DNA
<213> ORGANISM: Homo sapiens

<400> SEQUENCE: 204
taactaagac atattttctt gaatttgcag aatctagatt tccaagcact agaagaaact 60
acagaatatg acggtggcta taccagggac tctgttctga ttaggtgagg tacttagttc 120
ttcagaggaa gatt 134

<210> SEQ ID NO 205
<211> LENGTH: 204
<212> TYPE: DNA
<213> ORGANISM: Homo sapiens

<400> SEQUENCE: 205
tgaaaccagt attgtatttt ttctcattag ggagttctgg gaaatcgttc attcatttac 60
agatgaacag aaaagactct tcttgcagtt tacaacgggc acagacagag cacctgtggg 120
aggactagga aaattaaaga tgattatagc caaaaatggc ccagacacag aaaggtaggt 180
aattattaac ttgtgactgt atac 204

<210> SEQ ID NO 206
<211> LENGTH: 181
<212> TYPE: DNA
<213> ORGANISM: Homo sapiens

<400> SEQUENCE: 206
tcctgttttt ttccccttt ctctatttag gttacctaca tctcatactt gctttaatgt 60
gcttttactt ccggaatact caagcaaaga aaaacttaaa gagagattgt tgaaggccat 120
cacgtatgcc aaaggatttg gcatgctgta aaacaaaaca aaacaaaata aaacaaaaaa 180
a 181

<210> SEQ ID NO 207
<211> LENGTH: 198
<212> TYPE: DNA
<213> ORGANISM: Homo sapiens

<400> SEQUENCE: 207
gaggggtttt ctggtgcgtc ctggtccacc atggccaaac caacaagcaa agattcaggc 60
ttgaaggaga agtttaagat tctgttggga ctgggaacac cgaggccaaa tcccaggtct 120
gcagagggta aacagacgga gtttatcatc accgcggaaa tactgagagt gagtgagcta 180
cctgtgtctt tgctaggc 198

<210> SEQ ID NO 208
<211> LENGTH: 147
<212> TYPE: DNA
<213> ORGANISM: Homo sapiens

<400> SEQUENCE: 208
gccccttttt cttctttcat ctctctccag gaactgagca tggaatgtgg cctcaacaat 60
cgcatccgga tgatagggca gatttgtgaa gtcgcaaaaa ccaagaaatt tgaagaggta 120
ggtttatcca gttgagctac tagagag 147

<210> SEQ ID NO 209
<211> LENGTH: 171
<212> TYPE: DNA
<213> ORGANISM: Homo sapiens

<400> SEQUENCE: 209
cctcaccgct gtcccctctg ctggtgacag cacgcagtgg aagcactctg gaaggcggtc 60
gcggatctgt tgcagccgga gcggccgctg gaggcccggc acgcggtgct ggctctgctg 120
aaggccatcg tgcaggggca ggtaaggccc agggcgacgc tgggatgggt g 171

<210> SEQ ID NO 210
<211> LENGTH: 205
<212> TYPE: DNA
<213> ORGANISM: Homo sapiens

<400> SEQUENCE: 210
ctctgctgat cctgtggctt ttgtctttag ggcgagcgtt tgggggtcct cagagccctc 60
ttctttaagg tcatcaagga ttacccttcc aacgaagacc ttcacgaaag gctggaggtt 120
ttcaaggccc tcacagacaa tgggagacac atcacctact tggaggaaga gctgggtggg 180
tgccaccttg ggttggaggt ttctc 205

<210> SEQ ID NO 211
<211> LENGTH: 178
<212> TYPE: DNA
<213> ORGANISM: Homo sapiens

<400> SEQUENCE: 211
cctcgcaaac tgccgccgct tctcccccag ctgactttgt cctgcagtgg atggatgttg 60
gcttgtcctc ggaattcctt ctggtgctgg tgaacttggt caaattcaat agctgttacc 120
tcgacgagta catcgcaagg atggttcagt aagaaaagaa ttgagatcct gttctgat 178

<210> SEQ ID NO 212
<211> LENGTH: 109
<212> TYPE: DNA
<213> ORGANISM: Homo sapiens

<400> SEQUENCE: 212
tgccgggact gagctcggtg ctccctgcag gatgatctgt ctgctgtgcg tccggaccgc 60
gtcctctgtg gacatagagg tcagtgcctc ccctccccag ggccggccc 109

<210> SEQ ID NO 213
<211> LENGTH: 186
<212> TYPE: DNA
<213> ORGANISM: Homo sapiens

<400> SEQUENCE: 213
acgggcgtga gccgtctccc tctccaccag gtctccctgc aggtgctgga cgccgtggtc 60
tgctacaact gcctgccggc tgagagcctc ccgctgttca tcgttaccct ctgtcgcacc 120
atcaacgtca aggagctctg cgagccttgc tggaaggtgg ggtttctgaa actgctctgg 180
aaggtt 186

<210> SEQ ID NO 214
<211> LENGTH: 134
<212> TYPE: DNA
<213> ORGANISM: Homo sapiens

<400> SEQUENCE: 214
ccagcccctg acacgcattg tgtctcgcag ctgatgcgga acctccttgg cacccacctg 60
ggccacagcg ccatctacaa catgtgccac ctcatggagg acaggtgagt gtggtgggtg 120
gggcgcaggg cagt 134

<210> SEQ ID NO 215
<211> LENGTH: 187
<212> TYPE: DNA
<213> ORGANISM: Homo sapiens

<400> SEQUENCE: 215
acattccgtc tctctgggga acacttttag agcctacatg gaggacgcgc ccctgctgag 60
aggagccgtg ttttttgtgg gcatggctct ctggggagcc caccggctct attctctcag 120
gaactcgccg acatctgtgt tgccatcatt ttaccaggta aggcggtttc tgtgtgcagt 180
gagctgg 187

<210> SEQ ID NO 216
<211> LENGTH: 204
<212> TYPE: DNA
<213> ORGANISM: Homo sapiens

<400> SEQUENCE: 216
ccctgtgtgc tggccgggct cgtgttccag gccatggcat gtccgaacga ggtggtgtcc 60
tatgagatcg tcctgtccat caccaggctc atcaagaagt ataggaagga gctccaggtg 120
gtggcgtggg acattctgct gaacatcatc gaacggctcc ttcagcagct ccaggtgggg 180
tgggggcagg agctccgggg agca 204

<210> SEQ ID NO 217
<211> LENGTH: 198
<212> TYPE: DNA
<213> ORGANISM: Homo sapiens

<400> SEQUENCE: 217
cagcctgtgt catcgtgcct ggtactgcag accttggaca gcccggagct caggaccatc 60
gtccatgacc tgttgaccac ggtggaggag ctgtgtgacc agaacgagtt ccacgggtct 120
caggagagat actttgaact ggtggagaga tgtgcggacc agaggcctgt gagacccccct 180 cctgggtggg gcctttgg 198

<210> SEQ ID NO 218
<211> LENGTH: 164
<212> TYPE: DNA
<213> ORGANISM: Homo sapiens

<400> SEQUENCE: 218
gaggggcaac accggctctt cttttgacag gagtcctccc tcctgaacct gatctcctat 60
agagcgcagt ccatccaccc ggccaaggac ggctggattc agaacctgca ggcgctgatg 120
gagagattct tcaggtaggg ggtcctctgt agccttgcct ggca 164

<210> SEQ ID NO 219
<211> LENGTH: 142
<212> TYPE: DNA
<213> ORGANISM: Homo sapiens

<400> SEQUENCE: 219
cacccgcccc agcaggctgc cgtcccgcag gagcgagtcc cgaggcgccg tgcgcatcaa 60
ggtgctggac gtgctgtcct ttgtgctgct catcaacagg cagttctatg aggtgcgtgt 120
ccaggcggcc gcagctgggg gc 142

<210> SEQ ID NO 220
<211> LENGTH: 216
<212> TYPE: DNA
<213> ORGANISM: Homo sapiens

<400> SEQUENCE: 220
cgctcattgg cctcccttgt gcctgtgcag gaggagctga ttaactcagt ggtcatctcg 60
cagctctccc acatccccga ggataaagac caccaggtcc gaaagctggc cacccagttg 120
ctggtggacc tggcagaggg ctgccacaca caccacttca acagcctgct ggacatcatc 180
gagaaggtga gagccgttgt acccggggcc gggtgc 216

<210> SEQ ID NO 221
<211> LENGTH: 177
<212> TYPE: DNA
<213> ORGANISM: Homo sapiens

<400> SEQUENCE: 221
tgtgtgtaag tcctggcctt ctcttcaaag gtgatggccc gctccctctc cccaccccg 60 gagctggaag aaagggatgt ggccgcatac tcggcctcct tggaggatgt gaagacagcc 120
gtcctggggc ttctggtcat ccttcaggtg ggtgttctgc acgaggcctc tgctccc 177

<210> SEQ ID NO 222
<211> LENGTH: 183
<212> TYPE: DNA
<213> ORGANISM: Homo sapiens

<400> SEQUENCE: 222
gccgtggtga gctgcgtcct ctctctgcag accaagctgt acaccctgcc tgcaagccac 60
gccacgcgtg tgtatgagat gctggtcagc cacattcagc tccactacaa gcacagctac 120
accctgccaa tcgcgagcag catccggctg caggtatggt ggctggggtt gcgcagccag 180
ttc 183

<210> SEQ ID NO 223
<211> LENGTH: 167
<212> TYPE: DNA
<213> ORGANISM: Homo sapiens

<400> SEQUENCE: 223
ctctggcttt caccatcctc ttcctgacag gcctttgact tcctgttgct gctgcgggcc 60
gactcactgc accgcctggg cctgcccaac aaggatggag tcgtgcggtt cagcccctac 120
tgcgtctgcg actacatgta cgcgggacct cgcccacggc ccatgag 167

<210> SEQ ID NO 224
<211> LENGTH: 211
<212> TYPE: DNA
<213> ORGANISM: Homo sapiens

<400> SEQUENCE: 224
tggcctcagc tgcttctctt gcttctgcag ggagccagag agaggctctg agaagaagac 60
cagcggcccc ctttctcctc ccacagggcc tcctggcccg gcgcctgcag gccccgccgt 120
gcggctgggg tccgtgccct actccctgct cttccgcgtc ctgctgcagt gcttgaagca 180
ggtgagtggg gccgggcagg gaccatccgt c 211

<210> SEQ ID NO 225
<211> LENGTH: 183
<212> TYPE: DNA
<213> ORGANISM: Homo sapiens

<400> SEQUENCE: 225
gccctgtcct gacgcctcct ctcctcgcag gagtctgact ggaaggtgct gaagctggtt 60
ctgggcaggc tgcctgagtc cctgcgctat aaagtgctca tctttacttc cccttgcagt 120
gtggaccagc tgtgctctgc tctctgctcc atggtaccat ggccggcctg gggttggggt 180
ggg 183

<210> SEQ ID NO 226
<211> LENGTH: 195
<212> TYPE: DNA
<213> ORGANISM: Homo sapiens

<400> SEQUENCE: 226
agaggtttca tgcctggatt tggtcatcag ctttcaggcc caaagacact ggagcggctc 60
cgaggcgccc cagaaggctt ctccagaact gacttgcacc tggccgtggt tccagtgctg 120
acagcattaa tctcttacca taactacctg gacaaaacca aacaggtagg aggtcagagc 180
aggacaggcg agctt 195

<210> SEQ ID NO 227
<211> LENGTH: 250
<212> TYPE: DNA
<213> ORGANISM: Homo sapiens

<400> SEQUENCE: 227
gtggggcctg aggtgtcctg tctcctgcag cgcgagatgg tctactgcct ggagcagggc 60
ctcatccacc gctgtgccag ccagtgcgtc gtggccttgt ccatctgcag cgtggagatg 120
cctgacatca tcatcaaggc gctgcctgtt ctggtggtga agctcacgca catctcagcc 180
acagccagca tggccgtccc actgctggag ttcctgtcca gtgagtcccc gccctgcctg 240
cgcatgcacc 250

<210> SEQ ID NO 228
<211> LENGTH: 154
<212> TYPE: DNA
<213> ORGANISM: Homo sapiens

<400> SEQUENCE: 228
ctcccctgac caccctctcc attaccgcag ctctggccag gctgccgcac ctctacagga 60
actttgccgc ggagcagtat gccagtgtgt tcgccatctc cctgccgtac accaacccct 120
ccaagtgagt ggtcgcccca ggccctgtgc ctcc 154

<210> SEQ ID NO 229
<211> LENGTH: 163
<212> TYPE: DNA
<213> ORGANISM: Homo sapiens

<400> SEQUENCE: 229
gatggagtgc cagccccctt ctcatctcag gtttaatcag tacatcgtgt gtctggccca 60
tcacgtcata gccatgtggt tcatcaggtg ccgcctgccc ttccggaagg attttgtccc 120
tttcatcact aaggtgggct cagggccggt gaaggctgtg tct 163

<210> SEQ ID NO 230
<211> LENGTH: 155
<212> TYPE: DNA
<213> ORGANISM: Homo sapiens

<400> SEQUENCE: 230
ctcactgtct gggtgtgctc actctgccag ggcctgcggt ccaatgtcct cttgtctttt 60
gatgacaccc ccgagaagga cagcttcagg gcccggagta ctagtctcaa cgagagaccc 120
aagaggtacg gcctgcgggg gtgtgcctgg agtcg 155

<210> SEQ ID NO 231
<211> LENGTH: 189
<212> TYPE: DNA
<213> ORGANISM: Homo sapiens

<400> SEQUENCE: 231
gggcgttggg gctccttcct cacccgatag tctgaggata gccagacccc ccaaacaagg 60
cttgaataac tctccacccg tgaaagaatt caaggagagc tctgcagccg aggccttccg 120
gtgccgcagc atcagtgtgt ctgaacatgt ggtccgcagg tagcgggact gtcgggtggg 180
gggcacgga 189

<210> SEQ ID NO 232
<211> LENGTH: 225
<212> TYPE: DNA
<213> ORGANISM: Homo sapiens

<400> SEQUENCE: 232
cctgaccctg gtcacggcct ctccctccag caggatacag acgtccctca ccagtgccag 60
cttggggtct gcagatgaga actccgtggc ccaggctgac gatagcctga aaaacctcca 120
cctggagctc acggaaacct gtctggacat gatggctcga tacgtcttct ccaacttcac 180
ggctgtcccg aagaggtcca ggcggcacta cagggctggg cgggc 225

<210> SEQ ID NO 233
<211> LENGTH: 213
<212> TYPE: DNA
<213> ORGANISM: Homo sapiens

<400> SEQUENCE: 233
aagctgggtt tcacgctccc tgtcttctag gtctcctgtg ggcgagttcc tcctagcggg 60
tggcaggacc aaaacctggc tggttgggaa caagcttgtc actgtgacga caagcgtggg 120
aaccgggacc cggtcgttac taggcctgga ctcgggggag ctgcagtccg gcccggagtc 180
gaggtgactg caccttcctt tcctccgcgc ctg 213

<210> SEQ ID NO 234
<211> LENGTH: 173
<212> TYPE: DNA
<213> ORGANISM: Homo sapiens

<400> SEQUENCE: 234
tccaccctgt gcgtgggatt ctcttctcag ctccagcccc ggggtgcatg tgagacagac 60
caaggaggcg ccggccaagc tggagtccca ggctgggcag caggtgtccc gtggggcccg 120
ggatcgggtc cgttccatgt cgggtgagcc ttggccccag ccacctccac aca 173

<210> SEQ ID NO 235
<211> LENGTH: 273
<212> TYPE: DNA
<213> ORGANISM: Homo sapiens

<400> SEQUENCE: 235
tggtcaccag tcctctgccc tcttcttcag ggggccatgg tcttcgagtt ggcgccctgg 60
acgtgccggc ctcccagttc ctgggcagtg ccacttctcc aggaccacgg actgcaccag 120
ccgcgaaacc tgagaaggcc tcagctggca cccgggttcc tgtgcaggag aagacgaacc 180
tggcggccta tgtgcccctg ctgacccagg gctgggcgga gatcctggtc cggaggccca 240
caggtactgg gcggggctgg cctgagcgcc atc 273

<210> SEQ ID NO 236
<211> LENGTH: 264
<212> TYPE: DNA
<213> ORGANISM: Homo sapiens

<400> SEQUENCE: 236
ctcaggccaa aggtgctgcc gcctccgcag ggaacaccag ctggctgatg agcctggaga 60
acccgctcag ccctttctcc tcggacatca acaacatgcc cctgcaggag ctgtctaacg 120
ccctcatggc ggctgagcgc ttcaaggagc accgggacac agccctgtac aagtcactgt 180
cggtgccggc agccagcacg gccaaacccc ctcctctgcc tcgctccaac acaggtgagt 240
ggcatggcgg gccttggcac gggc 264

<210> SEQ ID NO 237
<211> LENGTH: 129
<212> TYPE: DNA
<213> ORGANISM: Homo sapiens

<400> SEQUENCE: 237
gacgtggccg cacacggcct tcccttgcag tggcctcttt ctcctccctg taccagtcca 60
gctgccaagg acagctgcac aggagcgttt cctgggcagg tatcgcctct cagagggaag 120
cggttggct 129

<210> SEQ ID NO 238
<211> LENGTH: 182
<212> TYPE: DNA
<213> ORGANISM: Homo sapiens

<400> SEQUENCE: 238
catccagcag ccccgtctgt gtcctcccag actccgccgt ggtcatggag gagggaagtc 60
cgggcgaggt tcctgtgctg gtggagcccc cagggttgga ggacgttgag gcagcgctag 120
gcatggacag gcgcacggat gcctacagca gggtgagtgt ggctcagagc ctggaccctg 180
ct 182

<210> SEQ ID NO 239
<211> LENGTH: 548
<212> TYPE: DNA
<213> ORGANISM: Homo sapiens

<400> SEQUENCE: 239
aggggttctc tttgggatgg tcctttctag tcgtcctcag tctccagcca ggaggagaag 60
tcgctccacg cggaggagct ggttggcagg ggcatcccca tcgagcgagt cgtctcctcg 120
gagggtggcc ggccctctgt ggacctctcc ttccagccct cgcagcccct gagcaagtcc 180
agctcctctc ccgagctgca gactctgcag gacatcctcg gggaccctgg ggacaaggcc 240
gacgtgggcc ggctgagccc tgaggttaag gcccggtcac agtcagggac cctggacggg 300
gaaagtgctg cctggtcggc ctcgggcgaa gacagtcggg gccagcccga gggtcccttg 360
ccttccagct ccccccgctc gcccagtggc ctccggcccc gaggttacac catctccgac 420
tcggccccat cacgcagggg caagagagta gagagggacg ccttaaagag cagagccaca 480
gcctccaatg cagagaaagt gccaggcatc aaccccaggt gggcctcttg cttccgggcg 540
gggctcct 548

<210> SEQ ID NO 240
<211> LENGTH: 136
<212> TYPE: DNA
<213> ORGANISM: Homo sapiens

<400> SEQUENCE: 240
ctgggtgccc accatcccct ccctgtgcag tttcgtgttc ctgcagctct accattcccc 60
cttctttggc gacgagtcaa acaagccaat cctgctgccc aatgaggtag gcgtggcctc 120
cctctcctgc atccgc 136

<210> SEQ ID NO 241
<211> LENGTH: 153
<212> TYPE: DNA

<213> ORGANISM: Homo sapiens

<400> SEQUENCE: 241
ggggctcagg cagggctctg tgtgccacag tcacagtcct ttgagcggtc ggtgcagctc 60
ctcgaccaga tcccatcata cgacacccac aagatcgccg tcctgtatgt tggagaaggc 120
caggtgaggc tgcggggccg gcctaggtgc ctg 153

<210> SEQ ID NO 242
<211> LENGTH: 247
<212> TYPE: DNA
<213> ORGANISM: Homo sapiens

<400> SEQUENCE: 242
tgccaccctg cctctcccct ctccccacag agcaacagcg agctcgccat cctgtccaat 60
gagcatggct cctacaggta cacggagttc ctgacgggcc tgggccggct catcgagctg 120
aaggactgcc agccggacaa ggtgtacctg ggaggcctgg acgtgtgtgg tgaggacggc 180
cagttcacct actgctggca cgatgacatc atgcaaggta cggcctggcg cctacccgct 240
cctgctg 247

<210> SEQ ID NO 243
<211> LENGTH: 200
<212> TYPE: DNA
<213> ORGANISM: Homo sapiens

<400> SEQUENCE: 243
acaaacccat ccggccctgc tcaccctcag ccgtcttcca catcgccacc ctgatgccca 60
ccaaggacgt ggacaagcac cgctgcgaca agaagcgcca cctgggcaac gactttgtgt 120
ccattgtcta caatgactcc ggtgaggact tcaagcttgg caccatcaag gtgagtgagg 180
ggccgtcagt gaggctgggc 200

<210> SEQ ID NO 244
<211> LENGTH: 139
<212> TYPE: DNA
<213> ORGANISM: Homo sapiens

<400> SEQUENCE: 244
cggggatgac cctttctctt gtccgggcag ggccagttca actttgtcca cgtgatcgtc 60
accccgctgg actacgagtg caacctggtg tccctgcagt gcaggaaagg tagggccggg 120
tggggccctg cagtgcagg 139

<210> SEQ ID NO 245
<211> LENGTH: 152
<212> TYPE: DNA
<213> ORGANISM: Homo sapiens

<400> SEQUENCE: 245
gggcctggcg tgaccaccaa gtctccccag acatggaggg ccttgtggac accagcgtgg 60
ccaagatcgt gtctgaccgc aacctgccct tcgtggcccg ccagatggcc ctgcacgcaa 120
atgtgagtgg gggtgggtcc aggcgtgagc tg 152

<210> SEQ ID NO 246
<211> LENGTH: 159
<212> TYPE: DNA
<213> ORGANISM: Homo sapiens

<400> SEQUENCE: 246
agtgagctca ccccctgcct acgtccccag atggcctcac aggtgcatca tagccgctcc 60
aaccccaccg atatctaccc ctccaagtgg attgcccggc tccgccacat caagcggctc 120
cgccagcggg tagggaatat ggggctccct cagcggggt 159

<210> SEQ ID NO 247
<211> LENGTH: 225
<212> TYPE: DNA
<213> ORGANISM: Homo sapiens

<400> SEQUENCE: 247
acttactgcc caagccgcct ctgccttcag atctgcgagg aagccgccta ctccaacccc 60
agcctacctc tggtgcaccc tccgtcccat agcaaagccc ctgcacagac tccagccgag 120
cccacacctg gctatgaggt gggccagcgg aagcgcctca tctcctcggt ggaggacttc 180
accgagtttg tgtgaggccg gggccctccc tcctgcactg gcctt 225

<210> SEQ ID NO 248
<211> LENGTH: 152
<212> TYPE: DNA
<213> ORGANISM: Homo sapiens

<400> SEQUENCE: 248
gcgccgccgc cgccggcccg cggagccccg atgctggccc ggaggaagcc ggtgctgccg 60
gcgctcacca tcaaccctac catcgccgag ggcccatccc ctaccagcga gggcgcctcc 120
gagtgagtgg gcaggggtca gccggaggct tg 152

<210> SEQ ID NO 249
<211> LENGTH: 271
<212> TYPE: DNA
<213> ORGANISM: Homo sapiens

<400> SEQUENCE: 249
gctaacccct accctggggg gtctctgcag ggcaaacctg gtggacctgc agaagaagct 60
ggaggagctg gaacttgacg agcagcagaa gaagcggctg gaagcctttc tcacccagaa 120
agccaaggtc ggcgaactca aagacgatga cttcgaaagg atctcagagc tgggcgcggg 180
caacggcggg gtggtcacca aagtccagca cagaccctcg ggcctcatca tggccaggaa 240
ggtgagcact gcggggtcgg ggaggtcggg g 271

<210> SEQ ID NO 250
<211> LENGTH: 207
<212> TYPE: DNA
<213> ORGANISM: Homo sapiens

<400> SEQUENCE: 250
caagccagtc tcgcccctct ccccttgcag ctgatccacc ttgagatcaa gccggccatc 60
cggaaccaga tcatccgcga gctgcaggtc ctgcacgaat gcaactcgcc gtacatcgtg 120
ggcttctacg gggccttcta cagtgacggg gagatcagca tttgcatgga acacatggtg 180
agtgcgtccg gggcaggggc aggggca 207

<210> SEQ ID NO 251
<211> LENGTH: 138
<212> TYPE: DNA
<213> ORGANISM: Homo sapiens

<400> SEQUENCE: 251

```
gcctgcactc actccttgtg tgccctctag gacggcggct ccctggacca ggtgctgaaa    60

gaggccaaga ggattcccga ggagatcctg gggaaagtca gcatcgcggt gagtccaccg   120

cagacccaca tcgcgccc                                                 138
```

<210> SEQ ID NO 252
<211> LENGTH: 112
<212> TYPE: DNA
<213> ORGANISM: Homo sapiens

<400> SEQUENCE: 252

```
tcccgtgact ccctccgcgc tccctgcag gttctccggg gcttggcgta cctccgagag    60

aagcaccaga tcatgcaccg aggtaaggcc cagcccgccc tccccagagc cc           112
```

<210> SEQ ID NO 253
<211> LENGTH: 185
<212> TYPE: DNA
<213> ORGANISM: Homo sapiens

<400> SEQUENCE: 253

```
cgcccctcac ccgcagcctg ccgcctccag atgtgaagcc ctccaacatc ctcgtgaact    60

ctagagggga gatcaagctg tgtgacttcg gggtgagcgg ccagctcatc gactccatgg   120

ccaactcctt cgtgggcacg cgctcctaca tggctgtgag tccccgctgg ctctcccctc   180

cagct                                                               185
```

<210> SEQ ID NO 254
<211> LENGTH: 274
<212> TYPE: DNA
<213> ORGANISM: Homo sapiens

<400> SEQUENCE: 254

```
tgggctcttt cctccctggc tctgctgcag ccggagcggt tgcagggcac acattactcg    60

gtgcagtcgg acatctggag catgggcctg tccctggtgg agctggccgt cggaaggtac   120

cccatccccc cgcccgacgc caaagagctg gaggccatct ttggccggcc cgtggtcgac   180

ggggaagaag gagagcctca cagcatctcg cctcggccga ggccccccgg gcgccccgtc   240

agcggtacgg cctgaatctg caacttccgg tctg                               274
```

<210> SEQ ID NO 255
<211> LENGTH: 125
<212> TYPE: DNA
<213> ORGANISM: Homo sapiens

<400> SEQUENCE: 255

```
catctcacct ccatctctct ccctgtgcag gtcacgggat ggatagccgg cctgccatgg    60

ccatctttga actcctggac tatattgtga acgaggtttg tgcttgatgc cttttggctt   120

ttctt                                                               125
```

<210> SEQ ID NO 256
<211> LENGTH: 122
<212> TYPE: DNA
<213> ORGANISM: Homo sapiens

<400> SEQUENCE: 256

```
gctgacccca ccctctgttc tcctccacag ccacctccta agctgcccaa cggtgtgttc    60

acccccgact tccaggagtt tgtcaataaa tggtaggtgg agccgggctg cccacacccc   120

tg                                                                  122
```

<210> SEQ ID NO 257
<211> LENGTH: 106
<212> TYPE: DNA
<213> ORGANISM: Homo sapiens

<400> SEQUENCE: 257
cctcccggtc ctgcctcttg gaacccccag cctcatcaag aacccagcgg agcgggcgga 60
cctgaagatg ctcacagtga gtgatgccag cgggttctgg gaccgg 106

<210> SEQ ID NO 258
<211> LENGTH: 171
<212> TYPE: DNA
<213> ORGANISM: Homo sapiens

<400> SEQUENCE: 258
cgggtgctca cggctcccct ttccttgcag aaccacacct tcatcaagcg gtccgaggtg 60
gaagaagtgg attttgccgg ctggttgtgt aaaaccctgc ggctgaacca gcccggcaca 120
cccacgcgca ccgccgtgtg acagtggccg ggctccctgc gtcccgctgg t 171

<210> SEQ ID NO 259
<211> LENGTH: 123
<212> TYPE: DNA
<213> ORGANISM: Homo sapiens

<400> SEQUENCE: 259
agcggccccg gcccgggccc cggcgcgggg atggacggcc ccggggccag cgccgtggtc 60
gtgcgcgtcg gcatcccgga cctgcagcag acggtgagcc ccgccgccct gggcccggcc 120
gtg 123

<210> SEQ ID NO 260
<211> LENGTH: 264
<212> TYPE: DNA
<213> ORGANISM: Homo sapiens

<400> SEQUENCE: 260
acctgagctc acgagcccgc tccgctgcag aagtgcctgc gcctggaccc ggccgcgccc 60
gtgtgggccg ccaagcagcg cgtgctctgc gccctcaacc acagcctcca ggacgcgctc 120
aactatgggc ttttccagcc gccctcccgg ggccgcgccg gcaagttcct ggatgaggag 180
cggctcctgc aggagtaccc gcccaacctg gacacgcccc tgccctacct ggaggtaagt 240
ggccggcgcg ggggtgagct gagg 264

<210> SEQ ID NO 261
<211> LENGTH: 132
<212> TYPE: DNA
<213> ORGANISM: Homo sapiens

<400> SEQUENCE: 261
attttctcta ccttttcttt atctgagcag tttcgataca agcggcgagt ttatgcccag 60
aacctcatcg atgataagca gtttgcaaag cttcacacaa aggtaaagga tcacggggag 120
ggggctcctg ag 132

<210> SEQ ID NO 262
<211> LENGTH: 169
<212> TYPE: DNA
<213> ORGANISM: Homo sapiens

```
<400> SEQUENCE: 262

tgccaggctg actgacggcc ggtgttccag gcgaacctga agaagttcat ggactacgtc    60

cagctgcata gcacggacaa ggtggcacgc ctgttggaca aggggctgga ccccaacttc   120

catgaccctg actcaggagg tgaggagtgg agtcggggag gggcatggc              169

<210> SEQ ID NO 263
<211> LENGTH: 212
<212> TYPE: DNA
<213> ORGANISM: Homo sapiens

<400> SEQUENCE: 263

agcctgaccc ttatctgtct gtgaacccag agtgccccct gagcctcgca gcccagctgg    60

acaacgccac ggacctgcta aaggtgctga agaatggtgg tgcccacctg gacttccgca   120

ctcgcgatgg gctcactgcc gtgcactgtg ccacacgcca gcggaatgcg gcagcactga   180

cggtcagtga gggcgggggcc tggcctggag gg                                212

<210> SEQ ID NO 264
<211> LENGTH: 228
<212> TYPE: DNA
<213> ORGANISM: Homo sapiens

<400> SEQUENCE: 264

ggtgtggata ctgaggctgc tcaccctcag accctgctgg acctgggggc ttcacctgac    60

tacaaggaca gccgcggctt gacacccctc taccacagcg ccctgggggg tggggatgcc   120

ctctgctgtg agctgcttct ccacgaccac gctcagctgg ggatcaccga cgagaatggc   180

tggcaggaga tccaccaggt gtgcagggag ccgaggtggg gtcccggc                228

<210> SEQ ID NO 265
<211> LENGTH: 177
<212> TYPE: DNA
<213> ORGANISM: Homo sapiens

<400> SEQUENCE: 265

ggaccctaca gcaccttgct cttcccccag gcctgccgct ttgggcacgt gcagcatctg    60

gagcacctgc tgttctatgg ggcagacatg ggggcccaga acgcctcggg gaacacagcc   120

ctgcacatct gtgccctcta caaccaggtg cgactgtgtg tcctgcacat gcctgca      177

<210> SEQ ID NO 266
<211> LENGTH: 138
<212> TYPE: DNA
<213> ORGANISM: Homo sapiens

<400> SEQUENCE: 266

ccagctgtga ttccctcttc cccgcaacag gagagctgtg ctcgtgtcct gctcttccgt    60

ggagctaaca gggatgtccg caactacaac agccagacag ccttccaggt acaccggtgg   120

tttacaggag ctcaaggc                                                 138

<210> SEQ ID NO 267
<211> LENGTH: 127
<212> TYPE: DNA
<213> ORGANISM: Homo sapiens

<400> SEQUENCE: 267

ctcaaggcct tgacctcccc tttccctcag gtggccatca tcgcagggaa ctttgagctt    60

gcagaggtta tcaagaccca caaagactcg gatgttggtg agttctgccc acctgggcga   120
```

ccctgct 127

<210> SEQ ID NO 268
<211> LENGTH: 334
<212> TYPE: DNA
<213> ORGANISM: Homo sapiens

<400> SEQUENCE: 268
cagagtctta cctatgcccc cttaccccag taccattcag ggaaaccccc agctatgcga 60
agcggcggcg actggctggc cccagtggct tggcatcccc tcggcctctg cagcgctcag 120
ccagcgatat caacctgaag gggaggcac agccagcagc ttctcctgga ccctcgctga 180
gaagcctccc ccaccagctg ctgctccagc ggctgcaaga ggagaaagat cgtgaccggg 240
atgccgacca ggagagcaac atcagtggcc ctttagcagg cagggccggc caaagcaaga 300
tcaggtagga gggggctggc aggccctgga gggg 334

<210> SEQ ID NO 269
<211> LENGTH: 109
<212> TYPE: DNA
<213> ORGANISM: Homo sapiens

<400> SEQUENCE: 269
cccaggccta gagggggact gggcacccag cgatccgggc cctggacctg gaggggtggg 60
gggggcgccc ctccctcccg ttcaccggct ccaggcggct ttgctggtg 109

<210> SEQ ID NO 270
<211> LENGTH: 253
<212> TYPE: DNA
<213> ORGANISM: Homo sapiens

<400> SEQUENCE: 270
gggcgcgggg cggccgcggc atggagcgag cctggcgcgc ccaggagctg tattcgaatt 60
cgagctcggt tccccgcgcc ccctgcgccc cccgcaccgc cgccccgggg cccgaagcgg 120
aaactttaca gcgccgtccc cggccgcaag ttcatcgccg tgaaggcgca cagcccgcag 180
ggtgaaggcg agatcccgct gcaccgcggc gaggccgtga agggtgaggg gcgcgggggg 240
gcgcgggggg gcg 253

<210> SEQ ID NO 271
<211> LENGTH: 174
<212> TYPE: DNA
<213> ORGANISM: Homo sapiens

<400> SEQUENCE: 271
actgacggcc tgtctggctt cttcctccag tgctcagcat tggggagggc ggtttctggg 60
agggaaccgt gaaaggccgc acgggctggt tcccggccga ctgcgtggag gaagtgcaga 120
tgaggcagca tgacacacgg cctggtgagt gaccccacgg ctccccgggc agct 174

<210> SEQ ID NO 272
<211> LENGTH: 136
<212> TYPE: DNA
<213> ORGANISM: Homo sapiens

<400> SEQUENCE: 272
ctgtccatca gctcccgata ctcccttcag aaacgcggga ggaccggacg aagcggctct 60
ttcggcacta cacagtgggc tcctacgaca gcctcacctc acacaggtac gtgcagggac 120
cctggctggc gggagc 136

<210> SEQ ID NO 273
<211> LENGTH: 143
<212> TYPE: DNA
<213> ORGANISM: Homo sapiens

<400> SEQUENCE: 273
acctcactcc tccctgcttt ccttcatcag cgattatgtc attgatgaca aagtggctgt 60
cctgcagaaa cgggaccacg agggctttgg ttttgtgctc cggggagcca aaggtaatgg 120
ggagtgggtg cccgggggtc agg 143

<210> SEQ ID NO 274
<211> LENGTH: 185
<212> TYPE: DNA
<213> ORGANISM: Homo sapiens

<400> SEQUENCE: 274
gtgaagcgcc ttcctaattg ccccccgcag cagagacccc catcgaggag ttcacgccca 60
cgccagcctt cccggcgctg cagtatctcg agtcggtgga cgtggagggt gtggcctgga 120
gggccgggct gcgcacggga gacttcctca tcgaggtgag gtcgttctgg ccggtgctgc 180
ccagt 185

<210> SEQ ID NO 275
<211> LENGTH: 193
<212> TYPE: DNA
<213> ORGANISM: Homo sapiens

<400> SEQUENCE: 275
cgtccccacc cagctgcctg tctatcccag gtgaacgggg tgaacgtggt gaaggtcgga 60
cacaagcagg tggtggctct gattcgccag ggtggcaacc gcctcgtcat gaaggttgtg 120
tctgtgacaa ggaagccaga agaggacggg gctcggcgca gaggtgaggg gtcacgcttc 180
aggcctctgt gcc 193

<210> SEQ ID NO 276
<211> LENGTH: 141
<212> TYPE: DNA
<213> ORGANISM: Homo sapiens

<400> SEQUENCE: 276
ggaggtccaa ggcctccctc ttctttgcag ccccaccgcc ccccaagagg gcccccagca 60
ccacactgac cctgcgctcc aagtccatga cagctgagct cgaggaactt ggtgagtggc 120
gggggtggcg gtggaggtgg a 141

<210> SEQ ID NO 277
<211> LENGTH: 84
<212> TYPE: DNA
<213> ORGANISM: Homo sapiens

<400> SEQUENCE: 277
actcccttta ctctgtttct tgattccaag cctccattcg gagaagaaaa gggggtgagt 60
catctgcctg tgtccccagg gcct 84

<210> SEQ ID NO 278
<211> LENGTH: 191
<212> TYPE: DNA
<213> ORGANISM: Homo sapiens

<400> SEQUENCE: 278
cagctgagat ggagcctcct tgctgtgcag agaagctgga cgagatgctg gcagccgccg 60
cagagccaac gctgcggcca gacatcgcag acgcagactc cagagccgcc accgtcaaac 120
agaggcccac cagtcggagg atcacacccg ccgagattag cgtaagggcc acgggcggct 180
gggagcgctg g 191

<210> SEQ ID NO 279
<211> LENGTH: 145
<212> TYPE: DNA
<213> ORGANISM: Homo sapiens

<400> SEQUENCE: 279
cctccatatt cccctccctg acccccacag tcattgtttg aacgccaggg cctcccaggc 60
ccagagaagc tgccgggctc cttgcggaag gggattccac ggaccaagtc tgtaggtatg 120
gctgcgctgt ggggctgcat ggggt 145

<210> SEQ ID NO 280
<211> LENGTH: 2314
<212> TYPE: DNA
<213> ORGANISM: Homo sapiens

<400> SEQUENCE: 280
ggctggtctc accggccctt ccgtccgcag gggaggacga gaagctggcg tccctgctgg 60
aagggcgctt cccgcggagc acctcgatgc aagacccggt gcgcgagggt cgcggcatcc 120
cgcccccgcc gcagaccgcg ccgcctcccc cgcccgcgcc ctactacttc gactcggggc 180
cgcccccggc cttctcgccg ccgcccccgc cgggccgcgc ctacgacacg gtgcgctcca 240
gcttcaagcc cggcctggag gcgcgcctgg gcgcgggcgc tgccggcctg tacgagccgg 300
gcgcggccct cggcccgctg ccgtatcccg agcggcagaa gcgcgcgcgc tccatgatca 360
tcctgcagga ctcggcgccc gagtcgggcg acgcccctcg acccccgccc gcggccaccc 420
cgcccgagcg acccaagcgc cggccgcggc cgcccggccc cgacagcccc tacgccaacc 480
tgggcgcctt cagcgccagc ctcttcgctc cgtccaagcc gcagcgccgc aagagccccc 540
tggtgaagca gctgcaggtg gaggacgcgc aggagcgcgc ggccctggcc gtgggcagcc 600
ccggtcccgg cggcggcagc ttcgcccgcg agccctcccc gacccaccgc ggtccgcgcc 660
cgggtggcct cgactacggc gcgggcgatg gcccggggct cgcgttcggc ggcccgggcc 720
cggccaagga ccggcggctg gaggagcggc gccgctccac tgtgttcctg tccgtggggg 780
ccatcgaggg cagcgccccc ggcgcggatc tgccatccct acagccctcc cgctccatcg 840
acgagcgcct cctggggacc ggccccaccg ccggccgcga cctgctgctg ccctccccgg 900
tgtctgccct gaagccgttg gtcagcggcc cgagcctggg gccctcgggt tccaccttca 960
tccacccact caccggcaaa cccctggacc ccagctcacc cctggccctt gccctggctg 1020
cccgagagcg agctctggcc tcccaggcgc cctcccggtc ccccacaccc gtgcacagtc 1080
ccgacgccga ccgccccgga cccctgtttg tggatgtaca ggcccgggac ccagagcgag 1140
ggtccctggc ttccccggct ttctccccac ggagcccagc ctggattcct gtgcctgctc 1200
gcagggaggc agagaaggtc cccgggaggg agcggaagtc acccgaggac aagaagtcca 1260
tgatcctcag cgtcctggac acatccctgc agcggccagc tggcctcatc gttgtgcacg 1320
ccaccagcaa cgggcaggag cccagcaggc tgggggggc cgaagaggag cgcccgggca 1380

-continued

```
ccccggagtt ggccccggcc cccatgcagt cagcggctgt ggcagagccc ctgcccagcc   1440

cccgggccca gccccctggt ggcaccccgg cagacgccgg gccaggccag ggcagctcag   1500

aggaagagcc agagctggtg tttgctgtga acctgccacc tgcccagctg tcgtccagcg   1560

atgaggagac cagggaggag ctggcccgaa ttgggttggt gccacccccct gaagagtttg  1620

ccaacggggt cctgctggcc accccactcg ctggcccggg cccctcgccc accacggtgc   1680

ccagcccggc ctcagggaag cccagcagtg agccaccccc tgcccctgag tctgcagccg   1740

actctggggt ggaggaggct gacacacgca gctccagcga cccccacctg gagaccacaa   1800

gcaccatctc cacggtgtcc agcatgtcca ccttgagctc ggagagcggg gaactcactg   1860

acacccacac ctccttcgct gacggacaca cttttctact cgagaagcca ccagtgcctc   1920

ccaagcccaa gctcaagtcc ccgctgggga aggggccggt gaccttcagg gacccgctgc   1980

tgaagcagtc ctcggacagc gagctcatgg cccagcagca ccacgccgcc tctgccgggc   2040

tggcctctgc cgccgggcct gcccgccctc gctacctctt ccagagaagg tccaagctat   2100

ggggggaccc cgtggagagc cgggggctcc ctgggcctga agacgacaaa ccaactgtga   2160

tcagtgagct cagctcccgc ctgcagcagc tgaacaagga cacgcgttcc ctgggggagg   2220

aaccagttgg tggcctgggc agcctgctgg accctgccaa gaagtcgccc atcgcagcag   2280

ctcggtgagc agggcggtgc ggggagggat ccgt                               2314
```

```
<210> SEQ ID NO 281
<211> LENGTH: 652
<212> TYPE: DNA
<213> ORGANISM: Homo sapiens

<400> SEQUENCE: 281

cacctggcgc tgacccctct ccctccgcag gctcttcagc agcctcggtg agctgagctc     60

catttcagcg cagcgcagcc ccgggggccc gggcggcggg gcctcgtact cggtgaggcc    120

cagtggccgc taccccgtgg cgagacgcgc cccgagcccg gtgaagcccg cgtcgctgga    180

gcgggtggag gggctggggg cgggcgcggg gggcgcaggg cggcccttcg gcctcacgcc    240

ccccaccatc ctcaagtcgt ccagcctctc catcccgcac gagcccaagg aggtgcgctt    300

cgtggtgcgc agcgtgagcg cgcgcagtcg ctccccctcg ccgtcgccgc tgccctcgcc    360

cgcgtccggc cccggccccg gcgcccccgg cccacgccga cccttccagc agaagccgct    420

gcagctctgg agcaagttcg acgtgggcga ctggctggag agcatccacc taggcgagca    480

ccgcgaccgc ttcgaggacc atgagataga aggcgcgcac ctacccgcgc ttaccaagga    540

cgacttcgtg gagctgggcg tcacgcgcgt gggccaccgc atgaacatcg agcgcgcgct    600

caggcagctg gacggcagct gacgccccac ccccactccc gccccggccg tg            652
```

METHODS FOR DIAGNOSING AUTISM SPECTRUM DISORDERS

RELATED APPLICATIONS

The present application is a divisional application of pending U.S. patent application Ser. No. 12/877,655, filed Sep. 8, 2010, entitled "Compositions and Methods for Diagnosing Autism Spectrum Disorders," which claimed priority under 35 USC 119(e) to U.S. Provisional Patent Application No. 61/240,469, filed Sep. 8, 2009. The disclosures of U.S. Provisional Patent Application No. 61/240,469 and U.S. patent application Ser. No. 12/877,655 are incorporated by reference in their entireties herein.

FIELD OF THE INVENTION

The invention generally relates to compositions and methods for diagnosing autism spectrum disorders.

BACKGROUND

Autism is a complex developmental disability that interferes with normal development of the brain in the areas of social interaction and communication skills. Typically, autistic children and adults have difficulties with verbal and non-verbal communication, social interactions, and leisure or play activities.

Autism generally is characterized as one of five disorders coming under the umbrella of Pervasive Developmental Disorders (PDD), a category of neurological disorders characterized by severe and pervasive impairment in several areas of development, including social interaction and communications skills. The five disorders under PDD include Autistic Disorder, Asperger's Disorder, Childhood Disintegrative Disorder (CDD), Rett's Disorder, and PDD-Not Otherwise Specified (PDD-NOS). Specific diagnostic criteria for each of these disorders can be found in the American Psychiatric Association: *Diagnostic and Statistical Manual of Mental Disorders*, Fourth Edition, Text Revision. Washington, D.C., American Psychiatric Association, 2000, as distributed by the American Psychiatric Association.

There is no definitive diagnostic test for biological manifestations of autism, and thus it remains one of the only neurological disorders that must be diagnosed almost entirely through behavioral symptoms. The DSM-IV classifies autism as a Pervasive Developmental Disorder (PDD) characterized by twelve diagnostic criteria. Those criteria fall into three categories: impairments in social interaction; impairments in communication; and a restricted repertoire of activities and interests. A diagnosis of autism requires that a child display at least six of the twelve symptoms.

If a child does not fit the definition of autism given above, he/she may be diagnosed with a condition called Pervasive Developmental Disorder Not Otherwise Specified (PDD-NOS). Such a diagnosis of non-specific forms of Pervasive Developmental Disorder (PDD) may include atypical types of autism that do not fall into the above categories because of late age of onset, for example, or sub-threshold or atypical symptoms. According to the DSM-IV, this diagnosis is to be used when autistic-like behaviors are present, in particular when there is severe impairment in the development of social and verbal communication skills, but the child does not meet the criteria for classic autism or any other specific Pervasive Developmental Disorder, Schizophrenia, Schizotypal Personality Disorder or Avoidant Personality Disorder.

A variety of agents have been postulated to be associated with the development of autism including, but not limited to, exposure to pesticides and/or agents that can cause birth defects. In at least some cases, it appears that autism may have a genetic basis. The genetics of autism appear to be complex. For example, copy number variation and chromosomal structural abnormalities (both large and small) have been shown be present in particular genomic regions in patients with autism or syndromes in which autistic behavior is common (Abrahams and Geschwind, Nature Reviews Genetics, 2008, 9:341-355). DNA hybridization studies have shown structural abnormalities in autistic populations. A causal role for genetic variation in many different genes has been suggested based on evidence from association or linkage studies. Still, genome wide association studies have failed to link specific common variants, acting singly or in combination, though such studies have identified association peaks that may point to other causative genes or pathways. There is some evidence that genetic variation may be the cause of at least non-syndromic autism.

Evaluations to diagnose a child are made by a team typically including doctors and the child's parents. Because diagnosis of autism spectrum disorders is subjective, misdiagnosis of a child can frequently occur. Thus, there is an unmet need for diagnostic tests that can provide an objective determination of whether a subject suffers from an autism spectrum disorder.

SUMMARY

The invention generally relates to compositions and methods for diagnosing the presence or an increased risk of developing autism spectrum disorders. The methods and compositions of the present invention may be used to obtain or provide genetic information from a subject in order to objectively diagnose the presence of an autism spectrum disorder (ASD), or an increased risk for that subject, or other subjects, to develop an autism spectrum disorder.

In one embodiment, the invention comprises methods for diagnosing the presence or an increased risk of developing an autism spectrum disorder in a subject. The method may comprise the steps of obtaining a nucleic acid from a biological sample (e.g., a tissue or body fluid sample) from a subject and conducting an assay to identify whether there is a variant sequence in the subject's nucleic acid. In certain embodiments, the method may comprise comparing the variant to known variants associated with an autism spectrum disorder and determining whether the variant is a variant that has been previously identified as being associated with autism. Or, the method may comprise identifying the variant as a new, previously uncharacterized or previously not described variant. If the variant is a new variant, the method may further comprise performing an analysis to determine whether the mutation is expected to be deleterious to expression of the gene and/or the function of the protein encoded by the gene. The method may further comprise using the variant profile (i.e., the compilation of mutations identified in the subject) to diagnose the presence of an autism spectrum disorder or an increased risk of developing an autism spectrum disorder. In some embodiments, the method may comprise obtaining a nucleic acid from a tissue or body fluid sample from a subject and sequencing at least a portion of a nucleic acid in order to obtain a sample nucleic acid sequence for at least one gene.

Yet other embodiments of the invention may comprise methods for identifying mutations (i.e., variants) correlated with the presence or increased risk of developing an autism spectrum disorder. The method may comprise the step of identifying a nucleic acid to be evaluated as having a sequence that if mutated may be associated with the development of autism. Also, the method may comprise obtaining a nucleic acid sample from a biological sample (e.g., a tissue or body fluid sample) from a subject having an autism spectrum disorder; and conducting an assay to identify whether there is a mutation in the nucleic acid sequence in the subject having autism as compared to the nucleic acid sequence in individuals who do not have an autism spectrum disorder, wherein the presence of the mutation in a subject with an autism spectrum disorder indicates that the mutation may be associated with the development of the autism spectrum disorder. If the variant is a new variant, the method may further comprise performing an analysis to determine whether the mutation is expected to be deleterious to expression of the gene and/or the function of the protein encoded by the gene. The method may further comprise compiling a panel of variant mutations that can be used to diagnose the presence of an autism spectrum disorder or an increased risk of developing an autism spectrum disorder.

In yet other embodiments, the invention comprises an isolated nucleic acid comprising a nucleic acid of at least one of the following genes or genomic regions: TSC1, TSC2, MECP2, SHANK3, GRM1, GRM5, ARC, EIF4E, HOMER1, HRAS, MAP2K1, MAP2K2, RAF1, PIK3CA, PIK3R1, FMR1, PTEN, RHEB or UBE3A, wherein the sequence comprises a variant that is indicative of or associated with an autism spectrum disorder.

There are additional features of the invention which will be described hereinafter. It is to be understood that the invention is not limited in its application to the details set forth in the following claims, description and figures. The invention is capable of other embodiments and of being practiced or carried out in various ways.

BRIEF DESCRIPTION OF THE FIGURES

Various features, aspects and advantages of the present invention will become more apparent with reference to the following figures.

FIG. 3, Panels A-LL, depicts the DNA sequences for the TSC1, TSC2, MECP2, SHANK3, GRM1, GRM5, ARC, EIF4E, HOMER1, HRAS, MAP2K1, MAP2K2, RAF1, PIK3CA, PIK3R1, FMR1, PTEN, RHEB and UBE3A genes and protein sequences encoded by these genes as SEQ ID NO: 1-38.

FIG. 4 depicts DNA sequences used to identify mutations in the TSC1, TSC2, MECP2, SHANK3, GRM1, GRM5, ARC, EIF4E, HOMER1, HRAS, MAP2K1, MAP2K2, RAF1, PIK3CA, PIK3R1, FMR1, PTEN, RHEB and UBE3A genes as SEQ ID NOs: 39-271 as well as the chromosomal location of the exon and flanking sequences used.

DETAILED DESCRIPTION

Figure 1:
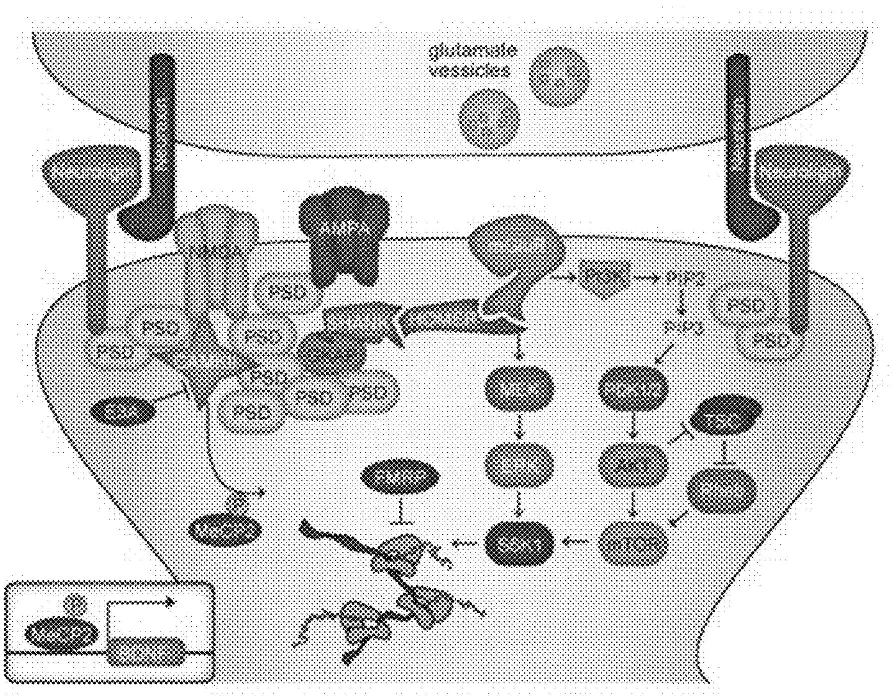
FIG. 1 shows genes that are involved in mGluR signaling in accordance with an embodiment of the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

It is further noted that, as used in this specification, the singular forms "a," "an," and "the" include plural referents unless expressly and unequivocally limited to one referent. The term "and/or" generally is used to refer to at least one or the other. In some case the term "and/or" is used interchangeably with the term "or".

Also, the terms "portion" and "fragment" are used interchangeably to refer to parts of a polypeptide, nucleic acid, or other molecular construct.

"Polypeptide" and "protein" are used interchangeably herein to describe protein molecules that may comprise either partial or full-length proteins. The term "peptide" is used to denote a less than full-length protein or a very short protein unless the context indicates otherwise.

As is known in the art, "proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. Typically, the amino acids making up a protein are numbered in order, starting at the amino terminal residue and increasing in the direction toward the carboxy terminal residue of the protein.

As is known in the art, conditions for hybridizing nucleic acid sequences to each other can be described as ranging from low to high stringency. Generally, highly stringent hybridization conditions refer to washing hybrids in low salt buffer at high temperatures. Hybridization may be to filter bound DNA using hybridization solutions standard in the art such as 0.5M $NaHPO_4$, 7% sodium dodecyl sulfate (SDS), at 65° C., and washing in 0.25 M $NaHPO_4$, 3.5% SDS followed by washing 0.1×SSC/0.1% SDS at a temperature ranging from room temperature to 68° C. depending on the length of the probe (see e.g. Ausubel, F. M. et al., *Short Protocols in Molecular Biology,* $4^{th}$ Ed., Chapter 2, John Wiley & Sons, N.Y). For example, a high stringency wash comprises washing in 6×SSC/0.05% sodium pyrophosphate at 37° C. for a 14 base oligonucleotide probe, or at 48° C. for a 17 base oligonucleotide probe, or at 55° C. for a 20 base oligonucleotide probe, or at 60° C. for a 25 base oligonucleotide probe, or at 65° C. for a nucleotide probe about 250 nucleotides in length. Nucleic acid probes may be labeled with radionucleotides by end-labeling with, for example, [$\gamma$-$^{32}$P]ATP, or incorporation of radiolabeled nucleotides such as [$\alpha$-$^{32}$P]dCTP by random primer labeling. Alternatively, probes may be labeled by incorporation of biotinylated or fluorescein labeled nucleotides, and the probe detected using Streptavidin or anti-fluorescein antibodies.

As used herein, the term "upstream" refers to a residue that is N-terminal to a second residue where the molecule is a protein, or 5' to a second residue where the molecule is a nucleic acid. Also as used herein, the term "downstream" refers to a residue that is C-terminal to a second residue where the molecule is a protein, or 3' to a second residue where the molecule is a nucleic acid. The protein, polypeptide and peptide sequences disclosed herein are all listed from N-terminal amino acid to C-terminal acid and the nucleic acid sequences disclosed herein are all listed from the 5' end of the molecule to the 3' end of the molecule.

Unless defined otherwise, all technical and scientific terms used herein have the same meaning as commonly understood by one of ordinary skill in the art. Practitioners are particularly directed to Current Protocols in Molecular Biology (Ausubel) for definitions and terms of the art. Abbreviations for amino acid residues are the standard 3-letter and/or 1-letter codes used in the art to refer to one of the 20 common L-amino acids.

A "nucleic acid" is a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues.

The terms "identity" or "percent identical" refers to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, 1981, *Adv. Appl. Math.* 2:482; Needleman and Wunsch, 1970, *J. Mol. Biol.* 48:443; Pearson and Lipman, 1988, *Proc. Natl. Acad. Sci., USA,* 85:2444) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. In other cases, commercially available software, such as GenomeQuest, may be used to determine percent identity. When utilizing BLAST and Gapped BLAST programs, the default parameters of the respective programs (e.g., BLASTN; available at the Internet site for the National Center for Biotechnology Information) may be used. In one embodiment, the percent identity of two sequences may be determined using GCG with a gap weight of 1, such that each amino acid gap is weighted as if it were a single amino acid mismatch between the two sequences. Or, the ALIGN program (version 2.0), which is part of the GCG (Accelrys, San Diego, Calif.) sequence alignment software package may be used.

As used herein, the term "conserved residues" refers to amino acids that are the same among a plurality of proteins having the same structure and/or function. A region of conserved residues may be important for protein structure or function. Thus, contiguous conserved residues as identified in a three-dimensional protein may be important for protein structure or function. To find conserved residues, or conserved regions of 3-D structure, a comparison of sequences for the same or similar proteins from different species, or of individuals of the same species, may be made.

As used herein, the term "similar" or "homologue" when referring to amino acid or nucleotide sequences means a polypeptide having a degree of homology or identity with the wild-type amino acid sequence. Homology comparisons can be conducted by eye, or more usually, with the aid of readily available sequence comparison programs. These commercially available computer programs can calculate percent homology between two or more sequences (e.g. Wilbur, W. J. and Lipman, D. J., 1983, Proc. Natl. Acad. Sci. USA, 80:726-730). For example, homologous sequences may be taken to include an amino acid sequences which in alternate embodiments are at least 70% identical, 75% identical, 80% identical, 85% identical, 90% identical, 95% identical, 97% identical, or 98% identical to each other.

As used herein, the term at least 90% identical thereto includes sequences that range from 90 to 100% identity to the indicated sequences and includes all ranges in between. Thus, the term at least 90% identical thereto includes sequences that are 91, 91.5, 92, 92.5, 93, 93.5. 94, 94.5, 95, 95.5, 96, 96.5, 97, 97.5, 98, 98.5, 99, 99.5 percent identical to the indicated sequence. Similarly the term "at least 70% identical includes sequences that range from 70 to 100% identical, with all ranges in between. The determination of percent identity is determined using the algorithms described herein.

As used herein, a polypeptide or protein "domain" comprises a region along a polypeptide or protein that comprises an independent unit. Domains may be defined in terms of structure, sequence and/or biological activity. In one embodiment, a polypeptide domain may comprise a region of a protein that folds in a manner that is substantially independent from the rest of the protein. Domains may be identified using domain databases such as, but not limited to PFAM, PRODOM, PROSITE, BLOCKS, PRINTS, SBASE, ISREC PROFILES, SAMRT, and PROCLASS.

As used herein a gene is a unit of heredity. Generally, a gene is a portion of DNA that encodes a protein or a functional RNA. A modern working definition of a gene is a locatable region of genomic sequence corresponding to a unit of inheritance. A gene may associated with regulatory regions, transcribed regions, and or other functional sequence regions.

As used herein a gene regulatory element or regulatory sequence is a segment of DNA where regulatory proteins, such as transcription factors, bind to regulate gene expression. Such regulatory regions are often upstream of the gene being regulated.

As used herein an exon is a nucleic acid sequence that is found in mature or processed RNA after other portions of the RNA (e.g., intervening regions known as introns) have been removed by RNA splicing. As such, exon sequences generally encode for proteins or portions of proteins. An intron is the portion of the RNA that is removed from surrounding exon sequences by RNA splicing.

As used herein expressed RNA is an RNA that encodes for a protein or polypeptide ("coding RNA"), and any other RNA that is transcribed but not translated ("non-coding RNA").

As used herein micro RNA is microRNAs (miRNAs) are short (20-24 nt) non-coding RNAs that are involved in post-transcriptional regulation of gene expression. microRNA can affect both the stability and translation of mRNAs. For example, microRNAs can bind to complementary sequences in the 3'UTR of target mRNAs and cause gene silencing. miRNAs are transcribed by RNA polymerase II as part of capped and polyadenylated primary transcripts (pri-miRNAs) that can be either protein-coding or non-coding. The primary transcript can be cleaved by the Drosha ribonuclease III enzyme to produce an approximately 70-nt stem-loop precursor miRNA (pre-miRNA), which can further be cleaved by the cytoplasmic Dicer ribonuclease to generate the mature miRNA and antisense miRNA star (miRNA*) products. The mature miRNA can be incorporated into a RNA-induced silencing complex (RISC), which can recognize target mRNAs through imperfect base pairing with the miRNA and most commonly results in translational inhibition or destabilization of the target mRNA.

As used herein, siRNA is essentially a double-stranded RNA molecule composed of about 20 complementary nucleotides. siRNA is created by the breakdown of larger double-stranded (ds) RNA molecules. siRNA can suppress gene expression by inherently splitting its corresponding mRNA in two by way of the interaction of the siRNA with the mRNA, leading to degradation of the mRNA. siRNAs can also interact with DNA to facilitate chromating silencing and the expansion of heterochromatin.

As used herein, an epigenetic element can change gene expression by a mechanism other than a change in the underlying DNA sequences. Such elements may include elements that regulate paramutation, imprinting, gene silencing, X chromosome inactivation, position effect, reprogramming, transvection, maternal effects, histone modification, and heterochromatin.

As used herein, the terms mutation and variant are used interchangeably to describe a nucleic acid or protein sequence change.

As used herein, "associated with an autism spectrum disorder" means that the variant is found with in patients with autism more than in non-autistic controls. Generally, the statistical significance of such association can be determined by assaying a plurality of patients.

As used herein, a region of interest is a portion of the chromosome that is being targeted for assaying for variants in the DNA sequence.

Methods and Compositions for Diagnosing Autism Spectrum Disorders

Embodiments of the present invention comprise compositions and methods for diagnosing presence or increased risk of developing autism spectrum disorders. The methods and compositions of the present invention may be used to obtain or provide genetic information from a subject in order to objectively diagnose the presence or increased risk for that subject, or other subjects to develop an autism spectrum disorder.

In one embodiment, the invention comprises methods for diagnosing the presence or an increased risk of developing an autism spectrum disorder in a subject. The method may comprise the steps of obtaining a nucleic acid from a tissue or body fluid sample from a subject and conducting an assay to identify whether there is a variant sequence (i.e., a mutation) in the subject's nucleic acid. In certain embodiments, the method may comprise comparing the variant to known variants associated with an autism spectrum disorder and determining whether the variant is a variant that has been previously identified as being associated with autism. Or, the method may comprise identifying the variant as a new, previously uncharacterized variant. If the variant is a new variant, the method may further comprise performing an analysis to determine whether the mutation is expected to be deleterious to expression of the gene and/or the function of the protein encoded by the gene. The method may further comprise using the variant profile (i.e., the compilation of mutations identified in the subject) to diagnose the presence of an autism spectrum disorder or an increased risk of developing an autism spectrum disorder.

In certain embodiments, the invention comprises a method for diagnosing the presence or an increased risk of developing an autism spectrum disorder in a subject, the method comprising: obtaining a nucleic acid from a tissue or body fluid sample from a subject; conducting an assay to identify whether there is a variant sequence, or a plurality of variant sequences, in the subject's nucleic acid; for each variant detected, determining if the variant is a known variant associated with an autism spectrum disorder or a previously undescribed variant; if the variant is a previously undescribed variant, determining if the variant is expected to have a deleterious effect on at least one of gene expression and/or protein function; and diagnosing the presence or an increased risk of developing the autism spectrum disorder based on the variant sequence or the plurality of variant sequences detected.

In some embodiments, the method may comprise obtaining a nucleic acid from a tissue or body fluid sample from a subject and sequencing at least a portion of a nucleic acid in order to obtain a sample nucleic acid sequence for at least one gene. In certain embodiments, the method may comprise comparing the variant to known variants associated with an autism spectrum disorder and determining whether the variant is a variant that has been previously identified as being associated with autism. Or, the method may comprise identifying the variant as a new, previously uncharacterized variant. If the variant is a new variant, or in some cases for previously characterized (i.e., identified) variants, the method may further comprise performing an analysis to determine whether the mutation is expected to be deleterious to expression of the gene and/or the function of the protein encoded by the gene. The method may further comprise using the variant profile (i.e., a compilation of variants identified in the subject) to diagnose the presence of an autism spectrum disorder or an increased risk of developing an autism spectrum disorder.

In embodiments of each of the methods of the invention, the method may comprise performing the assay (e.g., sequencing) in a plurality of individuals to determine the statistical significance of the association.

In various embodiments of the methods of the invention and as described in more detail herein, the assay comprises at least one of nucleic acid sequencing, hybrid capture, and/or epigenetic analysis. For example, in certain embodiments, next generation (massively-parallel sequencing) may be used. Or, Sanger sequencing may be used. Or, a combination of next generation (massively-parallel sequencing) and Sanger sequencing may be used. Additionally and/or alternatively, the sequencing comprises at least one of single-molecule sequencing-by-synthesis. Thus, in certain embodiments, a plurality of DNA samples are analyzed in a pool to identify samples that show a variation. Additionally or alternatively, in certain embodiments, a plurality of DNA samples are analyzed in a plurality of pools to identify an individual sample that shows the same variation in at least two pools.

Also, in various embodiments, the nucleic acid in the conducting step comprises a gene, an RNA, an exon, an intron, a gene regulatory element, an expressed RNA, an siRNA, or an epigenetic element. Also, regulatory elements, including splice sites, transcription factor binding, A-I editing sites, microRNA binding sites, and functional RNA structure sites may be evaluated for mutations (i.e., variants).

In certain embodiments, the nucleic acid selected for analyzing for a variant comprises a sequence selected from a sequence known or suspected to be associated with one or more autism spectrum disorders. For, example, the nucleic acid comprises at least a portion of one of the genes in Table 1. Or, the nucleic acid may comprise a gene that encodes for a protein involved in a biochemical pathway that can be important in the development of an autism spectrum disorder (ASD). For example, in certain embodiments, the nucleic acid is derived from a gene that encodes a protein in the metabotropic glutamate receptor signaling pathway. For example, in certain embodiments, the variant comprises at least one of the variants in Table 2. Thus, in certain embodiments of the methods of the invention, the nucleic acid comprises at least a portion of a gene for at least one of TSC1, TSC2, MECP2, SHANK3, GRM1, GRM5, ARC, EIF4E, HOMER1, HRAS, MAP2K1, MAP2K2, RAF1, PIK3CA, PIK3R1, FMR1, PTEN, RHEB or UBE3A. In some embodiments, the nucleic acid comprises at least a portion of a gene for at least one of TSC1, TSC2, SHANK3, or HOMER1. In certain embodiments, the variant comprises at least one of the following mutations: HOMER 1 c.195G>T, M65I; HOMER 1 c.290C>T, S97L; HOMER 1 c.425C>T, P142L; GRM5 c.3503T>C, L1168P; MAPK2 c.581-1G>T; HRAS c.383G>A, R128Q; a MECP2 c.1477G>T, E483X.

In the various embodiments of the methods of the invention, the autism spectrum disorder may be at least one of non-syndromic autism, classical autism, Asperger's syndrome, Rett's syndrome, childhood disintegrative disorder, or pervasive developmental disorder not otherwise specified (PDD-NOS). In certain embodiments, the autism spectrum disorder comprises non-syndromic autism (i.e., patients who display symptoms of autism but who do not exhibit physical manifestations often found with autism).

The methods of the invention may further comprise diagnosing a the presence of, or an increased risk of developing, a genetic syndrome linked to autism, wherein the genetic syndrome comprises a manifesting phenotype. For example, in certain embodiments, the genetic syndrome comprises at least one of Angelman syndrome, Prader-Willi syndrome, 15q11-q13 duplication, fragile X syndrome, fragile X premutation, deletion of chromosome 2q, XYY syndrome, Smith-Lemli-Opitz syndrome, Apert syndrome, mutations in the ARX gene, De Lange syndrome, Smith-Magenis syndrome, Williams syndrome, Noonan syndrome, Down syndrome, velo-cardio-facial syndrome, myotonic dystrophy, Steinert disease, tuberous sclerosis, Duchenne's disease, Timothy syndrome, 10p terminal deletion, Cowden syndrome, 45,X/46,XY mosaicism, Myhre syndrome, Sotos syndrome, Cohen syndrome, Goldenhar syndrome, Joubert syndrome, Lujan-Fryns syndrome, Moebius syndrome, hypomelanosis of Ito, neurofibromatosis type 1, CHARGE syndrome, and/or HEADD syndrome.

The methods may be used to assist in the diagnosis of individuals who do not yet display symptoms of an ASD, or for whom, the diagnosis is equivocal. For example, the subject may be a child or a fetus.

The techniques for sequencing nucleic acids (both DNA and RNA) are highly sensitive and therefore, can be used almost any biological sample (i.e., tissue or body fluid) taken from subject. For example, in alternate embodiments, the body fluid comprises at least one of cerebrospinal fluid, blood, amniotic fluid, maternal blood, or urine.

As noted above, in certain embodiments, the genes for which mutations are evaluated are genes that encode proteins in biochemical pathway or pathways that are relevant to the development of autism. For example, in certain embodiments, the genes are involved in the metabotropic glutamate receptor pathway. In one embodiment, the pathway is the mGluR5 signaling pathway and/or includes genes important to the activity of the mGluR5 receptor. Or, other biochemical pathways that are related to certain types of autism syndromes may be evaluated. For example, in certain embodiments, at least one of the genes and/or genomic regions in Table 1 may be evaluated.

Where the pathway is the mGluR5 signaling pathway and/or includes genes important to the activity of the mGluR5 receptor, the DNA sequences may be derived from genes or genomic regions comprising the genes shown in Table 2. In certain embodiments of the methods, the genes and/or genomic regions being evaluated for mutations that may be indicative of the presence or an increase risk of an ASD are ARC, EIF4E, FMR1, GRM1, GRM5, HOMER1, HRAS, MAP2K1, MAP2K2, MECP2, PIK3CA, PIK3R1, PTEN, RAF1, RHEB, SHANK3, TSC1, TSC2, and/or UBE3A. In certain embodiments, the native or non-variant sequence used in the assay comprises an exon sequence from at least one of the following genes: ARC, EIF4E, FMR1, GRM1, GRM5, HOMER1, HRAS, MAP2K1, MAP2K2, MECP2, PIK3CA, PIK3R1, PTEN, RAF1, RHEB, SHANK3, TSC1, TSC2, and/or UBE3A. For example, in certain embodiments, the gene sequence being evaluated for a variant comprises the exon sequences. Or, intron sequences or other non-coding regions may be evaluated for potentially deleterious mutations. In certain embodiments, the exon sequence and additional flanking sequence (e.g., about 5, 10, 15, 20, 25, 30, 35, 40, 45, 50, 55 or more nucleotides of UTR and/or intron sequence) is analyzed in the assay. Or portions of these sequences may be used. In certain embodiments, the gene sequence being evaluated comprises an exon sequence and/or flanking intron or UTR sequence from at least one of the following genes: HOMER1, SHANK3, TSC1, and/or TSC2. In certain embodiments, the gene sequence being evaluated comprises an exon sequence from the HOMER1 gene. Such variant gene sequences may include sequences having at least one of the mutations as shown in Table 2.

Yet other embodiments of the invention may comprise methods for identifying mutations correlated with the presence or increased risk of developing an autism spectrum disorder. The method may comprise the step of identifying a nucleic acid sequence, such as a gene or a genomic region, that if mutated may be associated with the development of autism. Also, the method may comprise obtaining a nucleic acid sample from a tissue or body fluid sample from a subject having an autism spectrum disorder; and conducting an assay to identify whether there is a mutation in the nucleic acid sequence in the subject having autism as compared to the nucleic acid sequence in individuals who do not have an autism spectrum disorder, wherein the presence of the mutation in a subject with an autism spectrum disorder indicates that the mutation may be associated with the development of the autism spectrum disorder. Or, the method may comprise analyzing the sequence of the selected gene or genomic region for new variants (i.e., previously undiscovered mutations). If the variant is a new variant, or in some cases for a previously identified variant, the method may further comprise performing an analysis to determine whether the mutation is expected to be deleterious to expression of the gene and/or the function of the protein encoded by the gene. The method may further comprise compiling a panel of variant mutations that can be used to diagnose the presence of an autism spectrum disorder or an increased risk of developing an autism spectrum disorder.

Thus, the method may comprise a method for identifying mutations correlated with the presence or increased risk of developing an autism spectrum disorder, comprising: identifying a nucleic acid to be evaluated as having a sequence that if mutated may be or is associated with the development of autism; obtaining a nucleic acid sample from a tissue or body fluid sample from a subject having an autism spectrum disorder; and conducting an assay to identify whether there is a mutation in the nucleic acid sequence in the subject having autism as compared to the nucleic acid sequence in individuals who do not have an autism spectrum disorder, wherein the presence of the mutation in a subject with an autism spectrum disorder indicates that the mutation may be associated with the development of the autism spectrum disorder.

In embodiments the methods of the invention for identifying new mutations, the method may comprise performing the assay (e.g., sequencing) in a plurality of individuals to determine the statistical significance of the association.

In certain embodiments, the mutation is a variant that has been previously associated with the development of an autism spectrum disorder. Or, the mutation may be a previously undescribed variant. The method may additionally comprise determining if the mutation is expected to have a deleterious effect on at least one of gene expression and/or protein function.

In certain embodiments, the nucleic acid selected for analyzing for a variant comprises a sequence selected from a sequence known or suspected to be associated with one or more autism spectrum disorders. For, example, the nucleic acid comprises at least a portion of one of the genes in Table 1. Or, the nucleic acid may comprise a gene that encodes for a protein involved in a biochemical pathway that can be important in the development of an autism spectrum disorder (ASD). For example, in certain embodiments, the nucleic acid is derived from a gene that encodes a protein in the metabotropic glutamate receptor signaling pathway. For example, in certain embodiments, the variant comprises at least one of the variants in Table 2. Thus, in certain embodiments of the methods of the invention, the nucleic acid comprises at least a portion of a gene for at least one of TSC1, TSC2, MECP2, SHANK3, GRM1, GRM5, ARC, EIF4E, HOMER1, HRAS, MAP2K1, MAP2K2, RAF1, PIK3CA, PIK3R1, FMR1, PTEN, RHEB or UBE3A. In some embodiments, the nucleic acid comprises at least a portion of a gene for at least one of TSC1, TSC2, SHANK3, or HOMER1.

In the various embodiments of the methods of the invention, the autism spectrum disorder may be at least one of non-syndromic autism, classical autism, Asperger's syndrome, Rett's syndrome, childhood disintegrative disorder, or pervasive developmental disorder not otherwise specified (PDD-NOS). In certain embodiments, the autism spectrum disorder comprises non-syndromic autism.

Or, the association of variants with other syndromes that are associated (e.g., genetically linked to) with autism, such as at least one of Angelman syndrome, Prader-Willi syndrome, 15q11-q13 duplication, fragile X syndrome, fragile X premutation, deletion of chromosome 2q, XYY syndrome, Smith-Lemli-Opitz syndrome, Apert syndrome, mutations in the ARX gene, De Lange syndrome, Smith-Magenis syndrome, Williams syndrome, Noonan syndrome, Down syndrome, velo-cardio-facial syndrome, myotonic dystrophy, Steinert disease, tuberous sclerosis, Duchenne's disease, Timothy syndrome, 10p terminal deletion, Cowden syndrome, 45,X/46,XY mosaicism, Myhre syndrome, Sotos syndrome, Cohen syndrome, Goldenhar syndrome, Joubert syndrome, Lujan-Fryns syndrome, Moebius syndrome, hypomelanosis of Ito, neurofibromatosis type 1, CHARGE syndrome, and/or HEADD syndrome.

In various embodiments, of the methods of the invention and as described in more detail herein, the assay comprises at least one of nucleic acid sequencing, hybrid capture, and epigenetic analysis. For example, in certain embodiments, next generation (massively-parallel sequencing) may be used. Or, Sanger sequencing may be used. Or, a combination of next generation (massively-parallel sequencing) and Sanger sequencing may be used. Additionally and/or alternatively, the sequencing comprises at least one of single-molecule sequencing-by-synthesis. Thus, in certain embodiments, a plurality of DNA samples are analyzed in a pool to identify samples that show a variation. Additionally or alternatively, in certain embodiments, a plurality of DNA samples are analyzed in a plurality of pools to identify an individual sample that shows the same variation in at least two pools.

Also, in various embodiments, the nucleic acid in the conducting step comprises a gene, an RNA, an exon, an intron, a gene regulatory element, an expressed RNA, an siRNA, or an epigenetic element. Also, regulatory elements, including splice sites, transcription factor binding, A-I editing sites, microRNA binding sites, and functional RNA structure sites may be evaluated for mutations (i.e., variants).

The methods may be used to assist in the diagnosis of individuals who do not yet display symptoms of an ASD, or for whom, the diagnosis is equivocal. For example, the subject may be a child or a fetus.

The techniques for sequencing nucleic acids (both DNA and RNA) are highly sensitive and therefore, can be used almost any biological sample (i.e., tissue or body fluid) taken from subject. For example, in alternate embodiments, the body fluid comprises at least one of cerebrospinal fluid, blood, amniotic fluid, maternal blood, or urine.

Again, in certain embodiments, the genes for which new mutations are evaluated are genes that encode proteins in biochemical pathway or pathways that are relevant to the development of autism. For example, in certain embodiments, the genes are involved in the metabotropic glutamate receptor pathway. In one embodiment, the pathway is the mGluR5 signaling pathway and/or includes genes important to the activity of the mGluR5 receptor. Or, other biochemical pathways that are related to certain types of autism syndromes may be evaluated. For example, in certain embodiments, at least one of the genes and/or genomic regions in Table 1 may be evaluated.

Where the pathway is the mGluR5 signaling pathway and/or includes genes important to the activity of the mGluR5 receptor the DNA sequences may be derived from genes or genomic regions comprising the genes shown in Table 2. In certain embodiments of the methods the genes and/or genomic regions being evaluated for new mutations that may be indicative of the presence or an increase risk of an ASD are ARC, EIF4E, FMR1, GRM1, GRM5, HOMER1, HRAS, MAP2K1, MAP2K2, MECP2, PIK3CA, PIK3R1, PTEN, RAF1, RHEB, SHANK3, TSC1, TSC2, and/or UBE3A. In certain embodiments, the native or non-variant sequence comprises an exon sequence from at least one of the following genes: ARC, EIF4E, FMR1, GRM1, GRM5, HOMER1, HRAS, MAP2K1, MAP2K2, MECP2, PIK3CA, PIK3R1, PTEN, RAF1, RHEB, SHANK3, TSC1, TSC2, and/or UBE3A. For example, in certain embodiments, the gene sequence being evaluated for a variant comprises the exon sequences. In certain embodiments, the exon sequence and additional flanking sequence (e.g., about 5, 10, 15, 20, 25, 30, 35, 40, 45, 50, 55 or more nucleotides of UTR and/or intron sequence) is analyzed in the assay. Or, intron sequences or other non-coding regions may be evaluated for potentially deleterious mutations. Or, portions of these sequences may be used. Such variant gene sequences may include sequences having at least one of the mutations as shown in Table 2.

Other embodiments of the invention provide isolated gene sequences containing mutations that relate to autism spectrum disorders. Such gene sequences may be used to objectively diagnose the presence or increased risk for a subject to develop an autism spectrum disorder. In certain embodiments, the isolated nucleic acid may contain a non-variant sequence or a variant sequence of any one or combination of ARC, EIF4E, FMR1, GRM1, GRM5, HOMER1, HRAS, MAP2K1, MAP2K2, MECP2, PIK3CA, PIK3R1, PTEN, RAF1, RHEB, SHANK3, TSC1, TSC2, and/or UBE3A. For example, in certain embodiments, the gene sequence comprises the exon sequences. In certain embodiments, the exon sequence and additional flanking sequence (e.g., about 5, 10, 15, 20, 25, 30, 35, 40, 45, 50, 55 or more nucleotides of UTR and/or intron sequence) is analyzed in the assay. Or, intron sequences or other non-coding regions may be used. Or, portions of these sequences may be used. In certain embodiments, the gene sequence comprises an exon sequence from at least one of the following genes: HOMER1, SHANK3, TSC1, and/or TSC2. In certain embodiments, the gene sequence comprises an exon sequence from the HOMER1 gene. Such variant gene sequences include sequences having at least one of the mutations as shown in Table 2. In an embodiment, the isolated nucleic acid may comprise at least one of the following variants: HOMER 1 c.195G>T, M65I; HOMER 1 c.290C>T, S97L; HOMER 1 c.425C>T, P142L; GRM5 c.3503T>C, L1168P; MAPK2 c.58'-1G>T; HRAS c.383G>A, R128Q; a MECP2 c.1477G>T, E483X.

Autism spectrum disorders are generally characterized as one of five disorders coming under the umbrella of Pervasive Developmental Disorders (PDD). The five disorders under PDD include autism (classical autism), Asperger's Syndrome, Rett's Syndrome, childhood disintegrative disorder, and pervasive developmental disorder not otherwise specified (PDD-NOS). According to the invention, one may analyze a panel of genes known or suspected to be associated with one of the five disorders and/or an autism spectrum disorder. In certain embodiments, the autism is non-syndromic autism. Or, the presence or increased risk of developing other types of autism spectrum disorders may be characterized.

The methods and compositions of the invention may further be used for diagnosing or predicting increased risk of developing a genetic syndrome linked to autism, thereby determining whether the subject is affected with, or at increased risk of developing, syndromic autism or non-syndromic autism or another autism spectrum disorder. Genetic disorders that are generally linked to autism include, for example, Angelman syndrome, Prader-Willi syndrome, 15q11-q13 duplication, fragile X syndrome, fragile X premutation, deletion of chromosome 2q, XYY syndrome, Smith-Lemli-Opitz syndrome, Apert syndrome, mutations in the ARX gene, De Lange syndrome, Smith-Magenis syndrome, Williams syndrome, Noonan syndrome, Down syndrome, velo-cardio-facial syndrome, myotonic dystrophy, Steinert disease, tuberous sclerosis, Duchenne's disease, Timothy syndrome, 10p terminal deletion, Cowden syndrome, 45,X/46,XY mosaicism, Myhre syndrome, Sotos syndrome, Cohen syndrome, Goldenhar syndrome, Joubert syndrome, Lujan-Fryns syndrome, Moebius syndrome, hypomelanosis of Ito, neurofibromatosis type 1, CHARGE syndrome, and HEADD syndrome.

The methods of the invention may utilize nucleic acid sequencing, hybridization, quantitative PCR or other techniques known in the art to identify variants associated with autism spectrum disorder. A description of such techniques may be found in textbooks used by those in the art. Or, newer sequencing technologies, such as those described in more detail herein may be used (see e.g., Bowers et al., 2009, Nature Methods, 6:593-595; Ozsolak et al., Nature, 2009, 461: 814-818. By utilizing an objective diagnostic test, methods of the invention greatly reduce and/or eliminate misdiagnoses associated with subjective methods of diagnosing an autism spectrum disorder.

For example, in certain embodiments, the invention provides methods for diagnosing presence or increased risk of developing an autism spectrum disorder in a subject (e.g., a child or a fetus) by obtaining a nucleic acid sample from the subject and identifying a sequence variant, rearrangement, copy number variant and the like that is indicative of an autism spectrum disorder. The sequence variant may be one that has been previously identified in a subject or subjects having an ASD. Or, the sequence variant may be new (i.e., previously undescribed). The identification of the variant may be empirical or may be made by comparison to known sequence alterations associated with one or more autism spectrum disorders as taught herein.

The nucleic acid source material may be obtained from a body fluid or tissue, such as cerebrospinal fluid, blood, amniotic fluid, maternal blood, buccal swab, sputum, or urine. Diagnosis may be made by analysis of any genetic element, such as, but not limited to, genes, exons, introns, gene regulatory elements, introns, expressed RNA, micro RNA, siRNA, and epigenetic elements. Sequencing methods sensitive enough to detect single copies of a gene may be used.

Yet other elements in the genome may be important to gene expression and as such, are contemplated as variants that may be used in the diagnostics of an ASD. For example, for the TSC1, TSC2, MECP2, SHANK3, GRM1, GRM5, ARC, EIF4E, HOMER1, HRAS, MAP2K1, MAP2K2, RAF1, PIK3CA, PIK3R1, FMR1, PTEN, RHEB and UBE3A genes, regulatory elements, including splice sites, transcription factor binding, A-I editing sites, microRNA binding sites, functional RNA structure sites, have been mapped and can be evaluated for mutations (variants) as described herein.

Thus, for each of the methods and compositions of the invention, the variant may comprise a nucleic acid sequence that encompasses at least one of the following: (1) A-to-I editing sites—adenosine-to-inosine (A-to-I) RNA editing exhibits precise regional specificity in the brain and is essential for normal behavior, and alterations in specific editing sites have been associated with a range of neuropathologies, including epilepsy and schizophrenia; (2) splice sites—it is estimated that nearly half of the causative mutations affect pre-mRNA splicing, and that many neurological diseases are caused by a splicing defect, including myotonic dystrophy and Parkinsonism linked to chromosome 17; (3) conserved functional RNA structures—single-stranded RNA-mediated regulation is structure dependent, and several core secondary structures are repeatedly used, such as hairpins and stem-loops, and alteration of these structures may affect their function to cause disease, as in the classical example of SEPN1-related myopathy; (4) validated transcription factor binding sites (TFBS)—the Encyclopedia of DNA Elements (ENCODE) project has validated the binding of several transcription factors to predicted transcription factor binding sites (TFBS) using CHiP-seq, and mutations in TFBS are associated with several psychiatric disorders, including schizophrenia and bipolar disorder; (5) microRNA (miRNA) binding sites—miRNAs are increasingly recognized as key regulators of brain development, inducing global shifts in gene expression programs by silencing target mRNAs, and mutations in microRNA binding sites have been implicated in Tourette Syndrome and TDP43-positive frontotemporal dementia; (6) polyadenylation sites—3 polyadenylation is necessary for mRNA stabilization, and polyadenylation defects may indirectly lead to altered expression of their mRNA, or, rarely have a direct gain of function effect, such as in oculopharyngeal muscular dystrophy; (7) known regulatory elements—the Open REGulatory ANNOtation database (ORegAnno) is a database for the curation of known regulatory elements from scientific literature; (8) miRNA genes encoded in the region of interest (ROI) as several miRNA genes are embedded within protein coding genes, and polymorphisms in miRNA genes are associated with Alzheimers disease and schizophrenia; (9) small nucleolar RNA genes encoded in the ROIs—several snoRNA genes are hosted in protein coding genes, and alterations in brain specific snoRNAs have been associated with certain diseases e.g., Prader-Willi Syndrome; (10) ultraconserved elements across placental mammals—ultraconserved elements have been under tremendous evolutionary pressure to prevent any sequence changes over millions of years, and as such are thought to carry a key functional role.

For example, embodiments of the invention provide methods for diagnosing the presence or an increased risk of developing an autism spectrum disorder in a subject, e.g., a child or a fetus. Such methods may include obtaining a nucleic acid from a tissue or body fluid sample from a subject, or, in the case of a fetus, from its mother. The method may further include the steps of sequencing the nucleic acid or determining the genomic arrangement or copy number of the nucleic acid to detect whether there is a variant or variants in the nucleic acid sequence or genomic arrangement or copy number. The method may further include the steps of assessing the clinical significance of a variant or variants in the nucleic acid sequence or genomic arrangement or copy number for autism spectrum disorders. Such analysis may include an evaluation of the extent of association of the variant sequence in affected populations (i.e., subjects having the disease). Such analysis may also include an analysis of the extent of effect the mutation may have on gene expression and/or protein function. The method may also include diagnosing presence or increased risk of developing the autism spectrum disorder based on results of this assessment.

Many different genomic analysis techniques can be used in order to make the assessments taught herein. For example, target resequencing, whole genome sequencing, single nucleotide polymorphism (SNP) analysis, copy number, epigenetic comparisons, rearrangements, deletions, and identification/analysis of other variants can be used to make the comparisons and identifications taught herein. The exemplification below is intended as illustrative and the skilled artisan understands that any available genomic analysis technique can be used in order to achieve the results specified herein.

Nucleic acid for analysis according to the invention may be obtained from a human sample, e.g. a human tissue or body fluid in any clinically acceptable manner. Nucleic acid can be obtained from adults or children or can be fetal material (e.g., fetal chromosomal materials from maternal serum or amniotic fluid). Any tissue or body fluid source is acceptable, including cellular material from tissue or fluids, such as mucous, blood, plasma, serum, serum derivatives, bile, blood, maternal blood, phlegm, saliva, sweat, amniotic fluid, mammary fluid, urine, and cerebrospinal fluid (CSF). A sample may also be a swab or a fine needle aspirate or biopsied tissue. A sample also may be media containing cells or biological material. In embodiments in which the subject is a fetus, the liquid sample can be obtained from either the amniotic fluid or the maternal blood.

The nucleic acid may be sequenced and/or its genomic arrangement and/or copy number is determined in order to detect variants (i.e., mutations) in the nucleic acid compared to a reference sequence derived from one or more individuals not known to suffer from an autism spectrum disorder at the time of sampling. As noted above, sequence variants may also be obtained empirically. The nucleic acid can include a plurality of nucleic acids derived from a plurality of genetic elements. Methods of detecting sequence variants or genomic arrangement or copy number are known in the art, and sequence variants or genomic arrangement or copy numbers can be detected by any sequencing method known in the art e.g., ensemble sequencing or single molecule sequencing, and by any method for detecting genomic arrangement or copy number known in the art, e.g., array comparative genomic hybridization.

One conventional method to perform sequencing is by chain termination and gel separation, as described by Sanger et al., 1977, Proc Natl Acad Sci USA, 74:5463-67. Another conventional sequencing method involves chemical degradation of nucleic acid fragments. See, Maxam et al., 1977, Proc. Natl. Acad. Sci., 74:560-564. Finally, methods have been developed based upon sequencing by hybridization. See, e.g., Harris et al., U.S. Patent Application Publication No. 20090156412. Each of these references are incorporated by reference in there entireties herein.

In certain embodiments, sequencing is performed by the Sanger sequencing technique. Classical Sanger sequencing involves a single-stranded DNA template, a DNA primer, a DNA polymerase, radioactively or fluorescently labeled nucleotides, and modified nucleotides that terminate DNA strand elongation. If the label is not attached to the dideoxynucleotide terminator (e.g., labeled primer), or is a monochromatic label (e.g., radioisotope), then the DNA sample is divided into four separate sequencing reactions, containing four standard deoxynucleotides (dATP, dGTP, dCTP and dTTP) and the DNA polymerase. To each reaction is added only one of the four dideoxynucleotides (ddATP, ddGTP, ddCTP, or ddTTP). These dideoxynucleotides are the chain-terminating nucleotides, lacking a 3'-OH group required for the formation of a phosphodiester bond between two nucleotides during DNA strand elongation. If each of the dideoxynucleotides carries a different label, however, (e.g., 4 different fluorescent dyes), then all the sequencing reactions can be carried out together without the need for separate reactions.

Incorporation of a dideoxynucleotide into the nascent, i.e., elongating, DNA strand terminates DNA strand extension, resulting in a nested set of DNA fragments of varying length. The newly synthesized and labeled DNA fragments are then denatured, and separated by size using gel electrophoresis on a denaturing polyacrylamide-urea gel capable of resolving single-base differences in chain length. If each of the four DNA synthesis reactions was labeled with the same, monochromatic label (e.g., radioisotope), then they are separated in one of four individual, adjacent lanes in the gel, in which each lane in the gel is designated according to the dideoxynucleotide used in the respective reaction, i.e., gel lanes A, T, G, C. If four different labels were utilized, then the reactions can be combined in a single lane on the gel. DNA bands are then visualized by autoradiography or fluorescence, and the DNA sequence can be directly read from the X-ray film or gel image or a continuous monitoring of fluorescence as the reaction products pass by a certain point in the gel.

The terminal nucleotide base is identified according to the dideoxynucleotide that was added in the reaction resulting in that band or its corresponding direct label. The relative positions of the different bands in the gel are then used to read (from shortest to longest) the DNA sequence as indicated. The Sanger sequencing process can be automated using a DNA sequencer, such as those commercially available from PerkinElmer, Beckman Coulter, Life Technologies, and others.

In other embodiments, sequencing of the nucleic acid is accomplished by massively parallel sequencing (also known as "next generation sequencing") of single-molecules or groups of largely identical molecules derived from single molecules by amplification through a method such as PCR. Massively parallel sequencing is shown for example in Lapidus et al., U.S. Pat. No. 7,169,560, Quake et al. U.S. Pat. No. 6,818,395, Harris U.S. Pat. No. 7,282,337 and Braslavsky, et al., PNAS (USA), 100: 3960-3964 (2003), the contents of each of which are incorporated by reference herein.

In next generation sequencing, PCR or whole genome amplification can be performed on the nucleic acid in order to obtain a sufficient amount of nucleic acid for analysis. In some forms of next generation sequencing, no amplification is required because the method is capable of evaluating DNA sequences from unamplified DNA. Once determined, the sequence and/or genomic arrangement and/or genomic copy number of the nucleic acid from the test sample is compared to a standard reference derived from one or more individuals not known to suffer from an autism spectrum disorder at the time their sample was taken. All differences between the sequence and/or genomic arrangement and/or genomic arrangement and/or copy number of the nucleic acid from the test sample and the standard reference are considered variants.

In next generation (massively parallel sequencing), all regions of interest are sequenced together, and the origin of each sequence read is determined by comparison (alignment) to a reference sequence. The regions of interest can be enriched together in one reaction, or they can be enriched separately and then combined before sequencing. In certain embodiments, and as described in more detail in the examples herein, the DNA sequences derived from coding exons of genes included in the assay are enriched by bulk hybridization of randomly fragmented genomic DNA to specific RNA probes. The same adapter sequences are attached to the ends of all fragments, allowing enrichment of all hybridization-captured fragments by PCR with one primer pair in one reaction. Regions that are less efficiently captured by hybridization are amplified by PCR with specific primers. In addition, PCR with specific primers is may be used to amplify exons for which similar sequences ("pseudo exons") exist elsewhere in the genome.

In certain embodiments where massively parallel sequencing is used, PCR products are concatenated to form long stretches of DNA, which are sheared into short fragments (e.g., by acoustic energy). This step ensures that the fragment ends are distributed throughout the regions of interest. Subsequently, a stretch of dA nucleotides is added to the 3' end of each fragment, which allows the fragments to bind to a planar surface coated with oligo(dT) primers (the "flow cell"). Each fragment may then be sequenced by extending the oligo(dT) primer with fluorescently-labeled nucleotides. During each sequencing cycle, only one type of nucleotide (A, G, T, or C) is added, and only one nucleotide is allowed to be incorporated through use of chain terminating nucleotides. For example, during the 1st sequencing cycle, a fluorescently labeled dCTP could be added. This nucleotide will only be incorporated into those growing complementary DNA strands that need a C as the next nucleotide. After each sequencing cycle, an image of the flow cell is taken to determine which fragment was extended. DNA strands that have incorporated a C will emit light, while DNA strands that have not incorporated a C will appear dark. Chain termination is reversed to make the growing DNA strands extendible again, and the process is repeated for a total of 120 cycles.

The images are converted into strings of bases, commonly referred to as "reads," which recapitulate the 3' terminal 25 to 60 bases of each fragment. The reads are then compared to the reference sequence for the DNA that was analyzed. Since any given string of 25 bases typically only occurs once in the human genome, most reads can be "aligned" to one specific place in the human genome. Finally, a consensus sequence of each genomic region may be built from the available reads and compared to the exact sequence of the reference at that position. Any differences between the consensus sequence and the reference are called as sequence variants.

Methods to Identify Autism Markers

In certain embodiments, the invention comprises methods to identify autism markers (i.e., variants in nucleic acid sequence that are associated with autism in a statistically significant manner). The genes and/or genomic regions assayed for new markers may be selected based upon their importance in biochemical pathways that show linkage and/or causation to autism. Or, the genes and/or genomic regions assayed for markers may be selected based on genetic linkage to DNA regions that are genetically linked to the inheritance of autism in families (e.g., Abrahams and Geschwind, 2008). Or, the genes and/or genomic regions assayed for markers may be evaluated systematically to cover certain regions of chromosomes not yet evaluated.

As discussed herein, autism spectrum disorders are generally characterized as one of five disorders coming under the umbrella of Pervasive Developmental Disorders (PDD). The five disorders under PDD include Autistic Disorder, Asperger's Disorder, Childhood Disintegrative Disorder (CDD), Rett's Disorder, and PDD-Not Otherwise Specified (PDD-NOS). In certain cases, the autism may be non-syndromic. Table 1 below provides a panel of genes or genomic regions that may be evaluated for new markers to diagnose an autism spectrum disorder according to the methods of the invention.

TABLE 1

| Gene | Protein encoded |
|---|---|
| EIF4E | Eukaryotic translation initiation factor 4E |
| EBP1 | Eukaryotic translation initiation factor 4E-binding protein 1 |
| EBP2 | Eukaryotic translation initiation factor 4E-binding protein 2 |
| AKT1 | RAC-alpha serine/threonine-protein kinase |
| AKT2 | RAC-beta serine/threonine-protein kinase |
| AKT3 | RAC-gamma serine/threonine-protein kinase |

TABLE 1-continued

| Gene | Protein encoded |
|---|---|
| PRKAA1 | 5'-AMP-activated protein kinase catalytic subunit alpha-1 |
| APP | Amyloid precursor protein |
| ARC | activity-regulated cytoskeleton-associated |
| ARX | Aristaless related homeobox |
| CACNA1C | calcium channel, voltage-dependent, L type, alpha 1C subunit |
| CAMK2G | Calcium/calmodulin-dependent protein kinase type II gamma chain |
| CDKL5 | cyclin-dependent kinase-like 5 |
| MET | MNNG (N-Methyl-N'-nitro-N-nitroso-guanidine) HOS transforming |
| CNTNAP2 | Contactin-associated protein-like 2 |
| DHCR7 | 7-dehydrocholesterol reductase |
| DRD3 | D(3) dopamine receptor |
| MAPK3 | Mitogen-activated protein kinase 3 |
| MAPK1 | Mitogen-activated protein kinase 1 |
| FKBP1A | Peptidyl-prolyl cis-trans isomerase FKBP1A |
| FMR1 | fragile X mental retardation 1 protein (FMRP) |
| AFF2 | AF4/FMR2 family member 2 |
| FOXP2 | Forkhead box protein P2 |
| FXR1 | Fragile X mental retardation syndrome-related protein 1 |
| FXR2 | Fragile X mental retardation syndrome-related protein 2 |
| GCH1 | GTP cyclohydrolase 1 |
| Gq-alpha | $G_q$ protein or $G_{q/11}$ |
| HLA-A | human leukocyte antigen |
| HOMER1 | Homer protein |
| HOXA1 | Homeobox protein Hox-A1 |
| HRAS | A ras oncogene |
| HTR3A | 5-hydroxytryptamine receptor 3A |
| HTR3C | 5-hydroxytryptamine receptor 3C |
| IGF1R | insulin-like growth factor 1 receptor |
| IGFBP1 | Insulin-like growth factor-binding protein 1 |
| MIRLET7B microRNA let-7b | A micro RNA (no protein) |
| MAP1B | Microtubule-associated protein 1B |
| MECP2 | Methyl CpG binding protein 2 |
| MAP2K1 | mitogen-activated protein kinase kinase 1 |
| MAP2K2 | mitogen-activated protein kinase kinase 1 |
| GRM1 | glutamate receptor, metabotropic 1 |
| GRM5 | glutamate receptor, metabotropic 5 |
| MKNK1 | MAP kinase-interacting serine/threonine-protein kinase 1 |
| MTOR | mammalian target of rapamycin (mTOR) |
| NF1 | Neurofibromatosis type I (NF-1) |
| NLGN3 | Neuroligin-3 |
| NLGN4 | Neuroligin-4 |
| NLGN4X | Neuroligin-4, X-linked |
| NLGN4Y | Neuroligin-4, X-linked |
| NRXN1 | Neurexin-1-alpha |
| OXTR | oxytocin receptor |
| PAK1 | Serine/threonine-protein kinase PAK 1 |
| PAK2 | Serine/threonine-protein kinase PAK 2 |
| PDPK1 | 3-phosphoinositide dependent protein kinase-1 |
| PDK1 | Pyruvate dehydrogenase [lipoamide] kinase isozyme 1, mitochondrial |
| PDK2 | Pyruvate dehydrogenase [lipoamide] kinase isozyme 2, mitochondrial |
| PIK3CA | Phosphatidylinositol 3-kinase, catalytic subunit |
| PIK3R1 | Phosphatidylinositol 3-kinase, catalytic subunit |
| PPP2CA | Protein phosphatase 2 (PP2) |
| PPP1CA | Serine/threonine-protein phosphatase PP1-alpha catalytic subunit |
| PPP1CC | Serine/threonine-protein phosphatase PP1-gamma catalytic subunit |
| PPP2R2B | Serine/threonine-protein phosphatase 2A 55 kDa regulatory subunit B beta isoform |
| PPP2R3B | Serine/threonine-protein phosphatase 2A regulatory subunit B subunit beta |
| PPP3CA | Calcineurin |
| PPP3CB | Serine/threonine-protein phosphatase 2B catalytic subunit beta isoform |
| PPP3CC | Serine/threonine-protein phosphatase 2B catalytic subunit gamma isoform |
| PRKCB | Protein kinase C beta type |
| DLG4 | Disks large homolog 4 |
| PTEN | Phosphatase and tensin homolog |
| PTPRD | Receptor-type tyrosine-protein phosphatase delta |
| PTPRF | Receptor-type tyrosine-protein phosphatase F |
| PTPRM | Receptor-type tyrosine-protein phosphatase mu |
| PTPRZ1 | Receptor-type tyrosine-protein phosphatase zeta |
| RAC1 | Ras-related C3 botulinum toxin substrate 1 |
| RAF1 | Map kinase |
| RPTOR | regulatory associated protein of MTOR complex |
| RELN | RELN protein |
| RGS4 | Regulator of G protein signaling 4 |
| RHEB | Ras homolog enriched in brain |
| RPS6KB1 | Ribosomal protein S6 kinase beta-1 |
| SHANK1 | Shank protein 1 |
| SHANK3 | Shank protein 3 |

TABLE 1-continued

| Gene | Protein encoded |
|---|---|
| SLC6A4 | Solute carrier family 6 (neurotransmitter transporter, serotonin) member |
| SNRPN | Small nuclear ribonucleoprotein-associated protein N |
| TSC1 | Tuberous sclerosis 1 |
| TSC2 | Tuberous sclerosis 2 |
| UBE3A | Ubiquitin protein ligase E3A |

In other embodiments, the genes or genomic regions evaluated for new markers may be part of a biochemical pathway that may be linked to the development of autism. For example, in certain embodiments, the genes and/or genomic regions are involved in the metabotropic glutamate receptor pathway. In one embodiment, the pathway is the mGluR5 signaling pathway and/or includes genes important to the activity of the mGluR5 receptor as the mGluR5 receptor. Thus, the mGluR5 receptor signaling pathway may, based upon its apparent importance in the development of fragile X syndrome and the association of several other components within the broadly defined mGluR5 signaling pathway with ASD, provide markers predictive of ASD. Cumulative contribution of individually rare sequence variants within multiple components of a given pathway to the same phenotype has been shown to occur for other genetic diseases. Or, other biochemical pathways that are related to certain types of autism syndromes may be evaluated.

For example, FIG. 1 provides a depiction of genes that are involved in the mGluR5 signaling pathway and that may be evaluated according to the invention to determine if mutations in such genes are linked to the development of autism. Where evidence indicates that such sequence variations may be linked to the development of autism, isolated sequences may be provided for use in DNA sequencing of patient samples to provide an indication of the presence and/or increased risk of developing autism in the subject. For example, and as described in more detail herein, Table 2 provides a subset of genes and/or genomic regions that may be evaluated, as well as mutations found in autistic subjects (i.e., patients diagnosed with non-sydromic autism).

Figure 2:
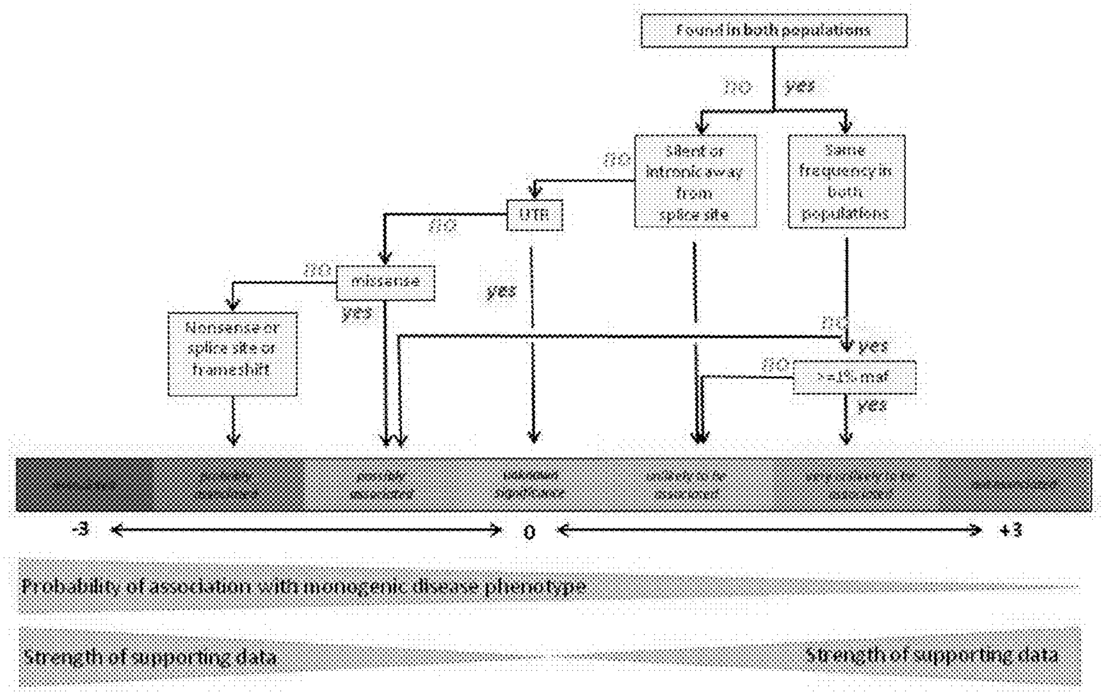
FIG. 2 shows a method for variant classification in accordance with an embodiment of the present invention.

As depicted in FIG. 2, the variants and/or variant combinations may be assessed for their clinical significance for autism spectrum disorders based on one or more of the following methods. If a variant or a variant combination is reported or known to occur more often in nucleic acid from subjects with, than in subjects without, autism spectrum disorders, it is considered to be at least potentially predisposing to autism spectrum disorders. If a variant or a variant combination is reported or known to be transmitted exclusively or preferentially to individuals with an autism spectrum disorder, it is considered to be at least potentially predisposing to autism spectrum disorders. Conversely, if a variant is found in both populations at a similar frequency, it is less likely to be associated with the development of an autism syndrome disorder (ASD) (see FIG. 2, right hand side).

If a variant or a variant combination is reported or known to have an overall deleterious effect on the function of a protein or a biological system in an experimental model system appropriate for measuring the function of this protein or this biological system, and if this variant or variant combination affects a gene or genes known to be associated with autism spectrum disorders, it is considered to be at least potentially predisposing to autism spectrum disorders. For example, if a variant or a variant combination is predicted to have an overall deleterious effect on a protein or gene expression (i.e., resulting in a nonsense mutation, a frameshift mutation, or a splice site mutation, or even a missense mutation), based on the predicted effect on the sequence and/or the structure of a protein or a nucleic acid, and if this variant or variant combination affects a gene or genes known to be associated with autism spectrum disorders, it is considered to be at least potentially predisposing to autism spectrum disorders (see FIG. 2, left-hand side).

Also, in certain embodiments, the overall number of variants may be important. If, in the test sample, a variant or several variants are detected that are, individually or in combination, assessed as at least probably associated with an autism spectrum disorder, then the individual in whose genetic material this variant or these variants were detected can be diagnosed as being affected with or at high risk of developing an autism spectrum disorder.

Methods and Compositions for Diagnosing an Autism Spectrum Disorder

In certain embodiments, diagnosis of the autism spectrum disorder is carried out by detecting variation in the sequence, genomic location or arrangement, and/or genomic copy number of a nucleic acid or a panel of nucleic acids. For example, in some embodiments, the gene or genomic regions assessed for variants is selected from the genes in Table 1. The panel can include at least 5, 10, 20, 30, 40, 50, 60, 70, 80, or 90 of the genes in Table 1. In other embodiments, the diagnosis is made with less than 5 genes from Table 1, and in certain embodiments, with only 1 gene from Table 1.

For example, Table 2 below provides a subset of genes from Table 1, at least some of which are involved in mGluR5 receptor signaling. Table 2 also provides variants for these genes that may be detected in subjects with autism. These variants may, in certain embodiments of the methods and compositions of the invention, be indicative of an autism spectrum disorder in a subject.

TABLE 2

Variants for detection in ASD from mGluR5 pathway

| Gene | Position | Variant | AA change | Type | Major allele | Minor allele | Variant type |
|---|---|---|---|---|---|---|---|
| ARC | 95 | c.65T>G | p.Val22Gly | missense | T | G | T>G |
| ARC | 155 | c.125T>G | p.Val42Gly | missense | T | G | T>G |
| ARC | 167 | c.137A>C | p.His46Pro | missense | A | C | A>C |
| ARC | 173 | c.143A>C | p.His48Pro | missense | A | C | A>C |

TABLE 2-continued

| Variants for detection in ASD from mGluR5 pathway | | | | | | | |
|---|---|---|---|---|---|---|---|
| Gene | Position | Variant | AA change | Type | Major allele | Minor allele | Variant type |
| ARC | 188 | c.158T>G | p.Val53Gly | missense | T | G | T>G |
| ARC | 200 | c.170T>G | p.Val57Gly | missense | T | G | T>G |
| ARC | 229 | c.199T>G | p.Ser67Ala | missense | T | G | T>G |
| ARC | 266 | c.236T>G | p.Val79Gly | missense | T | G | T>G |
| ARC | 341 | c.311A>C | p.Asn104Thr | missense | A | C | A>C |
| ARC | 376 | c.346T>G | p.Trp116Gly | missense | T | G | T>G |
| ARC | 413 | c.383A>C | p.Asp128Ala | missense | A | C | A>C |
| ARC | 469 | c.439A>C | p.Thr147Pro | missense | A | C | A>C |
| ARC | 479 | c.449T>G | p.Val150Gly | missense | T | G | T>G |
| ARC | 485 | c.455T>G | p.Val152Gly | missense | T | G | T>G |
| ARC | 503 | c.473A>C | p.Tyr158Ser | missense | A | C | A>C |
| ARC | 619 | c.589T>G | p.Trp197Gly | missense | T | G | T>G |
| ARC | 632 | c.602A>G | p.Glu201Gly | missense | A | G | A>G |
| ARC | 656 | c.626T>G | p.Val209Gly | missense | T | G | T>G |
| ARC | 698 | c.668A>C | p.His223Pro | missense | A | C | A>C |
| ARC | 722 | c.692T>-invalid | | deletion | T | — | T>-invalid |
| ARC | 722 | c.692T>G | p.Val231Gly | missense | T | G | T>G |
| ARC | 726 | c.696C>G | p.Gly232Gly | silent | C | G | C>G |
| ARC | 739 | c.709T>G | p.Tyr237Asp | missense | T | G | T>G |
| ARC | 748 | c.718T>G | p.Ser240Pro | missense | T | G | T>G |
| ARC | 787 | c.757T>G | p.Trp253Gly | missense | T | G | T>G |
| ARC | 790 | c.760T>G | p.Trp254Gly | missense | T | G | T>G |
| ARC | 859 | c.829G>A | p.Gly277Ser | missense | G | A | G>A |
| ARC | 1012 | c.982A>C | p.Thr328Pro | missense | A | C | A>C |
| ARC | 1043 | c.1013G>C | p.Arg338Pro | missense | G | C | G>C |
| ARC | 1046 | c.1016A>C | p.His339Pro | missense | A | C | A>C |
| ARC | 1060 | c.1030A>C | p.Thr344Pro | missense | A | C | A>C |
| ARC | 1094 | c.1064T>G | p.Val355Gly | missense | T | G | T>G |
| ARC | 1136 | c.1106A>C | | missense | A | C | A>C |
| ARC | 1139 | c.1109T>C | p.Leu370Pro | missense | T | C | T>C |
| ARC | 1145 | c.1115T>G | p.Val372Gly | missense | T | G | T>G |
| ARC | 1162 | c.1132A>C | p.Thr378Pro | missense | A | C | A>C |
| ARC | 1166 | c.1136T>C | p.Leu379Pro | missense | T | C | T>C |
| ARC | 1168 | c.1138A>C | p.Thr380Pro | missense | A | C | A>C |
| ARC | 1181 | c.1151A>C | p.Asn384Thr | missense | A | C | A>C |
| ARC | 1200 | c.1170T>G | p.Ser390Arg | missense | T | G | T>G |
| ARC | 1202 | c.1172A>C | p.Asp391Ala | missense | A | C | A>C |
| ARC | 1219 | c.1189T>G | p.X397Glu | missense | T | G | T>G |
| EIF4E | 113 | c.622G>A | p.Gly208Ser | missense | G | A | G>A |
| GRM1 | 56 | c.26T>-invalid | | deletion | T | — | T>-invalid |
| GRM1 | 443 | c.413A>C | p.Asn138Thr | missense | A | C | A>C |
| GRM1 | 654 | c.624C>T | p.Asp208Asp | silent | C | T | C>T |
| GRM1 | 71 | c.1643C>T | p.Thr548Met | missense | C | T | C>T |
| GRM1 | 35 | c.1734T>G | p.Cys578Trp | missense | T | G | T>G |
| GRM1 | 63 | c.1762T>G | p.Trp588Gly | missense | T | G | T>G |
| GRM1 | 183 | c.1882C>G | p.Arg628Gly | missense | C | G | C>G |
| GRM1 | 240 | c.1939A>C | p.Thr647Pro | missense | A | C | A>C |
| GRM1 | 261 | c.1960A>C | p.Thr654Pro | missense | A | C | A>C |
| GRM1 | 284 | c.1983C>T | p.Arg661Arg | silent | C | T | C>T |
| GRM1 | 399 | c.2098T>G | p.Phe700Val | missense | T | G | T>G |
| GRM1 | 486 | c.2185C>A | p.Pro729Thr | missense | C | A | C>A |
| GRM1 | 603 | c.2302A>C | p.Thr768Pro | missense | A | C | A>C |
| GRM1 | 641 | c.2340C>T | p.Asn780Asn | silent | C | T | C>T |
| GRM1 | 882 | c.2581G>A | p.Gly861Ser | missense | G | A | G>A |
| GRM1 | 95 | c.2725A>C | p.Met909Leu | missense | A | C | A>C |
| GRM1 | 163 | c.2793G>-invalid | | deletion | G | — | G>-invalid |
| GRM1 | 229 | c.2859C>T | p.Thr953Thr | silent | C | T | C>T |
| GRM1 | 332 | c.2962A>C | p.Thr988Pro | missense | A | C | A>C |
| GRM1 | 538 | c.3168T>-invalid | | deletion | T | — | T>-invalid |
| GRM1 | 580 | c.3210A>C | p.Pro1070Pro | silent | A | C | A>C |
| GRM1 | 583 | c.3213T>G | p.Pro1071Pro | silent | T | G | T>G |
| GRM1 | 620 | c.3250A>C | p.Thr1084Pro | missense | A | C | A>C |
| GRM1 | 727 | c.3357G>C | p.Thr1119Thr | silent | G | C | G>C |
| HOMER1 | 234 | c.1080C>T | | 3'UTR | C | T | C>T |
| HRAS | 21 | c.-10C>T | | 5'UTR | C | T | -C>T |
| HRAS | 56 | c.26T>G | p.Val9Gly | missense | T | G | T>G |
| HRAS | 69 | c.39T>G | p.Gly13Gly | silent | T | G | T>G |
| HRAS | 50 | c.131T>G | p.Val44Gly | missense | T | G | T>G |
| HRAS | 70 | c.151T>G | p.Cys51Gly | missense | T | G | T>G |
| GRM5 | 23 | c.-8T>G | | 5'UTR | T | G | -T>G |
| GRM5 | 117 | c.87T>C | p.Ala29Ala | silent | T | C | T>C |
| GRM5 | 126 | c.96G>A | p.Pro32Pro | silent | G | A | G>A |
| GRM5 | 390 | c.360A>G | p.Ser120Ser | silent | A | G | A>G |
| GRM5 | 96 | c.727G>T | p.Ala243Ser | missense | G | T | G>T |
| GRM5 | 50 | c.1167A>G | p.Thr389Thr | silent | A | G | A>G |

TABLE 2-continued

Variants for detection in ASD from mGluR5 pathway

| Gene | Position | Variant | AA change | Type | Major allele | Minor allele | Variant type |
|---|---|---|---|---|---|---|---|
| GRM5 | 207 | c.1563+8G>A | | intronic | G | A | +G>A |
| GRM5 | 27 | c.1691−4G>T | | intronic | G | T | −G>T |
| GRM5 | 120 | c.1780A>C | p.Thr594Pro | missense | A | C | A>C |
| GRM5 | 467 | c.2127T>A | p.Val709Val | silent | T | A | T>A |
| GRM5 | 719 | c.2379T>C | p.Phe793Phe | silent | T | C | T>C |
| GRM5 | 805 | c.2465T>G | p.Val822Gly | missense | T | G | T>G |
| GRM5 | 838 | c.2498T>G | p.Val833Gly | missense | T | G | T>G |
| GRM5 | 894 | c.2554T>G | p.Ser852Ala | missense | T | G | T>G |
| GRM5 | 52 | c.2652G>A | p.Thr884Thr | silent | G | A | G>A |
| GRM5 | 53 | c.2653T>G | p.Trp885Gly | missense | T | G | T>G |
| GRM5 | 63 | c.2663A>C | p.Asn888Thr | missense | A | C | A>C |
| GRM5 | 111 | c.2711A>C | p.His904Pro | missense | A | C | A>C |
| GRM5 | 147 | c.2747T>G | p.Val916Gly | missense | T | G | T>G |
| GRM5 | 344 | c.2944G>A | p.Ala982Thr | missense | G | A | G>A |
| GRM5 | 344 | c.2944G>T | p.Ala982Ser | missense | G | T | G>T |
| GRM5 | 345 | c.2945C>−invalid | | deletion | C | — | C>−invalid |
| GRM5 | 354 | c.2954G>A | p.Arg985His | missense | G | A | G>A |
| GRM5 | 354 | c.2954G>C | p.Arg985Pro | missense | G | C | G>C |
| GRM5 | 354 | c.2954G>T | p.Arg985Leu | missense | G | T | G>T |
| GRM5 | 355 | c.2955C>G | p.Arg985Arg | silent | C | G | C>G |
| GRM5 | 356 | c.2956T>A | p.Ser986Thr | missense | T | A | T>A |
| GRM5 | 356 | c.2956T>C | p.Ser986Pro | missense | T | C | T>C |
| GRM5 | 432 | c.3032A>C | p.His1011Pro | missense | A | C | A>C |
| GRM5 | 500 | c.3100A>C | p.Thr1034Pro | missense | A | C | A>C |
| GRM5 | 509 | c.3109A>C | p.Thr1037Pro | missense | A | C | A>C |
| GRM5 | 523 | c.3123C>T | p.Ser1041Ser | silent | C | T | C>T |
| GRM5 | 533 | c.3133T>C | p.Ser1045Pro | missense | T | C | T>C |
| GRM5 | 548 | c.3148A>C | p.Thr1050Pro | missense | A | C | A>C |
| GRM5 | 570 | c.3170T>G | p.Val1057Gly | missense | T | G | T>G |
| GRM5 | 626 | c.3226A>C | p.Thr1076Pro | missense | A | C | A>C |
| GRM5 | 754 | c.3354T>−invalid | | deletion | T | — | T>−invalid |
| GRM5 | 754 | c.3354T>G | p.Ala1118Ala | silent | T | G | T>G |
| GRM5 | 755 | c.3355G>−invalid | | deletion | G | — | G>−invalid |
| GRM5 | 756 | c.3356C>G | p.Ala1119Gly | missense | C | G | C>G |
| GRM5 | 763 | c.3363C>A | p.Ala1121Ala | silent | C | A | C>A |
| GRM5 | 786 | c.3386T>G | p.Val1129Gly | missense | T | G | T>G |
| GRM5 | 794 | c.3394A>C | p.Thr1132Pro | missense | A | C | A>C |
| GRM5 | 822 | c.3422T>G | p.Val1141Gly | missense | T | G | T>G |
| GRM5 | 851 | c.3451C>A | p.Pro1151Thr | missense | C | A | C>A |
| GRM5 | 884 | c.3484T>G | p.Ser1162Ala | missense | T | G | T>G |
| GRM5 | 899 | c.3499A>C | p.Thr1167Pro | missense | A | C | A>C |
| GRM5 | 903 | c.3503T>C | p.Leu1168Pro | missense | T | C | T>C |
| GRM5 | 920 | c.3520A>C | p.Thr1174Pro | missense | A | C | A>C |
| GRM5 | 920 | c.3520A>G | p.Thr1174Ala | missense | A | G | A>G |
| GRM5 | 946 | c.3546G>T | | 3'UTR | G | T | G>T |
| MAP2K1 | 54 | c.315C>T | p.Pro105Pro | silent | C | T | C>T |
| RAF1 | 152 | c.122G>A | p.Arg41Gln | missense | G | A | G>A |
| RAF1 | 66 | c.356C>T | p.Ala119Val | missense | C | T | C>T |
| RAF1 | 19 | c.1537−12T>G | | intronic | T | G | −T>G |
| RAF1 | 181 | c.1668+19G>T | | intronic | G | T | +G>T |
| RAF1 | 18 | c.1669−13T>C | | intronic | T | C | −T>C |
| RAF1 | 168 | c.1941C>T | p.Val647Val | silent | C | T | C>T |
| SHANK3 | 106 | c.524A>C | p.His175Pro | missense | A | C | A>C |
| SHANK3 | 120 | c.538A>C | p.Thr180Pro | missense | A | C | A>C |
| SHANK3 | 135 | c.553A>C | p.Thr185Pro | missense | A | C | A>C |
| SHANK3 | 54 | c.624A>C | p.Ser208Ser | silent | A | C | A>C |
| SHANK3 | 24 | c.769−7C>G | | intronic | C | G | −C>G |
| SHANK3 | 125 | c.863A>C | p.His288Pro | missense | A | C | A>C |
| SHANK3 | 43 | c.898C>T | p.Arg300Cys | missense | C | T | C>T |
| SHANK3 | 254 | c.1254G>A | p.Glu418Glu | silent | G | A | G>A |
| SHANK3 | 44 | c.2091C>G | p.Pro697Pro | silent | C | G | C>G |
| SHANK3 | 1217 | c.3585G>A | p.Lys1195Lys | silent | G | A | G>A |
| SHANK3 | 1559 | c.3927C>T | p.Ser1309Ser | silent | C | T | C>T |
| SHANK3 | 1781 | c.4149C>T | p.Asp1383Asp | silent | C | T | C>T |
| SHANK3 | 2000 | c.4368C>T | p.Ser1456Ser | silent | C | T | C>T |
| SHANK3 | 468 | c.5090A>C | p.His1697Pro | missense | A | C | A>C |
| MAP2K2 | 132 | c.405G>C | p.Gly135Gly | silent | G | C | G>C |
| MAP2K2 | 147 | c.420C>T | p.Asp140Asp | silent | C | T | C>T |
| MAP2K2 | 108 | c.528G>A | p.Ala176Ala | silent | G | A | G>A |
| MAP2K2 | 171 | c.846C>T | p.Pro282Pro | silent | C | T | C>T |
| MAP2K2 | 58 | c.1074G>A | p.Ala358Ala | silent | G | A | G>A |
| MECP2 | 27 | c.378−4A>C | | intronic | A | C | −A>C |
| MECP2 | 87 | c.434T>G | p.Val145Gly | missense | T | G | T>G |
| MECP2 | 90 | c.437G>T | p.Gly146Val | missense | G | T | G>T |
| MECP2 | 93 | c.440A>C | p.Asp147Ala | missense | A | C | A>C |

TABLE 2-continued

Variants for detection in ASD from mGluR5 pathway

| Gene | Position | Variant | AA change | Type | Major allele | Minor allele | Variant type |
|---|---|---|---|---|---|---|---|
| MECP2 | 105 | c.452A>C | p.Asp151Ala | missense | A | C | A>C |
| MECP2 | 138 | c.485G>T | p.Arg162Ile | missense | G | T | G>T |
| MECP2 | 220 | c.567A>C | p.Gly189Gly | silent | A | C | A>C |
| MECP2 | 235 | c.582C>T | p.Ser194Ser | silent | C | T | C>T |
| MECP2 | 242 | c.589A>C | p.Thr197Pro | missense | A | C | A>C |
| MECP2 | 271 | c.618T>G | p.Gly206Gly | silent | T | G | T>G |
| MECP2 | 338 | c.685T>G | p.Ser229Ala | missense | T | G | T>G |
| MECP2 | 355 | c.702T>G | p.Ala234Ala | silent | T | G | T>G |
| MECP2 | 364 | c.711T>-invalid | | deletion | T | — | T>-invalid |
| MECP2 | 364 | c.711T>G | p.Gly237Gly | silent | T | G | T>G |
| MECP2 | 387 | c.734T>G | p.Val245Gly | missense | T | G | T>G |
| MECP2 | 393 | c.740T>G | p.Val247Gly | missense | T | G | T>G |
| MECP2 | 403 | c.750C>T | p.Arg250Arg | silent | C | T | C>T |
| MECP2 | 406 | c.753C>T | p.Pro251Pro | silent | C | T | C>T |
| MECP2 | 436 | c.783T>G | p.Pro261Pro | silent | T | G | T>G |
| MECP2 | 516 | c.863T>G | p.Val288Gly | missense | T | G | T>G |
| MECP2 | 552 | c.899T>G | p.Val300Gly | missense | T | G | T>G |
| MECP2 | 555 | c.902T>C | p.Leu301Pro | missense | T | C | T>C |
| MECP2 | 555 | c.902T>G | p.Leu301Arg | missense | T | G | T>G |
| MECP2 | 609 | c.956T>G | p.Val319Gly | missense | T | G | T>G |
| MECP2 | 612 | c.959T>G | p.Val320Gly | missense | T | G | T>G |
| MECP2 | 627 | c.974T>G | p.Val325Gly | missense | T | G | T>G |
| MECP2 | 632 | c.979A>C | p.Thr327Pro | missense | A | C | A>C |
| MECP2 | 640 | c.987T>G | p.Gly329Gly | silent | T | G | T>G |
| MECP2 | 649 | c.996C>A | p.Ser332Arg | missense | C | A | C>A |
| MECP2 | 649 | c.996C>T | p.Ser332Ser | silent | C | T | C>T |
| MECP2 | 733 | c.1080A>C | p.Ser360Ser | silent | A | C | A>C |
| MECP2 | 805 | c.1152A>C | p.Pro384Pro | silent | A | C | A>C |
| MECP2 | 815 | c.1162C>T | p.Pro388Ser | missense | C | T | C>T |
| MECP2 | 817 | c.1164A>C | p.Pro388Pro | silent | A | C | A>C |
| MECP2 | 823 | c.1170A>C | p.Pro390Pro | silent | A | C | A>C |
| MECP2 | 842 | c.1189G>A | p.Glu397Lys | missense | G | A | G>A |
| MECP2 | 851 | c.1198A>C | p.Thr400Pro | missense | A | C | A>C |
| MECP2 | 882 | c.1229G>T | p.Ser410Ile | missense | G | T | G>T |
| MECP2 | 910 | c.1257C>T | p.Pro419Pro | silent | C | T | C>T |
| MECP2 | 933 | c.1280A>C | p.Asp427Ala | missense | A | C | A>C |
| MECP2 | 977 | c.1324A>C | p.Thr442Pro | missense | A | C | A>C |
| MECP2 | 986 | c.1333A>C | p.Thr445Pro | missense | A | C | A>C |
| MECP2 | 1088 | c.1435A>C | p.Thr479Pro | missense | A | C | A>C |
| MECP2 | 1090 | c.1437G>A | p.Thr479Thr | silent | G | A | G>A |
| MECP2 | 1095 | c.1442T>G | p.Val481Gly | missense | T | G | T>G |
| PIK3CA | 114 | c.1143C>G | p.Pro381Pro | silent | C | G | C>G |
| PIK3CA | 76 | c.1297A>C | p.Thr433Pro | missense | A | C | A>C |
| PIK3CA | 155 | c.1529A>C | p.His510Pro | missense | A | C | A>C |
| PIK3CA | 35 | c.1544A>G | p.Asn515Ser | missense | A | G | A>G |
| PIK3CA | 72 | c.1788A>G | p.Glu596Glu | silent | A | G | A>G |
| PIK3CA | 53 | c.2439A>G | p.Thr813Thr | silent | A | G | A>G |
| PIK3CA | 154 | c.3060A>G | p.Ala1020Ala | silent | A | G | A>G |
| PIK3CA | 169 | c.3075C>T | p.Thr1025Thr | silent | C | T | C>T |
| PIK3R1 | 18 | c.837-13C>T | | intronic | C | T | -C>T |
| TSC1 | 166 | c.346T>G | p.Leu116Val | missense | T | G | T>G |
| TSC1 | 52 | c.935A>C | p.Tyr312Ser | missense | A | C | A>C |
| TSC1 | 123 | c.1006C>T | p.Arg336Trp | missense | C | T | C>T |
| TSC1 | 67 | c.1178C>T | p.Thr393Ile | missense | C | T | C>T |
| TSC1 | 115 | c.1523A>C | p.Tyr508Ser | missense | A | C | A>C |
| TSC1 | 151 | c.1559A>C | p.His520Pro | missense | A | C | A>C |
| TSC1 | 172 | c.1580A>G | p.Gln527Arg | missense | A | G | A>G |
| TSC1 | 200 | c.1608A>C | p.Leu536Phe | missense | A | C | A>C |
| TSC1 | 202 | c.1610A>C | p.His537Pro | missense | A | C | A>C |
| TSC1 | 275 | c.1683T>G | p.Ser561Arg | missense | T | G | T>G |
| TSC1 | 373 | c.1781T>G | p.Val594Gly | missense | T | G | T>G |
| TSC1 | 391 | c.1799A>C | p.Gln600Pro | missense | A | C | A>C |
| TSC1 | 421 | c.1829T>G | p.Val610Gly | missense | T | G | T>G |
| TSC1 | 435 | c.1843A>C | p.Thr615Pro | missense | A | C | A>C |
| TSC1 | 436 | c.1844C>A | p.Thr615Lys | missense | C | A | C>A |
| TSC1 | 509 | c.1917T>G | p.Gly639Gly | silent | T | G | T>G |
| TSC1 | 535 | c.1943T>G | p.Val648Gly | missense | T | G | T>G |
| TSC1 | 550 | c.1958T>G | p.Ile653Arg | missense | T | G | T>G |
| TSC1 | 552 | c.1960C>A | p.Gln654Lys | missense | C | A | C>A |
| TSC1 | 552 | c.1960C>G | p.Gln654Glu | missense | C | G | C>G |
| TSC1 | 555 | c.1963C>A | p.Gln655Lys | missense | C | A | C>A |
| TSC1 | 591 | c.1997+2T>G | | splice site | T | G | +T>G |
| TSC1 | 183 | c.2194C>T | p.His732Tyr | missense | C | T | C>T |
| TSC1 | 82 | c.2865C>T | p.Thr955Thr | silent | C | T | C>T |
| TSC1 | 97 | c.3042C>T | p.His1014His | silent | C | T | C>T |

TABLE 2-continued

| Variants for detection in ASD from mGluR5 pathway | | | | | | | |
|---|---|---|---|---|---|---|---|
| Gene | Position | Variant | AA change | Type | Major allele | Minor allele | Variant type |
| TSC1 | 114 | c.3059C>T | p.Thr1020Ile | missense | C | T | C>T |
| TSC1 | 157 | c.3102T>G | p.Gly1034Gly | silent | T | G | T>G |
| TSC1 | 160 | c.3105T>G | p.Gly1035Gly | silent | T | G | T>G |
| UBE3A | 301 | c.333C>G | p.Asn111Lys | missense | C | G | C>G |
| UBE3A | 126 | c.457G>A | p.Val153Ile | missense | G | A | G>A |
| UBE3A | 261 | c.592G>A | p.Ala198Thr | missense | G | A | G>A |
| UBE3A | 287 | c.618A>T | p.Ala206Ala | silent | A | T | A>T |
| UBE3A | 823 | c.1154T>G | p.Val385Gly | missense | T | G | T>G |
| UBE3A | 1007 | c.1338T>C | p.Phe446Phe | silent | T | C | T>C |
| UBE3A | 1097 | c.1428A>G | p.Thr476Thr | silent | A | G | A>G |
| TSC2 | 80 | c.275A>T | p.Glu92Val | missense | A | T | A>T |
| TSC2 | 127 | c.433G>A | p.Ala145Thr | missense | G | A | G>A |
| TSC2 | 26 | c.649−5A>C | | intronic | A | C | −A>C |
| TSC2 | 118 | c.736A>C | p.Thr246Pro | missense | A | C | A>C |
| TSC2 | 52 | c.796A>C | p.Thr266Pro | missense | A | C | A>C |
| TSC2 | 119 | c.848+15T>G | | intronic | T | G | +T>G |
| TSC2 | 65 | c.1292C>T | p.Ala431Val | missense | C | T | C>T |
| TSC2 | 66 | c.1875A>C | p.Ser625Ser | silent | A | C | A>C |
| TSC2 | 190 | c.3126G>T | p.Pro1042Pro | silent | G | T | G>T |
| TSC2 | 45 | c.3299T>G | p.Val1100Gly | missense | T | G | T>G |
| TSC2 | 198 | c.3778A>C | p.Thr1260Pro | missense | A | C | A>C |
| TSC2 | 43 | c.3827C>T | p.Ser1276Phe | missense | C | T | C>T |
| TSC2 | 61 | c.3914C>T | p.Pro1305Leu | missense | C | T | C>T |
| TSC2 | 133 | c.3986G>A | p.Arg1329His | missense | G | A | G>A |
| TSC2 | 23 | c.4006−8C>T | | intronic | C | T | −C>T |
| TSC2 | 76 | c.4051G>A | p.Glu1351Lys | missense | G | A | G>A |
| TSC2 | 294 | c.4269G>A | p.Leu1423Leu | silent | G | A | G>A |
| TSC2 | 310 | c.4285G>T | p.Ala1429Ser | missense | G | T | G>T |
| TSC2 | 24 | c.4990−7C>T | | intronic | C | T | −C>T |
| TSC2 | 69 | c.5028G>A | p.Leu1676Leu | silent | G | A | G>A |
| TSC2 | 23 | c.5069−8C>T | | intronic | C | T | −C>T |
| TSC2 | 130 | c.5359G>A | p.Gly1787Ser | missense | G | A | G>A |
| TSC2 | 200 | c.5429G>A | | 3'UTR | G | A | G>A |

In Table 2, all numbers and names for variants are relative to the human reference sequence as published at the genome.ucsc.edu web-site March of 2006 (hg18) and according to the system suggested by the Human Genome Variation Society. According to the HGVS system, the start of the coding sequence (i.e., the "A" of the start codon ATG) is designated as +1. All coding nucleotides, i.e., all exonic nucleotides, in the designated mRNA isoform are numbered consecutively. Intronic nucleotides are numbered relative to the nearest exonic nucleotide. For example, the first three nucleotides of a gene (atg) would be numbered 1, 2, and 3 respectively with non-exon elements numbered as shown below (see e.g., Correlagen web-site for a discussion).

c.4_5insT), or substitutions of a group of nucleotides for a group of different nucleotides, where the number of deleted and inserted nucleotides can be different (e.g., c.4_6delinsT).

Mutations, even a single nucleotide substitution, can have very different results. Splice site mutations destroy an existing splice site or create a new splice site. Both types of variations can lead to altered mRNA processing and thus, a dramatically different mature mRNA and different protein.

Nonsense mutations introduce a stop codon in the middle of a coding region, which leads to truncation of the protein. Missense mutations change one amino acid in the protein

| Variant Numbering | | | | | | | | | | | | | | | | | | | | | | | | | |
|---|---|---|---|---|---|---|---|---|---|---|---|---|---|---|---|---|---|---|---|---|---|---|---|---|---|
| Exon 1 | | | | | | | Exon 2 | | | | | | | | | | | | Exon 3 | | | | | | |
| 5'UTR | | | Intron 1 | | | | 5'UTR | | Met | | | Glu | | | Intron 2 | | | | Val | | | stop | | | 3'UTR |
| G | A | G | T | T | A | G | G | T | A | T | G | G | A | G | G | T | A | G | G | T | A | T | G | A | G | A |
| −5 | −4 | −3 | −3 + 1 | −3 + 2 | −2 − 2 | −2 − 1 | −2 | −1 | 1 | 2 | 3 | 4 | 5 | 6 | 6 + 1 | 6 + 2 | 7 − 2 | 7 − 1 | 7 | 8 | 9 | 10 | 11 | 12 | 13 | 14 |

As shown in Table 2, sequence variants are named according to the change they cause in the DNA sequence and the resultant change (if any) to the peptide sequence. The most common types of changes are substitutions of one nucleotide for another nucleotide (e.g., c.3G>T). Other types of variants include deletions of one or more nucleotides (e.g., c.4_6delGAA), insertions of one or more nucleotides (e.g., into another. Synonymous mutations are mutations that do not change the amino acid sequence.

Frameshift mutations cause a shift in reading frame leading to a complete change of the amino acid sequence downstream of the mutation (i.e., the frameshift site). A frameshift mutation is caused by a net deletion or insertion of a number of nucleotides not divisible by 3.In-frame deletions and/or insertions lead to deletion or insertion of one or more amino acids in the protein, but do not alter the reading frame and so, do not change the amino acid sequence downstream of the deletion or insertion site.

The variants in Table 2 have been detected in subjects with non-syndromic autism using the methods described herein. In certain embodiments, diagnosis of the autism spectrum disorder can be carried out by comparing a sample nucleic acid including the variant(s) to a panel of nucleic acids including the nucleic acid variants selected from the genes in Table 2. Or, novel variants may be included in the panel. The panel can include at least 1, 2, 3, 5, 10, 15, 16 or all of the genes in Table 2. In other embodiments, the diagnosis is made with less than 3 genes from Table 2, and in certain embodiments, with only 1 gene from Table 2.

Thus, ARC (activity-regulated cytoskeleton-associated) encodes a protein that is important for consolidation of synaptic plasticity as well as formation of long-term memory. ARC also regulates endocytosis of AMPA receptors in response to synaptic activity and is involved in homeostatic synaptic scaling of AMPA receptors. The ARC gene is located on chromosome 8 at 8q24.3, starting 143, 689,412 bp from the p-terminus and ending 143,692,835 bp from the p-terminus (3,424 bases; orientation: minus strand). The genomic sequence of ARC is found in GenBank at accession number NC_000008. The gene sequence (NM_015193) is shown in FIG. 3A as SEQ ID NO: 1 (coding sequence from 202-1392); the protein sequence is shown in FIG. 3B as SEQ ID NO: 2. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

EIF4E (eukaryotic translation initiation factor 4E) encodes the eukaryotic translation initiation factor 4E. EIF4E is a eukaryotic translation initiation factor involved in directing ribosomes to the 7-methyl-gaunosine cap structure of mRNA. EI4FE is part of the EIF4E pre-initiation complex. The genomic sequence of EIF4E is found in GenBank at accession number NC_000004. The gene sequence (NM_001968) is shown in FIG. 3C as SEQ ID NO: 3 (coding sequence from 1524-2177); the protein sequence is shown in FIG. 3D as SEQ ID NO: 4. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

FMR1 (fragile X mental retardation 1) encodes fragile X mental retardation protein (FMRP). This protein is normally made in many tissues and may play a role in the development of synaptic connections between nerve cells in the brain. FMRP may be involved in the regulation of synaptic plasticity, which can be important in memory and learning. The FMR1 gene is located on the long arm of the X chromosome at position 27.3, from base pair 146,699,054 to base pair 146,736,156. A genomic sequence of FMR1 is found in GenBank at accession number NC_000023. The gene sequence (NM_002024) is shown in FIG. 3E as SEQ ID NO: 5 (coding sequence from 230-2128); the protein sequence is shown in FIG. 3F as SEQ ID NO: 6. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

GRM1 (glutamate receptor, metabotropic 1) encodes the metabotropic glutamate receptor 1 (mGluR1) protein. GRM5 (glutamate receptor, metabotropic 5) encodes the metabotropic glutamate receptor 5 (mGluR5) protein. L-glutamate is the major excitatory neurotransmitter in the central nervous system and activates both ionotropic and metabotropic glutamate receptors. Glutamatergic neurotransmission is involved in most aspects of normal brain function and can be perturbed in many neuropathologic conditions. The metabotropic glutamate receptors are a family of G protein-coupled receptors, that have been divided into 3 groups on the basis of sequence homology, putative signal transduction mechanisms, and pharmacologic properties. Group I includes GRM1 and GRM5 and these receptors have been shown to activate phospholipase C. Group II includes GRM2 and GRM3 while Group III includes GRM4, GRM6, GRM7 and GRM8. Group II and III receptors are linked to the inhibition of the cyclic AMP cascade but differ in their agonist selectivities.

The GRM1 gene is located on chromosome 6 at 6q24, starting 146,390,611 bp from the p-terminus and ending 146,800,427 bp from the p-terminus (409,817 bases; orientation: plus strand). The genomic sequence of GRM1 is found in GenBank at accession number NC_000006. The gene sequence (NM_000838) is shown in FIG. 3G as SEQ ID NO: 7 (coding sequence from 471-4055); the protein sequence is shown in FIG. 3H as SEQ ID NO: 8. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

The GRM5 gene is located on chromosome 11 at 11q14.2-q14.3, starting 87,880,626 bp from the p-terminus and ending 88,438,761 bp from the p-terminus (558,136 bases; orientation: minus strand). The genomic sequence of GRM5 is found in GenBank at accession number NC_000011. The gene sequence (NM_000842) is shown in FIG. 3I as SEQ ID NO: 9 (coding sequence from 369-3911); the protein sequence is shown in FIG. 3J as SEQ ID NO: 10. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

HOMER1 encodes a member of the homer family of dendritic proteins. Members of this family regulate group 1 metabotrophic glutamate receptor function. The HOMER1 gene is located on chromosome 5 at 5q14.2, starting 78,704, 215 bp from the p-terminus and ending 78,845,796 bp from the p-terminus (141,582 bases; orientation: minus strand). The genomic sequence of HOMER1 is found in GenBank at accession number NC_000005. The gene sequence (NM_004272) is shown in FIG. 3K as SEQ ID NO: 11 (coding sequence from 1104-2168); the protein sequence is shown in FIG. 3L as SEQ ID NO: 12. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

HRAS belongs to the Ras oncogene family, whose members are related to the transforming genes of mammalian sarcoma retroviruses. The products encoded by these genes function in signal transduction pathways. These proteins can bind GTP and GDP, and they have intrinsic GTPase activity. The HRAS gene is located on chromosome 11 at 11p15.5, starting 522,242 bp from the p-terminus and ending 525,591 bp from the p-terminus (3,350 bases; orientation: minus strand). The genomic sequence of HRAS is found in GenBank at accession number NC_000011. The gene sequence (NM_176795) is shown in FIG. 3M as SEQ ID NO: 13 (coding sequence from 189-701); the protein sequence is shown in FIG. 3N as SEQ ID NO: 14. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

MAP2K1 (mitogen-activated protein kinase kinase 1) encodes a protein known as MEK1 protein kinase. MAP2K2 (mitogen-activated protein kinase kinase 2) encodes a protein known as MEK2 protein kinase. These proteins are part of a signaling pathway called the RAS/MAPK pathway, which transmits chemical signals from outside the cell to the cell's nucleus. RAS/MAPK signaling helps control the growth and division (proliferation) of cells, the process by which cells mature to carry out specific functions (differentiation), cell movement, and the self-destruction of cells (apoptosis).

The MAP2K1 gene is located on chromosome 15 at 15q22.1-q22.33, starting 64,466,674 bp from the p-terminus and ending 64,570,936 bp from the p-terminus (104,263 bases; orientation: plus strand). The genomic sequence of MAP2K1 is found in GenBank at accession number NC_000015. The gene sequence (NM_002755) is shown in FIG. 3O as SEQ ID NO: 15 (coding sequence from 476-1657); the protein sequence is shown in FIG. 3P as SEQ ID NO: 17. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

The MAP2K2 gene is located on chromosome 19 at 19p13.3, starting 4,041,319 bp from the p-terminus and ending 4,075,126 bp from the p-terminus (33,808 bases; orientation: minus strand). The genomic sequence of MAP2K2 is found in GenBank at accession number NC_000019. The gene sequence (NM_030662) is shown in FIG. 3Q as SEQ ID NO: 17 (coding sequence from 255-1457); the protein sequence is shown in FIG. 3R as SEQ ID NO: 18. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

The MECP2 gene (methyl CpG binding protein 2) encodes a protein (MeCP2) that is essential for normal brain development. This protein seems to be important for the function of nerve cells in the brain and is present in high levels in mature nerve cells. Studies suggest that the MeCP2 protein plays a role in forming synapses between nerve cells, where cell-to-cell communication occurs. This protein silences several other genes, preventing them from making proteins. The MECP2 gene is located on chromosome X at Xq28, starting 152,940,218 bp from the p-terminus and ending 153,016,406 bp from the p-terminus (76,189 bases; orientation: minus strand). The genomic sequence of MECP2 is found in GenBank at accession number NC_000023. The gene sequence (NM_004992) is shown in FIG. 3S as SEQ ID NO: 19 (coding sequence from 227-1687); the protein sequence is shown in FIG. 3R as SEQ ID NO: 20. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

PIK3CA encodes a protein that represents the catalytic subunit of Phosphatidylinositol 3-kinase, which uses ATP to phosphorylate PtdIns, PtdIns4P and PtdIns(4,5)P2. The gene is located on chromosome 3 at 3q26.3, starting 180,349,005 bp from the p-terminus and ending 180,435,194 bp from the p-terminus (86,190 bases; orientation: plus strand). The genomic sequence of is found in GenBank at accession number NC_000003. The gene sequence (NM_006218) is shown in FIG. 3U as SEQ ID NO: 21 (coding sequence from 158-3364); the protein sequence is shown in FIG. 3V as SEQ ID NO: 22. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

PIK3R1 encodes a protein that represents the 85 kD regulatory unit of Phosphatidylinositol 3-kinase. The gene is located on chromosome 5 at 5q13.1, starting 67,558,218 bp from the p-terminus and ending 67,633,405 bp from the p-terminus (75,188 bases; orientation: plus strand). The genomic sequence of is found in GenBank at accession number NC_000005. The gene sequence (NM_181523) is shown in FIG. 3W as SEQ ID NO: 23 (coding sequence from 43-2217); the protein sequence is shown in FIG. 3X as SEQ ID NO: 24. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

PTEN encodes the phosphatase and tensin homology protein, is a 3,4,5-triphosphate 3-phosphatase that contains a tensin like domain as well as a catalytic domain similar to that of the dual specificity protein tyrosine phosphatases. The PTEN protein preferentially dephosphorylates phosphoinositide substrates, and negatively regulate intracellular levels of phosphatidylinosito-3,4,5-triphosphate in cells. The PTEN protein is involved in the regulation of the cell cycle, preventing cells from growing too rapidly. The genomic sequence of is found in GenBank at accession number NC_007466. The gene sequence (NM_000314) is shown in FIG. 3Y as SEQ ID NO: 25 (coding sequence from 1032-2243); the protein sequence is shown in FIG. 3Z as SEQ ID NO: 26. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

RAF1 encodes a MAP kinase that functions downstream of the Ras family of membrane associated GTPases to which it binds directly. Once activated, the cellular RAF1 protein can phosphorylate to activate the dual specificity protein kinases MEK1 and MEK2, which in turn phosphorylate to activate the serine/threonine specific protein kinases, ERK1 and ERK2. Activated ERKs are pleiotropic effectors of cell physiology and play an important role in the control of gene expression involved in the cell division cycle, apoptosis, cell differentiation and cell migration. The RAF1 gene is located on chromosome 3 at 3p25, starting 12,600,108 bp from the p-terminus and ending 12,680,678 bp from the p-terminus (80,571 bases; orientation: minus strand). The genomic sequence of RAF1 is found in GenBank at accession number NC_000003. The gene sequence (NM_002880) is shown in FIG. 3AA as SEQ ID NO: 27 (coding sequence from 416-2362); the protein sequence is shown in FIG. 3BB as SEQ ID NO: 28. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

RHEB encodes the GTP-binding protein known as Ras Homology Enriched in Brain. Rheb is a member of the Ras superfamily and may be involved in neural plasticity. The protein is a member of the small GTPase superfamily and encodes a lipid-anchored cell membrane protein with five repeats of the Ras-related GTP-binding region. A genomic sequence of RHEB is found in GenBank at accession number NC_000007. The gene sequence (NM_005614) is shown in FIG. 3CC as SEQ ID NO: 29 (coding sequence from 414-968); the protein sequence is shown in FIG. 3DD as SEQ ID NO: 30. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

SHANK3 encodes proteins necessary to construct synapses in the brain. Shank proteins are multidomain scaffold proteins of the postsynaptic density that connect neurotransmitter receptors, ion channels, and other membrane proteins to the actin cytoskeleton and G-protein-coupled signaling pathways. Shank proteins also play a role in synapse formation and dendritic spine maturation. The gene is located on chromosome 22 at 22q13.3, starting 49,459,936 bp from the p-terminus and ending 49,518,507 bp from the p-terminus (58,572 bases; orientation: plus strand). A genomic sequence of SHANK3 is found in GenBank at accession number NC_000022. The gene sequence (NM_001080420) is shown in FIG. 3EE as SEQ ID NO: 31 (coding sequence from 1-5244); the protein sequence is shown in FIG. 3FF as SEQ ID NO: 32. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

TSC1 (Tuberous sclerosis 1) encodes a peripheral membrane protein that has been implicated as a tumor suppressor. TSC1 is also involved in vesicular transport and docking, in complex with TSC2. The TSC1 gene is located on chromosome 9 at 9q34, starting 134,756,557 bp from the p-terminus and ending 134,809,841 bp from the p-terminus (53,285 bases; orientation: minus strand). The gene sequence of TSC1 is found in GenBank at accession number NC_000009. The gene sequence (NM_000368) is shown in FIG. 3GG as SEQ ID NO: 33 (coding sequence from 235-3729); the protein sequence is shown in FIG. 3HH as SEQ ID NO: 34. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

The gene TSC2 (Tuberous sclerosis 2) encodes a protein called tuberin and has been implicated as a tumor suppressor. Its gene product associates with hamartin in a cytosolic complex, acting as a chaperone for hamartin. TSC2 has a function in vesicular transport, and interaction between TSC1 and TSC2 facilitates vesicular docking Gene products of TSC1 and TSC2 work together to help control cell growth and size. The TSC2 gene is located on chromosome 16 at 16p13.3, starting 2,037,991 bp from the p-terminus and ending 2,078,714 bp from the p-terminus (40,724 bases; orientation: plus strand). A genomic sequence of TSC2 is found in GenBank at accession number NC_000016. The gene sequence (NM_000548) is shown in FIG. 3II as SEQ ID NO: 35 (coding sequence from 107-5530); the protein sequence is shown in FIG. 3JJ as SEQ ID NO: 36. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

UBE3A (ubiquitin protein ligase E3A) encodes an enzyme called ubiquitin protein ligase E3A. This enzyme is involved in targeting proteins to be broken down (degraded) within cells. The gene is located on chromosome 15 at 15q11-q13, starting 23,133,489 bp from the p-terminus and ending 23,235,221 bp from the p-terminus (101,733 bases; orientation: minus strand). A genomic sequence of is found in GenBank at accession number NC_000015. The gene sequence (NM_130839) is shown in FIG. 3KK as SEQ ID NO: 37 (coding sequence from 658-3276); the protein sequence is shown in FIG. 3LL as SEQ ID NO: 38. Except as noted herein, variants in this sequence are believed to have not previously been shown to be associated with at least some autism spectrum disorders (e.g., non-syndromic autism), and variants in Table 2 have not previously been shown to be associated with non-syndromic autism or syndromic autism.

For example, for the first ARC variant in Table 2, one may use the DNA sequence of SEQ ID NO: 1 to determine the coding sequence of the gene encoding the variant: c65T>G, and the protein sequence of the protein having the variant p.Val22Gly to determine that this variant comprises a missense mutation. The nature of the mutation may further be assessed on the protein sequence (SEQ ID NO: 2) and function. For example, this mutation may be expected to have a moderate to minor effect as the amino acid substitution of Gly for Val may be considered to be a conservative substitution. Or, a more detailed analysis of three-dimensional conformational data for the protein may indicate that the mutation may be deleterious to protein function. A similar analysis may be performed for each of the variants described in Table 2, using the sequences provided in FIG. 4, panes A-LL.

Thus, in certain embodiments, the number and nature of DNA sequence variants in the coding regions and contiguous RNA regulatory regions in 19 genes that code for a number of the key proteins involved in the mGluR5 pathway in samples from patients with an ASD (e.g., non-syndromic autism) and from controls (i.e., non-autistic individuals) may be examined. Target regions may be enriched in pools of samples and sequenced by next-generation technology to enable the detection of rare variants. An embodiment of such methods are discussed in more detail in the Examples herein. Such sequencing is generally performed under conditions of high sensitivity and low false discovery rates at acceptable cost using the methods described herein. Sensitivity of variant detection may generally depend on the number of reads covering this position (known as "depth" or "coverage"), i.e., the amount of sequence information available for that particular position. Since both the enrichment methods and the sequencing step are influenced by the sequence context, coverage may vary from region to region. In addition, sensitivity of variant detection also differs by type of variant (substitution versus deletion and/or insertion). At high coverages (i.e., sequencing a region ≥30×), sensitivity is in certain embodiments, about 99% for detecting substitution variants, 90% for detecting deletions and/or insertions spanning ≤5 bases, and approximately 30% for detecting deletions and/or insertions spanning from 6 to about 40 bases. Also in certain embodiments, insertions and/or deletions spanning ≤5 bases or ≥6 bases account for about 10% and 1%, respectively, of all variant occurrences and for about 16% and 2.6%, respectively, of all pathogenic variant occurrences. Taking into account coverage at each base position within the sequenced regions, length of the sequenced regions, and variant-type specific sensitivity, an overall sensitivity of variant detection for each gene included in the assay may be provided. For example, if 80% of the analyzed bases in a gene have a coverage corresponding to 97% sensitivity, 15% have a coverage corresponding to 92% sensitivity, and 5% have a coverage corresponding to 80% sensitivity, the overall sensitivity for that gene would be calculated as 95%. Generally, exons with a sensitivity of less than 50% are not included in the overall sensitivity estimate per gene, but are reported separately as segments not sequenced.

In certain embodiments, all sequence variants detected by next-generation sequencing that are known or predicted to be pathogenic as well as all sequence variants that are novel (i.e., not previously described in the literature or a database) are confirmed by uni-directional Sanger sequencing. Therefore, the false positive rate of reported variants is generally very low. Using this method, a statistically significant increase in the number of rare variants overall as well as rare, potentially disruptive variants in cases compared to controls in several different genes may be detected.

For example, in an embodiment, the variants depicted in Table 2 were found in samples from individuals with a type of autism syndrome (i.e., non-syndromic autism) that are not seen in unaffected individuals.

For example, Tables 3-5 provide an analysis of variants associated with mGluR5 signaling as found in individuals that either did not display the symptoms of autism (i.e., controls), or that were diagnosed with non-syndromic autism. As described in more detail in the Examples herein, the variants in Table 2 were found in samples from 290 individuals with an autism-spectrum disorder (non-syndromic autism).

As shown in Tables 3-5, at least 4 of these genes (SHANK 3, TSC1, TSC2 and HOMER 1) had mutations that based upon an increased detection in autism patients. Also, for these genes, and at least some of the other genes assayed, the severity of the mutation with respect to gene expression or protein function indicated that the variants may be associated with the development of non-syndromic autism. These mutations may also be involved in other types of autism syndromes. At least one of these genes (HOMER1) has not previously been associated with autism either functionally, or genetically.

Table 3 shows a comparison of the number of common and rare variants in samples from patients with non-syndromic autism as provided by the AGRE sample database, as compared to controls (i.e., individuals who do not have autism or ASD). It can be seen that for some of the genes, there is a distinct increase in the number of rare variants in the individuals from the patient pool, whereas the more common variants exhibit similar frequencies in both groups.

TABLE 3

| | Total # | Number of rare variants | | Number of common variants | |
|---|---|---|---|---|---|
| Gene | variants | AGRE | Controls | AGRE | Controls |
| ARC | 14 | 6 | 9 | 2 | 2 |
| EIF4E | 7 | 4 | 5 | 1 | 1 |
| FMR1 | 10 | 3 | 7 | 2 | 3 |
| GRM1 | 41 | 23 | 28 | 7 | 7 |
| GRM5 | 71 | 38 | 36 | 22 | 21 |
| HOMER1 | 13 | 8 | 2 | 4 | 4 |
| HRAS | 7 | 3 | 2 | 3 | 3 |
| MAP2K1 | 8 | 5 | 4 | 2 | 3 |
| MAP2K2 | 32 | 21 | 19 | 5 | 6 |
| MECP2 | 21 | 15 | 15 | | 1 |
| PIK3CA | 27 | 9 | 4 | 16 | 16 |
| PIK3R1 | 18 | 9 | 8 | 6 | 6 |
| PTEN | 6 | 5 | 5 | 1 | 1 |
| RAF1 | 10 | 7 | 8 | 1 | |
| RHEB | 3 | 1 | 2 | 1 | 1 |
| SHANK3 | 98 | 81 | 61 | 7 | 6 |
| TSC1 | 31 | 26 | 13 | 3 | 5 |
| TSC2 | 107 | 64 | 73 | 14 | 12 |
| UBE3A | 12 | 8 | 9 | 2 | 1 |
| Grand Total | 536 | 336 | 310 | 99 | 99 |

Table 4 shows a comparison of the number of rare and potentially disruptive mutations, (i.e., based on the nature of the mutation, these mutations are expected to disrupt gene expression or protein function, in patients with non-syndromic autism as compared to controls. It can be seen that for some of the genes, there is a distinct increase in the number of potentially disruptive variants in the AGRE population as compared to the controls.

TABLE 4

| | Number of rare, potentially disruptive variants | | |
|---|---|---|---|
| Gene | Total | AGRE | Controls |
| ARC | 6 | 5 | 3 |
| EIF4E | 2 | 2 | 2 |
| FMR1 | 3 | | 2 |
| GRM1 | 19 | 10 | 14 |
| GRM5 | 31 | 13 | 17 |
| HOMER1 | 6 | 6 | 1 |
| HRAS | 2 | 1 | |
| MAP2K1 | 3 | 2 | 3 |
| MAP2K2 | 8 | 6 | 4 |
| MECP2 | 6 | 4 | 6 |
| PIK3CA | 13 | 2 | 3 |
| PIK3R1 | 4 | 2 | 1 |
| PTEN | 1 | 1 | 1 |
| RAF1 | 4 | 2 | 2 |
| RHEB | 1 | 1 | 1 |
| SHANK3 | 42 | 37 | 26 |
| TSC1 | 18 | 17 | 8 |
| TSC2 | 44 | 35 | 27 |
| UBE3A | 3 | 1 | 1 |
| Total | 216 | 147 | 122 |

Table 5 shows the number of rare, potentially disruptive variants that were found in only one sample source. It can be seen that for at least four genes (HOMER, SHANK 3, TSC1 and TSC2, there are mutations that are found in the patient (AGRE) population, but are not found in the controls. This demonstrates a statistically significant difference between rare (i.e., novel in that these variants have never been reported before) variants in specific genes in the mGluR5 pathway and non-syndromic autism.

TABLE 5

| | Number of rare, potentially disruptive variants found in only one sample source | | | Fisher's 2 |
|---|---|---|---|---|
| Gene | Total | AGRE | Control | tailed test |
| ARC | 4 | 3 | 1 | 0.3654 |
| FMR1 | 3 | | 2 | 0.2412 |
| GRM1 | 8 | 2 | 6 | 0.2863 |
| GRM5 | 9 | 3 | 6 | 0.505 |
| HOMER1 | 5 | 5 | | 0.0282 |
| HRAS | 1 | 1 | | 0.4915 |
| MAP2K1 | 1 | | 1 | 0.4915 |
| MAP2K2 | 4 | 3 | 1 | 0.3654 |
| MECP2 | 2 | | 2 | 0.4994 |
| PIK3CA | 3 | 1 | 2 | 1 |
| PIK3R1 | 1 | 1 | | 0.4915 |
| RAF1 | 4 | 2 | 2 | 1 |
| SHANK3 | 17 | 14 | 3 | 0.006 |
| TSC1 | 8 | 8 | | 0.0032 |
| TSC2 | 19 | 14 | 5 | 0.0356 |
| UBE3A | 1 | 1 | | 0.4915 |
| Grand Total | 90 | 58 | 31 | 0.0012 |

Thus, in certain embodiments, the present invention provides methods and or nucleic acid sequences that can be used to determine if a subject has, or is at increased risk for developing an ASD. As noted above, in some cases, the variant nucleic acid may be a novel (i.e., not previously reported) variant, or it may be a variant that has previously been found to be associated with an ASD. In certain embodiments, the variant may be a novel variant, or a previously reported variant in one of the genes that is important to the metabotropic glutamate receptor pathway. Or, genes from other biochemical pathways may be analyzed. For example, in at least one embodiment, at least four genes (HOMER, SHANK 3, TSC1 and TSC2), there are mutations that are found in patients with non-syndromic autism but that are not found in the controls.

In an embodiment, the variant (mutation) may be one of the variants listed in Table 2. Or, the variant may be at least one of a HOMER 1 such as, but not limited to: a c.195G>T, M65I; a c.290C>T, S97L mutation; or a c.425C>T, P142L mutation. Additionally or alternatively, the mutation may comprise a GRM5 c.3503T>C, L1168P mutation. Additionally or alternatively, the mutation may comprise a MAPK2 c.581-1G>T mutation and/or a HRAS c.383G>A, R128Q mutation. Additionally or alternatively, the mutation may comprise a MECP2 c.1477G>T, E483X mutation.

For example, two of HOMER1 variants (c.195G>T, M65I and c.290C>T, S97L) are located in the EVH1 domain in Homer1, which interacts with the Pro-Pro-Ser-Pro-Phe motifs in mGluR1 and mGluR5. A third potentially damaging variant in HOMER1 (c.425C>T, P142L) affects one of the conserved prolines within the P-motif of the CRH1 domain, which serves as an internal binding site for the EVH1 domain. It has been proposed that EVH1 binding to mGluR induces homo-multimerization of Homer1, while EVH1 binding to the internal P-motif in Homer1 arrests this homo-multimerization. Interestingly, one of the GRM5 variants (c.3503T>C, L1168P) detected in AGRE samples is located relatively close to the conserved Pro-Pro-Ser-Pro-Phe Homer1 binding motif in mGluR5.

In other embodiments, the mutations detected are in either the TSC1 or the TSC2 genes (see Table 2). In yet other embodiments, the mutations detected are in either the SHANK 3 gene (see Table 2).

In other embodiments, AGRE samples may have a variant in MAP2K2 that affects a conserved splice-site and is thus highly likely to be damaging (c.581-1G>T). In yet other embodiments, a potentially damaging variant was also detected in HRAS, another gene in the RAS/MAPK signalling pathway. This HRAS variant (c.383G>A, R128Q) disrupts an arginine at position 128 that plays an important role in membrane binding and function of GTP-bound H-ras.

In yet other embodiments, the method may further detect a nonsense mutation (c.1477G>T, E483X) in MECP2 in a single AGRE sample, a gene known to be associated with Rett's syndrome, another syndromic form of ASD.

EXAMPLES

The method is exemplified by the following non-limiting examples.

Example 1

Variant Discovery in Autism Candidate Genes

All coding exons of 19 candidate genes hypothesized to be associated with autism spectrum disorders and of 4 control genes known to be associated with hypertrophic cardiomyopathy in 290 samples from the AGRE collection and 290 ethnically matched samples from the Coriell collection were amplified. Before amplification, the DNA concentration in each sample was determined by measurement on a NANODROP spectrophotometer, and equal amounts of DNA were then used to generate 15 pools of 20 AGRE samples each and 15 pools of 20 Coriell samples each.

Ten samples of each collection were represented in two pools, allowing for independent replication of variant detection in those samples. For each pool, a total of 293 PCR products were generated, encompassing about 116,000 bases in total. PCR products covered all coding regions of every mRNA isoform as well as flanking intronic regions. A high-fidelity polymerase was used for PCR amplification, to minimize introduction of errors during PCR. PCR primers were tailed with sequences containing a NotI restriction site. Following PCR amplification, PCR products were pooled and subjected to digestion with NotI restriction enzyme. The NotI-digested PCR products were ligated to generate concatemers of several kb in length. Concatemers were then randomly sheared into fragments 200 to 250 bp in length. Following ILLUMINA's protocol, the fragments were end-repaired, A-tailed, and ligated to forked adapter molecules. Adapter-ligated fragments were selectively enriched by PCR. During the enrichment step, a 6-bp index was added to the fragments. Indexing of the fragments allowed sequencing of fragments from different sample pools on the same lane of the Illumina GA2 instrument.

Sequencing was performed for 50 cycles on the ILLUMINA GA2. Minimal yield per lane was 5 million reads. Fragment libraries from two different sample pools were sequenced per ILLUMINA GA2 lane, for an average target coverage of 800 fold per base and sample pool, or 40 fold per individual (20 fold per individual chromosome). This average coverage was sufficient to detect occurrence of a single heterozygous variant in a pool of 20 samples. It was found that coverage and thus detection sensitivity varied within and between amplified regions, as well as between fragment libraries.

Sequence data derived from each ILLUMINA GA2 lane were processed through BUSTARD for base calling, and the output data then separated into different files based on index. Only index reads differing by 1 or less bases from the actual index sequence were used. After index-splitting, sequence data were analyzed using the pipeline developed at Boston College by Dr. Gabor Marth, which is comprised of an aligner (MOSAIK) and a variant caller (GIGABAYES). Sequence reads were aligned to a reference sequence assembled from the hg18-derived sequence for all coding exons represented in the original PCR-product library plus about 30 nucleotides of flanking non-coding sequence. For a read to be considered aligned, at least 60% of the bases had to be aligned with a maximum of 1 mismatch. Variant calling in the pooled data was based on the successive application of three types of filters followed by use of the Bayesian-based variant calling algorithm employed by GIGABAYES. The filters were designed to reduce the false-positive rate while maintaining 80-90% sensitivity for detecting single heterozygous variant occurrences in a pool of 20 samples by adhering to the following experimental conditions: (1) The QV value of the base call had to be at least 20; (2) a minimum number of minor allele calls had to be derived from each DNA strand (coding and non-coding); and (3) the minor allele frequency had to reach a certain value.

Filters were applied as follows. Minor alleles that occurred at least 4 times on each DNA strand at a QV of at least 20 were kept in consideration as potential variants. At positions where the total coverage (i.e., the total number of base calls of any QV value) was below 1200, minor alleles that occurred at least 3 times on each DNA strand at a QV of at least 20 were kept in consideration as potential variants. At positions where the total coverage was below 900, minor alleles that occurred at least 2 times on each DNA strand at a QV of at least 20 were kept in consideration as potential variants. At all positions where a potential variant was called based on the criteria described above, all variant calls with any filter in any other sample pools were then kept in consideration as potential variants. All potential variant calls were then subjected to the GIGABAYES variant calling algorithm with the appropriate settings for variant calling in pooled samples. Of the resulting variant calls, only those with a minor allele frequency of 1.5% or more were accepted.

Example 2

Number of Variants Found in AGRE and Control Samples

A total of 536 variants were detected in the AGRE and/or the control samples on both the GA2 and the HELISCOPE platform (Table 3). These variants were called 'common' if found with an allele frequency ≥1% and rare if found with an allele frequency of <1%. 336 and 310 of the variants detected in AGRE samples and in controls, respectively, were rare. The number of both common and rare variants differed between individual genes. Table 2 shows at least some of the variants that were detected.

The method may include selecting for rare variants with a potentially disruptive effect. In this group, variants which create a missense or nonsense change on the protein level, affect a conserved splice-site, or are located in the 3'UTR or 5' UTR and may thus impact mRNA transcription or processing were included. Of a total of 216 rare potentially disruptive variants, 147 were found in AGRE and 122 in controls (Table 4). Of those, 58 were only found in AGRE samples and 31 only in controls (Table 5), indicating as statistically significant enrichment of rare, potentially disruptive variants in AGRE samples. On the level of the individual genes, the enrichment reached statistical significance for the genes HOMER1, SHANK3, TSC1, and TSC2 (Table 5).

Three of these genes (SHANK3, TSC1, and TSC2) have previously demonstrated causal roles in autism. Notably, however, autism due to variants in TSC1 or TSC2 is typically seen in the context of tuberous sclerosis, while in the current study, samples from individuals with syndromic forms of ASD were excluded. The fourth gene (HOMER1) has not previously been causally related to autism. Two of HOMER1 variants (c.195G>T, M65I and c.290C>T, S97L) are located in the EVH1 domain in Homer1, which has been shown to interact with the Pro-Pro-Ser-Pro-Phe motifs in mGluR1 and mGluR5. A third potentially damaging variant in HOMER1 (c.425C>T, P142L) affects one of the conserved prolines within the P-motif of the CRH1 domain, which serves as an internal binding site for the EVH1 domain. It has been proposed that EVH1 binding to mGluR induces homo-multimerization of Homer1, while EVH1 binding to the internal P-motif in Homer1 arrests this homo-multimerization. Interestingly, one of the GRM5 variants (c.3503T>C, L1168P) detected in AGRE samples is located relatively close to the conserved Pro-Pro-Ser-Pro-Phe Homer1 binding motif in mGluR5.

Several of the rare, potentially disruptive TSC1 and TSC2 variants observed only in AGRE samples have been classified by others as rare polymorphism because they were seen together with clear disease variants and/or did not clearly segregate with a tuberous sclerosis phenotype. These variants may thus represent hypomorphic variants with regard to tuberous sclerosis and act as modifiers when occurring together with other variants in TSC1 and TSC2. The pleomorphic nature of monogenic disorders and the role of hypomorphic variants in milder forms of monogenic disease is increasingly well recognized.

While the enrichment of rare, potentially disruptive variants in AGRE samples reached statistical significance for four of the genes with this initial sampling, specific single variants suggest causal relationship of additional genes to ASD. Specifically, one AGRE sample harbored a variant in MAP2K2 that affects a conserved splice-site and is thus highly likely to be damaging (c.581-1G>T). A potentially damaging variant was also detected in HRAS, another gene in the RAS/MAPK signalling pathway. This HRAS variant (c.383G>A, R128Q) disrupts an arginine at position 128 that has been shown to play an important role in membrane binding and function of GTP-bound H-ras. MAP2K2 and HRAS are known to be associated cardiofaciocutaneous and Costello syndrome, respectively, both monogenic disorders associated with mental delay and retardation. However, MAP2K2 has not previously been linked to autism, while early association studies did suggest a link between HRAS and ASD.

The method further detected one nonsense mutation (c.1477G>T, E483X) in MECP2 in a single AGRE sample, a gene known to be associated with Rett's syndrome, another syndromic form of ASD. Interestingly, this nonsense mutation causes a deletion of only the 3 C-terminal amino acids of MECP2, and may thus also represent a hypomorphic variant.

The average coverage for each gene in each pool at all positions where a variant was detected in any or the pools was determined. Low coverage in one or a few pools has little effect on detection of common variants, since the variant will be found in many different pools. However, rare variants may be missed if they occur only in a pool of lower coverage. To appreciate these effects two measures were evaluated: (1) the number of pools with coverage below a certain cut-off value (e.g., 160 for the 20-specimen pools and 120 for the 15-specimen pools); and (2) the relative frequency of common and rare variants. Both presence of low coverage in several pools and an unbalanced ratio of common and rare variants between populations lower the detection confidence for rare variants in a given gene.

As the methods of the invention provide for the discovery of rare variants in candidate genes, assays were performed to determine that that the sample-pool size did not limit sensitivity of variant detection.

To validate sensitivity of variant detection in the larger (20-sample) pools, a validation pool from 20 samples that had previously been Sanger sequenced for all coding exons of the genes MYBPC3, MHY7, TNNT2, and TNNI3 was constructed and enriched for these targets using PCR. The PCR products were concatenated, sheared, and sequenced on the GA2 sequencer under conditions of high coverage. Sequencing detected all of the 46 single-nucleotide variants previously detected by Sanger sequencing, including 20 variants that were heterozygously present in only 1 of the 20 samples (singletons), demonstrating the high sensitivity of variant detection in such pools (e.g., 20-sample pools on the GA2 under conditions of high coverage). Although for some of the singletons, the allele frequency detected in the pool deviated from the theoretical value of 0.025, all singletons were detected at an allele frequency of ≥0.012, or half the theoretical value. At this allele-frequency cut-off, however, an additional 82 variants were detected that had not been found by Sanger sequencing and are thus likely to be false positives, for a false-discovery rate (FDR) of 64%.

Example 3

Methods

Sample Selection

DNA samples (n=290) from individuals with an autism-spectrum disorder (ASD) were obtained from the Autism Genetic Research Exchange (AGRE) collection, based on the following inclusion criteria: diagnosis of autism by Autism Diagnostic Interview, Revised (ADI-R) and Autism Diagnostic Schedule (ADOS); idiopathic (i.e., non-syndromic) autism; at least one affected family member; and availability of complete data for RAVEN, Peobody, and SRS. Sample ethnicity was given as white, not Hispanic or Latino, and not more than one race for 221 individuals; as white, not Hispanic or Latino, and more than one race for 11 individuals; as Hispanic or Latino for 53 individuals; and as Asian for 5 individuals. Three hundred (300) control DNA samples were obtained from the Coriell collection and consisted of 248 samples with Caucasian or European ethnicities and 52 with Hispanic or Latino ethnicities.

Next-Generation Sequencing

DNA concentration was determined for all samples using a NANODROP analysis system, and equal amounts of control sample DNAs were combined into orthogonal pools of either 20 samples each and 15 samples. Each pool then served as a one DNA template for PCR amplification of all coding exons of the longest isoform of each of the 19 candidate genes, using specific PCR primers tailed at the 5' end with a 14-bp sequence containing a Not1 restriction site. All PCR products derived from the same template (i.e., sample pool) were pooled, digested with Not1, and ligated to form concatemers, which were subsequently randomly sheared into fragments with a mean size of 150 to 300 bp, using a COVARIS S2 instrument. These fragments were prepared for sequencing on either an ILLUMINA GA2 (20-sample pools) or a HELICOS HELISCOPE (15-sample pools) according to the manufacturers' instructions. ILLUMINA sequencing was performed for 50 cycles, resulting in a read length of up close to 50 bases, and HELISCOPE sequencing was performed for 120 cycles or 30 quads, resulting in an average read length of about 32 bases.

Analysis of Next-Generation Sequencing Data

Reads were aligned to a reference sequence that included the hg18-derived sequence of each amplified exon "padded" on each side with 30 flanking non-coding bases. The aligner MOSAIK was used for the GA2 reads, and the aligner INDEXDP for the HELISCOPE reads. Variant calling was performed with GIGABAYES for the GA2 reads, but without invoking the Bayesian-based algorithm, and with SNPSNIFFER for the HELISCOPE reads. SNPSNIFFER required a minimum minor allele frequency threshold of 1%. No minimum minor allele frequency threshold was set in GIGABAYES. In both cases, variant calls were only accepted if they occurred at least once on each DNA strand. No other filters were used during the initial variant calling.

Sanger Sequencing

Sanger sequencing was performed for selected gene regions and selected samples, to confirm variants detected during next-generation sequencing. PCR primers and conditions were the same as before, except that individual samples were used as template instead of sample pools. Each PCR product was then cycle-sequenced using ABI BIGDYE reagents, with the specific PCR primers serving as sequencing primers, and the sequencing products were separated on an ABI3730exl. Sequencing traces were visualized using SEQUENCESCANNER (ABI), and presence or absence of a given mutation determined by manual comparison to the reference sequence.

References and citations to other documents, such as patents, patent applications, patent publications, journals, books, papers, web contents, have been made throughout this disclosure. All such documents are hereby incorporated herein by reference in their entirety for all purposes.

Various modifications and equivalents of the invention and many further embodiments thereof, in addition to those shown and described herein, will become apparent to those skilled in the art from the full contents of this document, including references to the scientific and patent literature cited herein. The subject matter herein contains information, exemplification and guidance that can be adapted to the practice of this invention in its various embodiments and equivalents thereof.

What is claimed is:

1. A method for detecting a mutation associated with the presence or an increased risk of developing an autism spectrum disorder in a subject, the method comprising:

obtaining a nucleic acid from a tissue or body fluid sample from a subject;

conducting an assay to identify a HOMER 1 c.195G>T, M65I variant sequence in the nucleic acid;

conducting an assay to identify a HOMER 1 c.290C>T, S97L variant sequence in the nucleic acid; and conducting an assay to identify a HOMER 1 c.425C>T, P142L variant sequence in the nucleic acid.

2. The method according to claim 1, wherein the assay comprises at least one of nucleic acid sequencing, hybrid capture, and epigenetic analysis.

3. The method according to claim 1, further comprising conducting an assay to identify an additional variant sequence in at least one of a TSC1, TSC2, MECP2, SHANK3, GRM1, GRM5, ARC, EIF4E, HOMER1, HRAS, MAP2K1, MAP2K2, RAF1, PIK3CA, PIK3R1, FMR1, PTEN, RHEB or UBE3A gene.

4. The method of claim 3, wherein the nucleic acid in the conducting step comprises a gene, an exon, an intron, a gene regulatory element, an expressed RNA, an siRNA, or an epigenetic element.

5. The method according to claim 3, wherein the variant comprises at least one of the following mutations: GRM5 c.3503T>C, L1168P; MAPK2 c.581-1G>T; HRAS c.383G>A, R128Q; a MECP2 c.1477G>T, E483X.

6. The method according to claim 1, further comprising conducting an assay to identify an additional variant sequence in at least one of a TSC1, TSC2, SHANKS3, or HOMER1 gene.

7. The method according to claim 2, wherein the nucleic acid sequencing comprises at least one of single-molecule sequencing-by-synthesis or massively parallel sequencing.

8. The method according to claim 2, wherein the nucleic acids from individual subjects are combined and analyzed as a pooled sample to identify at least one nucleic acid that shows a variation.

9. The method according to claim 8, wherein a plurality of the pooled samples are analyzed to identify at least one nucleic acid that shows the same variation in at least two pooled samples.

10. The method according to claim 1, wherein the autism spectrum disorder comprises at least one of non-syndromic autism, classical autism, Asperger's syndrome, Rett's syndrome, childhood disintegrative disorder, or pervasive developmental disorder not otherwise specified (PDD-NOS).

11. The method according to claim 1, wherein the autism spectrum disorder comprises non-syndromic autism.

12. The method according to claim 1, wherein the subject is a child.

13. The method according to claim 1, wherein the subject is a fetus.

14. The method according to claim 1, wherein the body fluid comprise at least one of cerebrospinal fluid, blood, amniotic fluid, maternal blood, and urine.

* * * * *